United States Patent [19]
Bischofberger et al.

[11] Patent Number: 5,952,375
[45] Date of Patent: *Sep. 14, 1999

[54] COMPOUNDS AND METHODS FOR SYNTHESIS AND THERAPY

[75] Inventors: Norbert W. Bischofberger; Choung U. Kim, both of San Carlos; Willard Lew, San Mateo; Hongtao Liu; Matthew A. Williams, both of Foster City, all of Calif.

[73] Assignee: Gilead Sciences, Inc., Foster City, Calif.

[*] Notice: This patent is subject to a terminal disclaimer.

[21] Appl. No.: 08/606,624

[22] Filed: Feb. 26, 1996

Related U.S. Application Data

[63] Continuation-in-part of application No. 08/580,567, Dec. 29, 1995, abandoned, which is a continuation-in-part of application No. 08/476,946, Jun. 6, 1995, Pat. No. 5,866,601, which is a continuation-in-part of application No. 08/395,245, Feb. 27, 1995, abandoned.

[51] Int. Cl.$^6$ .......................... A61K 31/35; A61K 31/28
[52] U.S. Cl. ............................. 514/459; 514/492
[58] Field of Search ...................... 514/459, 492

[56] References Cited

U.S. PATENT DOCUMENTS

| | | | |
|---|---|---|---|
| 4,968,788 | 11/1990 | Farquhar | 536/27 |
| 5,175,273 | 12/1992 | Bischofberger et al. | 536/27 |
| 5,206,400 | 4/1993 | Witiak et al. | |
| 5,292,938 | 3/1994 | Mease et al. | |
| 5,428,073 | 6/1995 | Kunisch et al. | 514/561 |
| 5,512,596 | 4/1996 | Kim et al. | 514/568 |
| 5,514,798 | 5/1996 | Bischofberger et al. | 544/243 |
| 5,536,734 | 7/1996 | Mueller et al. | 514/336 |
| 5,556,963 | 9/1996 | Liav et al. | |
| 5,597,933 | 1/1997 | Searle et al. | |
| 5,622,916 | 4/1997 | Kunisch et al. | 504/269 |
| 5,714,509 | 2/1998 | Luo et al. | 514/415 |

FOREIGN PATENT DOCUMENTS

| | | |
|---|---|---|
| PJ 9800 | 11/1991 | Australia. |
| PK 2896 | 11/1991 | Australia. |
| PK 4537 | 11/1991 | Australia. |
| 654815 | 11/1994 | Australia. |
| 0 534 216 A1 | 9/1992 | European Pat. Off.. |
| 0 539 204 A1 | 10/1992 | European Pat. Off.. |
| 9510141 | 5/1995 | United Kingdom. |
| 9516276 | 8/1995 | United Kingdom. |
| 9525389 | 12/1995 | United Kingdom. |
| WO 91/16320 | 10/1991 | WIPO. |
| WO 92/06691 | 4/1992 | WIPO. |
| WO 93/12105 | 6/1993 | WIPO. |
| WO 93/16049 | 8/1993 | WIPO. |
| WO 94/07885 | 4/1994 | WIPO. |
| WO 94/07886 | 4/1994 | WIPO. |
| WO 94/28956 | 12/1994 | WIPO. |
| WO 94/29476 | 12/1994 | WIPO. |
| WO 95/00503 | 1/1995 | WIPO. |
| WO 95/16680 | 6/1995 | WIPO. |
| WO 95/18800 | 7/1995 | WIPO. |
| WO 95/20583 | 8/1995 | WIPO. |
| WO 95/32712 | 12/1995 | WIPO. |
| WO 96/04265 | 2/1996 | WIPO. |
| WO 96/26933 | 9/1996 | WIPO. |
| WO 96/30329 | 10/1996 | WIPO. |
| WO 96/36628 | 11/1996 | WIPO. |
| WO 96/39838 | 12/1996 | WIPO. |

OTHER PUBLICATIONS

Luo et al., "Abstract of Presentation C52: Designed Non–Carbohydrates Inhibitors or Influenza Virus Neuraminidase And Accompanying Notes," International Antiviral Conference, Nice, France, Jun. 10 (1994).

Ranner et al., Aust J Chem, 43:609–616 (1990).

Smith et al., "Novel Inhibitors of Influenza Sialidases Related to GC167," Bioorg Med Chem Lett 6(24):2931–2936 (1996).

Bamford et al., "Synthesis of 6–,7–and 8–carbon sugar analogues of potent anti–influenza 2,3–didehydro–2,3–dideoxy–N–acetylneuraminic acid derivatives," J Chem Soc Perkin Trans I pp. 1181–1187 (1995).

Bamford, Mark J., "Neuraminidase Inhibitors as Potential Anti–Influenza Drugs," J Enzyme Inhibition 10:1–16 (1995).

Carless et al., "Synthesis of Psuedo–alpha–L–fucopyranose from Toluene," J Chem Soc (C) pp. 2447–2448 (1995).

Chandler et al., "Approaches to carbocyclic analogues of the potent neuraminidase inhibitor 4–guanidino–Neu5Ac2en. X–Ray molecular structure of N[(1–S,2S,6R)–2–azido–6–benzylaoxymethyl–4–formylcyclohex–3–enyl] acetamide," J Chem Soc Perkin Trans I pp. 1189–1197 (1995).

Chandler et al., "Synthesis of the potent influenza neuraminidase inhibitor 4–guanidino Neu5Ac2en. X–Ray molecular structure of 5–acetamido–4–amino–2,6–anhydro–3,4,5–trideoxy–D–erythro–L–gluco–nononic acid," J Chem Soc Perkin Trans I pp. 1173–1180 (1995).

Ciccotosto et al., "Synthesis of Methyl 5–Acetamido–3,4,5–trideoxy–4–Guanidinyl–D–glycero–D–galacto–2– nonulopryanosidonic acid (4–deoxy–4–guanidino–Neu5Ac–alpha2Me)," Tet Lett 36(30):5405–5408 (1995).

Colman, P.M., "Influenza virus neuraminidase: Structure, antibodies, and inhibitors," Protein Science 3:1687–1696 (1994).

Dernick, Rudolf, "Sterical Requirements for Inhibitors of Viral Neuraminidases," Chem Ab 96:256 (1982).

(List continued on next page.)

Primary Examiner—Kevin E. Weddington
Attorney, Agent, or Firm—Mark L. Bosse

[57] ABSTRACT

Novel compounds are described. The compounds generally comprise an acidic group, a basic group, a substituted amino or N-acyl and a group having an optionally hydroxylated alkane moiety. Pharmaceutical compositions comprising the inhibitors of the invention are also described. Methods of inhibiting neuraminidase in samples suspected of containing neuraminidase are also described. Antigenic materials, polymers, antibodies, conjugates of the compounds of the invention with labels, and assay methods for detecting neuraminidase activity are also described.

8 Claims, 8 Drawing Sheets

OTHER PUBLICATIONS

Douglas, R. Gordon, Jr., "Prophylaxis and Treatment of Influenza," N Engl J Med 322(7):443–450 (2/15/90).

Ganem, Bruce, "Tetrahedron Report Number 59. From Glucose to Aromatics: Recent Developments in Natural Products of the Shikimic Acid Pathway," Tetrahedron 34:3353–3383 (1978).

Grewe et al, "Abbau der Chinasaure nach Hunsdiecker," Chem Ber 98:104–110 (1965).

Grewe et al, "Darstellung und Eigenschaften des Chinaaldehyds," Liuebigs Ann Chem 658:113–119 (1962).

Grewe et al, Die Totalsynthese der Chinasaure, Chem Ber 87:793–802 (1954).

Grewe et al, Die Uberfuhrung der Shikimisaure in Chinasaure, Chem Ber 86:928–938 (1953).

Grewe et al, Eine einfache Synthese der Shikimisaure, Chem Ber 100:2546–2553 (1967).

Grewe et al, Eine neue Syntheses der Shikimisaure, Chem Ber 97:443–448 (1964).

Grewe et al, Synthese der Homochinasaure und des beta–Chino–athylamins, Liebigs Ann Chem 575:1–17 (1952).

Grewe et al, Uberfuhrung der Chinasaue in ungesattigte Verbindugen vom Typ der Shikimisaure, Angew Chem Int Ed 69:61 (1957).

Hanessian et al, "Anomeric Deoxygenation of 2–Ulosonic Acids Using SmI2: Rapid Access to 2–Deoxy–KDO and 2–Deoxy–NANA," Synlett pp. 863–864 (Oct. 1994).

Hayden et al., "Safety and Efficacy of the Neuraminidase Inhibitor GG167 in Experimental Human Influenza," JAMA 275(4):295–299 (Jan. 1996).

Janakiraman et al., "Structure of Influenze Virus Neuraminidase B/Lee/40 Complexed with Sialic Acid and a Dehydro Analog at 1.8–Angstrom Resolution: Implications for the Catalytic Mechanism," Biochem 33:8172–8179 (1994).

Kiefel et al., "Synthesis and Biological Evaluation of N–Acetylneuraminic Acid–Based Rotavirus Inhibitors," J Med Chem 39:1314–1320 (1996).

Kong et al., "The First Synthesis of a C–7 Nitrogen–containing Sialic Acid Analogue, 5–Acetamido–7–azido–3,5,7–trideoxy–D–glycero–D–galacto–2–nonulopyranosonic acid (7–azido–7–deoxy–Neu5Ac)," Tet Lett 36(6):957–960 (1995).

Kudo et al., "Synthesis of the Potent Inhibitors of Neuraminidase, N–(1,2–Dihydroxypropyl) Derivatives of Siastatin B and its 4–Deoxy Analogs," J Antibiot 46(2):300–309 (Feb. 1993).

McCauley et al., "4–Guanidino–Neu5Ac2en fails to protect chickens from infection with highly pathogenic avian influenza virus," Antiviral Res 27:179–186 (1995).

McKimm–Breschkin et al., Generation and Characterization of Variants of NWS/G70C Influenza Virus after in Vitro Passage in 4–Amino–neu5Ac2en and 4–Guanidino–Neu5Ac2en, Antimicro AG & Chemo 40(1):40–46 (Jan. 1996).

Nishimura et al., "Design of Potential Neuraminidase Inhibitors By Dehydration, Deoxygenation and Epimerization of Siastatin B," Natural Product Letters 1(1):39–44 (1992).

Ogawa et al., "Synthesis of a Carbocyclic Analogue of N–Acetylneuraminic Acid (Pseudo–N–acetylneuraminic Acid)," J Chem Soc (C) pp. 406–408 (1992).

Ogawa et al., "Synthesis of carbocyclic analogues of 3–deoxy–D–manno–2–octulosonic acid and N–acetylneuraminic acid," Carb Res 269:53–78 (1995).

Ryan et al., "Inhibition of Influenza Virus Replication in Mice GG167 (4–Guanidino–2,3–Dehydro–N–Acetylneuraminic Acid) Is Consistent with Extracellular Activity of Viral Neuraminidase (Sialidase)," Antimicro Ag & Chem 38(10):2270–2275 (Oct. 1994).

Saito et al., "Steps in Maturation of Influenza A Virus Neuraminidase," J Virol 69(8):5011–5017 (Aug. 1995).

Singh et al., "Structure–Based Inhibitors of Influenza Virus Sialidase. A Benzoic Acid Lead with Novel Interaction," J Med Chem 38:3217–3225 (1995).

Smith et al., "Synthesis and influenza virus sialidase inhibitory activity of analogues of 4–guanidino–Neu5Ac2en (GG167) with modified 5–substituents," Eur J Med Chem 31:143–150 (Jun. 22, 1995).

Sollis et al., "Novel Inhibitors of Influenza Sialidase Related to GG167," Bioorg Med Chem Lett 6(15):1805–1808, Abstract, Table of Contents (1996).

Starkey et al., "Synthesis and Influenza Virus Sialidase Inhibitory Activity of the 5–Desacetamido Analogue of 2, 3–Didehydro–2, 4–dideoxy–4–guanidinyl–N–acetylneuraminic acid," Tet Lett 36(2):299–302 (1995).

Staschke et al., "Molecular Basis for the Resistance of Influenza Viruses to 4–Guanidino–Neu5Ac2en," Virology 214:642–646 (1995).

Ulmer et al., "Heterologuous Protection Against Influenza by Injection of DNA Encoding a Viral Protein," Science 259:17845–1749 (Mar. 19, 1993).

Wu et al., "Non–Sialate Inhibitor of Influenza A/WSN/33 Neuraminidase," Biochem 34:7154–7160 (1995).

von Itzstein et al, "Rational design of potent sialidase–based inhibitors of influenza virus replication," Nature 363:418–423 (1993).

von Itzstein et al, "A Study of the Active Site of Influenza Virus Sialidase: An Approach to the Rational Design of Novel Anti–Influenza Drugs," J Med Chem 39:388–391 (1996).

Berger, Alfred, "Relation of Chemical Structure and Biological Activity," Medicinal Chemistry Third edition, part 1, pp. 73–75 (1979).

Chahoua et al., "Synthesis of (–)–Shikimate and (–)–Quinate 3–Phosphates by Differentiation of the Hydroxyl Functions of (–)–Shikimic and (–)–Quinic Acids",57:5798–5801, J Org Chem, 1992.

Fernandez et al., "New and Efficient Enantiospecific Synthesis of (–)–Methyl 5–epi–Shikimate and Methyl 5–epi–Quinate from (–)–Quinic Acid", 38(29):5225–5228, Tet Lett, 1997.

Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti–Influenza Activity", 119:681–690, J Am Chem Soc, 1997.

Meindl et al., "2–Deoxy–2,3–dehydrosialic acids. 3. Inhibitionof Vibrio cholerae[comma]neuraminidase by oxidation products of 2–deoxy–2,3–dehydro–N–acetylneuraminic acid", 73:42027b, Chem Ab, 1970.

Ulibarri et al., "Construction of the Bicyclic Core Structure of the Enediyne Antibiotic Esperamicin–A1 in Either Anatiomeric Form from (–)–Quinic Acid", 60:2753–2761, J Org Chem, 1995.

Kudo et al., "Synthesis and Activities of N–Substituted Derivatives of Siastatin B", 45(10):1662–1668, The Journal of Antibiotics, Oct. 1992.

Microbial Chem Res Found, "Siastatin B Derivative as Novel Antiviral Substance and its Production", Publication No. 04089481, Patent Abstracts of Japan, Mar. 23, 1992.

Nishimura et al., "The First L–Iduronic Acid–Type 1–N–Iminosugars Having Inhibitory Activity of Experimental Metastasis", 118:3051–3052, J Am Chem Soc, 1996.

Nishimura et al., "Totally Synthetic Analogues fo Siastatin B. III. Trifluoroacetamide Analogues Having Inhibitory Activity for Tumor Metastasis", 47(1):101–107, The Journal of Antibiotics, Jan. 1994.

Nishimura, et al., "Potent Inhibitory of Neuraminidase by N–(1,2–Dihydroxypropyl) Derivatives of Siastatin B and its Analogs", 1(1):33–38, Natural Product Letters, 1992.

Funded Research Agreement, "Agreement between Gilead Sciences, Inc. and the University of California Berkeley", 2 pages, Dec. 7, 1995.

Stevens, Ray, "Letters from Assistant Prof. Ray Stevens to Dr. Choung Kim", 2 pages, Feb. 18, 1996.

COMPOUNDS AND METHODS FOR SYNTHESIS AND THERAPY

CROSS REFERENCE TO RELATED APPLICATIONS

This application is a continuation-in-part application of U.S. patent application Ser. No. 08/580,567, filed Dec. 29, 1995, abandoned which was a continuation-in-part application of U.S. patent application Ser. No. 08/476,946, filed Jun. 6, 1995, now U.S. Pat. No. 5,866,601 which was a continuation-in-part application of U.S. patent application Ser. No. 08/395,245, filed Feb. 27, 1995, abandoned all of which are now pending and are incorporated herein by reference in their entirety.

BACKGROUND OF THE INVENTION

1. Field of the Invention

Neuraminidase (also known as sialidase, acylneuraminyl hydrolase, and EC 3.2.1.18) is an enzyme common among animals and a number of microorganisms. It is a glycohydrolase that cleaves terminal alphaketosidically linked sialic acids from glycoproteins, glycolipids and oligosaccharides. Many of the microorganisms containing neuraminidase are pathogenic to man and other animals including fowl, horses, swine and seals. These pathogenic organisms include influenza virus.

Neuraminidase has been implicated in the pathogenicity of influenza viruses. It is thought to help the elution of newly synthesized virons from infected cells and assist in the movement of the virus (through its hydrolase activity) through the mucus of the respiratory tract.

2. Brief Description of Related Art

Itzstein, M. von et al.; "Nature", 363(6428):418–423 (1993), discloses the rational design of sialidase-based inhibitors of influenza virus replication.

Colman, P. M. et al.; International Patent Publication No. WO 92/06691 (Int. App. No. PCT/AU90/00501, publication date Apr. 30, 1992), Itzstein, L. M. von et al.; European Patent Publication No. 0 539 204 A1 (EP App. No. 92309684.6, publication date Apr. 28, 1993), and Itzstein, L. M. von et al.; International Publication No. WO 91/16320 (Int. App. No. PCT/AU91/00161, publication date Oct. 31, 1991) disclose compounds that bind neuraminidase and are asserted to exhibited antiviral activity in vivo.

OBJECTS OF THE INVENTION

A principal object of the invention is inhibition of viruses, in particular influenza viruses. In particular, an object is inhibition of glycolytic enzymes such as neuraminidase, in particular the selective inhibition of viral or bacterial neuraminidases. inhibitors that have a retarded rate of urinary excretion, that enter into nasal or pulmonary secretions from the systemic circulation, that have sufficient oral bioavailability to be therapeutically effective, that possess elevated potency, that exhibit clinically acceptable toxicity profiles and have other desirable pharmacologic properties.

Another object is to provide improved and less costly methods for synthesis of neuraminidase inhibitors.

A still further object is to provide improved methods for administration of known and novel neuraminidase inhibitors.

An additional object is to provide compositions useful in preparing polymers, surfactants or immunogens and for use in other industrial processes and articles.

These and other objects will be readily apparent to the ordinary artisan from consideration of the invention as a whole.

SUMMARY OF THE INVENTION

Compounds, or compositions having formula (I) or (II) are provided herein:

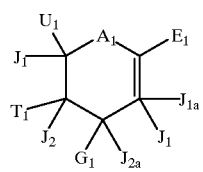

(I)

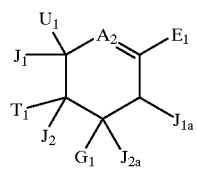

(II)

wherein
$A_1$ is —C($J_1$)═, or —N═;
$A_2$ is —C($J_1$)$_2$—, —N($J_1$)—, —N(O)($J_1$)—, —N(O)═, —S—, —S(O)—, —S(O)$_2$— or —O—;
$E_1$ is —(CR$_1$R$_1$)$_{m1}$W$_1$;
$G_1$ is N$_3$, —CN, —OH, —OR$_{6a}$, —NO$_2$, or —(CR$_1$R$_1$)$_{m1}$W$_2$;
$T_1$ is —NR$_1$W$_3$, a heterocycle, or is taken together with $U_1$ or $G_1$ to form a group having the structure

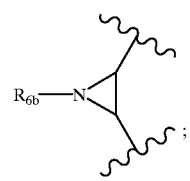

$U_1$ is H or —X$_1$W$_6$;
$J_1$ and $J_{1a}$ are independently R$_1$, Br, Cl, F, I, CN, NO$_2$ or N$_3$;
$J_2$ and $J_{2a}$ are independently H or R$_1$;
R$_1$ is independently H or alkyl of 1 to 12 carbon atoms;
R$_2$ is independently R$_3$ or R$_4$ wherein each R$_4$ is independently substituted with 0 to 3 R$_3$ groups;
R$_3$ is independently F, Cl, Br, I, —CN, N$_3$, —NO$_2$, —OR$_{6a}$—OR$_1$, —N(R$_1$)$_2$, —N(R$_1$)(R$_{6b}$), —N(R$_{6b}$)$_2$, —SR$_1$,—SR$_{6a}$,—S(O)$_2$R$_1$,—S(O)$_2$R$_1$,—S(O)OR$_1$,—S(O)OR$_{6a}$, —S(O)$_2$OR$_1$, —S(O)$_2$OR$_{6a}$, —C(O)OR$_1$, C(O)R$_{6c}$, C(O)OR$_{6a}$, —OC(O)R$_1$,—N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_1$))(N(R$_1$)(R$_{6b}$)), —N(R$_1$)C(N(R$_{6b}$))(N(R$_1$)(R$_{6b}$)), —N(R$_1$)C(N(R$_1$))(N(R$_{6b}$)$_2$), —N(R$_{6b}$)C(N(R$_{6b}$))(N(R$_1$)(R$_{6b}$)), —N(R$_{6b}$)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), ═O, ═S, ═N(R$_1$) or ═N(R$_{6b}$);

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is a group comprising an acidic hydrogen, a protected acidic group, or an $R_{6c}$ amide of the group comprising an acidic hydrogen;

$W_2$ is a group comprising a basic heteroatom or a protected basic heteroatom, or an $R_{6b}$ amide of the basic heteroatom;

$W_3$ is $W_4$ or $W_5$;

$W_4$ is $R_5$ or —C(O)$R_5$, —C(O)$W_5$, —SO$_2R_5$, or —SO$_2W_5$;

$W_5$ is carbocyde or heterocycle wherein $W_5$ is independently substituted with 0 to 3 $R_2$ groups;

$W_6$ is —$R_5$, —$W_5$, —$R_{5a}W_5$, —C(O)O$R_{6a}$, —C(O)$R_{6c}$, —C(O)N($R_{6b}$)$_2$, —C(N$R_{6b}$)(N($R_{6b}$)$_2$), —C(N$R_{6b}$)(N(H)($R_{6b}$)), —C(N(H)(N($R_{6b}$)$_2$), —C(S)N($R_{6b}$)$_2$, or —C(O)$R_2$;

$X_1$ is a bond, —O—, —N(H)—, —N($W_6$)—, —N(OH)—, —N(O$W_6$)—, —N(NH$_2$)—, —N(N(H)($W_6$))—, —N(N($W_6$)$_2$)—, —N(H)N($W_6$)—, —S—, —SO—, or —SO$_2$—, and each $m_1$ is independently an integer from 0 to 2;

provided, however, that compounds are excluded wherein:

(a) $A_1$ is —CH= or —N= and $A_2$ is —CH$_2$—;

(b) $E_1$ is COOH, P(O)(OH)$_2$, SOOH, SO$_3$H, or tetrazol;

(c) $G_1$ is CN, N(H)$R_{20}$, N$_3$, S$R_{20}$, O$R_{20}$, guanidino, —N(H)CN

[structures: N(R$_{20}$)(OR$_{20}$), NR$_{20}$, N→O with R$_{20}$, NH—N(R$_{20}$)(R$_{20}$), pyridine ring, pyridine ring with CH$_2$—];

(d) $T_1$ is —NHR$_{20}$;

(e) $R_{20}$ is H; an acyl group having 1 to 4 carbon atoms; a linear or cyclic alkyl group having 1 to 6 carbon atoms, or a halogen-substituted analogue thereof; an allyl group or an unsubstituted aryl group or an aryl substituted by a halogen, an OH group, an NO$_2$ group, an NH$_2$ group or a COOH group;

(f) $J_1$ is H; and $J_{1a}$ is H, FCl, Br or CN;

(g) $J_2$ is H and $J_{2a}$ is H, CN or N$_3$;

(h) $U_1$ is CH$_2$YR$_{20a}$, CHYR$_{20a}$CH$_2$YR$_{20a}$ or CHYR$_{20a}$CHYR$_{20a}$CH$_2$YR$_{20a}$;

(i) $R_{20a}$ is H or acyl having 1 to 4 carbon atoms;

(j) Y is O, S, H or NH;

(k) 0 to 2 YR$_{20a}$ are H, and (l) successive Y moieties in a $U_1$ group are the same or different, and when Y is H then $R_{20a}$ is a covalent bond, and provided that if $G_1$ is N$_3$ then $U_1$ is not —CH$_{20}$CH$_2$Ph and the pharmaceutically acceptable salts and solvates thereof;

and the salts, solvates, resolved enantiomers and purified diastereomers thereof.

Another embodiment of the invention is directed to compounds of the formula:

(III)

[structure of cyclohexene with substituents $U_1$, $J_1$, $E_1$, $J_1$, $J_{1a}$, $T_1$, $J_2$, $G_1$, $J_{2a}$]

(IV)

[structure of cyclohexene with substituents $U_1$, $J_1$, $J_1$, $E_1$, $J_1$, $J_{1a}$, $T_1$, $J_2$, $G_1$, $J_{2a}$]

wherein $E_1$ is —(CR$_1$R$_1$)$_{m1}$W$_1$;

$G_1$ is N$_3$, —CN, —OH, —OR$_{6a}$ —NO$_2$, or —(CR$_1$R$_1$)$_{m1}$W$_2$;

$T_1$ is —NR$_1$W$_3$, a heterocycle, or is taken together with $U_1$ or $G_1$ to form a group having the structure

[aziridine structure with R$_{6b}$—N];

$U_1$ is H or —X$_1$W$_6$ and, if —X$_1$W$_6$, then $U_1$ is a branched chain;

$J_1$ and $J_{1a}$ are independently R$_1$, Br, Cl, F, I, CN, NO$_2$ or N$_3$;

$J_2$ and $J_{2a}$ are independently H or R$_1$;

$R_1$ is independently H or alkyl of 1 to 12 carbon atoms;

$R_2$ is independently R$_3$ or R wherein each R$_4$ is independently substituted with 0 to 3 R$_3$ groups;

$R_3$ is independently F, Cl, Br, I, —CN, N$_3$, —NO$_2$, —OR$_{6a}$, —OR$_1$, —N(R$_1$)$_2$, —N(R$_1$)(R$_{6b}$), —N(R$_{6b}$)$_2$, —SR$_1$, —SR$_{6a}$, —S(O)$_2$R$_1$, —S(O)$_2$R$_1$, —S(O)OR$_1$, —S(O)OR$_{6a}$, —S(O)$_2$OR$_1$, —S(O)$_2$OR$_{6a}$, —C(O)OR$_1$, C(O)R$_{6c}$, —C(O)OR$_{6a}$, —OC(O)R$_1$, —N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_{6b}$))(N(R$_1$)$_2$), —N(R$_{6b}$)C(N(R$_1$))(N(R)(R$_{6b}$)), —N(R$_1$)C(N(R$_{6b}$))(N(R)(R$_{6b}$)), —N(R$_1$)C(N(R$_1$))(N(R$_{6b}$)$_2$), —N(R$_{6b}$)C(N(R$_{6b}$))(N(R$_1$)(R$_{6b}$)), —N(R$_{6b}$)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), =O, =S, =N(R$_1$) or =N(R$_{6b}$);

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms which is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is a group comprising an acidic hydrogen, a protected acidic group, or an $R_{6c}$ amide of the group comprising an acidic hydrogen;

$W_2$ is a group comprising a basic heteroatom or a protected basic heteroatom, or an $R_{6b}$ amide of the basic heteroatom;

$W_3$ is $W_4$ or $W_5$;

$W_4$ is $R_5$ or —C(O)$R_5$, —C(O)$W_5$, —SO$_2R_5$, or —SO$_2W_5$;

$W_5$ is carbocycle or heterocycle wherein $W_5$ is independently substituted with 0 to 3 $R_2$ groups;

$W_6$ is —$R_5$, —$W_5$, —$R_{5a}W_5$, —C(O)O$R_{6a}$, —C(O)$R_{6c}$, —C(O)N($R_{6b}$)$_2$, —C(N$R_{6b}$)(N($R_{6b}$)$_2$), —C(S)N($R_{6b}$)$_2$, or —C(O)$R_2$;

$X_1$ is a bond, —O—, —N(H)—, —N($W_6$)—, —N(OH)—, —N(O$W_6$)—, —N(NH$_2$)—, —N(N(H)($W_6$))—, —N(N($W_6$)$_2$)—, —N(H)N($W_6$)—, —S—, —SO—, or —SO$_2$—, and each $m_1$ is independently an integer from 0 to 2; and the salts, solvates, resolved enantiomers and purified diastereomers Another embodiment of the invention is directed to compounds of the formula:

(III)

wherein $E_1$ is —(C$R_1R_1$)$_{m1}W_1$;

$G_1$ is $N_3$, —CN, —OH, —O$R_{6a}$, —NO$_2$, or —(C$R_1R_1$)$_{m1}W_2$;

$T_1$ is —N$R_1W_3$, a heterocycle, or is taken together with $U_1$ or $G_1$ to form a group having the structure $U_1$ is H or —$X_1W_6$;

$J_1$ and $J_{1a}$ are independently $R_1$, Br, Cl, F, I, CN, NO$_2$ or $N_3$;

$J_2$ and $J_{2a}$ are independently H or $R_1$;

$R_1$ is independently H or alkyl of 1 to 12 carbon atoms;

$R_2$ is independently $R_3$ or $R_4$ wherein each R is independently substituted with 0 to 3 $R_3$ groups;

$R_3$ is independently F, Cl, Br, I, —CN, $N_3$, —NO$_2$, O$R_{6a}$, —O$R_1$, —N($R_1$)$_2$, —N($R_1$)($R_{6b}$), —N($R_{6b}$)$_2$, —S$R_1$, —S$R_{6a}$, —S(O)$R_1$, —S(O)$_2R_1$, —S(O)O$R_1$, —S(O)O$R_{6a}$, —S(O)$_2$O$R_1$, —S(O)$_2$O$R_{6a}$, —C(O)O$R_1$, —C(O)$R_{6c}$, —C(O)O$R_{6a}$, —OC(O)$R_1$, —N($R_1$)(C(O)$R_1$), —N($R_{6b}$)(C(O)$R_1$), —N($R_1$)(C(O)O$R_1$), —N($R_{6b}$)(C(O)O$R_1$), —C(O)N($R_1$)$_2$, —C(O)N($R_{6b}$)($R_1$), —C(O)N($R_{6b}$)$_2$, —C(N$R_1$)(N($R_1$)$_2$), —C(N($R_{6b}$))(N($R_1$)$_2$), —C(N($R_1$))(N($R_1$)($R_{6b}$)), —C(N($R_{6b}$))(N($R_1$)($R_{6b}$)), —C(N($R_1$))(N($R_{6b}$)$_2$), —C(N($R_{6b}$))(N($R_{6b}$)$_2$), —N($R_1$)C(N($R_1$))(N($R_1$)$_2$), —N($R_1$)C(N($R_1$))(N($R_1$)($R_{6b}$)), —N($R_1$)C(N($R_{6b}$))(N($R_1$)$_2$), —N($R_{6b}$)C(N($R_1$))(N($R_1$)$_2$), —N($R_{6b}$)C(N($R_{6b}$))(N($R_1$)$_2$), —N($R_{6b}$)C(N($R_1$))(N($R_{6b}$)), —N($R_1$)C(N($R_{6b}$))(N($R_1$) ($R_{6b}$)), —N($R_1$)C(N($R_1$))(N($R_{6b}$)$_2$), —N($R_{6b}$)C(N($R_{6b}$))(N($R_1$)($R_{6b}$)), —N($R_{6b}$)C(N($R_1$))(N($R_{6b}$)$_2$), —N($R_1$)C(N($R_{6b}$))(N($R_{6b}$)$_2$), —N($R_{6b}$)C(N($R_{6b}$))(N($R_{6b}$)$_2$), =O, =S, =N($R_1$) or =N($R_{6b}$);

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms which is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is a group comprising an acidic hydrogen, a protected acidic group, or an $R_{6c}$ amide of the group comprising an acidic hydrogen;

$W_2$ is a group comprising a basic heteroatom or a protected basic heteroatom, or an $R_{6b}$ amide of the basic heteroatom;

$W_3$ is $W_4$ or $W_5$;

$W_4$ is $R_5$ or —C(O)$R_5$, —C(O)$W_5$, —SO$_2R_5$, or —SO$_2W_5$;

$W_5$ is carbocyde or heterocycle wherein $W_5$ is independently substituted with 0 to 3 $R_2$ groups;

$W_6$ is —$R_5$, —$W_5$, —$R_5W_5$, —C(O)O$R_{6a}$, —C(O)$R_{6c}$ —C(O)N($R_{6b}$)$_2$, —C(N$R_{6b}$)(N($R_{6b}$)$_2$), —C(S)N($R_{6b}$)$_2$, or —C(O)$R_2$;

$X_1$ is —O—, —N(H)—, —N($W_6$)—, —N(OH)—, —N(O$W_6$)—, —N(NH$_2$)—, —N(N(H)($W_6$))—, —N(N($W_6$)$_2$)—, —N(H)N($W_6$)—, —S—, —SO—, or —SO$_2$—, and each $m_1$ is independently an integer from 0 to 2; and the salts, solvates, resolved enantiomers and purified diastereomers thereof.

Another embodiment of the invention is directed to compounds of the formula:

wherein:

$E_1$ is —CO$_2R_1$;

$G_1$ is —NH$_2$, —N(H)($R_5$) or —N(H)(C(N(H))(NH$_2$));

$T_1$ is —N(H)(C(O)CH$_3$);

$U_1$ is —O$R_{60}$;

$R_1$ is H or an alkyl of 1, 2, 3, 4, 5, 6, 7, 8, 9, 10, 11, or 12 carbon atoms; and $R_{60}$ is a branched alkyl of 3, 4, 5, 6, 7, 8, 9, 10, 11, or 12 carbon atoms; and the salts, solvates, resolved enantiomers and purified diastereomers thereof.

Another embodiment of the invention is directed to compounds of formulas (VII) or (VIII):

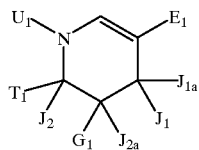
(VII)

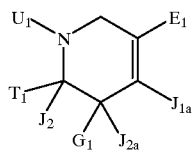
(VIII)

wherein
$E_1$ is $-(CR_1R_1)_{m1}W_1$;
$G_1$ is $N_3$, $-CN$, $-OH$, $-OR_{6a}$, $-NO_2$, or $-(CR_1R_1)_{m1}W_2$;
$T_1$ is $-NR_1W_3$, a heterocycle, or is taken together with $G_1$ to form a group having the structure

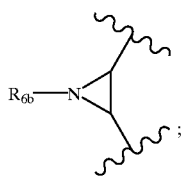

$U_1$ is $-X_1W_6$;
$J_1$ and $J_{1a}$ are independently $R_1$, Br, Cl, F, I, CN, $NO_2$ or $N_3$;
$J_2$ and $J_{2a}$ are independently H or $R_1$;
$R_1$ is independently H or alkyl of 1 to 12 carbon atoms;
$R_2$ is independently $R_3$ or $R_4$ wherein each $R_4$ is independently substituted with 0 to 3 $R_3$ groups;
$R_3$ is independently F, Cl, Br, I, $-CN$, $N_3$, $-NO_2$, $OR_{6a}$, $OR_1$, $-N(R_1)_2$, $-N(R_1)(R_{6b})$, $-N(R_{6b})_2$, $-SR_1$, $-SR_{6a}$, $-S(O)R_1$, $-S(O)_2R_1$, $-S(O)OR_1$, $-S(O)OR_{6a}$, $-S(O)_2OR_1$, $-S(O)_2OR_{6a}$, $C(O)OR_1$, $C(O)R_{6c}$, $-C(O)OR_a$, $OC(O)R_1$, $-N(R_1)(C(O)R_1)$, $-N(R_{6b})(C(O)R_1)$, $-N(R_1)(C(O)OR_1)$, $-N(R_{6b})(C(O)OR_1)$, $-C(O)N(R_1)(R_2)$, $-C(O)N(R_{6b})_1$, $-C(O)N(R_{6b})_2$, $-C(NR_1)(N(R_1)_2)$, $-C(N(R_{6b}))(N(R_1)_2)$, $C(N(R_1))(N(R_1)(R_{6b}))$, $C(N(R_{6b}))(N(R_1)(R_{6b}))$, $-C(N(R_1))(N(R_{6b})_2)$, $C(N(R_{6b}))(N(R_{6b})_2)$, $-N(R_1)C(N(R_1))(N(R_1)_2)$, $-N(R_1)C(N(R_1))(N(R_1)(R_{6b}))$, $-N(R_1)C(N(R_{6b}))(N(R_1)_2)$, $-N(R_{6b})C(N(R_1))(N(R_1)_2)$, $-N(R_{6b})C(N(R_{6b}))(N(R_1)_2)$, $-N(R_{6b})C(N(R_1))(N(R_1)(R_{6b}))$, $-N(R_1)C(N(R_{6b}))(N(R_1)(R_{6b}))$, $-N(R_1)C(N(R_1))(N(R_{6b})_2)$, $-N(R_{6b})C(N(R_{6b}))(N(R_1)(R_{6b}))$, $-N(R_{6b})C(N(R_1))(N(R_{6b})_2)$, $-N(R_1)C(N(R_{6b}))(N(R_{6b})_2)$, $-N(R_{6b})C(N(R_{6b}))(N(R_{6b})_2)$, $=O$, $=S$, $=N(R_1)$ or $=N(R_{6b})$;
$R_4$ is independently alkyl of 1 to 12 carbon atoms, alkenyl of 2 to 12 carbon atoms, or alkynyl of 2 to 12 carbon atoms;
$R_5$ is independently $R_4$ wherein each $R_4$ is substituted with 0 to 3 $R_3$ groups;
$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;
$R_{6a}$ is independently H or a protecting group for hydroxyl or thio;

$R_{6b}$ is independently H, a protecting group for amino or the residue of a carboxyl-containing compound;
$R_{6c}$ is independently H or the residue of an amino-containing compound;
$W_1$ is a group comprising an acidic hydrogen, a protected acidic group, or an $R_{6c}$ amide of the group comprising an acidic hydrogen;
$W_2$ is a group comprising a basic heteroatom or a protected basic heteroatom, or an $R_{6b}$ amide of the basic heteroatom;
$W_3$ is $W_4$ or $W_5$;
$W_4$ is $R_5$ or $C(O)R_5$, $-C(O)W_5$, $-SO_2R_5$, or $-SO_2W_5$;
$W_5$ is carbocycle or heterocycle wherein $W_5$ is independently substituted with 0 to 3 $R_2$ groups;
$W_6$ is $-R_5$, $-W_5$, $-R_{5a}W_5$, $-C(O)OR_{6a}$, $-C(O)R_{6c}$, $-C(O)N(R_{6b})_2$, $-C(NR_{6b})(N(R_{6b})_2)$, $-C(NR_{6b})(N(H)(R_{6b}))$, $-C(N(H))(N(R_{6b})_2)$, $-C(S)N(R_{6b})_2$, or $C(O)R_2$;
$X_1$ is a bond, $-O-$, $-N(H)-$, $-N(W_6)-$, $-S-$, $-SO-$, or $-SO_2-$; and
each $m_1$ is independently an integer from 0 to 2; provided, however, that compounds are excluded wherein $U_1$ is H or $-CH_2CH(OH)CH_2(OH)$;
and the salts, solvates, resolved enantiomers and purified diastereomers thereof.

In another embodiment of the invention a compound or composition of the invention is provided that further comprises a pharmaceutically-acceptable carrier.

In another embodiment of the invention the activity of neuraminidase is inhibited by a method comprising the step of treating a sample suspected of containing neuraminidase with a compound or composition of the invention.

Another embodiment of the invention provides a method for inhibiting the activity of neuraminidase comprising the step of contacting a sample suspected of containing neuraminidase with the composition embodiments of the invention.

Another embodiment of this invention is a method for the treatment or prophylaxis of viruses, particularly influenza virus infection in a host comprising administration to the host, by a route other than topically to the respiratory tract, of a therapeutically effective dose of an antivirally active compound described in WO 91/16320, WO 92/06691 or U.S. Pat. No. 5,360,817.

In other embodiments, novel methods for synthesis of the compounds of this invention are provided. In one such embodiment, a method is provided for using a compound of the formula 281 wherein the method comprises treating compound 281 with a compound of the formula $R_5-X_1-H$ to form a compound of the formula 281.1

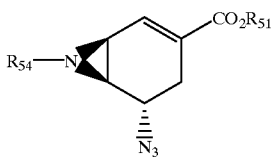
281

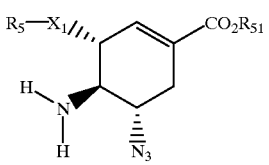
281.1 wherein:
$X_1$ and $R_5$ are as described above;

$R_{51}$ is an acid stable protecting group for a carboxylic acid; and $R_{54}$ aziridine activating group.

In another embodiment, a method is provided for using a compound of the formula:

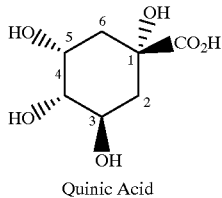

Quinic Acid wherein the method comprises treating Quinic acid with a geminal dialkoxyalkane or geminal dialkoxy cycloalkane and acid to form a compound of the formula:

274

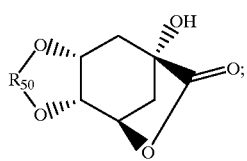

treating compound 274 with a metal alkoxide and an alkanol to form a compound of the formula:

275

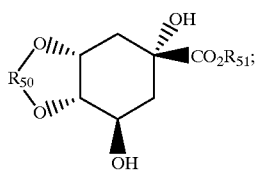

treating compound 275 with a sulfonic acid halide and an amine to form a compound of the formula:

276

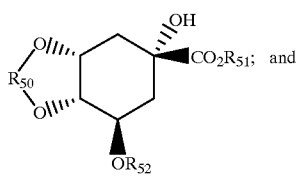

treating compound 276 with a dehydrating agent followed by an acid and an alkanol to form a compound of the formula:

272

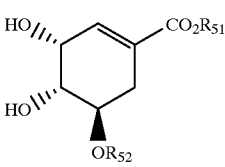

wherein:

$R_{50}$ is a 1,2 diol protecting group;

$R_{51}$ is an acid stable carboxylic acid protecting group; and $R_{52}$ is a hydroxy activating group.

BRIEF DESCRIPTION OF THE DRAWINGS

FIG. 3: 150 mpk of each of compound 203 and GG167, 100 mpk ribavirin; FIG. 4: 50 mpk of each of compound 203 and GG167, 32 mpk of ribavirin; FIG. 5: 10 mpk of each of compound 203 and GG167, 10 mpk of ribavirin.

FIG. 6: mpk of each of the test compounds; FIG. 7: 1 mpk of each test compound; FIG. 8: 0.1 mpk of each test compound.

DETAILED DESCRIPTION

Compositions of the Invention

Figure 1:
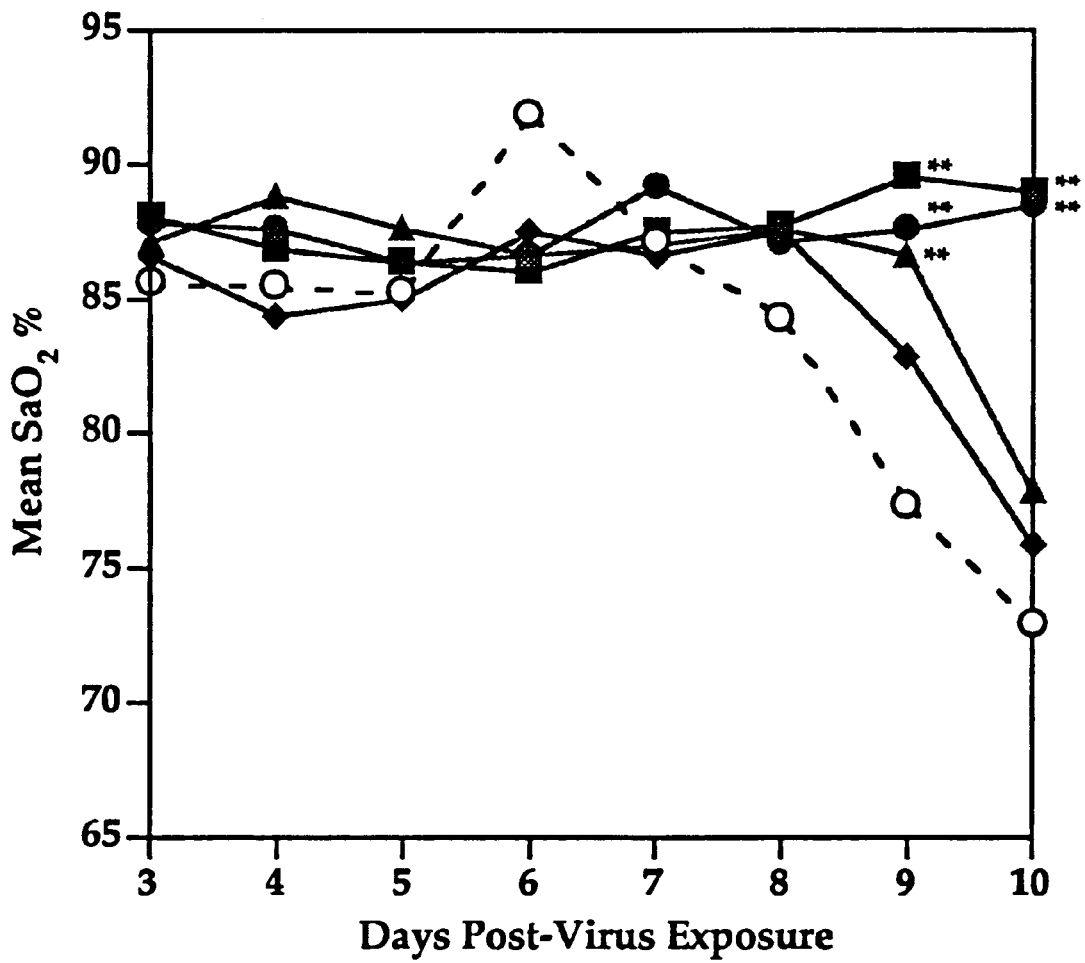
FIGS. 1 and 2 depict the arterial oxygen saturation ($SaO_2$) levels of influenza-A infected mice treated with varying i.p. doses of GG167 (4-guanidino-2,4-dideoxy-2,3-dehydro-N-acetylneuraminic acid), a known anti-influenza compound (FIG. 1) and compound 203 of this invention (FIG. 2): 50, 10, 2 and 0.5 mpk (mg/kg/day) of test compounds and saline control are designated, respectively, by squares, solid circles, triangles, diamonds and open circles. In all Figures, *$P<0.05$, **$P<0.01$ compared to the saline controls.

The compounds of this invention exclude compounds heretofore known. However, as will be further apparent below in other embodiments it is within the invention to use for antiviral purposes known compounds heretofore only produced and used as intermediates in the preparation of antiviral compounds. With respect to the United States, the compounds or compositions herein exclude compounds that are anticipated under 35 USC §102 or obvious under 35 USC §103. In particular, the claims herein shall be construed as excluding the compounds which are anticipated by or not possessing novelty over WO 91/16320, WO 92/06691, U.S. Pat. No. 5,360,817 or Chandler, M.; et al.; *J. Chem. Soc. Perkin Trans.* 1, 1995, 1189–1197.

The foregoing notwithstanding, in an embodiment of the invention one identifies compounds that may fall within the generic scope of WO 91/16320, WO 92/06691, or U.S. Pat. No. 5,360,817 but which have (a) formula Ia of the '320 application, (b) carbon for group "A" in the '320 application, and (c) $R^5$ of the '320 and '691 applications being "—$CH_2YR^6$, —$CHYR^6CH_2YR^6$ or —$CHYR^6CHYR^6CH_2YR^6$" where $YR^6$ cannot be either OH or protected OH in which the protecting group is capable of hydrolysis to yield the free OH under conditions of the human gastrointestinal tract, i.e. the compounds are stable to hydrolysis in the gastrointestinal tract. Thus, typically excluded from this embodiment are compounds of the '320 or '691 applications where $R^5$ therein is acetyl or other carbacyl having 1–4 carbon atoms.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Such compounds are suitable for use in this embodiment. Note that simply because the compounds are stable to the gastrointestinal tract does not mean that they cannot be hydroyzed in vivo. Prodrugs typically will be stable in the digestive system but are substantially hydroyzed to the parental drug in the digestive lunem, liver or other metabolic organ, or within cells in general.

It should be understood, however, that other embodiments of this invention more fully described below contemplate the use of compounds that are in fact specifically disclosed in WO 91/16320, WO 92/06691, or U.S. Pat. No. 5,360,817, including those in which $YR^6$ is free hydroxyl, or hydroxyl protected by a readily hydrolyzable group such as acetyl. In this instance, however, the compounds are delivered by novel routes of administration.

In another embodiment, the compounds herein exclude those in which (a) $E_1$ is —$CO_2H$, —$P(O)(OH)_2$, —$NO_2$, —$SO_2H$, —$SO_3H$, tetrazolyl, —$CH_2CHO$, —CHO, or —CH(CHO)$_2$;

(b) $G_1$ is —CN, $N_3$, —$NHR_{20}$, $NR_{20}$, —$OR_{20}$, guanidino, $SR_{20}$, —$N(R_{20})$→O, —$N(R_{20})(OR_{20})$, —$N(H)(R_{20})N(R_{20})_2$, unsubstituted pyrimidinyl, or unsubstituted (pyrimidinyl)methyl;

(c) $T_1$ is —$NHR_{20}$, —$NO_2$; and $R_{20}$ is H; an acyl group having 1 to 4 carbon atoms; a linear or cyclic alkyl group having 1 to 6 carbon atoms, or a halogen-substituted analogue thereof; an allyl group or an unsubstituted aryl group or an aryl substituted by a halogen, an OH group, an $NO_2$ group, an $NH_2$ group or a COOH group;

(d) each $J_1$ is H; and (e) $X_1$ is a bond, —$CH_2$— or —$CH_2CH_2$—;
in which case $W_6$ is not H, $W_7$ or —$CH_2W_7$ wherein $W_7$ is H, —$OR_{6a}$, —$OR_1$, —$N(R_1)_2$, —$N(R_1)(R_{6b})$, —$N(R_{6b})_2$, —$SR_1$, or —$SR_{6a}$.

In a further embodiment, the compounds of this invention are those in which $U_1$ is not —$CH_2OH$, —$CH_2OAc$, or —$CH_2OCH_2Ph$.

In a further embodiment, the compounds of this invention are those in which $E_1$ is not —$CH_2OH$, —$CH_2OTMS$, or —CHO.

In a further embodiment, the compounds of this invention are those in which $U_1$ is not bonded directly to the nuclear ring by a carbon atom or $U_1$ is not substituted with hydroxyl or hydroxyester, in particular $U_1$ is not polyhydroxyalkane, especially —CH(OH)CH(OH)$CH_2OH$. In a further embodiment, $U_1$ is a branched chain group $R_5$ as described below or a carbocycle which is substituted with at least one group $R_5$.

In a further embodiments, excluded from the invention are compounds of the formula:

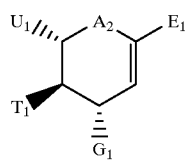
(V)

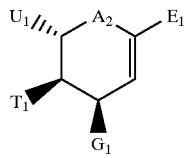
(VI)

wherein:
1. In formula (V):
$A_2$ is —O— or —$CH_2$—;
$E_1$ is —$CO_2H$;
$G_1$ is —N(H)(C(NH)(NH$_2$));
$T_1$ is —N(H)(Ac); and
$U_1$ is of the formula:

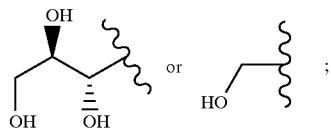

2. In formula (V):
$A_2$ is —O— or —$CH_2$—;
$E_1$ is —$CO_2H$;
$G_1$ is —$NH_2$;
$T_1$ is —N(H)(Ac); and
$U_1$ is —$CH_2OH$;
3. In formula (V):
$A_2$—$CH_2$—;
$E_1$ is —$CH_2OH$ or —$CH_2OTMS$;
$G_1$ is —$N_3$;
$T_1$ is —N(H)(Ac); and
$U_1$ is —$CH_2OCH_2Ph$;
4. In formula (V):
$A_2$—$CH_2$—;
$E_1$ is —$CO_2H$ or —$CO_2CH_3$;
$G_1$ is —$N_3$;
$T_1$ is —N(H)(Ac); and
$U_1$ is —$CH_2OH$;
5. In formula (V):
$A_2$—$CH_2$—;
$E_1$ is —$CO_2H$, —CHO, or —$CH_2OH$;
$G_1$ is —$N_3$;
$T_1$ is —N(H)(Ac); and
$U_1$ is —$CH_2OCH_2Ph$;
6. In formula (VI):
$A_2$—$CH_2$—;
$E_1$ is —$CO_2H$;
$G_1$ is —$OCH_3$;
$T_1$ is —$NH_2$; and
$U_1$ is —$CH_2OH$; and
7. In formula (VI):
$A_2$—$CH_2$—;
$E_1$ is —$CO_2H$;
$G_1$ is —$OCH_3$;
$T_1$ is —N(H)(Ac); and
$U_1$ is —$CH_2OAc$.

Whenever a compound described herein is substituted with more than one of the same designated group, e.g., "$R_1$" or "$R_{6a}$", then it will be understood that the groups may be the same or different, i.e., each group is independently selected.

"Heterocycle" as used herein includes by way of example and not limitation these heterocycles described in Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" John Wiley & Sons, New York, 1950 to present), in particular Volumes 13, 14, 16, 19, and 28; and "J. Am. Chem. Soc.", 82:5566 (1960).

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Alkyl" as used herein, unless stated to the contrary, is $C_1$–$C_{12}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ ($CH_2CH_2CH_3$)), 2-methyl-2-pentyl (—$C(CH_3)_2CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)$ $C(CH_3)_3$). Examples of alkyl groups appear in Table 2 as groups 2–5, 7, 9, and 100–399.

The compositions of the invention comprise compounds of either formula:

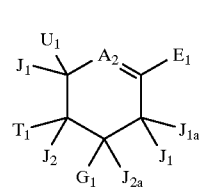

(I)

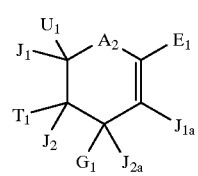

(II)

In the typical embodiment, the compounds of Formula I are chosen.

$J_1$ and $J_{1a}$ are independently $R_1$, Br, Cl, F, I, CN, $NO_2$ or $N_3$, typically $R_1$ or F, more typically H or F, more typically yet H.

$J_2$ and $J_{2a}$ are independently H or $R_1$, typically H.

$A_1$ is —$C(J_1)$=, or —N=, typically —$C(J_1)$=, more typically —CH=.

$A_2$ is —$C(J_1)_2$—, —$N(J_1)$—, —$N(O)(J_1)$—, —N(O)=, —S—, —S(O)—, —$S(O)_2$— or —O—, typically —$C(J_1)_2$—, —$N(J_1)$—, —S—, or —O—, more typically —$C(J_1)_2$—, or —O—, more typically yet —$CH_2$— or —O—, still more typically —$CH_2$—.

$E_1$ is —$(CR_1R_1)_{m1}W_1$.

Typically, $R_1$ is H or alkyl of 1 to 12 carbon atoms, usually H or an alkyl of 1 to 4 or 5 to 10 carbon atoms, still more typically, H or an alkyl of 1, 2, 3, 4, 5, 6, 7, 8, 9, 10, 11, or 12 carbon atoms, more typically yet, H or an alkyl of 1 to 3 carbon atoms selected from methyl, ethyl, n-propyl, and i-propyl. Most typically $R_1$ is H.

$m_1$ is an integer of 0 to 2, typically 0 or 1, most typically 0.

$m_2$ is an integer of 0 to 1.

$m_3$ is an integer of 1 to 3.

$W_1$ is a group comprising an acidic hydrogen, a protected acidic group or an $R_{6c}$ amide of the group comprising an acidic hydrogen which, within the context of the invention, means a group having a hydrogen atom that can be removed by a base yielding an anion or its corresponding salt or solvate. The general principles of acidity and basicity of organic materials are well understood and are to be understood as defining $W_1$. They will not be detailed here. However, a description appears in Streitwieser, A.; and Heathcock, C. H.; "Introduction to Organic Chemistry, Second Edition" (Macmillan, New York, 1981), pages 60–64. Generally, acidic groups of the invention have pK values less than that of water, usually less than pK=10, typically less than pK=8, and frequently less than pK=6. They include tetrazoles and the acids of carbon, sulfur, phosphorous and nitrogen, typically the carboxylic, sulfuric, sulfonic sulfinic, phosphoric and phosphonic acids, together with the $R_{6c}$ amides and $R_{6b}$ esters of those acids ($R_{6a}$ and $R_{6c}$ are defined below). Exemplary $W_1$ are —$CO_2H$, —$CO_2R_{6a}$. —$OSO_3H$, —$SO_3H$, —$SO_2H$, —$OPO_3H_2$, —$PO_3(R_{6a})_2$, —$PO_3H_2$, —$PO_3(H)(R_{6a})$, and —$OPO_3(R_{6a})_2$. $W_1$ typically is $E_1$, and $E_1$ typically is —$CO_2H$, —$CO_2R_{6a}$, —$CO_2R_4$ or $CO_2R_1$, and most typically is $CO_2R_{14}$ wherein $R_{14}$ is normal or terminally secondary $C_1$–$C_6$ alkyl.

$W_1$ may also be a protected acidic group, which, within the context of the invention means an acidic group as described above that has been protected by one of the groups commonly used in the art for such groups and are described below under $R_{6a}$. More typically, protected $W_1$ is —$CO_2R_1$, $SO_3R_1$, —$S(O)OR_1$, —$P(O)(OR_1)_2$, —$C(O)NHSO_2R_4$, or —$SO_2NHC(O)$—$R_4$, wherein $R_1$ is defined above.

Most typically, $E_1$ is selected from —$C(O)O(CH_2)_b CH((CH_2)_c CH_3)_2$ where b=0 to 4, c=0 to 4, and b+c=1 to 4, or from the group of

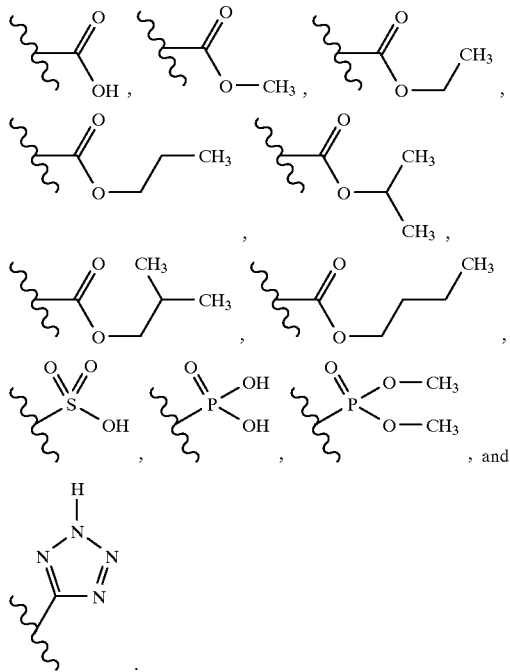

Exemplary $E_1$ groups are listed in Tables 3a through 3b.

$G_1$ is $N_3$, —CN, —OH, $OR_{6a}$, —$NO_2$ or —$(CR_1R_1)_{m1}W_2$, wherein $R_1$ and m1 are defined above. Ordinarily, $G_1$ is —$(CR_1R_1)_{m1}W_2$.

$W_2$ is a group comprising a basic heteroatom, a protected basic heteroatom or an $R_{6b}$ amide of the basic heteroatom. $W_2$ generally comprises a basic heteroatom, which, within the context of the invention means an atom other than carbon which is capable of protonation, typically by an acidic hydrogen having an acidity in the range described above for $W_1$. The basic principles of basicity are described in Streitwieser and Heathcock (op. cit.) and provide meaning for the term basic heteroatom as will be understood by those ordinarily skilled in the art. Generally, the basic heteroatoms employed in the compounds of the invention have pK values for the corresponding protonated form that are in the range of values described above for $W_1$. Basic heteroatoms include the heteroatoms common in organic compounds which have an un-shared, non-bonding, n-type, or the like, electron pair. By way of example and not limitation, typical basic heteroatoms include the oxygen, nitrogen, and sulfur atoms of groups such as alcohols, amines, amidines, guanidines, sulfides, and the like, frequently, amines, amidines and guanidines. Ordinarily, $W_2$ is amino or an amino alkyl (generally lower alkyl) group such as aminomethyl, aminoethyl or aminopropyl; an amidinyl, or an amidinoalkyl group such as amidinomethyl, amidinoethyl, or amidinopropyl; or guanidinyl, or a guanidinoalkyl group such as guanidinomethyl, guanidinoethyl, or guanidinopropyl (in each instance wherein the alkyl group serves to bridge the basic substituent to the carbocyclic ring). More typically, $W_2$ is amino, amidino, guanidino, heterocycle, heterocycle substituted with 1 or 2 amino or guanidino groups (usually 1), or an alkyl of 2 to 3 carbon atoms substituted with amino or guanidino, or such alkyl substituted with an amino and a second group selected from the group consisting of hydroxy and amino. The heterocycles useful as $W_2$ include typically N or S-containing 5 or 6 membered rings, wherein the ring contains 1 or 2 heteroatoms. Such heterocycles generally are substituted at ring carbon atoms. They may be saturated or unsaturated and may be linked to the core cyclohexene by lower alkyl (m1=1 or 2) or by —$NR_1$—. Still more typically, $W_2$ is —$NHR_1$, —$C(NH)(NH_2)$, —$NR_1$—$C(NR_1)(NR_1R_3)$, —NH—$C(NH)(NHR_3)$, —NH—$C(NH)(NHR_1)$, —NH—$C(NH)NH_2$, —$CH(CH_2NHR_1)(CH_2OH)$, —$CH(CH_2NHR_1)(CH_2NHR_1)$, —$CH(NHR_1)$—$(CR_1R_1)_{m2}$—$CH(NHR_1)R_1$, —$CH(OH)$—$(CR_1R_1)_{m2}$—$CH(NHR_1)R_1$, or —$CH(NHR_1)$—$(CR_1R_1)_{m2}$—$CH(OH)R_1$, —$(CR_1R_1)_{m2}$—S—$C(NH)NH_2$, —N=$C(NHR_1)(R_3)$, —N=$C(SR_1)N(R_1)_2$, —$N(R_1)C(NH)N(R_1)C$=N, or —N=$C(NHR_1)(R_1)$; wherein each m2 is ordinarily 0, and ordinarily $R_1$ is H and $R_3$ is $C(O)N(R_1)_2$.

$W_2$ optionally is a protected basic heteroatom which within the context of the invention means a basic heteroatom as described above that has been protected by $R_{6b}$ such as one of the groups common in the art. Such groups are described in detail in Greene (op. cit.) as set forth below. Such groups include by way of example and not limitation, amides, carbamates, amino acetals, imines, enamines, N-alkyl or N-aryl phosphinyls, N-alkyl or N-aryl sulfenyls or sulfonyls, N-alkyl or N-aryl silyls, thioethers, thioesters, disulfides, sulfenyls, and the like. In some embodiments, the protecting group $R_{6b}$ will be cleavable under physiological conditions, typically it will be cleavable in vivo where, for example, the basic heteroatom forms an amide with an organic acid or an amino acid such as a naturally occurring amino acid or a polypeptide as described below for the $R_{6a}$ group.

Typically $G_1$ is selected from the group consisting of:

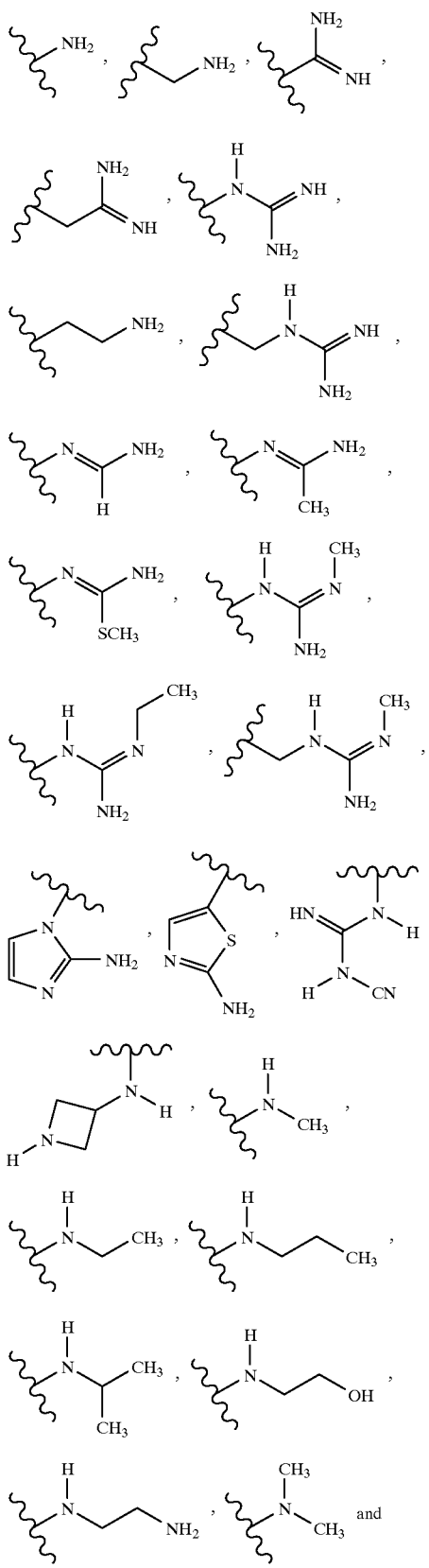

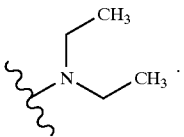

Further exemplary $G_1$ groups are listed in Table 4.

$T_1$ is $—NR_1W_3$ or heterocycle, or is taken together with $U_1$ or $G_1$ to form a group having the structure

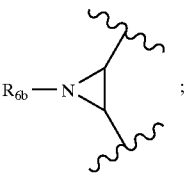

where $R_{6b}$ is defined below, and $R_1$ and $W_3$ are defined above. Generally $T_1$ is selected from the group consisting of:

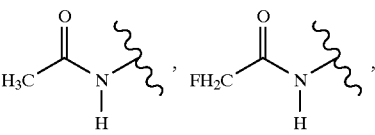

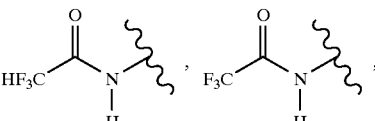

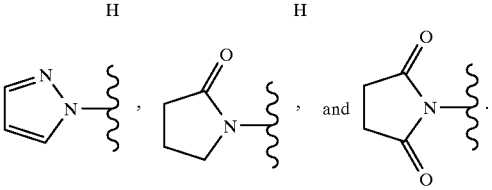

Exemplary $T_1$ groups are listed in Table 5.

$W_3$ is $W_4$ or $W_5$, wherein $W_4$ is $R_1$ or $—C(O)R_5$, $—C(O)W_5$, $—SO_2R_5$, or $—SO_2W_5$. Typically, $W_3$ is $—C(O)R_5$ or $W_5$.

$R_2$ is independently $R_3$ or $R_4$ as defined below, with the proviso that each $R_4$ is independently substituted with 0 to 3 $R_3$ groups;

$R_3$ is independently F, Cl, Br, I, $—CN$, $N_3$, $—NO_2$, $—OR_{6a}$, $—OR_1$, $—N(R_1)_2$, $—N(R_1)(R_{6b})$, $—N(R_{6b})_2$, $—SR_1$, $—SR_{6a}$, $—S(O)R_1$, $—S(O)_2R_1$, $—S(O)OR_1$, $—S(O)OR_{6a}$, $—S(O)_2OR_1$, $—S(O)_2OR_{6a}$, $—C(O)OR_1$, $—C(O)R_{6c}$, $—C(O)OR_{6a}$, $—OC(O)R_1$, $—N(R_1)(C(O)R_1)$, $—N(R_{6b})(C(O)R_1)$, $—N(R_1)(C(O)OR_1)$, $—N(R_{6b})(C(O)OR_1)$, $—C(O)N(R_1)_2$, $—C(O)N(R_{6b})(R_1)$, $—C(O)N(R_{6b})_2$, $—C(NR_1)(N(R_1)_2)$, $—C(N(R_{6b}))(N(R_1)_2)$, $—C(N(R_1))(N(R_1)(R_{6b}))$, $—C(N(R_{6b}))(N(R_1)(R_{6b}))$, $—C(N(R_1))(N(R_{6b})_2)$, $—C(N(R_{6b}))(N(R_{6b})_2)$, $—N(R_1)C(N(R_1))(N(R_1)_2)$, $—N(R_1)C(N(R_{6b}))(N(R_1)_2)$, $—N(R_1)C(N(R_1))(N(R_1)(R_{6b}))$, $—N(R_{6b})C(N(R_1))(N(R_1)_2)$, $—N(R_{6b})C(N(R_{6b}))(N(R_1)_2)$, $—N(R_{6b})C(N(R_1))(N(R_1)(R_{6b}))$, $—N(R_1)C(N(R_{6b}))(N(R_1)(R_{6b}))$, $—N(R_1)C(N(R_1))(N(R_{6b})_2)$, $—N(R_{6b})C(N(R_{6b}))(N(R_1)(R_{6b}))$, $—N(R_{6b})C(N(R_1))(N(R_{6b})_2)$, $—N(R_1)C(N(R_{6b}))(N(R_{6b})_2)$, $—N(R_{6b})C(N(R_{6b}))(N(R_{6b})_2)$, $=O$, $=S$, $=N(R_1)$ or $=N(R_{6b})$. Typically $R_3$ is F, Cl, $—CN$, $N_3$, $NO_2$, $—OR_{6a}$, $—OR_1$, $—N(R_1)_2$, $—N(R_1)$ ($R_{6b}$), —$N(R_{6b})_2$, —$SR_1$, —$SR_{6a}$, —C(O)$OR_1$, —C(O)$R_{6c}$, —C(O)$OR_{6a}$, —OC(O)$R_1$, —$NR_1C(O)R_1$, —$N(R_{6b})C(O)R_1$, —C(O)$N(R_1)_2$, —C(O)$N(R_{6b})(R_1)$, —C(O)$N(R_{6b})_2$, or =O. More typical $R_3$ groups comprising $R_{6b}$ include —C(O)$N(R_{6b})_2$, —C(O)$N(R_{6b})(R_1)$, —C(S)$N(R_{6b})_2$, or —C(S)$N(R_{6b})(R_1)$. More typically yet $R_3$ is F, Cl, —CN, $N_3$, —$OR_1$, —$N(R_1)_2$, —$SR_1$, —C(O)$OR_1$, —OC(O)$R_1$, or =O. More typically still, $R_3$ is F, —$OR_1$, —$N(R_1)_2$, or =O. In the context of the present application, "=O" denotes a double bonded oxygen atom (oxo), and "=S"=$N(R_{6b})$ and "=$N(R_1)$" denote the sulfur and nitrogen analogs.

$R_4$ is alkyl of 1 to 12 carbon atoms, and alkynyl or alkenyl of 2 to 12 carbon atoms. The alkyl $R_4$'s are typically of 1, 2, 3, 4, 5, 6, 7, 8, 9, 10, 11, or 12 carbon atoms and the alkenyl and alkynyl $R_4$'s are typically of 2, 3, 4, 5, 6, 7, 8, 9, 10, 11, or 12 carbon atoms. $R_4$ ordinarily is alkyl (as defined above). When $R_4$ is alkenyl it is typically ethenyl (—CH=$CH_2$), 1-prop-1-enyl (—CH=$CHCH_3$), 1-prop-2-enyl (—$CH_2$CH=$CH_2$), 2-prop-1-enyl (—C(=$CH_2$)($CH_3$)), 1-but-1-enyl (—CH=$CHCH_2CH_3$), 1-but-2-enyl (—$CH_2$CH=$CHCH_3$), 1-but-3-enyl (—$CH_2CH_2$CH=$CH_2$), 2-methyl-1-prop-1-enyl (—CH=C($CH_3$)$_2$), 2-methyl-1-prop-2-enyl (—$CH_2$C(=$CH_2$)($CH_3$)), 2-but-1-enyl (—C(=$CH_2$)$CH_2CH_3$), 2-but-2-enyl (—C($CH_3$)=$CHCH_3$), 2-but-3-enyl (—CH($CH_3$)CH=$CH_2$), 1-pent-1-enyl (C=$CHCH_2CH_2CH_3$), 1-pent-2-enyl (—CHCH=$CHCH_2CH_3$), 1-pent-3-enyl (—$CHCH_2$CH=$CHCH_3$), 1-pent-4-enyl (—$CHCH_2CH_2$CH=$CH_2$), 2-pent-1-enyl (—C(=$CH_2$)$CH_2CH_2CH_3$), 2-pent-2-enyl (—C($CH_3$)=$CH_2CH_2CH_3$), 2-pent-3-enyl (—CH($CH_3$)CH=$CHCH_3$), 2-pent-4-enyl (—CH($CH_3$)$CH_2$CH=$CH_2$) or 3-methyl-ibut-2-enyl (—$CH_2$CH=C($CH_3$)$_2$). More typically, $R_4$ alkenyl groups are of 2,3 or 4 carbon atoms. When $R_4$ is alkynyl it is typically ethynyl (—CCH), 1-prop-1-ynyl (—$CCCH_3$), 1-prop-2-ynyl (—$CH_2$CCH), 1-but-1-ynyl (—$CCCH_2CH_3$), 1-but-2-ynyl (—$CH_2CCCH_3$), 1-but-3-ynyl (—$CH_2CH_2$CCH), 2-but-3-ynyl (CH($CH_3$)CCH), 1-pent-1-ynyl (—$CCCH_2CH_2CH_3$), 1-pent-2-ynyl (—$CH_2CCCH_2CH_3$), 1-pent-3-ynyl (—$CH_2CH_2CCCH_3$) or 1-pent-4-ynyl (—$CH_2CH_2CH_2$CCH). More typically, $R_4$ alkynyl groups are of 2, 3 or 4 carbon atoms.

$R_5$ is $R_4$, as defined above, or $R_4$ substituted with 0 to 3 $R_3$ groups. Typically $R_5$ is an alkyl of 1 to 4 carbon atoms substituted with 0 to 3 fluorine atoms.

$R_{5a}$ is alkylene of 1 to 12 carbon atoms, alkenylene of 2 to 12 carbon atoms, or alkynylene of 2–12 carbon atoms which is substituted with 0–3 $R_3$ groups. As defined above for $R_4$, $R_{5a}$'s are of 1, 2, 3, 4, 5, 6, 7, 8, 9, 10, 11, or 12 carbon atoms when alkylene and of 2, 3, 4, 5, 6, 7, 8, 9, 10, 11, or 12 carbon atoms when alkenylene or alkynylene. Each of the typical $R_4$ groups is a typically $R_{5a}$ group with the proviso that one of the hydrogen atoms of the described $R_4$ group is removed to form the open valence to a carbon atom through which the second bond to the $R_{5a}$ is attached.

$R_{10}$ is alkyl, alkenyl, alkynyl of 1 to 12 carbon atoms substituted with 0 to 3 $R_2$.

$R_{11}$ is independently H or $R_{10}$.

$R_{12}$ is a cycloalkyl of 3 to 10 carbon atoms, or cycloalkenyl of 4 to 10 carbon atoms.

$R_{14}$ is normal or terminally secondary $C_1$–$C_6$ alkyl.

$W_5$ is a carbocycle or heterocycle, with the proviso that each $W_5$ is independently substituted with 0 to 3 $R_2$ groups. $W_5$ carbocycles and $T_1$ and $W_5$ heterocycles are stable chemical structures. Such structures are isolatable in measurable yield, with measurable purity, from reaction mixtures at temperatures from −78° C. to 200° C. Each $W_5$ is independently substituted with 0 to 3 $R_2$ groups. Typically, $T_1$ and $W_5$ are a saturated, unsaturated or aromatic ring comprising a mono- or bicyclic carbocycle or heterocycle. More typically, $T_1$ or $W_5$ has 3 to 10 ring atoms, still more typically, 3 to 7 ring atoms, and ordinarily 3 to 6 ring atoms. The $T_1$ and $W_5$ rings are saturated when containing 3 ring atoms, saturated or monounsaturated when containing 4 ring atoms, saturated, or mono- or diunsaturated when containing 5 ring atoms, and saturated, mono- or diunsaturated, or aromatic when containing 6 ring atoms.

When $W_5$ is carbocyclic, it is typically a 3 to 7 carbon monocycle or a 7 to 12 carbon atom bicycle. More typically, $W_5$ monocyclic carbocycles have 3 to 6 ring atoms, still more typically 5 or 6 ring atoms. $W_5$ bicyclic carbocycles have 7 to 12 ring atoms arranged as a bicyclo [4,5], [5,5], [5,6] or [6,6] system, still more typically, 9 or 10 ring atoms arranged as a bicyclo [5,6] or [6,6] system. Examples include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

A $T_1$ or $W_5$ heterocycle is typically a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). More typically, $T_1$ and $W_5$ heterocyclic monocycles have 3 to 6 ring atoms (2 to 5 carbon atoms and 1 to 2 heteroatoms selected from N, 0, and S), still more typically, 5 or 6 ring atoms (3 to 5 carbon atoms and 1 to 2 heteroatoms selected from N and S). $T_1$ and $W_5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system, still more typically, 9 to 10 ring atoms (8 to 9 carbon atoms and 1 to 2 hetero atoms selected from N and S) arranged as a bicyclo [5,6] or [6,6] system.

Typically $T_1$ and $W_5$ heterocycles are selected from pyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, or pyrrolyl.

More typically, the heterocycle of $T_1$ and $W_5$ is bonded through a carbon atom or nitrogen atom thereof. Still more typically $T_1$ heterocycles are bonded by a stable covalent bond through a nitrogen atom thereof to the cyclohexene ring of the compositions of the invention and $W_5$ heterocycles are bonded by a stable covalent bond through a carbon or nitrogen atom thereof to the cyclohexene ring of the compositions of the invention. Stable covalent bonds are chemically stable structures as described above.

$W_5$ optionally is selected from the group consisting of:

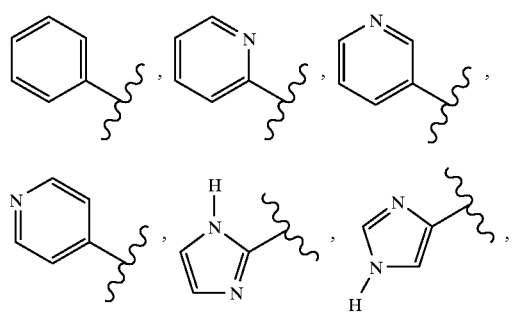

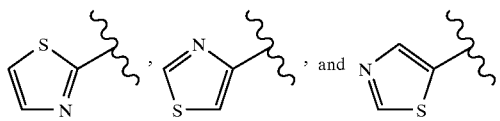

$U_1$ is H or $-X_1W_6$, but typically the latter.

$X_1$ is a bond, $-CR_5R_5-$, $-(CR_5R_5)_2-$, $-O-$, $-N(H)-$, $-N(W_6)-$, $-N(OH)-$, $-N(OW_6)-$, $-N(NH_2)-$, $-N(N(H)(W_6))-$, $-N(N(W_6)_2)-$, $-N(H)N(W_6)-$, $-S-$, $-SO-$, or $-SO_2-$, typically, $X_1$ is a bond, $-CR_5R_5-O-$, $-(CR_5R_5)_2-$, $-$, $-N(H)-$, $-N(R_5)-$, $-N(OH)-$, $-N(OR_5)-$, $-N(NH_2)-$, $-N(N(H)(R_5))-$, $-N(N(R_5)_2)-$, $-N(H)N(R_5)-$, $-S-$, $-SO-$, or $-SO_2-$, more typically $X_1$ is a bond, $-CR_1R_1-$, $-(CR_1R_1)_2-$, $-O-$, $-NR_1-$, $-N(OR_1)-$, $-N(NR_1R_1)-$, $-S-$, $-SO-$, or $-SO_2-$. Ordinarily $X_1$ is $-O-$, $-NH-$, $-S-$, $-SO-$, or $-SO_2-$;

$W_6$ is $-R_5$, $-W_5$, $-R_{5a}W_5$, $-C(O)OR_{6a}$, $-C(O)R_{6c}$, $-C(O)N(R_{6b})_2$, $-C(NR_{6b})(N(R_{6b})_2)$, $-C(NR_{6b})(N(H)(R_{6b}))$, $-C(N(H))(N(R_{6b})_2)$, $-C(S)N(R_{6b})_2$, or $-C(O)R_2$, typically is $-R_5$, $-W_5$, or $-R_{5a}W_5$; in some embodiments, $W_6$ is $R_1$, $-C(O)-R_1$, $-CHR_1W_7$, $-CH(R_1)_aW_7$, $-CH(W7)_2$, (where a is 0 or 1, but is 0 when $W_7$ is divalent) or $-C(O)W_7$. In some embodiments, $W_6$ is $-CHR_1W_7$ or $-C(O)W_7$, or $W_6$ is $-(CH_2)_{m1}CH((CH_2)_{m3}R_3)_2$, $-(CH_2)_{m1}C((CH_2)_{m3}R_3)_3$; $-(CH_2)_{m1}CH((CH_2)_{m3}R_{5a}W_5)_2$; $-(CH_2)_{m1}CH((CH_2)_{m3}R_3)((CH_2)_{m3}R_{5a}W_5)$; $-(CH_2)_{m1}C((CH_2)_{m3}R_3)_2(CH_2)_{m3}R_{5a}W_5)$, $(CH_2)_{m1}C((CH_2)_{m3}R_{5a}W_5)_3$ or $-(CH_2)_{m1}C((CH_2)_{m3}R_3)((CH_2)_{m3}R_{5a}W_5)_2$; and wherein m3 is an integer from 1 to 3.

$W_7$ is $R_3$ or $R_5$, but typically is alkyl of 1 to 12 carbons substituted with, 0 to 3 $R_3$ groups, the latter typically selected from the group consisting of $-NR_1(R_{6b})$, $-N(R_{6b})_2$, $-OR_{6a}$, or $SR_{6a}$ More typically, $W_7$ is $-OR_1$ or an alkyl of 3 to 12 carbon atoms substituted with $OR_1$.

In general, $U_1$ is $R_1O-$, $-OCHR_1W_7$,

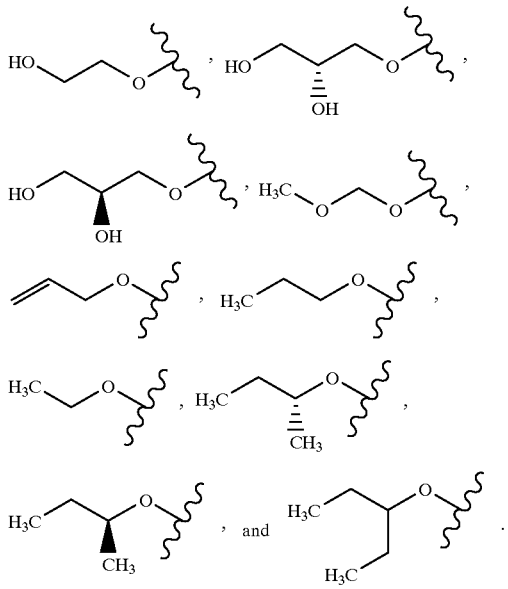

Exemplary $U_1$ groups are listed in Table 2.

An embodiment of the invention comprises a compound of the formula:

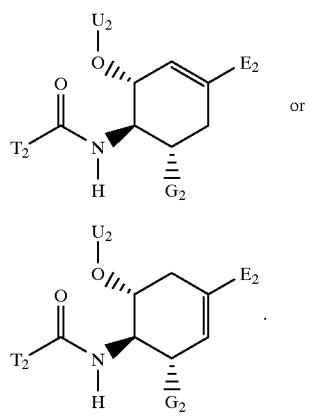

wherein $E_2$ is $E_1$, but is typically selected from the group consisting of:

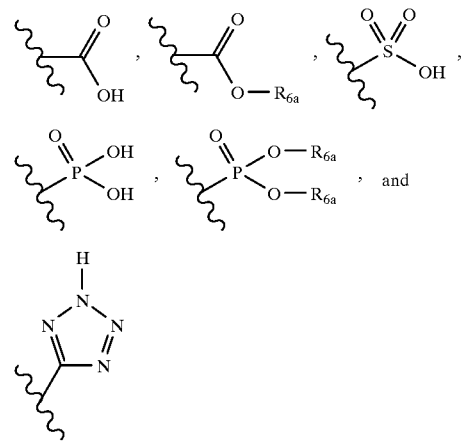

and wherein $G_2$ is $G_1$, but is typically selected from the group consisting of:

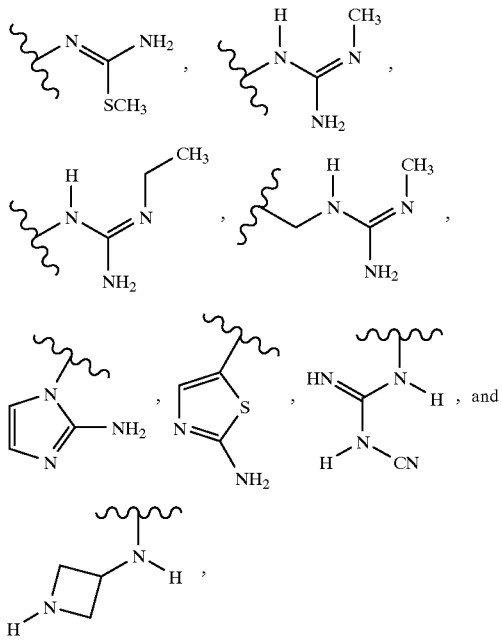

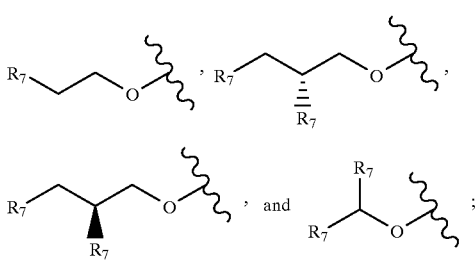

and wherein $T_2$ is $R_4$ or $R_5$. Generally, $T_2$ is alkyl of 1 to 2 carbon atoms substituted with 0 to 3 fluorine atoms.

$U_2$ is one of:

wherein $R_7$ is H, —$CH_3$, —$CH_2CH_3$, —$CH_2CH_2CH_3$, —$OCH_3$, —OAc (—O—C(O)$CH_3$), —OH, —$NH_2$, or —SH, typically H, —$CH_3$ or —$CH_2CH_3$.

Groups $R_{6a}$ and $R_{6b}$ are not critical functionalities and may vary widely. When not H, their function is to serve as intermediates for the parental drug substance. This does not mean that they are biologically inactive. On the contrary, a principal function of these groups is to convert the parental drug into a prodrug, whereby the parental drug is released upon conversion of the prodrug in vivo. Because active prodrugs are absorbed more effectively than the parental drug they in fact often possess greater potency in vivo than the parental drug. $R_{6a}$ and $R_{6b}$ are removed either in vitro, in the instance of chemical intermediates, or in vivo, in the case of prodrugs. With chemical intermediates, it is not particularly important that the resulting profunctionality products, e.g. alcohols, be physiologically acceptable, although in general it is more desirable if the products are pharmacologically innocuous.

$R_{6a}$ is H or an ether- or ester-forming group. "Ether-forming group" means a group which is capable of forming a stable, covalent bond between the parental molecule and a group having the formula:

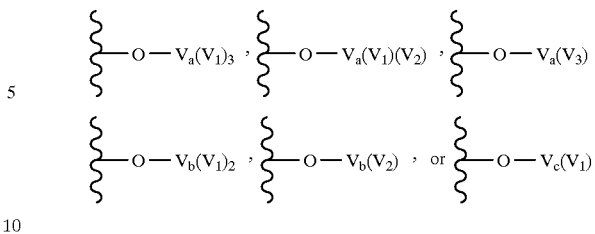

Wherein $V_a$ is a tetravalent atom typically selected from C and Si; $V_b$ is a trivalent atom typically selected from B, Al, N, and P, more typically N and P; $V_c$ is a divalent atom typically selected from O, S, and Se, more typically S; $V_1$ is a group bonded to $V_a$, $V_b$ or $V_c$ by a stable, single covalent bond, typically $V_1$ is $W_6$ groups, more typically $V_1$ is H, $R_2$, $W_5$, or —$R_{5a}W_5$, still more typically H or $R_2$; $V_2$ is a group bonded to $V_a$ or $V_b$ by a stable, double covalent bond, provided that $V_2$ is not =O, =S or =N—, typically $V_2$ is =$C(V_1)_2$ wherein $V_1$ is as described above; and $V_3$ is a group bonded to $V_a$ by a stable, triple covalent bond, typically $V_3$ is ≡—$C(V_1)$ wherein $V_1$ is as described above.

"Ester-forming group" means a group which is capable of forming a stable, covalent bond between the parental molecule and a group having the formula:

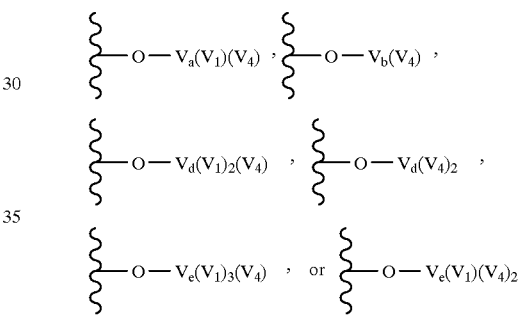

Wherein $V_a$, $V_b$, and $V_1$, are as described above; $V_d$ is a pentavalent atom typically selected from P and N; $V_e$ is a hexavalent atom typically S; and $V_4$ is a group bonded to $V_a$, $V_b$, $V_d$ or $V_e$ by a stable, double covalent bond, provided that at least one $V_4$ is =O, =S or =N-$V_1$, typically $V_4$, when other than =O, =S or =N—, is =$C(V_1)_2$ wherein $V_1$ is as described above.

Protecting groups for —OH functions (whether hydroxy, acid or other functions) are embodiments of "ether- or ester-forming groups".

Particularly of interest are ether- or ester-forming groups that are capable of functioning as protecting groups in the synthetic schemes set forth herein. However, some hydroxyl and thio protecting groups are neither ether- nor ester-forming groups, as will be understood by those skilled in the art, and are included with amides, discussed under $R_{6c}$ below. $R_{6c}$ is capable of protecting hydroxyl or thio groups such that hydrolysis from the parental molecule yields hydroxyl or thio.

In its ester-forming role, $R_{6a}$ typically is bound to any acidic group such as, by way of example and not limitation, a —$CO_2H$ or —C(S)OH group, thereby resulting in —$CO_2R_{6a}$. $R_{6a}$ for example is deduced from the enumerated ester groups of WO 95/07920.

Examples of $R_{6a}$ include
$C_3$–$C_{12}$ heterocycle (described above) or aryl. These aromatic groups optionally are polycyclic or monocyclic.

Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$–$C_{12}$ heterocycle or aryl substituted with halo, $R_1$, $R_1$—O—$C_1$–$C_{12}$ alkylene, $C_1$–$C_{12}$ alkoxy, CN, $NO_2$, OH, carboxy, carboxyester, thiol, thioester, $C_1$–$C_{12}$ haloalkyl (1–6 halogen atoms), $C_2$–$C_{12}$ alkenyl or $C_2$–$C_{12}$ alkynyl. Such groups include 2-, 3- and 4-alkoxyphenyl ($C_1$–$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$–$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$–$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$–$C_4$ alkyl, including 2-, 3- and 4-ethylsalicylphenyl), 2-, 3- and 4-acetylphehyl, 1,8-dihydroxynaphthyl (—$C_{10}H_6$—OH) and aryloxy ethyl [$C_6$–$C_9$ aryl (including phenoxy ethyl)], 2,2'-dihydroxybiphenyl, 2-, 3- and 4-N,N-dialkylaminophenol, —$C_6H_4CH_2N(CH_3)_2$, trimethoxybenzyl, triethoxybenzyl, 2-alkyl pyridinyl ($C_{1-4}$ alkyl);

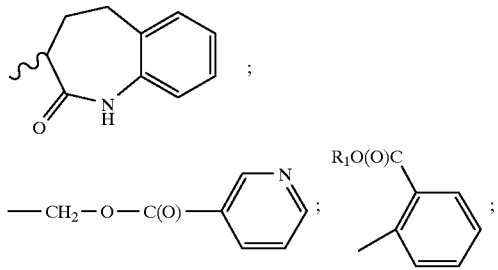

$C_4$–$C_8$ esters of 2-carboxyphenyl; and $C_1$–$C_4$ alkylene-$C_3$–$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$–$C_{12}$ alkoxy (including methoxy and ethoxy), cyano, nitro, OH, $C_1$–$C_{12}$ haloalkyl (1 to 6 halogen atoms; including —$CH_2$—$CCl_3$), $C_1$–$C_{12}$ alkyl (including methyl and ethyl), $C_2$–$C_{12}$ alkenyl or $C_2$–$C_{12}$ alkynyl;

alkoxy ethyl [$C_1$–$C_6$ alkyl including —$CH_2$—$CH_2$—O—$CH_3$ (methoxy ethyl)];

alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, —$CH_2CH_2F$, —$CH_2CH_2Cl$, —$CH_2CF_3$, and —$CH_2CCl_3$);

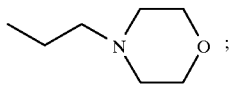

—N-2-propylmorpholino, 2,3-dihydro-6-hydroxyindene, sesamol, catechol monoester, —$CH_2$—C(O)—N($R_1$)$_2$, —$CH_2$—S(O)($R^1$), —$CH_2$—S(O)$_2$($R^1$), —$CH_2$—CH(OC(O)$CH_2R^1$)—$CH_2$(OC(O)$CH_2R^1$), cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* 5(6):670–671 [1974]);

cyclic carbonates such as (5-$R_d$-2-oxo-1,3-dioxolen-4-yl) methyl esters (Sakamoto et al., *Chem. Pharm. Bull.* 32(6)2241–2248 [1984]) where $R_d$ is $R_1$, $R_4$ or aryl; and

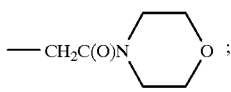

The hydroxyl groups of the compounds of this invention optionally are substituted with one of groups III, IV or V disclosed in WO94/21604, or with isopropyl.

As further embodiments, Table A lists examples of $R_{6a}$ ester moieties that for example can be bonded via oxygen to —C(O)O— and —P(O)(O—)$_2$ groups. Several $R_{6c}$ amidates also are shown, which are bound directly to —C(O)— or —P(O)$_2$. Esters of structures 1–5, 8–10 and 16, 17, 19–22 are synthesized by reacting the compound herein having a free hydroxyl with the corresponding halide (chloride or acyl chloride and the like) and N,N-dicylohexyl-N-morpholine carboxamidine (or another base such as DBU, triethylamine, $CsCO_3$, N,N-dimethylaniline and the like) in DMF (or other solvent such as acetonitrile or N-methylpyrrolidone). When $W_1$ is phosphonate, the esters of structures 5–7, 11, 12, 21, and 23–26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

1. —CH$_2$—C(O)—N(R$_1$)$_2$*
2. —CH$_2$—S(O)(R$_1$)
3. —CH$_2$—S(O)$_2$(R$_1$)
4. —CH$_2$—O—C(O)—CH$_2$—C$_6$H$_5$
5. 3-cholesteryl
6. 3-pyridyl 7. N-ethylmorpholino

8. —CH$_2$—O—C(O)—C$_6$H$_5$

9. —CH$_2$—O—C(O)—CH$_2$CH$_3$

10. —CH$_2$—O—C(O)—C(CH$_3$)$_3$

11. —CH$_2$—CCl$_3$

12. —C$_6$H$_5$

13. —NH—CH$_2$—C(O)O—CH$_2$CH$_3$

14. —N(CH$_3$)—CH$_2$—C(O)O—CH$_2$CH$_3$
15. —NHR$_1$
16. —CH$_2$—O—C(O)—C$_{10}$H$_{15}$
17. —CH$_2$—O—C(O)—CH(CH$_3$)$_2$
18. —CH$_2$—C#H(OC(O)CH$_2$R$_1$)—CH$_2$—(OC(O)CH$_2$R$_1$)*

19. 
—CH$_2$C(O)N⟨morpholino⟩

20. 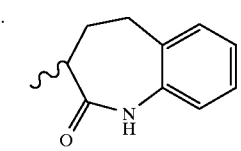

21. 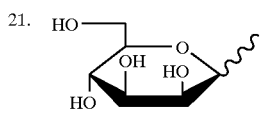

22. 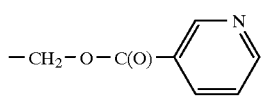
—CH$_2$—O—C(O)—(3-pyridyl)

23. 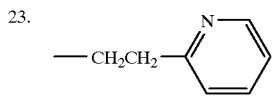
—CH$_2$CH$_2$—(2-pyridyl)

24. 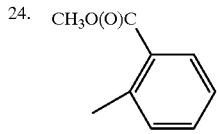
CH$_3$O(O)C— (o-methylbenzyl)

25. 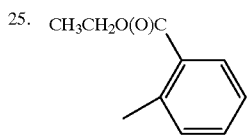
CH$_3$CH$_2$O(O)C— (o-methylbenzyl)

26. 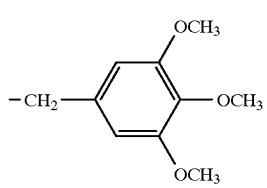
—CH$_2$—(3,4,5-trimethoxyphenyl)

—chiral center is (R), (S) or racemate.

Other esters that are suitable for use herein are described in EP 632,048.

R$_{6a}$ also includes "double ester" forming profunctionalities such as

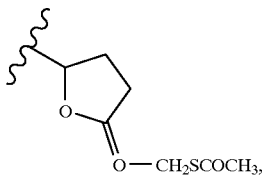

O—CH$_2$SCOCH$_3$,

—CH$_2$OCON(CH$_3$)$_2$, or alkyl- or aryl-acyloxyalkyl groups of the structure —CH(R$_1$ or W$_5$)O((CO)R$_{37}$) or —CH(R$_1$ or W$_5$)((CO)OR$_{38}$) (linked to oxygen of the acidic group) wherein R$_{37}$ and R$_{38}$ are alkyl, aryl, or alkylaryl groups (see U.S. Pat. No. 4,968,788). Frequently R$_{37}$ and R$_{38}$ are bulky groups such as branched alkyl, ortho-substituted aryl, meta-substituted aryl, or combinations thereof, including normal, secondary, iso- and tertiary alkyls of 1–6 carbon atoms. An example is the pivaloyloxymethyl group. These are of particular use with prodrugs for oral administration. Examples of such useful R$_{6a}$ groups are alkylacyloxymethyl esters and their derivatives, including —CH(CH$_2$CH$_2$OCH$_3$)OC(O)C(CH$_3$)$_3$,

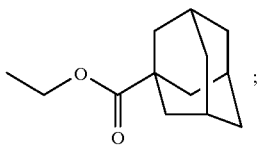

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

For prodrug purposes, the ester typically chosen is one heretofore used for antibiotic drugs, in particular the cyclic carbonates, double esters, or the phthalidyl, aryl or alkyl esters.

As noted, R$_{6a}$, R$_{6c}$ and R$_{6b}$ groups optionally are used to prevent side reactions with the protected group during synthetic procedures, so they function as protecting groups (PRT) during synthesis. For the most part the decision as to which groups to protect, when to do so, and the nature of the PRT will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect carboxyl, hydroxyl or amino groups. The order of deprotection to yield free groups is dependent upon the intended direction of the synthesis and the reaction conditions to be encountered, and may occur in any order as determined by the artisan.

A very large number of R$_{6a}$ hydroxy protecting groups and R$_{6c}$ amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21–94, Chapter 3, Diol Protecting Groups, pages 95–117, Chapter 4, Carboxyl Protecting Groups, pages 118–154, Chapter 5, Carbonyl Protecting Groups, pages 155–184. For R$_{6a}$ carboxylic acid, phosphonic acid, phosphonate, sulfonic acid and other protecting groups for W$_1$ acids see Greene as set forth below. Such groups include by way of example and not limitation, esters, amides, hydrazides, and the like.

In some embodiments the R$_{6a}$ protected acidic group is an ester of the acidic group and R$_{6a}$ is the residue of a hydroxyl-containing functionality. In other embodiments, an R$_{6c}$ amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11–18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical R$_{6a}$ esters for protecting W$_1$ acidic functionalities are also described in WO 95/07920, again understanding that the same esters can be formed with the acidic groups herein as with the phosphonate of the '920 publication. Typical ester groups are defined at least on WO 95/07920 pages 89–93 (under R$^{31}$ or R$^{35}$), the table on page 105, and pages 21–23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C$_1$–C$_4$ alkylestercarboxyphenyl (salicylate C$_1$–C$_{12}$ alkylesters).

The protected acidic groups W$_1$, particularly when using the esters or amides of WO 95/07920, are useful as prodrugs for oral administration. However, it is not essential that the W$_1$ acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical R$_{6a}$ hydroxy protecting groups described in Greene (pages 14–118) include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl) phenylmethyl, Tri(p-methoxyphenyl)methyl, 4-(4'-Bromophenacyloxy)phenyldiphenylmethyl, 4,4',4"-Tris(4, 5-dichlorophthalimidophenyl)methyl, 4,4',4"-Tris (levulinoyloxyphenyl)methyl, 4,4',4"-Tris (benzoyloxyphenyl)methyl, 3(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl) ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl) benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, $R_{6a}$ hydroxy protecting groups include substituted methyl ethers, substituted benzyl ethers, silyl ethers, and esters including sulfonic acid esters, still more typically, trialkylsilyl ethers, tosylates and acetates.

Typical 1,2-diol protecting groups (thus, generally where two OH groups are taken together with the $R_{6a}$ protecting functionality) are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

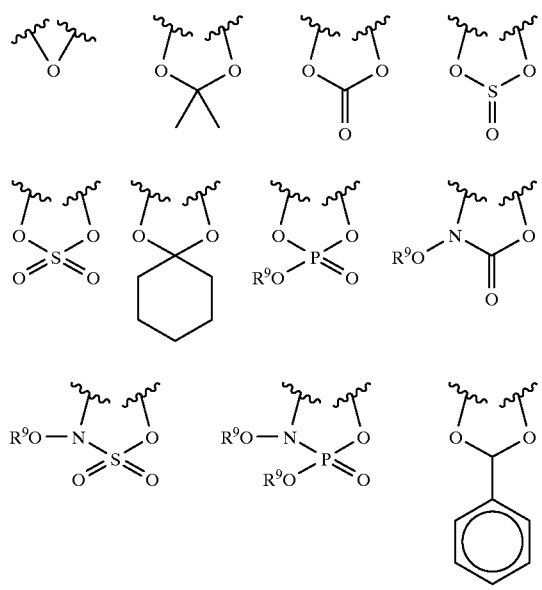

wherein $R^9$ is $C_1$–$C_6$ alkyl.

$R_{6b}$ is H, a protecting group for amino or the residue of a carboxyl-containing compound, in particular H, —C(O) $R_4$, an amino acid, a polypeptide or a protecting group not —C(O)$R_4$, amino acid or polypeptide. Amide-forming $R_{6b}$ are found for instance in group $G_1$. When $R_{6b}$ is an amino acid or polypeptide it has the structure $R_{15}$NHCH($R_{16}$)C (O)—, where $R_{15}$ is H, an amino acid or polypeptide residue, or $R_5$, and $R_{16}$ is defined below.

$R_{16}$ is lower alkyl or lower alkyl ($C_1$–$C_6$) substituted with amino, carboxyl, amide, carboxyl ester, hydroxyl, $C_6$–$C_7$ aryl, guanidinyl, imidazolyl, indolyl, sulfhydryl, sulfoxide, and/or alkylphosphate. $R_{10}$ also is taken together with the amino acid α N to form a proline residue ($R_{10}$=—$CH_2$) $_3$—). However, $R_{10}$ is generally the side group of a naturally-occuring amino acid such as H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—$SH$, —$CH_2C_6H_4OH$, —$CH_2$—$CO$—$NH_2$, —$CH_2$—$CH_2$—$CO$—$NH_2$, —$CH_2$—$COOH$, —$CH_2$—$CH_2$—$COOH$, —$(CH_2)_4$—$NH_2$ and —$(CH_2)_3$—$NH$—$C$ ($NH_2$)—$NH_2$. $R_{10}$ also includes 1-guanidinoprop-3-yl, benzyl, 4-hydroxybenzyl, imidazol-4-yl, indol-3-yl, methoxyphenyl and ethoxyphenyl.

$R_{6b}$ are residues of carboxylic acids for the most part, but any of the typical amino protecting groups described by Greene at pages 315–385 are useful. They include Carbamates (methyl and ethyl, 9-fluorenylmethyl, 9(2-sulfo) fluoroenylmethyl, 9-(2,7-dibromo)fluorenylmethyl, 2,7-di-t-buthyl-[9(10,10-dioxo-10,10,10,10-tetrahydrothioxanthyl)] methyl, 4-methoxyphenacyl); Substituted Ethyl (2,2,2-trichoroethyl, 2-trimethylsilylethyl, 2-phenylethyl, 1(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl) benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-lodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl) methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl) mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl) phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N-N Derivatives (N-nitro, N-nitroso, N-oxide); N-P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N-Si Derivatives; N-S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)R$_1$ or —N=CR$_1$N(R$_1$)$_2$. Another protecting group, also usefull as a prodrug at the G$_1$ site, particularly for amino or —NH(R$_5$), is:

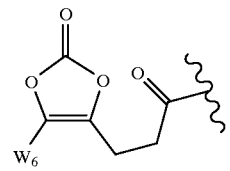

see for example Alexander, J.; et al.; *J. Med. Chem.* 1996, 39, 480–486.

R$_{6c}$ is H or the residue of an amino-containing compound, in particular an amino acid, a polypeptide, a protecting group, —NHSO$_2$R$_4$, NHC(O)R$_4$, —N(R$_4$)$_2$, NH$_2$ or —NH (R$_4$)(H), whereby for example the carboxyl or phosphonic acid groups of W$_1$ are reacted with the amine to form an amide, as in —C(O)R$_{6c}$, —P(O)(R$_{6c}$)$_2$ or —P(O)(OH)(R$_{6c}$). In general, R$_{6c}$ has the structure R$_{17}$C(O)CH(R$_{16}$)NH—, where R$_{17}$ is OH, OR$_{6a}$, OR$_5$, an amino acid or a polypeptide residue.

Amino acids are low molecular weight compounds, on the order of less than about 1,000 MW, that contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono-or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline.

When $R_{6b}$ and $R_{6c}$ are single amino acid residues or polypeptides they usually are substituted at $R_3$, $W_6$, $W_1$ and/or $W_2$, but typically only $W_1$ or $W_2$. These conjugates are produced by forming an amide bond between a carboxyl group of the amino acid (or C-terminal amino acid of a polypeptide for example) and $W_2$. Similarly, conjugates are formed between $W_1$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of $W_1$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g. by $R_{6a}$, esterified with $R_5$ or amidated with $R_{6c}$. Similarly, the amino side chains $R_{16}$ optionally will be blocked with $R_{6b}$ or substituted with $R_5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R_{6b}$ and $R_{6c}$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$–$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, aaminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, γ-hydroxynorvaline, δ-hydroxynorvaline and epsilon-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α amino acids such as the phenyl- or cyclohexylamino acids α-aminophenylacetic acid, aaminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro-, o-, m- or p-methyl-, 2,4, 6-trimethyl-, 2-ethoxy-5-nitro-, 2-hydroxy-5-nitro- and p-nitrophenylalanine); furyl-, thienyl-, pyridyl-, pyrimidinyl-, purinyl- or naphthylalanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 150014 5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In embodiments where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as $R_{6b}$ or $R_{6c}$. When $W_1$ is phosphonate, the sequence -X4-pro-X5- (where X4 is any amino acid residue and X5 is an amino acid residue, a carboxyl ester of proline, or hydrogen) will be cleaved by luminal carboxypeptidase to yield X4 with a free carboxyl, which in turn is expected to autocatalytically cleave the phosphonoamidate bond. The carboxy group of X5 optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., "Pharm Res." 9:969–978 (1992). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N (EC 3.4.11.2). In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A (EC 3.4.11.7), di- or tripeptides lacking amino acid residues on the N-terminal side of hydrophobic amino acids (leu, tyr, phe, val, trp) are poor substrates for endopeptidase 24.11 (EC 3.4.24.11), and peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Another embodiment of the invention relates to compositions of the formula (VII) or (VIII):

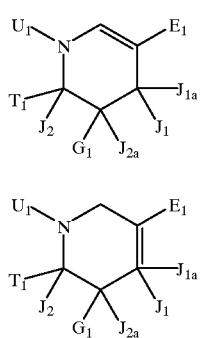

(VII)

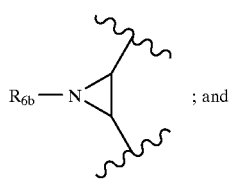

(VIII)

wherein $E_1$, $G_1$, $T_1$, $U_1$, $J_1$, $J_{1a}$, $J_2$ and $J_{2a}$ are as defined above except:

$T_1$ is —$NR_1W_3$, a heterocycle, or is taken together with $G_1$ to form a group having the structure

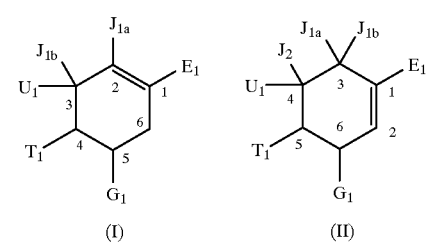
; and $X_1$ is a bond, —O—, —N(H)—, —N($R_5$)—, —S—, —SO—, or —$SO_2$—; and provided, however, that compounds are excluded wherein $U_1$ is H or $CH_2CH(OH)CH_2(OH)$;

and the salts, solvates, resolved enantiomers and purified diastereomers thereof.

Each of the typical or ordinary embodiments of formula (I)–(VI) detailed above are also typical embodiments of formula (VII) and (VIII).

The synthesis of a number of compounds of the formula (VII) and (VIII) wherein $U_1$ is H or —$CH_2CH(OH)CH_2(OH)$ are provided in Nishimura, Y.; et al.; *J. Antibiotics*, 1993, 46(2), 300; 46(12), 1883; and *Nat. Prod. Lett.* 1992, 1(1), 39. Attachement of $U_1$ groups of the present invention proceed as described therein.

Stereoisomers

The compounds of the invention are enriched or resolved optical isomers at any or all asymmetric atoms. For example, the chiral centers apparent from the depictions are provided as the chiral isomers or racemic mixtures. Both racemic and diasteromeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Exemplary stereochemistry of the compounds of this invention is set forth below in Table C.

TABLE C

Formula (I)

| $E_1$ | $J_{1a}$ | $J_{1b}$ | $U_1$ | $T_1$ | $G_1$ |
|---|---|---|---|---|---|
| — | — | α | β | α | α |
| — | — | β | α | α | α |
| — | — | α | β | β | α |
| — | — | α | β | α | β |
| — | — | β | α | β | α |
| — | — | β | α | α | β |
| — | — | α | β | β | β |
| — | — | β | α | β | β |

| $E_1$ | $J_{1a}$ | $J_{1b}$ | $J_2$ | $U_1$ | $T_1$ | $G_1$ |
|---|---|---|---|---|---|---|
| — | α | β | α | β | α | α |
| — | β | α | α | β | α | α |
| — | α | β | β | α | α | α |
| — | α | β | α | β | β | α |
| — | α | β | α | β | α | β |
| — | β | α | β | α | α | α |
| — | β | α | α | β | β | α |
| — | β | α | α | β | α | β |
| — | α | β | β | α | β | α |
| — | α | β | α | α | α | β |
| — | β | α | β | α | β | α |
| — | β | α | β | α | β | β |
| — | β | α | α | β | β | β |
| — | α | β | β | α | β | β |
| — | β | α | β | α | β | β |

The compounds of the invention can also exist as tautomeric isomers in certain cases. For example, ene-amine tautomers can exist for imidazole, guanidine, amidine, and tetrazole systems and all their possible tautomeric forms are within the scope of the invention.

Exemplary Enumerated Compounds

By way of example and not limitation, embodiment compounds are named below in tabular format (Table 6). Generally, each compound is depicted as a substituted nucleus in which the nucleus is designated by capital letter and each substituent is designated in order by lower case letter or number. Tables 1a and 1b are a schedule of nuclei which differ principally by the position of ring unsaturation and the nature of ring substituents. Each nucleus is given a alphabetical designation from Tables 1a and 1b, and this designation appears first in each compound name. Similarly, Tables 2a–av, 3a–b, 4a–c, and 5a–d list the selected $Q_1$, $Q_2$, $Q_3$ and $Q_4$ substituents, again by letter or number designation. Accordingly, each named compound will be depicted by a capital letter designating the nucleus from Table 1a–1b, followed by a number designating the $Q_1$ substituent, a lower case letter designating the $Q_2$ substituent, a number designating the $Q_3$ substituent, and a lower case letter or letters designating the $Q_4$ substituent. Thus, structure 8, scheme 1, is represented by A.49.a.4.i. $Q_1$–$Q_4$, it should be understood, do not represent groups or atoms but are simply connectivity designations.

TABLE 1a
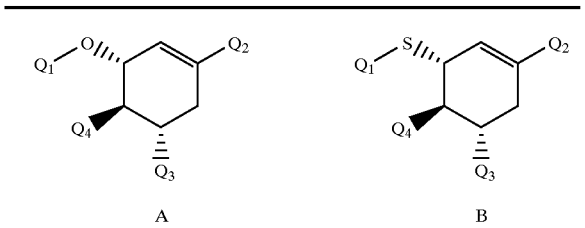
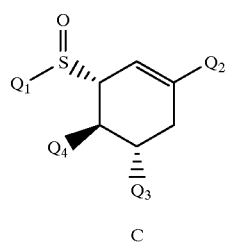
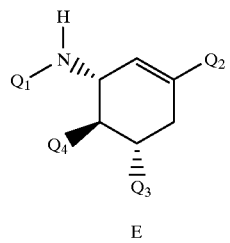
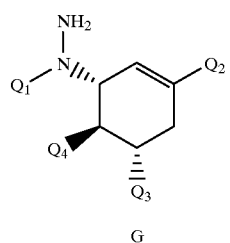
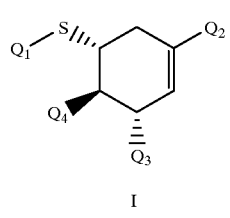
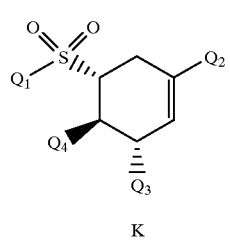
TABLE 1a-continued
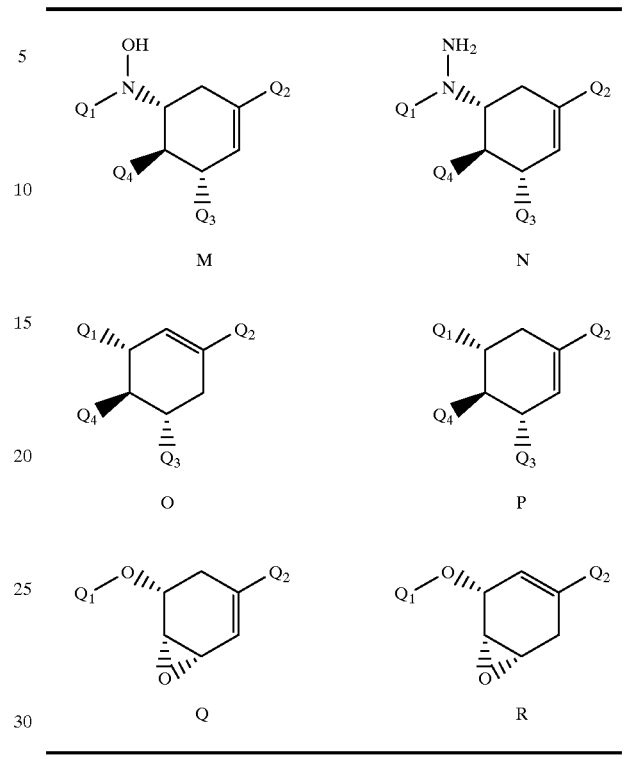
TABLE 1b
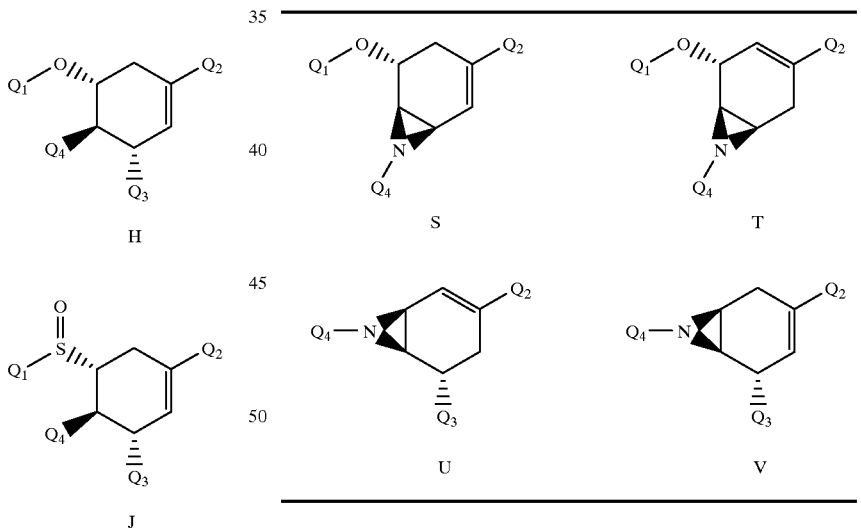
TABLE 2a
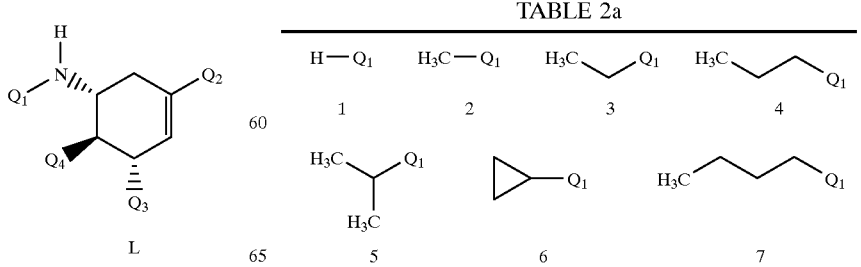

TABLE 2a-continued
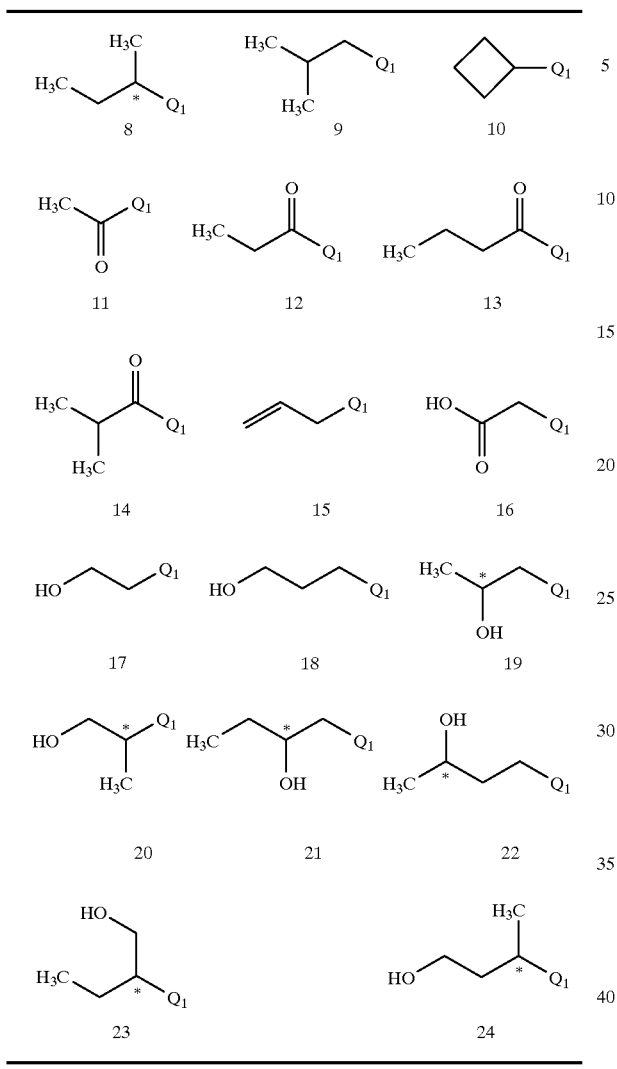
TABLE 2b
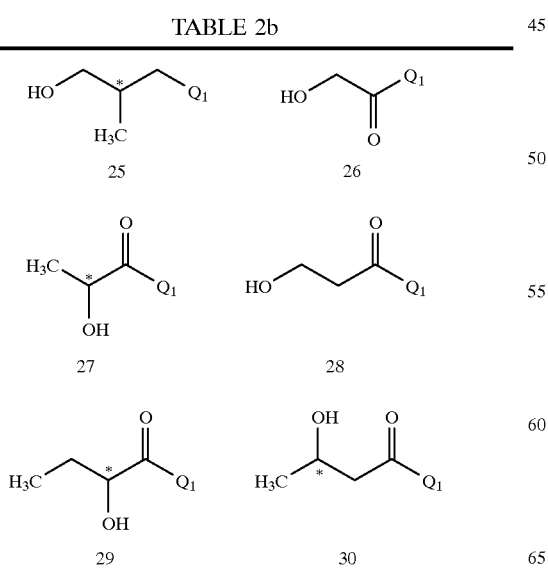
TABLE 2b-continued
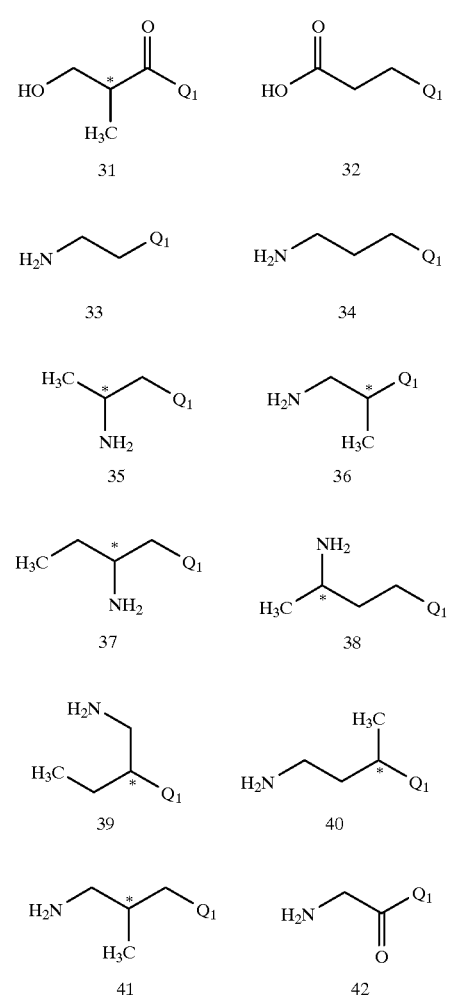
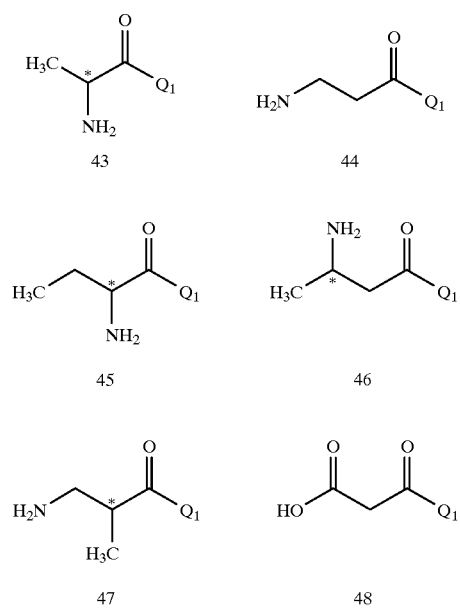

TABLE 2c

[Structure 49: HOCH₂-C*H(OH)-CH₂-Q₁ with OH]

[Structure 50: HOCH₂-C*H(Q₁)-CH₂-OH]

[Structure 51: H₃C-C*H(OH)-C*H(OH)-Q₁]

[Structure 52: H₃C-C*H(OH)-C*H(OH)-CH₂-Q₁ (arrangement)]

[Structure 53: HO-CH₂-CH₂-C*H(OH)-Q₁]

[Structure 54: H₃C-C*H(Q₁)-C*H(OH)-CH₂OH]

[Structure 55: HOCH₂-CH(CH₂OH)-CH₂-Q₁]

[Structure 56: HO-C*H(OH)-C(=O)-Q₁]

[Structure 57: H₃C-C*H(OH)-C*H(OH)-C(=O)-Q₁]

[Structure 58: HO-CH₂-CH₂-C*H(OH)-C(=O)-Q₁]

[Structure 59: HO-CH₂-C*H(OH)-CH₂-C(=O)-Q₁]

[Structure 60: HOCH₂-CH(CH₂OH)-C(=O)-Q₁]

[Structure 61: H₂N-CH₂-C*H(NH₂)-CH₂-Q₁]

[Structure 62: H₂N-CH₂-C*H(Q₁)-CH₂-NH₂]

[Structure 63: H₃C-C*H(NH₂)-C*H(NH₂)-CH₂-Q₁]

[Structure 64: H₃C-C*H(NH₂)-C*H(NH₂)-CH₂-Q₁ (variant)]

TABLE 2c-continued

[Structure 65: H₂N-CH₂-C*H(Q₁)-CH₂-CH₂-NH₂]

[Structure 66: H₃C-C*H(Q₁)-C*H(NH₂)-CH₂-NH₂]

TABLE 2d

[Structure 67: H₂N-CH₂-CH(CH₂NH₂)-CH₂-Q₁]

[Structure 68: H₂N-CH₂-C*H(NH₂)-C(=O)-Q₁]

[Structure 69: H₂N-C*H(NH₂)-C*H(NH₂)-C(=O)-Q₁]

[Structure 70: H₂N-CH₂-CH₂-C*H(NH₂)-C(=O)-Q₁]

[Structure 71: H₂N-CH₂-CH(CH₂NH₂)-C(=O)-Q₁]

[Structure 72: H₂N-C(=O)-Q₁]

[Structure 73: HO-CH₂-C*H(NH₂)-CH₂-Q₁]

[Structure 74: H₂N-CH₂-C*H(OH)-CH₂-Q₁]

[Structure 75: HO-CH₂-C*H(Q₁)-CH₂-NH₂]

[Structure 76: H₃C-C*H(OH)-C*H(NH₂)-CH₂-Q₁]

[Structure 77: H₃C-C*H(NH₂)-C*H(OH)-CH₂-Q₁]

[Structure 78: H₃C-C*H(OH)-C*H(NH₂)-CH₂-Q₁ (variant)]

[Structure 79: H₃C-C*H(OH)-C*H(Q₁)-CH₂-NH₂]

[Structure 80: HO-CH₂-C*H(NH₂)-C*H(CH₃)-Q₁]

TABLE 2d-continued
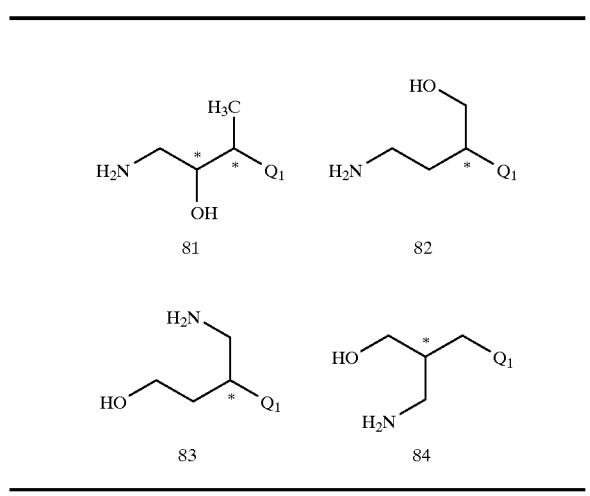
TABLE 2e
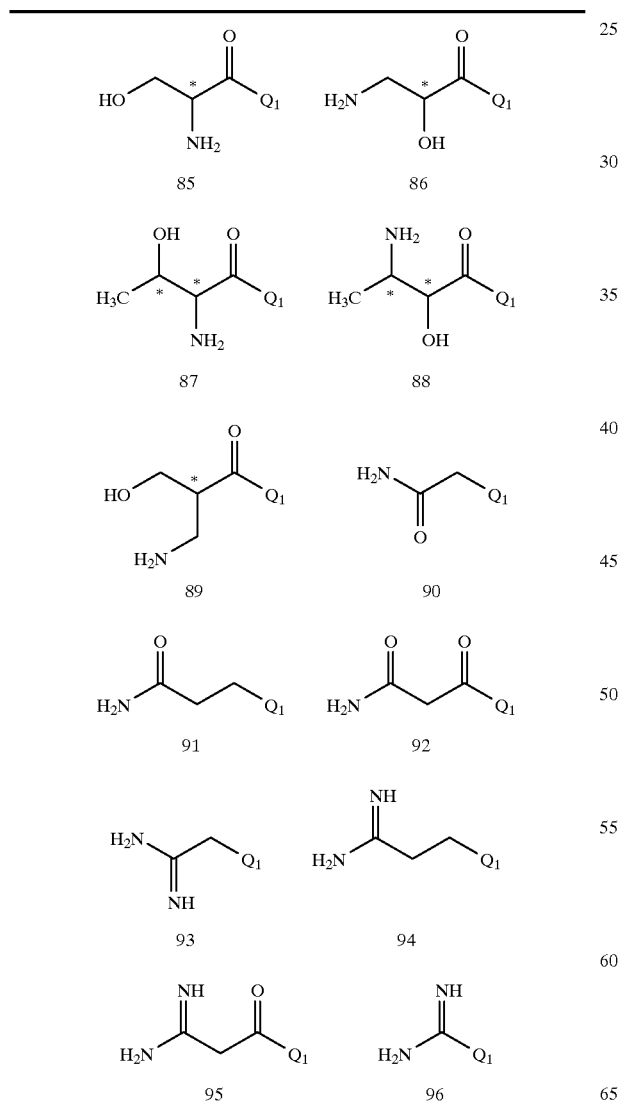
TABLE 2e-continued
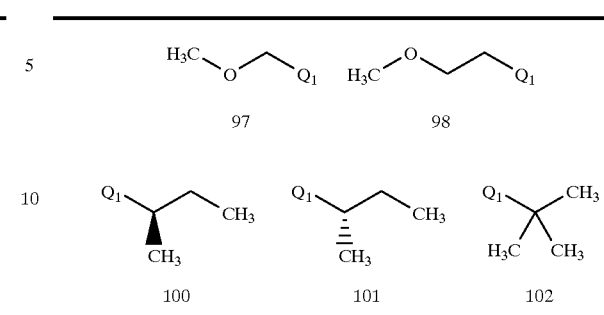
TABLE 2f
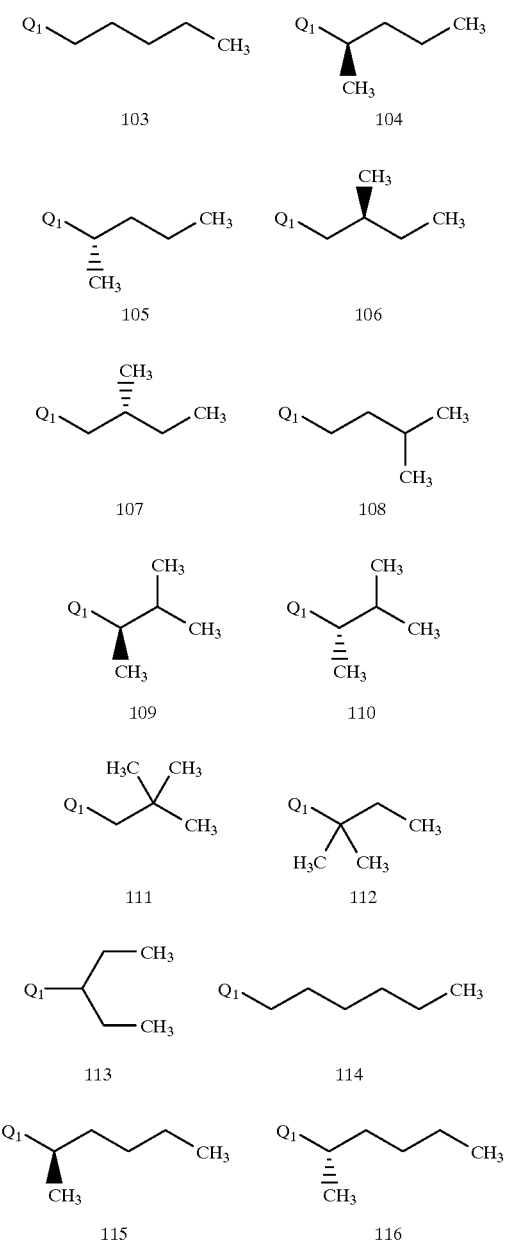

TABLE 2f-continued
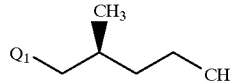 117
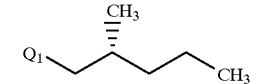 118
 119
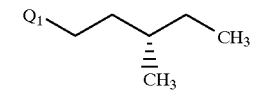 120
TABLE 2g
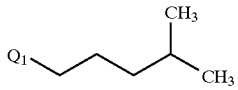 121
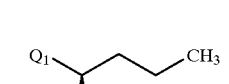 122
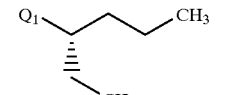 123
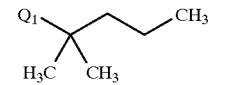 124
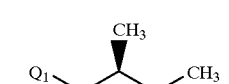 125
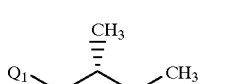 126
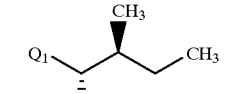 127
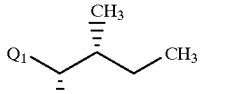 128
 129
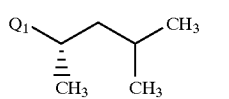 130
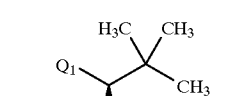 131
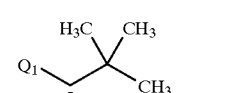 132
TABLE 2g-continued
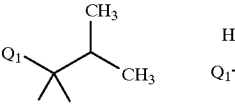 133
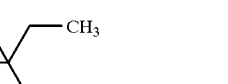 134
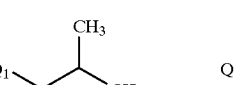 135
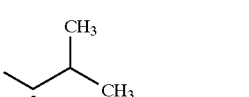 136
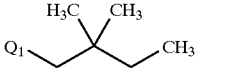 137
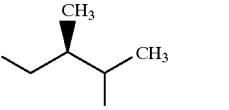 138
TABLE 2h
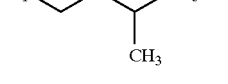 139
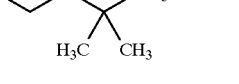 140
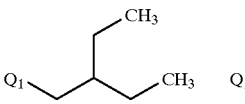 141
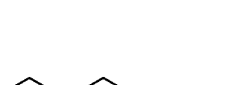 142
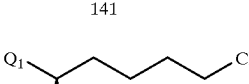 143
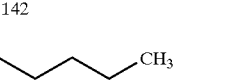 144
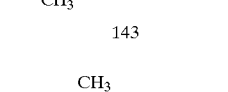 145
 146
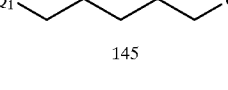 147
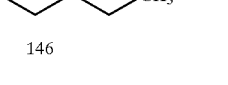 148
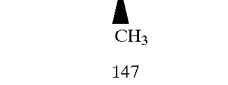 149
 150

TABLE 2h-continued
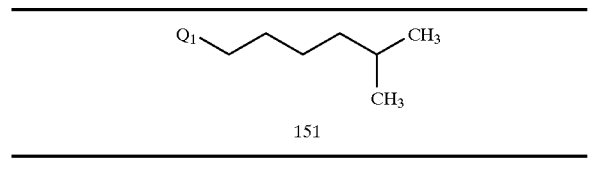
151
TABLE 2i
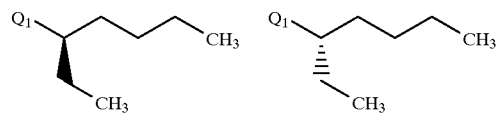
152     153
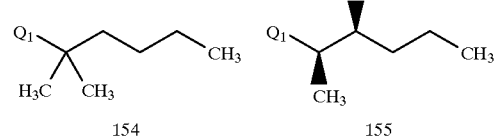
154     155
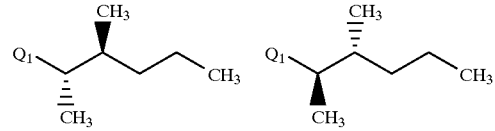
156     157
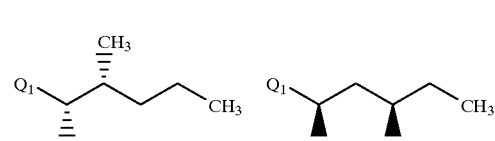
158     159
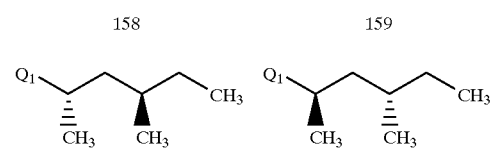
160     161
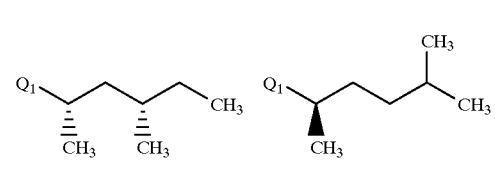
162     163
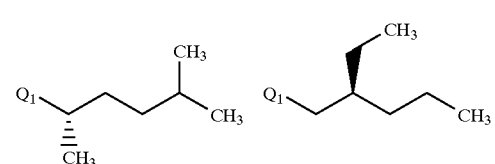
164     165
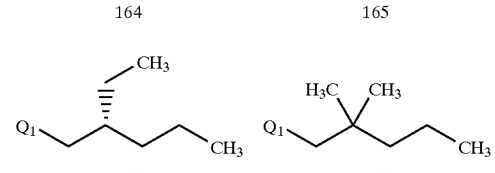
166     167
TABLE 2i-continued
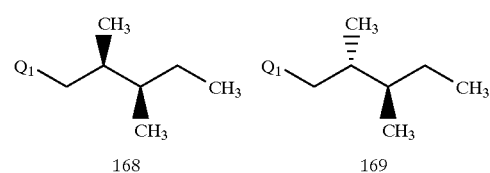
168     169
TABLE 2j
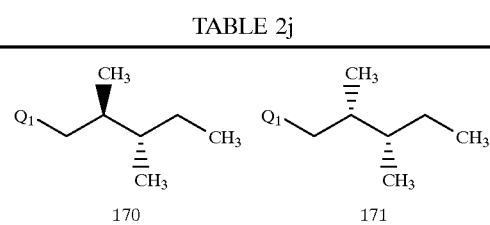
170     171
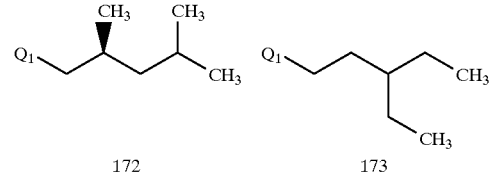
172     173
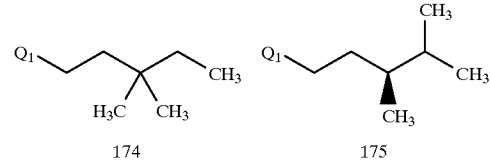
174     175
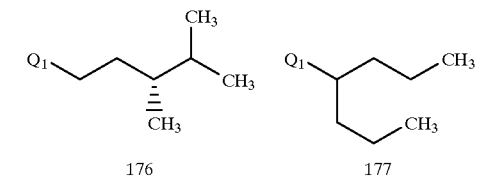
176     177
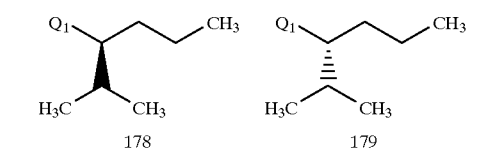
178     179
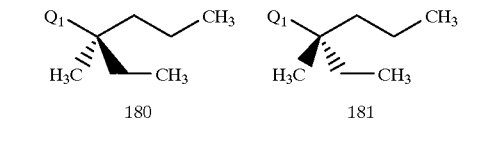
180     181
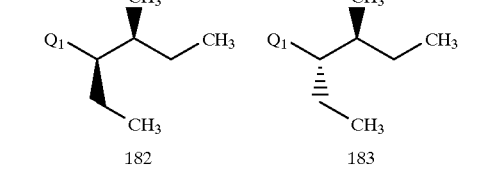
182     183

TABLE 2j-continued

[Structures 184, 185, 186, 187 - chiral branched alkyl groups attached to Q₁]

TABLE 2k

[Structures 188–199 - chiral branched alkyl groups attached to Q₁]

TABLE 2k-continued

[Structures 200, 201, 202, 203, 204 - chiral branched alkyl groups attached to Q₁]

TABLE 2l

[Structures 205–214 - chiral branched alkyl groups attached to Q₁]

TABLE 2l-continued
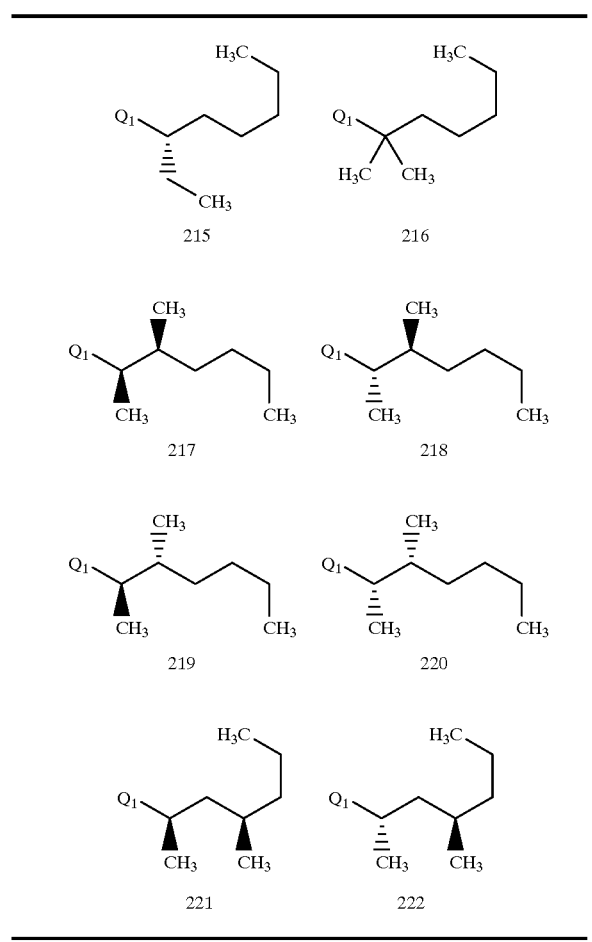
TABLE 2m
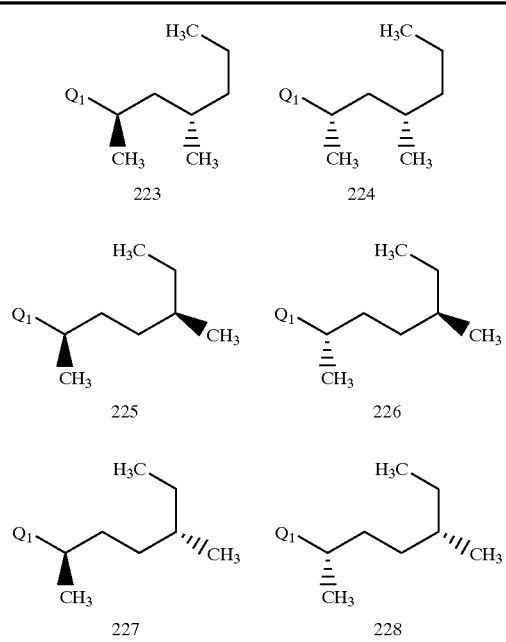
TABLE 2m-continued
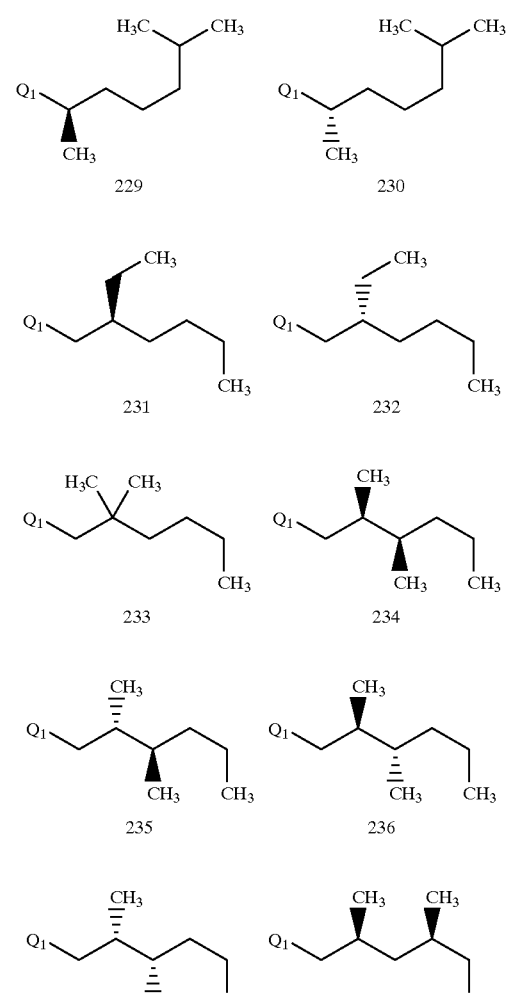
TABLE 2n
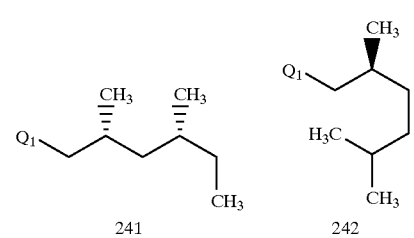

TABLE 2n-continued
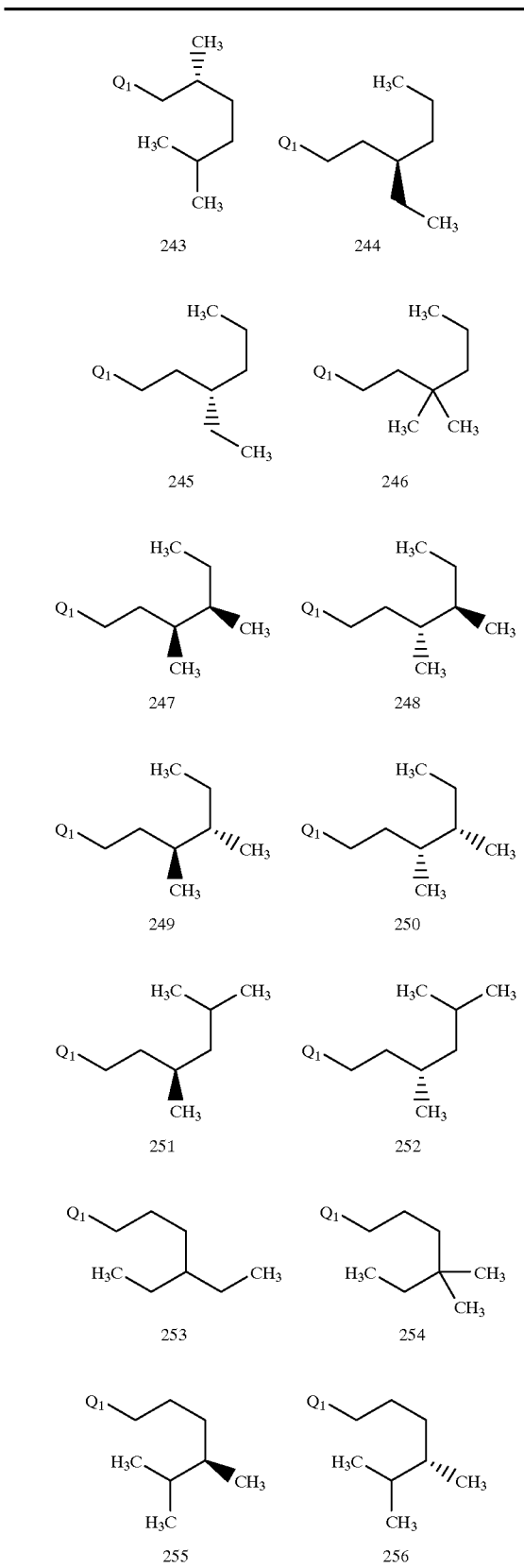
TABLE 2n-continued
TABLE 2o
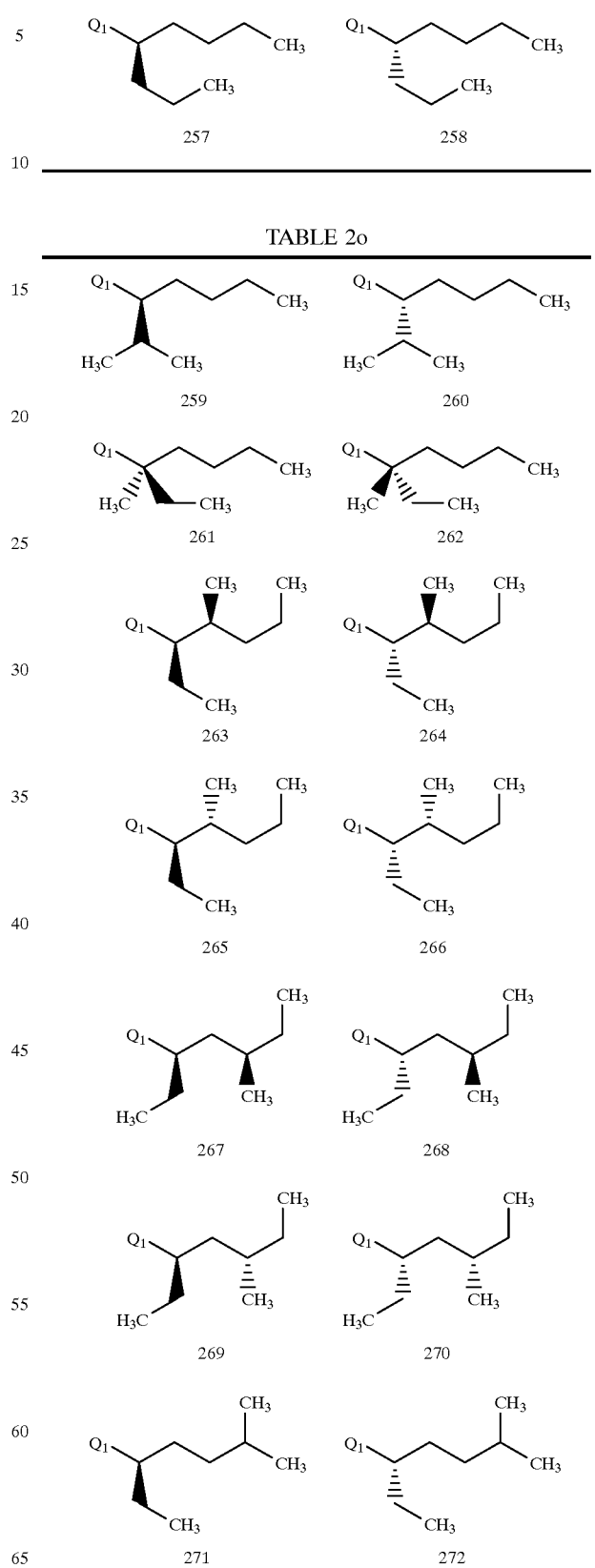

TABLE 2o-continued
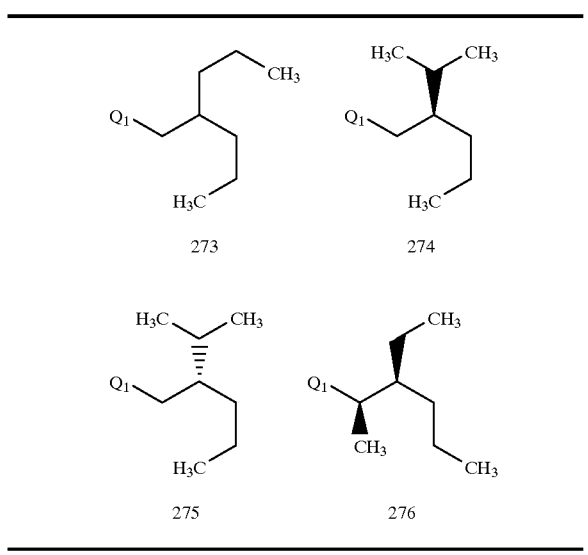
TABLE 2p
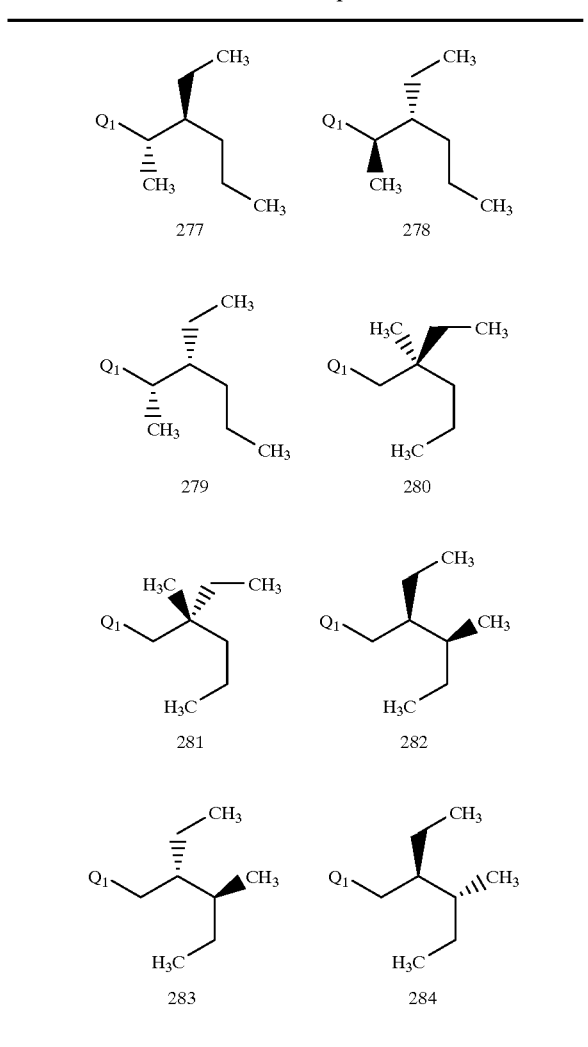
TABLE 2p-continued
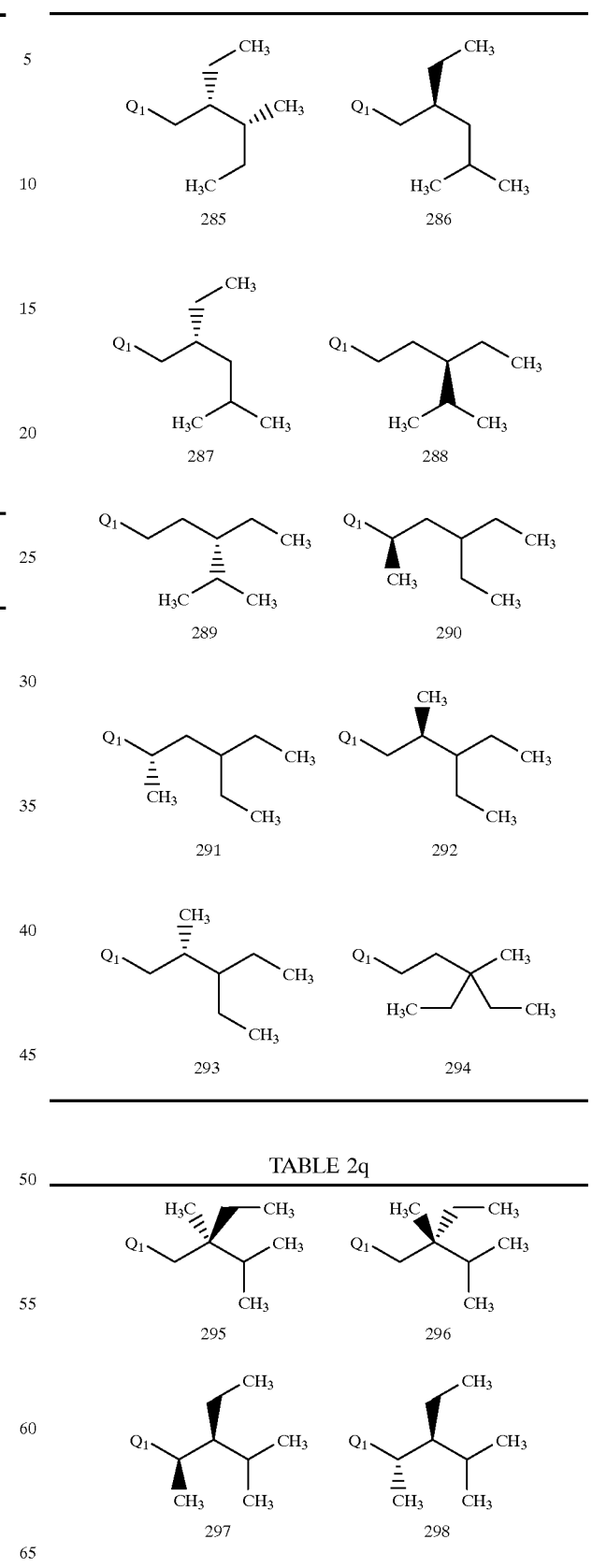

TABLE 2q-continued 299, 300, 301, 302, 303, 304, 305, 306, 307, 308, 309, 310, 311, 312

TABLE 2r 313, 314

TABLE 2r-continued 315, 316, 317, 318, 319, 320, 321, 322, 323, 324, 325, 326, 327, 328, 329, 330

TABLE 2s
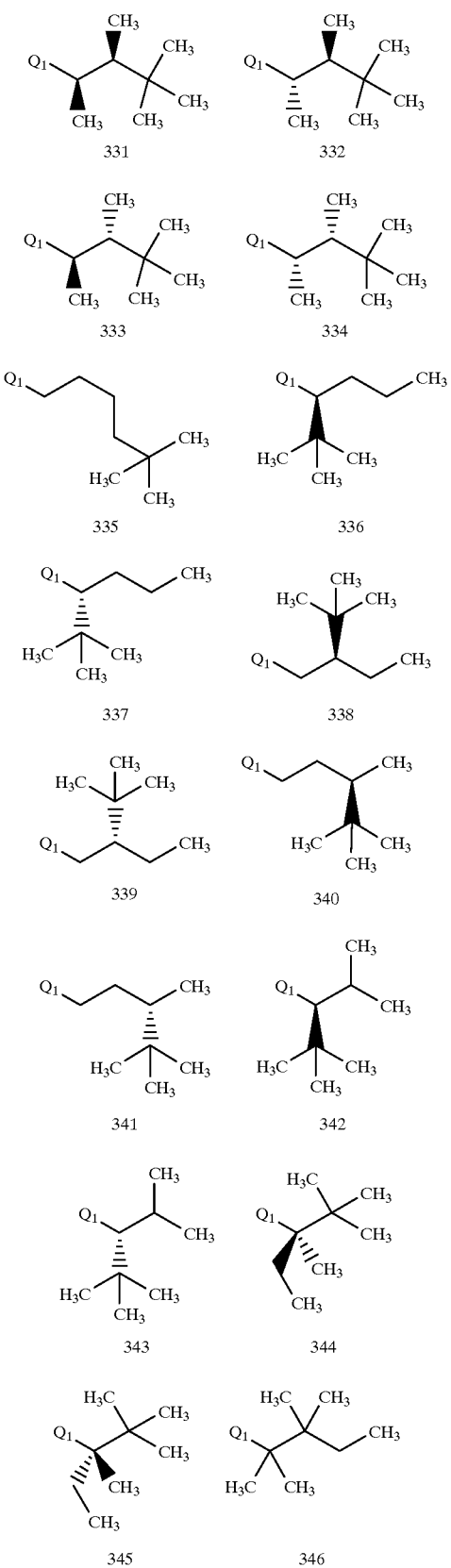
TABLE 2s-continued
TABLE 2t
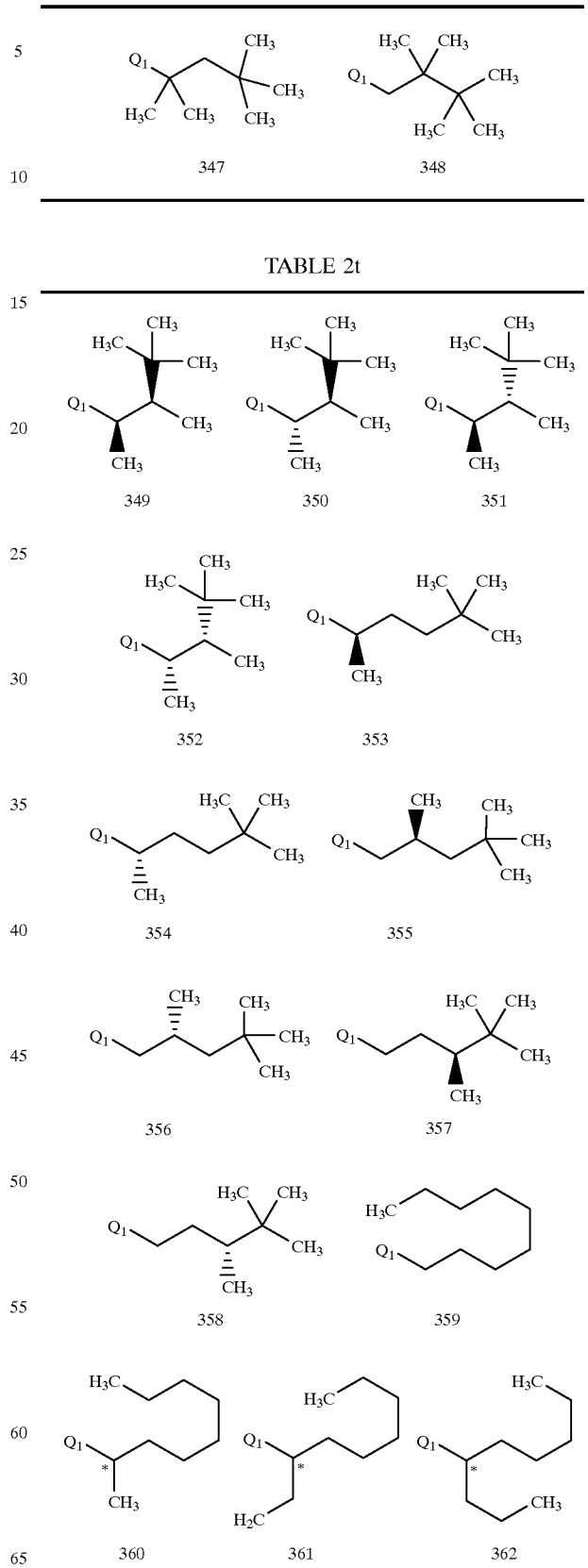

TABLE 2t-continued
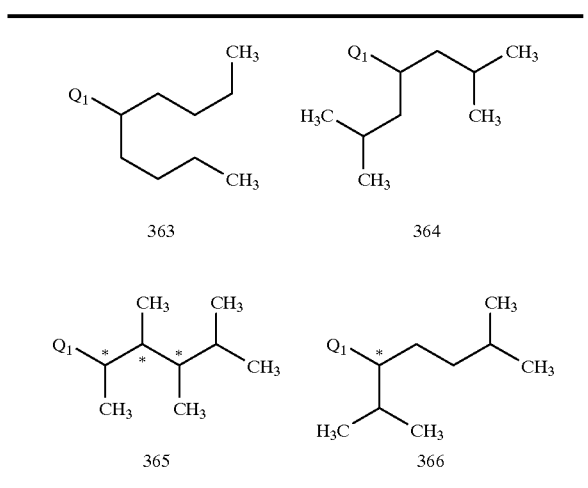
363  364
365  366
TABLE 2u
367  368
369  370
371  372
373  374
TABLE 2u-continued
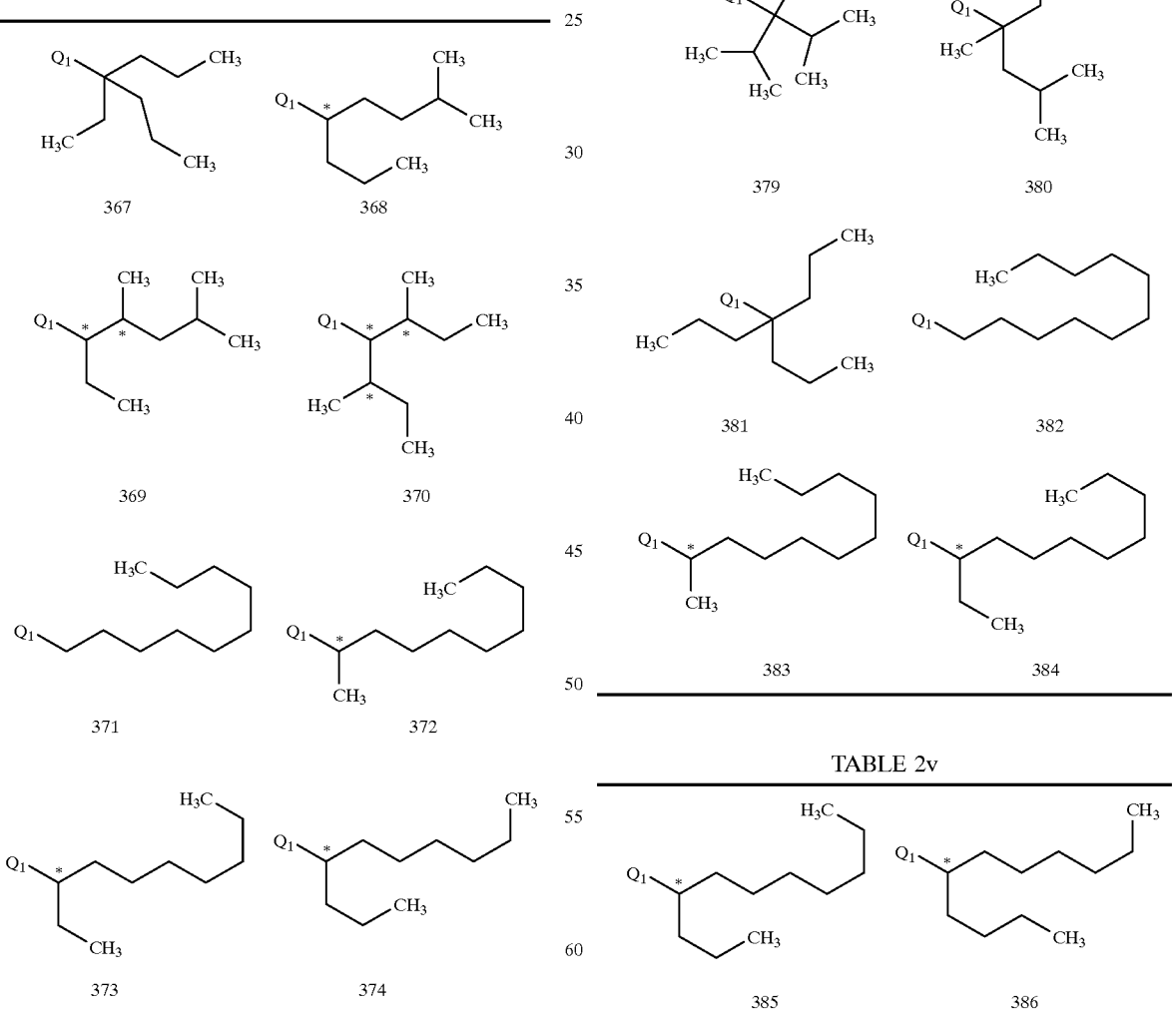
375  376
377  378
379  380
381  382
383  384
TABLE 2v
385  386

TABLE 2v-continued
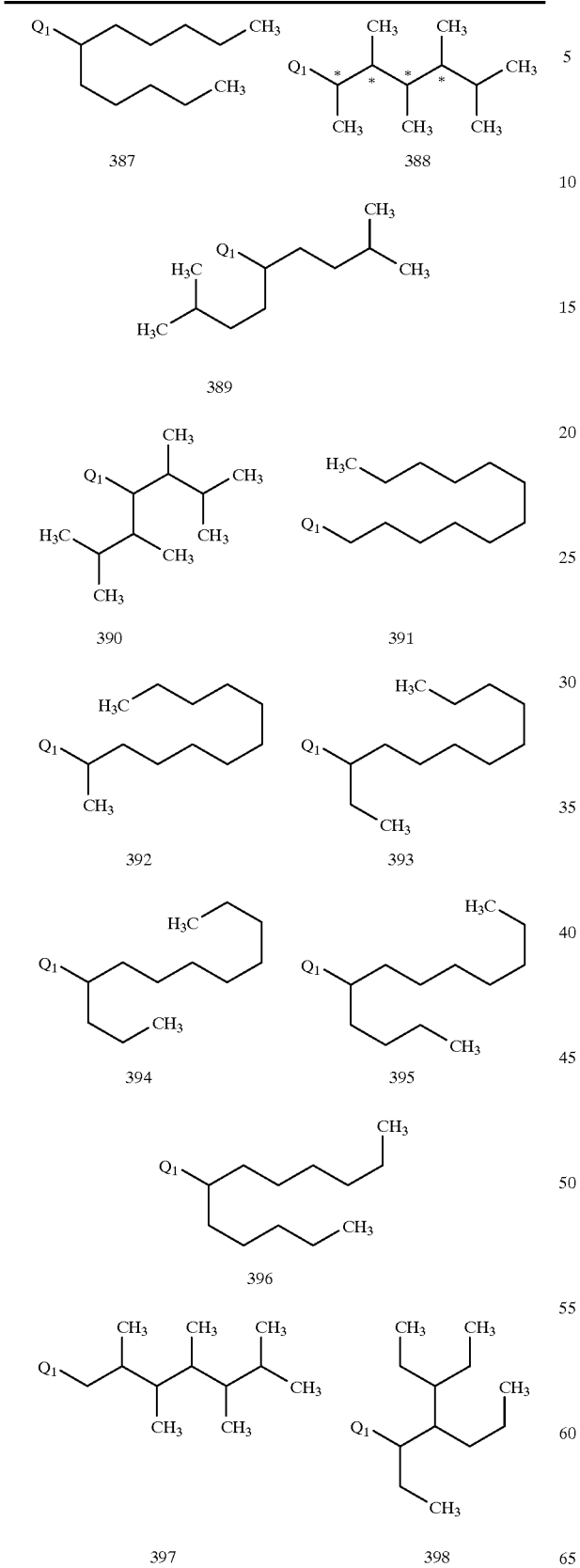
TABLE 2v-continued
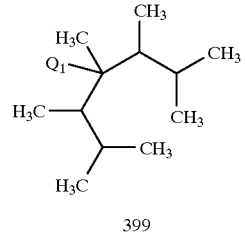
TABLE 2w
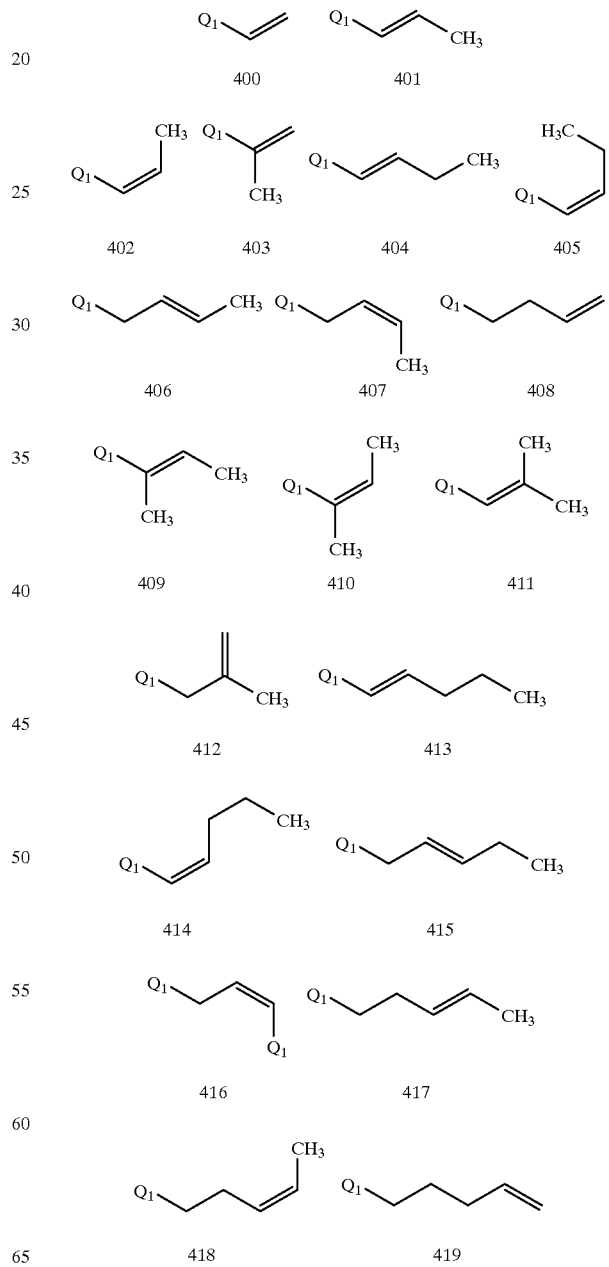

TABLE 2x
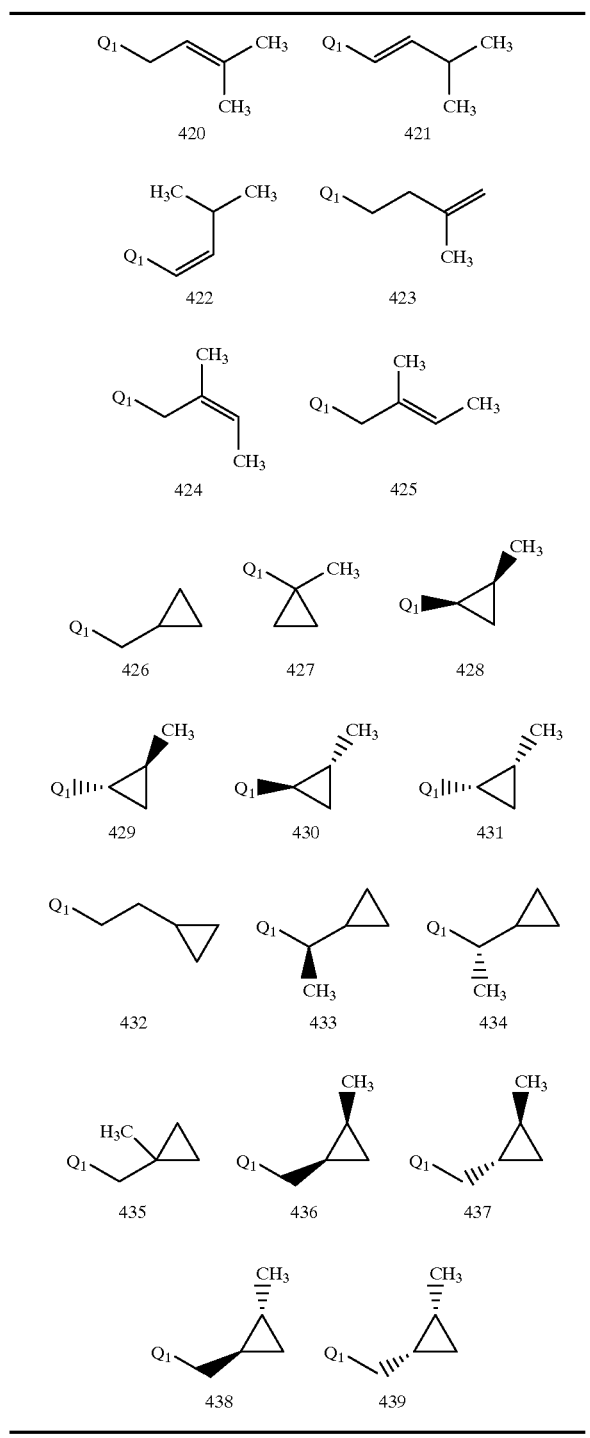
TABLE 2y
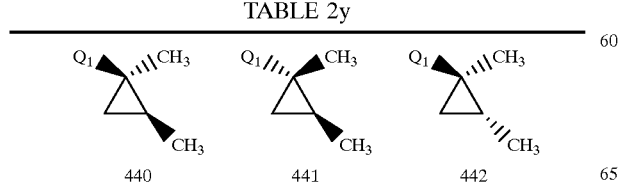
TABLE 2y-continued
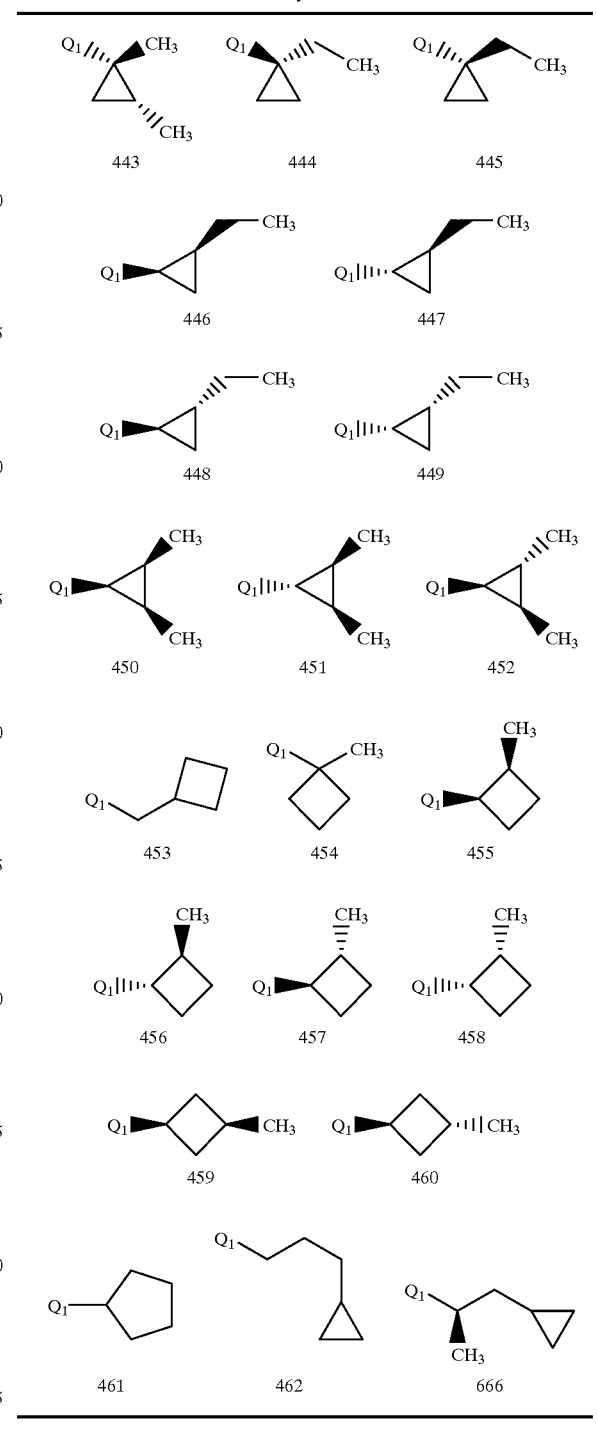
TABLE 2z
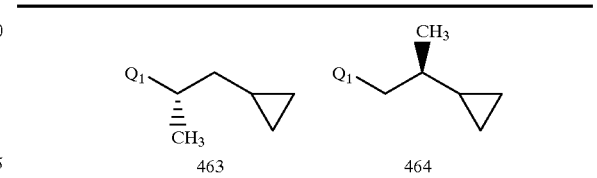

TABLE 2z-continued
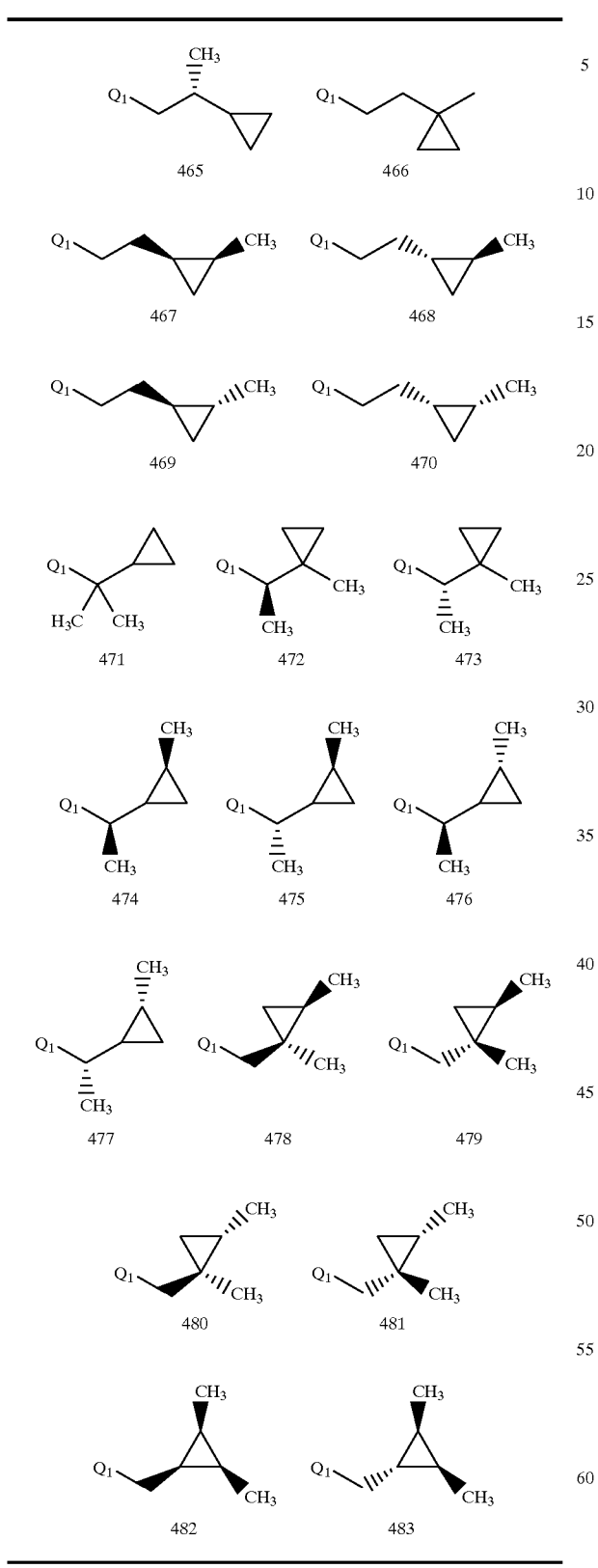
TABLE 2aa
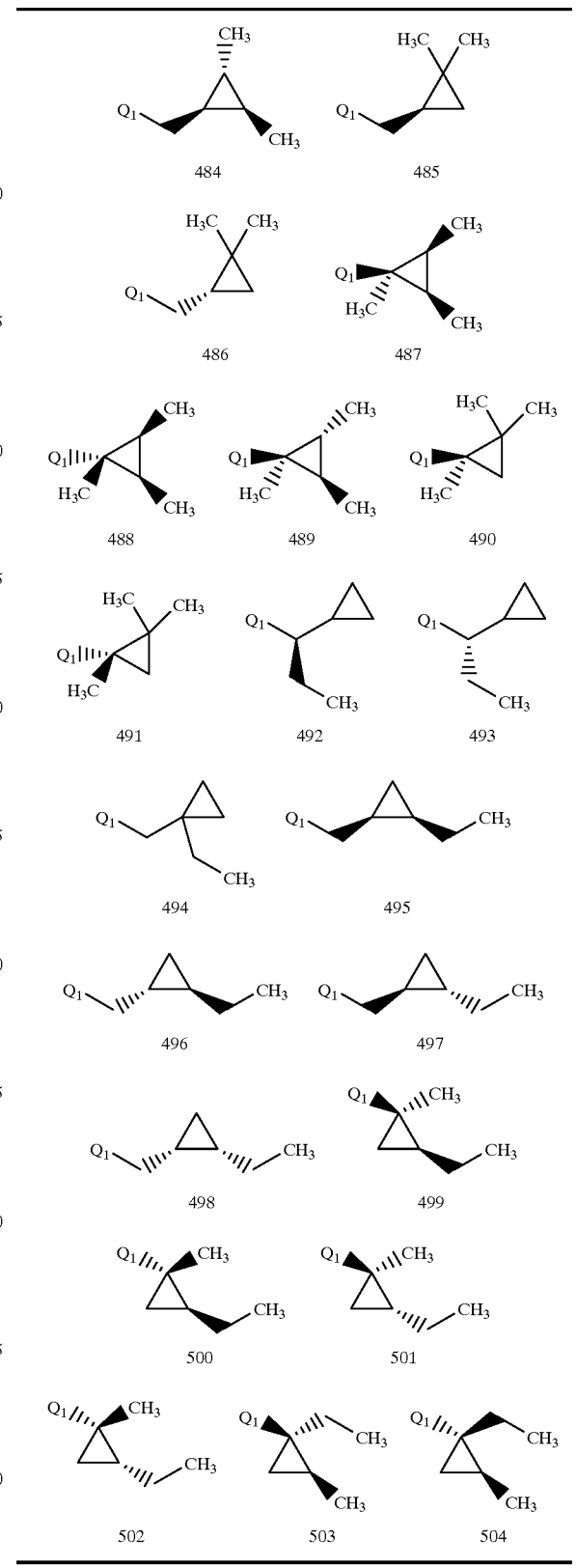

TABLE 2ab
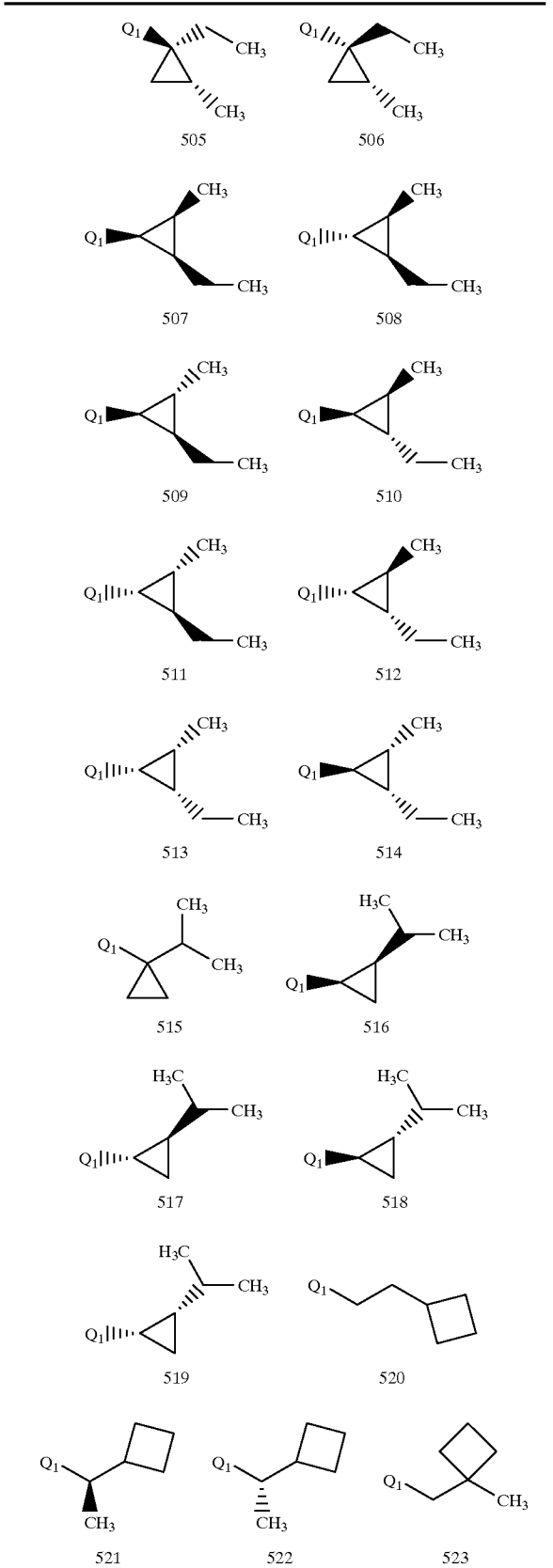
TABLE 2ab-continued
TABLE 2ac
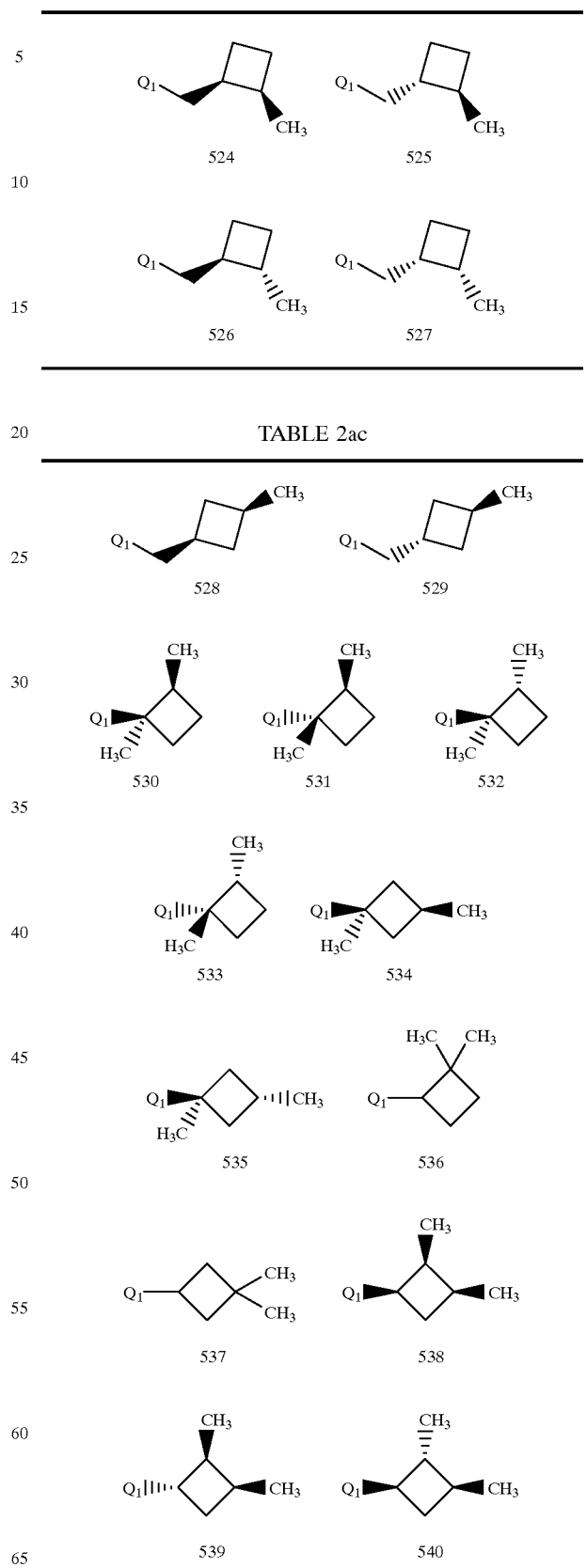

TABLE 2ac-continued 541, 542, 543, 544, 545, 546, 547, 548

TABLE 2ad 549, 550, 551, 552, 553, 554, 555, 556, 557, 558

TABLE 2ad-continued 559, 560, 561, 562, 563, 564, 565, 566, 567, 568, 569

TABLE 2ae 570, 571, 572, 573, 574, 575

TABLE 2ae-continued 576, 577, 578, 579, 580, 581, 582, 583, 584, 585, 586, 587, 588, 589, 590

TABLE 2af 591, 592, 593, 594

TABLE 2af-continued 595, 596, 597, 598, 599, 600, 601, 602, 603, 604, 605, 606, 607

TABLE 2ag 608, 609

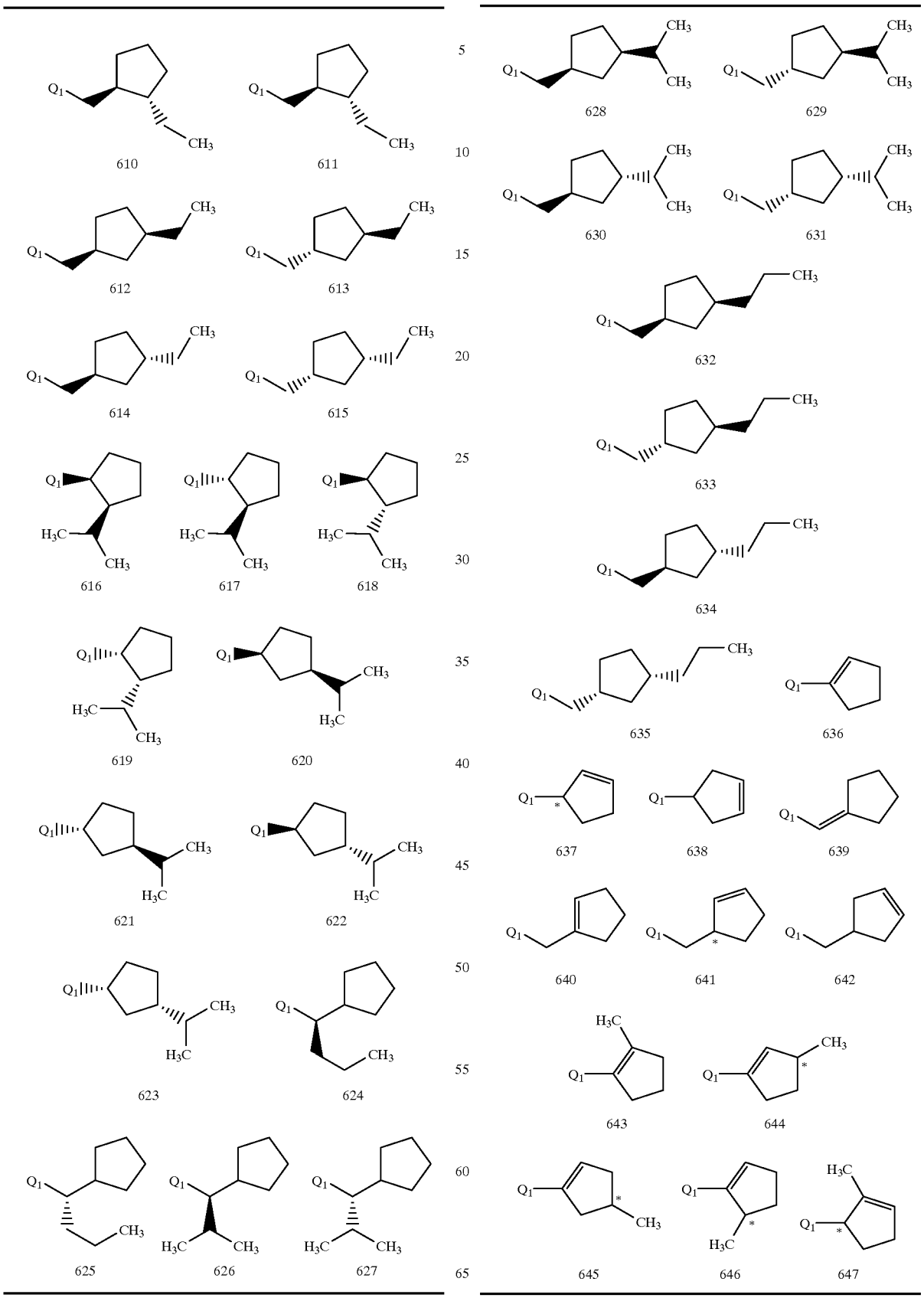

TABLE 2ai
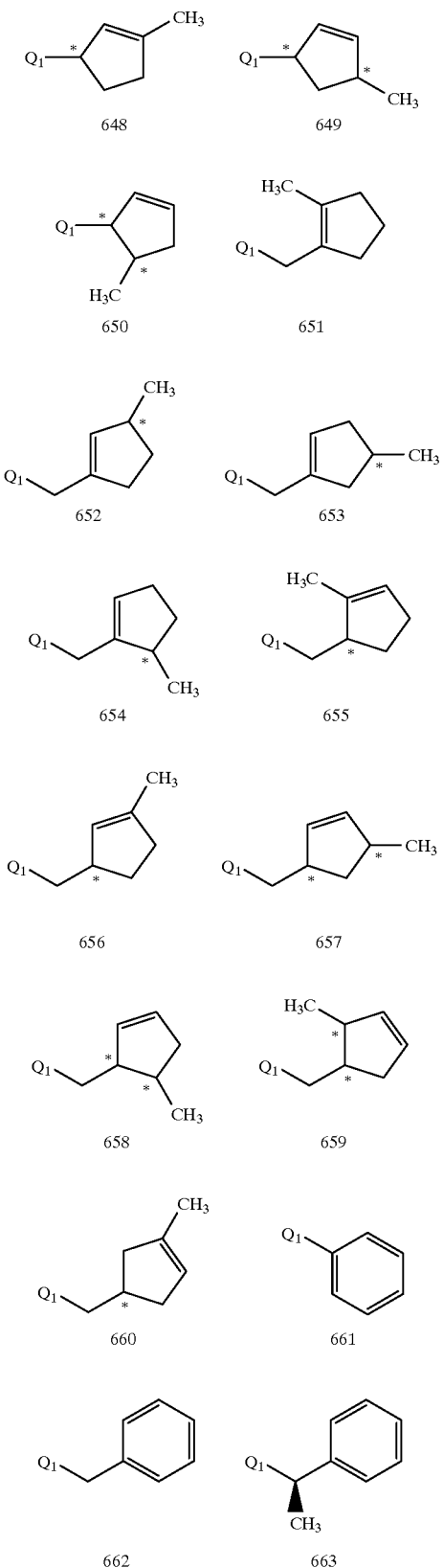
TABLE 2ai-continued
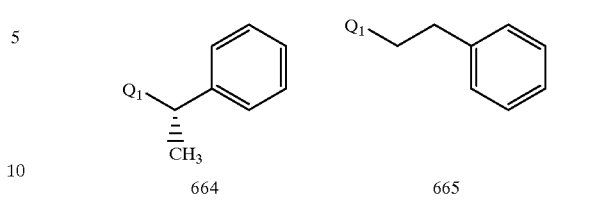
TABLE 3a
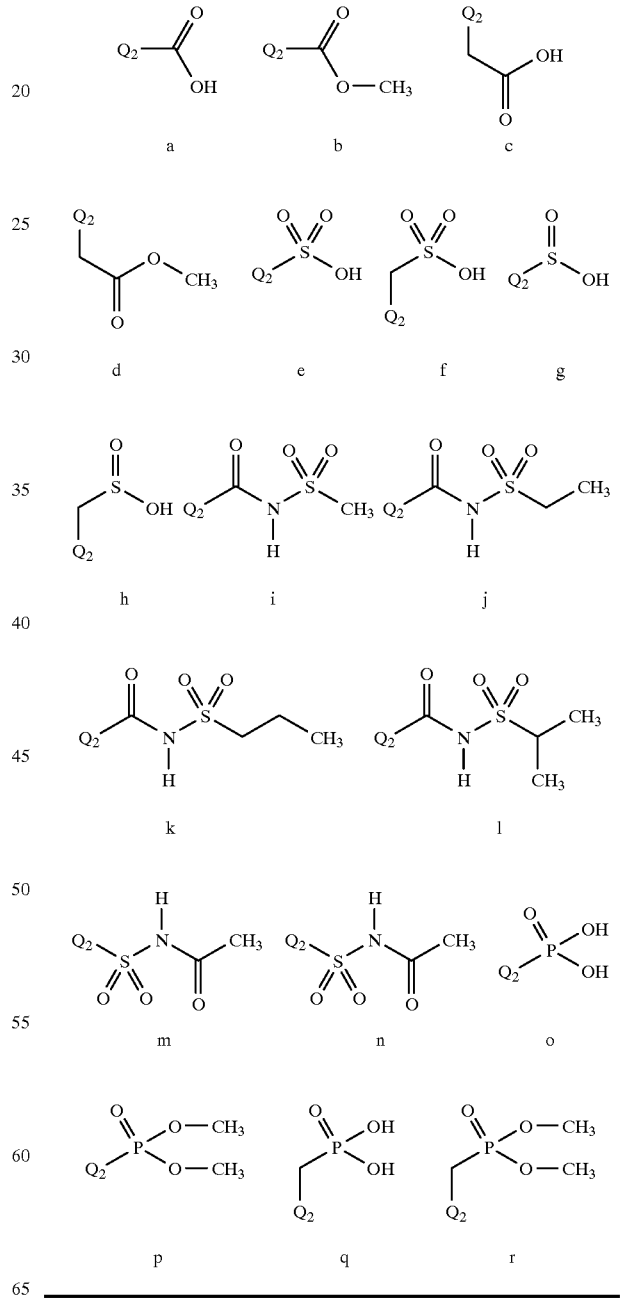

TABLE 3b
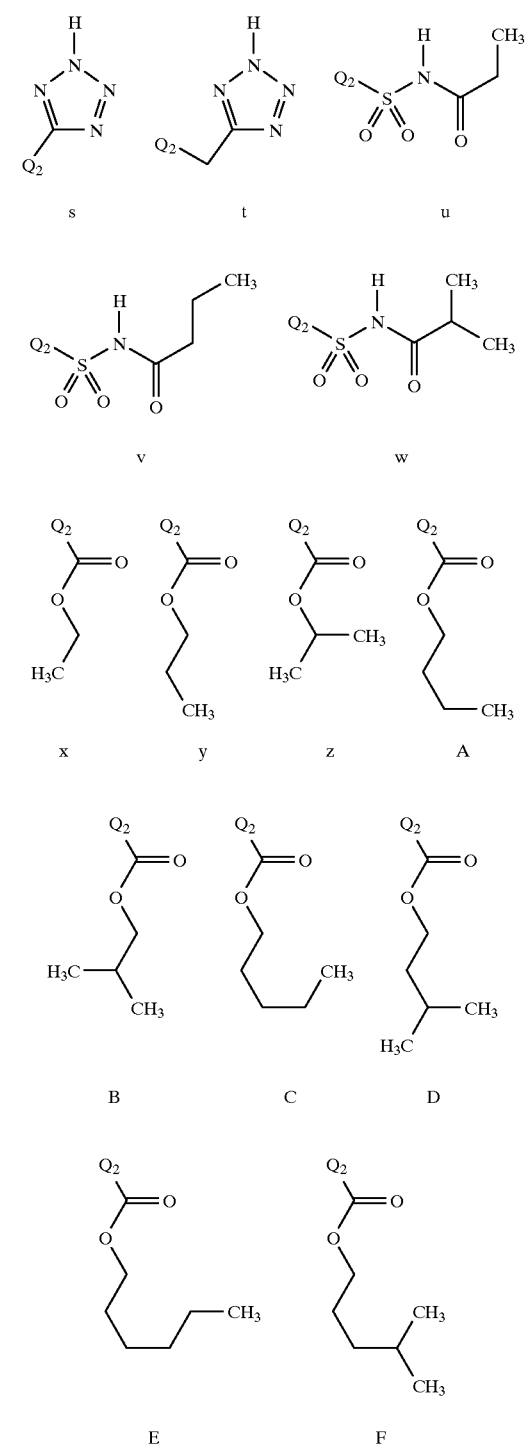
TABLE 4a-continued
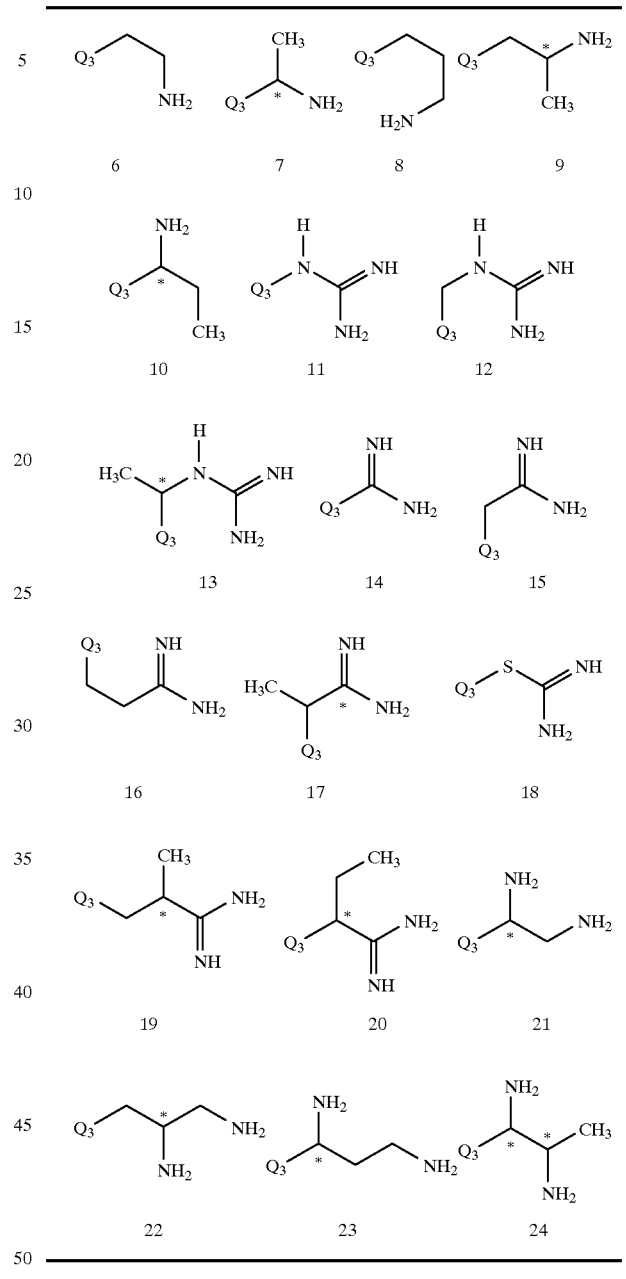
TABLE 4a
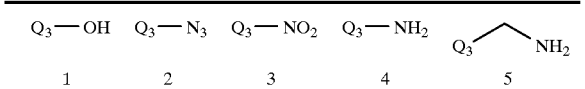
TABLE 4b
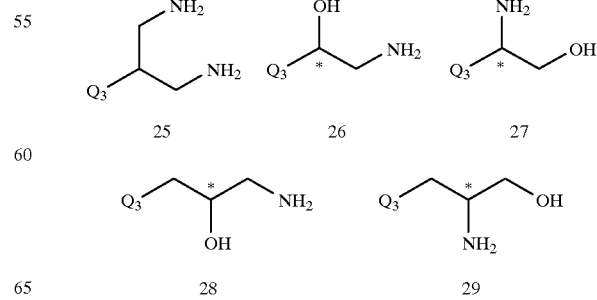

TABLE 4b-continued
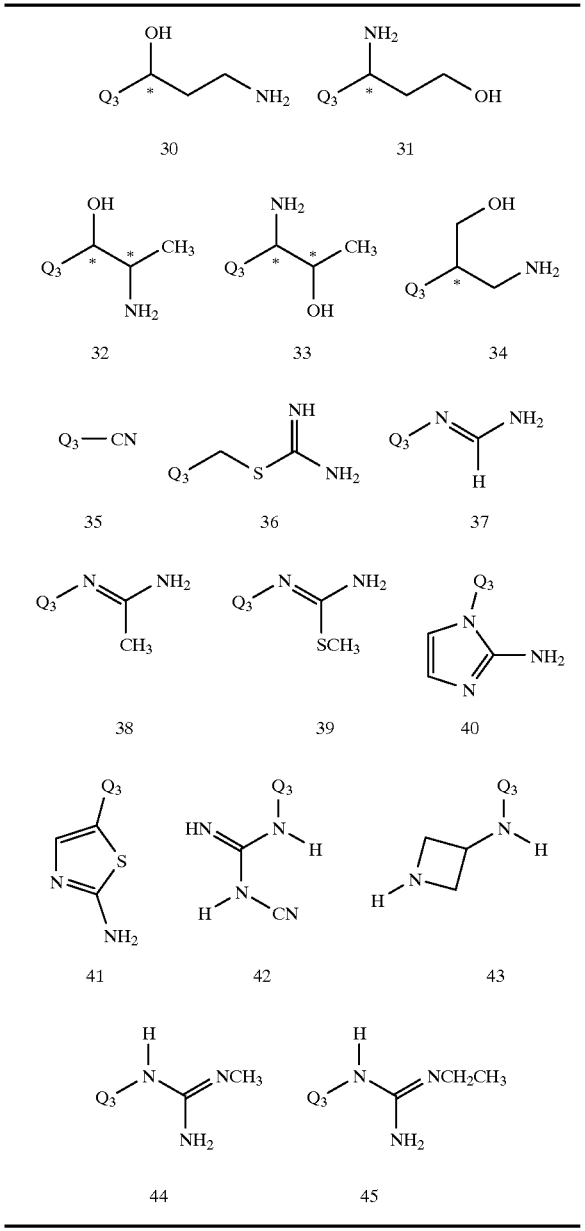
TABLE 4c
TABLE 4c-continued
TABLE 5a
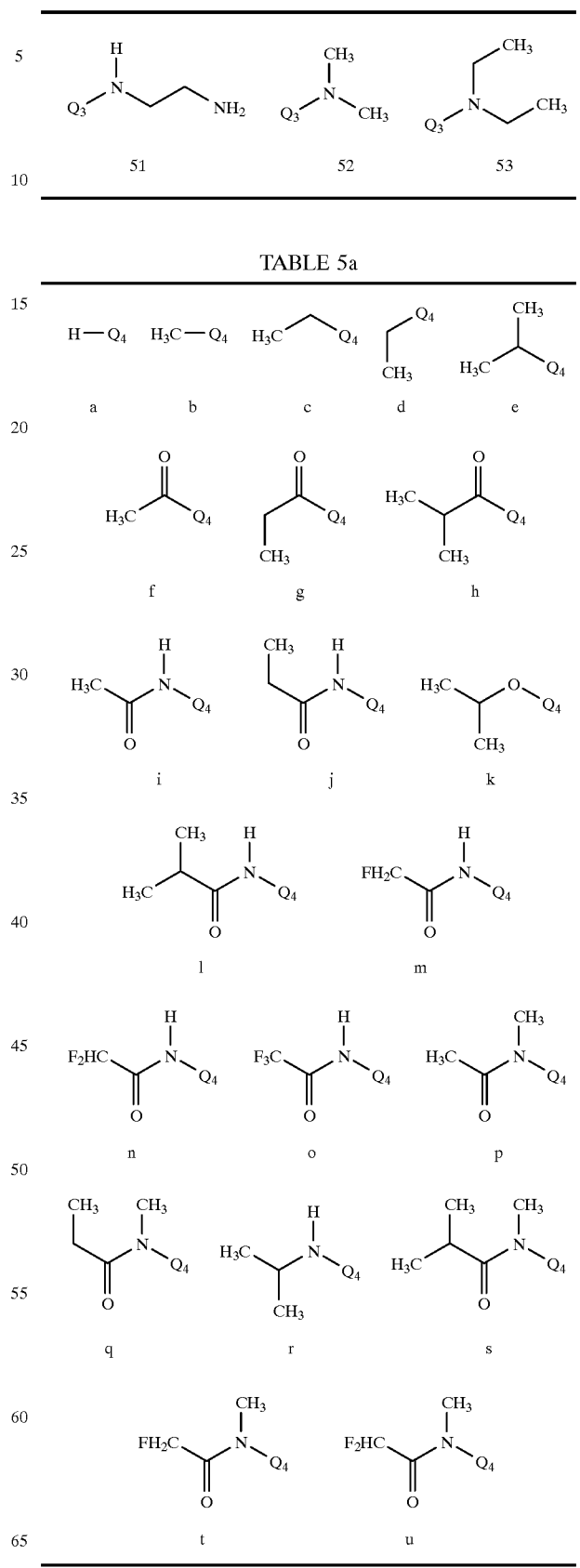

TABLE 5b
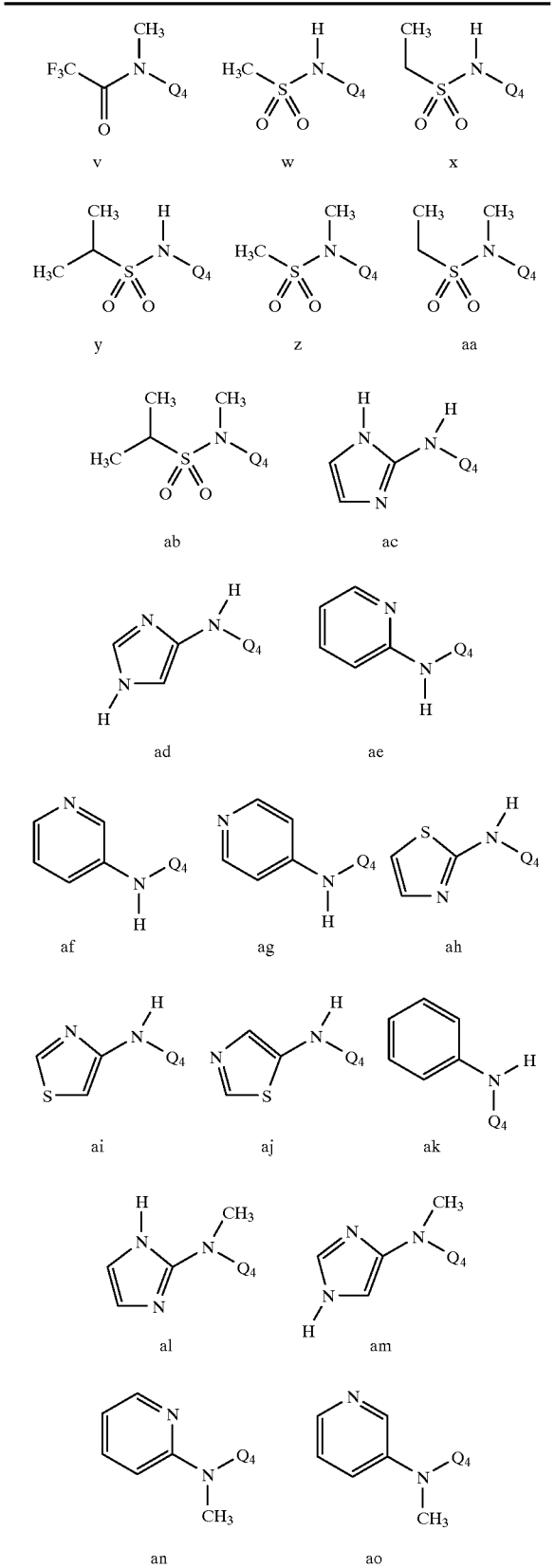
TABLE 5c
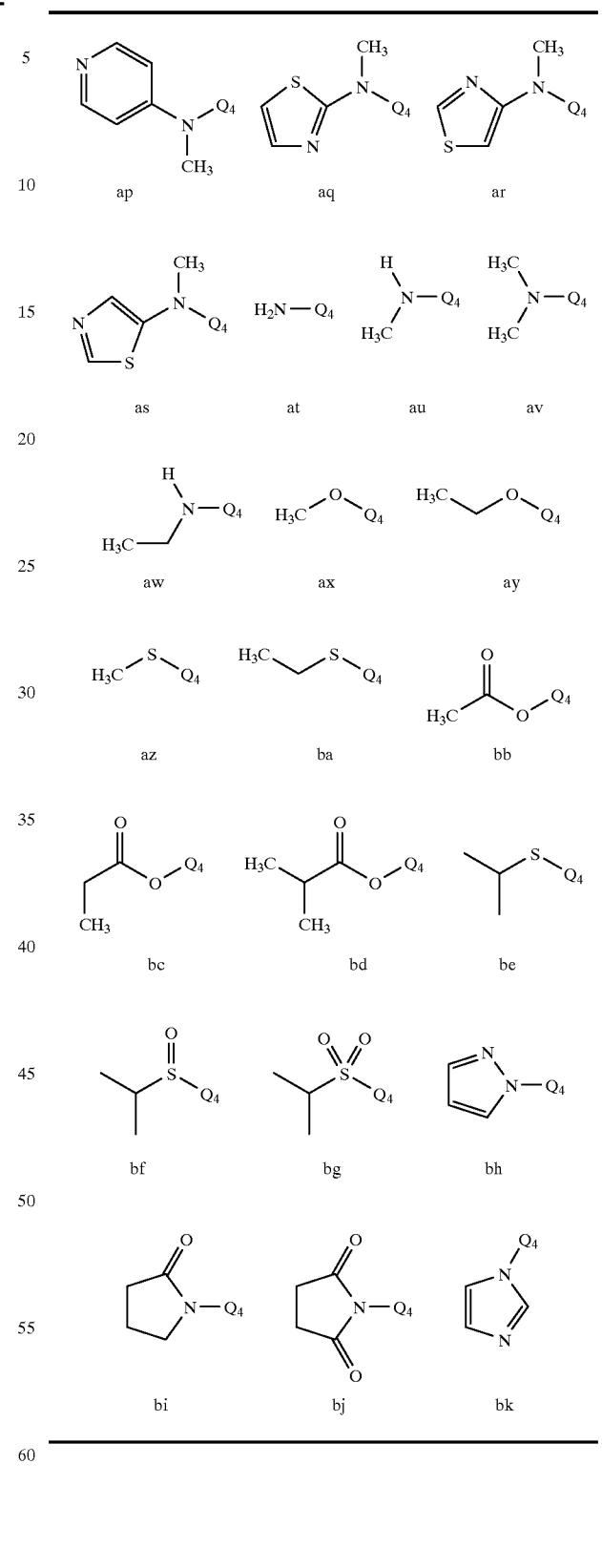

TABLE 6

Exemplary Enumerated Compounds

A.17.a.4.i; A.17.a.4.v; A.17.a.6.i; A.17.a.6.v; A.17.a.11.i; A.17.a.11.v; A.17.a.14.i;
A.17.a.14.v; A.17.a.15.i; A.17.a.15.v; A.17.a.18.i; A.17.a.18.v; A.17.a.25.i;
A.17.a.25.v; A.17.e.4.i; A.17.e.4.v; A.17.e.6.i; A.17.e.6.v; A.17.e.11.i; A.17.e.11.v;
A.17.e.14.i; A.17.e.14.v; A.17.e.15.i; A.17.e.15.v; A.17.e.18.i; A.17.e.18.v;
A.17.e.25.i; A.17.e.25.v; A.17.g.4.i; A.17.g.4.v; A.17.g.6.i; A.17.g.6.v; A.17.g.11.i;
A.17.g.11.v; A.17.g.14.i; A.17.g.14.v; A.17.g.15.i; A.17.g.15.v; A.17.g.18.i;
A.17.g.18.v; A.17.g.25.i; A.17.g.25.v; A.17.l.4.i; A.17.l.4.v; A.17.l.6.i; A.17.l.6.v;
A.17.l.11.i; A.17.l.11.v; A.17.l.14.i; A.17.l.14.v; A.17.l.15.i; A.17.l.15.v; A.17.l.18.i;
A.17.l.18.v; A.17.l.25.i; A.17.l.25.v; A.17.m.4.i; A.17.m.4.v; A.17.m.6.i;
A.17.m.6.v; A.17.m.11.i; A.17.m.11.v; A.17.m.14.i; A.17.m.14.v; A.17.m.15.i;
A.17.m.15.v; A.17.m.18.i; A.17.m.18.v; A.17.m.25.i; A.17.m.25.v; A.17.o.4.i;
A.17.o.4.v; A.17.o.6.i; A.17.o.6.v; A.17.o.11.i; A.17.o.11.v; A.17.o.14.i;
A.17.o.14.v; A.17.o.15.i; A.17.o.15.v; A.17.o.18.i; A.17.o.18.v; A.17.o.25.i;
A.17.o.25.v; A.33.a.4.i; A.33.a.4.v; A.33.a.6.i; A.33.a.6.v; A.33.a.11.i; A.33.a.11.v;
A.33.a.14.i; A.33.a.14.v; A.33.a.15.i; A.33.a.15.v; A.33.a.18.i; A.33.a.18.v;
A.33.a.25.i; A.33.a.25.v; A.33.e.4.i; A.33.e.4.v; A.33.e.6.i; A.33.e.6.v; A.33.e.11.i;
A.33.e.11.v; A.33.e.14.i; A.33.e.14.v; A.33.e.15.i; A.33.e.15.v; A.33.e.18.i;
A.33.e.18.v; A.33.e.25.i; A.33.e.25.v; A.33.g.4.i; A.33.g.4.v; A.33.g.6.i; A.33.g.6.v;
A.33.g.11.i; A.33.g.11.v; A.33.g.14.i; A.33.g.14.v; A.33.g.15.i; A.33.g.15.v;
A.33.g.18.i; A.33.g.18.v; A.33.g.25.i; A.33.g.25.v; A.33.l.4.i; A.33.l.4.v; A.33.l.6.i;
A.33.l.6.v; A.33.l.11.i; A.33.l.11.v; A.33.l.14.i; A.33.l.14.v; A.33.l.15.i; A.33.l.15.v;
A.33.l.18.i; A.33.l.18.v; A.33.l.25.i; A.33.l.25.v; A.33.m.4.i; A.33.m.4.v;
A.33.m.6.i; A.33.m.6.v; A.33.m.11.i; A.33.m.11.v; A.33.m.14.i; A.33.m.14.v;
A.33.m.15.i; A.33.m.15.v; A.33.m.18.i; A.33.m.18.v; A.33.m.25.i; A.33.m.25.v;
A.33.o.4.i; A.33.o.4.v; A.33.o.6.i; A.33.o.6.v; A.33.o.11.i; A.33.o.11.v; A.33.o.14.i;
A.33.o.14.v; A.33.o.15.i; A.33.o.15.v; A.33.o.18.i; A.33.o.18.v; A.33.o.25.i;
A.33.o.25.v; A.49.a.4.i; A.49.a.4.v; A.49.a.6.i; A.49.a.6.v; A.49.a.11.i; A.49.a.11.v;
A.49.a.14.i; A.49.a.14.v; A.49.a.15.i; A.49.a.15.v; A.49.a.18.i; A.49.a.18.v;
A.49.a.25.i; A.49.a.25.v; A.49.e.4.i; A.49.e.4.v; A.49.e.6.i; A.49.e.6.v; A.49.e.11.i;
A.49.e.11.v; A.49.e.14.i; A.49.e.14.v; A.49.e.15.i; A.49.e.15.v; A.49.e.18.i;
A.49.e.18.v; A.49.e.25.i; A.49.e.25.v; A.49.g.4.i; A.49.g.4.v; A.49.g.6.i; A.49.g.6.v;
A.49.g.11.i; A.49.g.11.v; A.49.g.14.i; A.49.g.14.v; A.49.g.15.i; A.49.g.15.v;
A.49.g.18.i; A.49.g.18.v; A.49.g.25.i; A.49.g.25.v; A.49.l.4.i; A.49.l.4.v; A.49.l.6.i;
A.49.l.6.v; A.49.l.11.i; A.49.l.11.v; A.49.l.14.i; A.49.l.14.v; A.49.l.15.i; A.49.l.15.v;
A.49.l.18.i; A.49.l.18.v; A.49.l.25.i; A.49.l.25.v; A.49.m.4.i; AA9.m.4.v;
A.49.m.6.i; A.49.m.6.v; A.49.m.11.i; A.49.m.11.v; A.49.m.14.i; A.49.m.14.v;
A.49.m.15.i; A.49.m.15.v; A.49.m.18.i; A.49.m.18.v; A.49.m.25.i; A.49.m.25.v;
A.49.o.4.i; A.49.o.4.v; A.49.o.6.i; A.49.o.6.v; A.49.o.11.i; A.49.o.11.v; A.49.o.14.i;
A.49.o.14.v; A.49.o.15.i; A.49.o.15.v; A.49.o.18.i; A.49.o.18.v; A.49.o.25.i;
A.49.o.25.v; B.17.a.4.i; B.17.a.4.v; B.17.a.6.i; B.17.a.6.v; B.17.a.11.i; B.17.a.11.v;
B.17.a.14.i; B.17.a.14.v; B.17.a.15.i; B.17.a.15.v; B.17.a.18.i; B.17.a.18.v; B.17.a.25.i;
B.17.a.25.v; B.17.e.4.i; B.17.e.4.v; B.17.e.6.i; B.17.e.6.v; B.17.e.11.i; B.17.e.11.v;
B.17.e.14.i; B.17.e.14.v; B.17.e.15.i; B.17.e.15.v; B.17.e.18.i; B.17.e.18.v; B.17.e.25.i;
B.17.e.25.v; B.17.g.4.i; B.17.g.4.v; B.17.g.6.i; B.17.g.6.v; B.17.g.11.i; B.17.g.11.v;
B.17.g.14.i; B.17.g.14.v; B.17.g.15.i; B.17.g.15.v; B.17.g.18.i; B.17.g.18.v; B.17.g.25.i;
B.17.g.25.v; B.17.l.4.i; B.17.l.4.v; B.17.l.6.i; B.17.l.6.v; B.17.l.11.i; B.17.l.11.v;
B.17.l.14.i; B.17.l.14.v; B.17.l.15.i; B.17.l.15.v; B.17.l.18.i; B.17.l.18.v; B.17.l.25.i;
B.17.l.25.v; B.17.m.4.i; B.17.m.4.v; B.17.m.6.i; B.17.m.6.v; B.17.m.11.i;
B.17.m.11.v; B.17.m.14.i; B.17.m.14.v; B.17.m.15.i; B.17.m.15.v; B.17.m.18.i;
B.17.m.18.v; B.17.m.25.i; B.17.m.25.v; B.17.o.4.i; B.17.o.4.v; B.17.o.6.i; B.17.o.6.v;
B.17.o.11.i; B.17.o.11.v; B.17.o.14.i; B.17.o.14.v; B.17.o.15.i; B.17.o.15.v;
B.17.o.18.i; B.17.o.18.v; B.17.o.25.i; B.17.o.25.v; B.33.a.4.i; B.33.a.4.v; B.33.a.6.i;
B.33.a.6.v; B.33.a.11.i; B.33.a.11.v; B.33.a.14.i; B.33.a.14.v; B.33.a.15.i; B.33.a.15.v;
B.33.a.18.i; B.33.a.18.v; B.33.a.25.i; B.33.a.25.v; B.33.e.4.i; B.33.e.4.v; B.33.e.6.i;
B.33.e.6.v; B.33.e.11.i; B.33.e.11.v; B.33.e.14.i; B.33.e.14.v; B.33.e.15.i; B.33.e.15.v;
B.33.e.18.i; B.33.e.18.v; B.33.e.25.i; B.33.e.25.v; B.33.g.4.i; B.33.g.4.v; B.33.g.6.i;
B.33.g.6.v; B.33.g.11.i; B.33.g.11.v; B.33.g.14.i; B.33.g.14.v; B.33.g.15.i; B.33.g.15.v;
B.33.g.18.i; B.33.g.18.v; B.33.g.25.i; B.33.g.25.v; B.33.l.4.i; B.33.l.4.v; B.33.l.6.i;
B.33.l.6.v; B.33.l.11.i; B.33.l.11.v; B.33.l.14.i; B.33.l.14.v; B.33.l.15.i; B.33.l.15.v;
B.33.l.18.i; B.33.l.18.v; B.33.l.25.i; B.33.l.25.v; B.33.m.4.i; B.33.m.4.v; B.33.m.6.i;
B.33.m.6.v; B.33.m.11.i; B.33.m.11.v; B.33.m.14.i; B.33.m.14.v; B.33.m.15.i;
B.33.m.15.v; B.33.m.18.i; B.33.m.18.v; B.33.m.25.i; B.33.m.25.v; B.33.o.4.i;
B.33.o.4.v; B.33.o.6.i; B.33.o.6.v; B.33.o.11.i; B.33.o.11.v; B.33.o.14.i; B.33.o.14.v;
B.33.o.15.i; B.33.o.15.v; B.33.o.18.i; B.33.o.18.v; B.33.o.25.i; B.33.o.25.v; B.49.a.4.i;
B.49.a.4.v; B.49.a.6.i; B.49.a.6.v; B.49.a.11.i; B.49.a.11.v; B.49.a.14.i; B.49.a.14.v;
B.49.a.15.i; B.49.a.15.v; B.49.a.18.i; B.49.a.18.v; B.49.a.25.i; B.49.a.25.v; B.49.e.4.i;
B.49.e.4.v; B.49.e.6.i; B.49.e.6.v; B.49.e.11.i; B.49.e.11.v; B.49.e.14.i; B.49.e.14.v;
B.49.e.15.i; B.49.e.15.v; B.49.e.18.i; B.49.e.18.v; B.49.e.25.i; B.49.e.25.v; B.49.g.4.i;
B.49.g.4.v; B.49.g.6.i; B.49.g.6.v; B.49.g.11.i; B.49.g.11.v; B.49.g.14.i; B.49.g.14.v;
B.49.g.15.i; B.49.g.15.v; B.49.g.18.i; B.49.g.18.v; B.49.g.25.i; B.49.g.25.v; B.49.l.4.i;
B.49.l.4.v; B.49.l.6.i; B.49.l.6.v; B.49.l.11.i; B.49.l.11.v; B.49.l.14.i; B.49.l.14.v;
B.49.l.15.i; B.49.l.15.v; B.49.l.18.i; B.49.l.18.v; B.49.l.25.i; B.49.l.25.v; B.49.m.4.i;
B.49.m.4.v; B.49.m.6.i; B.49.m.6.v; B.49.m.11.i; B.49.m.11.v; B.49.m.14.i;
B.49.m.14.v; B.49.m.15.i; B.49.m.15.v; B.49.m.18.i; B.49.m.18.v; B.49.m.25.i;
B.49.m.25.v; B.49.o.4.i; B.49.o.4.v; B.49.o.6.i; B.49.o.6.v; B.49.o.11.i; B.49.o.11.v;
B.49.o.14.i; B.49.o.14.v; B.49.o.15.i; B.49.o.15.v; B.49.o.18.i; B.49.o.18.v;
B.49.o.25.i; B.49.o.25.v; E.17.a.4.i; E.17.a.4.v; E.17.a.6.i; E.17.a.6.v; E.17.a.11.i;

TABLE 6-continued

Exemplary Enumerated Compounds

E.17.a.11.v; E.17.a.14.i; E.17.a.14.v; E.17.a.15.i; E.17.a.15.v; E.17.a.18.i; E.17.a.18.v;
E.17.a.25.i; E.17.a.25.v; E.17.e.4.i; E.17.e.4.v; E.17.e.6.i; E.17.e.6.v; E.17.e.11.i;
E.17.e.11.v; E.17.e.14.i; E.17.e.14.v; E.17.e.15.i; E.17.e.15.v; E.17.e.18.i; E.17.e.18.v;
E.17.e.25.i; E.17.e.25.v; E.17.g.4.i; E.17.g.4.v; E.17.g.6.i; E.17.g.6.v; E.17.g.11.i;
E.17.g.11.v; E.17.g.14.i; E.17.g.14.v; E.17.g.15.i; E.17.g.15.v; E.17.g.18.i; E.17.g.18.v;
E.17.g.25.i; E.17.g.25.v; E.17.l.4.i; E.17.l.4.v; E.17.l.6.i; E.17.l.6.v; E.17.l.11.i;
E.17.l.11.v; E.17.l.14.i; E.17.l.14.v; E.17.l.15.i; E.17.l.15.v; E.17.l.18.i; E.17.l.18.v;
E.17.l.25.i; E.17.l.25.v; E.17.m.4.i; E.17.m.4.v; E.17.m.6.i; E.17.m.6.v; E.17.m.11.i;
E.17.m.11.v; E.17.m.14.i; E.17.m.14.v; E.17.m.15.i; E.17.m.15.v; E.17.m.18.i;
E.17.m.18.v; E.17.m.25.i; E.17.m.25.v; E.17.o.4.i; E.17.o.4.v; E.17.o.6.i; E.17.o.6.v;
E.17.o.11.i; E.17.o.11.v; E.17.o.14.i; E.17.o.14.v; E.17.o.15.i; E.17.o.15.v; E.17.o.18.i;
E.17.o.18.v; E.17.o.25.i; E.17.o.25.v; E.33.a.4.i; E.33.a.4.v; E.33.a.6.i; E.33.a.6.v;
E.33.a.11.i; E.33.a.11.v; E.33.a.14.i; E.33.a.14.v; E.33.a.15.i; E.33.a.15.v; E.33.a.18.i;
E.33.a.18.v; E.33.a.25.i; E.33.a.25.v; E.33.e.4.i; E.33.e.4.v; E.33.e.6.i; E.33.e.6.v;
E.33.e.11.i; E.33.e.11.v; E.33.e.14.i; E.33.e.14.v; E.33.e.15.i; E.33.e.15.v; E.33.e.18.i;
E.33.e.18.v; E.33.e.25.i; E.33.e.25.v; E.33.g.4.i; E.33.g.4.v; E.33.g.6.i; E.33.g.6.v;
E.33.g.11.i; E.33.g.11.v; E.33.g.14.i; E.33.g.14.v; E.33.g.15.i; E.33.g.15.v; E.33.g.18.i;
E.33.g.18.v; E.33.g.25.i; E.33.g.25.v; E.33.l.4.i; E.33.l.4.v; E.33.l.6.i; E.33.l.6.v;
E.33.l.11.i; E.33.l.11.v; E.33.l.14.i; E.33.l.14.v; E.33.l.15.i; E.33.l.15.v; E.33.l.18.i;
E.33.l.18.v; E.33.l.25.i; E.33.l.25.v; E.33.m.4.i; E.33.m.4.v; E.33.m.6.i; E.33.m.6.v;
E.33.m.11.i; E.33.m.11.v; E.33.m.14.i; E.33.m.14.v; E.33.m.15.i; E.33.m.15.v;
E.33.m.18.i; E.33.m.18.v; E.33.m.25.i; E.33.m.25.v; E.33.o.4.i; E.33.o.4.v; E.33.o.6.i;
E.33.o.6.v; E.33.o.11.i; E.33.o.11.v; E.33.o.14.i; E.33.o.14.v; E.33.o.15.i; E.33.o.15.v;
E.33.o.18.i; E.33.o.18.v; E.33.o.25.i; E.33.o.25.v; E.49.a.4.i; E.49.a.4.v; E.49.a.6.i;
E.49.a.6.v; E.49.a.11.i; E.49.a.11.v; E.49.a.14.i; E.49.a.14.v; E.49.a.15.i; E.49.a.15.v;
E.49.a.18.i; E.49.a.18.v; E.49.a.25.i; E.49.a.25.v; E.49.e.4.i; E.49.e.4.v; E.49.e.6.i;
E.49.e.6.v; E.49.e.11.i; E.49.e.11.v; E.49.e.14.i; E.49.e.14.v; E.49.e.15.i; E.49.e.15.v;
E.49.e.18.i; E.49.e.18.v; E.49.e.25.i; E.49.e.25.v; E.49.g.4.i; E.49.g.4.v; E.49.g.6.i,
E.49.g.6.v; E.49.g.11.i; E.49.g.11.v; E.49.g.14.i; E.49.g.14.v; E.49.g.15.i; E.49.g.15.v;
E.49.g.18.i; E.49.g.18.v; E.49.g.25.i; E.49.g.25.v; E.49.l.4.i; E.49.l.4.v; E.49.l.6.i;
E.49.l.6.v; E.49.l.11.i; E.49.l.11.v; E.49.l.14.i; E.49.l.14.v; E.49.l.15.i; E.49.l.15.v;
E.49.l.18.i; E.49.l.18.v; E.49.l.25.i; E.49.l.25.v; E.49.m.4.i; E.49.m.4.v; E.49.m.6.i;
E.49.m.6.v; E.49.m.11.i; E.49.m.11.v; E.49.m.14.i; E.49.m.14.v; E.49.m.15.i;
E.49.m.15.v; E.49.m.18.i; E.49.m.18.v; E.49.m.25.i; E.49.m.25.v; E.49.o.4.i;
E.49.o.4.v; E.49.o.6.i; E.49.o.6.v; E.49.o.11.i; E.49.o.11.v; E.49.o.14.i; E.49.o.14.v;
E.49.o.15.i; E.49.o.15.v; E.49.o.18.i; E.49.o.18.v; E.49.o.25.i; E.49.o.25.v; H.17.a.4.i;
H.17.a.4.v; H.17.a.6.i; H.17.a.6.v; H.17.a.11.i; H.17.a.11.v; H.17.a.14.i; H.17.a.14.v;
H.17.a.15.i; H.17.a.15.v; H.17.a.18.i; H.17.a.18.v; H.17.a.25.i; H.17.a.25.v;
H.17.e.4.i; H.17.e.4.v; H.17.e.6.i; H.17.e.6.v; H.17.e.11.i; H.17.e.11.v; H.17.e.14.i;
H.17.e.14.v; H.17.e.15.i; H.17.e.15.v; H.17.e.18.i; H.17.e.18.v; H.17.e.25.i;
H.17.e.25.v; H.17.g.4.i; H.17.g.4.v; H.17.g.6.i; H.17.g.6.v; H.17.g.11.i; H.17.g.11.v;
H.17.g.14.i; H.17.g.14.v; H.17.g.15.i; H.17.g.15.v; H.17.g.18.i; H.17.g.18.v;
H.17.g.25.i; H.17.g.25.v; H.17.l.4.i; H.17.l.4.v; H.17.l.6.i; H.17.l.6.v; H.17.l.11.i;
H.17.l.11.v; H.17.l.14.i; H.17.l.14.v; H.17.l.15.i; H.17.l.15.v; H.17.l.18.i; H.17.l.18.v;
H.17.l.25.i; H.17.l.25.v; H.17.m.4.i; H.17.m.4.v; H.17.m.6.i; H.17.m.6.v;
H.17.m.11.i; H.17.m.11.v; H.17.m.14.i; H.17.m.14.v; H.17.m.15.i; H.17.m.15.v;
H.17.m.18.i; H.17.m.18.v; H.17.m.25.i; H.17.m.25.v; H.17.o.4.i; H.17.o.4.v;
H.17.o.6.i; H.17.o.6.v; H.17.o.11.i; H.17.o.11.v; H.17.o.14.i; H.17.o.14.v;
H.17.o.15.i; H.17.o.15.v; H.17.o.18.i; H.17.o.18.v; H.17.o.25.i; H.17.o.25.v;
H.33.a.4.i; H.33.a.4.v; H.33.a.6.i; H.33.a.6.v; H.33.a.11.i; H.33.a.11.v; H.33.a.14.i;
H.33.a.14.v; H.33.a.15.i; H.33.a.15.v; H.33.a.18.i; H.33.a.18.v; H.33.a.25.i;
H.33.a.25.v; H.33.e.4.i; H.33.e.4.v; H.33.e.6.i; H.33.e.6.v; H.33.e.11.i; H.33.e.11.v;
H.33.e.14.i; H.33.e.14.v; H.33.e.15.i; H.33.e.15.v; H.33.e.18.i; H.33.e.18.v;
H.33.e.25.i; H.33.e.25.v; H.33.g.4.i; H.33.g.4.v; H.33.g.6.i; H.33.g.6.v; H.33.g.11.i;
H.33.g.11.v; H.33.g.14.i; H.33.g.14.v; H.33.g.15.i; H.33.g.15.v; H.33.g.18.i;
H.33.g.18.v; H.33.g.25.i; H.33.g.25.v; H.33.l.4.i; H.33.l.4.v; H.33.l.6.i; H.33.l.6.v;
H.33.l.11.i; H.33.l.11.v; H.33.l.14.i; H.33.l.14.v; H.33.l.15.i; H.33.l.15.v; H.33.l.18.i;
H.33.l.18.v; H.33.l.25.i; H.33.l.25.v; H.33.m.4.i; H.33.m.4.v; H.33.m.6.i;
H.33.m.6.v; H.33.m.11.i; H.33.m.11.v; H.33.m.14.i; H.33.m.14.v; H.33.m.15.i;
H.33.m.15.v; H.33.m.18.i; H.33.m.18.v; H.33.m.25.i; H.33.m.25.v; H.33.o.4.i;
H.33.o.4.v; H.33.o.6.i; H.33.o.6.v; H.33.o.11.i; H.33.o.11.v; H.33.o.14.i;
H.33.o.14.v; H.33.o.15.i; H.33.o.15.v; H.33.o.18.i; H.33.o.18.v; H.33.o.25.i;
H.33.o.25.v; H.49.a.4.i; H.49.a.4.v; H.49.a.6.i; H.49.a.6.v; H.49.a.11.i; H.49.a.11.v;
H.49.a.14.i; H.49.a.14.v; H.49.a.15.i; H.49.a.15.v; H.49.a.18.i; H.49.a.18.v;
H.49.a.25.i; H.49.a.25.v; H.49.e.4.i; H.49.e.4.v; H.49.e.6.i; H.49.e.6.v; H.49.e.11.i;
H.49.e.11.v; H.49.e.14.i; H.49.e.14.v; H.49.e.15.i; H.49.e.15.v; H.49.e.18.i;
H.49.e.18.v; H.49.e.25.i; H.49.e.25.v; H.49.g.4.i; H.49.g.4.v; H.49.g.6.i; H.49.g.6.v;
H.49.g.11.i; H.49.g.11.v; H.49.g.14.i; H.49.g.14.v; H.49.g.15.i; H.49.g.15.v;
H.49.g.18.i; H.49.g.18.v; H.49.g.25.i; H.49.g.25.v; H.49.l.4.i; H.49.l.4.v; H.49.l.6.i;
H.49.l.6.v; H.49.l.11.i; H.49.l.11.v; H.49.l.14.i; H.49.l.14.v; H.49.l.15.i; H.49.l.15.v;
H.49.l.18.i; H.49.l.18.v; H.49.l.25.i; H.49.l.25.v; H.49.m.4.i; H.49.m.4.v;
H.49.m.6.i; H.49.m.6.v; H.49.m.11.i; H.49.m.11.v; H.49.m.14.i; H.49.m.14.v;
H.49.m.15.i; H.49.m.15.v; H.49.m.18.i; H.49.m.18.v; H.49.m.25.i; H.49.m.25.v;
H.49.o.4.i; H.49.o.4.v; H.49.o.6.i; H.49.o.6.v; H.49.o.11.i; H.49.o.11.v; H.49.o.14.i;
H.49.o.14.v; H.49.o.15.i; H.49.o.15.v; H.49.o.18.i; H.49.o.18.v; H.49.o.25.i;
H.49.o.25.v; I.17.a.4.i; I.17.a.4.v; I.17.a.6.i; I.17.a.6.v; I.17.a.11.i; I.17.a.11.v;
I.17.a.14.i; I.17.a.14.v; I.17.a.15.i; I.17.a.15.v; I.17.a.18.i; I.17.a.18.v; I.17.a.25.i;

TABLE 6-continued

Exemplary Enumerated Compounds

I.17.a.25.v; I.17.e.4.i; I.17.e.4.v; I.17.e.6.i; I.17.e.6.v; I.17.e.11.i; I.17.e.11.v;
I.17.e.14.i; I.17.e.14.v; I.17.e.15.i; I.17.e.15.v; I.17.e.18.i; I.17.e.18.v; I.17.e.25.i;
I.17.e.25.v; I.17.g.4.i; I.17.g.4.v; I.17.g.6.i; I.17.g.6.v; I.17.g.11.i; I.17.g.11.v;
I.17.g.14.i; I.17.g.14.v; I.17.g.15.i; I.17.g.15.v; I.17.g.18.i; I.17.g.18.v; I.17.g.25.i;
I.17.g.25.v; I.17.l.4.i; I.17.l.4.v; I.17.l.6.i; I.17.l.6.v; I.17.l.11.i; I.17.l.11.v; I.17.l.14.i;
I.17.l.14.v; I.17.l.15.i; I.17.l.15.v; I.17.l.18.i; I.17.l.18.v; I.17.l.25.i; I.17.l.25.v;
I.17.m.4.i; I.17.m.4.v; I.17.m.6.i; I.17.m.6.v; I.17.m.11.i; I.17.m.11.v; I.17.m.14.i;
I.17.m.14.v; I.17.m.15.i; I.17.m.15.v; I.17.m.18.i; I.17.m.18.v; I.17.m.25.i;
I.17.m.25.v; I.17.o.4.i; I.17.o.4.v; I.17.o.6.i; I.17.o.6.v; I.17.o.11.i; I.17.o.11.v;
I.17.o.14.i; I.17.o.14.v; I.17.o.15.i; I.17.o.15.v; I.17.o.18.i; I.17.o.18.v; I.17.o.25.i;
I.17.o.25.v; I.33.a.4.i; I.33.a.4.v; I.33.a.6.i; I.33.a.6.v; I.33.a.11.i; I.33.a.11.v;
I.33.a.14.i; I.33.a.14.v; I.33.a.15.i; I.33.a.15.v; I.33.a.18.i; I.33.a.18.v; I.33.a.25.i;
I.33.a.25.v; I.33.e.4.i; I.33.e.4.v; I.33.e.6.i; I.33.e.6.v; I.33.e.11.i; I.33.e.11.v;
I.33.e.14.i; I.33.e.14.v; I.33.e.15.i; I.33.e.15.v; I.33.e.18.i; I.33.e.18.v; I.33.e.25.i;
I.33.e.25.v; I.33.g.4.i; I.33.g.4.v; I.33.g.6.i; I.33.g.6.v; I.33.g.11.i; I.33.g.11.v;
I.33.g.14.i; I.33.g.14.v; I.33.g.15.i; I.33.g.15.v; I.33.g.18.i; I.33.g.18.v; I.33.g.25.i;
I.33.g.25.v; I.33.l.4.i; I.33.l.4.v; I.33.l.6.i; I.33.l.6.v; I.33.l.11.i; I.33.l.11.v; I.33.l.14.i;
I.33.l.14.v; I.33.l.15.i; I.33.l.15.v; I.33.l.18.i; I.33.l.18.v; I.33.l.25.i; I.33.l.25.v;
I.33.m.4.i; I.33.m.4.v; I.33.m.6.i; I.33.m.6.v; I.33.m.11.i; I.33.m.11.v; I.33.m.14.i;
I.33.m.14.v; I.33.m.15.i; I.33.m.15.v; I.33.m.18.i; I.33.m.18.v; I.33.m.25.i;
I.33.m.25.v; I.33.o.4.i; I.33.o.4.v; I.33.o.6.i; I.33.o.6.v; I.33.o.11.i; I.33.o.11.v;
I.33.o.14.i; I.33.o.14.v; I.33.o.15.i; I.33.o.15.v; I.33.o.18.i; I.33.o.18.v; I.33.o.25.i;
I.33.o.25.v; I.49.a.4.i; I.49.a.4.v; I.49.a.6.i; I.49.a.6.v; I.49.a.11.i; I.49.a.11.v;
I.49.a.14.i; I.49.a.14.v; I.49.a.15.i; I.49.a.15.v; I.49.a.18.i; I.49.a.18.v; I.49.a.25.i;
I.49.a.25.v; I.49.e.4.i; I.49.e.4.v; I.49.e.6.i; I.49.e.6.v; I.49.e.11.i; I.49.e.11.v;
I.49.e.14.i; I.49.e.14.v; I.49.e.15.i; I.49.e.15.v; I.49.e.18.i; I.49.e.18.v; I.49.e.25.i;
I.49.e.25.v; I.49.g.4.i; I.49.g.4.v; I.49.g.6.i; I.49.g.6.v; I.49.g.11.i; I.49.g.11.v;
I.49.g.14.i; I.49.g.14.v; I.49.g.15.i; I.49.g.15.v; I.49.g.18.i; I.49.g.18.v; I.49.g.25.i;
I.49.g.25.v; I.49.l.4.i; I.49.l.4.v; I.49.l.6.i; I.49.l.6.v; I.49.l.11.i; I.49.l.11.v; I.49.l.14.i;
I.49.l.14.v; I.49.l.15.i; I.49.l.15.v; I.49.l.18.i; I.49.l.18.v; I.49.l.25.i; I.49.l.25.v;
I.49.m.4.i; I.49.m.4.v; I.49.m.6.i; I.49.m.6.v; I.49.m.11.i; I.49.m.11.v; I.49.m.14.i;
I.49.m.14.v; I.49.m.15.i; I.49.m.15.v; I.49.m.18.i; I.49.m.18.v; I.49.m.25.i;
I.49.m.25.v; I.49.o.4.i; I.49.o.4.v; I.49.o.6.i; I.49.o.6.v; I.49.o.11.i; I.49.o.11.v;
I.49.o.14.i; I.49.o.14.v; I.49.o.15.i; I.49.o.15.v; I.49.o.18.i; I.49.o.18.v; I.49.o.25.i;
I.49.o.25.v; L.17.a.4.i; L.17.a.4.v; L.17.a.6.i; L.17.a.6.v; L.17.a.11.i; L.17.a.11.v;
L.17.a.14.i; L.17.a.14.v; L.17.a.15.i; L.17.a.15.v; L.17.a.18.i; L.17.a.18.v; L.17.a.25.i;
L.17.a.25.v; L.17.e.4.i; L.17.e.4.v; L.17.e.6.i; L.17.e.6.v; L.17.e.11.i; L.17.e.11.v;
L.17.e.14.i; L.17.e.14.v; L.17.e.15.i; L.17.e.15.v; L.17.e.18.i; L.17.e.18.v; L.17.e.25.i;
L.17.e.25.v; L.17.g.4.i; L.17.g.4.v; L.17.g.6.i; L.17.g.6.v; L.17.g.11.i; L.17.g.11.v;
L.17.g.14.i; L.17.g.14.v; L.17.g.15.i; L.17.g.15.v; L.17.g.18.i; L.17.g.18.v; L.17.g.25.i;
L.17.g.25.v; L.17.l.4.i; L.17.l.4.v; L.17.l.6.i; L.17.l.6.v; L.17.l.11.i; L.17.l.11.v;
L.17.l.14.v; L.17.l.15.i; L.17.l.15.v; L.17.l.18.i; L.17.l.18.v; L.17.l.25.i; L.17.l.25.v;
L.17.l.25.v; L.17.m.4.i; L.17.m.4.v; L.17.m.6.i; L.17.m.6.v; L.17.m.11.i;
L.17.m.11.v; L.17.m.14.i; L.17.m.14.v; L.17.m.15.i; L.17.m.15.v; L.17.m.18.i;
L.17.m.18.v; L.17.m.25.i; L.17.m.25.v; L.17.o.4.i; L.17.o.4.v; L.17.o.6.i; L.17.o.6.v;
L.17.o.11.i; L.17.o.11.v; L.17.o.14.i; L.17.o.14.v; L.17.o.15.i; L.17.o.15.v; L.17.o.18.i;
L.17.o.18.v; L.17.o.25.i; L.17.o.25.v; L.33.a.4.i; L.33.a.4.v; L.33.a.6.i; L.33.a.6.v;
L.33.a.11.i; L.33.a.11.v; L.33.a.14.i; L.33.a.14.v; L.33.a.15.i; L.33.a.15.v; L.33.a.18.i;
L.33.a.18.v; L.33.a.25.i; L.33.a.25.v; L.33.e.4.i; L.33.e.4.v; L.33.e.6.i; L.33.e.6.v;
L.33.e.11.i; L.33.e.11.v; L.33.e.14.i; L.33.e.14.v; L.33.e.15.i; L.33.e.15.v; L.33.e.18.i;
L.33.e.18.v; L.33.e.25.i; L.33.e.25.v; L.33.g.4.i; L.33.g.4.v; L.33.g.6.i; L.33.g.6.v;
L.33.g.11.i; L.33.g.11.v; L.33.g.14.i; L.33.g.14.v; L.33.g.15.i; L.33.g.15.v; L.33.g.18.i;
L.33.g.18.v; L.33.g.25.i; L.33.g.25.v; L.33.l.4.i; L.33.l.4.v; L.33.l.6.i; L.33.l.6.v;
L.33.l.11.i; L.33.l.11.v; L.33.l.14.i; L.33.l.14.v; L.33.l.15.i; L.33.l.15.v; L.33.l.18.i;
L.33.l.18.v; L.33.l.25.i; L.33.l.25.v; L.33.m.4.i; L.33.m.4.v; L.33.m.6.i; L.33.m.6.v;
L.33.m.11.i; L.33.m.11.v; L.33.m.14.i; L.33.m.14.v; L.33.m.15.i; L.33.m.15.v;
L.33.m.18.i; L.33.m.18.v; L.33.m.25.i; L.33.m.25.v; L.33.o.4.i; L.33.o.4.v; L.33.o.6.i;
L.33.o.6.v; L.33.o.11.i; L.33.o.11.v; L.33.o.14.i; L.33.o.14.v; L.33.o.15.i; L.33.o.15.v;
L.33.o.18.i; L.33.o.18.v; L.33.o.25.i; L.33.o.25.v; L.49.a.4.i; L.49.a.4.v; L.49.a.6.i;
L.49.a.6.v; L.49.a.11.i; L.49.a.11.v; L.49.a.14.i; L.49.a.14.v; L.49.a.15.i; L.49.a.15.v;
L.49.a.18.i; L.49.a.18.v; L.49.a.25.i; L.49.a.25.v; L.49.e.4.i; L.49.e.4.v; L.49.e.6.i;
L.49.e.6.v; L.49.e.11.i; L.49.e.11.v; L.49.e.14.i; L.49.e.14.v; L.49.e.15.i; L.49.e.15.v;
L.49.e.18.i; L.49.e.18.v; L.49.e.25.i; L.49.e.25.v; L.49.g.4.i; L.49.g.4.v; L.49.g.6.i;
L.49.g.6.v; L.49.g.11.i; L.49.g.11.v; L.49.g.14.i; L.49.g.14.v; L.49.g.15.i; L.49.g.15.v;
L.49.g.18.i; L.49.g.18.v; L.49.g.25.i; L.49.g.25.v; L.49.l.4.i; L.49.l.4.v; L.49.l.6.i;
L.49.l.6.v; L.49.l.11.i; L.49.l.11.v; L.49.l.14.i; L.49.l.14.v; L.49.l.15.i; L.49.l.15.v;
L.49.l.18.i; L.49.l.18.v; L.49.l.25.i; L.49.l.25.v; L.49.m.4.i; L.49.m.4.v; L.49.m.6.i;
L.49.m.6.v; L.49.m.11.i; L.49.m.11.v; L.49.m.14.i; L.49.m.14.v; L.49.m.15.i;
L.49.m.15.v; L.49.m.18.i; L.49.m.18.v; L.49.m.25.i; L.49.m.25.v; L.49.o.4.i;
L.49.o.4.v; L.49.o.6.i; L.49.o.6.v; L.49.o.11.i; L.49.o.11.v; L.49.o.14.i; L.49.o.14.v;
L.49.o.15.i; L.49.o.15.v; L.49.o.18.i; L.49.o.18.v; L.49.o.25.i; L.49.o.25.v; B.93.a.4.i;
B.93.a.4.v; B.93.a.6.i; B.93.a.6.v; B.93.a.11.i; B.93.a.11.v; B.93.a.14.i; B.93.a.14.v;
B.93.a.15.i; B.93.a.15.v; B.93.a.18.i; B.93.a.18.v; B.93.a.25.i; B.93.a.25.v; B.93.e.4.i;
B.93.e.4.v; B.93.e.6.i; B.93.e.6.v; B.93.e.11.i; B.93.e.11.v; B.93.e.14.i; B.93.e.14.v;
B.93.e.15.i; B.93.e.15.v; B.93.e.18.i; B.93.e.18.v; B.93.e.25.i; B.93.e.25.v; B.93.g.4.i;
B.93.g.4.v; B.93.g.6.i; B.93.g.6.v; B.93.g.11.i; B.93.g.11.v; B.93.g.14.i; B.93.g.14.v;
B.93.g.15.i; B.93.g.15.v; B.93.g.18.i; B.93.g.18.v; B.93.g.25.i; B.93.g.25.v; B.93.l.4.i;

TABLE 6-continued

Exemplary Enumerated Compounds

B.93.l.4.v; B.93.l.6.i; B.93.l.6.v; B.93.l.11.i; B.93.l.11.v; B.93.l.14.i; B.93.l.14.v;
B.93.l.15.i; B.93.l.15.v; B.93.l.18.i; B.93.l.18.v; B.93.l.25.i; B.93.l.25.v; B.93.m.4.i;
B.93.m.4.v; B.93.m.6.i; B.93.m.6.v; B.93.m.11.i; B.93.m.11.v; B.93.m.14.i;
B.93.m.14.v; B.93.m.15.i; B.93.m.15.v; B.93.m.18.i; B.93.m.18.v; B.93.m.25.i;
B.93.m.25.v; B.93.o.4.i; B.93.o.4.v; B.93.o.6.i; B.93.o.6.v; B.93.o.11.i; B.93.o.11.v;
B.93.o.14.i; B.93.o.14.v; B.93.o.15.i; B.93.o.15.v; B.93.o.18.i; B.93.o.18.v;
B.93.o.25.i; B.93.o.25.v; B.94.a.4.i; B.94.a.4.v; B.94.a.6.i; B.94.a.6.v; B.94.a.11.i;
B.94.a.11.v; B.94.a.14.i; B.94.a.14.v; B.94.a.15.i; B.94.a.15.v; B.94.a.18.i; B.94.a.18.v;
B.94.a.25.i; B.94.a.25.v; B.94.e.4.i; B.94.e.4.v; B.94.e.6.i; B.94.e.6.v; B.94.e.11.i;
B.94.e.11.v; B.94.e.14.i; B.94.e.14.v; B.94.e.15.i; B.94.e.15.v; B.94.e.18.i; B.94.e.18.v;
B.94.e.25.i; B.94.e.25.v; B.94.g.4.i; B.94.g.4.v; B.94.g.6.i; B.94.g.6.v; B.94.g.11.i;
B.94.g.11.v; B.94.g.14.i; B.94.g.14.v; B.94.g.15.i; B.94.g.15.v; B.94.g.18.i; B.94.g.18.v;
B.94.g.25.i; B.94.g.25.v; B.94.l.4.i; B.94.l.4.v; B.94.l.6.i; B.94.l.6.v; B.94.l.11.i;
B.94.l.11.v; B.94.l.14.i; B.94.l.14.v; B.94.l.15.i; B.94.l.15.v; B.94.l.18.i; B.94.l.18.v;
B.94.l.25.i; B.94.l.25.v; B.94.m.4.i; B.94.m.4.v; B.94.m.6.i; B.94.m.6.v; B.94.m.11.i;
B.94.m.11.v; B.94.m.14.i; B.94.m.14.v; B.94.m.15.i; B.94.m.15.v; B.94.m.18.i;
B.94.m.18.v; B.94.m.25.i; B.94.m.25.v; B.94.o.4.i; B.94.o.4.v; B.94.o.6.i; B.94.o.6.v;
B.94.o.11.i; B.94.o.11.v; B.94.o.14.i; B.94.o.14.v; B.94.o.15.i; B.94.o.15.v;
B.94.o.18.i; B.94.o.18.v; B.94.o.25.i; B.94.o.25.v; E.93.a.4.i; E.93.a.4.v; E.93.a.6.i;
E.93.a.6.v; E.93.a.11.i; E.93.a.11.v; E.93.a.14.i; E.93.a.14.v; E.93.a.15.i; E.93.a.15.v;
E.93.a.18.i; E.93.a.18.v; E.93.a.25.i; E.93.a.25.v; E.93.e.4.i; E.93.e.4.v; E.93.e.6.i;
E.93.e.6.v; E.93.e.11.i; E.93.e.11.v; E.93.e.14.i; E.93.e.14.v; E.93.e.15.i; E.93.e.15.v;
E.93.e.18.i; E.93.e.18.v; E.93.e.25.i; E.93.e.25.v; E.93.g.4.i; E.93.g.4.v; E.93.g.6.i;
E.93.g.6.v; E.93.g.11.i; E.93.g.11.v; E.93.g.14.i; E.93.g.14.v; E.93.g.15.i; E.93.g.15.v;
E.93.g.18.i; E.93.g.18.v; E.93.g.25.i; E.93.g.25.v; E.93.l.4.i; E.93.l.4.v; E.93.l.6.i;
E.93.l.6.v; E.93.l.11.i; E.93.l.11.v; E.93.l.14.i; E.93.l.14.v; E.93.l.15.i; E.93.l.15.v;
E.93.l.18.i; E.93.l.18.v; E.93.l.25.i; E.93.l.25.v; E.93.m.4.i; E.93.m.4.v; E.93.m.6.i;
E.93.m.6.v; E.93.m.11.i; E.93.m.11.v; E.93.m.14.i; E.93.m.14.v; E.93.m.15.i;
E.93.m.15.v; E.93.m.18.i; E.93.m.18.v; E.93.m.25.i; E.93.m.25.v; E.93.o.4.i;
E.93.o.4.v; E.93.o.6.i; E.93.o.6.v; E.93.o.11.i; E.93.o.11.v; E.93.o.14.i; E.93.o.14.v;
E.93.o.15.i; E.93.o.15.v; E.93.o.18.i; E.93.o.18.v; E.93.o.25.i; E.93.o.25.v; E.94.a.4.i;
E.94.a.4.v; E.94.a.6.i; E.94.a.6.v; E.94.a.11.i; E.94.a.11.v; E.94.a.14.i; E.94.a.14.v;
E.94.a.15.i; E.94.a.15.v; E.94.a.18.i; E.94.a.18.v; E.94.a.25.i; E.94.a.25.v; E.94.e.4.i;
E.94.e.4.v; E.94.e.6.i; E.94.e.6.v; E.94.e.11.i; E.94.e.11.v; E.94.e.14.i; E.94.e.14.v;
E.94.e.15.i; E.94.e.15.v; E.94.e.18.i; E.94.e.18.v; E.94.e.25.i; E.94.e.25.v; E.94.g.4.i;
E.94.g.4.v; E.94.g.6.i; E.94.g.6.v; E.94.g.11.i; E.94.g.11.v; E.94.g.14.i; E.94.g.14.v;
E.94.g.15.i; E.94.g.15.v; E.94.g.18.i; E.94.g.18.v; E.94.g.25.i; E.94.g.25.v; E.94.l.4.i;
E.94.l.4.v; E.94.l.6.i; E.94.l.6.v; E.94.l.11.i; E.94.l.11.v; E.94.l.14.i; E.94.l.14.v;
E.94.l.15.i; E.94.l.15.v; E.94.l.18.i; E.94.l.18.v; E.94.l.25.i; E.94.l.25.v; E.94.m.4.i;
E.94.m.4.v; E.94.m.6.i; E.94.m.6.v; E.94.m.11.i; E.94.m.11.v; E.94.m.14.i;
E.94.m.14.v; E.94.m.15.i; E.94.m.15.v; E.94.m.18.i; E.94.m.18.v; E.94.m.25.i;
E.94.m.25.v; E.94.o.4.i; E.94.o.4.v; E.94.o.6.i; E.94.o.6.v; E.94.o.11.i; E.94.o.11.v;
E.94.o.14.i; E.94.o.14.v; E.94.o.15.i; E.94.o.15.v; E.94.o.18.i; E.94.o.18.v; E.94.o.25.i;
E.94.o.25.v; I.93.a.4.i; I.93.a.4.v; I.93.a.6.i; I.93.a.6.v; I.93.a.11.i; I.93.a.11.v;
I.93.a.14.i; I.93.a.14.v; I.93.a.15.i; I.93.a.15.v; I.93.a.18.i; I.93.a.18.v; I.93.a.25.i;
I.93.a.25.v; I.93.e.4.i; I.93.e.4.v; I.93.e.6.i; I.93.e.6.v; I.93.e.11.i; I.93.e.11.v;
I.93.e.14.i; I.93.e.14.v; I.93.e.15.i; I.93.e.15.v; I.93.e.18.i; I.93.e.18.v; I.93.e.25.i;
I.93.e.25.v; I.93.g.4.i; I.93.g.4.v; I.93.g.6.i; I.93.g.6.v; I.93.g.11.i; I.93.g.11.v;
I.93.g.14.i; I.93.g.14.v; I.93.g.15.i; I.93.g.15.v; I.93.g.18.i; I.93.g.18.v; I.93.g.25.i;
I.93.g.25.v; I.93.l.4.i; I.93.l.4.v; I.93.l.6.i; I.93.l.6.v; I.93.l.11.i; I.93.l.11.v; I.93.l.14.i;
I.93.l.14.v; I.93.l.15.i; I.93.l.15.v; I.93.l.18.i; I.93.l.18.v; I.93.l.25.i; I.93.l.25.v;
I.93.m.4.i; I.93.m.4.v; I.93.m.6.i; I.93.m.6.v; I.93.m.11.i; I.93.m.11.v; I.93.m.14.i;
I.93.m.14.v; I.93.m.15.i; I.93.m.15.v; I.93.m.18.i; I.93.m.18.v; I.93.m.25.i;
I.93.m.25.v; I.93.o.4.i; I.93.o.4.v; I.93.o.6.i; I.93.o.6.v; I.93.o.11.i; I.93.o.11.v;
I.93.o.14.i; I.93.o.14.v; I.93.o.15.i; I.93.o.15.v; I.93.o.18.i; I.93.o.18.v; I.93.o.25.i;
I.93.o.25.v; I.94.a.4.i; I.94.a.4.v; I.94.a.6.i; I.94.a.6.v; I.94.a.11.i; I.94.a.11.v;
I.94.a.14.i; I.94.a.14.v; I.94.a.15.i; I.94.a.15.v; I.94.a.18.i; I.94.a.18.v; I.94.a.25.i;
I.94.a.25.v; I.94.e.4.i; I.94.e.4.v; I.94.e.6.i; I.94.e.6.v; I.94.e.11.i; I.94.e.11.v;
I.94.e.14.i; I.94.e.14.v; I.94.e.15.i; I.94.e.15.v; I.94.e.18.i; I.94.e.18.v; I.94.e.25.i;
I.94.e.25.v; I.94.g.4.i; I.94.g.4.v; I.94.g.6.i; I.94.g.6.v; I.94.g.11.i; I.94.g.11.v;
I.94.g.14.i; I.94.g.14.v; I.94.g.15.i; I.94.g.15.v; I.94.g.18.i; I.94.g.18.v; I.94.g.25.i;
I.94.g.25.v; I.94.l.4.i; I.94.l.4.v; I.94.l.6.i; I.94.l.6.v; I.94.l.11.i; I.94.l.11.v; I.94.l.14.i;
I.94.l.14.v; I.94.l.15.i; I.94.l.15.v; I.94.l.18.i; I.94.l.18.v; I.94.l.25.i; I.94.l.25.v;
I.94.m.4.i; I.94.m.4.v; I.94.m.6.i; I.94.m.6.v; I.94.m.11.i; I.94.m.11.v; I.94.m.14.i;
I.94.m.14.v; I.94.m.15.i; I.94.m.15.v; I.94.m.18.i; I.94.m.18.v; I.94.m.25.i;
I.94.m.25.v; I.94.o.4.i; I.94.o.4.v; I.94.o.6.i; I.94.o.6.v; I.94.o.11.i; I.94.o.11.v;
I.94.o.14.i; I.94.o.14.v; I.94.o.15.i; I.94.o.15.v; I.94.o.18.i; I.94.o.18.v; I.94.o.25.i;
I.94.o.25.v; L.93.a.4.i; L.93.a.4.v; L.93.a.6.i; L.93.a.6.v; L.93.a.11.i; L.93.a.11.v;
L.93.a.14.i; L.93.a.14.v; L.93.a.15.i; L.93.a.15.v; L.93.a.18.i; L.93.a.18.v; L.93.a.25.i;
L.93.a.25.v; L.93.e.4.i; L.93.e.4.v; L.93.e.6.i; L.93.e.6.v; L.93.e.11.i; L.93.e.11.v;
L.93.e.14.i; L.93.e.14.v; L.93.e.15.i; L.93.e.15.v; L.93.e.18.i; L.93.e.18.v; L.93.e.25.i;
L.93.e.25.v; L.93.g.4.i; L.93.g.4.v; L.93.g.6.i; L.93.g.6.v; L.93.g.11.i; L.93.g.11.v;
L.93.g.14.i; L.93.g.14.v; L.93.g.15.i; L.93.g.15.v; L.93.g.18.i; L.93.g.18.v; L.93.g.25.i;
L.93.g.25.v; L.93.l.4.i; L.93.l.4.v; L.93.l.6.i; L.93.l.6.v; L.93.l.11.i; L.93.l.11.v;
L.93.l.14.i; L.93.l.14.v; L.93.l.15.i; L.93.l.15.v; L.93.l.18.i; L.93.l.18.v; L.93.l.25.i;
L.93.l.25.v; L.93.m.4.i; L.93.m.4.v; L.93.m.6.i; L.93.m.6.v; L.93.m.11.i;
L.93.m.11.v; L.93.m.14.i; L.93.m.14.v; L.93.m.15.i; L.93.m.15.v; L.93.m.18.i;

TABLE 6-continued

Exemplary Enumerated Compounds

L.93.m.18.v; L.93.m.25.i; L.93.m.25.v; L.93.o.4.i; L.93.o.4.v; L.93.o.6.i; L.93.o.6.v;
L.93.o.11.i; L.93.o.11.v; L.93.o.14.i; L.93.o.14.v; L.93.o.15.i; L.93.o.15.v; L.93.o.18.i;
L.93.o.18.v; L.93.o.25.i; L.93.o.25.v; L.94.a.4.i; L.94.a.4.v; L.94.a.6.i; L.94.a.6.v;
L.94.a.11.i; L.94.a.11.v; L.94.a.14.i; L.94.a.14.v; L.94.a.15.i; L.94.a.15.v; L.94.a.18.i;
L.94.a.18.v; L.94.a.25.i; L.94.a.25.v; L.94.e.4.i; L.94.e.4.v; L.94.e.6.i; L.94.e.6.v;
L.94.e.11.i; L.94.e.11.v; L.94.e.14.i; L.94.e.14.v; L.94.e.15.i; L.94.e.15.v; L.94.e.18.i;
L.94.e.18.v; L.94.e.25.i; L.94.e.25.v; L.94.g.4.i; L.94.g.4.v; L.94.g.6.i; L.94.g.6.v;
L.94.g.11.i; L.94.g.11.v; L.94.g.14.i; L.94.g.14.v; L.94.g.15.i; L.94.g.15.v; L.94.g.18.i;
L.94.g.18.v; L.94.g.25.i; L.94.g.25.v; L.94.l.4.i; L.94.l.4.v; L.94.l.6.i; L.94.l.6.v;
L.94.l.11.i; L.94.l.11.v; L.94.l.14.i; L.94.l.14.v; L.94.l.15.i; L.94.l.15.v; L.94.l.18.i;
L.94.l.18.v; L.94.l.25.i; L.94.l.25.v; L.94.m.4.i; L.94.m.4.v; L.94.m.6.i; L.94.m.6.v;
L.94.m.11.i; L.94.m.11.v; L.94.m.14.i; L.94.m.14.v; L.94.m.15.i; L.94.m.15.v;
L.94.m.18.i; L.94.m.18.v; L.94.m.25.i; L.94.m.25.v; L.94.o.4.i; L.94.o.4.v; L.94.o.6.i;
L.94.o.6.v; L.94.o.11.i; L.94.o.11.v; L.94.o.14.i; L.94.o.14.v; L.94.o.15.i; L.94.o.15.v;
L.94.o.18.i; L.94.o.18.v; L.94.o.25.i; L.94.o.25.v; O.93.a.4.i; O.93.a.4.v; O.93.a.6.i;
O.93.a.6.v; O.93.a.11.i; O.93.a.11.v; O.93.a.14.i; O.93.a.14.v; O.93.a.15.i;
O.93.a.15.v; O.93.a.18.i; O.93.a.18.v; O.93.a.25.i; O.93.a.25.v; O.93.e.4.i; O.93.e.4.v;
O.93.e.6.i; O.93.e.6.v; O.93.e.11.i; O.93.e.11.v; O.93.e.14.i; O.93.e.14.v; O.93.e.15.i;
O.93.e.15.v; O.93.e.18.i; O.93.e.18.v; O.93.e.25.i; O.93.e.25.v; O.93.g.4.i; O.93.g.4.v;
O.93.g.6.i; O.93.g.6.v; O.93.g.11.i; O.93.g.11.v; O.93.g.14.i; O.93.g.14.v; O.93.g.15.i;
O.93.g.15.v; O.93.g.18.i; O.93.g.18.v; O.93.g.25.i; O.93.g.25.v; O.93.l.4.i; O.93.l.4.v;
O.93.l.6.i; O.93.l.6.v; O.93.l.11.i; O.93.l.11.v; O.93.l.14.i; O.93.l.14.v; O.93.l.15.i;
O.93.l.15.v; O.93.l.18.i; O.93.l.18.v; O.93.l.25.i; O.93.l.25.v; O.93.m.4.i; O.93.mA.v;
O.93.m.6.i; O.93.m.6.v; O.93.m.11.i; O.93.m.11.v; O.93.m.14.i; O.93.m.14.v;
O.93.m.15.i; O.93.m.15.v; O.93.m.18.i; O.93.m.18.v; O.93.m.25.i; O.93.m.25.v;
O.93.o.4.i; O.93.o.4.v; O.93.o.6.i; O.93.o.6.v; O.93.o.11.i; O.93.o.11.v; O.93.o.14.i;
O.93.o.14.v; O.93.o.15.i; O.93.o.15.v; O.93.o.18.i; O.93.o.18.v; O.93.o.25.i;
O.93.o.25.v; O.94.a.4.i; O.94.a.4.v; O.94.a.6.i; O.94.a.6.v; O.94.a.11.i; O.94.a.11.v;
O.94.a.14.i; O.94.a.14.v; O.94.a.15.i; O.94.a.15.v; O.94.a.18.i; O.94.a.18.v;
O.94.a.25.i; O.94.a.25.v; O.94.e.4.i; O.94.e.4.v; O.94.e.6.i; O.94.e.6.v; O.94.e.11.i;
O.94.e.11.v; O.94.e.14.i; O.94.e.14.v; O.94.e.15.i; O.94.e.15.v; O.94.e.18.i;
O.94.e.18.v; O.94.e.25.i; O.94.e.25.v; O.94.g.4.i; O.94.g.4.v; O.94.g.6.i; O.94.g.6.v;
O.94.g.11.i; O.94.g.11.v; O.94.g.14.i; O.94.g.14.v; O.94.g.15.i; O.94.g.15.v;
O.94.g.18.i; O.94.g.18.v; O.94.g.25.i; O.94.g.25.v; O.94.l.4.i; O.94.l.4.v; O.94.l.6.i;
O.94.l.6.v; O.94.l.11.i; O.94.l.11.v; O.94.l.14.i; O.94.l.14.v; O.94.l.15.i; O.94.l.15.v;
O.94.l.18.i; O.94.l.18.v; O.94.l.25.i; O.94.l.25.v; O.94.m.4.i; O.94.m.4.v; O.94.m.6.i;
O.94.m.6.v; O.94.m.11.i; O.94.m.11.v; O.94.m.14.i; O.94.m.14.v; O.94.m.15.i;
O.94.m.15.v; O.94.m.18.i; O.94.m.18.v; O.94.m.25.i; O.94.m.25.v; O.94.o.4.i;
O.94.o.4.v; O.94.o.6.i; O.94.o.6.v; O.94.o.11.i; O.94.o.11.v; O.94.o.14.i; O.94.o.14.v;
O.94.o.15.i; O.94.o.15.v; O.94.o.18.i; O.94.o.18.v; O.94.o.25.i; O.94.o.25.v;
P.93.a.4.i; P.93.a.4.v; P.93.a.6.i; P.93.a.6.v; P.93.a.11.i; P.93.a.11.v; P.93.a.14.i;
P.93.a.14.v; P.93.a.15.i; P.93.a.15.v; P.93.a.18.i; P.93.a.18.v; P.93.a.25.i; P.93.a.25.v;
P.93.e.4.i; P.93.e.4.v; P.93.e.6.i; P.93.e.6.v; P.93.e.11.i; P.93.e.11.v; P.93.e.14.i;
P.93.e.14.v; P.93.e.15.i; P.93.e.15.v; P.93.e.18.i; P.93.e.18.v; P.93.e.25.i; P.93.e.25.v;
P.93.g.4.i; P.93.g.4.v; P.93.g.6.i; P.93.g.6.v; P.93.g.11.i; P.93.g.11.v; P.93.g.14.i;
P.93.g.14.v; P.93.g.15.i; P.93.g.15.v; P.93.g.18.i; P.93.g.18.v; P.93.g.25.i; P.93.g.25.v;
P.93.l.4.i; P.93.l.4.v; P.93.l.6.i; P.93.l.6.v; P.93.l.11.i; P.93.l.11.v; P.93.l.14.i;
P.93.l.14.v; P.93.l.15.i; P.93.l.15.v; P.93.l.18.i; P.93.l.18.v; P.93.l.25.i; P.93.l.25.v;
P.93.m.4.i; P.93.m.4.v; P.93.m.6.i; P.93.m.6.v; P.93.m.11.i; P.93.m.11.v;
P.93.m.14.i; P.93.m.14.v; P.93.m.15.i; P.93.m.15.v; P.93.m.18.i; P.93.m.18.v;
P.93.m.25.i; P.93.m.25.v; P.93.o.4.i; P.93.o.4.v; P.93.o.6.i; P.93.o.6.v; P.93.o.11.i;
P.93.o.11.v; P.93.o.14.i; P.93.o.14.v; P.93.o.15.i; P.93.o.15.v; P.93.o.18.i; P.93.o.18.v;
P.93.o.25.i; P.93.o.25.v; P.94.a.4.i; P.94.a.4.v; P.94.a.6.i; P.94.a.6.v; P.94.a.11.i;
P.94.a.11.v; P.94.a.14.i; P.94.a.14.v; P.94.a.15.i; P.94.a.15.v; P.94.a.18.i; P.94.a.18.v;
P.94.a.25.i; P.94.a.25.v; P.94.e.4.i; P.94.e.4.v; P.94.e.6.i; P.94.e.6.v; P.94.e.11.i;
P.94.e.11.v; P.94.e.14.i; P.94.e.14.v; P.94.e.15.i; P.94.e.15.v; P.94.e.18.i; P.94.e.18.v;
P.94.e.25.i; P.94.e.25.v; P.94.g.4.i; P.94.g.4.v; P.94.g.6.i; P.94.g.6.v; P.94.g.11.i;
P.94.g.11.v; P.94.g.14.i; P.94.g.14.v; P.94.g.15.i; P.94.g.15.v; P.94.g.18.i; P.94.g.18.v;
P.94.g.25.i; P.94.g.25.v; P.94.l.4.i; P.94.l.4.v; P.94.l.6.i; P.94.l.6.v; P.94.l.11.i;
P.94.l.11.v; P.94.l.14.i; P.94.l.14.v; P.94.l.15.i; P.94.l.15.v; P.94.l.18.i; P.94.l.18.v;
P.94.l.25.i; P.94.l.25.v; P.94.m.4.i; P.94.m.4.v; P.94.m.6.i; P.94.m.6.v; P.94.m.11.i;
P.94.m.11.v; P.94.m.14.i; P.94.m.14.v; P.94.m.15.i; P.94.m.15.v; P.94.m.18.i;
P.94.m.18.v; P.94.m.25.i; P.94.m.25.v; P.94.o.4.i; P.94.o.4.v; P.94.o.6.i; P.94.o.6.v;
P.94.o.11.i; P.94.o.11.v; P.94.o.14.i; P.94.o.14.v; P.94.o.15.i; P.94.o.15.v; P.94.o.18.i;
P.94.o.18.v; P.94.o.25.i; P.94.o.25.v; A.2.a.4.o; A.2.a.4.bh; A.2.a.4.bi; A.2.a.4.bj;
A.2.a.4.bk; A.2.a.11.o; A.2.a.11.bh; A.2.a.11.bi; A.2.a.11.bj; A.2.a.11.bk; A.2.a.15.i;
A.2.a.15.o; A.2.a.15.bh; A.2.a.15.bi; A.2.a.15.bj; A.2.a.15.bk; A.2.a.37.i; A.2.a.37.o;
A.2.a.37.bh; A.2.a.37.bi; A.2.a.37.bj; A.2.a.37.bk; A.2.a.38.i; A.2.a.38.o; A.2.a.38.bh;
A.2.a.38.bi; A.2.a.38.bj; A.2.a.38.bk; A.2.a.39.i; A.2.a.39.o; A.2.a.39.bh; A.2.a.39.bi;
A.2.a.39.bj; A.2.a.39.bk; A.2.a.40.i; A.2.a.40.o; A.2.a.40.bh; A.2.a.40.bi; A.2.a.40.bj;
A.2.a.40.bk; A.2.a.41.i; A.2.a.41.o; A.2.a.41.bh; A:2.a.41.bi; A.2.a.41.bj; A.2.a.41.bk;
A.2.a.42.i; A.2.a.42.o; A.2.a.42.bh; A.2.a.42.bi; A.2.a.42.bj; A.2.a.42.bk; A.2.a.43.i;
A.2.a.43.o; A.2.a.43.bh; A.2.a.43.bi; A.2.a.43.bj; A.2.a.43.bk;
A.3.a.4.o; A.3.a.4.bh; A.3.a.4.bi; A.3.a.4.bj; A.3.a.4.bk; A.3.a.11.o; A.3.a.11.bh;
A.3.a.11.bi; A.3.a.11.bj; A.3.a.11.bk; A.3.a.15.i; A.3.a.15.o; A.3.a.15.bh; A.3.a.15.bi;
A.3.a.15.bj; A.3.a.15.bk; A.3.a.37.i; A.3.a.37.o; A.3.a.37.bh; A.3.a.37.bi; A.3.a.37.bj;
A.3.a.37.bk; A.3.a.38.i; A.3.a.38.o; A.3.a.38.bh; A.3.a.38.bi; A.3.a.38.bj; A.3.a.38.bk;

TABLE 6-continued

Exemplary Enumerated Compounds

A.3.a.39.i; A.3.a.39.o; A.3.a.39.bh; A.3.a.39.bi; A.3.a.39.bj; A.3.a.39.bk; A.3.a.40.i;
A.3.a.40.o; A.3.a.40.bh; A.3.a.40.bi; A.3.a.40.bj; A.3.a.40.bk; A.3.a.41.i; A.3.a.41.o;
A.3.a.41.bh; A.3.a.41.bi; A.3.a.41.bj; A.3.a.41.bk; A.3.a.42.i; A.3.a.42.o; A.3.a.42.bh;
A.3.a.42.bi; A.3.a.42.bj; A.3.a.42.bk; A.3.a.43.i; A.3.a.43.o; A.3.a.43.bh; A.3.a.43.bi;
A.3.a.43.bj; A.3.a.43.bk; A.4.a.4.o; A.4.a.4.bh; A.4.a.4.bi; A.4.a.4.bj; A.4.a.4.bk;
A.4.a.11.o; A.4.a.11.bh; A.4.a.11.bi; A.4.a.11.bj; A.4.a.11.bk; A.4.a.15.i; A.4.a.15.o;
A.4.a.15.bh; A.4.a.15.bi; A.4.a.15.bj; A.4.a.15.bk; A.4.a.37.i; A.4.a.37.o; A.4.a.37.bh;
A.4.a.37.bi; A.4.a.37.bj; A.4.a.37.bk; A.4.a.38.i; A.4.a.38.o; A.4.a.38.bh; A.4.a.38.bi;
A.4.a.38.bj; A.4.a.38.bk; A.4.a.39.i; A.4.a.39.o; A.4.a.39.bh; A.4.a.39.bi; A.4.a.39.bj;
A.4.a.39.bk; A.4.a.40.i; A.4.a.40.o; A.4.a.40.bh; A.4.a.40.bi; A.4.a.40.bj; A.4.a.40.bk;
A.4.a.41.i; A.4.a.41.o; A.4.a.41.bh; A.4.a.41.bi; A.4.a.41.bj; A.4.a.41.bk; A.4.a.42.i;
A.4.a.42.o; A.4.a.42.bh; A.4.a.42.bi; A.4.a.42.bj; A.4.a.42.bk; A.4.a.43.i; A.4.a.43.o;
A.4.a.43.bh; A.4.a.43.bi; A.4.a.43.bj; A.4.a.43.bk; A.7.a.4.o; A.7.a.4.bh; A.7.a.4.bi;
A.7.a.4.bj; A.7.a.4.bk; A.7.a.11.o; A.7.a.11.bh; A.7.a.11.bi; A.7.a.11.bj; A.7.a.11.bk;
A.7.a.15.i; A.7.a.15.o; A.7.a.15.bh; A.7.a.15.bi; A.7.a.15.bj; A.7.a.15.bk; A.7.a.37.i;
A.7.a.37.o; A.7.a.37.bh; A.7.a.37.bi; A.7.a.37.bj; A.7.a.37.bk; A.7.a.38.i; A.7.a.38.o;
A.7.a.38.bh; A.7.a.38.bi; A.7.a.38.bj; A.7.a.38.bk; A.7.a.39.i; A.7.a.39.o; A.7.a.39.bh;
A.7.a.39.bi; A.7.a.39.bj; A.7.a.39.bk; A.7.a.40.i; A.7.a.40.o; A.7.a.40.bh; A.7.a.40.bi;
A.7.a.40.bj; A.7.a.40.bk; A.7.a.41.i; A.7.a.41.o; A.7.a.41.bh; A.7.a.41.bi; A.7.a.41.bj;
A.7.a.41.bk; A.7.a.42.i; A.7.a.42.o; A.7.a.42.bh; A.7.a.42.bi; A.7.a.42.bj; A.7.a.42.bk;
A.7.a.43.i; A.7.a.43.o; A.7.a.43.bh; A.7.a.43.bi; A.7.a.43.bj; A.7.a.43.bk;
A.17.a.4.i; A.17.a.4.o; A.17.a.4.bh; A.17.a.4.bi; A.17.a.4.bj; A.17.a.4.bk; A.17.a.11.i;
A.17.a.11.o; A.17.a.11.bh; A.17.a.11.bi; A.17.a.11.bj; A.17.a.11.bk; A.17.a.15.i;
A.17.a.15.o; A.17.a.15.bh; A.17.a.15.bi; A.17.a.15.bj; A.17.a.15.bk; A.17.a.37.i;
A.17.a.37.o; A.17.a.37.bh; A.17.a.37.bi; A.17.a.37.bj; A.17.a.37.bk; A.17.a.38.i;
A.17.a.38.o; A.17.a.38.bh; A.17.a.38.bi; A.17.a.38.bj; A.17.a.38.bk; A.17.a.39.i;
A.17.a.39.o; A.17.a.39.bh; A.17.a.39.bi; A.17.a.39.bj; A.17.a.39.bk; A.17.a.40.i;
A.17.a.40.o; A.17.a.40.bh; A.17.a.40.bi; A.17.a.40.bj; A.17.a.40.bk; A.17.a.41.i;
A.17.a.41.o; A.17.a.41.bh; A.17.a.41.bi; A.17.a.41.bj; A.17.a.41.bk; A.17.a.42.i;
A.17.a.42.o; A.17.a.42.bh; A.17.a.42.bi; A.17.a.42.bj; A.17.a.42.bk; A.17.a.43.i;
A.17.a.43.o; A.17.a.43.bh; A.17.a.43.bi; A.17.a.43.bj; A.17.a.43.bk; A.18.a.4.i;
A.18.a.4.o; A.18.a.4.bh; A.18.a.4.bi; A.18.a.4.bj; A.18.a.4.bk; A.18.a.11.i;
A.18.a.11.o; A.18.a.11.bh; A.18.a.11.bi; A.18.a.11.bj; A.18.a.11.bk; A.18.a.15.i;
A.18.a.15.o; A.18.a.15.bh; A.18.a.15.bi; A.18.a.15.bj; A.18.a.15.bk; A.18.a.37.i;
A.18.a.37.o; A.18.a.37.bh; A.18.a.37.bi; A.18.a.37.bj; A.18.a.37.bk; A.18.a.38.i;
A.18.a.38.o; A.18.a.38.bh; A.18.a.38.bi; A.18.a.38.bj; A.18.a.38.bk; A.18.a.39.i;
A.18.a.39.o; A.18.a.39.bh; A.18.a.39.bi; A.18.a.39.bj; A.18.a.39.bk; A.18.a.40.i;
A.18.a.40.o; A.18.a.40.bh; A.18.a.40.bi; A.18.a.40.bj; A.18.a.40.bk; A.18.a.41.i;
A.18.a.41.o; A.18.a.41.bh; A.18.a.41.bi; A.18.a.41.bj; A.18.a.41.bk; A.18.a.42.i;
A.18.a.42.o; A.18.a.42.bh; A.18.a.42.bi; A.18.a.42.bj; A.18.a.42.bk; A.18.a.43.i;
A.18.a.43.o; A.18.a.43.bh; A.18.a.43.bi; A.18.a.43.bj; A.18.a.43.bk; A.19.a.4.i;
A.19.a.4.o; A.19.a.4.bh; A.19.a.4.bi; A.19.a.4.bj; A.19.a.4.bk; A.19.a.11.i;
A.19.a.11.o; A.19.a.11.bh; A.19.a.11.bi; A.19.a.11.bj; A.19.a.11.bk; A.19.a.15.i;
A.19.a.15.o; A.19.a.15.bh; A.19.a.15.bi; A.19.a.15.bj; A.19.a.15.bk; A.19.a.37.i;
A.19.a.37.o; A.19.a.37.bh; A.19.a.37.bi; A.19.a.37.bj; A.19.a.37.bk; A.19.a.38.i;
A.19.a.38.o; A.19.a.38.bh; A.19.a.38.bi; A.19.a.38.bj; A.19.a.38.bk; A.19.a.39.i;
A.19.a.39.o; A.19.a.39.bh; A.19.a.39.bi; A.19.a.39.bj; A.19.a.39.bk; A.19.a.40.i;
A.19.a.40.o; A.19.a.40.bh; A.19.a.40.bi; A.19.a.40.bj; A.19.a.40.bk; A.19.a.41.i;
A.19.a.41.o; A.19.a.41.bh; A.19.a.41.bi; A.19.a.41.bj; A.19.a.41.bk; A.19.a.42.i;
A.19.a.42.o; A.19.a.42.bh; A.19.a.42.bi; A.19.a.42.bj; A.19.a.42.bk; A.19.a.43.i;
A.19.a.43.o; A.19.a.43.bh; A.19.a.43.bi; A.19.a.43.bj; A.19.a.43.bk; A.97.a.4.i;
A.97.a.4.o; A.97.a.4.bh; A.97.a.4.bi; A.97.a.4.bj; A.97.a.4.bk; A.97.a.11.i;
A.97.a.11.o; A.97.a.11.bh; A.97.a.11.bi; A.97.a.11.bj; A.97.a.11.bk; A.97.a.15.i;
A.97.a.15.o; A.97.a.15.bh; A.97.a.15.bi; A.97.a.15.bj; A.97.a.15.bk; A.97.a.37.i;
A.97.a.37.o; A.97.a.37.bh; A.97.a.37.bi; A.97.a.37.bj; A.97.a.37.bk; A.97.a.38.i;
A.97.a.38.o; A.97.a.38.bh; A.97.a.38.bi; A.97.a.38.bj; A.97.a.38.bk; A.97.a.39.i;
A.97.a.39.o; A.97.a.39.bh; A.97.a.39.bi; A.97.a.39.bj; A.97.a.39.bk; A.97.a.40.i;
A.97.a.40.o; A.97.a.40.bh; A.97.a.40.bi; A.97.a.40.bj; A.97.a.40.bk; A.97.a.41.i;
A.97.a.41.o; A.97.a.41.bh; A.97.a.41.bi; A.97.a.41.bj; A.97.a.41.bk; A.97.a.42.i;
A.97.a.42.o; A.97.a.42.bh; A.97.a.42.bi; A.97.a.42.bj; A.97.a.42.bk; A.97.a.43.i;
A.97.a.43.o; A.97.a.43.bh; A.97.a.43.bi; A.97.a.43.bj; A.97.a.43.bk; A.98.a.4.i;
A.98.a.4.o; A.98.a.4.bh; A.98.a.4.bi; A.98.a.4.bj; A.98.a.4.bk; A.98.a.11.i;
A.98.a.11.o; A.98.a.11.bh; A.98.a.11.bi; A.98.a.11.bj; A.98.a.11.bk; A.98.a.15.i;
A.98.a.15.o; A.98.a.15.bh; A.98.a.15.bi; A.98.a.15.bj; A.98.a.15.bk; A.98.a.37.i;
A.98.a.37.o; A.98.a.37.bh; A.98.a.37.bi; A.98.a.37.bj; A.98.a.37.bk; A.98.a.38.i;
A.98.a.38.o; A.98.a.38.bh; A.98.a.38.bi; A.98.a.38.bj; A.98.a.38.bk; A.98.a.39.i;
A.98.a.39.o; A.98.a.39.bh; A.98.a.39.bi; A.98.a.39.bj; A.98.a.39.bk; A.98.a.40.i;
A.98.a.40.o; A.98.a.40.bh; A.98.a.40.bi; A.98.a.40.bj; A.98.a.40.bk; A.98.a.41.i;
A.98.a.41.o; A.98.a.41.bh; A.98.a.41.bi; A.98.a.41.bj; A.98.a.41.bk; A.98.a.42.i;
A.98.a.42.o; A.98.a.42.bh; A.98.a.42.bi; A.98.a.42.bj; A.98.a.42.bk; A.98.a.43.i;
A.98.a.43.o; A.98.a.43.bh; A.98.a.43.bi; A.98.a.43.bj; A.98.a.43.bk; A.2.a.4.i;
A.3.a.4.i; A.4.a.4.i; A.5.a.4.i; A.6.a.4.i; A.7.a.4.i; A.9.a.4.i; A.10.a.4.i; A.15.a.4.i;
A.100.a.4.i; A.101.a.4.i; A.102.a.4.i; A.103.a.4.i; A.104.a.4.i; A.105.a.4.i; A.106.a.4.i;
A.107.a.4.i; A.108.a.4.i; A.109.a.4.i; A.110.a.4.i; A.111.a.4.i; A.112.a.4.i; A.113.a.4.i;
A.114.a.4.i; A.115.a.4.i; A.116.a.4.i; A.117.a.4.i; A.118.a.4.i; A.119.a.4.i; A.120.a.4.i;
A.121.a.4.i; A.122.a.4.i; A.123.a.4.i; A.124.a.4.i; A.125.a.4.i; A.126.a.4.i; A.127.a.4.i;
A.128.a.4.i; A.129.a.4.i; A.130.a.4.i; A.131.a.4.i; A.132.a.4.i; A.133.a.4.i; A.134.a.4.i;

TABLE 6-continued

Exemplary Enumerated Compounds

A.135.a.4.i; A.136.a.4.i; A.137.a.4.i; A.138.a.4.i; A.139.a.4.i; A.140.a.4.i; A.141.a.4.i;
A.142.a.4.i; A.143.a.4.i; A.144.a.4.i; A.145.a.4.i; A.146.a.4.i; A.147.a.4.i; A.148.a.4.i;
A.149.a.4.i; A.150.a.4.i; A.151.a.4.i; A.152.a.4.i; A.153.a.4.i; A.154.a.4.i; A.155.a.4.i;
A.156.a.4.i; A.157.a.4.i; A.158.a.4.i; A.159.a.4.i; A.160.a.4.i; A.161.a.4.i; A.162.a.4.i;
A.163.a.4.i; A.164.a.4.i; A.165.a.4.i; A.166.a.4.i; A.167.a.4.i; A.168.a.4.i; A.169.a.4.i;
A.170.a.4.i; A.171.a.4.i; A.172.a.4.i; A.173.a.4.i; A.174.a.4.i; A.175.a.4.i; A.176.a.4.i;
A.177.a.4.i; A.178.a.4.i; A.179.a.4.i; A.180.a.4.i; A.181.a.4.i; A.182.a.4.i; A.183.a.4.i;
A.184.a.4.i; A.185.a.4.i; A.186.a.4.i; A.187.a.4.i; A.188.a.4.i; A.189.a.4.i; A.190.a.4.i;
A.191.a.4.i; A.192.a.4.i; A.193.a.4.i; A.194.a.4.i; A.195.a.4.i; A.196.a.4.i; A.197.a.4.i;
A.198.a.4.i; A.199.a.4.i; A.200.a.4.i; A.201.a.4.i; A.202.a.4.i; A.203.a.4.i; A.204.a.4.i;
A.205.a.4.i; A.206.a.4.i; A.207.a.4.i; A.208.a.4.i; A.209.a.4.i; A.210.a.4.i; A.211.a.4.i;
A.212.a.4.i; A.213.a.4.i; A.214.a.4.i; A.215.a.4.i; A.216.a.4.i; A.217.a.4.i; A.218.a.4.i;
A.219.a.4.i; A.220.a.4.i; A.221.a.4.i; A.222.a.4.i; A.223.a.4.i; A.224.a.4.i; A.225.a.4.i;
A.226.a.4.i; A.227.a.4.i; A.228.a.4.i; A.229.a.4.i; A.230.a.4.i; A.231.a.4.i; A.232.a.4.i;
A.233.a.4.i; A.234.a.4.i; A.235.a.4.i; A.236.a.4.i; A.237.a.4.i; A.238.a.4.i; A.239.a.4.i;
A.240.a.4.i; A.241.a.4.i; A.242.a.4.i; A.243.a.4.i; A.244.a.4.i; A.245.a.4.i; A.246.a.4.i;
A.247.a.4.i; A.248.a.4.i; A.249.a.4.i; A.250.a.4.i; A.251.a.4.i; A.252.a.4.i; A.253.a.4.i;
A.254.a.4.i; A.255.a.4.i; A.256.a.4.i; A.257.a.4.i; A.258.a.4.i; A.259.a.4.i; A.260.a.4.i;
A.261.a.4.i; A.262.a.4.i; A.263.a.4.i; A.264.a.4.i; A.265.a.4.i; A.266.a.4.i; A.267.a.4.i;
A.268.a.4.i; A.269.a.4.i; A.270.a.4.i; A.271.a.4.i; A.272.a.4.i; A.273.a.4.i; A.274.a.4.i;
A.275.a.4.i; A.276.a.4.i; A.277.a.4.i; A.278.a.4.i; A.279.a.4.i; A.280.a.4.i; A.281.a.4.i;
A.282.a.4.i; A.283.a.4.i; A.284.a.4.i; A.285.a.4.i; A.286.a.4.i; A.287.a.4.i; A.288.a.4.i;
A.289.a.4.i; A.290.a.4.i; A.291.a.4.i; A.292.a.4.i; A.293.a.4.i; A.294.a.4.i; A.295.a.4.i;
A.296.a.4.i; A.297.a.4.i; A.298.a.4.i; A.299.a.4.i; A.300.a.4.i; A.301.a.4.i; A.302.a.4.i;
A.303.a.4.i; A.304.a.4.i; A.305.a.4.i; A.306.a.4.i; A.307.a.4.i; A.308.a.4.i; A.309.a.4.i;
A.310.a.4.i; A.311.a.4.i; A.312.a.4.i; A.313.a.4.i; A.314.a.4.i; A.315.a.4.i; A.316.a.4.i;
A.317.a.4.i; A.318.a.4.i; A.319.a.4.i; A.320.a.4.i; A.321.a.4.i; A.323.a.4.i; A.324.a.4.i;
A.325.a.4.i; A.326.a.4.i; A.327.a.4.i; A.328.a.4.i; A.329.a.4.i; A.330.a.4.i; A.331.a.4.i;
A.332.a.4.i; A.333.a.4.i; A.334.a.4.i; A.335.a.4.i; A.336.a.4.i; A.337.a.4.i; A.338.a.4.i;
A.339.a.4.i; A.340.a.4.i; A.341.a.4.i; A.342.a.4.i; A.343.a.4.i; A.344.a.4.i; A.345.a.4.i;
A.346.a.4.i; A.347.a.4.i; A.348.a.4.i; A.349.a.4.i; A.350.a.4.i; A.351.a.4.i; A.352.a.4.i;
A.353.a.4.i; A.354.a.4.i; A.355.a.4.i; A.356.a.4.i; A.357.a.4.i; A.358.a.4.i; A.359.a.4.i;
A.360.a.4.i; A.361.a.4.i; A.362.a.4.i; A.363.a.4.i; A.364.a.4.i; A.365.a.4.i; A.366.a.4.i;
A.367.a.4.i; A.368.a.4.i; A.369.a.4.i; A.370.a.4.i; A.371.a.4.i; A.372.a.4.i; A.373.a.4.i;
A.374.a.4.i; A.375.a.4.i; A.376.a.4.i; A.377.a.4.i; A.378.a.4.i; A.379.a.4.i; A.380.a.4.i;
A.381.a.4.i; A.382.a.4.i; A.383.a.4.i; A.384.a.4.i; A.385.a.4.i; A.386.a.4.i; A.387.a.4.i;
A.388.a.4.i; A.389.a.4.i; A.390.a.4.i; A.391.a.4.i; A.392.a.4.i; A.393.a.4.i; A.394.a.4.i;
A.395.a.4.i; A.396.a.4.i; A.397.a.4.i; A.398.a.4.i; A.399.a.4.i; A.400.a.4.i; A.401.a.4.i;
A.402.a.4.i; A.403.a.4.i; A.404.a.4.i; A.405.a.4.i; A.406.a.4.i; A.407.a.4.i; A.408.a.4.i;
A.409.a.4.i; A.410.a.4.i; A.411.a.4.i; A.412.a.4.i; A.413.a.4.i; A.414.a.4.i; A.415.a.4.i;
A.416.a.4.i; A.417.a.4.i; A.418.a.4.i; A.419.a.4.i; A.420.a.4.i; A.421.a.4.i; A.422.a.4.i;
A.423.a.4.i; A.424.a.4.i; A.425.a.4.i; A.426.a.4.i; A.427.a.4.i; A.428.a.4.i; A.429.a.4.i;
A.430.a.4.i; A.431.a.4.i; A.432.a.4.i; A.433.a.4.i; A.434.a.4.i; A.435.a.4.i; A.436.a.4.i;
A.437.a.4.i; A.438.a.4.i; A.439.a.4.i; A.440.a.4.i; A.441.a.4.i; A.442.a.4.i; A.443.a.4.i;
A.444.a.4.i; A.445.a.4.i; A.446.a.4.i; A.447.a.4.i; A.448.a.4.i; A.449.a.4.i; A.450.a.4.i;
A.451.a.4.i; A.452.a.4.i; A.453.a.4.i; A.454.a.4.i; A.455.a.4.i; A.456.a.4.i; A.457.a.4.i;
A.458.a.4.i; A.459.a.4.i; A.460.a.4.i; A.461.a.4.i; A.462.a.4.i; A.463.a.4.i; A.464.a.4.i;
A.465.a.4.i; A.466.a.4.i; A.467.a.4.i; A.468.a.4.i; A.469.a.4.i; A.470.a.4.i; A.471.a.4.i;
A.472.a.4.i; A.473.a.4.i; A.474.a.4.i; A.475.a.4.i; A.476.a.4.i; A.477.a.4.i; A.478.a.4.i;
A.479.a.4.i; A.480.a.4.i; A.481.a.4.i; A.482.a.4.i; A.483.a.4.i; A.484.a.4.i; A.485.a.4.i;
A.486.a.4.i; A.487.a.4.i; A.488.a.4.i; A.489.a.4.i; A.490.a.4.i; A.491.a.4.i; A.492.a.4.i;
A.493.a.4.i; A.494.a.4.i; A.495.a.4.i; A.496.a.4.i; A.497.a.4.i; A.498.a.4.i; A.499.a.4.i;
A.500.a.4.i; A.501.a.4.i; A.502.a.4.i; A.503.a.4.i; A.504.a.4.i; A.505.a.4.i; A.506.a.4.i;
A.507.a.4.i; A.508.a.4.i; A.509.a.4.i; A.510.a.4.i; A.511.a.4.i; A.512.a.4.i; A.512.a.4.i;
A.513.a.4.i; A.514.a.4.i; A.515.a.4.i; A.516.a.4.i; A.517.a.4.i; A.518.a.4.i; A.519.a.4.i;
A.520.a.4.i; A.521.a.4.i; A.522.a.4.i; A.523.a.4.i; A.524.a.4.i; A.525.a.4.i; A.526.a.4.i;
A.527.a.4.i; A.528.a.4.i; A.529.a.4.i; A.530.a.4.i; A.531.a.4.i; A.532.a.4.i; A.533.a.4.i;
A.534.a.4.i; A.535.a.4.i; A.536.a.4.i; A.537.a.4.i; A.538.a.4.i; A.539.a.4.i; A.540.a.4.i;
A.541.a.4.i; A.542.a.4.i; A.543.a.4.i; A.544.a.4.i; A.545.a.4.i; A.546.a.4.i; A.547.a.4.i;
A.548.a.4.i; A.549.a.4.i; A.550.a.4.i; A.551.a.4.i; A.552.a.4.i; A.553.a.4.i; A.554.a.4.i;
A.555.a.4.i; A.556.a.4.i; A.557.a.4.i; A.558.a.4.i; A.559.a.4.i; A.560.a.4.i; A.561.a.4.i;
A.562.a.4.i; A.563.a.4.i; A.564.a.4.i; A.565.a.4.i; A.566.a.4.i; A.567.a.4.i; A.568.a.4.i;
A.569.a.4.i; A.570.a.4.i; A.571.a.4.i; A.572.a.4.i; A.573.a.4.i; A.574.a.4.i; A.575.a.4.i;
A.576.a.4.i; A.577.a.4.i; A.578.a.4.i; A.579.a.4.i; A.580.a.4.i; A.581.a.4.i; A.582.a.4.i;
A.583.a.4.i; A.584.a.4.i; A.585.a.4.i; A.586.a.4.i; A.587.a.4.i; A.588.a.4.i; A.589.a.4.i;
A.590.a.4.i; A.591.a.4.i; A.592.a.4.i; A.593.a.4.i; A.594.a.4.i; A.595.a.4.i; A.596.a.4.i;
A.597.a.4.i; A.598.a.4.i; A.599.a.4.i; A.600.a.4.i; A.601.a.4.i; A.602.a.4.i; A.603.a.4.i;
A.604.a.4.i; A.605.a.4.i; A.606.a.4.i; A.607.a.4.i; A.608.a.4.i; A.609.a.4.i; A.610.a.4.i;
A.611.a.4.i; A.612.a.4.i; A.613.a.4.i; A.614.a.4.i; A.615.a.4.i; A.616.a.4.i; A.617.a.4.i;
A.618.a.4.i; A.619.a.4.i; A.620.a.4.i; A.621.a.4.i; A.622.a.4.i; A.623.a.4.i; A.624.a.4.i;
A.625.a.4.i; A.626.a.4.i; A.627.a.4.i; A.628.a.4.i; A.629.a.4.i; A.630.a.4.i; A.631.a.4.i;
A.632.a.4.i; A.633.a.4.i; A.634.a.4.i; A.635.a.4.i; A.636.a.4.i; A.637.a.4.i; A.638.a.4.i;
A.639.a.4.i; A.640.a.4.i; A.641.a.4.i; A.642.a.4.i; A.643.a.4.i; A.644.a.4.i; A.645.a.4.i;
A.646.a.4.i; A.647.a.4.i; A.648.a.4.i; A.649.a.4.i; A.650.a.4.i; A.651.a.4.i; A.652.a.4.i;
A.653.a.4.i; A.654.a.4.i; A.655.a.4.i; A.656.a.4.i; A.657.a.4.i; A.658.a.4.i; A.659.a.4.i;
A.660.a.4.i; A.2.a.11.i; A.3.a.11.i; A.4.a.11.i; A.5.a.11.i; A.6.a.11.i; A.7.a.11.i;
A.9.a.11.i; A.10.a.11.i; A.15.a.11.i; A.100.a.11.i; A.101.a.11.i; A.102.a.11.i;

TABLE 6-continued

Exemplary Enumerated Compounds

A.103.a.11.i; A.104.a.11.i; A.105.a.11.i; A.106.a.11.i; A.107.a.11.i; A.108.a.11.i;
A.109.a.11.i; A.110.a.11.i; A.111.a.11.i; A.112.a.11.i; A.113.a.11.i; A.114.a.11.i;
A.115.a.11.i; A.116.a.11.i; A.117.a.11.i; A.118.a.11.i; A.119.a.11.i; A.120.a.11.i;
A.121.a.11.i; A.122.a.11.i; A.123.a.11.i; A.124.a.11.i; A.125.a.11.i; A.126.a.11.i;
A.127.a.11.i; A.128.a.11.i; A.129.a.11.i; A.130.a.11.i; A.131.a.11.i; A.132.a.11.i;
A.133.a.11.i; A.134.a.11.i; A.135.a.11.i; A.136.a.11.i; A.137.a.11.i; A.138.a.11.i;
A.139.a.11.i; A.140.a.11.i; A.141.a.11.i; A.142.a.11.i; A.143.a.11.i; A.144.a.11.i;
A.145.a.11.i; A.146.a.11.i; A.147.a.11.i; A.148.a.11.i; A.149.a.11.i; A.150.a.11.i;
A.151.a.11.i; A.152.a.11.i; A.153.a.11.i; A.154.a.11.i; A.155.a.11.i; A.156.a.11.i;
A.157.a.11.i; A.158.a.11.i; A.159.a.11.i; A.160.a.11.i; A.161.a.11.i; A.162.a.11.i;
A.163.a.11.i; A.164.a.11.i; A.165.a.11.i; A.166.a.11.i; A.167.a.11.i; A.168.a.11.i;
A.169.a.11.i; A.170.a.11.i; A.171.a.11.i; A.172.a.11.i; A.173.a.11.i; A.174.a.11.i;
A.175.a.11.i; A.176.a.11.i; A.177.a.11.i; A.178.a.11.i; A.179.a.11.i; A.180.a.11.i;
A.181.a.11.i; A.182.a.11.i; A.183.a.11.i; A.184.a.11.i; A.185.a.11.i; A.186.a.11.i;
A.187.a.11.i; A.188.a.11.i; A.189.a.11.i; A.190.a.11.i; A.191.a.11.i; A.192.a.11.i;
A.193.a.11.i; A.194.a.11.i; A.195.a.11.i; A.196.a.11.i; A.197.a.11.i; A.198.a.11.i;
A.199.a.11.i; A.200.a.11.i; A.201.a.11.i; A.202.a.11.i; A.203.a.11.i; A.204.a.11.i;
A.205.a.11.i; A.206.a.11.i; A.207.a.11.i; A.208.a.11.i; A.209.a.11.i; A.210.a.11.i;
A.211.a.11.i; A.212.a.11.i; A.213.a.11.i; A.214.a.11.i; A.215.a.11.i; A.216.a.11.i;
A.217.a.11.i; A.218.a.11.i; A.219.a.11.i; A.220.a.11.i; A.221.a.11.i; A.222.a.11.i;
A.223.a.11.i; A.224.a.11.i; A.225.a.11.i; A.226.a.11.i; A.227.a.11.i; A.228.a.11.i;
A.229.a.11.i; A.230.a.11.i; A.231.a.11.i; A.232.a.11.i; A.233.a.11.i; A.234.a.11.i;
A.235.a.11.i; A.236.a.11.i; A.237.a.11.i; A.238.a.11.i; A.239.a.11.i; A.240.a.11.i;
A.241.a.11.i; A.242.a.11.i; A.243.a.11.i; A.244.a.11.i; A.245.a.11.i; A.246.a.11.i;
A.247.a.11.i; A.248.a.11.i; A.249.a.11.i; A.250.a.11.i; A.251.a.11.i; A.252.a.11.i;
A.253.a.11.i; A.254.a.11.i; A.255.a.11.i; A.256.a.11.i; A.257.a.11.i; A.258.a.11.i;
A.259.a.11.i; A.260.a.11.i; A.261.a.11.i; A.262.a.11.i; A.263.a.11.i; A.264.a.11.i;
A.265.a.11.i; A.266.a.11.i; A.267.a.11.i; A.268.a.11.i; A.269.a.11.i; A.270.a.11.i;
A.271.a.11.i; A.272.a.11.i; A.273.a.11.i; A.274.a.11.i; A.275.a.11.i; A.276.a.11.i;
A.277.a.11.i; A.278.a.11.i; A.279.a.11.i; A.280.a.11.i; A.281.a.11.i; A.282.a.11.i;
A.283.a.11.i; A.284.a.11.i; A.285.a.11.i; A.286.a.11.i; A.287.a.11.i; A.288.a.11.i;
A.289.a.11.i; A.290.a.11.i; A.291.a.11.i; A.292.a.11.i; A.293.a.11.i; A.294.a.11.i;
A.295.a.11.i; A.296.a.11.i; A.297.a.11.i; A.298.a.11.i; A.299.a.11.i; A.300.a.11.i;
A.301.a.11.i; A.302.a.11.i; A.303.a.11.i; A.304.a.11.i; A.305.a.11.i; A.306.a.11.i;
A.307.a.11.i; A.308.a.11.i; A.309.a.11.i; A.310.a.11.i; A.311.a.11.i; A.312.a.11.i;
A.313.a.11.i; A.314.a.11.i; A.315.a.11.i; A.316.a.11.i; A.317.a.11.i; A.318.a.11.i;
A.319.a.11.i; A.320.a.11.i; A.321.a.11.i; A.323.a.11.i; A.324.a.11.i; A.325.a.11.i;
A.326.a.11.i; A.327.a.11.i; A.328.a.11.i; A.329.a.11.i; A.330.a.11.i; A.331.a.11.i;
A.332.a.11.i; A.333.a.11.i; A.334.a.11.i; A.335.a.11.i; A.336.a.11.i; A.337.a.11.i;
A.338.a.11.i; A.339.a.11.i; A.340.a.11.i; A.341.a.11.i; A.342.a.11.i; A.343.a.11.i;
A.344.a.11.i; A.345.a.11.i; A.346.a.11.i; A.347.a.11.i; A.348.a.11.i; A.349.a.11.i;
A.350.a.11.i; A.351.a.11.i; A.352.a.11.i; A.353.a.11.i; A.354.a.11.i; A.355.a.11.i;
A.356.a.11.i; A.357.a.11.i; A.358.a.11.i; A.359.a.11.i; A.360.a.11.i; A.361.a.11.i;
A.362.a.11.i; A.363.a.11.i; A.364.a.11.i; A.365.a.11.i; A.366.a.11.i; A.367.a.11.i;
A.368.a.11.i; A.369.a.11.i; A.370.a.11.i; A.371.a.11.i; A.372.a.11.i; A.373.a.11.i;
A.374.a.11.i; A.375.a.11.i; A.376.a.11.i; A.377.a.11.i; A.378.a.11.i; A.379.a.11.i;
A.380.a.11.i; A.381.a.11.i; A.382.a.11.i; A.383.a.11.i; A.384.a.11.i; A.385.a.11.i;
A.386.a.11.i; A.387.a.11.i; A.388.a.11.i; A.389.a.11.i; A.390.a.11.i; A.391.a.11.i;
A.392.a.11.i; A.393.a.11.i; A.394.a.11.i; A.395.a.11.i; A.396.a.11.i; A.397.a.11.i;
A.398.a.11.i; A.399.a.11.i; A.400.a.11.i; A.401.a.11.i; A.402.a.11.i; A.403.a.11.i;
A.404.a.11.i; A.405.a.11.i; A.406.a.11.i; A.407.a.11.i; A.408.a.11.i; A.409.a.11.i;
A.410.a.11.i; A.411.a.11.i; A.412.a.11.i; A.413.a.11.i; A.414.a.11.i; A.415.a.11.i;
A.416.a.11.i; A.417.a.11.i; A.418.a.11.i; A.419.a.11.i; A.420.a.11.i; A.421.a.11.i;
A.422.a.11.i; A.423.a.11.i; A.424.a.11.i; A.425.a.11.i; A.426.a.11.i; A.427.a.11.i;
A.428.a.11.i; A.429.a.11.i; A.430.a.11.i; A.431.a.11.i; A.432.a.11.i; A.433.a.11.i;
A.434.a.11.i; A.435.a.11.i; A.436.a.11.i; A.437.a.11.i; A.438.a.11.i; A.439.a.11.i;
A.440.a.11.i; A.441.a.11.i; A.442.a.11.i; A.443.a.11.i; A.444.a.11.i; A.445.a.11.i;
A.446.a.11.i; A.447.a.11.i; A.448.a.11.i; A.449.a.11.i; A.450.a.11.i; A.451.a.11.i;
A.452.a.11.i; A.453.a.11.i; A.454.a.11.i; A.455.a.11.i; A.456.a.11.i; A.457.a.11.i;
A.458.a.11.i; A.459.a.11.i; A.460.a.11.i; A.461.a.11.i; A.462.a.11.i; A.463.a.11.i;
A.464.a.11.i; A.465.a.11.i; A.466.a.11.i; A.467.a.11.i; A.468.a.11.i; A.469.a.11.i;
A.470.a.11.i; A.471.a.11.i; A.472.a.11.i; A.473.a.11.i; A.474.a.11.i; A.475.a.11.i;
A.476.a.11.i; A.477.a.11.i; A.478.a.11.i; A.479.a.11.i; A.480.a.11.i; A.481.a.11.i;
A.482.a.11.i; A.483.a.11.i; A.484.a.11.i; A.485.a.11.i; A.486.a.11.i; A.487.a.11.i;
A.488.a.11.i; A.489.a.11.i; A.490.a.11.i; A.491.a.11.i; A.492.a.11.i; A.493.a.11.i;
A.494.a.11.i; A.495.a.11.i; A.496.a.11.i; A.497.a.11.i; A.498.a.11.i; A.499.a.11.i;
A.500.a.11.i; A.501.a.11.i; A.502.a.11.i; A.503.a.11.i; A.504.a.11.i; A.505.a.11.i;
A.506.a.11.i; A.507.a.11.i; A.508.a.11.i; A.509.a.11.i; A.510.a.11.i; A.511.a.11.i;
A.512.a.11.i; A.512.a.11.i; A.513.a.11.i; A.514.a.11.i; A.515.a.11.i; A.516.a.11.i;
A.517.a.11.i; A.518.a.11.i; A.519.a.11.i; A.520.a.11.i; A.521.a.11.i; A.522.a.11.i;
A.523.a.11.i; A.524.a.11.i; A.525.a.11.i; A.526.a.11.i; A.527.a.11.i; A.528.a.11.i;
A.529.a.11.i; A.530.a.11.i; A.531.a.11.i; A.532.a.11.i; A.533.a.11.i; A.534.a.11.i;
A.535.a.11.i; A.536.a.11.i; A.537.a.11.i; A.538.a.11.i; A.539.a.11.i; A.540.a.11.i;
A.541.a.11.i; A.542.a.11.i; A.543.a.11.i; A.544.a.11.i; A.545.a.11.i; A.546.a.11.i;
A.547.a.11.i; A.548.a.11.i; A.549.a.11.i; A.550.a.11.i; A.551.a.11.i; A.552.a.11.i;
A.553.a.11.i; A.554.a.11.i; A.555.a.11.i; A.556.a.11.i; A.557.a.11.i; A.558.a.11.i;
A.559.a.11.i; A.560.a.11.i; A.561.a.11.i; A.562.a.11.i; A.563.a.11.i; A.564.a.11.i;

TABLE 6-continued

Exemplary Enumerated Compounds

A.565.a.11.i; A.566.a.11.i; A.567.a.11.i; A.568.a.11.i; A.569.a.11.i; A.570.a.11.i;
A.571.a.11.i; A.572.a.11.i; A.573.a.11.i; A.574.a.11.i; A.575.a.11.i; A.576.a.11.i;
A.577.a.11.i; A.578.a.11.i; A.579.a.11.i; A.580.a.11.i; A.581.a.11.i; A.582.a.11.i;
A.583.a.11.i; A.584.a.11.i; A.585.a.11.i; A.586.a.11.i; A.587.a.11.i; A.588.a.11.i;
A.589.a.11.i; A.590.a.11.i; A.591.a.11.i; A.592.a.11.i; A.593.a.11.i; A.594.a.11.i;
A.595.a.11.i; A.596.a.11.i; A.597.a.11.i; A.598.a.11.i; A.599.a.11.i; A.600.a.11.i;
A.601.a.11.i; A.602.a.11.i; A.603.a.11.i; A.604.a.11.i; A.605.a.11.i; A.606.a.11.i;
A.607.a.11.i; A.608.a.11.i; A.609.a.11.i; A.610.a.11.i; A.611.a.11.i; A.612.a.11.i;
A.613.a.11.i; A.614.a.11.i; A.615.a.11.i; A.616.a.11.i; A.617.a.11.i; A.618.a.11.i;
A.619.a.11.i; A.620.a.11.i; A.621.a.11.i; A.622.a.11.i; A.623.a.11.i; A.624.a.11.i;
A.625.a.11.i; A.626.a.11.i; A.627.a.11.i; A.628.a.11.i; A.629.a.11.i; A.630.a.11.i;
A.631.a.11.i; A.632.a.11.i; A.633.a.11.i; A.634.a.11.i; A.635.a.11.i; A.636.a.11.i;
A.637.a.11.i; A.638.a.11.i; A.639.a.11.i; A.640.a.11.i; A.641.a.11.i; A.642.a.11.i;
A.643.a.11.i; A.644.a.11.i; A.645.a.11.i; A.646.a.11.i; A.647.a.11.i; A.648.a.11.i;
A.649.a.11.i; A.650.a.11.i; A.651.a.11.i; A.652.a.11.i; A.653.a.11.i; A.654.a.11.i;
A.655.a.11.i; A.656.a.11.i; A.657.a.11.i; A.658.a.11.i; A.659.a.11.i; A.660.a.11.i;
A.2.b.4.i; A.3.b.4.i; A.4.b.4.i; A.5.b.4.i; A.6.b.4.i; A.7.b.4.i; A.9.b.4.i; A.10.b.4.i;
A.15.b.4.i; A.100.b.4.i; A.101.b.4.i; A.102.b.4.i; A.103.b.4.i; A.104.b.4.i; A.105.b.4.i;
A.106.b.4.i; A.107.b.4.i; A.108.b.4.i; A.109.b.4.i; A.110.b.4.i; A.111.b.4.i; A.112.b.4.i;
A.113.b.4.i; A.114.b.4.i; A.115.b.4.i; A.116.b.4.i; A.117.b.4.i; A.118.b.4.i; A.119.b.4.i;
A.120.b.4.i; A.121.b.4.i; A.122.b.4.i; A.123.b.4.i; A.124.b.4.i; A.125.b.4.i; A.126.b.4.i;
A.127.b.4.i; A.128.b.4.i; A.129.b.4.i; A.130.b.4.i; A.131.b.4.i; A.132.b.4.i; A.133.b.4.i;
A.134.b.4.i; A.135.b.4.i; A.136.b.4.i; A.137.b.4.i; A.138.b.4.i; A.139.b.4.i; A.140.b.4.i;
A.141.b.4.i; A.142.b.4.i; A.143.b.4.i; A.144.b.4.i; A.145.b.4.i; A.146.b.4.i; A.147.b.4.i;
A.148.b.4.i; A.149.b.4.i; A.150.b.4.i; A.151.b.4.i; A.152.b.4.i; A.153.b.4.i; A.154.b.4.i;
A.155.b.4.i; A.156.b.4.i; A.157.b.4.i; A.158.b.4.i; A.159.b.4.i; A.160.b.4.i; A.161.b.4.i;
A.162.b.4.i; A.163.b.4.i; A.164.b.4.i; A.165.b.4.i; A.166.b.4.i; A.167.b.4.i; A.168.b.4.i;
A.169.b.4.i; A.170.b.4.i; A.171.b.4.i; A.172.b.4.i; A.173.b.4.i; A.174.b.4.i; A.175.b.4.i;
A.176.b.4.i; A.177.b.4.i; A.178.b.4.i; A.179.b.4.i; A.180.b.4.i; A.181.b.4.i; A.182.b.4.i;
A.183.b.4.i; A.184.b.4.i; A.185.b.4.i; A.186.b.4.i; A.187.b.4.i; A.188.b.4.i; A.189.b.4.i;
A.190.b.4.i; A.191.b.4.i; A.192.b.4.i; A.193.b.4.i; A.194.b.4.i; A.195.b.4.i; A.196.b.4.i;
A.197.b.4.i; A.198.b.4.i; A.199.b.4.i; A.200.b.4.i; A.201.b.4.i; A.202.b.4.i; A.203.b.4.i;
A.204.b.4.i; A.205.b.4.i; A.206.b.4.i; A.207.b.4.i; A.208.b.4.i; A.209.b.4.i; A.210.b.4.i;
A.211.b.4.i; A.212.b.4.i; A.213.b.4.i; A.214.b.4.i; A.215.b.4.i; A.216.b.4.i; A.217.b.4.i;
A.218.b.4.i; A.219.b.4.i; A.220.b.4.i; A.221.b.4.i; A.222.b.4.i; A.223.b.4.i; A.224.b.4.i;
A.225.b.4.i; A.226.b.4.i; A.227.b.4.i; A.228.b.4.i; A.229.b.4.i; A.230.b.4.i; A.231.b.4.i;
A.232.b.4.i; A.233.b.4.i; A.234.b.4.i; A.235.b.4.i; A.236.b.4.i; A.237.b.4.i; A.238.b.4.i;
A.239.b.4.i; A.240.b.4.i; A.241.b.4.i; A.242.b.4.i; A.243.b.4.i; A.244.b.4.i; A.245.b.4.i;
A.246.b.4.i; A.247.b.4.i; A.248.b.4.i; A.249.b.4.i; A.250.b.4.i; A.251.b.4.i; A.252.b.4.i;
A.253.b.4.i; A.254.b.4.i; A.255.b.4.i; A.256.b.4.i; A.257.b.4.i; A.258.b.4.i; A.259.b.4.i;
A.260.b.4.i; A.261.b.4.i; A.262.b.4.i; A.263.b.4.i; A.264.b.4.i; A.265.b.4.i; A.266.b.4.i;
A.267.b.4.i; A.268.b.4.i; A.269.b.4.i; A.270.b.4.i; A.271.b.4.i; A.272.b.4.i; A.273.b.4.i;
A.274.b.4.i; A.275.b.4.i; A.276.b.4.i; A.277.b.4.i; A.278.b.4.i; A.279.b.4.i; A.280.b.4.i;
A.281.b.4.i; A.282.b.4.i; A.283.b.4.i; A.284.b.4.i; A.285.b.4.i; A.286.b.4.i; A.287.b.4.i;
A.288.b.4.i; A.289.b.4.i; A.290.b.4.i; A.291.b.4.i; A.292.b.4.i; A.293.b.4.i; A.294.b.4.i;
A.295.b.4.i; A.296.b.4.i; A.297.b.4.i; A.298.b.4.i; A.299.b.4.i; A.300.b.4.i; A.301.b.4.i;
A.302.b.4.i; A.303.b.4.i; A.304.b.4.i; A.305.b.4.i; A.306.b.4.i; A.307.b.4.i; A.308.b.4.i;
A.309.b.4.i; A.310.b.4.i; A.311.b.4.i; A.312.b.4.i; A.313.b.4.i; A.314.b.4.i; A.315.b.4.i;
A.316.b.4.i; A.317.b.4.i; A.318.b.4.i; A.319.b.4.i; A.320.b.4.i; A.321.b.4.i; A.323.b.4.i;
A.324.b.4.i; A.325.b.4.i; A.326.b.4.i; A.327.b.4.i; A.328.b.4.i; A.329.b.4.i; A.330.b.4.i;
A.331.b.4.i; A.332.b.4.i; A.333.b.4.i; A.334.b.4.i; A.335.b.4.i; A.336.b.4.i; A.337.b.4.i;
A.338.b.4.i; A.339.b.4.i; A.340.b.4.i; A.341.b.4.i; A.342.b.4.i; A.343.b.4.i; A.344.b.4.i;
A.345.b.4.i; A.346.b.4.i; A.347.b.4.i; A.348.b.4.i; A.349.b.4.i; A.350.b.4.i; A.351.b.4.i;
A.352.b.4.i; A.353.b.4.i; A.354.b.4.i; A.355.b.4.i; A.356.b.4.i; A.357.b.4.i; A.358.b.4.i;
A.359.b.4.i; A.360.b.4.i; A.361.b.4.i; A.362.b.4.i; A.363.b.4.i; A.364.b.4.i; A.365.b.4.i;
A.366.b.4.i; A.367.b.4.i; A.368.b.4.i; A.369.b.4.i; A.370.b.4.i; A.371.b.4.i; A.372.b.4.i;
A.373.b.4.i; A.374.b.4.i; A.375.b.4.i; A.376.b.4.i; A.377.b.4.i; A.378.b.4.i; A.379.b.4.i;
A.380.b.4.i; A.381.b.4.i; A.382.b.4.i; A.383.b.4.i; A.384.b.4.i; A.385.b.4.i; A.386.b.4.i;
A.387.b.4.i; A.388.b.4.i; A.389.b.4.i; A.390.b.4.i; A.391.b.4.i; A.392.b.4.i; A.393.b.4.i;
A.394.b.4.i; A.395.b.4.i; A.396.b.4.i; A.397.b.4.i; A.398.b.4.i; A.399.b.4.i; A.400.b.4.i;
A.401.b.4.i; A.402.b.4.i; A.403.b.4.i; A.404.b.4.i; A.405.b.4.i; A.406.b.4.i; A.407.b.4.i;
A.408.b.4.i; A.409.b.4.i; A.410.b.4.i; A.411.b.4.i; A.412.b.4.i; A.413.b.4.i; A.414.b.4.i;
A.415.b.4.i; A.416.b.4.i; A.417.b.4.i; A.418.b.4.i; A.419.b.4.i; A.420.b.4.i; A.421.b.4.i;
A.422.b.4.i; A.423.b.4.i; A.424.b.4.i; A.425.b.4.i; A.426.b.4.i; A.427.b.4.i; A.428.b.4.i;
A.429.b.4.i; A.430.b.4.i; A.431.b.4.i; A.432.b.4.i; A.433.b.4.i; A.434.b.4.i; A.435.b.4.i;
A.436.b.4.i; A.437.b.4.i; A.438.b.4.i; A.439.b.4.i; A.440.b.4.i; A.441.b.4.i; A.442.b.4.i;
A.443.b.4.i; A.444.b.4.i; A.445.b.4.i; A.446.b.4.i; A.447.b.4.i; A.448.b.4.i; A.449.b.4.i;
A.450.b.4.i; A.451.b.4.i; A.452.b.4.i; A.453.b.4.i; A.454.b.4.i; A.455.b.4.i; A.456.b.4.i;
A.457.b.4.i; A.458.b.4.i; A.459.b.4.i; A.460.b.4.i; A.461.b.4.i; A.462.b.4.i; A.463.b.4.i;
A.464.b.4.i; A.465.b.4.i; A.466.b.4.i; A.467.b.4.i; A.468.b.4.i; A.469.b.4.i; A.470.b.4.i;
A.471.b.4.i; A.472.b.4.i; A.473.b.4.i; A.474.b.4.i; A.475.b.4.i; A.476.b.4.i; A.477.b.4.i;
A.478.b.4.i; A.479.b.4.i; A.480.b.4.i; A.481.b.4.i; A.482.b.4.i; A.483.b.4.i; A.484.b.4.i;
A.485.b.4.i; A.486.b.4.i; A.487.b.4.i; A.488.b.4.i; A.489.b.4.i; A.490.b.4.i; A.491.b.4.i;
A.492.b.4.i; A.493.b.4.i; A.494.b.4.i; A.495.b.4.i; A.496.b.4.i; A.497.b.4.i; A.498.b.4.i;
A.499.b.4.i; A.500.b.4.i; A.501.b.4.i; A.502.b.4.i; A.503.b.4.i; A.504.b.4.i; A.505.b.4.i;
A.506.b.4.i; A.507.b.4.i; A.508.b.4.i; A.509.b.4.i; A.510.b.4.i; A.511.b.4.i; A.512.b.4.i;
A.512.b.4.i; A.513.b.4.i; A.514.b.4.i; A.515.b.4.i; A.516.b.4.i; A.517.b.4.i; A.518.b.4.i;

TABLE 6-continued

Exemplary Enumerated Compounds

A.519.b.4.i; A.520.b.4.i; A.521.b.4.i; A.522.b.4.i; A.523.b.4.i; A.524.b.4.i; A.525.b.4.i;
A.526.b.4.i; A.527.b.4.i; A.528.b.4.i; A.529.b.4.i; A.530.b.4.i; A.531.b.4.i; A.532.b.4.i;
A.533.b.4.i; A.534.b.4.i; A.535.b.4.i; A.536.b.4.i; A.537.b.4.i; A.538.b.4.i; A.539.b.4.i;
A.540.b.4.i; A.541.b.4.i; A.542.b.4.i; A.543.b.4.i; A.544.b.4.i; A.545.b.4.i; A.546.b.4.i;
A.547.b.4.i; A.548.b.4.i; A.549.b.4.i; A.550.b.4.i; A.551.b.4.i; A.552.b.4.i; A.553.b.4.i;
A.554.b.4.i; A.555.b.4.i; A.556.b.4.i; A.557.b.4.i; A.558.b.4.i; A.559.b.4.i; A.560.b.4.i;
A.561.b.4.i; A.562.b.4.i; A.563.b.4.i; A.564.b.4.i; A.565.b.4.i; A.566.b.4.i; A.567.b.4.i;
A.568.b.4.i; A.569.b.4.i; A.570.b.4.i; A.571.b.4.i; A.572.b.4.i; A.573.b.4.i; A.574.b.4.i;
A.575.b.4.i; A.576.b.4.i; A.577.b.4.i; A.578.b.4.i; A.579.b.4.i; A.580.b.4.i; A.581.b.4.i;
A.582.b.4.i; A.583.b.4.i; A.584.b.4.i; A.585.b.4.i; A.586.b.4.i; A.587.b.4.i; A.588.b.4.i;
A.589.b.4.i; A.590.b.4.i; A.591.b.4.i; A.592.b.4.i; A.593.b.4.i; A.594.b.4.i; A.595.b.4.i;
A.596.b.4.i; A.597.b.4.i; A.598.b.4.i; A.599.b.4.i; A.600.b.4.i; A.601.b.4.i; A.602.b.4.i;
A.603.b.4.i; A.604.b.4.i; A.605.b.4.i; A.606.b.4.i; A.607.b.4.i; A.608.b.4.i; A.609.b.4.i;
A.610.b.4.i; A.611.b.4.i; A.612.b.4.i; A.613.b.4.i; A.614.b.4.i; A.615.b.4.i; A.616.b.4.i;
A.617.b.4.i; A.618.b.4.i; A.619.b.4.i; A.620.b.4.i; A.621.b.4.i; A.622.b.4.i; A.623.b.4.i;
A.624.b.4.i; A.625.b.4.i; A.626.b.4.i; A.627.b.4.i; A.628.b.4.i; A.629.b.4.i; A.630.b.4.i;
A.631.b.4.i; A.632.b.4.i; A.633.b.4.i; A.634.b.4.i; A.635.b.4.i; A.636.b.4.i; A.637.b.4.i;
A.638.b.4.i; A.639.b.4.i; A.640.b.4.i; A.641.b.4.i; A.642.b.4.i; A.643.b.4.i; A.644.b.4.i;
A.645.b.4.i; A.646.b.4.i; A.647.b.4.i; A.648.b.4.i; A.649.b.4.i; A.650.b.4.i; A.651.b.4.i;
A.652.b.4.i; A.653.b.4.i; A.654.b.4.i; A.655.b.4.i; A.656.b.4.i; A.657.b.4.i; A.658.b.4.i;
A.659.b.4.i; A.660.b.4.i; A.2.b.11.i; A.3.b.11.i; A.4.b.11.i; A.5.b.11.i; A.6.b.11.i;
A.7.b.11.i; A.9.b.11.i; A.10.b.11.i; A.15.b.11.i; A.100.b.11.i; A.101.b.11.i;
A.102.b.11.i; A.103.b.11.i; A.104.b.11.i; A.105.b.11.i; A.106.b.11.i; A.107.b.11.i;
A.108.b.11.i; A.109.b.11.i; A.110.b.11.i; A.111.b.11.i; A.112.b.11.i; A.113.b.11.i;
A.114.b.11.i; A.115.b.11.i; A.116.b.11.i; A.117.b.11.i; A.118.b.11.i; A.119.b.11.i;
A.120.b.11.i; A.121.b.11.i; A.122.b.11.i; A.123.b.11.i; A.124.b.11.i; A.125.b.11.i;
A.126.b.11.i; A.127.b.11.i; A.128.b.11.i; A.129.b.11.i; A.130.b.11.i; A.131.b.11.i;
A.132.b.11.i; A.133.b.11.i; A.134.b.11.i; A.135.b.11.i; A.136.b.11.i; A.137.b.11.i;
A.138.b.11.i; A.139.b.11.i; A.140.b.11.i; A.141.b.11.i; A.142.b.11.i; A.143.b.11.i;
A.144.b.11.i; A.145.b.11.i; A.146.b.11.i; A.147.b.11.i; A.148.b.11.i; A.149.b.11.i;
A.150.b.11.i; A.151.b.11.i; A.152.b.11.i; A.153.b.11.i; A.154.b.11.i; A.155.b.11.i;
A.156.b.11.i; A.157.b.11.i; A.158.b.11.i; A.159.b.11.i; A.160.b.11.i; A.161.b.11.i;
A.162.b.11.i; A.163.b.11.i; A.164.b.11.i; A.165.b.11.i; A.166.b.11.i; A.167.b.11.i;
A.168.b.11.i; A.169.b.11.i; A.170.b.11.i; A.171.b.11.i; A.172.b.11.i; A.173.b.11.i;
A.174.b.11.i; A.175.b.11.i; A.176.b.11.i; A.177.b.11.i; A.178.b.11.i; A.179.b.11.i;
A.180.b.11.i; A.181.b.11.i; A.182.b.11.i; A.183.b.11.i; A.184.b.11.i; A.185.b.11.i;
A.186.b.11.i; A.187.b.11.i; A.188.b.11.i; A.189.b.11.i; A.190.b.11.i; A.191.b.11.i;
A.192.b.11.i; A.193.b.11.i; A.194.b.11.i; A.195.b.11.i; A.196.b.11.i; A.197.b.11.i;
A.198.b.11.i; A.199.b.11.i; A.200.b.11.i; A.201.b.11.i; A.202.b.11.i; A.203.b.11.i;
A.204.b.11.i; A.205.b.11.i; A.206.b.11.i; A.207.b.11.i; A.208.b.11.i; A.209.b.11.i;
A.210.b.11.i; A.211.b.11.i; A.212.b.11.i; A.213.b.11.i; A.214.b.11.i; A.215.b.11.i;
A.216.b.11.i; A.217.b.11.i; A.218.b.11.i; A.219.b.11.i; A.220.b.11.i; A.221.b.11.i;
A.222.b.11.i; A.223.b.11.i; A.224.b.11.i; A.225.b.11.i; A.226.b.11.i; A.227.b.11.i;
A.228.b.11.i; A.229.b.11.i; A.230.b.11.i; A.231.b.11.i; A.232.b.11.i; A.233.b.11.i;
A.234.b.11.i; A.235.b.11.i; A.236.b.11.i; A.237.b.11.i; A.238.b.11.i; A.239.b.11.i;
A.240.b.11.i; A.241.b.11.i; A.242.b.11.i; A.243.b.11.i; A.244.b.11.i; A.245.b.11.i;
A.246.b.11.i; A.247.b.11.i; A.248.b.11.i; A.249.b.11.i; A.250.b.11.i; A.251.b.11.i;
A.252.b.11.i; A.253.b.11.i; A.254.b.11.i; A.255.b.11.i; A.256.b.11.i; A.257.b.11.i;
A.258.b.11.i; A.259.b.11.i; A.260.b.11.i; A.261.b.11.i; A.262.b.11.i; A.263.b.11.i;
A.264.b.11.i; A.265.b.11.i; A.266.b.11.i; A.267.b.11.i; A.268.b.11.i; A.269.b.11.i;
A.270.b.11.i; A.271.b.11.i; A.272.b.11.i; A.273.b.11.i; A.274.b.11.i; A.275.b.11.i;
A.276.b.11.i; A.277.b.11.i; A.278.b.11.i; A.279.b.11.i; A.280.b.11.i; A.281.b.11.i;
A.282.b.11.i; A.283.b.11.i; A.284.b.11.i; A.285.b.11.i; A.286.b.11.i; A.287.b.11.i;
A.288.b.11.i; A.289.b.11.i; A.290.b.11.i; A.291.b.11.i; A.292.b.11.i; A.293.b.11.i;
A.294.b.11.i; A.295.b.11.i; A.296.b.11.i; A.297.b.11.i; A.298.b.11.i; A.299.b.11.i;
A.300.b.11.i; A.301.b.11.i; A.302.b.11.i; A.303.b.11.i; A.304.b.11.i; A.305.b.11.i;
A.306.b.11.i; A.307.b.11.i; A.308.b.11.i; A.309.b.11.i; A.310.b.11.i; A.311.b.11.i;
A.312.b.11.i; A.313.b.11.i; A.314.b.11.i; A.315.b.11.i; A.316.b.11.i; A.317.b.11.i;
A.318.b.11.i; A.319.b.11.i; A.320.b.11.i; A.321.b.11.i; A.323.b.11.i; A.324.b.11.i;
A.325.b.11.i; A.326.b.11.i; A.327.b.11.i; A.328.b.11.i; A.329.b.11.i; A.330.b.11.i;
A.331.b.11.i; A.332.b.11.i; A.333.b.11.i; A.334.b.11.i; A.335.b.11.i; A.336.b.11.i;
A.337.b.11.i; A.338.b.11.i; A.339.b.11.i; A.340.b.11.i; A.341.b.11.i; A.342.b.11.i;
A.343.b.11.i; A.344.b.11.i; A.345.b.11.i; A.346.b.11.i; A.347.b.11.i; A.348.b.11.i;
A.349.b.11.i; A.350.b.11.i; A.351.b.11.i; A.352.b.11.i; A.353.b.11.i; A.354.b.11.i;
A.355.b.11.i; A.356.b.11.i; A.357.b.11.i; A.358.b.11.i; A.359.b.11.i; A.360.b.11.i;
A.361.b.11.i; A.362.b.11.i; A.363.b.11.i; A.364.b.11.i; A.365.b.11.i; A.366.b.11.i;
A.367.b.11.i; A.368.b.11.i; A.369.b.11.i; A.370.b.11.i; A.371.b.11.i; A.372.b.11.i;
A.373.b.11.i; A.374.b.11.i; A.375.b.11.i; A.376.b.11.i; A.377.b.11.i; A.378.b.11.i;
A.379.b.11.i; A.380.b.11.i; A.381.b.11.i; A.382.b.11.i; A.383.b.11.i; A.384.b.11.i;
A.385.b.11.i; A.386.b.11.i; A.387.b.11.i; A.388.b.11.i; A.389.b.11.i; A.390.b.11.i;
A.391.b.11.i; A.392.b.11.i; A.393.b.11.i; A.394.b.11.i; A.395.b.11.i; A.396.b.11.i;
A.397.b.11.i; A.398.b.11.i; A.399.b.11.i; A.400.b.11.i; A.401.b.11.i; A.402.b.11.i;
A.403.b.11.i; A.404.b.11.i; A.405.b.11.i; A.406.b.11.i; A.407.b.11.i; A.408.b.11.i;
A.409.b.11.i; A.410.b.11.i; A.411.b.11.i; A.412.b.11.i; A.413.b.11.i; A.414.b.11.i;
A.415.b.11.i; A.416.b.11.i; A.417.b.11.i; A.418.b.11.i; A.419.b.11.i; A.420.b.11.i;
A.421.b.11.i; A.422.b.11.i; A.423.b.11.i; A.424.b.11.i; A.425.b.11.i; A.426.b.11.i;
A.427.b.11.i; A.428.b.11.i; A.429.b.11.i; A.430.b.11.i; A.431.b.11.i; A.432.b.11.i;

TABLE 6-continued

Exemplary Enumerated Compounds

A.433.b.11.i; A.434.b.11.i; A.435.b.11.i; A.436.b.11.i; A.437.b.11.i; A.438.b.11.i;
A.439.b.11.i; A.440.b.11.i; A.441.b.11.i; A.442.b.11.i; A.443.b.11.i; A.444.b.11.i;
A.445.b.11.i; A.446.b.11.i; A.447.b.11.i; A.448.b.11.i; A.449.b.11.i; A.450.b.11.i;
A.451.b.11.i; A.452.b.11.i; A.453.b.11.i; A.454.b.11.i; A.455.b.11.i; A.456.b.11.i;
A.457.b.11.i; A.458.b.11.i; A.459.b.11.i; A.460.b.11.i; A.461.b.11.i; A.462.b.11.i;
A.463.b.11.i; A.464.b.11.i; A.465.b.11.i; A.466.b.11.i; A.467.b.11.i; A.468.b.11.i;
A.469.b.11.i; A.470.b.11.i; A.471.b.11.i; A.472.b.11.i; A.473.b.11.i; A.474.b.11.i;
A.475.b.11.i; A.476.b.11.i; A.477.b.11.i; A.478.b.11.i; A.479.b.11.i; A.480.b.11.i;
A.481.b.11.i; A.482.b.11.i; A.483.b.11.i; A.484.b.11.i; A.485.b.11.i; A.486.b.11.i;
A.487.b.11.i; A.488.b.11.i; A.489.b.11.i; A.490.b.11.i; A.491.b.11.i; A.492.b.11.i;
A.493.b.11.i; A.494.b.11.i; A.495.b.11.i; A.496.b.11.i; A.497.b.11.i; A.498.b.11.i;
A.499.b.11.i; A.500.b.11.i; A.501.b.11.i; A.502.b.11.i; A.503.b.11.i; A.504.b.11.i;
A.505.b.11.i; A.506.b.11.i; A.507.b.11.i; A.508.b.11.i; A.509.b.11.i; A.510.b.11.i;
A.511.b.11.i; A.512.b.11.i; A.512.b.11.i; A.513.b.11.i; A.514.b.11.i; A.515.b.11.i;
A.516.b.11.i; A.517.b.11.i; A.518.b.11.i; A.519.b.11.i; A.520.b.11.i; A.521.b.11.i;
A.522.b.11.i; A.523.b.11.i; A.524.b.11.i; A.525.b.11.i; A.526.b.11.i; A.527.b.11.i;
A.528.b.11.i; A.529.b.11.i; A.530.b.11.i; A.531.b.11.i; A.532.b.11.i; A.533.b.11.i;
A.534.b.11.i; A.535.b.11.i; A.536.b.11.i; A.537.b.11.i; A.538.b.11.i; A.539.b.11.i;
A.540.b.11.i; A.541.b.11.i; A.542.b.11.i; A.543.b.11.i; A.544.b.11.i; A.545.b.11.i;
A.546.b.11.i; A.547.b.11.i; A.548.b.11.i; A.549.b.11.i; A.550.b.11.i; A.551.b.11.i;
A.552.b.11.i; A.553.b.11.i; A.554.b.11.i; A.555.b.11.i; A.556.b.11.i; A.557.b.11.i;
A.558.b.11.i; A.559.b.11.i; A.560.b.11.i; A.561.b.11.i; A.562.b.11.i; A.563.b.11.i;
A.564.b.11.i; A.565.b.11.i; A.566.b.11.i; A.567.b.11.i; A.568.b.11.i; A.569.b.11.i;
A.570.b.11.i; A.571.b.11.i; A.572.b.11.i; A.573.b.11.i; A.574.b.11.i; A.575.b.11.i;
A.576.b.11.i; A.577.b.11.i; A.578.b.11.i; A.579.b.11.i; A.580.b.11.i; A.581.b.11.i;
A.582.b.11.i; A.583.b.11.i; A.584.b.11.i; A.585.b.11.i; A.586.b.11.i; A.587.b.11.i;
A.588.b.11.i; A.589.b.11.i; A.590.b.11.i; A.591.b.11.i; A.592.b.11.i; A.593.b.11.i;
A.594.b.11.i; A.595.b.11.i; A.596.b.11.i; A.597.b.11.i; A.598.b.11.i; A.599.b.11.i;
A.600.b.11.i; A.601.b.11.i; A.602.b.11.i; A.603.b.11.i; A.604.b.11.i; A.605.b.11.i;
A.606.b.11.i; A.607.b.11.i; A.608.b.11.i; A.609.b.11.i; A.610.b.11.i; A.611.b.11.i;
A.612.b.11.i; A.613.b.11.i; A.614.b.11.i; A.615.b.11.i; A.616.b.11.i; A.617.b.11.i;
A.618.b.11.i; A.619.b.11.i; A.620.b.11.i; A.621.b.11.i; A.622.b.11.i; A.623.b.11.i;
A.624.b.11.i; A.625.b.11.i; A.626.b.11.i; A.627.b.11.i; A.628.b.11.i; A.629.b.11.i;
A.630.b.11.i; A.631.b.11.i; A.632.b.11.i; A.633.b.11.i; A.634.b.11.i; A.635.b.11.i;
A.636.b.11.i; A.637.b.11.i; A.638.b.11.i; A.639.b.11.i; A.640.b.11.i; A.641.b.11.i;
A.642.b.11.i; A.643.b.11.i; A.644.b.11.i; A.645.b.11.i; A.646.b.11.i; A.647.b.11.i;
A.648.b.11.i; A.649.b.11.i; A.650.b.11.i; A.651.b.11.i; A.652.b.11.i; A.653.b.11.i;
A.654.b.11.i; A.655.b.11.i; A.656.b.11.i; A.657.b.11.i; A.658.b.11.i; A.659.b.11.i;
A.660.b.11.i; A.2.x.4.i; A.3.x.4.i; A.4.x.4.i; A.5.x.4.i; A.6.x.4.i; A.7.x.4.i; A.9.x.4.i;
A.10.x.4.i; A.15.x.4.i; A.100.x.4.i; A.101.x.4.i; A.102.x.4.i; A.103.x.4.i; A.104.x.4.i;
A.105.x.4.i; A.106.x.4.i; A.107.x.4.i; A.108.x.4.i; A.109.x.4.i; A.110.x.4.i; A.111.x.4.i;
A.112.x.4.i; A.113.x.4.i; A.114.x.4.i; A.115.x.4.i; A.116.x.4.i; A.117.x.4.i; A.118.x.4.i;
A.119.x.4.i; A.120.x.4.i; A.121.x.4.i; A.122.x.4.i; A.123.x.4.i; A.124.x.4.i; A.125.x.4.i;
A.126.x.4.i; A.127.x.4.i; A.128.x.4.i; A.129.x.4.i; A.130.x.4.i; A.131.x.4.i; A.132.x.4.i;
A.133.x.4.i; A.134.x.4.i; A.135.x.4.i; A.136.x.4.i; A.137.x.4.i; A.138.x.4.i; A.139.x.4.i;
A.140.x.4.i; A.141.x.4.i; A.142.x.4.i; A.143.x.4.i; A.144.x.4.i; A.145.x.4.i; A.146.x.4.i;
A.147.x.4.i; A.148.x.4.i; A.149.x.4.i; A.150.x.4.i; A.151.x.4.i; A.152.x.4.i; A.153.x.4.i;
A.154.x.4.i; A.155.x.4.i; A.156.x.4.i; A.157.x.4.i; A.158.x.4.i; A.159.x.4.i; A.160.x.4.i;
A.161.x.4.i; A.162.x.4.i; A.163.x.4.i; A.164.x.4.i; A.165.x.4.i; A.166.x.4.i; A.167.x.4.i;
A.168.x.4.i; A.169.x.4.i; A.170.x.4.i; A.171.x.4.i; A.172.x.4.i; A.173.x.4.i; A.174.x.4.i;
A.175.x.4.i; A.176.x.4.i; A.177.x.4.i; A.178.x.4.i; A.179.x.4.i; A.180.x.4.i; A.181.x.4.i;
A.182.x.4.i; A.183.x.4.i; A.184.x.4.i; A.185.x.4.i; A.186.x.4.i; A.187.x.4.i; A.188.x.4.i;
A.189.x.4.i; A.190.x.4.i; A.191.x.4.i; A.192.x.4.i; A.193.x.4.i; A.194.x.4.i; A.195.x.4.i;
A.196.x.4.i; A.197.x.4.i; A.198.x.4.i; A.199.x.4.i; A.200.x.4.i; A.201.x.4.i; A.202.x.4.i;
A.203.x.4.i; A.204.x.4.i; A.205.x.4.i; A.206.x.4.i; A.207.x.4.i; A.208.x.4.i; A.209.x.4.i;
A.210.x.4.i; A.211.x.4.i; A.212.x.4.i; A.213.x.4.i; A.214.x.4.i; A.215.x.4.i; A.216.x.4.i;
A.217.x.4.i; A.218.x.4.i; A.219.x.4.i; A.220.x.4.i; A.221.x.4.i; A.222.x.4.i; A.223.x.4.i;
A.224.x.4.i; A.225.x.4.i; A.226.x.4.i; A.227.x.4.i; A.228.x.4.i; A.229.x.4.i; A.230.x.4.i;
A.231.x.4.i; A.232.x.4.i; A.233.x.4.i; A.234.x.4.i; A.235.x.4.i; A.236.x.4.i; A.237.x.4.i;
A.238.x.4.i; A.239.x.4.i; A.240.x.4.i; A.241.x.4.i; A.242.x.4.i; A.243.x.4.i; A.244.x.4.i;
A.245.x.4.i; A.246.x.4.i; A.247.x.4.i; A.248.x.4.i; A.249.x.4.i; A.250.x.4.i; A.251.x.4.i;
A.252.x.4.i; A.253.x.4.i; A.254.x.4.i; A.255.x.4.i; A.256.x.4.i; A.257.x.4.i; A.258.x.4.i;
A.259.x.4.i; A.260.x.4.i; A.261.x.4.i; A.262.x.4.i; A.263.x.4.i; A.264.x.4.i; A.265.x.4.i;
A.266.x.4.i; A.267.x.4.i; A.268.x.4.i; A.269.x.4.i; A.270.x.4.i; A.271.x.4.i; A.272.x.4.i;
A.273.x.4.i; A.274.x.4.i; A.275.x.4.i; A.276.x.4.i; A.277.x.4.i; A.278.x.4.i; A.279.x.4.i;
A.280.x.4.i; A.281.x.4.i; A.282.x.4.i; A.283.x.4.i; A.284.x.4.i; A.285.x.4.i; A.286.x.4.i;
A.287.x.4.i; A.288.x.4.i; A.289.x.4.i; A.290.x.4.i; A.291.x.4.i; A.292.x.4.i; A.293.x.4.i;
A.294.x.4.i; A.295.x.4.i; A.296.x.4.i; A.297.x.4.i; A.298.x.4.i; A.299.x.4.i; A.300.x.4.i;
A.301.x.4.i; A.302.x.4.i; A.303.x.4.i; A.304.x.4.i; A.305.x.4.i; A.306.x.4.i; A.307.x.4.i;
A.308.x.4.i; A.309.x.4.i; A.310.x.4.i; A.311.x.4.i; A.312.x.4.i; A.313.x.4.i; A.314.x.4.i;
A.315.x.4.i; A.316.x.4.i; A.317.x.4.i; A.318.x.4.i; A.319.x.4.i; A.320.x.4.i; A.321.x.4.i;
A.323.x.4.i; A.324.x.4.i; A.325.x.4.i; A.326.x.4.i; A.327.x.4.i; A.328.x.4.i; A.329.x.4.i;
A.330.x.4.i; A.331.x.4.i; A.332.x.4.i; A.333.x.4.i; A.334.x.4.i; A.335.x.4.i; A.336.x.4.i;
A.337.x.4.i; A.338.x.4.i; A.339.x.4.i; A.340.x.4.i; A.341.x.4.i; A.342.x.4.i; A.343.x.4.i;
A.344.x.4.i; A.345.x.4.i; A.346.x.4.i; A.347.x.4.i; A.348.x.4.i; A.349.x.4.i; A.350.x.4.i;
A.351.x.4.i; A.352.x.4.i; A.353.x.4.i; A.354.x.4.i; A.355.x.4.i; A.356.x.4.i; A.357.x.4.i;
A.358.x.4.i; A.359.x.4.i; A.360.x.4.i; A.361.x.4.i; A.362.x.4.i; A.363.x.4.i; A.364.x.4.i;

TABLE 6-continued

Exemplary Enumerated Compounds

A.365.x.4.i; A.366.x.4.i; A.367.x.4.i; A.368.x.4.i; A.369.x.4.i; A.370.x.4.i; A.371.x.4.i;
A.372.x.4.i; A.373.x.4.i; A.374.x.4.i; A.375.x.4.i; A.376.x.4.i; A.377.x.4.i; A.378.x.4.i;
A.379.x.4.i; A.380.x.4.i; A.381.x.4.i; A.382.x.4.i; A.383.x.4.i; A.384.x.4.i; A.385.x.4.i;
A.386.x.4.i; A.387.x.4.i; A.388.x.4.i; A.389.x.4.i; A.390.x.4.i; A.391.x.4.i; A.392.x.4.i;
A.393.x.4.i; A.394.x.4.i; A.395.x.4.i; A.396.x.4.i; A.397.x.4.i; A.398.x.4.i; A.399.x.4.i;
A.400.x.4.i; A.401.x.4.i; A.402.x.4.i; A.403.x.4.i; A.404.x.4.i; A.405.x.4.i; A.406.x.4.i;
A.407.x.4.i; A.408.x.4.i; A.409.x.4.i; A.410.x.4.i; A.411.x.4.i; A.412.x.4.i; A.413.x.4.i;
A.414.x.4.i; A.415.x.4.i; A.416.x.4.i; A.417.x.4.i; A.418.x.4.i; A.419.x.4.i; A.420.x.4.i;
A.421.x.4.i; A.422.x.4.i; A.423.x.4.i; A.424.x.4.i; A.425.x.4.i; A.426.x.4.i; A.427.x.4.i;
A.428.x.4.i; A.429.x.4.i; A.430.x.4.i; A.431.x.4.i; A.432.x.4.i; A.433.x.4.i; A.434.x.4.i;
A.435.x.4.i; A.436.x.4.i; A.437.x.4.i; A.438.x.4.i; A.439.x.4.i; A.440.x.4.i; A.441.x.4.i;
A.442.x.4.i; A.443.x.4.i; A.444.x.4.i; A.445.x.4.i; A.446.x.4.i; A.447.x.4.i; A.448.x.4.i;
A.449.x.4.i; A.450.x.4.i; A.451.x.4.i; A.452.x.4.i; A.453.x.4.i; A.454.x.4.i; A.455.x.4.i;
A.456.x.4.i; A.457.x.4.i; A.458.x.4.i; A.459.x.4.i; A.460.x.4.i; A.461.x.4.i; A.462.x.4.i;
A.463.x.4.i; A.464.x.4.i; A.465.x.4.i; A.466.x.4.i; A.467.x.4.i; A.468.x.4.i; A.469.x.4.i;
A.470.x.4.i; A.471.x.4.i; A.472.x.4.i; A.473.x.4.i; A.474.x.4.i; A.475.x.4.i; A.476.x.4.i;
A.477.x.4.i; A.478.x.4.i; A.479.x.4.i; A.480.x.4.i; A.481.x.4.i; A.482.x.4.i; A.483.x.4.i;
A.484.x.4.i; A.485.x.4.i; A.486.x.4.i; A.487.x.4.i; A.488.x.4.i; A.489.x.4.i; A.490.x.4.i;
A.491.x.4.i; A.492.x.4.i; A.493.x.4.i; A.494.x.4.i; A.495.x.4.i; A.496.x.4.i; A.497.x.4.i;
A.498.x.4.i; A.499.x.4.i; A.500.x.4.i; A.501.x.4.i; A.502.x.4.i; A.503.x.4.i; A.504.x.4.i;
A.505.x.4.i; A.506.x.4.i; A.507.x.4.i; A.508.x.4.i; A.509.x.4.i; A.510.x.4.i; A.511.x.4.i;
A.512.x.4.i; A.512.x.4.i; A.513.x.4.i; A.514.x.4.i; A.515.x.4.i; A.516.x.4.i; A.517.x.4.i;
A.518.x.4.i; A.519.x.4.i; A.520.x.4.i; A.521.x.4.i; A.522.x.4.i; A.523.x.4.i; A.524.x.4.i;
A.525.x.4.i; A.526.x.4.i; A.527.x.4.i; A.528.x.4.i; A.529.x.4.i; A.530.x.4.i; A.531.x.4.i;
A.532.x.4.i; A.533.x.4.i; A.534.x.4.i; A.535.x.4.i; A.536.x.4.i; A.537.x.4.i; A.538.x.4.i;
A.539.x.4.i; A.540.x.4.i; A.541.x.4.i; A.542.x.4.i; A.543.x.4.i; A.544.x.4.i; A.545.x.4.i;
A.546.x.4.i; A.547.x.4.i; A.548.x.4.i; A.549.x.4.i; A.550.x.4.i; A.551.x.4.i; A.552.x.4.i;
A.553.x.4.i; A.554.x.4.i; A.555.x.4.i; A.556.x.4.i; A.557.x.4.i; A.558.x.4.i; A.559.x.4.i;
A.560.x.4.i; A.561.x.4.i; A.562.x.4.i; A.563.x.4.i; A.564.x.4.i; A.565.x.4.i; A.566.x.4.i;
A.567.x.4.i; A.568.x.4.i; A.569.x.4.i; A.570.x.4.i; A.571.x.4.i; A.572.x.4.i; A.573.x.4.i;
A.574.x.4.i; A.575.x.4.i; A.576.x.4.i; A.577.x.4.i; A.578.x.4.i; A.579.x.4.i; A.580.x.4.i;
A.581.x.4.i; A.582.x.4.i; A.583.x.4.i; A.584.x.4.i; A.585.x.4.i; A.586.x.4.i; A.587.x.4.i;
A.588.x.4.i; A.589.x.4.i; A.590.x.4.i; A.591.x.4.i; A.592.x.4.i; A.593.x.4.i; A.594.x.4.i;
A.595.x.4.i; A.596.x.4.i; A.597.x.4.i; A.598.x.4.i; A.599.x.4.i; A.600.x.4.i; A.601.x.4.i;
A.602.x.4.i; A.603.x.4.i; A.604.x.4.i; A.605.x.4.i; A.606.x.4.i; A.607.x.4.i; A.608.x.4.i;
A.609.x.4.i; A.610.x.4.i; A.611.x.4.i; A.612.x.4.i; A.613.x.4.i; A.614.x.4.i; A.615.x.4.i;
A.616.x.4.i; A.617.x.4.i; A.618.x.4.i; A.619.x.4.i; A.620.x.4.i; A.621.x.4.i; A.622.x.4.i;
A.623.x.4.i; A.624.x.4.i; A.625.x.4.i; A.626.x.4.i; A.627.x.4.i; A.628.x.4.i; A.629.x.4.i;
A.630.x.4.i; A.631.x.4.i; A.632.x.4.i; A.633.x.4.i; A.634.x.4.i; A.635.x.4.i; A.636.x.4.i;
A.637.x.4.i; A.638.x.4.i; A.639.x.4.i; A.640.x.4.i; A.641.x.4.i; A.642.x.4.i; A.643.x.4.i;
A.644.x.4.i; A.645.x.4.i; A.646.x.4.i; A.647.x.4.i; A.648.x.4.i; A.649.x.4.i; A.650.x.4.i;
A.651.x.4.i; A.652.x.4.i; A.653.x.4.i; A.654.x.4.i; A.655.x.4.i; A.656.x.4.i; A.657.x.4.i;
A.658.x.4.i; A.659.x.4.i; A.660.x.4.i; A.2.x.11.i; A.3.x.11.i; A.4.x.11.i; A.5.x.11.i;
A.6.x.11.i; A.7.x.11.i; A.9.x.11.i; A.10.x.11.i; A.15.x.11.i; A.100.x.11.i; A.101.x.11.i;
A.102.x.11.i; A.103.x.11.i; A.104.x.11.i; A.105.x.11.i; A.106.x.11.i; A.107.x.11.i;
A.108.x.11.i; A.109.x.11.i; A.110.x.11.i; A.111.x.11.i; A.112.x.11.i; A.113.x.11.i;
A.114.x.11.i; A.115.x.11.i; A.116.x.11.i; A.117.x.11.i; A.118.x.11.i; A.119.x.11.i;
A.120.x.11.i; A.121.x.11.i; A.122.x.11.i; A.123.x.11.i; A.124.x.11.i; A.125.x.11.i;
A.126.x.11.i; A.127.x.11.i; A.128.x.11.i; A.129.x.11.i; A.130.x.11.i; A.131.x.11.i;
A.132.x.11.i; A.133.x.11.i; A.134.x.11.i; A.135.x.11.i; A.136.x.11.i; A.137.x.11.i;
A.138.x.11.i; A.139.x.11.i; A.140.x.11.i; A.141.x.11.i; A.142.x.11.i; A.143.x.11.i;
A.144.x.11.i; A.145.x.11.i; A.146.x.11.i; A.147.x.11.i; A.148.x.11.i; A.149.x.11.i;
A.150.x.11.i; A.151.x.11.i; A.152.x.11.i; A.153.x.11.i; A.154.x.11.i; A.155.x.11.i;
A.156.x.11.i; A.157.x.11.i; A.158.x.11.i; A.159.x.11.i; A.160.x.11.i; A.161.x.11.i;
A.162.x.11.i; A.163.x.11.i; A.164.x.11.i; A.165.x.11.i; A.166.x.11.i; A.167.x.11.i;
A.168.x.11.i; A.169.x.11.i; A.170.x.11.i; A.171.x.11.i; A.172.x.11.i; A.173.x.11.i;
A.174.x.11.i; A.175.x.11.i; A.176.x.11.i; A.177.x.11.i; A.178.x.11.i; A.179.x.11.i;
A.180.x.11.i; A.181.x.11.i; A.182.x.11.i; A.183.x.11.i; A.184.x.11.i; A.185.x.11.i;
A.186.x.11.i; A.187.x.11.i; A.188.x.11.i; A.189.x.11.i; A.190.x.11.i; A.191.x.11.i;
A.192.x.11.i; A.193.x.11.i; A.194.x.11.i; A.195.x.11.i; A.196.x.11.i; A.197.x.11.i;
A.198.x.11.i; A.199.x.11.i; A.200.x.11.i; A.201.x.11.i; A.202.x.11.i; A.203.x.11.i;
A.204.x.11.i; A.205.x.11.i; A.206.x.11.i; A.207.x.11.i; A.208.x.11.i; A.209.x.11.i;
A.210.x.11.i; A.211.x.11.i; A.212.x.11.i; A.213.x.11.i; A.214.x.11.i; A.215.x.11.i;
A.216.x.11.i; A.217.x.11.i; A.218.x.11.i; A.219.x.11.i; A.220.x.11.i; A.221.x.11.i;
A.222.x.11.i; A.223.x.11.i; A.224.x.11.i; A.225.x.11.i; A.226.x.11.i; A.227.x.11.i;
A.228.x.11.i; A.229.x.11.i; A.230.x.11.i; A.231.x.11.i; A.232.x.11.i; A.233.x.11.i;
A.234.x.11.i; A.235.x.11.i; A.236.x.11.i; A.237.x.11.i; A.238.x.11.i; A.239.x.11.i;
A.240.x.11.i; A.241.x.11.i; A.242.x.11.i; A.243.x.11.i; A.244.x.11.i; A.245.x.11.i;
A.246.x.11.i; A.247.x.11.i; A.248.x.11.i; A.249.x.11.i; A.250.x.11.i; A.251.x.11.i;
A.252.x.11.i; A.253.x.11.i; A.254.x.11.i; A.255.x.11.i; A.256.x.11.i; A.257.x.11.i;
A.258.x.11.i; A.259.x.11.i; A.260.x.11.i; A.261.x.11.i; A.262.x.11.i; A.263.x.11.i;
A.264.x.11.i; A.265.x.11.i; A.266.x.11.i; A.267.x.11.i; A.268.x.11.i; A.269.x.11.i;
A.270.x.11.i; A.271.x.11.i; A.272.x.11.i; A.273.x.11.i; A.274.x.11.i; A.275.x.11.i;
A.276.x.11.i; A.277.x.11.i; A.278.x.11.i; A.279.x.11.i; A.280.x.11.i; A.281.x.11.i;
A.282.x.11.i; A.283.x.11.i; A.284.x.11.i; A.285.x.11.i; A.286.x.11.i; A.287.x.11.i;
A.288.x.11.i; A.289.x.11.i; A.290.x.11.i; A.291.x.11.i; A.292.x.11.i; A.293.x.11.i;
A.294.x.11.i; A.295.x.11.i; A.296.x.11.i; A.297.x.11.i; A.298.x.11.i; A.299.x.11.i;

TABLE 6-continued

Exemplary Enumerated Compounds

A.300.x.11.i; A.301.x.11.i; A.302.x.11.i; A.303.x.11.i; A.304.x.11.i; A.305.x.11.i;
A.306.x.11.i; A.307.x.11.i; A.308.x.11.i; A.309.x.11.i; A.310.x.11.i; A.311.x.11.i;
A.312.x.11.i; A.313.x.11.i; A.314.x.11.i; A.315.x.11.i; A.316.x.11.i; A.317.x.11.i;
A.318.x.11.i; A.319.x.11.i; A.320.x.11.i; A.321.x.11.i; A.323.x.11.i; A.324.x.11.i;
A.325.x.11.i; A.326.x.11.i; A.327.x.11.i; A.328.x.11.i; A.329.x.11.i; A.330.x.11.i;
A.331.x.11.i; A.332.x.11.i; A.333.x.11.i; A.334.x.11.i; A.335.x.11.i; A.336.x.11.i;
A.337.x.11.i; A.338.x.11.i; A.339.x.11.i; A.340.x.11.i; A.341.x.11.i; A.342.x.11.i;
A.343.x.11.i; A.344.x.11.i; A.345.x.11.i; A.346.x.11.i; A.347.x.11.i; A.348.x.11.i;
A.349.x.11.i; A.350.x.11.i; A.351.x.11.i; A.352.x.11.i; A.353.x.11.i; A.354.x.11.i;
A.355.x.11.i; A.356.x.11.i; A.357.x.11.i; A.358.x.11.i; A.359.x.11.i; A.360.x.11.i;
A.361.x.11.i; A.362.x.11.i; A.363.x.11.i; A.364.x.11.i; A.365.x.11.i; A.366.x.11.i;
A.367.x.11.i; A.368.x.11.i; A.369.x.11.i; A.370.x.11.i; A.371.x.11.i; A.372.x.11.i;
A.373.x.11.i; A.374.x.11.i; A.375.x.11.i; A.376.x.11.i; A.377.x.11.i; A.378.x.11.i;
A.379.x.11.i; A.380.x.11.i; A.381.x.11.i; A.382.x.11.i; A.383.x.11.i; A.384.x.11.i;
A.385.x.11.i; A.386.x.11.i; A.387.x.11.i; A.388.x.11.i; A.389.x.11.i; A.390.x.11.i;
A.391.x.11.i; A.392.x.11.i; A.393.x.11.i; A.394.x.11.i; A.395.x.11.i; A.396.x.11.i;
A.397.x.11.i; A.398.x.11.i; A.399.x.11.i; A.400.x.11.i; A.401.x.11.i; A.402.x.11.i;
A.403.x.11.i; A.404.x.11.i; A.405.x.11.i; A.406.x.11.i; A.407.x.11.i; A.408.x.11.i;
A.409.x.11.i; A.410.x.11.i; A.411.x.11.i; A.412.x.11.i; A.413.x.11.i; A.414.x.11.i;
A.415.x.11.i; A.416.x.11.i; A.417.x.11.i; A.418.x.11.i; A.419.x.11.i; A.420.x.11.i;
A.421.x.11.i; A.422.x.11.i; A.423.x.11.i; A.424.x.11.i; A.425.x.11.i; A.426.x.11.i;
A.427.x.11.i; A.428.x.11.i; A.429.x.11.i; A.430.x.11.i; A.431.x.11.i; A.432.x.11.i;
A.433.x.11.i; A.434.x.11.i; A.435.x.11.i; A.436.x.11.i; A.437.x.11.i; A.438.x.11.i;
A.439.x.11.i; A.440.x.11.i; A.441.x.11.i; A.442.x.11.i; A.443.x.11.i; A.444.x.11.i;
A.445.x.11.i; A.446.x.11.i; A.447.x.11.i; A.448.x.11.i; A.449.x.11.i; A.450.x.11.i;
A.451.x.11.i; A.452.x.11.i; A.453.x.11.i; A.454.x.11.i; A.455.x.11.i; A.456.x.11.i;
A.457.x.11.i; A.458.x.11.i; A.459.x.11.i; A.460.x.11.i; A.461.x.11.i; A.462.x.11.i;
A.463.x.11.i; A.464.x.11.i; A.465.x.11.i; A.466.x.11.i; A.467.x.11.i; A.468.x.11.i;
A.469.x.11.i; A.470.x.11.i; A.471.x.11.i; A.472.x.11.i; A.473.x.11.i; A.474.x.11.i;
A.475.x.11.i; A.476.x.11.i; A.477.x.11.i; A.478.x.11.i; A.479.x.11.i; A.480.x.11.i;
A.481.x.11.i; A.482.x.11.i; A.483.x.11.i; A.484.x.11.i; A.485.x.11.i; A.486.x.11.i;
A.487.x.11.i; A.488.x.11.i; A.489.x.11.i; A.490.x.11.i; A.491.x.11.i; A.492.x.11.i;
A.493.x.11.i; A.494.x.11.i; A.495.x.11.i; A.496.x.11.i; A.497.x.11.i; A.498.x.11.i;
A.499.x.11.i; A.500.x.11.i; A.501.x.11.i; A.502.x.11.i; A.503.x.11.i; A.504.x.11.i;
A.505.x.11.i; A.506.x.11.i; A.507.x.11.i; A.508.x.11.i; A.509.x.11.i; A.510.x.11.i;
A.511.x.11.i; A.512.x.11.i; A.512.x.11.i; A.513.x.11.i; A.514.x.11.i; A.515.x.11.i;
A.516.x.11.i; A.517.x.11.i; A.518.x.11.i; A.519.x.11.i; A.520.x.11.i; A.521.x.11.i;
A.522.x.11.i; A.523.x.11.i; A.524.x.11.i; A.525.x.11.i; A.526.x.11.i; A.527.x.11.i;
A.528.x.11.i; A.529.x.11.i; A.530.x.11.i; A.531.x.11.i; A.532.x.11.i; A.533.x.11.i;
A.534.x.11.i; A.535.x.11.i; A.536.x.11.i; A.537.x.11.i; A.538.x.11.i; A.539.x.11.i;
A.540.x.11.i; A.541.x.11.i; A.542.x.11.i; A.543.x.11.i; A.544.x.11.i; A.545.x.11.i;
A.546.x.11.i; A.547.x.11.i; A.548.x.11.i; A.549.x.11.i; A.550.x.11.i; A.551.x.11.i;
A.552.x.11.i; A.553.x.11.i; A.554.x.11.i; A.555.x.11.i; A.556.x.11.i; A.557.x.11.i;
A.558.x.11.i; A.559.x.11.i; A.560.x.11.i; A.561.x.11.i; A.562.x.11.i; A.563.x.11.i;
A.564.x.11.i; A.565.x.11.i; A.566.x.11.i; A.567.x.11.i; A.568.x.11.i; A.569.x.11.i;
A.570.x.11.i; A.571.x.11.i; A.572.x.11.i; A.573.x.11.i; A.574.x.11.i; A.575.x.11.i;
A.576.x.11.i; A.577.x.11.i; A.578.x.11.i; A.579.x.11.i; A.580.x.11.i; A.581.x.11.i;
A.582.x.11.i; A.583.x.11.i; A.584.x.11.i; A.585.x.11.i; A.586.x.11.i; A.587.x.11.i;
A.588.x.11.i; A.589.x.11.i; A.590.x.11.i; A.591.x.11.i; A.592.x.11.i; A.593.x.11.i;
A.594.x.11.i; A.595.x.11.i; A.596.x.11.i; A.597.x.11.i; A.598.x.11.i; A.599.x.11.i;
A.600.x.11.i; A.601.x.11.i; A.602.x.11.i; A.603.x.11.i; A.604.x.11.i; A.605.x.11.i;
A.606.x.11.i; A.607.x.11.i; A.608.x.11.i; A.609.x.11.i; A.610.x.11.i; A.611.x.11.i;
A.612.x.11.i; A.613.x.11.i; A.614.x.11.i; A.615.x.11.i; A.616.x.11.i; A.617.x.11.i;
A.618.x.11.i; A.619.x.11.i; A.620.x.11.i; A.621.x.11.i; A.622.x.11.i; A.623.x.11.i;
A.624.x.11.i; A.625.x.11.i; A.626.x.11.i; A.627.x.11.i; A.628.x.11.i; A.629.x.11.i;
A.630.x.11.i; A.631.x.11.i; A.632.x.11.i; A.633.x.11.i; A.634.x.11.i; A.635.x.11.i;
A.636.x.11.i; A.637.x.11.i; A.638.x.11.i; A.639.x.11.i; A.640.x.11.i; A.641.x.11.i;
A.642.x.11.i; A.643.x.11.i; A.644.x.11.i; A.645.x.11.i; A.646.x.11.i; A.647.x.11.i;
A.648.x.11.i; A.649.x.11.i; A.650.x.11.i; A.651.x.11.i; A.652.x.11.i; A.653.x.11.i;
A.654.x.11.i; A.655.x.11.i; A.656.x.11.i; A.657.x.11.i; A.658.x.11.i; A.659.x.11.i;
A.660.x.11.i; A.2.y.4.i; A.3.y.4.i; A.4.y.4.i; A.5.y.4.i; A.6.y.4.i; A.7.y.4.i; A.9.y.4.i;
A.10.y.4.i; A.15.y.4.i; A.100.y.4.i; A.101.y.4.i; A.102.y.4.i; A.103.y.4.i; A.104.y.4.i;
A.105.y.4.i; A.106.y.4.i; A.107.y.4.i; A.108.y.4.i; A.109.y.4.i; A.110.y.4.i; A.111.y.4.i;
A.112.y.4.i; A.113.y.4.i; A.114.y.4.i; A.115.y.4.i; A.116.y.4.i; A.117.y.4.i; A.118.y.4.i;
A.119.y.4.i; A.120.y.4.i; A.121.y.4.i; A.122.y.4.i; A.123.y.4.i; A.124.y.4.i; A.125.y.4.i;
A.126.y.4.i; A.127.y.4.i; A.128.y.4.i; A.129.y.4.i; A.130.y.4.i; A.131.y.4.i; A.132.y.4.i;
A.133.y.4.i; A.134.y.4.i; A.135.y.4.i; A.136.y.4.i; A.137.y.4.i; A.138.y.4.i; A.139.y.4.i;
A.140.y.4.i; A.141.y.4.i; A.142.y.4.i; A.143.y.4.i; A.144.y.4.i; A.145.y.4.i; A.146.y.4.i;
A.147.y.4.i; A.148.y.4.i; A.149.y.4.i; A.150.y.4.i; A.151.y.4.i; A.152.y.4.i; A.153.y.4.i;
A.154.y.4.i; A.155.y.4.i; A.156.y.4.i; A.157.y.4.i; A.158.y.4.i; A.159.y.4.i; A.160.y.4.i;
A.161.y.4.i; A.162.y.4.i; A.163.y.4.i; A.164.y.4.i; A.165.y.4.i; A.166.y.4.i; A.167.y.4.i;
A.168.y.4.i; A.169.y.4.i; A.170.y.4.i; A.171.y.4.i; A.172.y.4.i; A.173.y.4.i; A.174.y.4.i;
A.175.y.4.i; A.176.y.4.i; A.177.y.4.i; A.178.y.4.i; A.179.y.4.i; A.180.y.4.i; A.181.y.4.i;
A.182.y.4.i; A.183.y.4.i; A.184.y.4.i; A.185.y.4.i; A.186.y.4.i; A.187.y.4.i; A.188.y.4.i;
A.189.y.4.i; A.190.y.4.i; A.191.y.4.i; A.192.y.4.i; A.193.y.4.i; A.194.y.4.i; A.195.y.4.i;
A.196.y.4.i; A.197.y.4.i; A.198.y.4.i; A.199.y.4.i; A.200.y.4.i; A.201.y.4.i; A.202.y.4.i;
A.203.y.4.i; A.204.y.4.i; A.205.y.4.i; A.206.y.4.i; A.207.y.4.i; A.208.y.4.i; A.209.y.4.i;

TABLE 6-continued

Exemplary Enumerated Compounds

A.210.y.4.i; A.211.y.4.i; A.212.y.4.i; A.213.y.4.i; A.214.y.4.i; A.215.y.4.i; A.216.y.4.i;
A.217.y.4.i; A.218.y.4.i; A.219.y.4.i; A.220.y.4.i; A.221.y.4.i; A.222.y.4.i; A.223.y.4.i;
A.224.y.4.i; A.225.y.4.i; A.226.y.4.i; A.227.y.4.i; A.228.y.4.i; A.229.y.4.i; A.230.y.4.i;
A.231.y.4.i; A.232.y.4.i; A.233.y.4.i; A.234.y.4.i; A.235.y.4.i; A.236.y.4.i; A.237.y.4.i;
A.238.y.4.i; A.239.y.4.i; A.240.y.4.i; A.241.y.4.i; A.242.y.4.i; A.243.y.4.i; A.244.y.4.i;
A.245.y.4.i; A.246.y.4.i; A.247.y.4.i; A.248.y.4.i; A.249.y.4.i; A.250.y.4.i; A.251.y.4.i;
A.252.y.4.i; A.253.y.4.i; A.254.y.4.i; A.255.y.4.i; A.256.y.4.i; A.257.y.4.i; A.258.y.4.i;
A.259.y.4.i; A.260.y.4.i; A.261.y.4.i; A.262.y.4.i; A.263.y.4.i; A.264.y.4.i; A.265.y.4.i;
A.266.y.4.i; A.267.y.4.i; A.268.y.4.i; A.269.y.4.i; A.270.y.4.i; A.271.y.4.i; A.272.y.4.i;
A.273.y.4.i; A.274.y.4.i; A.275.y.4.i; A.276.y.4.i; A.277.y.4.i; A.278.y.4.i; A.279.y.4.i;
A.280.y.4.i; A.281.y.4.i; A.282.y.4.i; A.283.y.4.i; A.284.y.4.i; A.285.y.4.i; A.286.y.4.i;
A.287.y.4.i; A.288.y.4.i; A.289.y.4.i; A.290.y.4.i; A.291.y.4.i; A.292.y.4.i; A.293.y.4.i;
A.294.y.4.i; A.295.y.4.i; A.296.y.4.i; A.297.y.4.i; A.298.y.4.i; A.299.y.4.i; A.300.y.4.i;
A.301.y.4.i; A.302.y.4.i; A.303.y.4.i; A.304.y.4.i; A.305.y.4.i; A.306.y.4.i; A.307.y.4.i;
A.308.y.4.i; A.309.y.4.i; A.310.y.4.i; A.311.y.4.i; A.312.y.4.i; A.313.y.4.i; A.314.y.4.i;
A.315.y.4.i; A.316.y.4.i; A.317.y.4.i; A.318.y.4.i; A.319.y.4.i; A.320.y.4.i; A.321.y.4.i;
A.323.y.4.i; A.324.y.4.i; A.325.y.4.i; A.326.y.4.i; A.327.y.4.i; A.328.y.4.i; A.329.y.4.i;
A.330.y.4.i; A.331.y.4.i; A.332.y.4.i; A.333.y.4.i; A.334.y.4.i; A.335.y.4.i; A.336.y.4.i;
A.337.y.4.i; A.338.y.4.i; A.339.y.4.i; A.340.y.4.i; A.341.y.4.i; A.342.y.4.i; A.343.y.4.i;
A.344.y.4.i; A.345.y.4.i; A.346.y.4.i; A.347.y.4.i; A.348.y.4.i; A.349.y.4.i; A.350.y.4.i;
A.351.y.4.i; A.352.y.4.i; A.353.y.4.i; A.354.y.4.i; A.355.y.4.i; A.356.y.4.i; A.357.y.4.i;
A.358.y.4.i; A.359.y.4.i; A.360.y.4.i; A.361.y.4.i; A.362.y.4.i; A.363.y.4.i; A.364.y.4.i;
A.365.y.4.i; A.366.y.4.i; A.367.y.4.i; A.368.y.4.i; A.369.y.4.i; A.370.y.4.i; A.371.y.4.i;
A.372.y.4.i; A.373.y.4.i; A.374.y.4.i; A.375.y.4.i; A.376.y.4.i; A.377.y.4.i; A.378.y.4.i;
A.379.y.4.i; A.380.y.4.i; A.381.y.4.i; A.382.y.4.i; A.383.y.4.i; A.384.y.4.i; A.385.y.4.i;
A.386.y.4.i; A.387.y.4.i; A.388.y.4.i; A.389.y.4.i; A.390.y.4.i; A.391.y.4.i; A.392.y.4.i;
A.393.y.4.i; A.394.y.4.i; A.395.y.4.i; A.396.y.4.i; A.397.y.4.i; A.398.y.4.i; A.399.y.4.i;
A.400.y.4.i; A.401.y.4.i; A.402.y.4.i; A.403.y.4.i; A.404.y.4.i; A.405.y.4.i; A.406.y.4.i;
A.407.y.4.i; A.408.y.4.i; A.409.y.4.i; A.410.y.4.i; A.411.y.4.i; A.412.y.4.i; A.413.y.4.i;
A.414.y.4.i; A.415.y.4.i; A.416.y.4.i; A.417.y.4.i; A.418.y.4.i; A.419.y.4.i; A.420.y.4.i;
A.421.y.4.i; A.422.y.4.i; A.423.y.4.i; A.424.y.4.i; A.425.y.4.i; A.426.y.4.i; A.427.y.4.i;
A.428.y.4.i; A.429.y.4.i; A.430.y.4.i; A.431.y.4.i; A.432.y.4.i; A.433.y.4.i; A.434.y.4.i;
A.435.y.4.i; A.436.y.4.i; A.437.y.4.i; A.438.y.4.i; A.439.y.4.i; A.440.y.4.i; A.441.y.4.i;
A.442.y.4.i; A.443.y.4.i; A.444.y.4.i; A.445.y.4.i; A.446.y.4.i; A.447.y.4.i; A.448.y.4.i;
A.449.y.4.i; A.450.y.4.i; A.451.y.4.i; A.452.y.4.i; A.453.y.4.i; A.454.y.4.i; A.455.y.4.i;
A.456.y.4.i; A.457.y.4.i; A.458.y.4.i; A.459.y.4.i; A.460.y.4.i; A.461.y.4.i; A.462.y.4.i;
A.463.y.4.i; A.464.y.4.i; A.465.y.4.i; A.466.y.4.i; A.467.y.4.i; A.468.y.4.i; A.469.y.4.i;
A.470.y.4.i; A.471.y.4.i; A.472.y.4.i; A.473.y.4.i; A.474.y.4.i; A.475.y.4.i; A.476.y.4.i;
A.477.y.4.i; A.478.y.4.i; A.479.y.4.i; A.480.y.4.i; A.481.y.4.i; A.482.y.4.i; A.483.y.4.i;
A.484.y.4.i; A.485.y.4.i; A.486.y.4.i; A.487.y.4.i; A.488.y.4.i; A.489.y.4.i; A.490.y.4.i;
A.491.y.4.i; A.492.y.4.i; A.493.y.4.i; A.494.y.4.i; A.495.y.4.i; A.496.y.4.i; A.497.y.4.i;
A.498.y.4.i; A.499.y.4.i; A.500.y.4.i; A.501.y.4.i; A.502.y.4.i; A.503.y.4.i; A.504.y.4.i;
A.505.y.4.i; A.506.y.4.i; A.507.y.4.i; A.508.y.4.i; A.509.y.4.i; A.510.y.4.i; A.511.y.4.i;
A.512.y.4.i; A.512.y.4.i; A.513.y.4.i; A.514.y.4.i; A.515.y.4.i; A.516.y.4.i; A.517.y.4.i;
A.518.y.4.i; A.519.y.4.i; A.520.y.4.i; A.521.y.4.i; A.522.y.4.i; A.523.y.4.i; A.524.y.4.i;
A.525.y.4.i; A.526.y.4.i; A.527.y.4.i; A.528.y.4.i; A.529.y.4.i; A.530.y.4.i; A.531.y.4.i;
A.532.y.4.i; A.533.y.4.i; A.534.y.4.i; A.535.y.4.i; A.536.y.4.i; A.537.y.4.i; A.538.y.4.i;
A.539.y.4.i; A.540.y.4.i; A.541.y.4.i; A.542.y.4.i; A.543.y.4.i; A.544.y.4.i; A.545.y.4.i;
A.546.y.4.i; A.547.y.4.i; A.548.y.4.i; A.549.y.4.i; A.550.y.4.i; A.551.y.4.i; A.552.y.4.i;
A.553.y.4.i; A.554.y.4.i; A.555.y.4.i; A.556.y.4.i; A.557.y.4.i; A.558.y.4.i; A.559.y.4.i;
A.560.y.4.i; A.561.y.4.i; A.562.y.4.i; A.563.y.4.i; A.564.y.4.i; A.565.y.4.i; A.566.y.4.i;
A.567.y.4.i; A.568.y.4.i; A.569.y.4.i; A.570.y.4.i; A.571.y.4.i; A.572.y.4.i; A.573.y.4.i;
A.574.y.4.i; A.575.y.4.i; A.576.y.4.i; A.577.y.4.i; A.578.y.4.i; A.579.y.4.i; A.580.y.4.i;
A.581.y.4.i; A.582.y.4.i; A.583.y.4.i; A.584.y.4.i; A.585.y.4.i; A.586.y.4.i; A.587.y.4.i;
A.588.y.4.i; A.589.y.4.i; A.590.y.4.i; A.591.y.4.i; A.592.y.4.i; A.593.y.4.i; A.594.y.4.i;
A.595.y.4.i; A.596.y.4.i; A.597.y.4.i; A.598.y.4.i; A.599.y.4.i; A.600.y.4.i; A.601.y.4.i;
A.602.y.4.i; A.603.y.4.i; A.604.y.4.i; A.605.y.4.i; A.606.y.4.i; A.607.y.4.i; A.608.y.4.i;
A.609.y.4.i; A.610.y.4.i; A.611.y.4.i; A.612.y.4.i; A.613.y.4.i; A.614.y.4.i; A.615.y.4.i;
A.616.y.4.i; A.617.y.4.i; A.618.y.4.i; A.619.y.4.i; A.620.y.4.i; A.621.y.4.i; A.622.y.4.i;
A.623.y.4.i; A.624.y.4.i; A.625.y.4.i; A.626.y.4.i; A.627.y.4.i; A.628.y.4.i; A.629.y.4.i;
A.630.y.4.i; A.631.y.4.i; A.632.y.4.i; A.633.y.4.i; A.634.y.4.i; A.635.y.4.i; A.636.y.4.i;
A.637.y.4.i; A.638.y.4.i; A.639.y.4.i; A.640.y.4.i; A.641.y.4.i; A.642.y.4.i; A.643.y.4.i;
A.644.y.4.i; A.645.y.4.i; A.646.y.4.i; A.647.y.4.i; A.648.y.4.i; A.649.y.4.i; A.650.y.4.i;
A.651.y.4.i; A.652.y.4.i; A.653.y.4.i; A.654.y.4.i; A.655.y.4.i; A.656.y.4.i; A.657.y.4.i;
A.658.y.4.i; A.659.y.4.i; A.660.y.4.i; A.2.y.11.i; A.3.y.11.i; A.4.y.11.i; A.5.y.11.i;
A.6.y.11.i; A.7.y.11.i; A.9.y.11.i; A.10.y.11.i; A.15.y.11.i; A.100.y.11.i; A.101.y.11.i;
A.102.y.11.i; A.103.y.11.i; A.104.y.11.i; A.105.y.11.i; A.106.y.11.i; A.107.y.11.i;
A.108.y.11.i; A.109.y.11.i; A.110.y.11.i; A.111.y.11.i; A.112.y.11.i; A.113.y.11.i;
A.114.y.11.i; A.115.y.11.i; A.116.y.11.i; A.117.y.11.i; A.118.y.11.i; A.119.y.11.i;
A.120.y.11.i; A.121.y.11.i; A.122.y.11.i; A.123.y.11.i; A.124.y.11.i; A.125.y.11.i;
A.126.y.11.i; A.127.y.11.i; A.128.y.11.i; A.129.y.11.i; A.130.y.11.i; A.131.y.11.i;
A.132.y.11.i; A.133.y.11.i; A.134.y.11.i; A.135.y.11.i; A.136.y.11.i; A.137.y.11.i;
A.138.y.11.i; A.139.y.11.i; A.140.y.11.i; A.141.y.11.i; A.142.y.11.i; A.143.y.11.i;
A.144.y.11.i; A.145.y.11.i; A.146.y.11.i; A.147.y.11.i; A.148.y.11.i; A.149.y.11.i;
A.150.y.11.i; A.151.y.11.i; A.152.y.11.i; A.153.y.11.i; A.154.y.11.i; A.155.y.11.i;
A.156.y.11.i; A.157.y.11.i; A.158.y.11.i; A.159.y.11.i; A.160.y.11.i; A.161.y.11.i;
A.162.y.11.i; A.163.y.11.i; A.164.y.11.i; A.165.y.11.i; A.166.y.11.i; A.167.y.11.i;

TABLE 6-continued

Exemplary Enumerated Compounds

A.168.y.11.i; A.169.y.11.i; A.170.y.11.i; A.171.y.11.i; A.172.y.11.i; A.173.y.11.i;
A.174.y.11.i; A.175.y.11.i; A.176.y.11.i; A.177.y.11.i; A.178.y.11.i; A.179.y.11.i;
A.180.y.11.i; A.181.y.11.i; A.182.y.11.i; A.183.y.11.i; A.184.y.11.i; A.185.y.11.i;
A.186.y.11.i; A.187.y.11.i; A.188.y.11.i; A.189.y.11.i; A.190.y.11.i; A.191.y.11.i;
A.192.y.11.i; A.193.y.11.i; A.194.y.11.i; A.195.y.11.i; A.196.y.11.i; A.197.y.11.i;
A.198.y.11.i; A.199.y.11.i; A.200.y.11.i; A.201.y.11.i; A.202.y.11.i; A.203.y.11.i;
A.204.y.11.i; A.205.y.11.i; A.206.y.11.i; A.207.y.11.i; A.208.y.11.i; A.209.y.11.i;
A.210.y.11.i; A.211.y.11.i; A.212.y.11.i; A.213.y.11.i; A.214.y.11.i; A.215.y.11.i;
A.216.y.11.i; A.217.y.11.i; A.218.y.11.i; A.219.y.11.i; A.220.y.11.i; A.221.y.11.i;
A.222.y.11.i; A.223.y.11.i; A.224.y.11.i; A.225.y.11.i; A.226.y.11.i; A.227.y.11.i;
A.228.y.11.i; A.229.y.11.i; A.230.y.11.i; A.231.y.11.i; A.232.y.11.i; A.233.y.11.i;
A.234.y.11.i; A.235.y.11.i; A.236.y.11.i; A.237.y.11.i; A.238.y.11.i; A.239.y.11.i;
A.240.y.11.i; A.241.y.11.i; A.242.y.11.i; A.243.y.11.i; A.244.y.11.i; A.245.y.11.i;
A.246.y.11.i; A.247.y.11.i; A.248.y.11.i; A.249.y.11.i; A.250.y.11.i; A.251.y.11.i;
A.252.y.11.i; A.253.y.11.i; A.254.y.11.i; A.255.y.11.i; A.256.y.11.i; A.257.y.11.i;
A.258.y.11.i; A.259.y.11.i; A.260.y.11.i; A.261.y.11.i; A.262.y.11.i; A.263.y.11.i;
A.264.y.11.i; A.265.y.11.i; A.266.y.11.i; A.267.y.11.i; A.268.y.11.i; A.269.y.11.i;
A.270.y.11.i; A.271.y.11.i; A.272.y.11.i; A.273.y.11.i; A.274.y.11.i; A.275.y.11.i;
A.276.y.11.i; A.277.y.11.i; A.278.y.11.i; A.279.y.11.i; A.280.y.11.i; A.281.y.11.i;
A.282.y.11.i; A.283.y.11.i; A.284.y.11.i; A.285.y.11.i; A.286.y.11.i; A.287.y.11.i;
A.288.y.11.i; A.289.y.11.i; A.290.y.11.i; A.291.y.11.i; A.292.y.11.i; A.293.y.11.i;
A.294.y.11.i; A.295.y.11.i; A.296.y.11.i; A.297.y.11.i; A.298.y.11.i; A.299.y.11.i;
A.300.y.11.i; A.301.y.11.i; A.302.y.11.i; A.303.y.11.i; A.304.y.11.i; A.305.y.11.i;
A.306.y.11.i; A.307.y.11.i; A.308.y.11.i; A.309.y.11.i; A.310.y.11.i; A.311.y.11.i;
A.312.y.11.i; A.313.y.11.i; A.314.y.11.i; A.315.y.11.i; A.316.y.11.i; A.317.y.11.i;
A.318.y.11.i; A.319.y.11.i; A.320.y.11.i; A.321.y.11.i; A.323.y.11.i; A.324.y.11.i;
A.325.y.11.i; A.326.y.11.i; A.327.y.11.i; A.328.y.11.i; A.329.y.11.i; A.330.y.11.i;
A.331.y.11.i; A.332.y.11.i; A.333.y.11.i; A.334.y.11.i; A.335.y.11.i; A.336.y.11.i;
A.337.y.11.i; A.338.y.11.i; A.339.y.11.i; A.340.y.11.i; A.341.y.11.i; A.342.y.11.i;
A.343.y.11.i; A.344.y.11.i; A.345.y.11.i; A.346.y.11.i; A.347.y.11.i; A.348.y.11.i;
A.349.y.11.i; A.350.y.11.i; A.351.y.11.i; A.352.y.11.i; A.353.y.11.i; A.354.y.11.i;
A.355.y.11.i; A.356.y.11.i; A.357.y.11.i; A.358.y.11.i; A.359.y.11.i; A.360.y.11.i;
A.361.y.11.i; A.362.y.11.i; A.363.y.11.i; A.364.y.11.i; A.365.y.11.i; A.366.y.11.i;
A.367.y.11.i; A.368.y.11.i; A.369.y.11.i; A.370.y.11.i; A.371.y.11.i; A.372.y.11.i;
A.373.y.11.i; A.374.y.11.i; A.375.y.11.i; A.376.y.11.i; A.377.y.11.i; A.378.y.11.i;
A.379.y.11.i; A.380.y.11.i; A.381.y.11.i; A.382.y.11.i; A.383.y.11.i; A.384.y.11.i;
A.385.y.11.i; A.386.y.11.i; A.387.y.11.i; A.388.y.11.i; A.389.y.11.i; A.390.y.11.i;
A.391.y.11.i; A.392.y.11.i; A.393.y.11.i; A.394.y.11.i; A.395.y.11.i; A.396.y.11.i;
A.397.y.11.i; A.398.y.11.i; A.399.y.11.i; A.400.y.11.i; A.401.y.11.i; A.402.y.11.i;
A.403.y.11.i; A.404.y.11.i; A.405.y.11.i; A.406.y.11.i; A.407.y.11.i; A.408.y.11.i;
A.409.y.11.i; A.410.y.11.i; A.411.y.11.i; A.412.y.11.i; A.413.y.11.i; A.414.y.11.i;
A.415.y.11.i; A.416.y.11.i; A.417.y.11.i; A.418.y.11.i; A.419.y.11.i; A.420.y.11.i;
A.421.y.11.i; A.422.y.11.i; A.423.y.11.i; A.424.y.11.i; A.425.y.11.i; A.426.y.11.i;
A.427.y.11.i; A.428.y.11.i; A.429.y.11.i; A.430.y.11.i; A.431.y.11.i; A.432.y.11.i;
A.433.y.11.i; A.434.y.11.i; A.435.y.11.i; A.436.y.11.i; A.437.y.11.i; A.438.y.11.i;
A.439.y.11.i; A.440.y.11.i; A.441.y.11.i; A.442.y.11.i; A.443.y.11.i; A.444.y.11.i;
A.445.y.11.i; A.446.y.11.i; A.447.y.11.i; A.448.y.11.i; A.449.y.11.i; A.450.y.11.i;
A.451.y.11.i; A.452.y.11.i; A.453.y.11.i; A.454.y.11.i; A.455.y.11.i; A.456.y.11.i;
A.457.y.11.i; A.458.y.11.i; A.459.y.11.i; A.460.y.11.i; A.461.y.11.i; A.462.y.11.i;
A.463.y.11.i; A.464.y.11.i; A.465.y.11.i; A.466.y.11.i; A.467.y.11.i; A.468.y.11.i;
A.469.y.11.i; A.470.y.11.i; A.471.y.11.i; A.472.y.11.i; A.473.y.11.i; A.474.y.11.i;
A.475.y.11.i; A.476.y.11.i; A.477.y.11.i; A.478.y.11.i; A.479.y.11.i; A.480.y.11.i;
A.481.y.11.i; A.482.y.11.i; A.483.y.11.i; A.484.y.11.i; A.485.y.11.i; A.486.y.11.i;
A.487.y.11.i; A.488.y.11.i; A.489.y.11.i; A.490.y.11.i; A.491.y.11.i; A.492.y.11.i;
A.493.y.11.i; A.494.y.11.i; A.495.y.11.i; A.496.y.11.i; A.497.y.11.i; A.498.y.11.i;
A.499.y.11.i; A.500.y.11.i; A.501.y.11.i; A.502.y.11.i; A.503.y.11.i; A.504.y.11.i;
A.505.y.11.i; A.506.y.11.i; A.507.y.11.i; A.508.y.11.i; A.509.y.11.i; A.510.y.11.i;
A.511.y.11.i; A.512.y.11.i; A.512.y.11.i; A.513.y.11.i; A.514.y.11.i; A.515.y.11.i;
A.516.y.11.i; A.517.y.11.i; A.518.y.11.i; A.519.y.11.i; A.520.y.11.i; A.521.y.11.i;
A.522.y.11.i; A.523.y.11.i; A.524.y.11.i; A.525.y.11.i; A.526.y.11.i; A.527.y.11.i;
A.528.y.11.i; A.529.y.11.i; A.530.y.11.i; A.531.y.11.i; A.532.y.11.i; A.533.y.11.i;
A.534.y.11.i; A.535.y.11.i; A.536.y.11.i; A.537.y.11.i; A.538.y.11.i; A.539.y.11.i;
A.540.y.11.i; A.541.y.11.i; A.542.y.11.i; A.543.y.11.i; A.544.y.11.i; A.545.y.11.i;
A.546.y.11.i; A.547.y.11.i; A.548.y.11.i; A.549.y.11.i; A.550.y.11.i; A.551.y.11.i;
A.552.y.11.i; A.553.y.11.i; A.554.y.11.i; A.555.y.11.i; A.556.y.11.i; A.557.y.11.i;
A.558.y.11.i; A.559.y.11.i; A.560.y.11.i; A.561.y.11.i; A.562.y.11.i; A.563.y.11.i;
A.564.y.11.i; A.565.y.11.i; A.566.y.11.i; A.567.y.11.i; A.568.y.11.i; A.569.y.11.i;
A.570.y.11.i; A.571.y.11.i; A.572.y.11.i; A.573.y.11.i; A.574.y.11.i; A.575.y.11.i;
A.576.y.11.i; A.577.y.11.i; A.578.y.11.i; A.579.y.11.i; A.580.y.11.i; A.581.y.11.i;
A.582.y.11.i; A.583.y.11.i; A.584.y.11.i; A.585.y.11.i; A.586.y.11.i; A.587.y.11.i;
A.588.y.11.i; A.589.y.11.i; A.590.y.11.i; A.591.y.11.i; A.592.y.11.i; A.593.y.11.i;
A.594.y.11.i; A.595.y.11.i; A.596.y.11.i; A.597.y.11.i; A.598.y.11.i; A.599.y.11.i;
A.600.y.11.i; A.601.y.11.i; A.602.y.11.i; A.603.y.11.i; A.604.y.11.i; A.605.y.11.i;
A.606.y.11.i; A.607.y.11.i; A.608.y.11.i; A.609.y.11.i; A.610.y.11.i; A.611.y.11.i;
A.612.y.11.i; A.613.y.11.i; A.614.y.11.i; A.615.y.11.i; A.616.y.11.i; A.617.y.11.i;
A.618.y.11.i; A.619.y.11.i; A.620.y.11.i; A.621.y.11.i; A.622.y.11.i; A.623.y.11.i;
A.624.y.11.i; A.625.y.11.i; A.626.y.11.i; A.627.y.11.i; A.628.y.11.i; A.629.y.11.i;

TABLE 6-continued

Exemplary Enumerated Compounds

A.630.y.11.i; A.631.y.11.i; A.632.y.11.i; A.633.y.11.i; A.634.y.11.i; A.635.y.11.i;
A.636.y.11.i; A.637.y.11.i; A.638.y.11.i; A.639.y.11.i; A.640.y.11.i; A.641.y.11.i;
A.642.y.11.i; A.643.y.11.i; A.644.y.11.i; A.645.y.11.i; A.646.y.11.i; A.647.y.11.i;
A.648.y.11.i; A.649.y.11.i; A.650.y.11.i; A.651.y.11.i; A.652.y.11.i; A.653.y.11.i;
A.654.y.11.i; A.655.y.11.i; A.656.y.11.i; A.657.y.11.i; A.658.y.11.i; A.659.y.11.i;
A.660.y.11.i; A.2.z.4.i; A.3.z.4.i; A.4.z.4.i; A.5.z.4.i; A.6.z.4.i; A.7.z.4.i; A.9.z.4.i;
A.10.z.4.i; A.15.z.4.i; A.100.z.4.i; A.101.z.4.i; A.102.z.4.i; A.103.z.4.i; A.104.z.4.i;
A.105.z.4.i; A.106.z.4.i; A.107.z.4.i; A.108.z.4.i; A.109.z.4.i; A.110.z.4.i; A.111.z.4.i;
A.112.z.4.i; A.113.z.4.i; A.114.z.4.i; A.115.z.4.i; A.116.z.4.i; A.117.z.4.i; A.118.z.4.i;
A.119.z.4.i; A.120.z.4.i; A.121.z.4.i; A.122.z.4.i; A.123.z.4.i; A.124.z.4.i; A.125.z.4.i;
A.126.z.4.i; A.127.z.4.i; A.128.z.4.i; A.129.z.4.i; A.130.z.4.i; A.131.z.4.i; A.132.z.4.i;
A.133.z.4.i; A.134.z.4.i; A.135.z.4.i; A.136.z.4.i; A.137.z.4.i; A.138.z.4.i; A.139.z.4.i;
A.140.z.4.i; A.141.z.4.i; A.142.z.4.i; A.143.z.4.i; A.144.z.4.i; A.145.z.4.i; A.146.z.4.i;
A.147.z.4.i; A.148.z.4.i; A.149.z.4.i; A.150.z.4.i; A.151.z.4.i; A.152.z.4.i; A.153.z.4.i;
A.154.z.4.i; A.155.z.4.i; A.156.z.4.i; A.157.z.4.i; A.158.z.4.i; A.159.z.4.i; A.160.z.4.i;
A.161.z.4.i; A.162.z.4.i; A.163.z.4.i; A.164.z.4.i; A.165.z.4.i; A.166.z.4.i; A.167.z.4.i;
A.168.z.4.i; A.169.z.4.i; A.170.z.4.i; A.171.z.4.i; A.172.z.4.i; A.173.z.4.i; A.174.z.4.i;
A.175.z.4.i; A.176.z.4.i; A.177.z.4.i; A.178.z.4.i; A.179.z.4.i; A.180.z.4.i; A.181.z.4.i;
A.182.z.4.i; A.183.z.4.i; A.184.z.4.i; A.185.z.4.i; A.186.z.4.i; A.187.z.4.i; A.188.z.4.i;
A.189.z.4.i; A.190.z.4.i; A.191.z.4.i; A.192.z.4.i; A.193.z.4.i; A.194.z.4.i; A.195.z.4.i;
A.196.z.4.i; A.197.z.4.i; A.198.z.4.i; A.199.z.4.i; A.200.z.4.i; A.201.z.4.i; A.202.z.4.i;
A.203.z.4.i; A.204.z.4.i; A.205.z.4.i; A.206.z.4.i; A.207.z.4.i; A.208.z.4.i; A.209.z.4.i;
A.210.z.4.i; A.211.z.4.i; A.212.z.4.i; A.213.z.4.i; A.214.z.4.i; A.215.z.4.i; A.216.z.4.i;
A.217.z.4.i; A.218.z.4.i; A.219.z.4.i; A.220.z.4.i; A.221.z.4.i; A.222.z.4.i; A.223.z.4.i;
A.224.z.4.i; A.225.z.4.i; A.226.z.4.i; A.227.z.4.i; A.228.z.4.i; A.229.z.4.i; A.230.z.4.i;
A.231.z.4.i; A.232.z.4.i; A.233.z.4.i; A.234.z.4.i; A.235.z.4.i; A.236.z.4.i; A.237.z.4.i;
A.238.z.4.i; A.239.z.4.i; A.240.z.4.i; A.241.z.4.i; A.242.z.4.i; A.243.z.4.i; A.244.z.4.i;
A.245.z.4.i; A.246.z.4.i; A.247.z.4.i; A.248.z.4.i; A.249.z.4.i; A.250.z.4.i; A.251.z.4.i;
A.252.z.4.i; A.253.z.4.i; A.254.z.4.i; A.255.z.4.i; A.256.z.4.i; A.257.z.4.i; A.258.z.4.i;
A.259.z.4.i; A.260.z.4.i; A.261.z.4.i; A.262.z.4.i; A.263.z.4.i; A.264.z.4.i; A.265.z.4.i;
A.266.z.4.i; A.267.z.4.i; A.268.z.4.i; A.269.z.4.i; A.270.z.4.i; A.271.z.4.i; A.272.z.4.i;
A.273.z.4.i; A.274.z.4.i; A.275.z.4.i; A.276.z.4.i; A.277.z.4.i; A.278.z.4.i; A.279.z.4.i;
A.280.z.4.i; A.281.z.4.i; A.282.z.4.i; A.283.z.4.i; A.284.z.4.i; A.285.z.4.i; A.286.z.4.i;
A.287.z.4.i; A.288.z.4.i; A.289.z.4.i; A.290.z.4.i; A.291.z.4.i; A.292.z.4.i; A.293.z.4.i;
A.294.z.4.i; A.295.z.4.i; A.296.z.4.i; A.297.z.4.i; A.298.z.4.i; A.299.z.4.i; A.300.z.4.i;
A.301.z.4.i; A.302.z.4.i; A.303.z.4.i; A.304.z.4.i; A.305.z.4.i; A.306.z.4.i; A.307.z.4.i;
A.308.z.4.i; A.309.z.4.i; A.310.z.4.i; A.311.z.4.i; A.312.z.4.i; A.313.z.4.i; A.314.z.4.i;
A.315.z.4.i; A.316.z.4.i; A.317.z.4.i; A.318.z.4.i; A.319.z.4.i; A.320.z.4.i; A.321.z.4.i;
A.323.z.4.i; A.324.z.4.i; A.325.z.4.i; A.326.z.4.i; A.327.z.4.i; A.328.z.4.i; A.329.z.4.i;
A.330.z.4.i; A.331.z.4.i; A.332.z.4.i; A.333.z.4.i; A.334.z.4.i; A.335.z.4.i; A.336.z.4.i;
A.337.z.4.i; A.338.z.4.i; A.339.z.4.i; A.340.z.4.i; A.341.z.4.i; A.342.z.4.i; A.343.z.4.i;
A.344.z.4.i; A.345.z.4.i; A.346.z.4.i; A.347.z.4.i; A.348.z.4.i; A.349.z.4.i; A.350.z.4.i;
A.351.z.4.i; A.352.z.4.i; A.353.z.4.i; A.354.z.4.i; A.355.z.4.i; A.356.z.4.i; A.357.z.4.i;
A.358.z.4.i; A.359.z.4.i; A.360.z.4.i; A.361.z.4.i; A.362.z.4.i; A.363.z.4.i; A.364.z.4.i;
A.365.z.4.i; A.366.z.4.i; A.367.z.4.i; A.368.z.4.i; A.369.z.4.i; A.370.z.4.i; A.371.z.4.i;
A.372.z.4.i; A.373.z.4.i; A.374.z.4.i; A.375.z.4.i; A.376.z.4.i; A.377.z.4.i; A.378.z.4.i;
A.379.z.4.i; A.380.z.4.i; A.381.z.4.i; A.382.z.4.i; A.383.z.4.i; A.384.z.4.i; A.385.z.4.i;
A.386.z.4.i; A.387.z.4.i; A.388.z.4.i; A.389.z.4.i; A.390.z.4.i; A.391.z.4.i; A.392.z.4.i;
A.393.z.4.i; A.394.z.4.i; A.395.z.4.i; A.396.z.4.i; A.397.z.4.i; A.398.z.4.i; A.399.z.4.i;
A.400.z.4.i; A.401.z.4.i; A.402.z.4.i; A.403.z.4.i; A.404.z.4.i; A.405.z.4.i; A.406.z.4.i;
A.407.z.4.i; A.408.z.4.i; A.409.z.4.i; A.410.z.4.i; A.411.z.4.i; A.412.z.4.i; A.413.z.4.i;
A.414.z.4.i; A.415.z.4.i; A.416.z.4.i; A.417.z.4.i; A.418.z.4.i; A.419.z.4.i; A.420.z.4.i;
A.421.z.4.i; A.422.z.4.i; A.423.z.4.i; A.424.z.4.i; A.425.z.4.i; A.426.z.4.i; A.427.z.4.i;
A.428.z.4.i; A.429.z.4.i; A.430.z.4.i; A.431.z.4.i; A.432.z.4.i; A.433.z.4.i; A.434.z.4.i;
A.435.z.4.i; A.436.z.4.i; A.437.z.4.i; A.438.z.4.i; A.439.z.4.i; A.440.z.4.i; A.441.z.4.i;
A.442.z.4.i; A.443.z.4.i; A.444.z.4.i; A.445.z.4.i; A.446.z.4.i; A.447.z.4.i; A.448.z.4.i;
A.449.z.4.i; A.450.z.4.i; A.451.z.4.i; A.452.z.4.i; A.453.z.4.i; A.454.z.4.i; A.455.z.4.i;
A.456.z.4.i; A.457.z.4.i; A.458.z.4.i; A.459.z.4.i; A.460.z.4.i; A.461.z.4.i; A.462.z.4.i;
A.463.z.4.i; A.464.z.4.i; A.465.z.4.i; A.466.z.4.i; A.467.z.4.i; A.468.z.4.i; A.469.z.4.i;
A.470.z.4.i; A.471.z.4.i; A.472.z.4.i; A.473.z.4.i; A.474.z.4.i; A.475.z.4.i; A.476.z.4.i;
A.477.z.4.i; A.478.z.4.i; A.479.z.4.i; A.480.z.4.i; A.481.z.4.i; A.482.z.4.i; A.483.z.4.i;
A.484.z.4.i; A.485.z.4.i; A.486.z.4.i; A.487.z.4.i; A.488.z.4.i; A.489.z.4.i; A.490.z.4.i;
A.491.z.4.i; A.492.z.4.i; A.493.z.4.i; A.494.z.4.i; A.495.z.4.i; A.496.z.4.i; A.497.z.4.i;
A.498.z.4.i; A.499.z.4.i; A.500.z.4.i; A.501.z.4.i; A.502.z.4.i; A.503.z.4.i; A.504.z.4.i;
A.505.z.4.i; A.506.z.4.i; A.507.z.4.i; A.508.z.4.i; A.509.z.4.i; A.510.z.4.i; A.511.z.4.i;
A.512.z.4.i; A.512.z.4.i; A.513.z.4.i; A.514.z.4.i; A.515.z.4.i; A.516.z.4.i; A.517.z.4.i;
A.518.z.4.i; A.519.z.4.i; A.520.z.4.i; A.521.z.4.i; A.522.z.4.i; A.523.z.4.i; A.524.z.4.i;
A.525.z.4.i; A.526.z.4.i; A.527.z.4.i; A.528.z.4.i; A.529.z.4.i; A.530.z.4.i; A.531.z.4.i;
A.532.z.4.i; A.533.z.4.i; A.534.z.4.i; A.535.z.4.i; A.536.z.4.i; A.537.z.4.i; A.538.z.4.i;
A.539.z.4.i; A.540.z.4.i; A.541.z.4.i; A.542.z.4.i; A.543.z.4.i; A.544.z.4.i; A.545.z.4.i;
A.546.z.4.i; A.547.z.4.i; A.548.z.4.i; A.549.z.4.i; A.550.z.4.i; A.551.z.4.i; A.552.z.4.i;
A.553.z.4.i; A.554.z.4.i; A.555.z.4.i; A.556.z.4.i; A.557.z.4.i; A.558.z.4.i; A.559.z.4.i;
A.560.z.4.i; A.561.z.4.i; A.562.z.4.i; A.563.z.4.i; A.564.z.4.i; A.565.z.4.i; A.566.z.4.i;
A.567.z.4.i; A.568.z.4.i; A.569.z.4.i; A.570.z.4.i; A.571.z.4.i; A.572.z.4.i; A.573.z.4.i;
A.574.z.4.i; A.575.z.4.i; A.576.z.4.i; A.577.z.4.i; A.578.z.4.i; A.579.z.4.i; A.580.z.4.i;
A.581.z.4.i; A.582.z.4.i; A.583.z.4.i; A.584.z.4.i; A.585.z.4.i; A.586.z.4.i; A.587.z.4.i;
A.588.z.4.i; A.589.z.4.i; A.590.z.4.i; A.591.z.4.i; A.592.z.4.i; A.593.z.4.i; A.594.z.4.i;

TABLE 6-continued

Exemplary Enumerated Compounds

A.595.z.4.i; A.596.z.4.i; A.597.z.4.i; A.598.z.4.i; A.599.z.4.i; A.600.z.4.i; A.601.z.4.i;
A.602.z.4.i; A.603.z.4.i; A.604.z.4.i; A.605.z.4.i; A.606.z.4.i; A.607.z.4.i; A.608.z.4.i;
A.609.z.4.i; A.610.z.4.i; A.611.z.4.i; A.612.z.4.i; A.613.z.4.i; A.614.z.4.i; A.615.z.4.i;
A.616.z.4.i; A.617.z.4.i; A.618.z.4.i; A.619.z.4.i; A.620.z.4.i; A.621.z.4.i; A.622.z.4.i;
A.623.z.4.i; A.624.z.4.i; A.625.z.4.i; A.626.z.4.i; A.627.z.4.i; A.628.z.4.i; A.629.z.4.i;
A.630.z.4.i; A.631.z.4.i; A.632.z.4.i; A.633.z.4.i; A.634.z.4.i; A.635.z.4.i; A.636.z.4.i;
A.637.z.4.i; A.638.z.4.i; A.639.z.4.i; A.640.z.4.i; A.641.z.4.i; A.642.z.4.i; A.643.z.4.i;
A.644.z.4.i; A.645.z.4.i; A.646.z.4.i; A.647.z.4.i; A.648.z.4.i; A.649.z.4.i; A.650.z.4.i;
A.651.z.4.i; A.652.z.4.i; A.653.z.4.i; A.654.z.4.i; A.655.z.4.i; A.656.z.4.i; A.657.z.4.i;
A.658.z.4.i; A.659.z.4.i; A.660.z.4.i; A.2.z.11.i; A.3.z.11.i; A.4.z.11.i; A.5.z.11.i;
A.6.z.11.i; A.7.z.11.i; A.9.z.11.i; A.10.z.11.i; A.15.z.11.i; A.100.z.11.i; A.101.z.11.i;
A.102.z.11.i; A.103.z.11.i; A.104.z.11.i; A.105.z.11.i; A.106.z.11.i; A.107.z.11.i;
A.108.z.11.i; A.109.z.11.i; A.110.z.11.i; A.111.z.11.i; A.112.z.11.i; A.113.z.11.i;
A.114.z.11.i; A.115.z.11.i; A.116.z.11.i; A.117.z.11.i; A.118.z.11.i; A.119.z.11.i;
A.120.z.11.i; A.121.z.11.i; A.122.z.11.i; A.123.z.11.i; A.124.z.11.i; A.125.z.11.i;
A.126.z.11.i; A.127.z.11.i; A.128.z.11.i; A.129.z.11.i; A.130.z.11.i; A.131.z.11.i;
A.132.z.11.i; A.133.z.11.i; A.134.z.11.i; A.135.z.11.i; A.136.z.11.i; A.137.z.11.i;
A.138.z.11.i; A.139.z.11.i; A.140.z.11.i; A.141.z.11.i; A.142.z.11.i; A.143.z.11.i;
A.144.z.11.i; A.145.z.11.i; A.146.z.11.i; A.147.z.11.i; A.148.z.11.i; A.149.z.11.i;
A.150.z.11.i; A.151.z.11.i; A.152.z.11.i; A.153.z.11.i; A.154.z.11.i; A.155.z.11.i;
A.156.z.11.i; A.157.z.11.i; A.158.z.11.i; A.159.z.11.i; A.160.z.11.i; A.161.z.11.i;
A.162.z.11.i; A.163.z.11.i; A.164.z.11.i; A.165.z.11.i; A.166.z.11.i; A.167.z.11.i;
A.168.z.11.i; A.169.z.11.i; A.170.z.11.i; A.171.z.11.i; A.172.z.11.i; A.173.z.11.i;
A.174.z.11.i; A.175.z.11.i; A.176.z.11.i; A.177.z.11.i; A.178.z.11.i; A.179.z.11.i;
A.180.z.11.i; A.181.z.11.i; A.182.z.11.i; A.183.z.11.i; A.184.z.11.i; A.185.z.11.i;
A.186.z.11.i; A.187.z.11.i; A.188.z.11.i; A.189.z.11.i; A.190.z.11.i; A.191.z.11.i;
A.192.z.11.i; A.193.z.11.i; A.194.z.11.i; A.195.z.11.i; A.196.z.11.i; A.197.z.11.i;
A.198.z.11.i; A.199.z.11.i; A.200.z.11.i; A.201.z.11.i; A.202.z.11.i; A.203.z.11.i;
A.204.z.11.i; A.205.z.11.i; A.206.z.11.i; A.207.z.11.i; A.208.z.11.i; A.209.z.11.i;
A.210.z.11.i; A.211.z.11.i; A.212.z.11.i; A.213.z.11.i; A.214.z.11.i; A.215.z.11.i;
A.216.z.11.i; A.217.z.11.i; A.218.z.11.i; A.219.z.11.i; A.220.z.11.i; A.221.z.11.i;
A.222.z.11.i; A.223.z.11.i; A.224.z.11.i; A.225.z.11.i; A.226.z.11.i; A.227.z.11.i;
A.228.z.11.i; A.229.z.11.i; A.230.z.11.i; A.231.z.11.i; A.232.z.11.i; A.233.z.11.i;
A.234.z.11.i; A.235.z.11.i; A.236.z.11.i; A.237.z.11.i; A.238.z.11.i; A.239.z.11.i;
A.240.z.11.i; A.241.z.11.i; A.242.z.11.i; A.243.z.11.i; A.244.z.11.i; A.245.z.11.i;
A.246.z.11.i; A.247.z.11.i; A.248.z.11.i; A.249.z.11.i; A.250.z.11.i; A.251.z.11.i;
A.252.z.11.i; A.253.z.11.i; A.254.z.11.i; A.255.z.11.i; A.256.z.11.i; A.257.z.11.i;
A.258.z.11.i; A.259.z.11.i; A.260.z.11.i; A.261.z.11.i; A.262.z.11.i; A.263.z.11.i;
A.264.z.11.i; A.265.z.11.i; A.266.z.11.i; A.267.z.11.i; A.268.z.11.i; A.269.z.11.i;
A.270.z.11.i; A.271.z.11.i; A.272.z.11.i; A.273.z.11.i; A.274.z.11.i; A.275.z.11.i;
A.276.z.11.i; A.277.z.11.i; A.278.z.11.i; A.279.z.11.i; A.280.z.11.i; A.281.z.11.i;
A.282.z.11.i; A.283.z.11.i; A.284.z.11.i; A.285.z.11.i; A.286.z.11.i; A.287.z.11.i;
A.288.z.11.i; A.289.z.11.i; A.290.z.11.i; A.291.z.11.i; A.292.z.11.i; A.293.z.11.i;
A.294.z.11.i; A.295.z.11.i; A.296.z.11.i; A.297.z.11.i; A.298.z.11.i; A.299.z.11.i;
A.300.z.11.i; A.301.z.11.i; A.302.z.11.i; A.303.z.11.i; A.304.z.11.i; A.305.z.11.i;
A.306.z.11.i; A.307.z.11.i; A.308.z.11.i; A.309.z.11.i; A.310.z.11.i; A.311.z.11.i;
A.312.z.11.i; A.313.z.11.i; A.314.z.11.i; A.315.z.11.i; A.316.z.11.i; A.317.z.11.i;
A.318.z.11.i; A.319.z.11.i; A.320.z.11.i; A.321.z.11.i; A.323.z.11.i; A.324.z.11.i;
A.325.z.11.i; A.326.z.11.i; A.327.z.11.i; A.328.z.11.i; A.329.z.11.i; A.330.z.11.i;
A.331.z.11.i; A.332.z.11.i; A.333.z.11.i; A.334.z.11.i; A.335.z.11.i; A.336.z.11.i;
A.337.z.11.i; A.338.z.11.i; A.339.z.11.i; A.340.z.11.i; A.341.z.11.i; A.342.z.11.i;
A.343.z.11.i; A.344.z.11.i; A.345.z.11.i; A.346.z.11.i; A.347.z.11.i; A.348.z.11.i;
A.349.z.11.i; A.350.z.11.i; A.351.z.11.i; A.352.z.11.i; A.353.z.11.i; A.354.z.11.i;
A.355.z.11.i; A.356.z.11.i; A.357.z.11.i; A.358.z.11.i; A.359.z.11.i; A.360.z.11.i;
A.361.z.11.i; A.362.z.11.i; A.363.z.11.i; A.364.z.11.i; A.365.z.11.i; A.366.z.11.i;
A.367.z.11.i; A.368.z.11.i; A.369.z.11.i; A.370.z.11.i; A.371.z.11.i; A.372.z.11.i;
A.373.z.11.i; A.374.z.11.i; A.375.z.11.i; A.376.z.11.i; A.377.z.11.i; A.378.z.11.i;
A.379.z.11.i; A.380.z.11.i; A.381.z.11.i; A.382.z.11.i; A.383.z.11.i; A.384.z.11.i;
A.385.z.11.i; A.386.z.11.i; A.387.z.11.i; A.388.z.11.i; A.389.z.11.i; A.390.z.11.i;
A.391.z.11.i; A.392.z.11.i; A.393.z.11.i; A.394.z.11.i; A.395.z.11.i; A.396.z.11.i;
A.397.z.11.i; A.398.z.11.i; A.399.z.11.i; A.400.z.11.i; A.401.z.11.i; A.402.z.11.i;
A.403.z.11.i; A.404.z.11.i; A.405.z.11.i; A.406.z.11.i; A.407.z.11.i; A.408.z.11.i;
A.409.z.11.i; A.410.z.11.i; A.411.z.11.i; A.412.z.11.i; A.413.z.11.i; A.414.z.11.i;
A.415.z.11.i; A.416.z.11.i; A.417.z.11.i; A.418.z.11.i; A.419.z.11.i; A.420.z.11.i;
A.421.z.11.i; A.422.z.11.i; A.423.z.11.i; A.424.z.11.i; A.425.z.11.i; A.426.z.11.i;
A.427.z.11.i; A.428.z.11.i; A.429.z.11.i; A.430.z.11.i; A.431.z.11.i; A.432.z.11.i;
A.433.z.11.i; A.434.z.11.i; A.435.z.11.i; A.436.z.11.i; A.437.z.11.i; A.438.z.11.i;
A.439.z.11.i; A.440.z.11.i; A.441.z.11.i; A.442.z.11.i; A.443.z.11.i; A.444.z.11.i;
A.445.z.11.i; A.446.z.11.i; A.447.z.11.i; A.448.z.11.i; A.449.z.11.i; A.450.z.11.i;
A.451.z.11.i; A.452.z.11.i; A.453.z.11.i; A.454.z.11.i; A.455.z.11.i; A.456.z.11.i;
A.457.z.11.i; A.458.z.11.i; A.459.z.11.i; A.460.z.11.i; A.461.z.11.i; A.462.z.11.i;
A.463.z.11.i; A.464.z.11.i; A.465.z.11.i; A.466.z.11.i; A.467.z.11.i; A.468.z.11.i;
A.469.z.11.i; A.470.z.11.i; A.471.z.11.i; A.472.z.11.i; A.473.z.11.i; A.474.z.11.i;
A.475.z.11.i; A.476.z.11.i; A.477.z.11.i; A.478.z.11.i; A.479.z.11.i; A.480.z.11.i;
A.481.z.11.i; A.482.z.11.i; A.483.z.11.i; A.484.z.11.i; A.485.z.11.i; A.486.z.11.i;
A.487.z.11.i; A.488.z.11.i; A.489.z.11.i; A.490.z.11.i; A.491.z.11.i; A.492.z.11.i;
A.493.z.11.i; A.494.z.11.i; A.495.z.11.i; A.496.z.11.i; A.497.z.11.i; A.498.z.11.i;

TABLE 6-continued

Exemplary Enumerated Compounds

A.499.z.11.i; A.500.z.11.i; A.501.z.11.i; A.502.z.11.i; A.503.z.11.i; A.504.z.11.i;
A.505.z.11.i; A.506.z.11.i; A.507.z.11.i; A.508.z.11.i; A.509.z.11.i; A.510.z.11.i;
A.511.z.11.i; A.512.z.11.i; A.512.z.11.i; A.513.z.11.i; A.514.z.11.i; A.515.z.11.i;
A.516.z.11.i; A.517.z.11.i; A.518.z.11.i; A.519.z.11.i; A.520.z.11.i; A.521.z.11.i;
A.522.z.11.i; A.523.z.11.i; A.524.z.11.i; A.525.z.11.i; A.526.z.11.i; A.527.z.11.i;
A.528.z.11.i; A.529.z.11.i; A.530.z.11.i; A.531.z.11.i; A.532.z.11.i; A.533.z.11.i;
A.534.z.11.i; A.535.z.11.i; A.536.z.11.i; A.537.z.11.i; A.538.z.11.i; A.539.z.11.i;
A.540.z.11.i; A.541.z.11.i; A.542.z.11.i; A.543.z.11.i; A.544.z.11.i; A.545.z.11.i;
A.546.z.11.i; A.547.z.11.i; A.548.z.11.i; A.549.z.11.i; A.550.z.11.i; A.551.z.11.i;
A.552.z.11.i; A.553.z.11.i; A.554.z.11.i; A.555.z.11.i; A.556.z.11.i; A.557.z.11.i;
A.558.z.11.i; A.559.z.11.i; A.560.z.11.i; A.561.z.11.i; A.562.z.11.i; A.563.z.11.i;
A.564.z.11.i; A.565.z.11.i; A.566.z.11.i; A.567.z.11.i; A.568.z.11.i; A.569.z.11.i;
A.570.z.11.i; A.571.z.11.i; A.572.z.11.i; A.573.z.11.i; A.574.z.11.i; A.575.z.11.i;
A.576.z.11.i; A.577.z.11.i; A.578.z.11.i; A.579.z.11.i; A.580.z.11.i; A.581.z.11.i;
A.582.z.11.i; A.583.z.11.i; A.584.z.11.i; A.585.z.11.i; A.586.z.11.i; A.587.z.11.i;
A.588.z.11.i; A.589.z.11.i; A.590.z.11.i; A.591.z.11.i; A.592.z.11.i; A.593.z.11.i;
A.594.z.11.i; A.595.z.11.i; A.596.z.11.i; A.597.z.11.i; A.598.z.11.i; A.599.z.11.i;
A.600.z.11.i; A.601.z.11.i; A.602.z.11.i; A.603.z.11.i; A.604.z.11.i; A.605.z.11.i;
A.606.z.11.i; A.607.z.11.i; A.608.z.11.i; A.609.z.11.i; A.610.z.11.i; A.611.z.11.i;
A.612.z.11.i; A.613.z.11.i; A.614.z.11.i; A.615.z.11.i; A.616.z.11.i; A.617.z.11.i;
A.618.z.11.i; A.619.z.11.i; A.620.z.11.i; A.621.z.11.i; A.622.z.11.i; A.623.z.11.i;
A.624.z.11.i; A.625.z.11.i; A.626.z.11.i; A.627.z.11.i; A.628.z.11.i; A.629.z.11.i;
A.630.z.11.i; A.631.z.11.i; A.632.z.11.i; A.633.z.11.i; A.634.z.11.i; A.635.z.11.i;
A.636.z.11.i; A.637.z.11.i; A.638.z.11.i; A.639.z.11.i; A.640.z.11.i; A.641.z.11.i;
A.642.z.11.i; A.643.z.11.i; A.644.z.11.i; A.645.z.11.i; A.646.z.11.i; A.647.z.11.i;
A.648.z.11.i; A.649.z.11.i; A.650.z.11.i; A.651.z.11.i; A.652.z.11.i; A.653.z.11.i;
A.654.z.11.i; A.655.z.11.i; A.656.z.11.i; A.657.z.11.i; A.658.z.11.i; A.659.z.11.i;
A.660.z.11.i; A.2.A.4.i; A.3.A.4.i; A.4.A.4.i; A.5.A.4.i; A.6.A.4.i; A.7.A.4.i;
A.9.A.4.i; A.10.A.4.i; A.15.A.4.i; A.100.A.4.i; A.101.A.4.i; A.102.A.4.i;
A.103.A.4.i; A.104.A.4.i; A.105.A.4.i; A.106.A.4.i; A.107.A.4.i; A.108.A.4.i;
A.109.A.4.i; A.110.A.4.i; A.111.A.4.i; A.112.A.4.i; A.113.A.4.i; A.115.A.4.i;
A.115.A.4.i; A.116.A.4.i; A.117.A.4.i; A.118.A.4.i; A.119.A.4.i; A.120.A.4.i;
A.121.A.4.i; A.122.A.4.i; A.123.A.4.i; A.124.A.4.i; A.125.A.4.i; A.126.A.4.i;
A.127.A.4.i; A.128.A.4.i; A.129.A.4.i; A.130.A.4.i; A.131.A.4.i; A.132.A.4.i;
A.133.A.4.i; A.134.A.4.i; A.135.A.4.i; A.136.A.4.i; A.137.A.4.i; A.138.A.4.i;
A.139.A.4.i; A.140.A.4.i; A.141.A.4.i; A.142.A.4.i; A.143.A.4.i; A.144.A.4.i;
A.145.A.4.i; A.146.A.4.i; A.147.A.4.i; A.148.A.4.i; A.149.A.4.i; A.150.A.4.i;
A.151.A.4.i; A.152.A.4.i; A.153.A.4.i; A.154.A.4.i; A.155.A.4.i; A.156.A.4.i;
A.157.A.4.i; A.158.A.4.i; A.159.A.4.i; A.160.A.4.i; A.161.A.4.i; A.162.A.4.i;
A.163.A.4.i; A.164.A.4.i; A.165.A.4.i; A.166.A.4.i; A.167.A.4.i; A.168.A.4.i;
A.169.A.4.i; A.170.A.4.i; A.171.A.4.i; A.172.A.4.i; A.173.A.4.i; A.174.A.4.i;
A.175.A.4.i; A.176.A.4.i; A.177.A.4.i; A.178.A.4.i; A.179.A.4.i; A.180.A.4.i;
A.181.A.4.i; A.182.A.4.i; A.183.A.4.i; A.184.A.4.i; A.185.A.4.i; A.186.A.4.i;
A.187.A.4.i; A.188.A.4.i; A.189.A.4.i; A.190.A.4.i; A.191.A.4.i; A.192.A.4.i;
A.193.A.4.i; A.194.A.4.i; A.195.A.4.i; A.196.A.4.i; A.197.A.4.i; A.198.A.4.i;
A.199.A.4.i; A.200.A.4.i; A.201.A.4.i; A.202.A.4.i; A.203.A.4.i; A.204.A.4.i;
A.205.A.4.i; A.206.A.4.i; A.207.A.4.i; A.208.A.4.i; A.209.A.4.i; A.210.A.4.i;
A.211.A.4.i; A.212.A.4.i; A.213.A.4.i; A.214.A.4.i; A.215.A.4.i; A.216.A.4.i;
A.217.A.4.i; A.218.A.4.i; A.219.A.4.i; A.220.A.4.i; A.221.A.4.i; A.222.A.4.i;
A.223.A.4.i; A.224.A.4.i; A.225.A.4.i; A.226.A.4.i; A.227.A.4.i; A.228.A.4.i;
A.229.A.4.i; A.230.A.4.i; A.231.A.4.i; A.232.A.4.i; A.233.A.4.i; A.234.A.4.i;
A.235.A.4.i; A.236.A.4.i; A.237.A.4.i; A.238.A.4.i; A.239.A.4.i; A.240.A.4.i;
A.241.A.4.i; A.242.A.4.i; A.243.A.4.i; A.244.A.4.i; A.245.A.4.i; A.246.A.4.i;
A.247.A.4.i; A.248.A.4.i; A.249.A.4.i; A.250.A.4.i; A.251.A.4.i; A.252.A.4.i;
A.253.A.4.i; A.254.A.4.i; A.255.A.4.i; A.256.A.4.i; A.257.A.4.i; A.258.A.4.i;
A.259.A.4.i; A.260.A.4.i; A.261.A.4.i; A.262.A.4.i; A.263.A.4.i; A.264.A.4.i;
A.265.A.4.i; A.266.A.4.i; A.267.A.4.i; A.268.A.4.i; A.269.A.4.i; A.270.A.4.i;
A.271.A.4.i; A.272.A.4.i; A.273.A.4.i; A.274.A.4.i; A.275.A.4.i; A.276.A.4.i;
A.277.A.4.i; A.278.A.4.i; A.279.A.4.i; A.280.A.4.i; A.281.A.4.i; A.282.A.4.i;
A.283.A.4.i; A.284.A.4.i; A.285.A.4.i; A.286.A.4.i; A.287.A.4.i; A.288.A.4.i;
A.289.A.4.i; A.290.A.4.i; A.291.A.4.i; A.292.A.4.i; A.293.A.4.i; A.294.A.4.i;
A.295.A.4.i; A.296.A.4.i; A.297.A.4.i; A.298.A.4.i; A.299.A.4.i; A.300.A.4.i;
A.301.A.4.i; A.302.A.4.i; A.303.A.4.i; A.304.A.4.i; A.305.A.4.i; A.306.A.4.i;
A.307.A.4.i; A.308.A.4.i; A.309.A.4.i; A.310.A.4.i; A.311.A.4.i; A.312.A.4.i;
A.313.A.4.i; A.314.A.4.i; A.315.A.4.i; A.316.A.4.i; A.317.A.4.i; A.318.A.4.i;
A.319.A.4.i; A.320.A.4.i; A.321.A.4.i; A.323.A.4.i; A.324.A.4.i; A.325.A.4.i;
A.326.A.4.i; A.327.A.4.i; A.328.A.4.i; A.329.A.4.i; A.330.A.4.i; A.331.A.4.i;
A.332.A.4.i; A.333.A.4.i; A.334.A.4.i; A.335.A.4.i; A.336.A.4.i; A.337.A.4.i;
A.338.A.4.i; A.339.A.4.i; A.340.A.4.i; A.341.A.4.i; A.342.A.4.i; A.343.A.4.i;
A.344.A.4.i; A.345.A.4.i; A.346.A.4.i; A.347.A.4.i; A.348.A.4.i; A.349.A.4.i;
A.350.A.4.i; A.351.A.4.i; A.352.A.4.i; A.353.A.4.i; A.354.A.4.i; A.355.A.4.i;
A.356.A.4.i; A.357.A.4.i; A.358.A.4.i; A.359.A.4.i; A.360.A.4.i; A.361.A.4.i;
A.362.A.4.i; A.363.A.4.i; A.364.A.4.i; A.365.A.4.i; A.366.A.4.i; A.367.A.4.i;
A.368.A.4.i; A.369.A.4.i; A.370.A.4.i; A.371.A.4.i; A.372.A.4.i; A.373.A.4.i;
A.374.A.4.i; A.375.A.4.i; A.376.A.4.i; A.377.A.4.i; A.378.A.4.i; A.379.A.4.i;
A.380.A.4.i; A.381.A.4.i; A.382.A.4.i; A.383.A.4.i; A.384.A.4.i; A.385.A.4.i;
A.386.A.4.i; A.387.A.4.i; A.388.A.4.i; A.389.A.4.i; A.390.A.4.i; A.391.A.4.i;

TABLE 6-continued

Exemplary Enumerated Compounds

A.392.A.4.i; A.393.A.4.i; A.394.A.4.i; A.395.A.4.i; A.396.A.4.i; A.397.A.4.i;
A.398.A.4.i; A.399.A.4.i; A.400.A.4.i; A.401.A.4.i; A.402.A.4.i; A.403.A.4.i;
A.404.A.4.i; A.405.A.4.i; A.406.A.4.i; A.407.A.4.i; A.408.A.4.i; A.409.A.4.i;
A.410.A.4.i; A.411.A.4.i; A.412.A.4.i; A.413.A.4.i; A.414.A.4.i; A.415.A.4.i;
A.416.A.4.i; A.417.A.4.i; A.418.A.4.i; A.419.A.4.i; A.420.A.4.i; A.421.A.4.i;
A.422.A.4.i; A.423.A.4.i; A.424.A.4.i; A.425.A.4.i; A.426.A.4.i; A.427.A.4.i;
A.428.A.4.i; A.429.A.4.i; A.430.A.4.i; A.431.A.4.i; A.432.A.4.i; A.433.A.4.i;
A.434.A.4.i; A.435.A.4.i; A.436.A.4.i; A.437.A.4.i; A.438.A.4.i; A.439.A.4.i;
A.440.A.4.i; A.441.A.4.i; A.442.A.4.i; A.443.A.4.i; A.444.A.4.i; A.445.A.4.i;
A.446.A.4.i; A.447.A.4.i; A.448.A.4.i; A.449.A.4.i; A.450.A.4.i; A.451.A.4.i;
A.452.A.4.i; A.453.A.4.i; A.454.A.4.i; A.455.A.4.i; A.456.A.4.i; A.457.A.4.i;
A.458.A.4.i; A.459.A.4.i; A.460.A.4.i; A.461.A.4.i; A.462.A.4.i; A.463.A.4.i;
A.464.A.4.i; A.465.A.4.i; A.466.A.4.i; A.467.A.4.i; A.468.A.4.i; A.469.A.4.i;
A.470.A.4.i; A.471.A.4.i; A.472.A.4.i; A.473.A.4.i; A.474.A.4.i; A.475.A.4.i;
A.476.A.4.i; A.477.A.4.i; A.478.A.4.i; A.479.A.4.i; A.480.A.4.i; A.481.A.4.i;
A.482.A.4.i; A.483.A.4.i; A.484.A.4.i; A.485.A.4.i; A.486.A.4.i; A.487.A.4.i;
A.488.A.4.i; A.489.A.4.i; A.490.A.4.i; A.491.A.4.i; A.492.A.4.i; A.493.A.4.i;
A.494.A.4.i; A.495.A.4.i; A.496.A.4.i; A.497.A.4.i; A.498.A.4.i; A.499.A.4.i;
A.500.A.4.i; A.501.A.4.i; A.502.A.4.i; A.503.A.4.i; A.504.A.4.i; A.505.A.4.i;
A.506.A.4.i; A.507.A.4.i; A.508.A.4.i; A.509.A.4.i; A.510.A.4.i; A.511.A.4.i;
A.512.A.4.i; A.512.A.4.i; A.513.A.4.i; A.514.A.4.i; A.515.A.4.i; A.516.A.4.i;
A.517.A.4.i; A.518.A.4.i; A.519.A.4.i; A.520.A.4.i; A.521.A.4.i; A.522.A.4.i;
A.523.A.4.i; A.524.A.4.i; A.525.A.4.i; A.526.A.4.i; A.527.A.4.i; A.528.A.4.i;
A.529.A.4.i; A.530.A.4.i; A.531.A.4.i; A.532.A.4.i; A.533.A.4.i; A.534.A.4.i;
A.535.A.4.i; A.536.A.4.i; A.537.A.4.i; A.538.A.4.i; A.539.A.4.i; A.540.A.4.i;
A.541.A.4.i; A.542.A.4.i; A.543.A.4.i; A.544.A.4.i; A.545.A.4.i; A.546.A.4.i;
A.547.A.4.i; A.548.A.4.i; A.549.A.4.i; A.550.A.4.i; A.551.A.4.i; A.552.A.4.i;
A.553.A.4.i; A.554.A.4.i; A.555.A.4.i; A.556.A.4.i; A.557.A.4.i; A.558.A.4.i;
A.559.A.4.i; A.560.A.4.i; A.561.A.4.i; A.562.A.4.i; A.563.A.4.i; A.564.A.4.i;
A.565.A.4.i; A.566.A.4.i; A.567.A.4.i; A.568.A.4.i; A.569.A.4.i; A.570.A.4.i;
A.571.A.4.i; A.572.A.4.i; A.573.A.4.i; A.574.A.4.i; A.575.A.4.i; A.576.A.4.i;
A.577.A.4.i; A.578.A.4.i; A.579.A.4.i; A.580.A.4.i; A.581.A.4.i; A.582.A.4.i;
A.583.A.4.i; A.584.A.4.i; A.585.A.4.i; A.586.A.4.i; A.587.A.4.i; A.588.A.4.i;
A.589.A.4.i; A.590.A.4.i; A.591.A.4.i; A.592.A.4.i; A.593.A.4.i; A.594.A.4.i;
A.595.A.4.i; A.596.A.4.i; A.597.A.4.i; A.598.A.4.i; A.599.A.4.i; A.600.A.4.i;
A.2.A.11.i; A.3.A.11.i; A.11.A.11.i; A.5.A.11.i; A.6.A.11.i; A.7.A.11.i; A.9.A.11.i;
A.10.A.11.i; A.15.A.11.i; A.100.A.11.i; A.101.A.11.i; A.102.A.11.i; A.103.A.11.i;
A.104.A.11.i; A.105.A.11.i; A.106.A.11.i; A.107.A.11.i; A.108.A.11.i; A.109.A.11.i;
A.110.A.11.i; A.111.A.11.i; A.112.A.11.i; A.113.A.11.i; A.115.A.11.i; A.115.A.11.i;
A.116.A.11.i; A.117.A.11.i; A.118.A.11.i; A.119.A.11.i; A.120.A.11.i; A.121.A.11.i;
A.122.A.11.i; A.123.A.11.i; A.124.A.11.i; A.125.A.11.i; A.126.A.11.i; A.127.A.11.i;
A.128.A.11.i; A.129.A.11.i; A.130.A.11.i; A.131.A.11.i; A.132.A.11.i; A.133.A.11.i;
A.134.A.11.i; A.135.A.11.i; A.136.A.11.i; A.137.A.11.i; A.138.A.11.i; A.139.A.11.i;
A.140.A.11.i; A.141.A.11.i; A.142.A.11.i; A.143.A.11.i; A.144.A.11.i; A.145.A.11.i;
A.146.A.11.i; A.147.A.11.i; A.148.A.11.i; A.149.A.11.i; A.150.A.11.i; A.151.A.11.i;
A.152.A.11.i; A.153.A.11.i; A.154.A.11.i; A.155.A.11.i; A.156.A.11.i; A.157.A.11.i;
A.158.A.11.i; A.159.A.11.i; A.160.A.11.i; A.161.A.11.i; A.162.A.11.i; A.163.A.11.i;
A.164.A.11.i; A.165.A.11.i; A.166.A.11.i; A.167.A.11.i; A.168.A.11.i; A.169.A.11.i;
A.170.A.11.i; A.171.A.11.i; A.172.A.11.i; A.173.A.11.i; A.174.A.11.i; A.175.A.11.i;
A.176.A.11.i; A.177.A.11.i; A.178.A.11.i; A.179.A.11.i; A.180.A.11.i; A.181.A.11.i;
A.182.A.11.i; A.183.A.11.i; A.184.A.11.i; A.185.A.11.i; A.186.A.11.i; A.187.A.11.i;
A.188.A.11.i; A.189.A.11.i; A.190.A.11.i; A.191.A.11.i; A.192.A.11.i; A.193.A.11.i;
A.194.A.11.i; A.195.A.11.i; A.196.A.11.i; A.197.A.11.i; A.198.A.11.i; A.199.A.11.i;
A.200.A.11.i; A.201.A.11.i; A.202.A.11.i; A.203.A.11.i; A.204.A.11.i; A.205.A.11.i;
A.206.A.11.i; A.207.A.11.i; A.208.A.11.i; A.209.A.11.i; A.210.A.11.i; A.211.A.11.i;
A.212.A.11.i; A.213.A.11.i; A.214.A.11.i; A.215.A.11.i; A.216.A.11.i; A.217.A.11.i;
A.218.A.11.i; A.219.A.11.i; A.220.A.11.i; A.221.A.11.i; A.222.A.11.i; A.223.A.11.i;
A.224.A.11.i; A.225.A.11.i; A.226.A.11.i; A.227.A.11.i; A.228.A.11.i; A.229.A.11.i;
A.230.A.11.i; A.231.A.11.i; A.232.A.11.i; A.233.A.11.i; A.234.A.11.i; A.235.A.11.i;
A.236.A.11.i; A.237.A.11.i; A.238.A.11.i; A.239.A.11.i; A.240.A.11.i; A.241.A.11.i;
A.242.A.11.i; A.243.A.11.i; A.244.A.11.i; A.245.A.11.i; A.246.A.11.i; A.247.A.11.i;
A.248.A.11.i; A.249.A.11.i; A.250.A.11.i; A.251.A.11.i; A.252.A.11.i; A.253.A.11.i;
A.254.A.11.i; A.255.A.11.i; A.256.A.11.i; A.257.A.11.i; A.258.A.11.i; A.259.A.11.i;
A.260.A.11.i; A.261.A.11.i; A.262.A.11.i; A.263.A.11.i; A.264.A.11.i; A.265.A.11.i;
A.266.A.11.i; A.267.A.11.i; A.268.A.11.i; A.269.A.11.i; A.270.A.11.i; A.271.A.11.i;
A.272.A.11.i; A.273.A.11.i; A.274.A.11.i; A.275.A.11.i; A.276.A.11.i; A.277.A.11.i;
A.278.A.11.i; A.279.A.11.i; A.280.A.11.i; A.281.A.11.i; A.282.A.11.i; A.283.A.11.i;
A.284.A.11.i; A.285.A.11.i; A.286.A.11.i; A.287.A.11.i; A.288.A.11.i; A.289.A.11.i;
A.290.A.11.i; A.291.A.11.i; A.292.A.11.i; A.293.A.11.i; A.294.A.11.i; A.295.A.11.i;
A.296.A.11.i; A.297.A.11.i; A.298.A.11.i; A.299.A.11.i; A.300.A.11.i; A.301.A.11.i;
A.302.A.11.i; A.303.A.11.i; A.304.A.11.i; A.305.A.11.i; A.306.A.11.i; A.307.A.11.i;
A.308.A.11.i; A.309.A.11.i; A.310.A.11.i; A.311.A.11.i; A.312.A.11.i; A.313.A.11.i;
A.314.A.11.i; A.315.A.11.i; A.316.A.11.i; A.317.A.11.i; A.318.A.11.i; A.319.A.11.i;
A.320.A.11.i; A.321.A.11.i; A.323.A.11.i; A.324.A.11.i; A.325.A.11.i; A.326.A.11.i;
A.327.A.11.i; A.328.A.11.i; A.329.A.11.i; A.330.A.11.i; A.331.A.11.i; A.332.A.11.i;
A.333.A.11.i; A.334.A.11.i; A.335.A.11.i; A.336.A.11.i; A.337.A.11.i; A.338.A.11.i;
A.339.A.11.i; A.340.A.11.i; A.341.A.11.i; A.342.A.11.i; A.343.A.11.i; A.344.A.11.i;

TABLE 6-continued

Exemplary Enumerated Compounds

A.345.A.11.i; A.346.A.11.i; A.347.A.11.i; A.348.A.11.i; A.349.A.11.i; A.350.A.11.i;
A.351.A.11.i; A.352.A.11.i; A.353.A.11.i; A.354.A.11.i; A.355.A.11.i; A.356.A.11.i;
A.357.A.11.i; A.358.A.11.i; A.359.A.11.i; A.360.A.11.i; A.361.A.11.i; A.362.A.11.i;
A.363.A.11.i; A.364.A.11.i; A.365.A.11.i; A.366.A.11.i; A.367.A.11.i; A.368.A.11.i;
A.369.A.11.i; A.370.A.11.i; A.371.A.11.i; A.372.A.11.i; A.373.A.11.i; A.374.A.11.i;
A.375.A.11.i; A.376.A.11.i; A.377.A.11.i; A.378.A.11.i; A.379.A.11.i; A.380.A.11.i;
A.381.A.11.i; A.382.A.11.i; A.383.A.11.i; A.384.A.11.i; A.385.A.11.i; A.386.A.11.i;
A.387.A.11.i; A.388.A.11.i; A.389.A.11.i; A.390.A.11.i; A.391.A.11.i; A.392.A.11.i;
A.393.A.11.i; A.394.A.11.i; A.395.A.11.i; A.396.A.11.i; A.397.A.11.i; A.398.A.11.i;
A.399.A.11.i; A.400.A.11.i; A.401.A.11.i; A.402.A.11.i; A.403.A.11.i; A.404.A.11.i;
A.405.A.11.i; A.406.A.11.i; A.407.A.11.i; A.408.A.11.i; A.409.A.11.i; A.410.A.11.i;
A.411.A.11.i; A.412.A.11.i; A.413.A.11.i; A.414.A.11.i; A.415.A.11.i; A.416.A.11.i;
A.417.A.11.i; A.418.A.11.i; A.419.A.11.i; A.420.A.11.i; A.421.A.11.i; A.422.A.11.i;
A.423.A.11.i; A.424.A.11.i; A.425.A.11.i; A.426.A.11.i; A.427.A.11.i; A.428.A.11.i;
A.429.A.11.i; A.430.A.11.i; A.431.A.11.i; A.432.A.11.i; A.433.A.11.i; A.434.A.11.i;
A.435.A.11.i; A.436.A.11.i; A.437.A.11.i; A.438.A.11.i; A.439.A.11.i; A.440.A.11.i;
A.441.A.11.i; A.442.A.11.i; A.443.A.11.i; A.444.A.11.i; A.445.A.11.i; A.446.A.11.i;
A.447.A.11.i; A.448.A.11.i; A.449.A.11.i; A.450.A.11.i; A.451.A.11.i; A.452.A.11.i;
A.453.A.11.i; A.454.A.11.i; A.455.A.11.i; A.456.A.11.i; A.457.A.11.i; A.458.A.11.i;
A.459.A.11.i; A.460.A.11.i; A.461.A.11.i; A.462.A.11.i; A.463.A.11.i; A.464.A.11.i;
A.465.A.11.i; A.466.A.11.i; A.467.A.11.i; A.468.A.11.i; A.469.A.11.i; A.470.A.11.i;
A.471.A.11.i; A.472.A.11.i; A.473.A.11.i; A.474.A.11.i; A.475.A.11.i; A.476.A.11.i;
A.477.A.11.i; A.478.A.11.i; A.479.A.11.i; A.480.A.11.i; A.481.A.11.i; A.482.A.11.i;
A.483.A.11.i; A.484.A.11.i; A.485.A.11.i; A.486.A.11.i; A.487.A.11.i; A.488.A.11.i;
A.489.A.11.i; A.490.A.11.i; A.491.A.11.i; A.492.A.11.i; A.493.A.11.i; A.494.A.11.i;
A.495.A.11.i; A.496.A.11.i; A.497.A.11.i; A.498.A.11.i; A.499.A.11.i; A.500.A.11.i;
A.501.A.11.i; A.502.A.11.i; A.503.A.11.i; A.504.A.11.i; A.505.A.11.i; A.506.A.11.i;
A.507.A.11.i; A.508.A.11.i; A.509.A.11.i; A.510.A.11.i; A.511.A.11.i; A.512.A.11.i;
A.512.A.11.i; A.513.A.11.i; A.514.A.11.i; A.515.A.11.i; A.516.A.11.i; A.517.A.11.i;
A.518.A.11.i; A.519.A.11.i; A.520.A.11.i; A.521.A.11.i; A.522.A.11.i; A.523.A.11.i;
A.524.A.11.i; A.525.A.11.i; A.526.A.11.i; A.527.A.11.i; A.528.A.11.i; A.529.A.11.i;
A.530.A.11.i; A.531.A.11.i; A.532.A.11.i; A.533.A.11.i; A.534.A.11.i; A.535.A.11.i;
A.536.A.11.i; A.537.A.11.i; A.538.A.11.i; A.539.A.11.i; A.540.A.11.i; A.541.A.11.i;
A.542.A.11.i; A.543.A.11.i; A.544.A.11.i; A.545.A.11.i; A.546.A.11.i; A.547.A.11.i;
A.548.A.11.i; A.549.A.11.i; A.550.A.11.i; A.551.A.11.i; A.552.A.11.i; A.553.A.11.i;
A.554.A.11.i; A.555.A.11.i; A.556.A.11.i; A.557.A.11.i; A.558.A.11.i; A.559.A.11.i;
A.560.A.11.i; A.561.A.11.i; A.562.A.11.i; A.563.A.11.i; A.564.A.11.i; A.565.A.11.i;
A.566.A.11.i; A.567.A.11.i; A.568.A.11.i; A.569.A.11.i; A.570.A.11.i; A.571.A.11.i;
A.572.A.11.i; A.573.A.11.i; A.574.A.11.i; A.575.A.11.i; A.576.A.11.i; A.577.A.11.i;
A.578.A.11.i; A.579.A.11.i; A.580.A.11.i; A.581.A.11.i; A.582.A.11.i; A.583.A.11.i;
A.584.A.11.i; A.585.A.11.i; A.586.A.11.i; A.587.A.11.i; A.588.A.11.i; A.589.A.11.i;
A.590.A.11.i; A.591.A.11.i; A.592.A.11.i; A.593.A.11.i; A.594.A.11.i; A.595.A.11.i;
A.596.A.11.i; A.597.A.11.i; A.598.A.11.i; A.599.A.11.i; A.600.A.11.i; A.601.A.11.i;
A.602.A.11.i; A.603.A.11.i; A.604.A.11.i; A.605.A.11.i; A.606.A.11.i; A.607.A.11.i;
A.608.A.11.i; A.609.A.11.i; A.610.A.11.i; A.611.A.11.i; A.612.A.11.i; A.613.A.11.i;
A.614.A.11.i; A.615.A.11.i; A.616.A.11.i; A.617.A.11.i; A.618.A.11.i; A.619.A.11.i;
A.620.A.11.i; A.621.A.11.i; A.622.A.11.i; A.623.A.11.i; A.624.A.11.i; A.625.A.11.i;
A.626.A.11.i; A.627.A.11.i; A.628.A.11.i; A.629.A.11.i; A.630.A.11.i; A.631.A.11.i;
A.632.A.11.i; A.633.A.11.i; A.634.A.11.i; A.635.A.11.i; A.636.A.11.i; A.637.A.11.i;
A.638.A.11.i; A.639.A.11.i; A.640.A.11.i; A.641.A.11.i; A.642.A.11.i; A.643.A.11.i;
A.644.A.11.i; A.645.A.11.i; A.646.A.11.i; A.647.A.11.i; A.648.A.11.i; A.649.A.11.i;
A.650.A.11.i; A.651.A.11.i; A.652.A.11.i; A.653.A.11.i; A.654.A.11.i; A.655.A.11.i;
A.656.A.11.i; A.657.A.11.i; A.658.A.11.i; A.659.A.11.i; A.660.A.11.i; A.2.B.4.i;
A.3.B.4.i; A.4.B.4.i; A.5.B.4.i; A.6.B.4.i; A.7.B.4.i; A.9.B.4.i; A.10.B.4.i; A.15.B.4.i;
A.100.B.4.i; A.101.B.4.i; A.102.B.4.i; A.103.B.4.i; A.104.B.4.i; A.105.B.4.i;
A.106.B.4.i; A.107.B.4.i; A.108.B.4.i; A.109.B.4.i; A.110.B.4.i; A.111.B.4.i;
A.112.B.4.i; A.113.B.4.i; A.115.B.4.i; A.115.B.4.i; A.116.B.4.i; A.117.B.4.i;
A.118.B.4.i; A.119.B.4.i; A.120.B.4.i; A.121.B.4.i; A.122.B.4.i; A.123.B.4.i;
A.124.B.4.i; A.125.B.4.i; A.126.B.4.i; A.127.B.4.i; A.128.B.4.i; A.129.B.4.i;
A.130.B.4.i; A.131.B.4.i; A.132.B.4.i; A.133.B.4.i; A.134.B.4.i; A.135.B.4.i;
A.136.B.4.i; A.137.B.4.i; A.138.B.4.i; A.139.B.4.i; A.140.B.4.i; A.141.B.4.i;
A.142.B.4.i; A.143.B.4.i; A.144.B.4.i; A.145.B.4.i; A.146.B.4.i; A.147.B.4.i;
A.148.B.4.i; A.149.B.4.i; A.150.B.4.i; A.151.B.4.i; A.152.B.4.i; A.153.B.4.i;
A.154.B.4.i; A.155.B.4.i; A.156.B.4.i; A.157.B.4.i; A.158.B.4.i; A.159.B.4.i;
A.160.B.4.i; A.161.B.4.i; A.162.B.4.i; A.163.B.4.i; A.164.B.4.i; A.165.B.4.i;
A.166.B.4.i; A.167.B.4.i; A.168.B.4.i; A.169.B.4.i; A.170.B.4.i; A.171.B.4.i;
A.172.B.4.i; A.173.B.4.i; A.174.B.4.i; A.175.B.4.i; A.176.B.4.i; A.177.B.4.i;
A.178.B.4.i; A.179.B.4.i; A.180.B.4.i; A.181.B.4.i; A.182.B.4.i; A.183.B.4.i;
A.184.B.4.i; A.185.B.4.i; A.186.B.4.i; A.187.B.4.i; A.188.B.4.i; A.189.B.4.i;
A.190.B.4.i; A.191.B.4.i; A.192.B.4.i; A.193.B.4.i; A.194.B.4.i; A.195.B.4.i;
A.196.B.4.i; A.197.B.4.i; A.198.B.4.i; A.199.B.4.i; A.200.B.4.i; A.201.B.4.i;
A.202.B.4.i; A.203.B.4.i; A.204.B.4.i; A.205.B.4.i; A.206.B.4.i; A.207.B.4.i;
A.208.B.4.i; A.209.B.4.i; A.210.B.4.i; A.211.B.4.i; A.212.B.4.i; A.213.B.4.i;
A.214.B.4.i; A.215.B.4.i; A.216.B.4.i; A.217.B.4.i; A.218.B.4.i; A.219.B.4.i;
A.220.B.4.i; A.221.B.4.i; A.222.B.4.i; A.223.B.4.i; A.224.B.4.i; A.225.B.4.i;
A.226.B.4.i; A.227.B.4.i; A.228.B.4.i; A.229.B.4.i; A.230.B.4.i; A.231.B.4.i;
A.232.B.4.i; A.233.B.4.i; A.234.B.4.i; A.235.B.4.i; A.236.B.4.i; A.237.B.4.i;

TABLE 6-continued

Exemplary Enumerated Compounds

A.238.B.4.i; A.239.B.4.i; A.240.B.4.i; A.241.B.4.i; A.242.B.4.i; A.243.B.4.i;
A.244.B.4.i; A.245.B.4.i; A.246.B.4.i; A.247.B.4.i; A.248.B.4.i; A.249.B.4.i;
A.250.B.4.i; A.251.B.4.i; A.252.B.4.i; A.253.B.4.i; A.254.B.4.i; A.255.B.4.i;
A.256.B.4.i; A.257.B.4.i; A.258.B.4.i; A.259.B.4.i; A.260.B.4.i; A.261.B.4.i;
A.262.B.4.i; A.263.B.4.i; A.264.B.4.i; A.265.B.4.i; A.266.B.4.i; A.267.B.4.i;
A.268.B.4.i; A.269.B.4.i; A.270.B.4.i; A.271.B.4.i; A.272.B.4.i; A.273.B.4.i;
A.274.B.4.i; A.275.B.4.i; A.276.B.4.i; A.277.B.4.i; A.278.B.4.i; A.279.B.4.i;
A.280.B.4.i; A.281.B.4.i; A.282.B.4.i; A.283.B.4.i; A.284.B.4.i; A.285.B.4.i;
A.286.B.4.i; A.287.B.4.i; A.288.B.4.i; A.289.B.4.i; A.290.B.4.i; A.291.B.4.i;
A.292.B.4.i; A.293.B.4.i; A.294.B.4.i; A.295.B.4.i; A.296.B.4.i; A.297.B.4.i;
A.298.B.4.i; A.299.B.4.i; A.300.B.4.i; A.301.B.4.i; A.302.B.4.i; A.303.B.4.i;
A.304.B.4.i; A.305.B.4.i; A.306.B.4.i; A.307.B.4.i; A.308.B.4.i; A.309.B.4.i;
A.310.B.4.i; A.311.B.4.i; A.312.B.4.i; A.313.B.4.i; A.314.B.4.i; A.315.B.4.i;
A.316.B.4.i; A.317.B.4.i; A.318.B.4.i; A.319.B.4.i; A.320.B.4.i; A.321.B.4.i;
A.323.B.4.i; A.324.B.4.i; A.325.B.4.i; A.326.B.4.i; A.327.B.4.i; A.328.B.4.i;
A.329.B.4.i; A.330.B.4.i; A.331.B.4.i; A.332.B.4.i; A.333.B.4.i; A.334.B.4.i;
A.335.B.4.i; A.336.B.4.i; A.337.B.4.i; A.338.B.4.i; A.339.B.4.i; A.340.B.4.i;
A.341.B.4.i; A.342.B.4.i; A.343.B.4.i; A.344.B.4.i; A.345.B.4.i; A.346.B.4.i;
A.347.B.4.i; A.348.B.4.i; A.349.B.4.i; A.350.B.4.i; A.351.B.4.i; A.352.B.4.i;
A.353.B.4.i; A.354.B.4.i; A.355.B.4.i; A.356.B.4.i; A.357.B.4.i; A.358.B.4.i;
A.359.B.4.i; A.360.B.4.i; A.361.B.4.i; A.362.B.4.i; A.363.B.4.i; A.364.B.4.i;
A.365.B.4.i; A.366.B.4.i; A.367.B.4.i; A.368.B.4.i; A.369.B.4.i; A.370.B.4.i;
A.371.B.4.i; A.372.B.4.i; A.373.B.4.i; A.374.B.4.i; A.375.B.4.i; A.376.B.4.i;
A.377.B.4.i; A.378.B.4.i; A.379.B.4.i; A.380.B.4.i; A.381.B.4.i; A.382.B.4.i;
A.383.B.4.i; A.384.B.4.i; A.385.B.4.i; A.386.B.4.i; A.387.B.4.i; A.388.B.4.i;
A.389.B.4.i; A.390.B.4.i; A.391.B.4.i; A.392.B.4.i; A.393.B.4.i; A.394.B.4.i;
A.395.B.4.i; A.396.B.4.i; A.397.B.4.i; A.398.B.4.i; A.399.B.4.i; A.400.B.4.i;
A.401.B.4.i; A.402.B.4.i; A.403.B.4.i; A.404.B.4.i; A.405.B.4.i; A.406.B.4.i;
A.407.B.4.i; A.408.B.4.i; A.409.B.4.i; A.410.B.4.i; A.411.B.4.i; A.412.B.4.i;
A.413.B.4.i; A.414.B.4.i; A.415.B.4.i; A.416.B.4.i; A.417.B.4.i; A.418.B.4.i;
A.419.B.4.i; A.420.B.4.i; A.421.B.4.i; A.422.B.4.i; A.423.B.4.i; A.424.B.4.i;
A.425.B.4.i; A.426.B.4.i; A.427.B.4.i; A.428.B.4.i; A.429.B.4.i; A.430.B.4.i;
A.431.B.4.i; A.432.B.4.i; A.433.B.4.i; A.434.B.4.i; A.435.B.4.i; A.436.B.4.i;
A.437.B.4.i; A.438.B.4.i; A.439.B.4.i; A.440.B.4.i; A.441.B.4.i; A.442.B.4.i;
A.443.B.4.i; A.444.B.4.i; A.445.B.4.i; A.446.B.4.i; A.447.B.4.i; A.448.B.4.i;
A.449.B.4.i; A.450.B.4.i; A.451.B.4.i; A.452.B.4.i; A.453.B.4.i; A.454.B.4.i;
A.455.B.4.i; A.456.B.4.i; A.457.B.4.i; A.458.B.4.i; A.459.B.4.i; A.460.B.4.i;
A.461.B.4.i; A.462.B.4.i; A.463.B.4.i; A.464.B.4.i; A.465.B.4.i; A.466.B.4.i;
A.467.B.4.i; A.468.B.4.i; A.469.B.4.i; A.470.B.4.i; A.471.B.4.i; A.472.B.4.i;
A.473.B.4.i; A.474.B.4.i; A.475.B.4.i; A.476.B.4.i; A.477.B.4.i; A.478.B.4.i;
A.479.B.4.i; A.480.B.4.i; A.481.B.4.i; A.482.B.4.i; A.483.B.4.i; A.484.B.4.i;
A.485.B.4.i; A.486.B.4.i; A.487.B.4.i; A.488.B.4.i; A.489.B.4.i; A.490.B.4.i;
A.491.B.4.i; A.492.B.4.i; A.493.B.4.i; A.494.B.4.i; A.495.B.4.i; A.496.B.4.i;
A.497.B.4.i; A.498.B.4.i; A.499.B.4.i; A.500.B.4.i; A.501.B.4.i; A.502.B.4.i;
A.503.B.4.i; A.504.B.4.i; A.505.B.4.i; A.506.B.4.i; A.507.B.4.i; A.508.B.4.i;
A.509.B.4.i; A.510.B.4.i; A.511.B.4.i; A.512.B.4.i; A.512.B.4.i; A.513.B.4.i;
A.514.B.4.i; A.515.B.4.i; A.516.B.4.i; A.517.B.4.i; A.518.B.4.i; A.519.B.4.i;
A.520.B.4.i; A.521.B.4.i; A.522.B.4.i; A.523.B.4.i; A.524.B.4.i; A.525.B.4.i;
A.526.B.4.i; A.527.B.4.i; A.528.B.4.i; A.529.B.4.i; A.530.B.4.i; A.531.B.4.i;
A.532.B.4.i; A.533.B.4.i; A.534.B.4.i; A.535.B.4.i; A.536.B.4.i; A.537.B.4.i;
A.538.B.4.i; A.539.B.4.i; A.540.B.4.i; A.541.B.4.i; A.542.B.4.i; A.543.B.4.i;
A.544.B.4.i; A.545.B.4.i; A.546.B.4.i; A.547.B.4.i; A.548.B.4.i; A.549.B.4.i;
A.550.B.4.i; A.551.B.4.i; A.552.B.4.i; A.553.B.4.i; A.554.B.4.i; A.555.B.4.i;
A.556.B.4.i; A.557.B.4.i; A.558.B.4.i; A.559.B.4.i; A.560.B.4.i; A.561.B.4.i;
A.562.B.4.i; A.563.B.4.i; A.564.B.4.i; A.565.B.4.i; A.566.B.4.i; A.567.B.4.i;
A.568.B.4.i; A.569.B.4.i; A.570.B.4.i; A.571.B.4.i; A.572.B.4.i; A.573.B.4.i;
A.574.B.4.i; A.575.B.4.i; A.576.B.4.i; A.577.B.4.i; A.578.B.4.i; A.579.B.4.i;
A.580.B.4.i; A.581.B.4.i; A.582.B.4.i; A.583.B.4.i; A.584.B.4.i; A.585.B.4.i;
A.586.B.4.i; A.587.B.4.i; A.588.B.4.i; A.589.B.4.i; A.590.B.4.i; A.591.B.4.i;
A.592.B.4.i; A.593.B.4.i; A.594.B.4.i; A.595.B.4.i; A.596.B.4.i; A.597.B.4.i;
A.598.B.4.i; A.599.B.4.i; A.600.B.4.i; A.601.B.4.i; A.602.B.4.i; A.603.B.4.i;
A.604.B.4.i; A.605.B.4.i; A.606.B.4.i; A.607.B.4.i; A.608.B.4.i; A.609.B.4.i;
A.610.B.4.i; A.611.B.4.i; A.612.B.4.i; A.613.B.4.i; A.614.B.4.i; A.615.B.4.i;
A.616.B.4.i; A.617.B.4.i; A.618.B.4.i; A.619.B.4.i; A.620.B.4.i; A.621.B.4.i;
A.622.B.4.i; A.623.B.4.i; A.624.B.4.i; A.625.B.4.i; A.626.B.4.i; A.627.B.4.i;
A.628.B.4.i; A.629.B.4.i; A.630.B.4.i; A.631.B.4.i; A.632.B.4.i; A.633.B.4.i;
A.634.B.4.i; A.635.B.4.i; A.636.B.4.i; A.637.B.4.i; A.638.B.4.i; A.639.B.4.i;
A.640.B.4.i; A.641.B.4.i; A.642.B.4.i; A.643.B.4.i; A.644.B.4.i; A.645.B.4.i;
A.646.B.4.i; A.647.B.4.i; A.648.B.4.i; A.649.B.4.i; A.650.B.4.i; A.651.B.4.i;
A.652.B.4.i; A.653.B.4.i; A.654.B.4.i; A.655.B.4.i; A.656.B.4.i; A.657.B.4.i;
A.658.B.4.i; A.659.B.4.i; A.660.B.4.i; A.2.B.11.i; A.3.B.11.i; A.4.B.11.i; A.5.B.11.i;
A.6.B.11.i; A.7.B.11.i; A.9.B.11.i; A.10.B.11.i; A.15.B.11.i; A.100.B.11.i;
A.101.B.11.i; A.102.B.11.i; A.103.B.11.i; A.104.B.11.i; A.105.B.11.i; A.106.B.11.i;
A.107.B.11.i; A.108.B.11.i; A.109.B.11.i; A.110.B.11.i; A.111.B.11.i; A.112.B.11.i;
A.113.B.11.i; A.115.B.11.i; A.115.B.11.i; A.116.B.11.i; A.117.B.11.i; A.118.B.11.i;
A.119.B.11.i; A.120.B.11.i; A.121.B.11.i; A.122.B.11.i; A.123.B.11.i; A.124.B.11.i;
A.125.B.11.i; A.126.B.11.i; A.127.B.11.i; A.128.B.11.i; A.129.B.11.i; A.130.B.11.i;

TABLE 6-continued

Exemplary Enumerated Compounds

A.131.B.11.i; A.132.B.11.i; A.133.B.11.i; A.134.B.11.i; A.135.B.11.i; A.136.B.11.i;
A.137.B.11.i; A.138.B.11.i; A.139.B.11.i; A.140.B.11.i; A.141.B.11.i; A.142.B.11.i;
A.143.B.11.i; A.144.B.11.i; A.145.B.11.i; A.146.B.11.i; A.147.B.11.i; A.148.B.11.i;
A.149.B.11.i; A.150.B.11.i; A.151.B.11.i; A.152.B.11.i; A.153.B.11.i; A.154.B.11.i;
A.155.B.11.i; A.156.B.11.i; A.157.B.11.i; A.158.B.11.i; A.159.B.11.i; A.160.B.11.i;
A.161.B.11.i; A.162.B.11.i; A.163.B.11.i; A.164.B.11.i; A.165.B.11.i; A.166.B.11.i;
A.167.B.11.i; A.168.B.11.i; A.169.B.11.i; A.170.B.11.i; A.171.B.11.i; A.172.B.11.i;
A.173.B.11.i; A.174.B.11.i; A.175.B.11.i; A.176.B.11.i; A.177.B.11.i; A.178.B.11.i;
A.179.B.11.i; A.180.B.11.i; A.181.B.11.i; A.182.B.11.i; A.183.B.11.i; A.184.B.11.i;
A.185.B.11.i; A.186.B.11.i; A.187.B.11.i; A.188.B.11.i; A.189.B.11.i; A.190.B.11.i;
A.191.B.11.i; A.192.B.11.i; A.193.B.11.i; A.194.B.11.i; A.195.B.11.i; A.196.B.11.i;
A.197.B.11.i; A.198.B.11.i; A.199.B.11.i; A.200.B.11.i; A.201.B.11.i; A.202.B.11.i;
A.203.B.11.i; A.204.B.11.i; A.205.B.11.i; A.206.B.11.i; A.207.B.11.i; A.208.B.11.i;
A.209.B.11.i; A.210.B.11.i; A.211.B.11.i; A.212.B.11.i; A.213.B.11.i; A.214.B.11.i;
A.215.B.11.i; A.216.B.11.i; A.217.B.11.i; A.218.B.11.i; A.219.B.11.i; A.220.B.11.i;
A.221.B.11.i; A.222.B.11.i; A.223.B.11.i; A.224.B.11.i; A.225.B.11.i; A.226.B.11.i;
A.227.B.11.i; A.228.B.11.i; A.229.B.11.i; A.230.B.11.i; A.231.B.11.i; A.232.B.11.i;
A.233.B.11.i; A.234.B.11.i; A.235.B.11.i; A.236.B.11.i; A.237.B.11.i; A.238.B.11.i;
A.239.B.11.i; A.240.B.11.i; A.241.B.11.i; A.242.B.11.i; A.243.B.11.i; A.244.B.11.i;
A.245.B.11.i; A.246.B.11.i; A.247.B.11.i; A.248.B.11.i; A.249.B.11.i; A.250.B.11.i;
A.251.B.11.i; A.252.B.11.i; A.253.B.11.i; A.254.B.11.i; A.255.B.11.i; A.256.B.11.i;
A.257.B.11.i; A.258.B.11.i; A.259.B.11.i; A.260.B.11.i; A.261.B.11.i; A.262.B.11.i;
A.263.B.11.i; A.264.B.11.i; A.265.B.11.i; A.266.B.11.i; A.267.B.11.i; A.268.B.11.i;
A.269.B.11.i; A.270.B.11.i; A.271.B.11.i; A.272.B.11.i; A.273.B.11.i; A.274.B.11.i;
A.275.B.11.i; A.276.B.11.i; A.277.B.11.i; A.278.B.11.i; A.279.B.11.i; A.280.B.11.i;
A.281.B.11.i; A.282.B.11.i; A.283.B.11.i; A.284.B.11.i; A.285.B.11.i; A.286.B.11.i;
A.287.B.11.i; A.288.B.11.i; A.289.B.11.i; A.290.B.11.i; A.291.B.11.i; A.292.B.11.i;
A.293.B.11.i; A.294.B.11.i; A.295.B.11.i; A.296.B.11.i; A.297.B.11.i; A.298.B.11.i;
A.299.B.11.i; A.300.B.11.i; A.301.B.11.i; A.302.B.11.i; A.303.B.11.i; A.304.B.11.i;
A.305.B.11.i; A.306.B.11.i; A.307.B.11.i; A.308.B.11.i; A.309.B.11.i; A.310.B.11.i;
A.311.B.11.i; A.312.B.11.i; A.313.B.11.i; A.314.B.11.i; A.315.B.11.i; A.316.B.11.i;
A.317.B.11.i; A.318.B.11.i; A.319.B.11.i; A.320.B.11.i; A.321.B.11.i; A.323.B.11.i;
A.324.B.11.i; A.325.B.11.i; A.326.B.11.i; A.327.B.11.i; A.328.B.11.i; A.329.B.11.i;
A.330.B.11.i; A.331.B.11.i; A.332.B.11.i; A.333.B.11.i; A.334.B.11.i; A.335.B.11.i;
A.336.B.11.i; A.337.B.11.i; A.338.B.11.i; A.339.B.11.i; A.340.B.11.i; A.341.B.11.i;
A.342.B.11.i; A.343.B.11.i; A.344.B.11.i; A.345.B.11.i; A.346.B.11.i; A.347.B.11.i;
A.348.B.11.i; A.349.B.11.i; A.350.B.11.i; A.351.B.11.i; A.352.B.11.i; A.353.B.11.i;
A.354.B.11.i; A.355.B.11.i; A.356.B.11.i; A.357.B.11.i; A.358.B.11.i; A.359.B.11.i;
A.360.B.11.i; A.361.B.11.i; A.362.B.11.i; A.363.B.11.i; A.364.B.11.i; A.365.B.11.i;
A.366.B.11.i; A.367.B.11.i; A.368.B.11.i; A.369.B.11.i; A.370.B.11.i; A.371.B.11.i;
A.372.B.11.i; A.373.B.11.i; A.374.B.11.i; A.375.B.11.i; A.376.B.11.i; A.377.B.11.i;
A.378.B.11.i; A.379.B.11.i; A.380.B.11.i; A.381.B.11.i; A.382.B.11.i; A.383.B.11.i;
A.384.B.11.i; A.385.B.11.i; A.386.B.11.i; A.387.B.11.i; A.388.B.11.i; A.389.B.11.i;
A.390.B.11.i; A.391.B.11.i; A.392.B.11.i; A.393.B.11.i; A.394.B.11.i; A.395.B.11.i;
A.396.B.11.i; A.397.B.11.i; A.398.B.11.i; A.399.B.11.i; A.400.B.11.i; A.401.B.11.i;
A.402.B.11.i; A.403.B.11.i; A.404.B.11.i; A.405.B.11.i; A.406.B.11.i; A.407.B.11.i;
A.408.B.11.i; A.409.B.11.i; A.410.B.11.i; A.411.B.11.i; A.412.B.11.i; A.413.B.11.i;
A.414.B.11.i; A.415.B.11.i; A.416.B.11.i; A.417.B.11.i; A.418.B.11.i; A.419.B.11.i;
A.420.B.11.i; A.421.B.11.i; A.422.B.11.i; A.423.B.11.i; A.424.B.11.i; A.425.B.11.i;
A.426.B.11.i; A.427.B.11.i; A.428.B.11.i; A.429.B.11.i; A.430.B.11.i; A.431.B.11.i;
A.432.B.11.i; A.433.B.11.i; A.434.B.11.i; A.435.B.11.i; A.436.B.11.i; A.437.B.11.i;
A.438.B.11.i; A.439.B.11.i; A.440.B.11.i; A.441.B.11.i; A.442.B.11.i; A.443.B.11.i;
A.444.B.11.i; A.445.B.11.i; A.446.B.11.i; A.447.B.11.i; A.448.B.11.i; A.449.B.11.i;
A.450.B.11.i; A.451.B.11.i; A.452.B.11.i; A.453.B.11.i; A.454.B.11.i; A.455.B.11.i;
A.456.B.11.i; A.457.B.11.i; A.458.B.11.i; A.459.B.11.i; A.460.B.11.i; A.461.B.11.i;
A.462.B.11.i; A.463.B.11.i; A.464.B.11.i; A.465.B.11.i; A.466.B.11.i; A.467.B.11.i;
A.468.B.11.i; A.469.B.11.i; A.470.B.11.i; A.471.B.11.i; A.472.B.11.i; A.473.B.11.i;
A.474.B.11.i; A.475.B.11.i; A.476.B.11.i; A.477.B.11.i; A.478.B.11.i; A.479.B.11.i;
A.480.B.11.i; A.481.B.11.i; A.482.B.11.i; A.483.B.11.i; A.484.B.11.i; A.485.B.11.i;
A.486.B.11.i; A.487.B.11.i; A.488.B.11.i; A.489.B.11.i; A.490.B.11.i; A.491.B.11.i;
A.492.B.11.i; A.493.B.11.i; A.494.B.11.i; A.495.B.11.i; A.496.B.11.i; A.497.B.11.i;
A.498.B.11.i; A.499.B.11.i; A.500.B.11.i; A.501.B.11.i; A.502.B.11.i; A.503.B.11.i;
A.504.B.11.i; A.505.B.11.i; A.506.B.11.i; A.507.B.11.i; A.508.B.11.i; A.509.B.11.i;
A.510.B.11.i; A.511.B.11.i; A.512.B.11.i; A.512.B.11.i; A.513.B.11.i; A.514.B.11.i;
A.515.B.11.i; A.516.B.11.i; A.517.B.11.i; A.518.B.11.i; A.519.B.11.i; A.520.B.11.i;
A.521.B.11.i; A.522.B.11.i; A.523.B.11.i; A.524.B.11.i; A.525.B.11.i; A.526.B.11.i;
A.527.B.11.i; A.528.B.11.i; A.529.B.11.i; A.530.B.11.i; A.531.B.11.i; A.532.B.11.i;
A.533.B.11.i; A.534.B.11.i; A.535.B.11.i; A.536.B.11.i; A.537.B.11.i; A.538.B.11.i;
A.539.B.11.i; A.540.B.11.i; A.541.B.11.i; A.542.B.11.i; A.543.B.11.i; A.544.B.11.i;
A.545.B.11.i; A.546.B.11.i; A.547.B.11.i; A.548.B.11.i; A.549.B.11.i; A.550.B.11.i;
A.551.B.11.i; A.552.B.11.i; A.553.B.11.i; A.554.B.11.i; A.555.B.11.i; A.556.B.11.i;
A.557.B.11.i; A.558.B.11.i; A.559.B.11.i; A.560.B.11.i; A.561.B.11.i; A.562.B.11.i;
A.563.B.11.i; A.564.B.11.i; A.565.B.11.i; A.566.B.11.i; A.567.B.11.i; A.568.B.11.i;
A.569.B.11.i; A.570.B.11.i; A.571.B.11.i; A.572.B.11.i; A.573.B.11.i; A.574.B.11.i;
A.575.B.11.i; A.576.B.11.i; A.577.B.11.i; A.578.B.11.i; A.579.B.11.i; A.580.B.11.i;
A.581.B.11.i; A.582.B.11.i; A.583.B.11.i; A.584.B.11.i; A.585.B.11.i; A.586.B.11.i;
A.587.B.11.i; A.588.B.11.i; A.589.B.11.i; A.590.B.11.i; A.591.B.11.i; A.592.B.11.i;

TABLE 6-continued

Exemplary Enumerated Compounds

A.593.B.11.i; A.594.B.11.i; A.595.B.11.i; A.596.B.11.i; A.597.B.11.i; A.598.B.11.i;
A.599.B.11.i; A.600.B.11.i; A.601.B.11.i; A.602.B.11.i; A.603.B.11.i; A.604.B.11.i;
A.605.B.11.i; A.606.B.11.i; A.607.B.11.i; A.608.B.11.i; A.609.B.11.i; A.610.B.11.i;
A.611.B.11.i; A.612.B.11.i; A.613.B.11.i; A.614.B.11.i; A.615.B.11.i; A.616.B.11.i;
A.617.B.11.i; A.618.B.11.i; A.619.B.11.i; A.620.B.11.i; A.621.B.11.i; A.622.B.11.i;
A.623.B.11.i; A.624.B.11.i; A.625.B.11.i; A.626.B.11.i; A.627.B.11.i; A.628.B.11.i;
A.629.B.11.i; A.630.B.11.i; A.631.B.11.i; A.632.B.11.i; A.633.B.11.i; A.634.B.11.i;
A.635.B.11.i; A.636.B.11.i; A.637.B.11.i; A.638.B.11.i; A.639.B.11.i; A.640.B.11.i;
A.641.B.11.i; A.642.B.11.i; A.643.B.11.i; A.644.B.11.i; A.645.B.11.i; A.646.B.11.i;
A.647.B.11.i; A.648.B.11.i; A.649.B.11.i; A.650.B.11.i; A.651.B.11.i; A.652.B.11.i;
A.653.B.11.i; A.654.B.11.i; A.655.B.11.i; A.656.B.11.i; A.657.B.11.i; A.658.B.11.i;
A.659.B.11.i; A.660.B.11.i; A.2.C.4.i; A.3.C.4.i; A.4.C.4.i; A.5.C.4.i; A.6.C.4.i;
A.7.C.4.i; A.9.C.4.i; A.10.C.4.i; A.15.C.4.i; A.100.C.4.i; A.101.C.4.i; A.102.C.4.i;
A.103.C.4.i; A.104.C.4.i; A.105.C.4.i; A.106.C.4.i; A.107.C.4.i; A.108.C.4.i;
A.109.C.4.i; A.110.C.4.i; A.111.C.4.i; A.112.C.4.i; A.113.C.4.i; A.115.C.4.i;
A.115.C.4.i; A.116.C.4.i; A.117.C.4.i; A.118.C.4.i; A.119.C.4.i; A.120.C.4.i;
A.121.C.4.i; A.122.C.4.i; A.123.C.4.i; A.124.C.4.i; A.125.C.4.i; A.126.C.4.i;
A.127.C.4.i; A.128.C.4.i; A.129.C.4.i; A.130.C.4.i; A.131.C.4.i; A.132.C.4.i;
A.133.C.4.i; A.134.C.4.i; A.135.C.4.i; A.136.C.4.i; A.137.C.4.i; A.138.C.4.i;
A.139.C.4.i; A.140.C.4.i; A.141.C.4.i; A.142.C.4.i; A.143.C.4.i; A.144.C.4.i;
A.145.C.4.i; A.146.C.4.i; A.147.C.4.i; A.148.C.4.i; A.149.C.4.i; A.150.C.4.i;
A.151.C.4.i; A.152.C.4.i; A.153.C.4.i; A.154.C.4.i; A.155.C.4.i; A.156.C.4.i;
A.157.C.4.i; A.158.C.4.i; A.159.C.4.i; A.160.C.4.i; A.161.C.4.i; A.162.C.4.i;
A.163.C.4.i; A.164.C.4.i; A.165.C.4.i; A.166.C.4.i; A.167.C.4.i; A.168.C.4.i;
A.169.C.4.i; A.170.C.4.i; A.171.C.4.i; A.172.C.4.i; A.173.C.4.i; A.174.C.4.i;
A.175.C.4.i; A.176.C.4.i; A.177.C.4.i; A.178.C.4.i; A.179.C.4.i; A.180.C.4.i;
A.181.C.4.i; A.182.C.4.i; A.183.C.4.i; A.184.C.4.i; A.185.C.4.i; A.186.C.4.i;
A.187.C.4.i; A.188.C.4.i; A.189.C.4.i; A.190.C.4.i; A.191.C.4.i; A.192.C.4.i;
A.193.C.4.i; A.194.C.4.i; A.195.C.4.i; A.196.C.4.i; A.197.C.4.i; A.198.C.4.i;
A.199.C.4.i; A.200.C.4.i; A.201.C.4.i; A.202.C.4.i; A.203.C.4.i; A.204.C.4.i;
A.205.C.4.i; A.206.C.4.i; A.207.C.4.i; A.208.C.4.i; A.209.C.4.i; A.210.C.4.i;
A.211.C.4.i; A.212.C.4.i; A.213.C.4.i; A.214.C.4.i; A.215.C.4.i; A.216.C.4.i;
A.217.C.4.i; A.218.C.4.i; A.219.C.4.i; A.220.C.4.i; A.221.C.4.i; A.222.C.4.i;
A.223.C.4.i; A.224.C.4.i; A.225.C.4.i; A.226.C.4.i; A.227.C.4.i; A.228.C.4.i;
A.229.C.4.i; A.230.C.4.i; A.231.C.4.i; A.232.C.4.i; A.233.C.4.i; A.234.C.4.i;
A.235.C.4.i; A.236.C.4.i; A.237.C.4.i; A.238.C.4.i; A.239.C.4.i; A.240.C.4.i;
A.241.C.4.i; A.242.C.4.i; A.243.C.4.i; A.244.C.4.i; A.245.C.4.i; A.246.C.4.i;
A.247.C.4.i; A.248.C.4.i; A.249.C.4.i; A.250.C.4.i; A.251.C.4.i; A.252.C.4.i;
A.253.C.4.i; A.254.C.4.i; A.255.C.4.i; A.256.C.4.i; A.257.C.4.i; A.258.C.4.i;
A.259.C.4.i; A.260.C.4.i; A.261.C.4.i; A.262.C.4.i; A.263.C.4.i; A.264.C.4.i;
A.265.C.4.i; A.266.C.4.i; A.267.C.4.i; A.268.C.4.i; A.269.C.4.i; A.270.C.4.i;
A.271.C.4.i; A.272.C.4.i; A.273.C.4.i; A.274.C.4.i; A.275.C.4.i; A.276.C.4.i;
A.277.C.4.i; A.278.C.4.i; A.279.C.4.i; A.280.C.4.i; A.281.C.4.i; A.282.C.4.i;
A.283.C.4.i; A.284.C.4.i; A.285.C.4.i; A.286.C.4.i; A.287.C.4.i; A.288.C.4.i;
A.289.C.4.i; A.290.C.4.i; A.291.C.4.i; A.292.C.4.i; A.293.C.4.i; A.294.C.4.i;
A.295.C.4.i; A.296.C.4.i; A.297.C.4.i; A.298.C.4.i; A.299.C.4.i; A.300.C.4.i;
A.301.C.4.i; A.302.C.4.i; A.303.C.4.i; A.304.C.4.i; A.305.C.4.i; A.306.C.4.i;
A.307.C.4.i; A.308.C.4.i; A.309.C.4.i; A.310.C.4.i; A.311.C.4.i; A.312.C.4.i;
A.313.C.4.i; A.314.C.4.i; A.315.C.4.i; A.316.C.4.i; A.317.C.4.i; A.318.C.4.i;
A.319.C.4.i; A.320.C.4.i; A.321.C.4.i; A.323.C.4.i; A.324.C.4.i; A.325.C.4.i;
A.326.C.4.i; A.327.C.4.i; A.328.C.4.i; A.329.C.4.i; A.330.C.4.i; A.331.C.4.i;
A.332.C.4.i; A.333.C.4.i; A.334.C.4.i; A.335.C.4.i; A.336.C.4.i; A.337.C.4.i;
A.338.C.4.i; A.339.C.4.i; A.340.C.4.i; A.341.C.4.i; A.342.C.4.i; A.343.C.4.i;
A.344.C.4.i; A.345.C.4.i; A.346.C.4.i; A.347.C.4.i; A.348.C.4.i; A.349.C.4.i;
A.350.C.4.i; A.351.C.4.i; A.352.C.4.i; A.353.C.4.i; A.354.C.4.i; A.355.C.4.i;
A.356.C.4.i; A.357.C.4.i; A.358.C.4.i; A.359.C.4.i; A.360.C.4.i; A.361.C.4.i;
A.362.C.4.i; A.363.C.4.i; A.364.C.4.i; A.365.C.4.i; A.366.C.4.i; A.367.C.4.i;
A.368.C.4.i; A.369.C.4.i; A.370.C.4.i; A.371.C.4.i; A.372.C.4.i; A.373.C.4.i;
A.374.C.4.i; A.375.C.4.i; A.376.C.4.i; A.377.C.4.i; A.378.C.4.i; A.379.C.4.i;
A.380.C.4.i; A.381.C.4.i; A.382.C.4.i; A.383.C.4.i; A.384.C.4.i; A.385.C.4.i;
A.386.C.4.i; A.387.C.4.i; A.388.C.4.i; A.389.C.4.i; A.390.C.4.i; A.391.C.4.i;
A.392.C.4.i; A.393.C.4.i; A.394.C.4.i; A.395.C.4.i; A.396.C.4.i; A.397.C.4.i;
A.398.C.4.i; A.399.C.4.i; A.400.C.4.i; A.401.C.4.i; A.402.C.4.i; A.403.C.4.i;
A.404.C.4.i; A.405.C.4.i; A.406.C.4.i; A.407.C.4.i; A.408.C.4.i; A.409.C.4.i;
A.410.C.4.i; A.411.C.4.i; A.412.C.4.i; A.413.C.4.i; A.414.C.4.i; A.415.C.4.i;
A.416.C.4.i; A.417.C.4.i; A.418.C.4.i; A.419.C.4.i; A.420.C.4.i; A.421.C.4.i;
A.422.C.4.i; A.423.C.4.i; A.424.C.4.i; A.425.C.4.i; A.426.C.4.i; A.427.C.4.i;
A.428.C.4.i; A.429.C.4.i; A.430.C.4.i; A.431.C.4.i; A.432.C.4.i; A.433.C.4.i;
A.434.C.4.i; A.435.C.4.i; A.436.C.4.i; A.437.C.4.i; A.438.C.4.i; A.439.C.4.i;
A.440.C.4.i; A.441.C.4.i; A.442.C.4.i; A.443.C.4.i; A.444.C.4.i; A.445.C.4.i;
A.446.C.4.i; A.447.C.4.i; A.448.C.4.i; A.449.C.4.i; A.450.C.4.i; A.451.C.4.i;
A.452.C.4.i; A.453.C.4.i; A.454.C.4.i; A.455.C.4.i; A.456.C.4.i; A.457.C.4.i;
A.458.C.4.i; A.459.C.4.i; A.460.C.4.i; A.461.C.4.i; A.462.C.4.i; A.463.C.4.i;
A.464.C.4.i; A.465.C.4.i; A.466.C.4.i; A.467.C.4.i; A.468.C.4.i; A.469.C.4.i;
A.470.C.4.i; A.471.C.4.i; A.472.C.4.i; A.473.C.4.i; A.474.C.4.i; A.475.C.4.i;
A.476.C.4.i; A.477.C.4.i; A.478.C.4.i; A.479.C.4.i; A.480.C.4.i; A.481.C.4.i;
A.482.C.4.i; A.483.C.4.i; A.484.C.4.i; A.485.C.4.i; A.486.C.4.i; A.487.C.4.i;

TABLE 6-continued

Exemplary Enumerated Compounds

A.488.C.4.i; A.489.C.4.i; A.490.C.4.i; A.491.C.4.i; A.492.C.4.i; A.493.C.4.i;
A.494.C.4.i; A.495.C.4.i; A.496.C.4.i; A.497.C.4.i; A.498.C.4.i; A.499.C.4.i;
A.500.C.4.i; A.501.C.4.i; A.502.C.4.i; A.503.C.4.i; A.504.C.4.i; A.505.C.4.i;
A.506.C.4.i; A.507.C.4.i; A.508.C.4.i; A.509.C.4.i; A.510.C.4.i; A.511.C.4.i;
A.512.C.4.i; A.513.C.4.i; A.514.C.4.i; A.515.C.4.i; A.516.C.4.i;
A.517.C.4.i; A.518.C.4.i; A.519.C.4.i; A.520.C.4.i; A.521.C.4.i; A.522.C.4.i;
A.523.C.4.i; A.524.C.4.i; A.525.C.4.i; A.526.C.4.i; A.527.C.4.i; A.528.C.4.i;
A.529.C.4.i; A.530.C.4.i; A.531.C.4.i; A.532.C.4.i; A.533.C.4.i; A.534.C.4.i;
A.535.C.4.i; A.536.C.4.i; A.537.C.4.i; A.538.C.4.i; A.539.C.4.i; A.540.C.4.i;
A.541.C.4.i; A.542.C.4.i; A.543.C.4.i; A.544.C.4.i; A.545.C.4.i; A.546.C.4.i;
A.547.C.4.i; A.548.C.4.i; A.549.C.4.i; A.550.C.4.i; A.551.C.4.i; A.552.C.4.i;
A.553.C.4.i; A.554.C.4.i; A.555.C.4.i; A.556.C.4.i; A.557.C.4.i; A.558.C.4.i;
A.559.C.4.i; A.560.C.4.i; A.561.C.4.i; A.562.C.4.i; A.563.C.4.i; A.564.C.4.i;
A.565.C.4.i; A.566.C.4.i; A.567.C.4.i; A.568.C.4.i; A.569.C.4.i; A.570.C.4.i;
A.571.C.4.i; A.572.C.4.i; A.573.C.4.i; A.574.C.4.i; A.575.C.4.i; A.576.C.4.i;
A.577.C.4.i; A.578.C.4.i; A.579.C.4.i; A.580.C.4.i; A.581.C.4.i; A.582.C.4.i;
A.583.C.4.i; A.584.C.4.i; A.585.C.4.i; A.586.C.4.i; A.587.C.4.i; A.588.C.4.i;
A.589.C.4.i; A.590.C.4.i; A.591.C.4.i; A.592.C.4.i; A.593.C.4.i; A.594.C.4.i;
A.595.C.4.i; A.596.C.4.i; A.597.C.4.i; A.598.C.4.i; A.599.C.4.i; A.600.C.4.i;
A.601.C.4.i; A.602.C.4.i; A.603.C.4.i; A.604.C.4.i; A.605.C.4.i; A.606.C.4.i;
A.607.C.4.i; A.608.C.4.i; A.609.C.4.i; A.610.C.4.i; A.611.C.4.i; A.612.C.4.i;
A.613.C.4.i; A.614.C.4.i; A.615.C.4.i; A.616.C.4.i; A.617.C.4.i; A.618.C.4.i;
A.619.C.4.i; A.620.C.4.i; A.621.C.4.i; A.622.C.4.i; A.623.C.4.i; A.624.C.4.i;
A.625.C.4.i; A.626.C.4.i; A.627.C.4.i; A.628.C.4.i; A.629.C.4.i; A.630.C.4.i;
A.631.C.4.i; A.632.C.4.i; A.633.C.4.i; A.634.C.4.i; A.635.C.4.i; A.636.C.4.i;
A.637.C.4.i; A.638.C.4.i; A.639.C.4.i; A.640.C.4.i; A.641.C.4.i; A.642.C.4.i;
A.643.C.4.i; A.644.C.4.i; A.645.C.4.i; A.646.C.4.i; A.647.C.4.i; A.648.C.4.i;
A.649.C.4.i; A.650.C.4.i; A.651.C.4.i; A.652.C.4.i; A.653.C.4.i; A.654.C.4.i;
A.655.C.4.i; A.656.C.4.i; A.657.C.4.i; A.658.C.4.i; A.659.C.4.i; A.660.C.4.i;
A.2.C.11.i; A.3.C.11.i; A.4.C.11.i; A.5.C.11.i; A.6.C.11.i; A.7.C.11.i; A.9.C.11.i;
A.10.C.11.i; A.15.C.11.i; A.100.C.11.i; A.101.C.11.i; A.102.C.11.i; A.103.C.11.i;
A.104.C.11.i; A.105.C.11.i; A.106.C.11.i; A.107.C.11.i; A.108.C.11.i; A.109.C.11.i;
A.110.C.11.i; A.111.C.11.i; A.112.C.11.i; A.113.C.11.i; A.114.C.11.i; A.115.C.11.i;
A.116.C.11.i; A.117.C.11.i; A.118.C.11.i; A.119.C.11.i; A.120.C.11.i; A.121.C.11.i;
A.122.C.11.i; A.123.C.11.i; A.124.C.11.i; A.125.C.11.i; A.126.C.11.i; A.127.C.11.i;
A.128.C.11.i; A.129.C.11.i; A.130.C.11.i; A.131.C.11.i; A.132.C.11.i; A.133.C.11.i;
A.134.C.11.i; A.135.C.11.i; A.136.C.11.i; A.137.C.11.i; A.138.C.11.i; A.139.C.11.i;
A.140.C.11.i; A.141.C.11.i; A.142.C.11.i; A.143.C.11.i; A.144.C.11.i; A.145.C.11.i;
A.146.C.11.i; A.147.C.11.i; A.148.C.11.i; A.149.C.11.i; A.150.C.11.i; A.151.C.11.i;
A.152.C.11.i; A.153.C.11.i; A.154.C.11.i; A.155.C.11.i; A.156.C.11.i; A.157.C.11.i;
A.158.C.11.i; A.159.C.11.i; A.160.C.11.i; A.161.C.11.i; A.162.C.11.i; A.163.C.11.i;
A.164.C.11.i; A.165.C.11.i; A.166.C.11.i; A.167.C.11.i; A.168.C.11.i; A.169.C.11.i;
A.170.C.11.i; A.171.C.11.i; A.172.C.11.i; A.173.C.11.i; A.174.C.11.i; A.175.C.11.i;
A.176.C.11.i; A.177.C.11.i; A.178.C.11.i; A.179.C.11.i; A.180.C.11.i; A.181.C.11.i;
A.182.C.11.i; A.183.C.11.i; A.184.C.11.i; A.185.C.11.i; A.186.C.11.i; A.187.C.11.i;
A.188.C.11.i; A.189.C.11.i; A.190.C.11.i; A.191.C.11.i; A.192.C.11.i; A.193.C.11.i;
A.194.C.11.i; A.195.C.11.i; A.196.C.11.i; A.197.C.11.i; A.198.C.11.i; A.199.C.11.i;
A.200.C.11.i; A.201.C.11.i; A.202.C.11.i; A.203.C.11.i; A.204.C.11.i; A.205.C.11.i;
A.206.C.11.i; A.207.C.11.i; A.208.C.11.i; A.209.C.11.i; A.210.C.11.i; A.211.C.11.i;
A.212.C.11.i; A.213.C.11.i; A.214.C.11.i; A.215.C.11.i; A.216.C.11.i; A.217.C.11.i;
A.218.C.11.i; A.219.C.11.i; A.220.C.11.i; A.221.C.11.i; A.222.C.11.i; A.223.C.11.i;
A.224.C.11.i; A.225.C.11.i; A.226.C.11.i; A.227.C.11.i; A.228.C.11.i; A.229.C.11.i;
A.230.C.11.i; A.231.C.11.i; A.232.C.11.i; A.233.C.11.i; A.234.C.11.i; A.235.C.11.i;
A.236.C.11.i; A.237.C.11.i; A.238.C.11.i; A.239.C.11.i; A.240.C.11.i; A.241.C.11.i;
A.242.C.11.i; A.243.C.11.i; A.244.C.11.i; A.245.C.11.i; A.246.C.11.i; A.247.C.11.i;
A.248.C.11.i; A.249.C.11.i; A.250.C.11.i; A.251.C.11.i; A.252.C.11.i; A.253.C.11.i;
A.254.C.11.i; A.255.C.11.i; A.256.C.11.i; A.257.C.11.i; A.258.C.11.i; A.259.C.11.i;
A.260.C.11.i; A.261.C.11.i; A.262.C.11.i; A.263.C.11.i; A.264.C.11.i; A.265.C.11.i;
A.266.C.11.i; A.267.C.11.i; A.268.C.11.i; A.269.C.11.i; A.270.C.11.i; A.271.C.11.i;
A.272.C.11.i; A.273.C.11.i; A.274.C.11.i; A.275.C.11.i; A.276.C.11.i; A.277.C.11.i;
A.278.C.11.i; A.279.C.11.i; A.280.C.11.i; A.281.C.11.i; A.282.C.11.i; A.283.C.11.i;
A.284.C.11.i; A.285.C.11.i; A.286.C.11.i; A.287.C.11.i; A.288.C.11.i; A.289.C.11.i;
A.290.C.11.i; A.291.C.11.i; A.292.C.11.i; A.293.C.11.i; A.294.C.11.i; A.295.C.11.i;
A.296.C.11.i; A.297.C.11.i; A.298.C.11.i; A.299.C.11.i; A.300.C.11.i; A.301.C.11.i;
A.302.C.11.i; A.303.C.11.i; A.304.C.11.i; A.305.C.11.i; A.306.C.11.i; A.307.C.11.i;
A.308.C.11.i; A.309.C.11.i; A.310.C.11.i; A.311.C.11.i; A.312.C.11.i; A.313.C.11.i;
A.314.C.11.i; A.315.C.11.i; A.316.C.11.i; A.317.C.11.i; A.318.C.11.i; A.319.C.11.i;
A.320.C.11.i; A.321.C.11.i; A.323.C.11.i; A.324.C.11.i; A.325.C.11.i; A.326.C.11.i;
A.327.C.11.i; A.328.C.11.i; A.329.C.11.i; A.330.C.11.i; A.331.C.11.i; A.332.C.11.i;
A.333.C.11.i; A.334.C.11.i; A.335.C.11.i; A.336.C.11.i; A.337.C.11.i; A.338.C.11.i;
A.339.C.11.i; A.340.C.11.i; A.341.C.11.i; A.342.C.11.i; A.343.C.11.i; A.344.C.11.i;
A.345.C.11.i; A.346.C.11.i; A.347.C.11.i; A.348.C.11.i; A.349.C.11.i; A.350.C.11.i;
A.351.C.11.i; A.352.C.11.i; A.353.C.11.i; A.354.C.11.i; A.355.C.11.i; A.356.C.11.i;
A.357.C.11.i; A.358.C.11.i; A.359.C.11.i; A.360.C.11.i; A.361.C.11.i; A.362.C.11.i;
A.363.C.11.i; A.364.C.11.i; A.365.C.11.i; A.366.C.11.i; A.367.C.11.i; A.368.C.11.i;
A.369.C.11.i; A.370.C.11.i; A.371.C.11.i; A.372.C.11.i; A.373.C.11.i; A.374.C.11.i;
A.375.C.11.i; A.376.C.11.i; A.377.C.11.i; A.378.C.11.i; A.379.C.11.i; A.380.C.11.i;

TABLE 6-continued

Exemplary Enumerated Compounds

A.381.C.11.i; A.382.C.11.i; A.383.C.11.i; A.384.C.11.i; A.385.C.11.i; A.386.C.11.i;
A.387.C.11.i; A.388.C.11.i; A.389.C.11.i; A.390.C.11.i; A.391.C.11.i; A.392.C.11.i;
A.393.C.11.i; A.394.C.11.i; A.395.C.11.i; A.396.C.11.i; A.397.C.11.i; A.398.C.11.i;
A.399.C.11.i; A.400.C.11.i; A.401.C.11.i; A.402.C.11.i; A.403.C.11.i; A.404.C.11.i;
A.405.C.11.i; A.406.C.11.i; A.407.C.11.i; A.408.C.11.i; A.409.C.11.i; A.410.C.11.i;
A.411.C.11.i; A.412.C.11.i; A.413.C.11.i; A.414.C.11.i; A.415.C.11.i; A.416.C.11.i;
A.417.C.11.i; A.418.C.11.i; A.419.C.11.i; A.420.C.11.i; A.421.C.11.i; A.422.C.11.i;
A.423.C.11.i; A.424.C.11.i; A.425.C.11.i; A.426.C.11.i; A.427.C.11.i; A.428.C.11.i;
A.429.C.11.i; A.430.C.11.i; A.431.C.11.i; A.432.C.11.i; A.433.C.11.i; A.434.C.11.i;
A.435.C.11.i; A.436.C.11.i; A.437.C.11.i; A.438.C.11.i; A.439.C.11.i; A.440.C.11.i;
A.441.C.11.i; A.442.C.11.i; A.443.C.11.i; A.444.C.11.i; A.445.C.11.i; A.446.C.11.i;
A.447.C.11.i; A.448.C.11.i; A.449.C.11.i; A.450.C.11.i; A.451.C.11.i; A.452.C.11.i;
A.453.C.11.i; A.454.C.11.i; A.455.C.11.i; A.456.C.11.i; A.457.C.11.i; A.458.C.11.i;
A.459.C.11.i; A.460.C.11.i; A.461.C.11.i; A.462.C.11.i; A.463.C.11.i; A.464.C.11.i;
A.465.C.11.i; A.466.C.11.i; A.467.C.11.i; A.468.C.11.i; A.469.C.11.i; A.470.C.11.i;
A.471.C.11.i; A.472.C.11.i; A.473.C.11.i; A.474.C.11.i; A.475.C.11.i; A.476.C.11.i;
A.477.C.11.i; A.478.C.11.i; A.479.C.11.i; A.480.C.11.i; A.481.C.11.i; A.482.C.11.i;
A.483.C.11.i; A.484.C.11.i; A.485.C.11.i; A.486.C.11.i; A.487.C.11.i; A.488.C.11.i;
A.489.C.11.i; A.490.C.11.i; A.491.C.11.i; A.492.C.11.i; A.493.C.11.i; A.494.C.11.i;
A.495.C.11.i; A.496.C.11.i; A.497.C.11.i; A.498.C.11.i; A.499.C.11.i; A.500.C.11.i;
A.501.C.11.i; A.502.C.11.i; A.503.C.11.i; A.504.C.11.i; A.505.C.11.i; A.506.C.11.i;
A.507.C.11.i; A.508.C.11.i; A.509.C.11.i; A.510.C.11.i; A.511.C.11.i; A.512.C.11.i;
A.512.C.11.i; A.513.C.11.i; A.514.C.11.i; A.515.C.11.i; A.516.C.11.i; A.517.C.11.i;
A.518.C.11.i; A.519.C.11.i; A.520.C.11.i; A.521.C.11.i; A.522.C.11.i; A.523.C.11.i;
A.524.C.11.i; A.525.C.11.i; A.526.C.11.i; A.527.C.11.i; A.528.C.11.i; A.529.C.11.i;
A.530.C.11.i; A.531.C.11.i; A.532.C.11.i; A.533.C.11.i; A.534.C.11.i; A.535.C.11.i;
A.536.C.11.i; A.537.C.11.i; A.538.C.11.i; A.539.C.11.i; A.540.C.11.i; A.541.C.11.i;
A.542.C.11.i; A.543.C.11.i; A.544.C.11.i; A.545.C.11.i; A.546.C.11.i; A.547.C.11.i;
A.548.C.11.i; A.549.C.11.i; A.550.C.11.i; A.551.C.11.i; A.552.C.11.i; A.553.C.11.i;
A.554.C.11.i; A.555.C.11.i; A.556.C.11.i; A.557.C.11.i; A.558.C.11.i; A.559.C.11.i;
A.560.C.11.i; A.561.C.11.i; A.562.C.11.i; A.563.C.11.i; A.564.C.11.i; A.565.C.11.i;
A.566.C.11.i; A.567.C.11.i; A.568.C.11.i; A.569.C.11.i; A.570.C.11.i; A.571.C.11.i;
A.572.C.11.i; A.573.C.11.i; A.574.C.11.i; A.575.C.11.i; A.576.C.11.i; A.577.C.11.i;
A.578.C.11.i; A.579.C.11.i; A.580.C.11.i; A.581.C.11.i; A.582.C.11.i; A.583.C.11.i;
A.584.C.11.i; A.585.C.11.i; A.586.C.11.i; A.587.C.11.i; A.588.C.11.i; A.589.C.11.i;
A.590.C.11.i; A.591.C.11.i; A.592.C.11.i; A.593.C.11.i; A.594.C.11.i; A.595.C.11.i;
A.596.C.11.i; A.597.C.11.i; A.598.C.11.i; A.599.C.11.i; A.600.C.11.i; A.601.C.11.i;
A.602.C.11.i; A.603.C.11.i; A.604.C.11.i; A.605.C.11.i; A.606.C.11.i; A.607.C.11.i;
A.608.C.11.i; A.609.C.11.i; A.610.C.11.i; A.611.C.11.i; A.612.C.11.i; A.613.C.11.i;
A.614.C.11.i; A.615.C.11.i; A.616.C.11.i; A.617.C.11.i; A.618.C.11.i; A.619.C.11.i;
A.620.C.11.i; A.621.C.11.i; A.622.C.11.i; A.623.C.11.i; A.624.C.11.i; A.625.C.11.i;
A.626.C.11.i; A.627.C.11.i; A.628.C.11.i; A.629.C.11.i; A.630.C.11.i; A.631.C.11.i;
A.632.C.11.i; A.633.C.11.i; A.634.C.11.i; A.635.C.11.i; A.636.C.11.i; A.637.C.11.i;
A.638.C.11.i; A.639.C.11.i; A.640.C.11.i; A.641.C.11.i; A.642.C.11.i; A.643.C.11.i;
A.644.C.11.i; A.645.C.11.i; A.646.C.11.i; A.647.C.11.i; A.648.C.11.i; A.649.C.11.i;
A.650.C.11.i; A.651.C.11.i; A.652.C.11.i; A.653.C.11.i; A.654.C.11.i; A.655.C.11.i;
A.656.C.11.i; A.657.C.11.i; A.658.C.11.i; A.659.C.11.i; A.660.C.11.i; A.2.D.4.i;
A.3.D.4.i; A.4.D.4.i; A.5.D.4.i; A.6.D.4.i; A.7.D.4.i; A.9.D.4.i; A.10.D.4.i; A.15.D.4.i;
A.100.D.4.i; A.101.D.4.i; A.102.D.4.i; A.103.D.4.i; A.104.D.4.i; A.105.D.4.i;
A.106.D.4.i; A.107.D.4.i; A.108.D.4.i; A.109.D.4.i; A.110.D.4.i; A.111.D.4.i;
A.112.D.4.i; A.113.D.4.i; A.115.D.4.i; A.115.D.4.i; A.116.D.4.i; A.117.D.4.i;
A.118.D.4.i; A.119.D.4.i; A.120.D.4.i; A.121.D.4.i; A.122.D.4.i; A.123.D.4.i;
A.124.D.4.i; A.125.D.4.i; A.126.D.4.i; A.127.D.4.i; A.128.D.4.i; A.129.D.4.i;
A.130.D.4.i; A.131.D.4.i; A.132.D.4.i; A.133.D.4.i; A.134.D.4.i; A.135.D.4.i;
A.136.D.4.i; A.137.D.4.i; A.138.D.4.i; A.139.D.4.i; A.140.D.4.i; A.141.D.4.i;
A.142.D.4.i; A.143.D.4.i; A.144.D.4.i; A.145.D.4.i; A.146.D.4.i; A.147.D.4.i;
A.148.D.4.i; A.149.D.4.i; A.150.D.4.i; A.151.D.4.i; A.152.D.4.i; A.153.D.4.i;
A.154.D.4.i; A.155.D.4.i; A.156.D.4.i; A.157.D.4.i; A.158.D.4.i; A.159.D.4.i;
A.160.D.4.i; A.161.D.4.i; A.162.D.4.i; A.163.D.4.i; A.164.D.4.i; A.165.D.4.i;
A.166.D.4.i; A.167.D.4.i; A.168.D.4.i; A.169.D.4.i; A.170.D.4.i; A.171.D.4.i;
A.172.D.4.i; A.173.D.4.i; A.174.D.4.i; A.175.D.4.i; A.176.D.4.i; A.177.D.4.i;
A.178.D.4.i; A.179.D.4.i; A.180.D.4.i; A.181.D.4.i; A.182.D.4.i; A.183.D.4.i;
A.184.D.4.i; A.185.D.4.i; A.186.D.4.i; A.187.D.4.i; A.188.D.4.i; A.189.D.4.i;
A.190.D.4.i; A.191.D.4.i; A.192.D.4.i; A.193.D.4.i; A.194.D.4.i; A.195.D.4.i;
A.196.D.4.i; A.197.D.4.i; A.198.D.4.i; A.199.D.4.i; A.200.D.4.i; A.201.D.4.i;
A.202.D.4.i; A.203.D.4.i; A.204.D.4.i; A.205.D.4.i; A.206.D.4.i; A.207.D.4.i;
A.208.D.4.i; A.209.D.4.i; A.210.D.4.i; A.211.D.4.i; A.212.D.4.i; A.213.D.4.i;
A.214.D.4.i; A.215.D.4.i; A.216.D.4.i; A.217.D.4.i; A.218.D.4.i; A.219.D.4.i;
A.220.D.4.i; A.221.D.4.i; A.222.D.4.i; A.223.D.4.i; A.224.D.4.i; A.225.D.4.i;
A.226.D.4.i; A.227.D.4.i; A.228.D.4.i; A.229.D.4.i; A.230.D.4.i; A.231.D.4.i;
A.232.D.4.i; A.233.D.4.i; A.234.D.4.i; A.235.D.4.i; A.236.D.4.i; A.237.D.4.i;
A.238.D.4.i; A.239.D.4.i; A.240.D.4.i; A.241.D.4.i; A.242.D.4.i; A.243.D.4.i;
A.244.D.4.i; A.245.D.4.i; A.246.D.4.i; A.247.D.4.i; A.248.D.4.i; A.249.D.4.i;
A.250.D.4.i; A.251.D.4.i; A.252.D.4.i; A.253.D.4.i; A.254.D.4.i; A.255.D.4.i;
A.256.D.4.i; A.257.D.4.i; A.258.D.4.i; A.259.D.4.i; A.260.D.4.i; A.261.D.4.i;
A.262.D.4.i; A.263.D.4.i; A.264.D.4.i; A.265.D.4.i; A.266.D.4.i; A.267.D.4.i;
A.268.D.4.i; A.269.D.4.i; A.270.D.4.i; A.271.D.4.i; A.272.D.4.i; A.273.D.4.i;

TABLE 6-continued

Exemplary Enumerated Compounds

A.274.D.4.i; A.275.D.4.i; A.276.D.4.i; A.277.D.4.i; A.278.D.4.i; A.279.D.4.i;
A.280.D.4.i; A.281.D.4.i; A.282.D.4.i; A.283.D.4.i; A.284.D.4.i; A.285.D.4.i;
A.286.D.4.i; A.287.D.4.i; A.288.D.4.i; A.289.D.4.i; A.290.D.4.i; A.291.D.4.i;
A.292.D.4.i; A.293.D.4.i; A.294.D.4.i; A.295.D.4.i; A.296.D.4.i; A.297.D.4.i;
A.298.D.4.i; A.299.D.4.i; A.300.D.4.i; A.301.D.4.i; A.302.D.4.i; A.303.D.4.i;
A.304.D.4.i; A.305.D.4.i; A.306.D.4.i; A.307.D.4.i; A.308.D.4.i; A.309.D.4.i;
A.310.D.4.i; A.311.D.4.i; A.312.D.4.i; A.313.D.4.i; A.314.D.4.i; A.315.D.4.i;
A.316.D.4.i; A.317.D.4.i; A.318.D.4.i; A.319.D.4.i; A.320.D.4.i; A.321.D.4.i;
A.323.D.4.i; A.324.D.4.i; A.325.D.4.i; A.326.D.4.i; A.327.D.4.i; A.328.D.4.i;
A.329.D.4.i; A.330.D.4.i; A.331.D.4.i; A.332.D.4.i; A.333.D.4.i; A.334.D.4.i;
A.335.D.4.i; A.336.D.4.i; A.337.D.4.i; A.338.D.4.i; A.339.D.4.i; A.340.D.4.i;
A.341.D.4.i; A.342.D.4.i; A.343.D.4.i; A.344.D.4.i; A.345.D.4.i; A.346.D.4.i;
A.347.D.4.i; A.348.D.4.i; A.349.D.4.i; A.350.D.4.i; A.351.D.4.i; A.352.D.4.i;
A.353.D.4.i; A.354.D.4.i; A.355.D.4.i; A.356.D.4.i; A.357.D.4.i; A.358.D.4.i;
A.359.D.4.i; A.360.D.4.i; A.361.D.4.i; A.362.D.4.i; A.363.D.4.i; A.364.D.4.i;
A.365.D.4.i; A.366.D.4.i; A.367.D.4.i; A.368.D.4.i; A.369.D.4.i; A.370.D.4.i;
A.371.D.4.i; A.372.D.4.i; A.373.D.4.i; A.374.D.4.i; A.375.D.4.i; A.376.D.4.i;
A.377.D.4.i; A.378.D.4.i; A.379.D.4.i; A.380.D.4.i; A.381.D.4.i; A.382.D.4.i;
A.383.D.4.i; A.384.D.4.i; A.385.D.4.i; A.386.D.4.i; A.387.D.4.i; A.388.D.4.i;
A.389.D.4.i; A.390.D.4.i; A.391.D.4.i; A.392.D.4.i; A.393.D.4.i; A.394.D.4.i;
A.395.D.4.i; A.396.D.4.i; A.397.D.4.i; A.398.D.4.i; A.399.D.4.i; A.400.D.4.i;
A.401.D.4.i; A.402.D.4.i; A.403.D.4.i; A.404.D.4.i; A.405.D.4.i; A.406.D.4.i;
A.407.D.4.i; A.408.D.4.i; A.409.D.4.i; A.410.D.4.i; A.411.D.4.i; A.412.D.4.i;
A.413.D.4.i; A.414.D.4.i; A.415.D.4.i; A.416.D.4.i; A.417.D.4.i; A.418.D.4.i;
A.419.D.4.i; A.420.D.4.i; A.421.D.4.i; A.422.D.4.i; A.423.D.4.i; A.424.D.4.i;
A.425.D.4.i; A.426.D.4.i; A.427.D.4.i; A.428.D.4.i; A.429.D.4.i; A.430.D.4.i;
A.431.D.4.i; A.432.D.4.i; A.433.D.4.i; A.434.D.4.i; A.435.D.4.i; A.436.D.4.i;
A.437.D.4.i; A.438.D.4.i; A.439.D.4.i; A.440.D.4.i; A.441.D.4.i; A.442.D.4.i;
A.443.D.4.i; A.444.D.4.i; A.445.D.4.i; A.446.D.4.i; A.447.D.4.i; A.448.D.4.i;
A.449.D.4.i; A.450.D.4.i; A.451.D.4.i; A.452.D.4.i; A.453.D.4.i; A.454.D.4.i;
A.455.D.4.i; A.456.D.4.i; A.457.D.4.i; A.458.D.4.i; A.459.D.4.i; A.460.D.4.i;
A.461.D.4.i; A.462.D.4.i; A.463.D.4.i; A.464.D.4.i; A.465.D.4.i; A.466.D.4.i;
A.467.D.4.i; A.468.D.4.i; A.469.D.4.i; A.470.D.4.i; A.471.D.4.i; A.472.D.4.i;
A.473.D.4.i; A.474.D.4.i; A.475.D.4.i; A.476.D.4.i; A.477.D.4.i; A.478.D.4.i;
A.479.D.4.i; A.480.D.4.i; A.481.D.4.i; A.482.D.4.i; A.483.D.4.i; A.484.D.4.i;
A.485.D.4.i; A.486.D.4.i; A.487.D.4.i; A.488.D.4.i; A.489.D.4.i; A.490.D.4.i;
A.491.D.4.i; A.492.D.4.i; A.493.D.4.i; A.494.D.4.i; A.495.D.4.i; A.496.D.4.i;
A.497.D.4.i; A.498.D.4.i; A.499.D.4.i; A.500.D.4.i; A.501.D.4.i; A.502.D.4.i;
A.503.D.4.i; A.504.D.4.i; A.505.D.4.i; A.506.D.4.i; A.507.D.4.i; A.508.D.4.i;
A.509.D.4.i; A.510.D.4.i; A.511.D.4.i; A.512.D.4.i; A.512.D.4.i; A.513.D.4.i;
A.514.D.4.i; A.515.D.4.i; A.516.D.4.i; A.517.D.4.i; A.518.D.4.i; A.519.D.4.i;
A.520.D.4.i; A.521.D.4.i; A.522.D.4.i; A.523.D.4.i; A.524.D.4.i; A.525.D.4.i;
A.526.D.4.i; A.527.D.4.i; A.528.D.4.i; A.529.D.4.i; A.530.D.4.i; A.531.D.4.i;
A.532.D.4.i; A.533.D.4.i; A.534.D.4.i; A.535.D.4.i; A.536.D.4.i; A.537.D.4.i;
A.538.D.4.i; A.539.D.4.i; A.540.D.4.i; A.541.D.4.i; A.542.D.4.i; A.543.D.4.i;
A.544.D.4.i; A.545.D.4.i; A.546.D.4.i; A.547.D.4.i; A.548.D.4.i; A.549.D.4.i;
A.550.D.4.i; A.551.D.4.i; A.552.D.4.i; A.553.D.4.i; A.554.D.4.i; A.555.D.4.i;
A.556.D.4.i; A.557.D.4.i; A.558.D.4.i; A.559.D.4.i; A.560.D.4.i; A.561.D.4.i;
A.562.D.4.i; A.563.D.4.i; A.564.D.4.i; A.565.D.4.i; A.566.D.4.i; A.567.D.4.i;
A.568.D.4.i; A.569.D.4.i; A.570.D.4.i; A.571.D.4.i; A.572.D.4.i; A.573.D.4.i;
A.574.D.4.i; A.575.D.4.i; A.576.D.4.i; A.577.D.4.i; A.578.D.4.i; A.579.D.4.i;
A.580.D.4.i; A.581.D.4.i; A.582.D.4.i; A.583.D.4.i; A.584.D.4.i; A.585.D.4.i;
A.586.D.4.i; A.587.D.4.i; A.588.D.4.i; A.589.D.4.i; A.590.D.4.i; A.591.D.4.i;
A.592.D.4.i; A.593.D.4.i; A.594.D.4.i; A.595.D.4.i; A.596.D.4.i; A.597.D.4.i;
A.598.D.4.i; A.599.D.4.i; A.600.D.4.i; A.601.D.4.i; A.602.D.4.i; A.603.D.4.i;
A.604.D.4.i; A.605.D.4.i; A.606.D.4.i; A.607.D.4.i; A.608.D.4.i; A.609.D.4.i;
A.610.D.4.i; A.611.D.4.i; A.612.D.4.i; A.613.D.4.i; A.614.D.4.i; A.615.D.4.i;
A.616.D.4.i; A.617.D.4.i; A.618.D.4.i; A.619.D.4.i; A.620.D.4.i; A.621.D.4.i;
A.622.D.4.i; A.623.D.4.i; A.624.D.4.i; A.625.D.4.i; A.626.D.4.i; A.627.D.4.i;
A.628.D.4.i; A.629.D.4.i; A.630.D.4.i; A.631.D.4.i; A.632.D.4.i; A.633.D.4.i;
A.634.D.4.i; A.635.D.4.i; A.636.D.4.i; A.637.D.4.i; A.638.D.4.i; A.639.D.4.i;
A.640.D.4.i; A.641.D.4.i; A.642.D.4.i; A.643.D.4.i; A.644.D.4.i; A.645.D.4.i;
A.646.D.4.i; A.647.D.4.i; A.648.D.4.i; A.649.D.4.i; A.650.D.4.i; A.651.D.4.i;
A.652.D.4.i; A.653.D.4.i; A.654.D.4.i; A.655.D.4.i; A.656.D.4.i; A.657.D.4.i;
A.658.D.4.i; A.659.D.4.i; A.660.D.4.i; A.2.D.11.i; A.3.D.11.i; A.4.D.11.i; A.5.D.11.i;
A.6.D.11.i; A.7.D.11.i; A.9.D.11.i; A.10.D.11.i; A.15.D.11.i; A.100.D.11.i;
A.101.D.11.i; A.102.D.11.i; A.103.D.11.i; A.104.D.11.i; A.105.D.11.i; A.106.D.11.i;
A.107.D.11.i; A.108.D.11.i; A.109.D.11.i; A.110.D.11.i; A.111.D.11.i; A.112.D.11.i;
A.113.D.11.i; A.115.D.11.i; A.115.D.11.i; A.116.D.11.i; A.117.D.11.i; A.118.D.11.i;
A.119.D.11.i; A.120.D.11.i; A.121.D.11.i; A.122.D.11.i; A.123.D.11.i; A.124.D.11.i;
A.125.D.11.i; A.126.D.11.i; A.127.D.11.i; A.128.D.11.i; A.129.D.11.i; A.130.D.11.i;
A.131.D.11.i; A.132.D.11.i; A.133.D.11.i; A.134.D.11.i; A.135.D.11.i; A.136.D.11.i;
A.137.D.11.i; A.138.D.11.i; A.139.D.11.i; A.140.D.11.i; A.141.D.11.i; A.142.D.11.i;
A.143.D.11.i; A.144.D.11.i; A.145.D.11.i; A.146.D.11.i; A.147.D.11.i; A.148.D.11.i;
A.149.D.11.i; A.150.D.11.i; A.151.D.11.i; A.152.D.11.i; A.153.D.11.i; A.154.D.11.i;
A.155.D.11.i; A.156.D.11.i; A.157.D.11.i; A.158.D.11.i; A.159.D.11.i; A.160.D.11.i;
A.161.D.11.i; A.162.D.11.i; A.163.D.11.i; A.164.D.11.i; A.165.D.11.i; A.166.D.11.i;

TABLE 6-continued

Exemplary Enumerated Compounds

A.167.D.11.i; A.168.D.11.i; A.169.D.11.i; A.170.D.11.i; A.171.D.11.i; A.172.D.11.i;
A.173.D.11.i; A.174.D.11.i; A.175.D.11.i; A.176.D.11.i; A.177.D.11.i; A.178.D.11.i;
A.179.D.11.i; A.180.D.11.i; A.181.D.11.i; A.182.D.11.i; A.183.D.11.i; A.184.D.11.i;
A.185.D.11.i; A.186.D.11.i; A.187.D.11.i; A.188.D.11.i; A.189.D.11.i; A.190.D.11.i;
A.191.D.11.i; A.192.D.11.i; A.193.D.11.i; A.194.D.11.i; A.195.D.11.i; A.196.D.11.i;
A.197.D.11.i; A.198.D.11.i; A.199.D.11.i; A.200.D.11.i; A.201.D.11.i; A.202.D.11.i;
A.203.D.11.i; A.204.D.11.i; A.205.D.11.i; A.206.D.11.i; A.207.D.11.i; A.208.D.11.i;
A.209.D.11.i; A.210.D.11.i; A.211.D.11.i; A.212.D.11.i; A.213.D.11.i; A.214.D.11.i;
A.215.D.11.i; A.216.D.11.i; A.217.D.11.i; A.218.D.11.i; A.219.D.11.i; A.220.D.11.i;
A.221.D.11.i; A.222.D.11.i; A.223.D.11.i; A.224.D.11.i; A.225.D.11.i; A.226.D.11.i;
A.227.D.11.i; A.228.D.11.i; A.229.D.11.i; A.230.D.11.i; A.231.D.11.i; A.232.D.11.i;
A.233.D.11.i; A.234.D.11.i; A.235.D.11.i; A.236.D.11.i; A.237.D.11.i; A.238.D.11.i;
A.239.D.11.i; A.240.D.11.i; A.241.D.11.i; A.242.D.11.i; A.243.D.11.i; A.244.D.11.i;
A.245.D.11.i; A.246.D.11.i; A.247.D.11.i; A.248.D.11.i; A.249.D.11.i; A.250.D.11.i;
A.251.D.11.i; A.252.D.11.i; A.253.D.11.i; A.254.D.11.i; A.255.D.11.i; A.256.D.11.i;
A.257.D.11.i; A.258.D.11.i; A.259.D.11.i; A.260.D.11.i; A.261.D.11.i; A.262.D.11.i;
A.263.D.11.i; A.264.D.11.i; A.265.D.11.i; A.266.D.11.i; A.267.D.11.i; A.268.D.11.i;
A.269.D.11.i; A.270.D.11.i; A.271.D.11.i; A.272.D.11.i; A.273.D.11.i; A.274.D.11.i;
A.275.D.11.i; A.276.D.11.i; A.277.D.11.i; A.278.D.11.i; A.279.D.11.i; A.280.D.11.i;
A.281.D.11.i; A.282.D.11.i; A.283.D.11.i; A.284.D.11.i; A.285.D.11.i; A.286.D.11.i;
A.287.D.11.i; A.288.D.11.i; A.289.D.11.i; A.290.D.11.i; A.291.D.11.i; A.292.D.11.i;
A.293.D.11.i; A.294.D.11.i; A.295.D.11.i; A.296.D.11.i; A.297.D.11.i; A.298.D.11.i;
A.299.D.11.i; A.300.D.11.i; A.301.D.11.i; A.302.D.11.i; A.303.D.11.i; A.304.D.11.i;
A.305.D.11.i; A.306.D.11.i; A.307.D.11.i; A.308.D.11.i; A.309.D.11.i; A.310.D.11.i;
A.311.D.11.i; A.312.D.11.i; A.313.D.11.i; A.314.D.11.i; A.315.D.11.i; A.316.D.11.i;
A.317.D.11.i; A.318.D.11.i; A.319.D.11.i; A.320.D.11.i; A.321.D.11.i; A.323.D.11.i;
A.324.D.11.i; A.325.D.11.i; A.326.D.11.i; A.327.D.11.i; A.328.D.11.i; A.329.D.11.i;
A.330.D.11.i; A.331.D.11.i; A.332.D.11.i; A.333.D.11.i; A.334.D.11.i; A.335.D.11.i;
A.336.D.11.i; A.337.D.11.i; A.338.D.11.i; A.339.D.11.i; A.340.D.11.i; A.341.D.11.i;
A.342.D.11.i; A.343.D.11.i; A.344.D.11.i; A.345.D.11.i; A.346.D.11.i; A.347.D.11.i;
A.348.D.11.i; A.349.D.11.i; A.350.D.11.i; A.351.D.11.i; A.352.D.11.i; A.353.D.11.i;
A.354.D.11.i; A.355.D.11.i; A.356.D.11.i; A.357.D.11.i; A.358.D.11.i; A.359.D.11.i;
A.360.D.11.i; A.361.D.11.i; A.362.D.11.i; A.363.D.11.i; A.364.D.11.i; A.365.D.11.i;
A.366.D.11.i; A.367.D.11.i; A.368.D.11.i; A.369.D.11.i; A.370.D.11.i; A.371.D.11.i;
A.372.D.11.i; A.373.D.11.i; A.374.D.11.i; A.375.D.11.i; A.376.D.11.i; A.377.D.11.i;
A.378.D.11.i; A.379.D.11.i; A.380.D.11.i; A.381.D.11.i; A.382.D.11.i; A.383.D.11.i;
A.384.D.11.i; A.385.D.11.i; A.386.D.11.i; A.387.D.11.i; A.388.D.11.i; A.389.D.11.i;
A.390.D.11.i; A.391.D.11.i; A.392.D.11.i; A.393.D.11.i; A.394.D.11.i; A.395.D.11.i;
A.396.D.11.i; A.397.D.11.i; A.398.D.11.i; A.399.D.11.i; A.400.D.11.i; A.401.D.11.i;
A.402.D.11.i; A.403.D.11.i; A.404.D.11.i; A.405.D.11.i; A.406.D.11.i; A.407.D.11.i;
A.408.D.11.i; A.409.D.11.i; A.410.D.11.i; A.411.D.11.i; A.412.D.11.i; A.413.D.11.i;
A.414.D.11.i; A.415.D.11.i; A.416.D.11.i; A.417.D.11.i; A.418.D.11.i; A.419.D.11.i;
A.420.D.11.i; A.421.D.11.i; A.422.D.11.i; A.423.D.11.i; A.424.D.11.i; A.425.D.11.i;
A.426.D.11.i; A.427.D.11.i; A.428.D.11.i; A.429.D.11.i; A.430.D.11.i; A.431.D.11.i;
A.432.D.11.i; A.433.D.11.i; A.434.D.11.i; A.435.D.11.i; A.436.D.11.i; A.437.D.11.i;
A.438.D.11.i; A.439.D.11.i; A.440.D.11.i; A.441.D.11.i; A.442.D.11.i; A.443.D.11.i;
A.444.D.11.i; A.445.D.11.i; A.446.D.11.i; A.447.D.11.i; A.448.D.11.i; A.449.D.11.i;
A.450.D.11.i; A.451.D.11.i; A.452.D.11.i; A.453.D.11.i; A.454.D.11.i; A.455.D.11.i;
A.456.D.11.i; A.457.D.11.i; A.458.D.11.i; A.459.D.11.i; A.460.D.11.i; A.461.D.11.i;
A.462.D.11.i; A.463.D.11.i; A.464.D.11.i; A.465.D.11.i; A.466.D.11.i; A.467.D.11.i;
A.468.D.11.i; A.469.D.11.i; A.470.D.11.i; A.471.D.11.i; A.472.D.11.i; A.473.D.11.i;
A.474.D.11.i; A.475.D.11.i; A.476.D.11.i; A.477.D.11.i; A.478.D.11.i; A.479.D.11.i;
A.480.D.11.i; A.481.D.11.i; A.482.D.11.i; A.483.D.11.i; A.484.D.11.i; A.485.D.11.i;
A.486.D.11.i; A.487.D.11.i; A.488.D.11.i; A.489.D.11.i; A.490.D.11.i; A.491.D.11.i;
A.492.D.11.i; A.493.D.11.i; A.494.D.11.i; A.495.D.11.i; A.496.D.11.i; A.497.D.11.i;
A.498.D.11.i; A.499.D.11.i; A.500.D.11.i; A.501.D.11.i; A.502.D.11.i; A.503.D.11.i;
A.504.D.11.i; A.505.D.11.i; A.506.D.11.i; A.507.D.11.i; A.508.D.11.i; A.509.D.11.i;
A.510.D.11.i; A.511.D.11.i; A.512.D.11.i; A.512.D.11.i; A.513.D.11.i; A.514.D.11.i;
A.515.D.11.i; A.516.D.11.i; A.517.D.11.i; A.518.D.11.i; A.519.D.11.i; A.520.D.11.i;
A.521.D.11.i; A.522.D.11.i; A.523.D.11.i; A.524.D.11.i; A.525.D.11.i; A.526.D.11.i;
A.527.D.11.i; A.528.D.11.i; A.529.D.11.i; A.530.D.11.i; A.531.D.11.i; A.532.D.11.i;
A.533.D.11.i; A.534.D.11.i; A.535.D.11.i; A.536.D.11.i; A.537.D.11.i; A.538.D.11.i;
A.539.D.11.i; A.540.D.11.i; A.541.D.11.i; A.542.D.11.i; A.543.D.11.i; A.544.D.11.i;
A.545.D.11.i; A.546.D.11.i; A.547.D.11.i; A.548.D.11.i; A.549.D.11.i; A.550.D.11.i;
A.551.D.11.i; A.552.D.11.i; A.553.D.11.i; A.554.D.11.i; A.555.D.11.i; A.556.D.11.i;
A.557.D.11.i; A.558.D.11.i; A.559.D.11.i; A.560.D.11.i; A.561.D.11.i; A.562.D.11.i;
A.563.D.11.i; A.564.D.11.i; A.565.D.11.i; A.566.D.11.i; A.567.D.11.i; A.568.D.11.i;
A.569.D.11.i; A.570.D.11.i; A.571.D.11.i; A.572.D.11.i; A.573.D.11.i; A.574.D.11.i;
A.575.D.11.i; A.576.D.11.i; A.577.D.11.i; A.578.D.11.i; A.579.D.11.i; A.580.D.11.i;
A.581.D.11.i; A.582.D.11.i; A.583.D.11.i; A.584.D.11.i; A.585.D.11.i; A.586.D.11.i;
A.587.D.11.i; A.588.D.11.i; A.589.D.11.i; A.590.D.11.i; A.591.D.11.i; A.592.D.11.i;
A.593.D.11.i; A.594.D.11.i; A.595.D.11.i; A.596.D.11.i; A.597.D.11.i; A.598.D.11.i;
A.599.D.11.i; A.600.D.11.i; A.601.D.11.i; A.602.D.11.i; A.603.D.11.i; A.604.D.11.i;
A.605.D.11.i; A.606.D.11.i; A.607.D.11.i; A.608.D.11.i; A.609.D.11.i; A.610.D.11.i;
A.611.D.11.i; A.612.D.11.i; A.613.D.11.i; A.614.D.11.i; A.615.D.11.i; A.616.D.11.i;
A.617.D.11.i; A.618.D.11.i; A.619.D.11.i; A.620.D.11.i; A.621.D.11.i; A.622.D.11.i;
A.623.D.11.i; A.624.D.11.i; A.625.D.11.i; A.626.D.11.i; A.627.D.11.i; A.628.D.11.i;

TABLE 6-continued

Exemplary Enumerated Compounds

A.629.D.11.i; A.630.D.11.i; A.631.D.11.i; A.632.D.11.i; A.633.D.11.i; A.634.D.11.i;
A.635.D.11.i; A.636.D.11.i; A.637.D.11.i; A.638.D.11.i; A.639.D.11.i; A.640.D.11.i;
A.641.D.11.i; A.642.D.11.i; A.643.D.11.i; A.644.D.11.i; A.645.D.11.i; A.646.D.11.i;
A.647.D.11.i; A.648.D.11.i; A.649.D.11.i; A.650.D.11.i; A.651.D.11.i; A.652.D.11.i;
A.653.D.11.i; A.654.D.11.i; A.655.D.11.i; A.656.D.11.i; A.657.D.11.i; A.658.D.11.i;
A.659.D.11.i; A.660.D.11.i; A.2.E.4.i; A.3.E.4.i; A.4.E.4.i; A.5.E.4.i; A.6.E.4.i;
A.7.E.4.i; A.9.E.4.i; A.10.E.4.i; A.15.E.4.i; A.100.E.4.i; A.101.E.4.i; A.102.E.4.i;
A.103.E.4.i; A.104.E.4.i; A.105.E.4.i; A.106.E.4.i; A.107.E.4.i; A.108.E.4.i;
A.109.E.4.i; A.110.E.4.i; A.111.E.4.i; A.112.E.4.i; A.113.E.4.i; A.115.E.4.i;
A.115.E.4.i; A.116.E.4.i; A.117.E.4.i; A.118.E.4.i; A.119.E.4.i; A.120.E.4.i;
A.121.E.4.i; A.122.E.4.i; A.123.E.4.i; A.124.E.4.i; A.125.E.4.i; A.126.E.4.i;
A.127.E.4.i; A.128.E.4.i; A.129.E.4.i; A.130.E.4.i; A.131.E.4.i; A.132.E.4.i;
A.133.E.4.i; A.134.E.4.i; A.135.E.4.i; A.136.E.4.i; A.137.E.4.i; A.138.E.4.i;
A.139.E.4.i; A.140.E.4.i; A.141.E.4.i; A.142.E.4.i; A.143.E.4.i; A.144.E.4.i;
A.145.E.4.i; A.146.E.4.i; A.147.E.4.i; A.148.E.4.i; A.149.E.4.i; A.150.E.4.i;
A.151.E.4.i; A.152.E.4.i; A.153.E.4.i; A.154.E.4.i; A.155.E.4.i; A.156.E.4.i;
A.157.E.4.i; A.158.E.4.i; A.159.E.4.i; A.160.E.4.i; A.161.E.4.i; A.162.E.4.i;
A.163.E.4.i; A.164.E.4.i; A.165.E.4.i; A.166.E.4.i; A.167.E.4.i; A.168.E.4.i;
A.169.E.4.i; A.170.E.4.i; A.171.E.4.i; A.172.E.4.i; A.173.E.4.i; A.174.E.4.i;
A.175.E.4.i; A.176.E.4.i; A.177.E.4.i; A.178.E.4.i; A.179.E.4.i; A.180.E.4.i;
A.181.E.4.i; A.182.E.4.i; A.183.E.4.i; A.184.E.4.i; A.185.E.4.i; A.186.E.4.i;
A.187.E.4.i; A.188.E.4.i; A.189.E.4.i; A.190.E.4.i; A.191.E.4.i; A.192.E.4.i;
A.193.E.4.i; A.194.E.4.i; A.195.E.4.i; A.196.E.4.i; A.197.E.4.i; A.198.E.4.i;
A.199.E.4.i; A.200.E.4.i; A.201.E.4.i; A.202.E.4.i; A.203.E.4.i; A.204.E.4.i;
A.205.E.4.i; A.206.E.4.i; A.207.E.4.i; A.208.E.4.i; A.209.E.4.i; A.210.E.4.i;
A.211.E.4.i; A.212.E.4.i; A.213.E.4.i; A.214.E.4.i; A.215.E.4.i; A.216.E.4.i;
A.217.E.4.i; A.218.E.4.i; A.219.E.4.i; A.220.E.4.i; A.221.E.4.i; A.222.E.4.i;
A.223.E.4.i; A.224.E.4.i; A.225.E.4.i; A.226.E.4.i; A.227.E.4.i; A.228.E.4.i;
A.229.E.4.i; A.230.E.4.i; A.231.E.4.i; A.232.E.4.i; A.233.E.4.i; A.234.E.4.i;
A.235.E.4.i; A.236.E.4.i; A.237.E.4.i; A.238.E.4.i; A.239.E.4.i; A.240.E.4.i;
A.241.E.4.i; A.242.E.4.i; A.243.E.4.i; A.244.E.4.i; A.245.E.4.i; A.246.E.4.i;
A.247.E.4.i; A.248.E.4.i; A.249.E.4.i; A.250.E.4.i; A.251.E.4.i; A.252.E.4.i;
A.253.E.4.i; A.254.E.4.i; A.255.E.4.i; A.256.E.4.i; A.257.E.4.i; A.258.E.4.i;
A.259.E.4.i; A.260.E.4.i; A.261.E.4.i; A.262.E.4.i; A.263.E.4.i; A.264.E.4.i;
A.265.E.4.i; A.266.E.4.i; A.267.E.4.i; A.268.E.4.i; A.269.E.4.i; A.270.E.4.i;
A.271.E.4.i; A.272.E.4.i; A.273.E.4.i; A.274.E.4.i; A.275.E.4.i; A.276.E.4.i;
A.277.E.4.i; A.278.E.4.i; A.279.E.4.i; A.280.E.4.i; A.281.E.4.i; A.282.E.4.i;
A.283.E.4.i; A.284.E.4.i; A.285.E.4.i; A.286.E.4.i; A.287.E.4.i; A.288.E.4.i;
A.289.E.4.i; A.290.E.4.i; A.291.E.4.i; A.292.E.4.i; A.293.E.4.i; A.294.E.4.i;
A.295.E.4.i; A.296.E.4.i; A.297.E.4.i; A.298.E.4.i; A.299.E.4.i; A.300.E.4.i;
A.301.E.4.i; A.302.E.4.i; A.303.E.4.i; A.304.E.4.i; A.305.E.4.i; A.306.E.4.i;
A.307.E.4.i; A.308.E.4.i; A.309.E.4.i; A.310.E.4.i; A.311.E.4.i; A.312.E.4.i;
A.313.E.4.i; A.314.E.4.i; A.315.E.4.i; A.316.E.4.i; A.317.E.4.i; A.318.E.4.i;
A.319.E.4.i; A.320.E.4.i; A.321.E.4.i; A.323.E.4.i; A.324.E.4.i; A.325.E.4.i;
A.326.E.4.i; A.327.E.4.i; A.328.E.4.i; A.329.E.4.i; A.330.E.4.i; A.331.E.4.i;
A.332.E.4.i; A.333.E.4.i; A.334.E.4.i; A.335.E.4.i; A.336.E.4.i; A.337.E.4.i;
A.338.E.4.i; A.339.E.4.i; A.340.E.4.i; A.341.E.4.i; A.342.E.4.i; A.343.E.4.i;
A.344.E.4.i; A.345.E.4.i; A.346.E.4.i; A.347.E.4.i; A.348.E.4.i; A.349.E.4.i;
A.350.E.4.i; A.351.E.4.i; A.352.E.4.i; A.353.E.4.i; A.354.E.4.i; A.355.E.4.i;
A.356.E.4.i; A.357.E.4.i; A.358.E.4.i; A.359.E.4.i; A.360.E.4.i; A.361.E.4.i;
A.362.E.4.i; A.363.E.4.i; A.364.E.4.i; A.365.E.4.i; A.366.E.4.i; A.367.E.4.i;
A.368.E.4.i; A.369.E.4.i; A.370.E.4.i; A.371.E.4.i; A.372.E.4.i; A.373.E.4.i;
A.374.E.4.i; A.375.E.4.i; A.376.E.4.i; A.377.E.4.i; A.378.E.4.i; A.379.E.4.i;
A.380.E.4.i; A.381.E.4.i; A.382.E.4.i; A.383.E.4.i; A.384.E.4.i; A.385.E.4.i;
A.386.E.4.i; A.387.E.4.i; A.388.E.4.i; A.389.E.4.i; A.390.E.4.i; A.391.E.4.i;
A.392.E.4.i; A.393.E.4.i; A.394.E.4.i; A.395.E.4.i; A.396.E.4.i; A.397.E.4.i;
A.398.E.4.i; A.399.E.4.i; A.400.E.4.i; A.401.E.4.i; A.402.E.4.i; A.403.E.4.i;
A.404.E.4.i; A.405.E.4.i; A.406.E.4.i; A.407.E.4.i; A.408.E.4.i; A.409.E.4.i;
A.410.E.4.i; A.411.E.4.i; A.412.E.4.i; A.413.E.4.i; A.414.E.4.i; A.415.E.4.i;
A.416.E.4.i; A.417.E.4.i; A.418.E.4.i; A.419.E.4.i; A.420.E.4.i; A.421.E.4.i;
A.422.E.4.i; A.423.E.4.i; A.424.E.4.i; A.425.E.4.i; A.426.E.4.i; A.427.E.4.i;
A.428.E.4.i; A.429.E.4.i; A.430.E.4.i; A.431.E.4.i; A.432.E.4.i; A.433.E.4.i;
A.434.E.4.i; A.435.E.4.i; A.436.E.4.i; A.437.E.4.i; A.438.E.4.i; A.439.E.4.i;
A.440.E.4.i; A.441.E.4.i; A.442.E.4.i; A.443.E.4.i; A.444.E.4.i; A.445.E.4.i;
A.446.E.4.i; A.447.E.4.i; A.448.E.4.i; A.449.E.4.i; A.450.E.4.i; A.451.E.4.i;
A.452.E.4.i; A.453.E.4.i; A.454.E.4.i; A.455.E.4.i; A.456.E.4.i; A.457.E.4.i;
A.458.E.4.i; A.459.E.4.i; A.460.E.4.i; A.461.E.4.i; A.462.E.4.i; A.463.E.4.i;
A.464.E.4.i; A.465.E.4.i; A.466.E.4.i; A.467.E.4.i; A.468.E.4.i; A.469.E.4.i;
A.470.E.4.i; A.471.E.4.i; A.472.E.4.i; A.473.E.4.i; A.474.E.4.i; A.475.E.4.i;
A.476.E.4.i; A.477.E.4.i; A.478.E.4.i; A.479.E.4.i; A.480.E.4.i; A.481.E.4.i;
A.482.E.4.i; A.483.E.4.i; A.484.E.4.i; A.485.E.4.i; A.486.E.4.i; A.487.E.4.i;
A.488.E.4.i; A.489.E.4.i; A.490.E.4.i; A.491.E.4.i; A.492.E.4.i; A.493.E.4.i;
A.494.E.4.i; A.495.E.4.i; A.496.E.4.i; A.497.E.4.i; A.498.E.4.i; A.499.E.4.i;
A.500.E.4.i; A.501.E.4.i; A.502.E.4.i; A.503.E.4.i; A.504.E.4.i; A.505.E.4.i;
A.506.E.4.i; A.507.E.4.i; A.508.E.4.i; A.509.E.4.i; A.510.E.4.i; A.511.E.4.i;
A.512.E.4.i; A.512.E.4.i; A.513.E.4.i; A.514.E.4.i; A.515.E.4.i; A.516.E.4.i;
A.517.E.4.i; A.518.E.4.i; A.519.E.4.i; A.520.E.4.i; A.521.E.4.i; A.522.E.4.i;

TABLE 6-continued

Exemplary Enumerated Compounds

A.523.E.4.i; A.524.E.4.i; A.525.E.4.i; A.526.E.4.i; A.527.E.4.i; A.528.E.4.i;
A.529.E.4.i; A.530.E.4.i; A.531.E.4.i; A.532.E.4.i; A.533.E.4.i; A.534.E.4.i;
A.535.E.4.i; A.536.E.4.i; A.537.E.4.i; A.538.E.4.i; A.539.E.4.i; A.540.E.4.i;
A.541.E.4.i; A.542.E.4.i; A.543.E.4.i; A.544.E.4.i; A.545.E.4.i; A.546.E.4.i;
A.547.E.4.i; A.548.E.4.i; A.549.E.4.i; A.550.E.4.i; A.551.E.4.i; A.552.E.4.i;
A.553.E.4.i; A.554.E.4.i; A.555.E.4.i; A.556.E.4.i; A.557.E.4.i; A.558.E.4.i;
A.559.E.4.i; A.560.E.4.i; A.561.E.4.i; A.562.E.4.i; A.563.E.4.i; A.564.E.4.i;
A.565.E.4.i; A.566.E.4.i; A.567.E.4.i; A.568.E.4.i; A.569.E.4.i; A.570.E.4.i;
A.571.E.4.i; A.572.E.4.i; A.573.E.4.i; A.574.E.4.i; A.575.E.4.i; A.576.E.4.i;
A.577.E.4.i; A.578.E.4.i; A.579.E.4.i; A.580.E.4.i; A.581.E.4.i; A.582.E.4.i;
A.583.E.4.i; A.584.E.4.i; A.585.E.4.i; A.586.E.4.i; A.587.E.4.i; A.588.E.4.i;
A.589.E.4.i; A.590.E.4.i; A.591.E.4.i; A.592.E.4.i; A.593.E.4.i; A.594.E.4.i;
A.595.E.4.i; A.596.E.4.i; A.597.E.4.i; A.598.E.4.i; A.599.E.4.i; A.600.E.4.i;
A.601.E.4.i; A.602.E.4.i; A.603.E.4.i; A.604.E.4.i; A.605.E.4.i; A.606.E.4.i;
A.607.E.4.i; A.608.E.4.i; A.609.E.4.i; A.610.E.4.i; A.611.E.4.i; A.612.E.4.i;
A.613.E.4.i; A.614.E.4.i; A.615.E.4.i; A.616.E.4.i; A.617.E.4.i; A.618.E.4.i;
A.619.E.4.i; A.620.E.4.i; A.621.E.4.i; A.622.E.4.i; A.623.E.4.i; A.624.E.4.i;
A.625.E.4.i; A.626.E.4.i; A.627.E.4.i; A.628.E.4.i; A.629.E.4.i; A.630.E.4.i;
A.631.E.4.i; A.632.E.4.i; A.633.E.4.i; A.634.E.4.i; A.635.E.4.i; A.636.E.4.i;
A.637.E.4.i; A.638.E.4.i; A.639.E.4.i; A.640.E.4.i; A.641.E.4.i; A.642.E.4.i;
A.643.E.4.i; A.644.E.4.i; A.645.E.4.i; A.646.E.4.i; A.647.E.4.i; A.648.E.4.i;
A.649.E.4.i; A.650.E.4.i; A.651.E.4.i; A.652.E.4.i; A.653.E.4.i; A.654.E.4.i;
A.655.E.4.i; A.656.E.4.i; A.657.E.4.i; A.658.E.4.i; A.659.E.4.i; A.660.E.4.i; A.2.E.11.i;
A.3.E.11.i; A.4.E.11.i; A.5.E.11.i; A.6.E.11.i; A.7.E.11.i; A.9.E.11.i; A.10.E.11.i;
A.15.E.11.i; A.100.E.11.i; A.101.E.11.i; A.102.E.11.i; A.103.E.11.i; A.104.E.11.i;
A.105.E.11.i; A.106.E.11.i; A.107.E.11.i; A.108.E.11.i; A.109.E.11.i; A.110.E.11.i;
A.111.E.11.i; A.112.E.11.i; A.113.E.11.i; A.115.E.11.i; A.115.E.11.i; A.116.E.11.i;
A.117.E.11.i; A.118.E.11.i; A.119.E.11.i; A.120.E.11.i; A.121.E.11.i; A.122.E.11.i;
A.123.E.11.i; A.124.E.11.i; A.125.E.11.i; A.126.E.11.i; A.127.E.11.i; A.128.E.11.i;
A.129.E.11.i; A.130.E.11.i; A.131.E.11.i; A.132.E.11.i; A.133.E.11.i; A.134.E.11.i;
A.135.E.11.i; A.136.E.11.i; A.137.E.11.i; A.138.E.11.i; A.139.E.11.i; A.140.E.11.i;
A.141.E.11.i; A.142.E.11.i; A.143.E.11.i; A.144.E.11.i; A.145.E.11.i; A.146.E.11.i;
A.147.E.11.i; A.148.E.11.i; A.149.E.11.i; A.150.E.11.i; A.151.E.11.i; A.152.E.11.i;
A.153.E.11.i; A.154.E.11.i; A.155.E.11.i; A.156.E.11.i; A.157.E.11.i; A.158.E.11.i;
A.159.E.11.i; A.160.E.11.i; A.161.E.11.i; A.162.E.11.i; A.163.E.11.i; A.164.E.11.i;
A.165.E.11.i; A.166.E.11.i; A.167.E.11.i; A.168.E.11.i; A.169.E.11.i; A.170.E.11.i;
A.171.E.11.i; A.172.E.11.i; A.173.E.11.i; A.174.E.11.i; A.175.E.11.i; A.176.E.11.i;
A.177.E.11.i; A.178.E.11.i; A.179.E.11.i; A.180.E.11.i; A.181.E.11.i; A.182.E.11.i;
A.183.E.11.i; A.184.E.11.i; A.185.E.11.i; A.186.E.11.i; A.187.E.11.i; A.188.E.11.i;
A.189.E.11.i; A.190.E.11.i; A.191.E.11.i; A.192.E.11.i; A.193.E.11.i; A.194.E.11.i;
A.195.E.11.i; A.196.E.11.i; A.197.E.11.i; A.198.E.11.i; A.199.E.11.i; A.200.E.11.i;
A.201.E.11.i; A.202.E.11.i; A.203.E.11.i; A.204.E.11.i; A.205.E.11.i; A.206.E.11.i;
A.207.E.11.i; A.208.E.11.i; A.209.E.11.i; A.210.E.11.i; A.211.E.11.i; A.212.E.11.i;
A.213.E.11.i; A.214.E.11.i; A.215.E.11.i; A.216.E.11.i; A.217.E.11.i; A.218.E.11.i;
A.219.E.11.i; A.220.E.11.i; A.221.E.11.i; A.222.E.11.i; A.223.E.11.i; A.224.E.11.i;
A.225.E.11.i; A.226.E.11.i; A.227.E.11.i; A.228.E.11.i; A.229.E.11.i; A.230.E.11.i;
A.231.E.11.i; A.232.E.11.i; A.233.E.11.i; A.234.E.11.i; A.235.E.11.i; A.236.E.11.i;
A.237.E.11.i; A.238.E.11.i; A.239.E.11.i; A.240.E.11.i; A.241.E.11.i; A.242.E.11.i;
A.243.E.11.i; A.244.E.11.i; A.245.E.11.i; A.246.E.11.i; A.247.E.11.i; A.248.E.11.i;
A.249.E.11.i; A.250.E.11.i; A.251.E.11.i; A.252.E.11.i; A.253.E.11.i; A.254.E.11.i;
A.255.E.11.i; A.256.E.11.i; A.257.E.11.i; A.258.E.11.i; A.259.E.11.i; A.260.E.11.i;
A.261.E.11.i; A.262.E.11.i; A.263.E.11.i; A.264.E.11.i; A.265.E.11.i; A.266.E.11.i;
A.267.E.11.i; A.268.E.11.i; A.269.E.11.i; A.270.E.11.i; A.271.E.11.i; A.272.E.11.i;
A.273.E.11.i; A.274.E.11.i; A.275.E.11.i; A.276.E.11.i; A.277.E.11.i; A.278.E.11.i;
A.279.E.11.i; A.280.E.11.i; A.281.E.11.i; A.282.E.11.i; A.283.E.11.i; A.284.E.11.i;
A.285.E.11.i; A.286.E.11.i; A.287.E.11.i; A.288.E.11.i; A.289.E.11.i; A.290.E.11.i;
A.291.E.11.i; A.292.E.11.i; A.293.E.11.i; A.294.E.11.i; A.295.E.11.i; A.296.E.11.i;
A.297.E.11.i; A.298.E.11.i; A.299.E.11.i; A.300.E.11.i; A.301.E.11.i; A.302.E.11.i;
A.303.E.11.i; A.304.E.11.i; A.305.E.11.i; A.306.E.11.i; A.307.E.11.i; A.308.E.11.i;
A.309.E.11.i; A.310.E.11.i; A.311.E.11.i; A.312.E.11.i; A.313.E.11.i; A.314.E.11.i;
A.315.E.11.i; A.316.E.11.i; A.317.E.11.i; A.318.E.11.i; A.319.E.11.i; A.320.E.11.i;
A.321.E.11.i; A.323.E.11.i; A.324.E.11.i; A.325.E.11.i; A.326.E.11.i; A.327.E.11.i;
A.328.E.11.i; A.329.E.11.i; A.330.E.11.i; A.331.E.11.i; A.332.E.11.i; A.333.E.11.i;
A.334.E.11.i; A.335.E.11.i; A.336.E.11.i; A.337.E.11.i; A.338.E.11.i; A.339.E.11.i;
A.340.E.11.i; A.341.E.11.i; A.342.E.11.i; A.343.E.11.i; A.344.E.11.i; A.345.E.11.i;
A.346.E.11.i; A.347.E.11.i; A.348.E.11.i; A.349.E.11.i; A.350.E.11.i; A.351.E.11.i;
A.352.E.11.i; A.353.E.11.i; A.354.E.11.i; A.355.E.11.i; A.356.E.11.i; A.357.E.11.i;
A.358.E.11.i; A.359.E.11.i; A.360.E.11.i; A.361.E.11.i; A.362.E.11.i; A.363.E.11.i;
A.364.E.11.i; A.365.E.11.i; A.366.E.11.i; A.367.E.11.i; A.368.E.11.i; A.369.E.11.i;
A.370.E.11.i; A.371.E.11.i; A.372.E.11.i; A.373.E.11.i; A.374.E.11.i; A.375.E.11.i;
A.376.E.11.i; A.377.E.11.i; A.378.E.11.i; A.379.E.11.i; A.380.E.11.i; A.381.E.11.i;
A.382.E.11.i; A.383.E.11.i; A.384.E.11.i; A.385.E.11.i; A.386.E.11.i; A.387.E.11.i;
A.388.E.11.i; A.389.E.11.i; A.390.E.11.i; A.391.E.11.i; A.392.E.11.i; A.393.E.11.i;
A.394.E.11.i; A.395.E.11.i; A.396.E.11.i; A.397.E.11.i; A.398.E.11.i; A.399.E.11.i;
A.400.E.11.i; A.401.E.11.i; A.402.E.11.i; A.403.E.11.i; A.404.E.11.i; A.405.E.11.i;
A.406.E.11.i; A.407.E.11.i; A.408.E.11.i; A.409.E.11.i; A.410.E.11.i; A.411.E.11.i;
A.412.E.11.i; A.413.E.11.i; A.414.E.11.i; A.415.E.11.i; A.416.E.11.i; A.417.E.11.i;

TABLE 6-continued

Exemplary Enumerated Compounds

A.418.E.11.i; A.419.E.11.i; A.420.E.11.i; A.421.E.11.i; A.422.E.11.i; A.423.E.11.i;
A.424.E.11.i; A.425.E.11.i; A.426.E.11.i; A.427.E.11.i; A.428.E.11.i; A.429.E.11.i;
A.430.E.11.i; A.431.E.11.i; A.432.E.11.i; A.433.E.11.i; A.434.E.11.i; A.435.E.11.i;
A.436.E.11.i; A.437.E.11.i; A.438.E.11.i; A.439.E.11.i; A.440.E.11.i; A.441.E.11.i;
A.442.E.11.i; A.443.E.11.i; A.444.E.11.i; A.445.E.11.i; A.446.E.11.i; A.447.E.11.i;
A.448.E.11.i; A.449.E.11.i; A.450.E.11.i; A.451.E.11.i; A.452.E.11.i; A.453.E.11.i;
A.454.E.11.i; A.455.E.11.i; A.456.E.11.i; A.457.E.11.i; A.458.E.11.i; A.459.E.11.i;
A.460.E.11.i; A.461.E.11.i; A.462.E.11.i; A.463.E.11.i; A.464.E.11.i; A.465.E.11.i;
A.466.E.11.i; A.467.E.11.i; A.468.E.11.i; A.469.E.11.i; A.470.E.11.i; A.471.E.11.i;
A.472.E.11.i; A.473.E.11.i; A.474.E.11.i; A.475.E.11.i; A.476.E.11.i; A.477.E.11.i;
A.478.E.11.i; A.479.E.11.i; A.480.E.11.i; A.481.E.11.i; A.482.E.11.i; A.483.E.11.i;
A.484.E.11.i; A.485.E.11.i; A.486.E.11.i; A.487.E.11.i; A.488.E.11.i; A.489.E.11.i;
A.490.E.11.i; A.491.E.11.i; A.492.E.11.i; A.493.E.11.i; A.494.E.11.i; A.495.E.11.i;
A.496.E.11.i; A.497.E.11.i; A.498.E.11.i; A.499.E.11.i; A.500.E.11.i; A.501.E.11.i;
A.502.E.11.i; A.503.E.11.i; A.504.E.11.i; A.505.E.11.i; A.506.E.11.i; A.507.E.11.i;
A.508.E.11.i; A.509.E.11.i; A.510.E.11.i; A.511.E.11.i; A.512.E.11.i; A.512.E.11.i;
A.513.E.11.i; A.514.E.11.i; A.515.E.11.i; A.516.E.11.i; A.517.E.11.i; A.518.E.11.i;
A.519.E.11.i; A.520.E.11.i; A.521.E.11.i; A.522.E.11.i; A.523.E.11.i; A.524.E.11.i;
A.525.E.11.i; A.526.E.11.i; A.527.E.11.i; A.528.E.11.i; A.529.E.11.i; A.530.E.11.i;
A.531.E.11.i; A.532.E.11.i; A.533.E.11.i; A.534.E.11.i; A.535.E.11.i; A.536.E.11.i;
A.537.E.11.i; A.538.E.11.i; A.539.E.11.i; A.540.E.11.i; A.541.E.11.i; A.542.E.11.i;
A.543.E.11.i; A.544.E.11.i; A.545.E.11.i; A.546.E.11.i; A.547.E.11.i; A.548.E.11.i;
A.549.E.11.i; A.550.E.11.i; A.551.E.11.i; A.552.E.11.i; A.553.E.11.i; A.554.E.11.i;
A.555.E.11.i; A.556.E.11.i; A.557.E.11.i; A.558.E.11.i; A.559.E.11.i; A.560.E.11.i;
A.561.E.11.i; A.562.E.11.i; A.563.E.11.i; A.564.E.11.i; A.565.E.11.i; A.566.E.11.i;
A.567.E.11.i; A.568.E.11.i; A.569.E.11.i; A.570.E.11.i; A.571.E.11.i; A.572.E.11.i;
A.573.E.11.i; A.574.E.11.i; A.575.E.11.i; A.576.E.11.i; A.577.E.11.i; A.578.E.11.i;
A.579.E.11.i; A.580.E.11.i; A.581.E.11.i; A.582.E.11.i; A.583.E.11.i; A.584.E.11.i;
A.585.E.11.i; A.586.E.11.i; A.587.E.11.i; A.588.E.11.i; A.589.E.11.i; A.590.E.11.i;
A.591.E.11.i; A.592.E.11.i; A.593.E.11.i; A.594.E.11.i; A.595.E.11.i; A.596.E.11.i;
A.597.E.11.i; A.598.E.11.i; A.599.E.11.i; A.600.E.11.i; A.601.E.11.i; A.602.E.11.i;
A.603.E.11.i; A.604.E.11.i; A.605.E.11.i; A.606.E.11.i; A.607.E.11.i; A.608.E.11.i;
A.609.E.11.i; A.610.E.11.i; A.611.E.11.i; A.612.E.11.i; A.613.E.11.i; A.614.E.11.i;
A.615.E.11.i; A.616.E.11.i; A.617.E.11.i; A.618.E.11.i; A.619.E.11.i; A.620.E.11.i;
A.621.E.11.i; A.622.E.11.i; A.623.E.11.i; A.624.E.11.i; A.625.E.11.i; A.626.E.11.i;
A.627.E.11.i; A.628.E.11.i; A.629.E.11.i; A.630.E.11.i; A.631.E.11.i; A.632.E.11.i;
A.633.E.11.i; A.634.E.11.i; A.635.E.11.i; A.636.E.11.i; A.637.E.11.i; A.638.E.11.i;
A.639.E.11.i; A.640.E.11.i; A.641.E.11.i; A.642.E.11.i; A.643.E.11.i; A.644.E.11.i;
A.645.E.11.i; A.646.E.11.i; A.647.E.11.i; A.648.E.11.i; A.649.E.11.i; A.650.E.11.i;
A.651.E.11.i; A.652.E.11.i; A.653.E.11.i; A.654.E.11.i; A.655.E.11.i; A.656.E.11.i;
A.657.E.11.i; A.658.E.11.i; A.659.E.11.i; A.660.E.11.i; A.2.F.4.i; A.3.F.4.i; A.4.F.4.i;
A.5.F.4.i; A.6A.7.F.4.i; A.9.F.4.i; A.10.F.4.i; A.15.F.4.i; A.100.F.4.i;
A.101.F.4.i; A.102.F.4.i; A.103.F.4.i; A.104.F.4.i; A.105.F.4.i; A.106.F.4.i;
A.107.F.4.i; A.108.F.4.i; A.109.F.4.i; A.110.F.4.i; A.111.F.4.i; A.112.F.4.i;
A.113.F.4.i; A.115.F.4.i; A.115.F.4.i; A.116.F.4.i; A.117.F.4.i; A.118.F.4.i;
A.119.F.4.i; A.120.F.4.i; A.121.F.4.i; A.122.F.4.i; A.123.F.4.i; A.124.F.4.i;
A.125.F.4.i; A.126.F.4.i; A.127.F.4.i; A.128.F.4.i; A.129.F.4.i; A.130.F.4.i;
A.131.F.4.i; A.132.F.4.i; A.133.F.4.i; A.134.F.4.i; A.135.F.4.i; A.136.F.4.i;
A.137.F.4.i; A.138.F.4.i; A.139.F.4.i; A.140.F.4.i; A.141.F.4.i; A.142.F.4.i;
A.143.F.4.i; A.144.F.4.i; A.145.F.4.i; A.146.F.4.i; A.147.F.4.i; A.148.F.4.i;
A.149.F.4.i; A.150.F.4.i; A.151.F.4.i; A.152.F.4.i; A.153.F.4.i; A.154.F.4.i;
A.155.F.4.i; A.156.F.4.i; A.157.F.4.i; A.158.F.4.i; A.159.F.4.i; A.160.F.4.i;
A.161.F.4.i; A.162.F.4.i; A.163.F.4.i; A.164.F.4.i; A.165.F.4.i; A.166.F.4.i;
A.167.F.4.i; A.168.F.4.i; A.169.F.4.i; A.170.F.4.i; A.171.F.4.i; A.172.F.4.i;
A.173.F.4.i; A.174.F.4.i; A.175.F.4.i; A.176.F.4.i; A.177.F.4.i; A.178.F.4.i;
A.179.F.4.i; A.180.F.4.i; A.181.F.4.i; A.182.F.4.i; A.183.F.4.i; A.184.F.4.i;
A.185.F.4.i; A.186.F.4.i; A.187.F.4.i; A.188.F.4.i; A.189.F.4.i; A.190.F.4.i;
A.191.F.4.i; A.192.F.4.i; A.193.F.4.i; A.194.F.4.i; A.195.F.4.i; A.196.F.4.i;
A.197.F.4.i; A.198.F.4.i; A.199.F.4.i; A.200.F.4.i; A.201.F.4.i; A.202.F.4.i;
A.203.F.4.i; A.204.F.4.i; A.205.F.4.i; A.206.F.4.i; A.207.F.4.i; A.208.F.4.i;
A.209.F.4.i; A.210.F.4.i; A.211.F.4.i; A.212.F.4.i; A.213.F.4.i; A.214.F.4.i;
A.215.F.4.i; A.216.F.4.i; A.217.F.4.i; A.218.F.4.i; A.219.F.4.i; A.220.F.4.i;
A.221.F.4.i; A.222.F.4.i; A.223.F.4.i; A.224.F.4.i; A.225.F.4.i; A.226.F.4.i;
A.227.F.4.i; A.228.F.4.i; A.229.F.4.i; A.230.F.4.i; A.231.F.4.i; A.232.F.4.i;
A.233.F.4.i; A.234.F.4.i; A.235.F.4.i; A.236.F.4.i; A.237.F.4.i; A.238.F.4.i;
A.239.F.4.i; A.240.F.4.i; A.241.F.4.i; A.242.F.4.i; A.243.F.4.i; A.244.F.4.i;
A.245.F.4.i; A.246.F.4.i; A.247.F.4.i; A.248.F.4.i; A.249.F.4.i; A.250.F.4.i;
A.251.F.4.i; A.252.F.4.i; A.253.F.4.i; A.254.F.4.i; A.255.F.4.i; A.256.F.4.i;
A.257.F.4.i; A.258.F.4.i; A.259.F.4.i; A.260.F.4.i; A.261.F.4.i; A.262.F.4.i;
A.263.F.4.i; A.264.F.4.i; A.265.F.4.i; A.266.F.4.i; A.267.F.4.i; A.268.F.4.i;
A.269.F.4.i; A.270.F.4.i; A.271.F.4.i; A.272.F.4.i; A.273.F.4.i; A.274.F.4.i;
A.275.F.4.i; A.276.F.4.i; A.277.F.4.i; A.278.F.4.i; A.279.F.4.i; A.280.F.4.i;
A.281.F.4.i; A.282.F.4.i; A.283.F.4.i; A.284.F.4.i; A.285.F.4.i; A.286.F.4.i;
A.287.F.4.i; A.288.F.4.i; A.289.F.4.i; A.290.F.4.i; A.291.F.4.i; A.292.F.4.i;
A.293.F.4.i; A.294.F.4.i; A.295.F.4.i; A.296.F.4.i; A.297.F.4.i; A.298.F.4.i;
A.299.F.4.i; A.300.F.4.i; A.301.F.4.i; A.302.F.4.i; A.303.F.4.i; A.304.F.4.i;
A.305.F.4.i; A.306.F.4.i; A.307.F.4.i; A.308.F.4.i; A.309.F.4.i; A.310.F.4.i;

TABLE 6-continued

Exemplary Enumerated Compounds

A.311.F.4.i; A.312.F.4.i; A.313.F.4.i; A.314.F.4.i; A.315.F.4.i; A.316.F.4.i;
A.317.F.4.i; A.318.F.4.i; A.319.F.4.i; A.320.F.4.i; A.321.F.4.i; A.323.F.4.i;
A.324.F.4.i; A.325.F.4.i; A.326.F.4.i; A.327.F.4.i; A.328.F.4.i; A.329.F.4.i;
A.330.F.4.i; A.331.F.4.i; A.332.F.4.i; A.333.F.4.i; A.334.F.4.i; A.335.F.4.i;
A.336.F.4.i; A.337.F.4.i; A.338.F.4.i; A.339.F.4.i; A.340.F.4.i; A.341.F.4.i;
A.342.F.4.i; A.343.F.4.i; A.344.F.4.i; A.345.F.4.i; A.346.F.4.i; A.347.F.4.i;
A.348.F.4.i; A.349.F.4.i; A.350.F.4.i; A.351.F.4.i; A.352.F.4.i; A.353.F.4.i;
A.354.F.4.i; A.355.F.4.i; A.356.F.4.i; A.357.F.4.i; A.358.F.4.i; A.359.F.4.i;
A.360.F.4.i; A.361.F.4.i; A.362.F.4.i; A.363.F.4.i; A.364.F.4.i; A.365.F.4.i;
A.366.F.4.i; A.367.F.4.i; A.368.F.4.i; A.369.F.4.i; A.370.F.4.i; A.371.F.4.i;
A.372.F.4.i; A.373.F.4.i; A.374.F.4.i; A.375.F.4.i; A.376.F.4.i; A.377.F.4.i;
A.378.F.4.i; A.379.F.4.i; A.380.F.4.i; A.381.F.4.i; A.382.F.4.i; A.383.F.4.i;
A.384.F.4.i; A.385.F.4.i; A.386.F.4.i; A.387.F.4.i; A.388.F.4.i; A.389.F.4.i;
A.390.F.4.i; A.391.F.4.i; A.392.F.4.i; A.393.F.4.i; A.394.F.4.i; A.395.F.4.i;
A.396.F.4.i; A.397.F.4.i; A.398.F.4.i; A.399.F.4.i; A.400.F.4.i; A.401.F.4.i;
A.402.F.4.i; A.403.F.4.i; A.404.F.4.i; A.405.F.4.i; A.406.F.4.i; A.407.F.4.i;
A.408.F.4.i; A.409.F.4.i; A.410.F.4.i; A.411.F.4.i; A.412.F.4.i; A.413.F.4.i;
A.414.F.4.i; A.415.F.4.i; A.416.F.4.i; A.417.F.4.i; A.418.F.4.i; A.419.F.4.i;
A.420.F.4.i; A.421.F.4.i; A.422.F.4.i; A.423.F.4.i; A.424.F.4.i; A.425.F.4.i;
A.426.F.4.i; A.427.F.4.i; A.428.F.4.i; A.429.F.4.i; A.430.F.4.i; A.431.F.4.i;
A.432.F.4.i; A.433.F.4.i; A.434.F.4.i; A.435.F.4.i; A.436.F.4.i; A.437.F.4.i;
A.438.F.4.i; A.439.F.4.i; A.440.F.4.i; A.441.F.4.i; A.442.F.4.i; A.443.F.4.i;
A.444.F.4.i; A.445.F.4.i; A.446.F.4.i; A.447.F.4.i; A.448.F.4.i; A.449.F.4.i;
A.450.F.4.i; A.451.F.4.i; A.452.F.4.i; A.453.F.4.i; A.454.F.4.i; A.455.F.4.i;
A.456.F.4.i; A.457.F.4.i; A.458.F.4.i; A.459.F.4.i; A.460.F.4.i; A.461.F.4.i;
A.462.F.4.i; A.463.F.4.i; A.464.F.4.i; A.465.F.4.i; A.466.F.4.i; A.467.F.4.i;
A.468.F.4.i; A.469.F.4.i; A.470.F.4.i; A.471.F.4.i; A.472.F.4.i; A.473.F.4.i;
A.474.F.4.i; A.475.F.4.i; A.476.F.4.i; A.477.F.4.i; A.478.F.4.i; A.479.F.4.i;
A.480.F.4.i; A.481.F.4.i; A.482.F.4.i; A.483.F.4.i; A.484.F.4.i; A.485.F.4.i;
A.486.F.4.i; A.487.F.4.i; A.488.F.4.i; A.489.F.4.i; A.490.F.4.i; A.491.F.4.i;
A.492.F.4.i; A.493.F.4.i; A.494.F.4.i; A.495.F.4.i; A.496.F.4.i; A.497.F.4.i;
A.498.F.4.i; A.499.F.4.i; A.500.F.4.i; A.501.F.4.i; A.502.F.4.i; A.503.F.4.i;
A.504.F.4.i; A.505.F.4.i; A.506.F.4.i; A.507.F.4.i; A.508.F.4.i; A.509.F.4.i;
A.510.F.4.i; A.511.F.4.i; A.512.F.4.i; A.513.F.4.i; A.514.F.4.i;
A.515.F.4.i; A.516.F.4.i; A.517.F.4.i; A.518.F.4.i; A.519.F.4.i; A.520.F.4.i;
A.521.F.4.i; A.522.F.4.i; A.523.F.4.i; A.524.F.4.i; A.525.F.4.i; A.526.F.4.i;
A.527.F.4.i; A.528.F.4.i; A.529.F.4.i; A.530.F.4.i; A.531.F.4.i; A.532.F.4.i;
A.533.F.4.i; A.534.F.4.i; A.535.F.4.i; A.536.F.4.i; A.537.F.4.i; A.538.F.4.i;
A.539.F.4.i; A.540.F.4.i; A.541.F.4.i; A.542.F.4.i; A.543.F.4.i; A.544.F.4.i;
A.545.F.4.i; A.546.F.4.i; A.547.F.4.i; A.548.F.4.i; A.549.F.4.i; A.550.F.4.i;
A.551.F.4.i; A.552.F.4.i; A.553.F.4.i; A.554.F.4.i; A.555.F.4.i; A.556.F.4.i;
A.557.F.4.i; A.558.F.4.i; A.559.F.4.i; A.560.F.4.i; A.561.F.4.i; A.562.F.4.i;
A.563.F.4.i; A.564.F.4.i; A.565.F.4.i; A.566.F.4.i; A.567.F.4.i; A.568.F.4.i;
A.569.F.4.i; A.570.F.4.i; A.571.F.4.i; A.572.F.4.i; A.573.F.4.i; A.574.F.4.i;
A.575.F.4.i; A.576.F.4.i; A.577.F.4.i; A.578.F.4.i; A.579.F.4.i; A.580.F.4.i;
A.581.F.4.i; A.582.F.4.i; A.583.F.4.i; A.584.F.4.i; A.585.F.4.i; A.586.F.4.i;
A.587.F.4.i; A.588.F.4.i; A.589.F.4.i; A.590.F.4.i; A.591.F.4.i; A.592.F.4.i;
A.593.F.4.i; A.594.F.4.i; A.595.F.4.i; A.596.F.4.i; A.597.F.4.i; A.598.F.4.i;
A.599.F.4.i; A.600.F.4.i; A.601.F.4.i; A.602.F.4.i; A.603.F.4.i; A.604.F.4.i;
A.605.F.4.i; A.606.F.4.i; A.607.F.4.i; A.608.F.4.i; A.609.F.4.i; A.610.F.4.i;
A.611.F.4.i; A.612.F.4.i; A.613.F.4.i; A.614.F.4.i; A.615.F.4.i; A.616.F.4.i;
A.617.F.4.i; A.618.F.4.i; A.619.F.4.i; A.620.F.4.i; A.621.F.4.i; A.622.F.4.i;
A.623.F.4.i; A.624.F.4.i; A.625.F.4.i; A.626.F.4.i; A.627.F.4.i; A.628.F.4.i;
A.629.F.4.i; A.630.F.4.i; A.631.F.4.i; A.632.F.4.i; A.633.F.4.i; A.634.F.4.i;
A.635.F.4.i; A.636.F.4.i; A.637.F.4.i; A.638.F.4.i; A.639.F.4.i; A.640.F.4.i;
A.641.F.4.i; A.642.F.4.i; A.643.F.4.i; A.644.F.4.i; A.645.F.4.i; A.646.F.4.i;
A.647.F.4.i; A.648.F.4.i; A.649.F.4.i; A.650.F.4.i; A.651.F.4.i; A.652.F.4.i;
A.653.F.4.i; A.654.F.4.i; A.655.F.4.i; A.656.F.4.i; A.657.F.4.i; A.658.F.4.i;
A.659.F.4.i; A.660.F.4.i; A.2.F.11.i; A.3.F.11.i; A.4.F.11.i; A.5.F.11.i; A.6.F.11.i;
A.7.F.11.i; A.9.F.11.i; A.10.F.11.i; A.15.F.11.i; A.100.F.11.i; A.101.F.11.i;
A.102.F.11.i; A.103.F.11.i; A.104.F.11.i; A.105.F.11.i; A.106.F.11.i; A.107.F.11.i;
A.108.F.11.i; A.109.F.11.i; A.110.F.11.i; A.111.F.11.i; A.112.F.11.i; A.113.F.11.i;
A.114.F.11.i; A.115.F.11.i; A.116.F.11.i; A.117.F.11.i; A.118.F.11.i; A.119.F.11.i;
A.120.F.11.i; A.121.F.11.i; A.122.F.11.i; A.123.F.11.i; A.124.F.11.i; A.125.F.11.i;
A.126.F.11.i; A.127.F.11.i; A.128.F.11.i; A.129.F.11.i; A.130.F.11.i; A.131.F.11.i;
A.132.F.11.i; A.133.F.11.i; A.134.F.11.i; A.135.F.11.i; A.136.F.11.i; A.137.F.11.i;
A.138.F.11.i; A.139.F.11.i; A.140.F.11.i; A.141.F.11.i; A.142.F.11.i; A.143.F.11.i;
A.144.F.11.i; A.145.F.11.i; A.146.F.11.i; A.147.F.11.i; A.148.F.11.i; A.149.F.11.i;
A.150.F.11.i; A.151.F.11.i; A.152.F.11.i; A.153.F.11.i; A.154.F.11.i; A.155.F.11.i;
A.156.F.11.i; A.157.F.11.i; A.158.F.11.i; A.159.F.11.i; A.160.F.11.i; A.161.F.11.i;
A.162.F.11.i; A.163.F.11.i; A.164.F.11.i; A.165.F.11.i; A.166.F.11.i; A.167.F.11.i;
A.168.F.11.i; A.169.F.11.i; A.170.F.11.i; A.171.F.11.i; A.172.F.11.i; A.173.F.11.i;
A.174.F.11.i; A.175.F.11.i; A.176.F.11.i; A.177.F.11.i; A.178.F.11.i; A.179.F.11.i;
A.180.F.11.i; A.181.F.11.i; A.182.F.11.i; A.183.F.11.i; A.184.F.11.i; A.185.F.11.i;
A.186.F.11.i; A.187.F.11.i; A.188.F.11.i; A.189.F.11.i; A.190.F.11.i; A.191.F.11.i;
A.192.F.11.i; A.193.F.11.i; A.194.F.11.i; A.195.F.11.i; A.196.F.11.i; A.197.F.11.i;
A.198.F.11.i; A.199.F.11.i; A.200.F.11.i; A.201.F.11.i; A.202.F.11.i; A.203.F.11.i;

TABLE 6-continued

Exemplary Enumerated Compounds

A.204.F.11.i; A.205.F.11.i; A.206.F.11.i; A.207.F.11.i; A.208.F.11.i; A.209.F.11.i;
A.210.F.11.i; A.211.F.11.i; A.212.F.11.i; A.213.F.11.i; A.214.F.11.i; A.215.F.11.i;
A.216.F.11.i; A.217.F.11.i; A.218.F.11.i; A.219.F.11.i; A.220.F.11.i; A.221.F.11.i;
A.222.F.11.i; A.223.F.11.i; A.224.F.11.i; A.225.F.11.i; A.226.F.11.i; A.227.F.11.i;
A.228.F.11.i; A.229.F.11.i; A.230.F.11.i; A.231.F.11.i; A.232.F.11.i; A.233.F.11.i;
A.234.F.11.i; A.235.F.11.i; A.236.F.11.i; A.237.F.11.i; A.238.F.11.i; A.239.F.11.i;
A.240.F.11.i; A.241.F.11.i; A.242.F.11.i; A.243.F.11.i; A.244.F.11.i; A.245.F.11.i;
A.246.F.11.i; A.247.F.11.i; A.248.F.11.i; A.249.F.11.i; A.250.F.11.i; A.251.F.11.i;
A.252.F.11.i; A.253.F.11.i; A.254.F.11.i; A.255.F.11.i; A.256.F.11.i; A.257.F.11.i;
A.258.F.11.i; A.259.F.11.i; A.260.F.11.i; A.261.F.11.i; A.262.F.11.i; A.263.F.11.i;
A.264.F.11.i; A.265.F.11.i; A.266.F.11.i; A.267.F.11.i; A.268.F.11.i; A.269.F.11.i;
A.270.F.11.i; A.271.F.11.i; A.272.F.11.i; A.273.F.11.i; A.274.F.11.i; A.275.F.11.i;
A.276.F.11.i; A.277.F.11.i; A.278.F.11.i; A.279.F.11.i; A.280.F.11.i; A.281.F.11.i;
A.282.F.11.i; A.283.F.11.i; A.284.F.11.i; A.285.F.11.i; A.286.F.11.i; A.287.F.11.i;
A.288.F.11.i; A.289.F.11.i; A.290.F.11.i; A.291.F.11.i; A.292.F.11.i; A.293.F.11.i;
A.294.F.11.i; A.295.F.11.i; A.296.F.11.i; A.297.F.11.i; A.298.F.11.i; A.299.F.11.i;
A.300.F.11.i; A.301.F.11.i; A.302.F.11.i; A.303.F.11.i; A.304.F.11.i; A.305.F.11.i;
A.306.F.11.i; A.307.F.11.i; A.308.F.11.i; A.309.F.11.i; A.310.F.11.i; A.311.F.11.i;
A.312.F.11.i; A.313.F.11.i; A.314.F.11.i; A.315.F.11.i; A.316.F.11.i; A.317.F.11.i;
A.318.F.11.i; A.319.F.11.i; A.320.F.11.i; A.321.F.11.i; A.323.F.11.i; A.324.F.11.i;
A.325.F.11.i; A.326.F.11.i; A.327.F.11.i; A.328.F.11.i; A.329.F.11.i; A.330.F.11.i;
A.331.F.11.i; A.332.F.11.i; A.333.F.11.i; A.334.F.11.i; A.335.F.11.i; A.336.F.11.i;
A.337.F.11.i; A.338.F.11.i; A.339.F.11.i; A.340.F.11.i; A.341.F.11.i; A.342.F.11.i;
A.343.F.11.i; A.344.F.11.i; A.345.F.11.i; A.346.F.11.i; A.347.F.11.i; A.348.F.11.i;
A.349.F.11.i; A.350.F.11.i; A.351.F.11.i; A.352.F.11.i; A.353.F.11.i; A.354.F.11.i;
A.355.F.11.i; A.356.F.11.i; A.357.F.11.i; A.358.F.11.i; A.359.F.11.i; A.360.F.11.i;
A.361.F.11.i; A.362.F.11.i; A.363.F.11.i; A.364.F.11.i; A.365.F.11.i; A.366.F.11.i;
A.367.F.11.i; A.368.F.11.i; A.369.F.11.i; A.370.F.11.i; A.371.F.11.i; A.372.F.11.i;
A.373.F.11.i; A.374.F.11.i; A.375.F.11.i; A.376.F.11.i; A.377.F.11.i; A.378.F.11.i;
A.379.F.11.i; A.380.F.11.i; A.381.F.11.i; A.382.F.11.i; A.383.F.11.i; A.384.F.11.i;
A.385.F.11.i; A.386.F.11.i; A.387.F.11.i; A.388.F.11.i; A.389.F.11.i; A.390.F.11.i;
A.391.F.11.i; A.392.F.11.i; A.393.F.11.i; A.394.F.11.i; A.395.F.11.i; A.396.F.11.i;
A.397.F.11.i; A.398.F.11.i; A.399.F.11.i; A.400.F.11.i; A.401.F.11.i; A.402.F.11.i;
A.403.F.11.i; A.404.F.11.i; A.405.F.11.i; A.406.F.11.i; A.407.F.11.i; A.408.F.11.i;
A.409.F.11.i; A.410.F.11.i; A.411.F.11.i; A.412.F.11.i; A.413.F.11.i; A.414.F.11.i;
A.415.F.11.i; A.416.F.11.i; A.417.F.11.i; A.418.F.11.i; A.419.F.11.i; A.420.F.11.i;
A.421.F.11.i; A.422.F.11.i; A.423.F.11.i; A.424.F.11.i; A.425.F.11.i; A.426.F.11.i;
A.427.F.11.i; A.428.F.11.i; A.429.F.11.i; A.430.F.11.i; A.431.F.11.i; A.432.F.11.i;
A.433.F.11.i; A.434.F.11.i; A.435.F.11.i; A.436.F.11.i; A.437.F.11.i; A.438.F.11.i;
A.439.F.11.i; A.440.F.11.i; A.441.F.11.i; A.442.F.11.i; A.443.F.11.i; A.444.F.11.i;
A.445.F.11.i; A.446.F.11.i; A.447.F.11.i; A.448.F.11.i; A.449.F.11.i; A.450.F.11.i;
A.451.F.11.i; A.452.F.11.i; A.453.F.11.i; A.454.F.11.i; A.455.F.11.i; A.456.F.11.i;
A.457.F.11.i; A.458.F.11.i; A.459.F.11.i; A.460.F.11.i; A.461.F.11.i; A.462.F.11.i;
A.463.F.11.i; A.464.F.11.i; A.465.F.11.i; A.466.F.11.i; A.467.F.11.i; A.468.F.11.i;
A.469.F.11.i; A.470.F.11.i; A.471.F.11.i; A.472.F.11.i; A.473.F.11.i; A.474.F.11.i;
A.475.F.11.i; A.476.F.11.i; A.477.F.11.i; A.478.F.11.i; A.479.F.11.i; A.480.F.11.i;
A.481.F.11.i; A.482.F.11.i; A.483.F.11.i; A.484.F.11.i; A.485.F.11.i; A.486.F.11.i;
A.487.F.11.i; A.488.F.11.i; A.489.F.11.i; A.490.F.11.i; A.491.F.11.i; A.492.F.11.i;
A.493.F.11.i; A.494.F.11.i; A.495.F.11.i; A.496.F.11.i; A.497.F.11.i; A.498.F.11.i;
A.499.F.11.i; A.500.F.11.i; A.501.F.11.i; A.502.F.11.i; A.503.F.11.i; A.504.F.11.i;
A.505.F.11.i; A.506.F.11.i; A.507.F.11.i; A.508.F.11.i; A.509.F.11.i; A.510.F.11.i;
A.511.F.11.i; A.512.F.11.i; A.512.F.11.i; A.513.F.11.i; A.514.F.11.i; A.515.F.11.i;
A.516.F.11.i; A.517.F.11.i; A.518.F.11.i; A.519.F.11.i; A.520.F.11.i; A.521.F.11.i;
A.522.F.11.i; A.523.F.11.i; A.524.F.11.i; A.525.F.11.i; A.526.F.11.i; A.527.F.11.i;
A.528.F.11.i; A.529.F.11.i; A.530.F.11.i; A.531.F.11.i; A.532.F.11.i; A.533.F.11.i;
A.534.F.11.i; A.535.F.11.i; A.536.F.11.i; A.537.F.11.i; A.538.F.11.i; A.539.F.11.i;
A.540.F.11.i; A.541.F.11.i; A.542.F.11.i; A.543.F.11.i; A.544.F.11.i; A.545.F.11.i;
A.546.F.11.i; A.547.F.11.i; A.548.F.11.i; A.549.F.11.i; A.550.F.11.i; A.551.F.11.i;
A.552.F.11.i; A.553.F.11.i; A.554.F.11.i; A.555.F.11.i; A.556.F.11.i; A.557.F.11.i;
A.558.F.11.i; A.559.F.11.i; A.560.F.11.i; A.561.F.11.i; A.562.F.11.i; A.563.F.11.i;
A.564.F.11.i; A.565.F.11.i; A.566.F.11.i; A.567.F.11.i; A.568.F.11.i; A.569.F.11.i;
A.570.F.11.i; A.571.F.11.i; A.572.F.11.i; A.573.F.11.i; A.574.F.11.i; A.575.F.11.i;
A.576.F.11.i; A.577.F.11.i; A.578.F.11.i; A.579.F.11.i; A.580.F.11.i; A.581.F.11.i;
A.582.F.11.i; A.583.F.11.i; A.584.F.11.i; A.585.F.11.i; A.586.F.11.i; A.587.F.11.i;
A.588.F.11.i; A.589.F.11.i; A.590.F.11.i; A.591.F.11.i; A.592.F.11.i; A.593.F.11.i;
A.594.F.11.i; A.595.F.11.i; A.596.F.11.i; A.597.F.11.i; A.598.F.11.i; A.599.F.11.i;
A.600.F.11.i; A.601.F.11.i; A.602.F.11.i; A.603.F.11.i; A.604.F.11.i; A.605.F.11.i;
A.606.F.11.i; A.607.F.11.i; A.608.F.11.i; A.609.F.11.i; A.610.F.11.i; A.611.F.11.i;
A.612.F.11.i; A.613.F.11.i; A.614.F.11.i; A.615.F.11.i; A.616.F.11.i; A.617.F.11.i;
A.618.F.11.i; A.619.F.11.i; A.620.F.11.i; A.621.F.11.i; A.622.F.11.i; A.623.F.11.i;
A.624.F.11.i; A.625.F.11.i; A.626.F.11.i; A.627.F.11.i; A.628.F.11.i; A.629.F.11.i;
A.630.F.11.i; A.631.F.11.i; A.632.F.11.i; A.633.F.11.i; A.634.F.11.i; A.635.F.11.i;
A.636.F.11.i; A.637.F.11.i; A.638.F.11.i; A.639.F.11.i; A.640.F.11.i; A.641.F.11.i;
A.642.F.11.i; A.643.F.11.i; A.644.F.11.i; A.645.F.11.i; A.646.F.11.i; A.647.F.11.i;
A.648.F.11.i; A.649.F.11.i; A.650.F.11.i; A.651.F.11.i; A.652.F.11.i; A.653.F.11.i;
A.654.F.11.i; A.655.F.11.i; A.656.F.11.i; A.657.F.11.i; A.658.F.11.i; A.659.F.11.i;
A.660.F.11.i; A.2.A.44.i; A.3.A.44.i; A.4.A.44.i; A.5.A.44.i; A.9.A.44.i; A.100.A.44.i;

TABLE 6-continued

Exemplary Enumerated Compounds

A.101.A.44.i; A.102.A.44.i; A.103.A.44.i; A.104.A.44.i; A.105.A.44.i; A.106.A.44.i;
A.107.A.44.i; A.108.A.44.i; A.109.A.44.i; A.110.A.44.i; A.111.A.44.i; A.112.A.44.i;
A.113.A.44.i; A.115.A.44.i; A.115.A.44.i; A.116.A.44.i; A.117.A.44.i; A.118.A.44.i;
A.119.A.44.i; A.120.A.44.i; A.121.A.44.i; A.122.A.44.i; A.123.A.44.i; A.124.A.44.i;
A.125.A.44.i; A.126.A.44.i; A.127.A.44.i; A.128.A.44.i; A.129.A.44.i; A.130.A.44.i;
A.131.A.44.i; A.132.A.44.i; A.133.A.44.i; A.134.A.44.i; A.135.A.44.i; A.136.A.44.i;
A.137.A.44.i; A.138.A.44.i; A.139.A.44.i; A.140.A.44.i; A.141.A.44.i; A.142.A.44.i;
A.143.A.44.i; A.144.A.44.i; A.145.A.44.i; A.146.A.44.i; A.147.A.44.i; A.148.A.44.i;
A.149.A.44.i; A.150.A.44.i; A.151.A.44.i; A.152.A.44.i; A.153.A.44.i; A.154.A.44.i;
A.155.A.44.i; A.156.A.44.i; A.157.A.44.i; A.158.A.44.i; A.159.A.44.i; A.160.A.44.i;
A.161.A.44.i; A.162.A.44.i; A.163.A.44.i; A.164.A.44.i; A.165.A.44.i; A.166.A.44.i;
A.167.A.44.i; A.168.A.44.i; A.169.A.44.i; A.170.A.44.i; A.171.A.44.i; A.172.A.44.i;
A.173.A.44.i; A.174.A.44.i; A.175.A.44.i; A.176.A.44.i; A.177.A.44.i; A.178.A.44.i;
A.179.A.44.i; A.180.A.44.i; A.181.A.44.i; A.182.A.44.i; A.183.A.44.i; A.184.A.44.i;
A.185.A.44.i; A.186.A.44.i; A.187.A.44.i; A.188.A.44.i; A.189.A.44.i; A.190.A.44.i;
A.191.A.44.i; A.192.A.44.i; A.193.A.44.i; A.194.A.44.i; A.195.A.44.i; A.196.A.44.i;
A.197.A.44.i; A.198.A.44.i; A.199.A.44.i; A.200.A.44.i; A.201.A.44.i; A.202.A.44.i;
A.203.A.44.i; A.204.A.44.i; A.205.A.44.i; A.206.A.44.i; A.207.A.44.i; A.208.A.44.i;
A.209.A.44.i; A.210.A.44.i; A.211.A.44.i; A.212.A.44.i; A.213.A.44.i; A.214.A.44.i;
A.215.A.44.i; A.216.A.44.i; A.217.A.44.i; A.218.A.44.i; A.219.A.44.i; A.220.A.44.i;
A.221.A.44.i; A.222.A.44.i; A.223.A.44.i; A.224.A.44.i; A.225.A.44.i; A.226.A.44.i;
A.227.A.44.i; A.228.A.44.i; A.229.A.44.i; A.230.A.44.i; A.231.A.44.i; A.232.A.44.i;
A.233.A.44.i; A.234.A.44.i; A.235.A.44.i; A.236.A.44.i; A.237.A.44.i; A.238.A.44.i;
A.239.A.44.i; A.240.A.44.i; A.241.A.44.i; A.242.A.44.i; A.243.A.44.i; A.244.A.44.i;
A.245.A.44.i; A.246.A.44.i; A.247.A.44.i; A.248.A.44.i; A.249.A.44.i; A.250.A.44.i;
A.251.A.44.i; A.252.A.44.i; A.253.A.44.i; A.254.A.44.i; A.255.A.44.i; A.256.A.44.i;
A.257.A.44.i; A.258.A.44.i; A.259.A.44.i; A.260.A.44.i; A.261.A.44.i; A.262.A.44.i;
A.263.A.44.i; A.264.A.44.i; A.265.A.44.i; A.266.A.44.i; A.267.A.44.i; A.268.A.44.i;
A.269.A.44.i; A.270.A.44.i; A.271.A.44.i; A.272.A.44.i; A.273.A.44.i; A.274.A.44.i;
A.275.A.44.i; A.276.A.44.i; A.277.A.44.i; A.278.A.44.i; A.279.A.44.i; A.280.A.44.i;
A.281.A.44.i; A.282.A.44.i; A.283.A.44.i; A.284.A.44.i; A.285.A.44.i; A.286.A.44.i;
A.287.A.44.i; A.288.A.44.i; A.289.A.44.i; A.290.A.44.i; A.291.A.44.i; A.292.A.44.i;
A.293.A.44.i; A.294.A.44.i; A.295.A.44.i; A.296.A.44.i; A.297.A.44.i; A.298.A.44.i;
A.299.A.44.i; A.300.A.44.i; A.301.A.44.i; A.302.A.44.i; A.303.A.44.i; A.304.A.44.i;
A.305.A.44.i; A.306.A.44.i; A.307.A.44.i; A.308.A.44.i; A.309.A.44.i; A.310.A.44.i;
A.311.A.44.i; A.312.A.44.i; A.313.A.44.i; A.314.A.44.i; A.315.A.44.i; A.316.A.44.i;
A.317.A.44.i; A.318.A.44.i; A.319.A.44.i; A.320.A.44.i; A.321.A.44.i; A.322.A.44.i;
A.323.A.44.i; A.324.A.44.i; A.325.A.44.i; A.326.A.44.i; A.327.A.44.i; A.328.A.44.i;
A.329.A.44.i; A.330.A.44.i; A.331.A.44.i; A.332.A.44.i; A.333.A.44.i; A.334.A.44.i;
A.335.A.44.i; A.336.A.44.i; A.337.A.44.i; A.338.A.44.i; A.339.A.44.i; A.340.A.44.i;
A.341.A.44.i; A.342.A.44.i; A.343.A.44.i; A.344.A.44.i; A.345.A.44.i; A.346.A.44.i;
A.347.A.44.i; A.348.A.44.i; A.349.A.44.i; A.350.A.44.i; A.351.A.44.i; A.352.A.44.i;
A.353.A.44.i; A.354.A.44.i; A.355.A.44.i; A.356.A.44.i; A.357.A.44.i; A.358.A.44.i;
B.2.a.44.i; B.3.a.44.i; B.4.a.44.i; B.5.a.44.i; B.9.a.44.i; B.100.a.44.i; B.101.a.44.i;
B.102.a.44.i; B.103.a.44.i; B.104.a.44.i; B.105.a.44.i; B.106.a.44.i; B.107.a.44.i;
B.108.a.44.i; B.109.a.44.i; B.110.a.44.i; B.111.a.44.i; B.112.a.44.i; B.113.a.44.i;
B.114.a.44.i; B.115.a.44.i; B.116.a.44.i; B.117.a.44.i; B.118.a.44.i; B.119.a.44.i;
B.120.a.44.i; B.121.a.44.i; B.122.a.44.i; B.123.a.44.i; B.124.a.44.i; B.125.a.44.i;
B.126.a.44.i; B.127.a.44.i; B.128.a.44.i; B.129.a.44.i; B.130.a.44.i; B.131.a.44.i;
B.132.a.44.i; B.133.a.44.i; B.134.a.44.i; B.135.a.44.i; B.136.a.44.i; B.137.a.44.i;
B.138.a.44.i; B.139.a.44.i; B.140.a.44.i; B.141.a.44.i; B.142.a.44.i; B.143.a.44.i;
B.144.a.44.i; B.145.a.44.i; B.146.a.44.i; B.147.a.44.i; B.148.a.44.i; B.149.a.44.i;
B.150.a.44.i; B.151.a.44.i; B.152.a.44.i; B.153.a.44.i; B.154.a.44.i; B.155.a.44.i;
B.156.a.44.i; B.157.a.44.i; B.158.a.44.i; B.159.a.44.i; B.160.a.44.i; B.161.a.44.i;
B.162.a.44.i; B.163.a.44.i; B.164.a.44.i; B.165.a.44.i; B.166.a.44.i; B.167.a.44.i;
B.168.a.44.i; B.169.a.44.i; B.170.a.44.i; B.171.a.44.i; B.172.a.44.i; B.173.a.44.i;
B.174.a.44.i; B.175.a.44.i; B.176.a.44.i; B.177.a.44.i; B.178.a.44.i; B.179.a.44.i;
B.180.a.44.i; B.181.a.44.i; B.182.a.44.i; B.183.a.44.i; B.184.a.44.i; B.185.a.44.i;
B.186.a.44.i; B.187.a.44.i; B.188.a.44.i; B.189.a.44.i; B.190.a.44.i; B.191.a.44.i;
B.192.a.44.i; B.193.a.44.i; B.194.a.44.i; B.195.a.44.i; B.196.a.44.i; B.197.a.44.i;
B.198.a.44.i; B.199.a.44.i; B.200.a.44.i; B.201.a.44.i; B.202.a.44.i; B.203.a.44.i;
B.204.a.44.i; B.205.a.44.i; B.206.a.44.i; B.207.a.44.i; B.208.a.44.i; B.209.a.44.i;
B.210.a.44.i; B.211.a.44.i; B.212.a.44.i; B.213.a.44.i; B.214.a.44.i; B.215.a.44.i;
B.216.a.44.i; B.217.a.44.i; B.218.a.44.i; B.219.a.44.i; B.220.a.44.i; B.221.a.44.i;
B.222.a.44.i; B.223.a.44.i; B.224.a.44.i; B.225.a.44.i; B.226.a.44.i; B.227.a.44.i;
B.228.a.44.i; B.229.a.44.i; B.230.a.44.i; B.231.a.44.i; B.232.a.44.i; B.233.a.44.i;
B.234.a.44.i; B.235.a.44.i; B.236.a.44.i; B.237.a.44.i; B.238.a.44.i; B.239.a.44.i;
B.240.a.44.i; B.241.a.44.i; B.242.a.44.i; B.243.a.44.i; B.244.a.44.i; B.245.a.44.i;
B.246.a.44.i; B.247.a.44.i; B.248.a.44.i; B.249.a.44.i; B.250.a.44.i; B.251.a.44.i;
B.252.a.44.i; B.253.a.44.i; B.254.a.44.i; B.255.a.44.i; B.256.a.44.i; B.257.a.44.i;
B.258.a.44.i; B.259.a.44.i; B.260.a.44.i; B.261.a.44.i; B.262.a.44.i; B.263.a.44.i;
B.264.a.44.i; B.265.a.44.i; B.266.a.44.i; B.267.a.44.i; B.268.a.44.i; B.269.a.44.i;
B.270.a.44.i; B.271.a.44.i; B.272.a.44.i; B.273.a.44.i; B.274.a.44.i; B.275.a.44.i;
B.276.a.44.i; B.277.a.44.i; B.278.a.44.i; B.279.a.44.i; B.280.a.44.i; B.281.a.44.i;
B.282.a.44.i; B.283.a.44.i; B.284.a.44.i; B.285.a.44.i; B.286.a.44.i; B.287.a.44.i;
B.288.a.44.i; B.289.a.44.i; B.290.a.44.i; B.291.a.44.i; B.292.a.44.i; B.293.a.44.i;
B.294.a.44.i; B.295.a.44.i; B.296.a.44.i; B.297.a.44.i; B.298.a.44.i; B.299.a.44.i;

TABLE 6-continued

Exemplary Enumerated Compounds

B.300.a.44.i; B.301.a.44.i; B.302.a.44.i; B.303.a.44.i; B.304.a.44.i; B.305.a.44.i;
B.306.a.44.i; B.307.a.44.i; B.308.a.44.i; B.309.a.44.i; B.310.a.44.i; B.311.a.44.i;
B.312.a.44.i; B.313.a.44.i; B.314.a.44.i; B.315.a.44.i; B.316.a.44.i; B.317.a.44.i;
B.318.a.44.i; B.319.a.44.i; B.320.a.44.i; B.321.a.44.i; B.322.a.44.i; B.323.a.44.i;
B.324.a.44.i; B.325.a.44.i; B.326.a.44.i; B.327.a.44.i; B.328.a.44.i; B.329.a.44.i;
B.330.a.44.i; B.331.a.44.i; B.332.a.44.i; B.333.a.44.i; B.334.a.44.i; B.335.a.44.i;
B.336.a.44.i; B.337.a.44.i; B.338.a.44.i; B.339.a.44.i; B.340.a.44.i; B.341.a.44.i;
B.342.a.44.i; B.343.a.44.i; B.344.a.44.i; B.345.a.44.i; B.346.a.44.i; B.347.a.44.i;
B.348.a.44.i; B.349.a.44.i; B.350.a.44.i; B.351.a.44.i; B.352.a.44.i; B.353.a.44.i;
B.354.a.44.i; B.355.a.44.i; B.356.a.44.i; B.357.a.44.i; B.358.a.44.i; E.2.a.44.i; E.3.a.44.i;
E.4.a.44.i; E.5.a.44.i; E.9.a.44.i; E.100.a.44.i; E.101.a.44.i; E.102.a.44.i; E.103.a.44.i;
B.104.a.44.i; B.105.a.44.i; B.106.a.44.i; B.107.a.44.i; B.108.a.44.i; B.109.a.44.i;
B.110.a.44.i; B.111.a.44.i; B.112.a.44.i; B.113.a.44.i; B.115.a.44.i; B.115.a.44.i;
B.116.a.44.i; B.117.a.44.i; B.118.a.44.i; B.119.a.44.i; B.120.a.44.i; B.121.a.44.i;
B.122.a.44.i; B.123.a.44.i; B.124.a.44.i; B.125.a.44.i; B.126.a.44.i; B.127.a.44.i;
B.128.a.44.i; B.129.a.44.i; B.130.a.44.i; B.131.a.44.i; B.132.a.44.i; B.133.a.44.i;
B.134.a.44.i; B.135.a.44.i; B.136.a.44.i; B.137.a.44.i; B.138.a.44.i; B.139.a.44.i;
B.140.a.44.i; B.141.a.44.i; B.142.a.44.i; B.143.a.44.i; B.144.a.44.i; B.145.a.44.i;
B.146.a.44.i; B.147.a.44.i; B.148.a.44.i; B.149.a.44.i; B.150.a.44.i; B.151.a.44.i;
B.152.a.44.i; B.153.a.44.i; B.154.a.44.i; B.155.a.44.i; B.156.a.44.i; B.157.a.44.i;
B.158.a.44.i; B.159.a.44.i; B.160.a.44.i; B.161.a.44.i; B.162.a.44.i; B.163.a.44.i;
B.164.a.44.i; B.165.a.44.i; B.166.a.44.i; B.167.a.44.i; B.168.a.44.i; B.169.a.44.i;
B.170.a.44.i; B.171.a.44.i; B.172.a.44.i; B.173.a.44.i; B.174.a.44.i; B.175.a.44.i;
B.176.a.44.i; B.177.a.44.i; B.178.a.44.i; B.179.a.44.i; B.180.a.44.i; B.181.a.44.i;
B.182.a.44.i; B.183.a.44.i; B.184.a.44.i; B.185.a.44.i; B.186.a.44.i; B.187.a.44.i;
B.188.a.44.i; B.189.a.44.i; B.190.a.44.i; B.191.a.44.i; B.192.a.44.i; B.193.a.44.i;
B.194.a.44.i; B.195.a.44.i; B.196.a.44.i; B.197.a.44.i; B.198.a.44.i; B.199.a.44.i;
B.200.a.44.i; B.201.a.44.i; B.202.a.44.i; B.203.a.44.i; B.204.a.44.i; B.205.a.44.i;
B.206.a.44.i; B.207.a.44.i; B.208.a.44.i; B.209.a.44.i; B.210.a.44.i; B.211.a.44.i;
B.212.a.44.i; B.213.a.44.i; B.214.a.44.i; B.215.a.44.i; B.216.a.44.i; B.217.a.44.i;
B.218.a.44.i; B.219.a.44.i; B.220.a.44.i; B.221.a.44.i; B.222.a.44.i; B.223.a.44.i;
B.224.a.44.i; B.225.a.44.i; B.226.a.44.i; B.227.a.44.i; B.228.a.44.i; B.229.a.44.i;
B.230.a.44.i; B.231.a.44.i; B.232.a.44.i; B.233.a.44.i; B.234.a.44.i; B.235.a.44.i;
B.236.a.44.i; B.237.a.44.i; B.238.a.44.i; B.239.a.44.i; B.240.a.44.i; B.241.a.44.i;
B.242.a.44.i; B.243.a.44.i; B.244.a.44.i; B.245.a.44.i; B.246.a.44.i; B.247.a.44.i;
B.248.a.44.i; B.249.a.44.i; B.250.a.44.i; B.251.a.44.i; B.252.a.44.i; B.253.a.44.i;
B.254.a.44.i; B.255.a.44.i; B.256.a.44.i; B.257.a.44.i; B.258.a.44.i; B.259.a.44.i;
B.260.a.44.i; B.261.a.44.i; B.262.a.44.i; B.263.a.44.i; B.264.a.44.i; B.265.a.44.i;
B.266.a.44.i; B.267.a.44.i; B.268.a.44.i; B.269.a.44.i; B.270.a.44.i; B.271.a.44.i;
B.272.a.44.i; B.273.a.44.i; B.274.a.44.i; B.275.a.44.i; B.276.a.44.i; B.277.a.44.i;
B.278.a.44.i; B.279.a.44.i; B.280.a.44.i; B.281.a.44.i; B.282.a.44.i; B.283.a.44.i;
B.284.a.44.i; B.285.a.44.i; B.286.a.44.i; B.287.a.44.i; B.288.a.44.i; B.289.a.44.i;
B.290.a.44.i; B.291.a.44.i; B.292.a.44.i; B.293.a.44.i; B.294.a.44.i; B.295.a.44.i;
B.296.a.44.i; B.297.a.44.i; B.298.a.44.i; B.299.a.44.i; B.300.a.44.i; B.301.a.44.i;
B.302.a.44.i; B.303.a.44.i; B.304.a.44.i; B.305.a.44.i; B.306.a.44.i; B.307.a.44.i;
B.308.a.44.i; B.309.a.44.i; B.310.a.44.i; B.311.a.44.i; B.312.a.44.i; B.313.a.44.i;
B.314.a.44.i; B.315.a.44.i; B.316.a.44.i; B.317.a.44.i; B.318.a.44.i; B.319.a.44.i;
B.320.a.44.i; B.321.a.44.i; B.322.a.44.i; B.323.a.44.i; B.324.a.44.i; B.325.a.44.i;
B.326.a.44.i; B.327.a.44.i; B.328.a.44.i; B.329.a.44.i; B.330.a.44.i; B.331.a.44.i;
B.332.a.44.i; B.333.a.44.i; B.334.a.44.i; B.335.a.44.i; B.336.a.44.i; B.337.a.44.i;
B.338.a.44.i; B.339.a.44.i; B.340.a.44.i; B.341.a.44.i; B.342.a.44.i; B.343.a.44.i;
B.344.a.44.i; B.345.a.44.i; B.346.a.44.i; B.347.a.44.i; B.348.a.44.i; B.349.a.44.i;
B.350.a.44.i; B.351.a.44.i; B.352.a.44.i; B.353.a.44.i; B.354.a.44.i; B.355.a.44.i;
B.356.a.44.i; B.357.a.44.i; B.358.a.44.i; B.2.a.4.i; B.3.a.4.i; B.4.a.4.i; B.5.a.4.i; B.9.a.4.1;
B.100.a.4.i; B.101.a.4.i; B.102.a.4.i; B.103.a.4.i; B.104.a.4.i; B.105.a.4.i; B.106.a.4.i;
B.107.a.4.i; B.108.a.4.i; B.109.a.4.i; B.110.a.4.i; B.111.a.4.i; B.112.a.4.i; B.113.a.4.i;
B.114.a.4.i; B.115.a.4.i; B.116.a.4.i; B.117.a.4.i; B.118.a.4.i; B.119.a.4.i; B.120.a.4.i;
B.121.a.4.i; B.122.a.4.i; B.123.a.4.i; B.124.a.4.i; B.125.a.4.i; B.126.a.4.i; B.127.a.4.i;
B.128.a.4.i; B.129.a.4.i; B.130.a.4.i; B.131.a.4.i; B.132.a.4.i; B.133.a.4.i; B.134.a.4.i;
B.135.a.4.i; B.136.a.4.i; B.137.a.4.i; B.138.a.4.i; B.139.a.4.i; B.140.a.4.i; B.141.a.4.i;
B.142.a.4.i; B.143.a.4.i; B.144.a.4.i; B.145.a.4.i; B.146.a.4.i; B.147.a.4.i; B.148.a.4.i;
B.149.a.4.i; B.150.a.4.i; B.151.a.4.i; B.152.a.4.i; B.153.a.4.i; B.154.a.4.i; B.155.a.4.i;
B.156.a.4.i; B.157.a.4.i; B.158.a.4.i; B.159.a.4.i; B.160.a.4.i; B.161.a.4.i; B.162.a.4.i;
B.163.a.4.i; B.164.a.4.i; B.165.a.4.i; B.166.a.4.i; B.167.a.4.i; B.168.a.4.i; B.169.a.4.i;
B.170.a.4.i; B.171.a.4.i; B.172.a.4.i; B.173.a.4.i; B.174.a.4.i; B.175.a.4.i; B.176.a.4.i;
B.177.a.4.i; B.178.a.4.i; B.179.a.4.i; B.180.a.4.i; B.181.a.4.i; B.182.a.4.i; B.183.a.4.i;
B.184.a.4.i; B.185.a.4.i; B.186.a.4.i; B.187.a.4.i; B.188.a.4.i; B.189.a.4.i; B.190.a.4.i;
B.191.a.4.i; B.192.a.4.i; B.193.a.4.i; B.194.a.4.i; B.195.a.4.i; B.196.a.4.i; B.197.a.4.i;
B.198.a.4.i; B.199.a.4.i; B.200.a.4.i; B.201.a.4.i; B.202.a.4.i; B.203.a.4.i; B.204.a.4.i;
B.205.a.4.i; B.206.a.4.i; B.207.a.4.i; B.208.a.4.i; B.209.a.4.i; B.210.a.4.i; B.211.a.4.i;
B.212.a.4.i; B.213.a.4.i; B.214.a.4.i; B.215.a.4.i; B.216.a.4.i; B.217.a.4.i; B.218.a.4.i;
B.219.a.4.i; B.220.a.4.i; B.221.a.4.i; B.222.a.4.i; B.223.a.4.i; B.224.a.4.i; B.225.a.4.i;
B.226.a.4.i; B.227.a.4.i; B.228.a.4.i; B.229.a.4.i; B.230.a.4.i; B.231.a.4.i; B.232.a.4.i;
B.233.a.4.i; B.234.a.4.i; B.235.a.4.i; B.236.a.4.i; B.237.a.4.i; B.238.a.4.i; B.239.a.4.i;
B.240.a.4.i; B.241.a.4.i; B.242.a.4.i; B.243.a.4.i; B.244.a.4.i; B.245.a.4.i; B.246.a.4.i;
B.247.a.4.i; B.248.a.4.i; B.249.a.4.i; B.250.a.4.i; B.251.a.4.i; B.252.a.4.i; B.253.a.4.i;
B.254.a.4.i; B.255.a.4.i; B.256.a.4.i; B.257.a.4.i; B.258.a.4.i; B.259.a.4.i; B.260.a.4.i;

TABLE 6-continued

Exemplary Enumerated Compounds

B.261.a.4.i; B.262.a.4.i; B.263.a.4.i; B.264.a.4.i; B.265.a.4.i; B.266.a.4.i; B.267.a.4.i;
B.268.a.4.i; B.269.a.4.i; B.270.a.4.i; B.271.a.4.i; B.272.a.4.i; B.273.a.4.i; B.274.a.4.i;
B.275.a.4.i; B.276.a.4.i; B.277.a.4.i; B.278.a.4.i; B.279.a.4.i; B.280.a.4.i; B.281.a.4.i;
B.282.a.4.i; B.283.a.4.i; B.284.a.4.i; B.285.a.4.i; B.286.a.4.i; B.287.a.4.i; B.288.a.4.i;
B.289.a.4.i; B.290.a.4.i; B.291.a.4.i; B.292.a.4.i; B.293.a.4.i; B.294.a.4.i; B.295.a.4.i;
B.296.a.4.i; B.297.a.4.i; B.298.a.4.i; B.299.a.4.i; B.300.a.4.i; B.301.a.4.i; B.302.a.4.i;
B.303.a.4.i; B.304.a.4.i; B.305.a.4.i; B.306.a.4.i; B.307.a.4.i; B.308.a.4.i; B.309.a.4.i;
B.310.a.4.i; B.311.a.4.i; B.312.a.4.i; B.313.a.4.i; B.314.a.4.i; B.315.a.4.i; B.316.a.4.i;
B.317.a.4.i; B.318.a.4.i; B.319.a.4.i; B.320.a.4.i; B.321.a.4.i; B.322.a.4.i; B.323.a.4.i;
B.324.a.4.i; B.325.a.4.i; B.326.a.4.i; B.327.a.4.i; B.328.a.4.i; B.329.a.4.i; B.330.a.4.i;
B.331.a.4.i; B.332.a.4.i; B.333.a.4.i; B.334.a.4.i; B.335.a.4.i; B.336.a.4.i; B.337.a.4.i;
B.338.a.4.i; B.339.a.4.i; B.340.a.4.i; B.341.a.4.i; B.342.a.4.i; B.343.a.4.i; B.344.a.4.i;
B.345.a.4.i; B.346.a.4.i; B.347.a.4.i; B.348.a.4.i; B.349.a.4.i; B.350.a.4.i; B.351.a.4.i;
B.352.a.4.i; B.353.a.4.i; B.354.a.4.i; B.355.a.4.i; B.356.a.4.i; B.357.a.4.i; B.358.a.4.i;
E.2.a.4.i; E.3.a.4.i; E.4.a.4.i; E.5.a.4.i; E.9.a.4.i; E.100.a.4.i; E.101.a.4.i; E.102.a.4.i;
E.103.a.4.i; E.104.a.4.i; E.105.a.4.i; E.106.a.4.i; E.107.a.4.i; E.108.a.4.i; E.109.a.4.i;
E.110.a.4.i; E.111.a.4.i; E.112.a.4.i; E.113.a.4.i; E.114.a.4.i; E.115.a.4.i; E.116.a.4.i;
E.117.a.4.i; E.118.a.4.i; E.119.a.4.i; E.120.a.4.i; E.121.a.4.i; E.122.a.4.i; E.123.a.4.i;
E.124.a.4.i; E.125.a.4.i; E.126.a.4.i; E.127.a.4.i; E.128.a.4.i; E.129.a.4.i; E.130.a.4.i;
E.131.a.4.i; E.132.a.4.i; E.133.a.4.i; E.134.a.4.i; E.135.a.4.i; E.136.a.4.i; E.137.a.4.i;
E.138.a.4.i; E.139.a.4.i; E.140.a.4.i; E.141.a.4.i; E.142.a.4.i; E.143.a.4.i; E.144.a.4.i;
E.145.a.4.i; E.146.a.4.i; E.147.a.4.i; E.148.a.4.i; E.149.a.4.i; E.150.a.4.i; E.151.a.4.i;
E.152.a.4.i; E.153.a.4.i; E.154.a.4.i; E.155.a.4.i; E.156.a.4.i; E.157.a.4.i; E.158.a.4.i;
E.159.a.4.i; E.160.a.4.i; E.161.a.4.i; E.162.a.4.i; E.163.a.4.i; E.164.a.4.i; E.165.a.4.i;
E.166.a.4.i; E.167.a.4.i; E.168.a.4.i; E.169.a.4.i; E.170.a.4.i; E.171.a.4.i; E.172.a.4.i;
E.173.a.4.i; E.174.a.4.i; E.175.a.4.i; E.176.a.4.i; E.177.a.4.i; E.178.a.4.i; E.179.a.4.i;
E.180.a.4.i; E.181.a.4.i; E.182.a.4.i; E.183.a.4.i; E.184.a.4.i; E.185.a.4.i; E.186.a.4.i;
E.187.a.4.i; E.188.a.4.i; E.189.a.4.i; E.190.a.4.i; E.191.a.4.i; E.192.a.4.i; E.193.a.4.i;
E.194.a.4.i; E.195.a.4.i; E.196.a.4.i; E.197.a.4.i; E.198.a.4.i; E.199.a.4.i; E.200.a.4.i;
E.201.a.4.i; E.202.a.4.i; E.203.a.4.i; E.204.a.4.i; E.205.a.4.i; E.206.a.4.i; E.207.a.4.i;
E.208.a.4.i; E.209.a.4.i; E.210.a.4.i; E.211.a.4.i; E.212.a.4.i; E.213.a.4.i; E.214.a.4.i;
E.215.a.4.i; E.216.a.4.i; E.217.a.4.i; E.218.a.4.i; E.219.a.4.i; E.220.a.4.i; E.221.a.4.i;
E.222.a.4.i; E.223.a.4.i; E.224.a.4.i; E.225.a.4.i; E.226.a.4.i; E.227.a.4.i; E.228.a.4.i;
E.229.a.4.i; E.230.a.4.i; E.231.a.4.i; E.232.a.4.i; E.233.a.4.i; E.234.a.4.i; E.235.a.4.i;
E.236.a.4.i; E.237.a.4.i; E.238.a.4.i; E.239.a.4.i; E.240.a.4.i; E.241.a.4.i; E.242.a.4.i;
E.243.a.4.i; E.244.a.4.i; E.245.a.4.i; E.246.a.4.i; E.247.a.4.i; E.248.a.4.i; E.249.a.4.i;
E.250.a.4.i; E.251.a.4.i; E.252.a.4.i; E.253.a.4.i; E.254.a.4.i; E.255.a.4.i; E.256.a.4.i;
E.257.a.4.i; E.258.a.4.i; E.259.a.4.i; E.260.a.4.i; E.261.a.4.i; E.262.a.4.i; E.263.a.4.i;
E.264.a.4.i; E.265.a.4.i; E.266.a.4.i; E.267.a.4.i; E.268.a.4.i; E.269.a.4.i; E.270.a.4.i;
E.271.a.4.i; E.272.a.4.i; E.273.a.4.i; E.274.a.4.i; E.275.a.4.i; E.276.a.4.i; E.277.a.4.i;
E.278.a.4.i; E.279.a.4.i; E.280.a.4.i; E.281.a.4.i; E.282.a.4.i; E.283.a.4.i; E.284.a.4.i;
E.285.a.4.i; E.286.a.4.i; E.287.a.4.i; E.288.a.4.i; E.289.a.4.i; E.290.a.4.i; E.291.a.4.i;
E.292.a.4.i; E.293.a.4.i; E.294.a.4.i; E.295.a.4.i; E.296.a.4.i; E.297.a.4.i; E.298.a.4.i;
E.299.a.4.i; E.300.a.4.i; E.301.a.4.i; E.302.a.4.i; E.303.a.4.i; E.304.a.4.i; E.305.a.4.i;
E.306.a.4.i; E.307.a.4.i; E.308.a.4.i; E.309.a.4.i; E.310.a.4.i; E.311.a.4.i; E.312.a.4.i;
E.313.a.4.i; E.314.a.4.i; E.315.a.4.i; E.316.a.4.i; E.317.a.4.i; E.318.a.4.i; E.319.a.4.i;
E.320.a.4.i; E.321.a.4.i; E.322.a.4.i; E.323.a.4.i; E.324.a.4.i; E.325.a.4.i; E.326.a.4.i;
E.327.a.4.i; E.328.a.4.i; E.329.a.4.i; E.330.a.4.i; E.331.a.4.i; E.332.a.4.i; E.333.a.4.i;
E.334.a.4.i; E.335.a.4.i; E.336.a.4.i; E.337.a.4.i; E.338.a.4.i; E.339.a.4.i; E.340.a.4.i;
E.341.a.4.i; E.342.a.4.i; E.343.a.4.i; E.344.a.4.i; E.345.a.4.i; E.346.a.4.i; E.347.a.4.i;
E.348.a.4.i; E.349.a.4.i; E.350.a.4.i; E.351.a.4.i; E.352.a.4.i; E.353.a.4.i; E.354.a.4.i;
E.355.a.4.i; E.356.a.4.i; E.357.a.4.i; E.358.a.4.i; B.2.a.11.i; B.3.a.11.i; B.4.a.11.i;
B.5.a.11.i; B.9.a.11.i; B.100.a.11.i; B.101.a.11.i; B.102.a.11.i; B.103.a.11.i;
B.104.a.11.i; B.105.a.11.i; B.106.a.11.i; B.107.a.11.i; B.108.a.11.i; B.109.a.11.i;
B.110.a.11.i; B.111.a.11.i; B.112.a.11.i; B.113.a.11.i; B.115.a.11.i; B.115.a.11.i;
B.116.a.11.i; B.117.a.11.i; B.118.a.11.i; B.119.a.11.i; B.120.a.11.i; B.121.a.11.i;
B.122.a.11.i; B.123.a.11.i; B.124.a.11.i; B.125.a.11.i; B.126.a.11.i; B.127.a.11.i;
B.128.a.11.i; B.129.a.11.i; B.130.a.11.i; B.131.a.11.i; B.132.a.11.i; B.133.a.11.i;
B.134.a.11.i; B.135.a.11.i; B.136.a.11.i; B.137.a.11.i; B.138.a.11.i; B.139.a.11.i;
B.140.a.11.i; B.141.a.11.i; B.142.a.11.i; B.143.a.11.i; B.144.a.11.i; B.145.a.11.i;
B.146.a.11.i; B.147.a.11.i; B.148.a.11.i; B.149.a.11.i; B.150.a.11.i; B.151.a.11.i;
B.152.a.11.i; B.153.a.11.i; B.154.a.11.i; B.155.a.11.i; B.156.a.11.i; B.157.a.11.i;
B.158.a.11.i; B.159.a.11.i; B.160.a.11.i; B.161.a.11.i; B.162.a.11.i; B.163.a.11.i;
B.164.a.11.i; B.165.a.11.i; B.166.a.11.i; B.167.a.11.i; B.168.a.11.i; B.169.a.11.i;
B.170.a.11.i; B.171.a.11.i; B.172.a.11.i; B.173.a.11.i; B.174.a.11.i; B.175.a.11.i;
B.176.a.11.i; B.177.a.11.i; B.178.a.11.i; B.179.a.11.i; B.180.a.11.i; B.181.a.11.i;
B.182.a.11.i; B.183.a.11.i; B.184.a.11.i; B.185.a.11.i; B.186.a.11.i; B.187.a.11.i;
B.188.a.11.i; B.189.a.11.i; B.190.a.11.i; B.191.a.11.i; B.192.a.11.i; B.193.a.11.i;
B.194.a.11.i; B.195.a.11.i; B.196.a.11.i; B.197.a.11.i; B.198.a.11.i; B.199.a.11.i;
B.200.a.11.i; B.201.a.11.i; B.202.a.11.i; B.203.a.11.i; B.204.a.11.i; B.205.a.11.i;
B.206.a.11.i; B.207.a.11.i; B.208.a.11.i; B.209.a.11.i; B.210.a.11.i; B.211.a.11.i;
B.212.a.11.i; B.213.a.11.i; B.214.a.11.i; B.215.a.11.i; B.216.a.11.i; B.217.a.11.i;
B.218.a.11.i; B.219.a.11.i; B.220.a.11.i; B.221.a.11.i; B.222.a.11.i; B.223.a.11.i;
B.224.a.11.i; B.225.a.11.i; B.226.a.11.i; B.227.a.11.i; B.228.a.11.i; B.229.a.11.i;
B.230.a.11.i; B.231.a.11.i; B.232.a.11.i; B.233.a.11.i; B.234.a.11.i; B.235.a.11.i;
B.236.a.11.i; B.237.a.11.i; B.238.a.11.i; B.239.a.11.i; B.240.a.11.i; B.241.a.11.i;
B.242.a.11.i; B.243.a.11.i; B.244.a.11.i; B.245.a.11.i; B.246.a.11.i; B.247.a.11.i;

TABLE 6-continued

Exemplary Enumerated Compounds

B.248.a.11.i; B.249.a.11.i; B.250.a.11.i; B.251.a.11.i; B.252.a.11.i; B.253.a.11.i;
B.254.a.11.i; B.255.a.11.i; B.256.a.11.i; B.257.a.11.i; B.258.a.11.i; B.259.a.11.i;
B.260.a.11.i; B.261.a.11.i; B.262.a.11.i; B.263.a.11.i; B.264.a.11.i; B.265.a.11.i;
B.266.a.11.i; B.267.a.11.i; B.268.a.11.i; B.269.a.11.i; B.270.a.11.i; B.271.a.11.i;
B.272.a.11.i; B.273.a.11.i; B.274.a.11.i; B.275.a.11.i; B.276.a.11.i; B.277.a.11.i;
B.278.a.11.i; B.279.a.11.i; B.280.a.11.i; B.281.a.11.i; B.282.a.11.i; B.283.a.11.i;
B.284.a.11.i; B.285.a.11.i; B.286.a.11.i; B.287.a.11.i; B.288.a.11.i; B.289.a.11.i;
B.290.a.11.i; B.291.a.11.i; B.292.a.11.i; B.293.a.11.i; B.294.a.11.i; B.295.a.11.i;
B.296.a.11.i; B.297.a.11.i; B.298.a.11.i; B.299.a.11.i; B.300.a.11.i; B.301.a.11.i;
B.302.a.11.i; B.303.a.11.i; B.304.a.11.i; B.305.a.11.i; B.306.a.11.i; B.307.a.11.i;
B.308.a.11.i; B.309.a.11.i; B.310.a.11.i; B.311.a.11.i; B.312.a.11.i; B.313.a.11.i;
B.314.a.11.i; B.315.a.11.i; B.316.a.11.i; B.317.a.11.i; B.318.a.11.i; B.319.a.11.i;
B.320.a.11.i; B.321.a.11.i; B.322.a.11.i; B.323.a.11.i; B.324.a.11.i; B.325.a.11.i;
B.326.a.11.i; B.327.a.11.i; B.328.a.11.i; B.329.a.11.i; B.330.a.11.i; B.331.a.11.i;
B.332.a.11.i; B.333.a.11.i; B.334.a.11.i; B.335.a.11.i; B.336.a.11.i; B.337.a.11.i;
B.338.a.11.i; B.339.a.11.i; B.340.a.11.i; B.341.a.11.i; B.342.a.11.i; B.343.a.11.i;
B.344.a.11.i; B.345.a.11.i; B.346.a.11.i; B.347.a.11.i; B.348.a.11.i; B.349.a.11.i;
B.350.a.11.i; B.351.a.11.i; B.352.a.11.i; B.353.a.11.i; B.354.a.11.i; B.355.a.11.i;
B.356.a.11.i; B.357.a.11.i; B.358.a.11.i; E.2.a.11.i; E.3.a.11.i; E.4.a.11; B.5.a.11.i;
E.9.a.11.i; E.100.a.11.i; E.101.a.11.i; E.102.a.11.i; E.103.a.11.i; E.104.a.11.i;
E.105.a.11.i; E.106.a.11.i; E.107.a.11.i; E.108.a.11.i; E.109.a.11.i; E.110.a.11.i;
E.111.a.11.i; E.112.a.11.i; E.113.a.11.i; E.115.a.11.i; E.115.a.11.i; E.116.a.11.i;
E.117.a.11.i; E.118.a.11.i; E.119.a.11.i; E.120.a.11.i; E.121.a.11.i; E.122.a.11.i;
E.123.a.11.i; E.124.a.11.i; E.125.a.11.i; E.126.a.11.i; E.127.a.11.i; E.128.a.11.i;
E.129.a.11.i; E.130.a.11.i; E.131.a.11.i; E.132.a.11.i; E.133.a.11.i; E.134.a.11.i;
E.135.a.11.i; E.136.a.11.i; E.137.a.11.i; E.138.a.11.i; E.139.a.11.i; E.140.a.11.i;
E.141.a.11.i; E.142.a.11.i; E.143.a.11.i; E.144.a.11.i; E.145.a.11.i; E.146.a.11.i;
E.147.a.11.i; E.148.a.11.i; E.149.a.11.i; E.150.a.11.i; E.151.a.11.i; E.152.a.11.i;
E.153.a.11.i; E.154.a.11.i; E.155.a.11.i; E.156.a.11.i; E.157.a.11.i; E.158.a.11.i;
E.159.a.11.i; E.160.a.11.i; E.161.a.11.i; E.162.a.11.i; E.163.a.11.i; E.164.a.11.i;
E.165.a.11.i; E.166.a.11.i; E.167.a.11.i; E.168.a.11.i; E.169.a.11.i; E.170.a.11.i;
E.171.a.11.i; E.172.a.11.i; E.173.a.11.i; E.174.a.11.i; E.175.a.11.i; E.176.a.11.i;
E.177.a.11.i; E.178.a.11.i; E.179.a.11.i; E.180.a.11.i; E.181.a.11.i; E.182.a.11.i;
E.183.a.11.i; E.184.a.11.i; E.185.a.11.i; E.186.a.11.i; E.187.a.11.i; E.188.a.11.i;
E.189.a.11.i; E.190.a.11.i; E.191.a.11.i; E.192.a.11.i; E.193.a.11.i; E.194.a.11.i;
E.195.a.11.i; E.196.a.11.i; E.197.a.11.i; E.198.a.11.i; E.199.a.11.i; E.200.a.11.i;
E.201.a.11.i; E.202.a.11.i; E.203.a.11.i; E.204.a.11.i; E.205.a.11.i; E.206.a.11.i;
E.207.a.11.i; E.208.a.11.i; E.209.a.11.i; E.210.a.11.i; E.211.a.11.i; E.212.a.11.i;
E.213.a.11.i; E.214.a.11.i; E.215.a.11.i; E.216.a.11.i; E.217.a.11.i; E.218.a.11.i;
E.219.a.11.i; E.220.a.11.i; E.221.a.11.i; E.222.a.11.i; E.223.a.11.i; E.224.a.11.i;
E.225.a.11.i; E.226.a.11.i; E.227.a.11.i; E.228.a.11.i; E.229.a.11.i; E.230.a.11.i;
E.231.a.11.i; E.232.a.11.i; E.233.a.11.i; E.234.a.11.i; E.235.a.11.i; E.236.a.11.i;
E.237.a.11.i; E.238.a.11.i; E.239.a.11.i; E.240.a.11.i; E.241.a.11.i; E.242.a.11.i;
E.243.a.11.i; E.244.a.11.i; E.245.a.11.i; E.246.a.11.i; E.247.a.11.i; E.248.a.11.i;
E.249.a.11.i; E.250.a.11.i; E.251.a.11.i; E.252.a.11.i; E.253.a.11.i; E.254.a.11.i;
E.255.a.11.i; E.256.a.11.i; E.257.a.11.i; E.258.a.11.i; E.259.a.11.i; E.260.a.11.i;
E.261.a.11.i; E.262.a.11.i; E.263.a.11.i; E.264.a.11.i; E.265.a.11.i; E.266.a.11.i;
E.267.a.11.i; E.268.a.11.i; E.269.a.11.i; E.270.a.11.i; E.271.a.11.i; E.272.a.11.i;
E.273.a.11.i; E.274.a.11.i; E.275.a.11.i; E.276.a.11.i; E.277.a.11.i; E.278.a.11.i;
E.279.a.11.i; E.280.a.11.i; E.281.a.11.i; E.282.a.11.i; E.283.a.11.i; E.284.a.11.i;
E.285.a.11.i; E.286.a.11.i; E.287.a.11.i; E.288.a.11.i; E.289.a.11.i; E.290.a.11.i;
E.291.a.11.i; E.292.a.11.i; E.293.a.11.i; E.294.a.11.i; E.295.a.11.i; E.296.a.11.i;
E.297.a.11.i; E.298.a.11.i; E.299.a.11.i; E.300.a.11.i; E.301.a.11.i; E.302.a.11.i;
E.303.a.11.i; E.304.a.11.i; E.305.a.11.i; E.306.a.11.i; E.307.a.11.i; E.308.a.11.i;
E.309.a.11.i; E.310.a.11.i; E.311.a.11.i; E.312.a.11.i; E.313.a.11.i; E.314.a.11.i;
E.315.a.11.i; E.316.a.11.i; E.317.a.11.i; E.318.a.11.i; E.319.a.11.i; E.320.a.11.i;
E.321.a.11.i; E.322.a.11.i; E.323.a.11.i; E.324.a.11.i; E.325.a.11.i; E.326.a.11.i;
E.327.a.11.i; E.328.a.11.i; E.329.a.11.i; E.330.a.11.i; E.331.a.11.i; E.332.a.11.i;
E.333.a.11.i; E.334.a.11.i; E.335.a.11.i; E.336.a.11.i; E.337.a.11.i; E.338.a.11.i;
E.339.a.11.i; E.340.a.11.i; E.341.a.11.i; E.342.a.11.i; E.343.a.11.i; E.344.a.11.i;
E.345.a.11.i; E.346.a.11.i; E.347.a.11.i; E.348.a.11.i; E.349.a.11.i; E.350.a.11.i;
E.351.a.11.i; E.352.a.11.i; E.353.a.11.i; E.354.a.11.i; E.355.a.11.i; E.356.a.11.i;
E.357.a.11.i; E.358.a.11.i; A.661.a.4.i; A.662.a.4.i; A.663.a.4.i; A.664.a.4.i;
A.665.a.4.i; B.661.a.4.i; B.662.a.4.i; B.663.a.4.i; B.664.a.4.i; B.665.a.4.i; C.661.a.4.i;
C.662.a.4.i; C.663.a.4.i; C.664.a.4.i; C.665.a.4.i; A.661.a.11.i; A.662.a.11.i;
A.663.a.11.i; A.664.a.11.i; A.665.a.11.i; B.661.a.11.i; B.662.a.11.i; B.663.a.11.i;
B.664.a.11.i; B.665.a.11.i; C.661.a.11.i; C.662.a.11.i; C.663.a.11.i; C.664.a.11.i;
C.665.a.11.i; A.661.a.44.i; A.662.a.44.i; A.663.a.44.i; A.664.a.44.i; A.665.a.44.i;
B.661.a.44.i; B.662.a.44.i; B.663.a.44.i; B.664.a.44.i; B.665.a.44.i; C.661.a.44.i;
C.662.a.44.i; C.663.a.44.i; C.664.a.44.i; C.665.a.44.i; A.666.a.4.i; A.666.a.11.i;
A.666.a.44.1; A.666.b.4.i; A.666.b.11.i; A.666.b.44.i; A.666.x.4.i; A.666.x.11.i;
A.666.x.44.i; A.666.y.4.i; A.666.y.11.i; A.666.y.44.i; A.666.z.4.i; A.666.z.11.i;
A.666.z.44.i; A.666.A.4.i; A.666.A.11.i; A.666.A.44.i; A.666.B.4.i; A.666.B.11.i;
A.666.B.44.i; A.666.C.4.i; A.666.C.11.i; A.666.C.44.i; A.666.D.4.i; A.666.D.11.i;
A.666.D.44.i; A.666.E.4.i; A.666.E.11.i; A.666.E.44.i; A.666.F.4.i; A.666.F.11.i;
A.666.F.44.i; B.666.a.4.i; B.666.a.11.i; B.666.a.44.1; B.666.b.4.i; B.666.b.11.i;
B.666.b.44.i; B.666.x.4.i; B.666.x.11.i; B.666.x.44.i; B.666.y.4.i; B.666.y.11.i;

TABLE 6-continued

Exemplary Enumerated Compounds

B.666.y.44.i; B.666.z.4.i; B.666.z.11.i; B.666.z.44.i; B.666.B.4.i; B.666.B.11.i;
B.666.B.44.i; B.666.B.4.i; B.666.B.11.i; B.666.B.44.i; B.666.C.4.i; B.666.C.11.i;
B.666.C.44.i; B.666.D.4.i; B.666.D.11.i; B.666.D.44.i; B.666.E.4.i; B.666.E.11.i;
B.666.E.44.i; B.666.F.4.i; B.666.F.11.i; B.666.F.44.i; E.666.a.4.i; E.666.a.11.i;
E.666.a.44.i; E.666.b.4.i; E.666.b.11.i; E.666.b.44.i; E.666.x.4.i; E.666.x.11.i;
E.666.x.44.i; E.666.y.4.i; E.666.y.11.i; E.666.y.44.i; E.666.z.4.i; E.666.z.11.i;
E.666.z.44.i; E.666.E.4.i; E.666.E.11.i; E.666.E.44.i; E.666.B.4.i; E.666.B.11.i;
E.666.B.44.i; E.666.C.4.i; E.666.C.11.i; E.666.C.44.i; E.666.D.4.i; E.666.D.11.i;
E.666.D.44.i; E.666.E.4.i; E.666.E.11.i; E.666.E.44.i; E.666.F.4.i; E.666.F.11.i;
E.666.F.44.i;
A.2.a.46.i; A.3.a.46.i; A.4.a.46.i; A.5.a.46.i; A.7.a.46.i; A.9.a.46.i; A.100.a.46.i;
A.101.a.46.i; A.102.a.46.i; A.103.a.46.i; A.104.a.46.i; A.105.a.46.i; A.106.a.46.i;
A.107.a.46.i; A.108.a.46.i; A.109.a.46.i; A.110.a.46.i; A.111.a.46.i; A.112.a.46.i;
A.113.a.46.i; A.114.a.46.i; A.115.a.46.i; A.116.a.46.i; A.117.a.46.i; A.118.a.46.i;
A.119.a.46.i; A.120.a.46.i; A.121.a.46.i; A.122.a.46.i; A.123.a.46.i; A.124.a.46.i;
A.125.a.46.i; A.126.a.46.i; A.127.a.46.i; A.128.a.46.i; A.129.a.46.i; A.130.a.46.i;
A.131.a.46.i; A.132.a.46.i; A.133.a.46.i; A.134.a.46.i; A.135.a.46.i; A.136.a.46.i;
A.137.a.46.i; A.138.a.46.i; A.139.a.46.i; A.140.a.46.i; A.141.a.46.i; A.2.a.47.i;
A.3.a.47.i; A.4.a.47.i; A.5.a.47.i; A.7.a.47.i; A.9.a.47.i; A.100.a.47.i; A.101.a.47.i;
A.102.a.47.i; A.103.a.47.i; A.104.a.47.i; A.105.a.47.i; A.106.a.47.i; A.107.a.47.i;
A.108.a.47.i; A.109.a.47.i; A.110.a.47.i; A.111.a.47.i; A.112.a.47.i; A.113.a.47.i;
A.114.a.47.i; A.115.a.47.i; A.116.a.47.i; A.117.a.47.i; A.118.a.47.i; A.119.a.47.i;
A.120.a.47.i; A.121.a.47.i; A.122.a.47.i; A.123.a.47.i; A.124.a.47.i; A.125.a.47.i;
A.126.a.47.i; A.127.a.47.i; A.128.a.47.i; A.129.a.47.i; A.130.a.47.i; A.131.a.47.i;
A.132.a.47.i; A.133.a.47.i; A.134.a.47.i; A.135.a.47.i; A.136.a.47.i; A.137.a.47.i;
A.138.a.47.i; A.139.a.47.i; A.140.a.47.i; A.141.a.47.i; A.2.a.48.i; A.3.a.48.i;
A.4.a.48.i; A.5.a.48.i; A.7.a.48.i; A.9.a.48.i; A.100.a.48.i; A.101.a.48.i; A.102.a.48.i;
A.103.a.48.i; A.104.a.48.i; A.105.a.48.i; A.106.a.48.i; A.107.a.48.i; A.108.a.48.i;
A.109.a.48.i; A.110.a.48.i; A.111.a.48.i; A.112.a.48.i; A.113.a.48.i; A.114.a.48.i;
A.115.a.48.i; A.116.a.48.i; A.117.a.48.i; A.118.a.48.i; A.119.a.48.i; A.120.a.48.i;
A.121.a.48.i; A.122.a.48.i; A.123.a.48.i; A.124.a.48.i; A.125.a.48.i; A.126.a.48.i;
A.127.a.48.i; A.128.a.48.i; A.129.a.48.i; A.130.a.48.i; A.131.a.48.i; A.132.a.48.i;
A.133.a.48.i; A.134.a.48.i; A.135.a.48.i; A.136.a.48.i; A.137.a.48.i; A.138.a.48.i;
A.139.a.48.i; A.140.a.48.i; A.141.a.48.i; A.2.a.49.i; A.3.a.49.i; A.4.a.49.i; A.5.a.49.i;
A.7.a.49.i; A.9.a.49.i; A.100.a.49.i; A.101.a.49.i; A.102.a.49.i; A.103.a.49.i;
A.104.a.49.i; A.105.a.49.i; A.106.a.49.i; A.107.a.49.i; A.108.a.49.i; A.109.a.49.i;
A.110.a.49.i; A.111.a.49.i; A.112.a.49.i; A.113.a.49.i; A.114.a.49.i; A.115.a.49.i;
A.116.a.49.i; A.117.a.49.i; A.118.a.49.i; A.119.a.49.i; A.120.a.49.i; A.121.a.49.i;
A.122.a.49.i; A.123.a.49.i; A.124.a.49.i; A.125.a.49.i; A.126.a.49.i; A.127.a.49.i;
A.128.a.49.i; A.129.a.49.i; A.130.a.49.i; A.131.a.49.i; A.132.a.49.i; A.133.a.49.i;
A.134.a.49.i; A.135.a.49.i; A.136.a.49.i; A.137.a.49.i; A.138.a.49.i; A.139.a.49.i;
A.140.a.49.i; A.141.a.49.i; A.2.a.50.i; A.3.a.50.i; A.4.a.50.i; A.5.a.50.i; A.7.a.50.i;
A.9.a.50.i; A.100.a.50.i; A.101.a.50.i; A.102.a.50.i; A.103.a.50.i; A.104.a.50.i;
A.105.a.50.i; A.106.a.50.i; A.107.a.50.i; A.108.a.50.i; A.109.a.50.i; A.110.a.50.i;
A.111.a.50.i; A.112.a.50.i; A.113.a.50.i; A.114.a.50.i; A.115.a.50.i; A.116.a.50.i;
A.117.a.50.i; A.118.a.50.i; A.119.a.50.i; A.120.a.50.i; A.121.a.50.i; A.122.a.50.i;
A.123.a.50.i; A.124.a.50.i; A.125.a.50.i; A.126.a.50.i; A.127.a.50.i; A.128.a.50.i;
A.129.a.50.i; A.130.a.50.i; A.131.a.50.i; A.132.a.50.i; A.133.a.50.i; A.134.a.50.i;
A.135.a.50.i; A.136.a.50.i; A.137.a.50.i; A.138.a.50.i; A.139.a.50.i; A.140.a.50.i;
A.141.a.50.i; A.2.a.51.i; A.3.a.51.i; A.4.a.51.i; A.5.a.51.i; A.7.a.51.i; A.9.a.51.i;
A.100.a.51.i; A.101.a.51.i; A.102.a.51.i; A.103.a.51.i; A.104.a.51.i; A.105.a.51.i;
A.106.a.51.i; A.107.a.51.i; A.108.a.51.i; A.109.a.51.i; A.110.a.51.i; A.111.a.51.i;
A.112.a.51.i; A.113.a.51.i; A.114.a.51.i; A.115.a.51.i; A.116.a.51.i; A.117.a.51.i;
A.118.a.51.i; A.119.a.51.i; A.120.a.51.i; A.121.a.51.i; A.122.a.51.i; A.123.a.51.i;
A.124.a.51.i; A.125.a.51.i; A.126.a.51.i; A.127.a.51.i; A.128.a.51.i; A.129.a.51.i;
A.130.a.51.i; A.131.a.51.i; A.132.a.51.i; A.133.a.51.i; A.134.a.51.i; A.135.a.51.i;
A.136.a.51.i; A.137.a.51.i; A.138.a.51.i; A.139.a.51.i; A.140.a.51.i; A.141.a.51.i;
A.2.b.46.i; A.3.b.46.i; A.4.b.46.i; A.5.b.46.i; A.7.b.46.i; A.9.b.46.i; A.100.b.46.i;
A.101.b.46.i; A.102.b.46.i; A.103.b.46.i; A.104.b.46.i; A.105.b.46.i; A.106.b.46.i;
A.107.b.46.i; A.108.b.46.i; A.109.b.46.i; A.110.b.46.i; A.111.b.46.i; A.112.b.46.i;
A.113.b.46.i; A.114.b.46.i; A.115.b.46.i; A.116.b.46.i; A.117.b.46.i; A.118.b.46.i;
A.119.b.46.i; A.120.b.46.i; A.121.b.46.i; A.122.b.46.i; A.123.b.46.i; A.124.b.46.i;
A.125.b.46.i; A.126.b.46.i; A.127.b.46.i; A.128.b.46.i; A.129.b.46.i; A.130.b.46.i;
A.131.b.46.i; A.132.b.46.i; A.133.b.46.i; A.134.b.46.i; A.135.b.46.i; A.136.b.46.i;
A.137.b.46.i; A.138.b.46.i; A.139.b.46.i; A.140.b.46.i; A.141.b.46.i; A.2.b.47.i;
A.3.b.47.i; A.4.b.47.i; A.5.b.47.i; A.7.b.47.i; A.9.b.47.i; A.100.b.47.i; A.101.b.47.i;
A.102.b.47.i; A.103.b.47.i; A.104.b.47.i; A.105.b.47.i; A.106.b.47.i; A.107.b.47.i;
A.108.b.47.i; A.109.b.47.i; A.110.b.47.i; A.111.b.47.i; A.112.b.47.i; A.113.b.47.i;
A.114.b.47.i; A.115.b.47.i; A.116.b.47.i; A.117.b.47.i; A.118.b.47.i; A.119.b.47.i;
A.120.b.47.i; A.121.b.47.i; A.122.b.47.i; A.123.b.47.i; A.124.b.47.i; A.125.b.47.i;
A.126.b.47.i; A.127.b.47.i; A.128.b.47.i; A.129.b.47.i; A.130.b.47.i; A.131.b.47.i;
A.132.b.47.i; A.133.b.47.i; A.134.b.47.i; A.135.b.47.i; A.136.b.47.i; A.137.b.47.i;
A.138.b.47.i; A.139.b.47.i; A.140.b.47.i; A.141.b.47.i; A.2.b.48.i; A.3.b.48.i;
A.4.b.48.i; A.5.b.48.i; A.7.b.48.i; A.9.b.48.i; A.100.b.48.i; A.101.b.48.i; A.102.b.48.i;
A.103.b.48.i; A.104.b.48.i; A.105.b.48.i; A.106.b.48.i; A.107.b.48.i; A.108.b.48.i;
A.109.b.48.i; A.110.b.48.i; A.111.b.48.i; A.112.b.48.i; A.113.b.48.i; A.114.b.48.i;
A.115.b.48.i; A.116.b.48.i; A.117.b.48.i; A.118.b.48.i; A.119.b.48.i; A.120.b.48.i;

TABLE 6-continued

Exemplary Enumerated Compounds

A.121.b.48.i; A.122.b.48.i; A.123.b.48.i; A.124.b.48.i; A.125.b.48.i; A.126.b.48.i;
A.127.b.48.i; A.128.b.48.i; A.129.b.48.i; A.130.b.48.i; A.131.b.48.i; A.132.b.48.i;
A.133.b.48.i; A.134.b.48.i; A.135.b.48.i; A.136.b.48.i; A.137.b.48.i; A.138.b.48.i;
A.139.b.48.i; A.140.b.48.i; A.141.b.48.i; A.2.b.49.i; A.3.b.49.i; A.4.b.49.i; A.5.b.49.i;
A.7.b.49.i; A.9.b.49.i; A.100.b.49.i; A.101.b.49.i; A.102.b.49.i; A.103.b.49.i;
A.104.b.49.i; A.105.b.49.i; A.106.b.49.i; A.107.b.49.i; A.108.b.49.i; A.109.b.49.i;
A.110.b.49.i; A.111.b.49.i; A.112.b.49.i; A.113.b.49.i; A.114.b.49.i; A.115.b.49.i;
A.116.b.49.i; A.117.b.49.i; A.118.b.49.i; A.119.b.49.i; A.120.b.49.i; A.121.b.49.i;
A.122.b.49.i; A.123.b.49.i; A.124.b.49.i; A.125.b.49.i; A.126.b.49.i; A.127.b.49.i;
A.128.b.49.i; A.129.b.49.i; A.130.b.49.i; A.131.b.49.i; A.132.b.49.i; A.133.b.49.i;
A.134.b.49.i; A.135.b.49.i; A.136.b.49.i; A.137.b.49.i; A.138.b.49.i; A.139.b.49.i;
A.140.b.49.i; A.141.b.49.i; A.2.b.50.i; A.3.b.50.i; A.4.b.50.i; A.5.b.50.i; A.7.b.50.i;
A.9.b.50.i; A.100.b.50.i; A.101.b.50.i; A.102.b.50.i; A.103.b.50.i; A.104.b.50.i;
A.105.b.50.i; A.106.b.50.i; A.107.b.50.i; A.108.b.50.i; A.109.b.50.i; A.110.b.50.i;
A.111.b.50.i; A.112.b.50.i; A.113.b.50.i; A.114.b.50.i; A.115.b.50.i; A.116.b.50.i;
A.117.b.50.i; A.118.b.50.i; A.119.b.50.i; A.120.b.50.i; A.121.b.50.i; A.122.b.50.i;
A.123.b.50.i; A.124.b.50.i; A.125.b.50.i; A.126.b.50.i; A.127.b.50.i; A.128.b.50.i;
A.129.b.50.i; A.130.b.50.i; A.131.b.50.i; A.132.b.50.i; A.133.b.50.i; A.134.b.50.i;
A.135.b.50.i; A.136.b.50.i; A.137.b.50.i; A.138.b.50.i; A.139.b.50.i; A.140.b.50.i;
A.141.b.50.i; A.2.b.51.i; A.3.b.51.i; A.4.b.51.i; A.5.b.51.i; A.7.b.51.i; A.9.b.51.i;
A.100.b.51.i; A.101.b.51.i; A.102.b.51.i; A.103.b.51.i; A.104.b.51.i; A.105.b.51.i;
A.106.b.51.i; A.107.b.51.i; A.108.b.51.i; A.109.b.51.i; A.110.b.51.i; A.111.b.51.i;
A.112.b.51.i; A.113.b.51.i; A.114.b.51.i; A.115.b.51.i; A.116.b.51.i; A.117.b.51.i;
A.118.b.51.i; A.119.b.51.i; A.120.b.51.i; A.121.b.51.i; A.122.b.51.i; A.123.b.51.i;
A.124.b.51.i; A.125.b.51.i; A.126.b.51.i; A.127.b.51.i; A.128.b.51.i; A.129.b.51.i;
A.130.b.51.i; A.131.b.51.i; A.132.b.51.i; A.133.b.51.i; A.134.b.51.i; A.135.b.51.i;
A.136.b.51.i; A.137.b.51.i; A.138.b.51.i; A.139.b.51.i; A.140.b.51.i; A.141.b.51.i;
A.2.x.46.i; A.3.x.46.i; A.4.x.46.i; A.5.x.46.i; A.7.x.46.i; A.9.x.46.i; A.100.x.46.i;
A.101.x.46.i; A.102.x.46.i; A.103.x.46.i; A.104.x.46.i; A.105.x.46.i; A.106.x.46.i;
A.107.x.46.i; A.108.x.46.i; A.109.x.46.i; A.110.x.46.i; A.111.x.46.i; A.112.x.46.i;
A.113.x.46.i; A.114.x.46.i; A.115.x.46.i; A.116.x.46.i; A.117.x.46.i; A.118.x.46.i;
A.119.x.46.i; A.120.x.46.i; A.121.x.46.i; A.122.x.46.i; A.123.x.46.i; A.124.x.46.i;
A.125.x.46.i; A.126.x.46.i; A.127.x.46.i; A.128.x.46.i; A.129.x.46.i; A.130.x.46.i;
A.131.x.46.i; A.132.x.46.i; A.133.x.46.i; A.134.x.46.i; A.135.x.46.i; A.136.x.46.i;
A.137.x.46.i; A.138.x.46.i; A.139.x.46.i; A.140.x.46.i; A.141.x.46.i; A.2.x.47.i;
A.3.x.47.i; A.4.x.47.i; A.5.x.47.i; A.7.x.47.i; A.9.x.47.i; A.100.x.47.i; A.101.x.47.i;
A.102.x.47.i; A.103.x.47.i; A.104.x.47.i; A.105.x.47.i; A.106.x.47.i; A.107.x.47.i;
A.108.x.47.i; A.109.x.47.i; A.110.x.47.i; A.111.x.47.i; A.112.x.47.i; A.113.x.47.i;
A.114.x.47.i; A.115.x.47.i; A.116.x.47.i; A.117.x.47.i; A.118.x.47.i; A.119.x.47.i;
A.120.x.47.i; A.121.x.47.i; A.122.x.47.i; A.123.x.47.i; A.124.x.47.i; A.125.x.47.i;
A.126.x.47.i; A.127.x.47.i; A.128.x.47.i; A.129.x.47.i; A.130.x.47.i; A.131.x.47.i;
A.132.x.47.i; A.133.x.47.i; A.134.x.47.i; A.135.x.47.i; A.136.x.47.i; A.137.x.47.i;
A.138.x.47.i; A.139.x.47.i; A.140.x.47.i; A.141.x.47.i; A.2.x.48.i; A.3.x.48.i;
A.4.x.48.i; A.5.x.48.i; A.7.x.48.i; A.9.x.48.i; A.100.x.48.i; A.101.x.48.i; A.102.x.48.i;
A.103.x.48.i; A.104.x.48.i; A.105.x.48.i; A.106.x.48.i; A.107.x.48.i; A.108.x.48.i;
A.109.x.48.i; A.110.x.48.i; A.111.x.48.i; A.112.x.48.i; A.113.x.48.i; A.114.x.48.i;
A.115.x.48.i; A.116.x.48.i; A.117.x.48.i; A.118.x.48.i; A.119.x.48.i; A.120.x.48.i;
A.121.x.48.i; A.122.x.48.i; A.123.x.48.i; A.124.x.48.i; A.125.x.48.i; A.126.x.48.i;
A.127.x.48.i; A.128.x.48.i; A.129.x.48.i; A.130.x.48.i; A.131.x.48.i; A.132.x.48.i;
A.133.x.48.i; A.134.x.48.i; A.135.x.48.i; A.136.x.48.i; A.137.x.48.i; A.138.x.48.i;
A.139.x.48.i; A.140.x.48.i; A.141.x.48.i; A.2.x.49.i; A.3.x.49.i; A.4.x.49.i; A.5.x.49.i;
A.7.x.49.i; A.9.x.49.i; A.100.x.49.i; A.101.x.49.i; A.102.x.49.i; A.103.x.49.i;
A.104.x.49.i; A.105.x.49.i; A.106.x.49.i; A.107.x.49.i; A.108.x.49.i; A.109.x.49.i;
A.110.x.49.i; A.111.x.49.i; A.112.x.49.i; A.113.x.49.i; A.114.x.49.i; A.115.x.49.i;
A.116.x.49.i; A.117.x.49.i; A.118.x.49.i; A.119.x.49.i; A.120.x.49.i; A.121.x.49.i;
A.122.x.49.i; A.123.x.49.i; A.124.x.49.i; A.125.x.49.i; A.126.x.49.i; A.127.x.49.i;
A.128.x.49.i; A.129.x.49.i; A.130.x.49.i; A.131.x.49.i; A.132.x.49.i; A.133.x.49.i;
A.134.x.49.i; A.135.x.49.i; A.136.x.49.i; A.137.x.49.i; A.138.x.49.i; A.139.x.49.i;
A.140.x.49.i; A.141.x.49.i; A.2.x.50.i; A.3.x.50.i; A.4.x.50.i; A.5.x.50.i; A.7.x.50.i;
A.9.x.50.i; A.100.x.50.i; A.101.x.50.i; A.102.x.50.i; A.103.x.50.i; A.104.x.50.i;
A.105.x.50.i; A.106.x.50.i; A.107.x.50.i; A.108.x.50.i; A.109.x.50.i; A.110.x.50.i;
A.111.x.50.i; A.112.x.50.i; A.113.x.50.i; A.114.x.50.i; A.115.x.50.i; A.116.x.50.i;
A.117.x.50.i; A.118.x.50.i; A.119.x.50.i; A.120.x.50.i; A.121.x.50.i; A.122.x.50.i;
A.123.x.50.i; A.124.x.50.i; A.125.x.50.i; A.126.x.50.i; A.127.x.50.i; A.128.x.50.i;
A.129.x.50.i; A.130.x.50.i; A.131.x.50.i; A.132.x.50.i; A.133.x.50.i; A.134.x.50.i;
A.135.x.50.i; A.136.x.50.i; A.137.x.50.i; A.138.x.50.i; A.139.x.50.i; A.140.x.50.i;
A.141.x.50.i; A.2.x.51.i; A.3.x.51.i; A.4.x.51.i; A.5.x.51.i; A.7.x.51.i; A.9.x.51.i;
A.100.x.51.i; A.101.x.51.i; A.102.x.51.i; A.103.x.51.i; A.104.x.51.i; A.105.x.51.i;
A.106.x.51.i; A.107.x.51.i; A.108.x.51.i; A.109.x.51.i; A.110.x.51.i; A.111.x.51.i;
A.112.x.51.i; A.113.x.51.i; A.114.x.51.i; A.115.x.51.i; A.116.x.51.i; A.117.x.51.i;
A.118.x.51.i; A.119.x.51.i; A.120.x.51.i; A.121.x.51.i; A.122.x.51.i; A.123.x.51.i;
A.124.x.51.i; A.125.x.51.i; A.126.x.51.i; A.127.x.51.i; A.128.x.51.i; A.129.x.51.i;
A.130.x.51.i; A.131.x.51.i; A.132.x.51.i; A.133.x.51.i; A.134.x.51.i; A.135.x.51.i;
A.136.x.51.i; A.137.x.51.i; A.138.x.51.i; A.139.x.51.i; A.140.x.51.i; A.141.x.51.i;
A.2.y.46.i; A.3.y.46.i; A.4.y.46.i; A.5.y.46.i; A.7.y.46.i; A.9.y.46.i; A.100.y.46.i;
A.101.y.46.i; A.102.y.46.i; A.103.y.46.i; A.104.y.46.i; A.105.y.46.i; A.106.y.46.i;
A.107.y.46.i; A.108.y.46.i; A.109.y.46.i; A.110.y.46.i; A.111.y.46.i; A.112.y.46.i;

TABLE 6-continued

Exemplary Enumerated Compounds

A.113.y.46.i; A.114.y.46.i; A.115.y.46.i; A.116.y.46.i; A.117.y.46.i; A.118.y.46.i;
A.119.y.46.i; A.120.y.46.i; A.121.y.46.i; A.122.y.46.i; A.123.y.46.i; A.124.y.46.i;
A.125.y.46.i; A.126.y.46.i; A.127.y.46.i; A.128.y.46.i; A.129.y.46.i; A.130.y.46.i;
A.131.y.46.i; A.132.y.46.i; A.133.y.46.i; A.134.y.46.i; A.135.y.46.i; A.136.y.46.i;
A.137.y.46.i; A.138.y.46.i; A.139.y.46.i; A.140.y.46.i; A.141.y.46.i; A.2.y.47.i;
A.3.y.47.i; A.4.y.47.i; A.5.y.47.i; A.7.y.47.i; A.9.y.47.i; A.100.y.47.i; A.101.y.47.i;
A.102.y.47.i; A.103.y.47.i; A.104.y.47.i; A.105.y.47.i; A.106.y.47.i; A.107.y.47.i;
A.108.y.47.i; A.109.y.47.i; A.110.y.47.i; A.111.y.47.i; A.112.y.47.i; A.113.y.47.i;
A.114.y.47.i; A.115.y.47.i; A.116.y.47.i; A.117.y.47.i; A.118.y.47.i; A.119.y.47.i;
A.120.y.47.i; A.121.y.47.i; A.122.y.47.i; A.123.y.47.i; A.124.y.47.i; A.125.y.47.i;
A.126.y.47.i; A.127.y.47.i; A.128.y.47.i; A.129.y.47.i; A.130.y.47.i; A.131.y.47.i;
A.132.y.47.i; A.133.y.47.i; A.134.y.47.i; A.135.y.47.i; A.136.y.47.i; A.137.y.47.i;
A.138.y.47.i; A.139.y.47.i; A.140.y.47.i; A.141.y.47.i; A.2.y.48.i; A.3.y.48.i;
A.4.y.48.i; A.5.y.48.i; A.7.y.48.i; A.9.y.48.i; A.100.y.48.i; A.101.y.48.i; A.102.y.48.i;
A.103.y.48.i; A.104.y.48.i; A.105.y.48.i; A.106.y.48.i; A.107.y.48.i; A.108.y.48.i;
A.109.y.48.i; A.110.y.48.i; A.111.y.48.i; A.112.y.48.i; A.113.y.48.i; A.114.y.48.i;
A.115.y.48.i; A.116.y.48.i; A.117.y.48.i; A.118.y.48.i; A.119.y.48.i; A.120.y.48.i;
A.121.y.48.i; A.122.y.48.i; A.123.y.48.i; A.124.y.48.i; A.125.y.48.i; A.126.y.48.i;
A.127.y.48.i; A.128.y.48.i; A.129.y.48.i; A.130.y.48.i; A.131.y.48.i; A.132.y.48.i;
A.133.y.48.i; A.134.y.48.i; A.135.y.48.i; A.136.y.48.i; A.137.y.48.i; A.138.y.48.i;
A.139.y.48.i; A.140.y.48.i; A.141.y.48.i; A.2.y.49.i; A.3.y.49.i; A.4.y.49.i; A.5.y.49.i;
A.7.y.49.i; A.9.y.49.i; A.100.y.49.i; A.101.y.49.i; A.102.y.49.i; A.103.y.49.i;
A.104.y.49.i; A.105.y.49.i; A.106.y.49.i; A.107.y.49.i; A.108.y.49.i; A.109.y.49.i;
A.110.y.49.i; A.111.y.49.i; A.112.y.49.i; A.113.y.49.i; A.114.y.49.i; A.115.y.49.i;
A.116.y.49.i; A.117.y.49.i; A.118.y.49.i; A.119.y.49.i; A.120.y.49.i; A.121.y.49.i;
A.122.y.49.i; A.123.y.49.i; A.124.y.49.i; A.125.y.49.i; A.126.y.49.i; A.127.y.49.i;
A.128.y.49.i; A.129.y.49.i; A.130.y.49.i; A.131.y.49.i; A.132.y.49.i; A.133.y.49.i;
A.134.y.49.i; A.135.y.49.i; A.136.y.49.i; A.137.y.49.i; A.138.y.49.i; A.139.y.49.i;
A.140.y.49.i; A.141.y.49.i; A.2.y.50.i; A.3.y.50.i; A.4.y.50.i; A.5.y.50.i; A.7.y.50.i;
A.9.y.50.i; A.100.y.50.i; A.101.y.50.i; A.102.y.50.i; A.103.y.50.i; A.104.y.50.i;
A.105.y.50.i; A.106.y.50.i; A.107.y.50.i; A.108.y.50.i; A.109.y.50.i; A.110.y.50.i;
A.111.y.50.i; A.112.y.50.i; A.113.y.50.i; A.114.y.50.i; A.115.y.50.i; A.116.y.50.i;
A.117.y.50.i; A.118.y.50.i; A.119.y.50.i; A.120.y.50.i; A.121.y.50.i; A.122.y.50.i;
A.123.y.50.i; A.124.y.50.i; A.125.y.50.i; A.126.y.50.i; A.127.y.50.i; A.128.y.50.i;
A.129.y.50.i; A.130.y.50.i; A.131.y.50.i; A.132.y.50.i; A.133.y.50.i; A.134.y.50.i;
A.135.y.50.i; A.136.y.50.i; A.137.y.50.i; A.138.y.50.i; A.139.y.50.i; A.140.y.50.i;
A.141.y.50.i; A.2.y.51.i; A.3.y.51.i; A.4.y.51.i; A.5.y.51.i; A.7.y.51.i; A.9.y.51.i;
A.100.y.51.i; A.101.y.51.i; A.102.y.51.i; A.103.y.51.i; A.104.y.51.i; A.105.y.51.i;
A.106.y.51.i; A.107.y.51.i; A.108.y.51.i; A.109.y.51.i; A.110.y.51.i; A.111.y.51.i;
A.112.y.51.i; A.113.y.51.i; A.114.y.51.i; A.115.y.51.i; A.116.y.51.i; A.117.y.51.i;
A.118.y.51.i; A.119.y.51.i; A.120.y.51.i; A.121.y.51.i; A.122.y.51.i; A.123.y.51.i;
A.124.y.51.i; A.125.y.51.i; A.126.y.51.i; A.127.y.51.i; A.128.y.51.i; A.129.y.51.i;
A.130.y.51.i; A.131.y.51.i; A.132.y.51.i; A.133.y.51.i; A.134.y.51.i; A.135.y.51.i;
A.136.y.51.i; A.137.y.51.i; A.138.y.51.i; A.139.y.51.i; A.140.y.51.i; A.141.y.51.i;
A.2.z.46.i; A.3.z.46.i; A.4.z.46.i; A.5.z.46.i; A.7.z.46.i; A.9.z.46.i; A.100.z.46.i;
A.101.z.46.i; A.102.z.46.i; A.103.z.46.i; A.104.z.46.i; A.105.z.46.i; A.106.z.46.i;
A.107.z.46.i; A.108.z.46.i; A.109.z.46.i; A.110.z.46.i; A.111.z.46.i; A.112.z.46.i;
A.113.z.46.i; A.114.z.46.i; A.115.z.46.i; A.116.z.46.i; A.117.z.46.i; A.118.z.46.i;
A.119.z.46.i; A.120.z.46.i; A.121.z.46.i; A.122.z.46.i; A.123.z.46.i; A.124.z.46.i;
A.125.z.46.i; A.126.z.46.i; A.127.z.46.i; A.128.z.46.i; A.129.z.46.i; A.130.z.46.i;
A.131.z.46.i; A.132.z.46.i; A.133.z.46.i; A.134.z.46.i; A.135.z.46.i; A.136.z.46.i;
A.137.z.46.i; A.138.z.46.i; A.139.z.46.i; A.140.z.46.i; A.141.z.46.i; A.2.z.47.i;
A.3.z.47.i; A.4.z.47.i; A.5.z.47.i; A.7.z.47.i; A.9.z.47.i; A.100.z.47.i; A.101.z.47.i;
A.102.z.47.i; A.103.z.47.i; A.104.z.47.i; A.105.z.47.i; A.106.z.47.i; A.107.z.47.i;
A.108.z.47.i; A.109.z.47.i; A.110.z.47.i; A.111.z.47.i; A.112.z.47.i; A.113.z.47.i;
A.114.z.47.i; A.115.z.47.i; A.116.z.47.i; A.117.z.47.i; A.118.z.47.i; A.119.z.47.i;
A.120.z.47.i; A.121.z.47.i; A.122.z.47.i; A.123.z.47.i; A.124.z.47.i; A.125.z.47.i;
A.126.z.47.i; A.127.z.47.i; A.128.z.47.i; A.129.z.47.i; A.130.z.47.i; A.131.z.47.i;
A.132.z.47.i; A.133.z.47.i; A.134.z.47.i; A.135.z.47.i; A.136.z.47.i; A.137.z.47.i;
A.138.z.47.i; A.139.z.47.i; A.140.z.47.i; A.141.z.47.i; A.2.z.48.i; A.3.z.48.i;
A.4.z.48.i; A.5.z.48.i; A.7.z.48.i; A.9.z.48.i; A.100.z.48.i; A.101.z.48.i; A.102.z.48.i;
A.103.z.48.i; A.104.z.48.i; A.105.z.48.i; A.106.z.48.i; A.107.z.48.i; A.108.z.48.i;
A.109.z.48.i; A.110.z.48.i; A.111.z.48.i; A.112.z.48.i; A.113.z.48.i; A.114.z.48.i;
A.115.z.48.i; A.116.z.48.i; A.117.z.48.i; A.118.z.48.i; A.119.z.48.i; A.120.z.48.i;
A.121.z.48.i; A.122.z.48.i; A.123.z.48.i; A.124.z.48.i; A.125.z.48.i; A.126.z.48.i;
A.127.z.48.i; A.128.z.48.i; A.129.z.48.i; A.130.z.48.i; A.131.z.48.i; A.132.z.48.i;
A.133.z.48.i; A.134.z.48.i; A.135.z.48.i; A.136.z.48.i; A.137.z.48.i; A.138.z.48.i;
A.139.z.48.i; A.140.z.48.i; A.141.z.48.i; A.2.z.49.i; A.3.z.49.i; A.4.z.49.i; A.5.z.49.i;
A.7.z.49.i; A.9.z.49.i; A.100.z.49.i; A.101.z.49.i; A.102.z.49.i; A.103.z.49.i;
A.104.z.49.i; A.105.z.49.i; A.106.z.49.i; A.107.z.49.i; A.108.z.49.i; A.109.z.49.i;
A.110.z.49.i; A.111.z.49.i; A.112.z.49.i; A.113.z.49.i; A.114.z.49.i; A.115.z.49.i;
A.116.z.49.i; A.117.z.49.i; A.118.z.49.i; A.119.z.49.i; A.120.z.49.i; A.121.z.49.i;
A.122.z.49.i; A.123.z.49.i; A.124.z.49.i; A.125.z.49.i; A.126.z.49.i; A.127.z.49.i;
A.128.z.49.i; A.129.z.49.i; A.130.z.49.i; A.131.z.49.i; A.132.z.49.i; A.133.z.49.i;
A.134.z.49.i; A.135.z.49.i; A.136.z.49.i; A.137.z.49.i; A.138.z.49.i; A.139.z.49.i;
A.140.z.49.i; A.141.z.49.i; A.2.z.50.i; A.3.z.50.i; A.4.z.50.i; A.5.z.50.i; A.7.z.50.i;
A.9.z.50.i; A.100.z.50.i; A.101.z.50.i; A.102.z.50.i; A.103.z.50.i; A.104.z.50.i;

TABLE 6-continued

Exemplary Enumerated Compounds

A.105.z.50.i; A.106.z.50.i; A.107.z.50.i; A.108.z.50.i; A.109.z.50.i; A.110.z.50.i;
A.111.z.50.i; A.112.z.50.i; A.113.z.50.i; A.114.z.50.i; A.115.z.50.i; A.116.z.50.i;
A.117.z.50.i; A.118.z.50.i; A.119.z.50.i; A.120.z.50.i; A.121.z.50.i; A.122.z.50.i;
A.123.z.50.i; A.124.z.50.i; A.125.z.50.i; A.126.z.50.i; A.127.z.50.i; A.128.z.50.i;
A.129.z.50.i; A.130.z.50.i; A.131.z.50.i; A.132.z.50.i; A.133.z.50.i; A.134.z.50.i;
A.135.z.50.i; A.136.z.50.i; A.137.z.50.i; A.138.z.50.i; A.139.z.50.i; A.140.z.50.i;
A.141.z.50.i; A.2.z.51.i; A.3.z.51.i; A.4.z.51.i; A.5.z.51.i; A.7.z.51.i; A.9.z.51.i;
A.100.z.51.i; A.101.z.51.i; A.102.z.51.i; A.103.z.51.i; A.104.z.51.i; A.105.z.51.i;
A.106.z.51.i; A.107.z.51.i; A.108.z.51.i; A.109.z.51.i; A.110.z.51.i; A.111.z.51.i;
A.112.z.51.i; A.113.z.51.i; A.114.z.51.i; A.115.z.51.i; A.116.z.51.i; A.117.z.51.i;
A.118.z.51.i; A.119.z.51.i; A.120.z.51.i; A.121.z.51.i; A.122.z.51.i; A.123.z.51.i;
A.124.z.51.i; A.125.z.51.i; A.126.z.51.i; A.127.z.51.i; A.128.z.51.i; A.129.z.51.i;
A.130.z.51.i; A.131.z.51.i; A.132.z.51.i; A.133.z.51.i; A.134.z.51.i; A.135.z.51.i;
A.136.z.51.i; A.137.z.51.i; A.138.z.51.i; A.139.z.51.i; A.140.z.51.i; A.141.z.51.i;
A.2.A.46.i; A.3.A.46.i; A.4.A.46.i; A.5.A.46.i; A.7.A.46.i; A.9.A.46.i; A.100.A.46.i;
A.101.A.46.i; A.102.A.46.i; A.103.A.46.i; A.104.A.46.i; A.105.A.46.i; A.106.A.46.i;
A.107.A.46.i; A.108.A.46.i; A.109.A.46.i; A.110.A.46.i; A.111.A.46.i; A.112.A.46.i;
A.113.A.46.i; A.114.A.46.i; A.115.A.46.i; A.116.A.46.i; A.117.A.46.i; A.118.A.46.i;
A.119.A.46.i; A.120.A.46.i; A.121.A.46.i; A.122.A.46.i; A.123.A.46.i; A.124.A.46.i;
A.125.A.46.i; A.126.A.46.i; A.127.A.46.i; A.128.A.46.i; A.129.A.46.i; A.130.A.46.i;
A.131.A.46.i; A.132.A.46.i; A.133.A.46.i; A.134.A.46.i; A.135.A.46.i; A.136.A.46.i;
A.137.A.46.i; A.138.A.46.i; A.139.A.46.i; A.140.A.46.i; A.141.A.46.i; A.2.A.47.i;
A.3.A.47.i; A.4.A.47.i; A.5.A.47.i; A.7.A.47.i; A.9.A.47.i; A.100.A.47.i;
A.101.A.47.i; A.102.A.47.i; A.103.A.47.i; A.104.A.47.i; A.105.A.47.i; A.106.A.47.i;
A.107.A.47.i; A.108.A.47.i; A.109.A.47.i; A.110.A.47.i; A.111.A.47.i; A.112.A.47.i;
A.113.A.47.i; A.114.A.47.i; A.115.A.47.i; A.116.A.47.i; A.117.A.47.i; A.118.A.47.i;
A.119.A.47.i; A.120.A.47.i; A.121.A.47.i; A.122.A.47.i; A.123.A.47.i; A.124.A.47.i;
A.125.A.47.i; A.126.A.47.i; A.127.A.47.i; A.128.A.47.i; A.129.A.47.i; A.130.A.47.i;
A.131.A.47.i; A.132.A.47.i; A.133.A.47.i; A.134.A.47.i; A.135.A.47.i; A.136.A.47.i;
A.137.A.47.i; A.138.A.47.i; A.139.A.47.i; A.140.A.47.i; A.141.A.47.i; A.2.A.48.i;
A.3.A.48.i; A.4.A.48.i; A.5.A.48.i; A.7.A.48.i; A.9.A.48.i; A.100.A.48.i;
A.101.A.48.i; A.102.A.48.i; A.103.A.48.i; A.104.A.48.i; A.105.A.48.i; A.106.A.48.i;
A.107.A.48.i; A.108.A.48.i; A.109.A.48.i; A.110.A.48.i; A.111.A.48.i; A.112.A.48.i;
A.113.A.48.i; A.114.A.48.i; A.115.A.48.i; A.116.A.48.i; A.117.A.48.i; A.118.A.48.i;
A.119.A.48.i; A.120.A.48.i; A.121.A.48.i; A.122.A.48.i; A.123.A.48.i; A.124.A.48.i;
A.125.A.48.i; A.126.A.48.i; A.127.A.48.i; A.128.A.48.i; A.129.A.48.i; A.130.A.48.i;
A.131.A.48.i; A.132.A.48.i; A.133.A.48.i; A.134.A.48.i; A.135.A.48.i; A.136.A.48.i;
A.137.A.48.i; A.138.A.48.i; A.139.A.48.i; A.140.A.48.i; A.141.A.48.i; A.2.A.49.i;
A.3.A.49.i; A.4.A.49.i; A.5.A.49.i; A.7.A.49.i; A.9.A.49.i; A.100.A.49.i;
A.101.A.49.i; A.102.A.49.i; A.103.A.49.i; A.104.A.49.i; A.105.A.49.i; A.106.A.49.i;
A.107.A.49.i; A.108.A.49.i; A.109.A.49.i; A.110.A.49.i; A.111.A.49.i; A.112.A.49.i;
A.113.A.49.i; A.114.A.49.i; A.115.A.49.i; A.116.A.49.i; A.117.A.49.i; A.118.A.49.i;
A.119.A.49.i; A.120.A.49.i; A.121.A.49.i; A.122.A.49.i; A.123.A.49.i; A.124.A.49.i;
A.125.A.49.i; A.126.A.49.i; A.127.A.49.i; A.128.A.49.i; A.129.A.49.i; A.130.A.49.i;
A.131.A.49.i; A.132.A.49.i; A.133.A.49.i; A.134.A.49.i; A.135.A.49.i; A.136.A.49.i;
A.137.A.49.i; A.138.A.49.i; A.139.A.49.i; A.140.A.49.i; A.141.A.49.i; A.2.A.50.i;
A.3.A.50.i; A.4.A.50.i; A.5.A.50.i; A.7.A.50.i; A.9.A.50.i; A.100.A.50.i;
A.101.A.50.i; A.102.A.50.i; A.103.A.50.i; A.104.A.50.i; A.105.A.50.i; A.106.A.50.i;
A.107.A.50.i; A.108.A.50.i; A.109.A.50.i; A.110.A.50.i; A.111.A.50.i; A.112.A.50.i;
A.113.A.50.i; A.114.A.50.i; A.115.A.50.i; A.116.A.50.i; A.117.A.50.i; A.118.A.50.i;
A.119.A.50.i; A.120.A.50.i; A.121.A.50.i; A.122.A.50.i; A.123.A.50.i; A.124.A.50.i;
A.125.A.50.i; A.126.A.50.i; A.127.A.50.i; A.128.A.50.i; A.129.A.50.i; A.130.A.50.i;
A.131.A.50.i; A.132.A.50.i; A.133.A.50.i; A.134.A.50.i; A.135.A.50.i; A.136.A.50.i;
A.137.A.50.i; A.138.A.50.i; A.139.A.50.i; A.140.A.50.i; A.141.A.50.i; A.2.A.51.i;
A.3.A.51.i; A.4.A.51.i; A.5.A.51.i; A.7.A.51.i; A.9.A.51.i; A.100.A.51.i;
A.101.A.51.i; A.102.A.51.i; A.103.A.51.i; A.104.A.51.i; A.105.A.51.i; A.106.A.51.i;
A.107.A.51.i; A.108.A.51.i; A.109.A.51.i; A.110.A.51.i; A.111.A.51.i; A.112.A.51.i;
A.113.A.51.i; A.114.A.51.i; A.115.A.51.i; A.116.A.51.i; A.117.A.51.i; A.118.A.51.i;
A.119.A.51.i; A.120.A.51.i; A.121.A.51.i; A.122.A.51.i; A.123.A.51.i; A.124.A.51.i;
A.125.A.51.i; A.126.A.51.i; A.127.A.51.i; A.128.A.51.i; A.129.A.51.i; A.130.A.51.i;
A.131.A.51.i; A.132.A.51.i; A.133.A.51.i; A.134.A.51.i; A.135.A.51.i; A.136.A.51.i;
A.137.A.51.i; A.138.A.51.i; A.139.A.51.i; A.140.A.51.i; A.141.A.51.i; A.2.B.46.i;
A.3.B.46.i; A.4.B.46.i; A.5.B.46.i; A.7.B.46.i; A.9.B.46.i; A.100.B.46.i; A.101.B.46.i;
A.102.B.46.i; A.103.B.46.i; A.104.B.46.i; A.105.B.46.i; A.106.B.46.i; A.107.B.46.i;
A.108.B.46.i; A.109.B.46.i; A.110.B.46.i; A.111.B.46.i; A.112.B.46.i; A.113.B.46.i;
A.114.B.46.i; A.115.B.46.i; A.116.B.46.i; A.117.B.46.i; A.118.B.46.i; A.119.B.46.i;
A.120.B.46.i; A.121.B.46.i; A.122.B.46.i; A.123.B.46.i; A.124.B.46.i; A.125.B.46.i;
A.126.B.46.i; A.127.B.46.i; A.128.B.46.i; A.129.B.46.i; A.130.B.46.i; A.131.B.46.i;
A.132.B.46.i; A.133.B.46.i; A.134.B.46.i; A.135.B.46.i; A.136.B.46.i; A.137.B.46.i;
A.138.B.46.i; A.139.B.46.i; A.140.B.46.i; A.141.B.46.i; A.2.B.47.i; A.3.B.47.i;
A.4.B.47.i; A.5.B.47.i; A.7.B.47.i; A.9.B.47.i; A.100.B.47.i; A.101.B.47.i;
A.102.B.47.i; A.103.B.47.i; A.104.B.47.i; A.105.B.47.i; A.106.B.47.i; A.107.B.47.i;
A.108.B.47.i; A.109.B.47.i; A.110.B.47.i; A.111.B.47.i; A.112.B.47.i; A.113.B.47.i;
A.114.B.47.i; A.115.B.47.i; A.116.B.47.i; A.117.B.47.i; A.118.B.47.i; A.119.B.47.i;
A.120.B.47.i; A.121.B.47.i; A.122.B.47.i; A.123.B.47.i; A.124.B.47.i; A.125.B.47.i;
A.126.B.47.i; A.127.B.47.i; A.128.B.47.i; A.129.B.47.i; A.130.B.47.i; A.131.B.47.i;
A.132.B.47.i; A.133.B.47.i; A.134.B.47.i; A.135.B.47.i; A.136.B.47.i; A.137.B.47.i;

TABLE 6-continued

Exemplary Enumerated Compounds

A.138.B.47.i; A.139.B.47.i; A.140.B.47.i; A.141.B.47.i; A.2.B.48.i; A.3.B.48.i;
A.4.B.48.i; A.5.B.48.i; A.7.B.48.i; A.9.B.48.i; A.100.B.48.i; A.101.B.48.i;
A.102.B.48.i; A.103.B.48.i; A.104.B.48.i; A.105.B.48.i; A.106.B.48.i; A.107.B.48.i;
A.108.B.48.i; A.109.B.48.i; A.110.B.48.i; A.111.B.48.i; A.112.B.48.i; A.113.B.48.i;
A.114.B.48.i; A.115.B.48.i; A.116.B.48.i; A.117.B.48.i; A.118.B.48.i; A.119.B.48.i;
A.120.B.48.i; A.121.B.48.i; A.122.B.48.i; A.123.B.48.i; A.124.B.48.i; A.125.B.48.i;
A.126.B.48.i; A.127.B.48.i; A.128.B.48.i; A.129.B.48.i; A.130.B.48.i; A.131.B.48.i;
A.132.B.48.i; A.133.B.48.i; A.134.B.48.i; A.135.B.48.i; A.136.B.48.i; A.137.B.48.i;
A.138.B.48.i; A.139.B.48.i; A.140.B.48.i; A.141.B.48.i; A.2.B.49.i; A.3.B.49.i;
A.4.B.49.i; A.5.B.49.i; A.7.B.49.i; A.9.B.49.i; A.100.B.49.i; A.101.B.49.i;
A.102.B.49.i; A.103.B.49.i; A.104.B.49.i; A.105.B.49.i; A.106.B.49.i; A.107.B.49.i;
A.108.B.49.i; A.109.B.49.i; A.110.B.49.i; A.111.B.49.i; A.112.B.49.i; A.113.B.49.i;
A.114.B.49.i; A.115.B.49.i; A.116.B.49.i; A.117.B.49.i; A.118.B.49.i; A.119.B.49.i;
A.120.B.49.i; A.121.B.49.i; A.122.B.49.i; A.123.B.49.i; A.124.B.49.i; A.125.B.49.i;
A.126.B.49.i; A.127.B.49.i; A.128.B.49.i; A.129.B.49.i; A.130.B.49.i; A.131.B.49.i;
A.132.B.49.i; A.133.B.49.i; A.134.B.49.i; A.135.B.49.i; A.136.B.49.i; A.137.B.49.i;
A.138.B.49.i; A.139.B.49.i; A.140.B.49.i; A.141.B.49.i; A.2.B.50.i; A.3.B.50.i;
A.4.B.50.i; A.5.B.50.i; A.7.B.50.i; A.9.B.50.i; A.100.B.50.i; A.101.B.50.i;
A.102.B.50.i; A.103.B.50.i; A.104.B.50.i; A.105.B.50.i; A.106.B.50.i; A.107.B.50.i;
A.108.B.50.i; A.109.B.50.i; A.110.B.50.i; A.111.B.50.i; A.112.B.50.i; A.113.B.50.i;
A.114.B.50.i; A.115.B.50.i; A.116.B.50.i; A.117.B.50.i; A.118.B.50.i; A.119.B.50.i;
A.120.B.50.i; A.121.B.50.i; A.122.B.50.i; A.123.B.50.i; A.124.B.50.i; A.125.B.50.i;
A.126.B.50.i; A.127.B.50.i; A.128.B.50.i; A.129.B.50.i; A.130.B.50.i; A.131.B.50.i;
A.132.B.50.i; A.133.B.50.i; A.134.B.50.i; A.135.B.50.i; A.136.B.50.i; A.137.B.50.i;
A.138.B.50.i; A.139.B.50.i; A.140.B.50.i; A.141.B.50.i; A.2.B.51.i; A.3.B.51.i;
A.4.B.51.i; A.5.B.51.i; A.7.B.51.i; A.9.B.51.i; A.100.B.51.i; A.101.B.51.i;
A.102.B.51.i; A.103.B.51.i; A.104.B.51.i; A.105.B.51.i; A.106.B.51.i; A.107.B.51.i;
A.108.B.51.i; A.109.B.51.i; A.110.B.51.i; A.111.B.51.i; A.112.B.51.i; A.113.B.51.i;
A.114.B.51.i; A.115.B.51.i; A.116.B.51.i; A.117.B.51.i; A.118.B.51.i; A.119.B.51.i;
A.120.B.51.i; A.121.B.51.i; A.122.B.51.i; A.123.B.51.i; A.124.B.51.i; A.125.B.51.i;
A.126.B.51.i; A.127.B.51.i; A.128.B.51.i; A.129.B.51.i; A.130.B.51.i; A.131.B.51.i;
A.132.B.51.i; A.133.B.51.i; A.134.B.51.i; A.135.B.51.i; A.136.B.51.i; A.137.B.51.i;
A.138.B.51.i; A.139.B.51.i; A.140.B.51.i; A.141.B.51.i; A.2.C.46.i; A.3.C.46.i;
A.4.C.46.i; A.5.C.46.i; A.7.C.46.i; A.9.C.46.i; A.100.C.46.i; A.101.C.46.i;
A.102.C.46.i; A.103.C.46.i; A.104.C.46.i; A.105.C.46.i; A.106.C.46.i; A.107.C.46.i;
A.108.C.46.i; A.109.C.46.i; A.110.C.46.i; A.111.C.46.i; A.112.C.46.i; A.113.C.46.i;
A.114.C.46.i; A.115.C.46.i; A.116.C.46.i; A.117.C.46.i; A.118.C.46.i; A.119.C.46.i;
A.120.C.46.i; A.121.C.46.i; A.122.C.46.i; A.123.C.46.i; A.124.C.46.i; A.125.C.46.i;
A.126.C.46.i; A.127.C.46.i; A.128.C.46.i; A.129.C.46.i; A.130.C.46.i; A.131.C.46.i;
A.132.C.46.i; A.133.C.46.i; A.134.C.46.i; A.135.C.46.i; A.136.C.46.i; A.137.C.46.i;
A.138.C.46.i; A.139.C.46.i; A.140.C.46.i; A.141.C.46.i; A.2.C.47.i; A.3.C.47.i;
A.4.C.47.i; A.5.C.47.i; A.7.C.47.i; A.9.C.47.i; A.100.C.47.i; A.101.C.47.i;
A.102.C.47.i; A.103.C.47.i; A.104.C.47.i; A.105.C.47.i; A.106.C.47.i; A.107.C.47.i;
A.108.C.47.i; A.109.C.47.i; A.110.C.47.i; A.111.C.47.i; A.112.C.47.i; A.113.C.47.i;
A.114.C.47.i; A.115.C.47.i; A.116.C.47.i; A.117.C.47.i; A.118.C.47.i; A.119.C.47.i;
A.120.C.47.i; A.121.C.47.i; A.122.C.47.i; A.123.C.47.i; A.124.C.47.i; A.125.C.47.i;
A.126.C.47.i; A.127.C.47.i; A.128.C.47.i; A.129.C.47.i; A.130.C.47.i; A.131.C.47.i;
A.132.C.47.i; A.133.C.47.i; A.134.C.47.i; A.135.C.47.i; A.136.C.47.i; A.137.C.47.i;
A.138.C.47.i; A.139.C.47.i; A.140.C.47.i; A.141.C.47.i; A.2.C.48.i; A.3.C.48.i;
A.4.C.48.i; A.5.C.48.i; A.7.C.48.i; A.9.C.48.i; A.100.C.48.i; A.101.C.48.i;
A.102.C.48.i; A.103.C.48.i; A.104.C.48.i; A.105.C.48.i; A.106.C.48.i; A.107.C.48.i;
A.108.C.48.i; A.109.C.48.i; A.110.C.48.i; A.111.C.48.i; A.112.C.48.i; A.113.C.48.i;
A.114.C.48.i; A.115.C.48.i; A.116.C.48.i; A.117.C.48.i; A.118.C.48.i; A.119.C.48.i;
A.120.C.48.i; A.121.C.48.i; A.122.C.48.i; A.123.C.48.i; A.124.C.48.i; A.125.C.48.i;
A.126.C.48.i; A.127.C.48.i; A.128.C.48.i; A.129.C.48.i; A.130.C.48.i; A.131.C.48.i;
A.132.C.48.i; A.133.C.48.i; A.134.C.48.i; A.135.C.48.i; A.136.C.48.i; A.137.C.48.i;
A.138.C.48.i; A.139.C.48.i; A.140.C.48.i; A.141.C.48.i; A.2.C.49.i; A.3.C.49.i;
A.4.C.49.i; A.5.C.49.i; A.7.C.49.i; A.9.C.49.i; A.100.C.49.i; A.101.C.49.i;
A.102.C.49.i; A.103.C.49.i; A.104.C.49.i; A.105.C.49.i; A.106.C.49.i; A.107.C.49.i;
A.108.C.49.i; A.109.C.49.i; A.110.C.49.i; A.111.C.49.i; A.112.C.49.i; A.113.C.49.i;
A.114.C.49.i; A.115.C.49.i; A.116.C.49.i; A.117.C.49.i; A.118.C.49.i; A.119.C.49.i;
A.120.C.49.i; A.121.C.49.i; A.122.C.49.i; A.123.C.49.i; A.124.C.49.i; A.125.C.49.i;
A.126.C.49.i; A.127.C.49.i; A.128.C.49.i; A.129.C.49.i; A.130.C.49.i; A.131.C.49.i;
A.132.C.49.i; A.133.C.49.i; A.134.C.49.i; A.135.C.49.i; A.136.C.49.i; A.137.C.49.i;
A.138.C.49.i; A.139.C.49.i; A.140.C.49.i; A.141.C.49.i; A.2.C.50.i; A.3.C.50.i;
A.4.C.50.i; A.5.C.50.i; A.7.C.50.i; A.9.C.50.i; A.100.C.50.i; A.101.C.50.i;
A.102.C.50.i; A.103.C.50.i; A.104.C.50.i; A.105.C.50.i; A.106.C.50.i; A.107.C.50.i;
A.108.C.50.i; A.109.C.50.i; A.110.C.50.i; A.111.C.50.i; A.112.C.50.i; A.113.C.50.i;
A.114.C.50.i; A.115.C.50.i; A.116.C.50.i; A.117.C.50.i; A.118.C.50.i; A.119.C.50.i;
A.120.C.50.i; A.121.C.50.i; A.122.C.50.i; A.123.C.50.i; A.124.C.50.i; A.125.C.50.i;
A.126.C.50.i; A.127.C.50.i; A.128.C.50.i; A.129.C.50.i; A.130.C.50.i; A.131.C.50.i;
A.132.C.50.i; A.133.C.50.i; A.134.C.50.i; A.135.C.50.i; A.136.C.50.i; A.137.C.50.i;
A.138.C.50.i; A.139.C.50.i; A.140.C.50.i; A.141.C.50.i; A.2.C.51.i; A.3.C.51.i;
A.4.C.51.i; A.5.C.51.i; A.7.C.51.i; A.9.C.51.i; A.100.C.51.i; A.101.C.51.i;
A.102.C.51.i; A.103.C.51.i; A.104.C.51.i; A.105.C.51.i; A.106.C.51.i; A.107.C.51.i;
A.108.C.51.i; A.109.C.51.i; A.110.C.51.i; A.111.C.51.i; A.112.C.51.i; A.113.C.51.i;
A.114.C.51.i; A.115.C.51.i; A.116.C.51.i; A.117.C.51.i; A.118.C.51.i; A.119.C.51.i;

TABLE 6-continued

Exemplary Enumerated Compounds

A.120.C.51.i; A.121.C.51.i; A.122.C.51.i; A.123.C.51.i; A.124.C.51.i; A.125.C.51.i;
A.126.C.51.i; A.127.C.51.i; A.128.C.51.i; A.129.C.51.i; A.130.C.51.i; A.131.C.51.i;
A.132.C.51.i; A.133.C.51.i; A.134.C.51.i; A.135.C.51.i; A.136.C.51.i; A.137.C.51.i;
A.138.C.51.i; A.139.C.51.i; A.140.C.51.i; A.141.C.51.i; A.2.D.46.i; A.3.D.46.i;
A.4.D.46.i; A.5.D.46.i; A.7.D.46.i; A.9.D.46.i; A.100.D.46.i; A.101.D.46.i;
A.102.D.46.i; A.103.D.46.i; A.104.D.46.i; A.105.D.46.i; A.106.D.46.i; A.107.D.46.i;
A.108.D.46.i; A.109.D.46.i; A.110.D.46.i; A.111.D.46.i; A.112.D.46.i; A.113.D.46.i;
A.114.D.46.i; A.115.D.46.i; A.116.D.46.i; A.117.D.46.i; A.118.D.46.i; A.119.D.46.i;
A.120.D.46.i; A.121.D.46.i; A.122.D.46.i; A.123.D.46.i; A.124.D.46.i; A.125.D.46.i;
A.126.D.46.i; A.127.D.46.i; A.128.D.46.i; A.129.D.46.i; A.130.D.46.i; A.131.D.46.i;
A.132.D.46.i; A.133.D.46.i; A.134.D.46.i; A.135.D.46.i; A.136.D.46.i; A.137.D.46.i;
A.138.D.46.i; A.139.D.46.i; A.140.D.46.i; A.141.D.46.i; A.2.D.47.i; A.3.D.47.i;
A.4.D.47.i; A.5.D.47.i; A.7.D.47.i; A.9.D.47.i; A.100.D.47.i; A.101.D.47.i;
A.102.D.47.i; A.103.D.47.i; A.104.D.47.i; A.105.D.47.i; A.106.D.47.i; A.107.D.47.i;
A.108.D.47.i; A.109.D.47.i; A.110.D.47.i; A.111.D.47.i; A.112.D.47.i; A.113.D.47.i;
A.114.D.47.i; A.115.D.47.i; A.116.D.47.i; A.117.D.47.i; A.118.D.47.i; A.119.D.47.i;
A.120.D.47.i; A.121.D.47.i; A.122.D.47.i; A.123.D.47.i; A.124.D.47.i; A.125.D.47.i;
A.126.D.47.i; A.127.D.47.i; A.128.D.47.i; A.129.D.47.i; A.130.D.47.i; A.131.D.47.i;
A.132.D.47.i; A.133.D.47.i; A.134.D.47.i; A.135.D.47.i; A.136.D.47.i; A.137.D.47.i;
A.138.D.47.i; A.139.D.47.i; A.140.D.47.i; A.141.D.47.i; A.2.D.48.i; A.3.D.48.i;
A.4.D.48.i; A.5.D.48.i; A.7.D.48.i; A.9.D.48.i; A.100.D.48.i; A.101.D.48.i;
A.102.D.48.i; A.103.D.48.i; A.104.D.48.i; A.105.D.48.i; A.106.D.48.i; A.107.D.48.i;
A.108.D.48.i; A.109.D.48.i; A.110.D.48.i; A.111.D.48.i; A.112.D.48.i; A.113.D.48.i;
A.114.D.48.i; A.115.D.48.i; A.116.D.48.i; A.117.D.48.i; A.118.D.48.i; A.119.D.48.i;
A.120.D.48.i; A.121.D.48.i; A.122.D.48.i; A.123.D.48.i; A.124.D.48.i; A.125.D.48.i;
A.126.D.48.i; A.127.D.48.i; A.128.D.48.i; A.129.D.48.i; A.130.D.48.i; A.131.D.48.i;
A.132.D.48.i; A.133.D.48.i; A.134.D.48.i; A.135.D.48.i; A.136.D.48.i; A.137.D.48.i;
A.138.D.48.i; A.139.D.48.i; A.140.D.48.i; A.141.D.48.i; A.2.D.49.i; A.3.D.49.i;
A.4.D.49.i; A.5.D.49.i; A.7.D.49.i; A.9.D.49.i; A.100.D.49.i; A.101.D.49.i;
A.102.D.49.i; A.103.D.49.i; A.104.D.49.i; A.105.D.49.i; A.106.D.49.i; A.107.D.49.i;
A.108.D.49.i; A.109.D.49.i; A.110.D.49.i; A.111.D.49.i; A.112.D.49.i; A.113.D.49.i;
A.114.D.49.i; A.115.D.49.i; A.116.D.49.i; A.117.D.49.i; A.118.D.49.i; A.119.D.49.i;
A.120.D.49.i; A.121.D.49.i; A.122.D.49.i; A.123.D.49.i; A.124.D.49.i; A.125.D.49.i;
A.126.D.49.i; A.127.D.49.i; A.128.D.49.i; A.129.D.49.i; A.130.D.49.i; A.131.D.49.i;
A.132.D.49.i; A.133.D.49.i; A.134.D.49.i; A.135.D.49.i; A.136.D.49.i; A.137.D.49.i;
A.138.D.49.i; A.139.D.49.i; A.140.D.49.i; A.141.D.49.i; A.2.D.50.i; A.3.D.50.i;
A.4.D.50.i; A.5.D.50.i; A.7.D.50.i; A.9.D.50.i; A.100.D.50.i; A.101.D.50.i;
A.102.D.50.i; A.103.D.50.i; A.104.D.50.i; A.105.D.50.i; A.106.D.50.i; A.107.D.50.i;
A.108.D.50.i; A.109.D.50.i; A.110.D.50.i; A.111.D.50.i; A.112.D.50.i; A.113.D.50.i;
A.114.D.50.i; A.115.D.50.i; A.116.D.50.i; A.117.D.50.i; A.118.D.50.i; A.119.D.50.i;
A.120.D.50.i; A.121.D.50.i; A.122.D.50.i; A.123.D.50.i; A.124.D.50.i; A.125.D.50.i;
A.126.D.50.i; A.127.D.50.i; A.128.D.50.i; A.129.D.50.i; A.130.D.50.i; A.131.D.50.i;
A.132.D.50.i; A.133.D.50.i; A.134.D.50.i; A.135.D.50.i; A.136.D.50.i; A.137.D.50.i;
A.138.D.50.i; A.139.D.50.i; A.140.D.50.i; A.141.D.50.i; A.2.D.51.i; A.3.D.51.i;
A.4.D.51.i; A.5.D.51.i; A.7.D.51.i; A.9.D.51.i; A.100.D.51.i; A.101.D.51.i;
A.102.D.51.i; A.103.D.51.i; A.104.D.51.i; A.105.D.51.i; A.106.D.51.i; A.107.D.51.i;
A.108.D.51.i; A.109.D.51.i; A.110.D.51.i; A.111.D.51.i; A.112.D.51.i; A.113.D.51.i;
A.114.D.51.i; A.115.D.51.i; A.116.D.51.i; A.117.D.51.i; A.118.D.51.i; A.119.D.51.i;
A.120.D.51.i; A.121.D.51.i; A.122.D.51.i; A.123.D.51.i; A.124.D.51.i; A.125.D.51.i;
A.126.D.51.i; A.127.D.51.i; A.128.D.51.i; A.129.D.51.i; A.130.D.51.i; A.131.D.51.i;
A.132.D.51.i; A.133.D.51.i; A.134.D.51.i; A.135.D.51.i; A.136.D.51.i; A.137.D.51.i;
A.138.D.51.i; A.139.D.51.i; A.140.D.51.i; A.141.D.51.i; A.2.E.46.i; A.3.E.46.i;
A.4.E.46.i; A.5.E.46.i; A.7.E.46.i; A.9.E.46.i; A.100.E.46.i; A.101.E.46.i; A.102.E.46.i;
A.103.E.46.i; A.104.E.46.i; A.105.E.46.i; A.106.E.46.i; A.107.E.46.i; A.108.E.46.i;
A.109.E.46.i; A.110.E.46.i; A.111.E.46.i; A.112.E.46.i; A.113.E.46.i; A.114.E.46.i;
A.115.E.46.i; A.116.E.46.i; A.117.E.46.i; A.118.E.46.i; A.119.E.46.i; A.120.E.46.i;
A.121.E.46.i; A.122.E.46.i; A.123.E.46.i; A.124.E.46.i; A.125.E.46.i; A.126.E.46.i;
A.127.E.46.i; A.128.E.46.i; A.129.E.46.i; A.130.E.46.i; A.131.E.46.i; A.132.E.46.i;
A.133.E.46.i; A.134.E.46.i; A.135.E.46.i; A.136.E.46.i; A.137.E.46.i; A.138.E.46.i;
A.139.E.46.i; A.140.E.46.i; A.141.E.46.i; A.2.E.47.i; A.3.E.47.i; A.4.E.47.i; A.5.E.47.i;
A.7.E.47.i; A.9.E.47.i; A.100.E.47.i; A.101.E.47.i; A.102.E.47.i; A.103.E.47.i;
A.104.E.47.i; A.105.E.47.i; A.106.E.47.i; A.107.E.47.i; A.108.E.47.i; A.109.E.47.i;
A.110.E.47.i; A.111.E.47.i; A.112.E.47.i; A.113.E.47.i; A.114.E.47.i; A.115.E.47.i;
A.116.E.47.i; A.117.E.47.i; A.118.E.47.i; A.119.E.47.i; A.120.E.47.i; A.121.E.47.i;
A.122.E.47.i; A.123.E.47.i; A.124.E.47.i; A.125.E.47.i; A.126.E.47.i; A.127.E.47.i;
A.128.E.47.i; A.129.E.47.i; A.130.E.47.i; A.131.E.47.i; A.132.E.47.i; A.133.E.47.i;
A.134.E.47.i; A.135.E.47.i; A.136.E.47.i; A.137.E.47.i; A.138.E.47.i; A.139.E.47.i;
A.140.E.47.i; A.141.E.47.i; A.2.E.48.i; A.3.E.48.i; A.4.E.48.i; A.5.E.48.i; A.7.E.48.i;
A.9.E.48.i; A.100.E.48.i; A.101.E.48.i; A.102.E.48.i; A.103.E.48.i; A.104.E.48.i;
A.105.E.48.i; A.106.E.48.i; A.107.E.48.i; A.108.E.48.i; A.109.E.48.i; A.110.E.48.i;
A.111.E.48.i; A.112.E.48.i; A.113.E.48.i; A.114.E.48.i; A.115.E.48.i; A.116.E.48.i;
A.117.E.48.i; A.118.E.48.i; A.119.E.48.i; A.120.E.48.i; A.121.E.48.i; A.122.E.48.i;
A.123.E.48.i; A.124.E.48.i; A.125.E.48.i; A.126.E.48.i; A.127.E.48.i; A.128.E.48.i;
A.129.E.48.i; A.130.E.48.i; A.131.E.48.i; A.132.E.48.i; A.133.E.48.i; A.134.E.48.i;
A.135.E.48.i; A.136.E.48.i; A.137.E.48.i; A.138.E.48.i; A.139.E.48.i; A.140.E.48.i;
A.141.E.48.i; A.2.E.49.i; A.3.E.49.i; A.4.E.49.i; A.5.E.49.i; A.7.E.49.i; A.9.E.49.i;
A.100.E.49.i; A.101.E.49.i; A.102.E.49.i; A.103.E.49.i; A.104.E.49.i; A.105.E.49.i;

TABLE 6-continued

Exemplary Enumerated Compounds

A.106.E.49.i; A.107.E.49.i; A.108.E.49.i; A.109.E.49.i; A.110.E.49.i; A.111.E.49.i;
A.112.E.49.i; A.113.E.49.i; A.114.E.49.i; A.115.E.49.i; A.116.E.49.i; A.117.E.49.i;
A.118.E.49.i; A.119.E.49.i; A.120.E.49.i; A.121.E.49.i; A.122.E.49.i; A.123.E.49.i;
A.124.E.49.i; A.125.E.49.i; A.126.E.49.i; A.127.E.49.i; A.128.E.49.i; A.129.E.49.i;
A.130.E.49.i; A.131.E.49.i; A.132.E.49.i; A.133.E.49.i; A.134.E.49.i; A.135.E.49.i;
A.136.E.49.i; A.137.E.49.i; A.138.E.49.i; A.139.E.49.i; A.140.E.49.i; A.141.E.49.i;
A.2.E.50.i; A.3.E.50.i; A.4.E.50.i; A.5.E.50.i; A.7.E.50.i; A.9.E.50.i; A.100.E.50.i;
A.101.E.50.i; A.102.E.50.i; A.103.E.50.i; A.104.E.50.i; A.105.E.50.i; A.106.E.50.i;
A.107.E.50.i; A.108.E.50.i; A.109.E.50.i; A.110.E.50.i; A.111.E.50.i; A.112.E.50.i;
A.113.E.50.i; A.114.E.50.i; A.115.E.50.i; A.116.E.50.i; A.117.E.50.i; A.118.E.50.i;
A.119.E.50.i; A.120.E.50.i; A.121.E.50.i; A.122.E.50.i; A.123.E.50.i; A.124.E.50.i;
A.125.E.50.i; A.126.E.50.i; A.127.E.50.i; A.128.E.50.i; A.129.E.50.i; A.130.E.50.i;
A.131.E.50.i; A.132.E.50.i; A.133.E.50.i; A.134.E.50.i; A.135.E.50.i; A.136.E.50.i;
A.137.E.50.i; A.138.E.50.i; A.139.E.50.i; A.140.E.50.i; A.141.E.50.i; A.2.E.51.i;
A.3.E.51.i; A.4.E.51.i; A.5.E.51.i; A.7.E.51.i; A.9.E.51.i; A.100.E.51.i; A.101.E.51.i;
A.102.E.51.i; A.103.E.51.i; A.104.E.51.i; A.105.E.51.i; A.106.E.51.i; A.107.E.51.i;
A.108.E.51.i; A.109.E.51.i; A.110.E.51.i; A.111.E.51.i; A.112.E.51.i; A.113.E.51.i;
A.114.E.51.i; A.115.E.51.i; A.116.E.51.i; A.117.E.51.i; A.118.E.51.i; A.119.E.51.i;
A.120.E.51.i; A.121.E.51.i; A.122.E.51.i; A.123.E.51.i; A.124.E.51.i; A.125.E.51.i;
A.126.E.51.i; A.127.E.51.i; A.128.E.51.i; A.129.E.51.i; A.130.E.51.i; A.131.E.51.i;
A.132.E.51.i; A.133.E.51.i; A.134.E.51.i; A.135.E.51.i; A.136.E.51.i; A.137.E.51.i;
A.138.E.51.i; A.139.E.51.i; A.140.E.51.i; A.141.E.51.i; A.2.F.46.i; A.3.F.46.i;
A.4.F.46.i; A.5.F.46.i; A.7.F.46.i; A.9.F.46.i; A.100.F.46.i; A.101.F.46.i; A.102.F.46.i;
A.103.F.46.i; A.104.F.46.i; A.105.F.46.i; A.106.F.46.i; A.107.F.46.i; A.108.F.46.i;
A.109.F.46.i; A.110.F.46.i; A.111.F.46.i; A.112.F.46.i; A.113.F.46.i; A.114.F.46.i;
A.115.F.46.i; A.116.F.46.i; A.117.F.46.i; A.118.F.46.i; A.119.F.46.i; A.120.F.46.i;
A.121.F.46.i; A.122.F.46.i; A.123.F.46.i; A.124.F.46.i; A.125.F.46.i; A.126.F.46.i;
A.127.F.46.i; A.128.F.46.i; A.129.F.46.i; A.130.F.46.i; A.131.F.46.i; A.132.F.46.i;
A.133.F.46.i; A.134.F.46.i; A.135.F.46.i; A.136.F.46.i; A.137.F.46.i; A.138.F.46.i;
A.139.F.46.i; A.140.F.46.i; A.141.F.46.i; A.2.F.47.i; A.3.F.47.i; A.4.F.47.i; A.5.F.47.i;
A.7.F.47.i; A.9.F.47.i; A.100.F.47.i; A.101.F.47.i; A.102.F.47.i; A.103.F.47.i;
A.104.F.47.i; A.105.F.47.i; A.106.F.47.i; A.107.F.47.i; A.108.F.47.i; A.109.F.47.i;
A.110.F.47.i; A.111.F.47.i; A.112.F.47.i; A.113.F.47.i; A.114.F.47.i; A.115.F.47.i;
A.116.F.47.i; A.117.F.47.i; A.118.F.47.i; A.119.F.47.i; A.120.F.47.i; A.121.F.47.i;
A.122.F.47.i; A.123.F.47.i; A.124.F.47.i; A.125.F.47.i; A.126.F.47.i; A.127.F.47.i;
A.128.F.47.i; A.129.F.47.i; A.130.F.47.i; A.131.F.47.i; A.132.F.47.i; A.133.F.47.i;
A.134.F.47.i; A.135.F.47.i; A.136.F.47.i; A.137.F.47.i; A.138.F.47.i; A.139.F.47.i;
A.140.F.47.i; A.141.F.47.i; A.2.F.48.i; A.3.F.48.i; A.4.F.48.i; A.5.F.48.i; A.7.F.48.i;
A.9.F.48.i; A.100.F.48.i; A.101.F.48.i; A.102.F.48.i; A.103.F.48.i; A.104.F.48.i;
A.105.F.48.i; A.106.F.48.i; A.107.F.48.i; A.108.F.48.i; A.109.F.48.i; A.110.F.48.i;
A.111.F.48.i; A.112.F.48.i; A.113.F.48.i; A.114.F.48.i; A.115.F.48.i; A.116.F.48.i;
A.117.F.48.i; A.118.F.48.i; A.119.F.48.i; A.120.F.48.i; A.121.F.48.i; A.122.F.48.i;
A.123.F.48.i; A.124.F.48.i; A.125.F.48.i; A.126.F.48.i; A.127.F.48.i; A.128.F.48.i;
A.129.F.48.i; A.130.F.48.i; A.131.F.48.i; A.132.F.48.i; A.133.F.48.i; A.134.F.48.i;
A.135.F.48.i; A.136.F.48.i; A.137.F.48.i; A.138.F.48.i; A.139.F.48.i; A.140.F.48.i;
A.141.F.48.i; A.2.F.49.i; A.3.F.49.i; A.4.F.49.i; A.5.F.49.i; A.7.F.49.i; A.9.F.49.i;
A.100.F.49.i; A.101.F.49.i; A.102.F.49.i; A.103.F.49.i; A.104.F.49.i; A.105.F.49.i;
A.106.F.49.i; A.107.F.49.i; A.108.F.49.i; A.109.F.49.i; A.110.F.49.i; A.111.F.49.i;
A.112.F.49.i; A.113.F.49.i; A.114.F.49.i; A.115.F.49.i; A.116.F.49.i; A.117.F.49.i;
A.118.F.49.i; A.119.F.49.i; A.120.F.49.i; A.121.F.49.i; A.122.F.49.i; A.123.F.49.i;
A.124.F.49.i; A.125.F.49.i; A.126.F.49.i; A.127.F.49.i; A.128.F.49.i; A.129.F.49.i;
A.130.F.49.i; A.131.F.49.i; A.132.F.49.i; A.133.F.49.i; A.134.F.49.i; A.135.F.49.i;
A.136.F.49.i; A.137.F.49.i; A.138.F.49.i; A.139.F.49.i; A.140.F.49.i; A.141.F.49.i;
A.2.F.50.i; A.3.F.50.i; A.4.F.50.i; A.5.F.50.i; A.7.F.50.i; A.9.F.50.i; A.100.F.50.i;
A.101.F.50.i; A.102.F.50.i; A.103.F.50.i; A.104.F.50.i; A.105.F.50.i; A.106.F.50.i;
A.107.F.50.i; A.108.F.50.i; A.109.F.50.i; A.110.F.50.i; A.111.F.50.i; A.112.F.50.i;
A.113.F.50.i; A.114.F.50.i; A.115.F.50.i; A.116.F.50.i; A.117.F.50.i; A.118.F.50.i;
A.119.F.50.i; A.120.F.50.i; A.121.F.50.i; A.122.F.50.i; A.123.F.50.i; A.124.F.50.i;
A.125.F.50.i; A.126.F.50.i; A.127.F.50.i; A.128.F.50.i; A.129.F.50.i; A.130.F.50.i;
A.131.F.50.i; A.132.F.50.i; A.133.F.50.i; A.134.F.50.i; A.135.F.50.i; A.136.F.50.i;
A.137.F.50.i; A.138.F.50.i; A.139.F.50.i; A.140.F.50.i; A.141.F.50.i; A.2.F.51.i;
A.3.F.51.i; A.4.F.51.i; A.5.F.51.i; A.7.F.51.i; A.9.F.51.i; A.100.F.51.i; A.101.F.51.i;
A.102.F.51.i; A.103.F.51.i; A.104.F.51.i; A.105.F.51.i; A.106.F.51.i; A.107.F.51.i;
A.108.F.51.i; A.109.F.51.i; A.110.F.51.i; A.111.F.51.i; A.112.F.51.i; A.113.F.51.i;
A.114.F.51.i; A.115.F.51.i; A.116.F.51.i; A.117.F.51.i; A.118.F.51.i; A.119.F.51.i;
A.120.F.51.i; A.121.F.51.i; A.122.F.51.i; A.123.F.51.i; A.124.F.51.i; A.125.F.51.i;
A.126.F.51.i; A.127.F.51.i; A.128.F.51.i; A.129.F.51.i; A.130.F.51.i; A.131.F.51.i;
A.132.F.51.i; A.133.F.51.i; A.134.F.51.i; A.135.F.51.i; A.136.F.51.i; A.137.F.51.i;
A.138.F.51.i; A.139.F.51.i; A.140.F.51.i; A.141.F.51.i;

Salts and Hydrates

The compositions of this invention optionally comprise salts of the compounds herein, especially pharmaceutically acceptable non-toxic salts containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety, typically the $W_1$ group carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, or organic sulfonic acids, to basic centers, typically amines of group $G_1$, or to acidic groups such as $E_1$. Finally, it is to be understood that the compositions herein comprise compounds of the invention in their un-ionized, as well as zwitterionic form, and combinations with stoiochimetric amounts of water as in hydrates.

Also included within the scope of this invention are the salts of the parental compounds with one or more amino acids. Any of the amino acids described above are suitable, especially the naturally-occuring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Neuraminidase

Another aspect of the invention relates to methods of inhibiting the activity of neuraminidase comprising the step of treating a sample suspected of containing neuraminidase with a compound of the invention.

Compositions of the invention act as inhibitors of neuraminidase, as intermediates for such inhibitors or have other utilities as described below. The inhibitors will bind to locations on the surface or in a cavity of neuraminidase having a geometry unique to neuraminidase. Compositions binding neuraminidase may bind with varying degrees of reversibility. Those compounds binding substantially irreversibly are ideal candidates for use in this method of the invention. Once labeled, the substantially irreversibly binding compositions are useful as probes for the detection of neuraminidase. Accordingly, the invention relates to methods of detecting neuraminidase in a sample suspected of containing neuraminidase comprising the steps of: treating a sample suspected of containing neuraminidase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces neuraminidase, frequently a pathogenic organism such as a virus. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of neuraminidase after application of the composition can be observed by any method including direct and indirect methods of detecting neuraminidase activity. Quantitative, qualitative, and semiquantitative methods of determining neuraminidase activity are all contemplated. Typically one of the screening methods described above are applied, however, any other method such as observation of the physiological properties of a living organism are also applicable.

Organisms that contain neuraminidase include bacteria (*Vibrio cholerae, Clostridium perfringens, Streptococcus pneumoniae,* and *Arthrobacter sialophilus*) and viruses (especially orthomyxoviruses or paramyxoviruses such as influenza virus A and B, parainfluenza virus, mumps virus, Newcastle disease virus, fowl plague virus, and sendai virus). Inhibition of neuraminidase activity obtained from or found within any of these organisms is within the objects of this invention. The virology of influenza viruses is described in "Fundamental Virology" (Raven Press, New York, 1986), Chapter 24. The compounds of this invention are useful in the treatment or prophylaxis of such infections in animals, e.g. duck, rodents, or swine, or in man.

However, in screening compounds capable of inhibiting influenza viruses it should be kept in mind that the results of enzyme assays may not correlate with cell culture assays, as shown Table 1 of Chandler et al., supra. Thus, a plaque reduction assay should be the primary screening tool.

Screens for Neuraminidase Inhibitors

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, Itzstein, M. von et al.; "Nature", 363(6428):418–423 (1993), in particular page 420, column 2, full paragraph 3, to page 421, column 2, first partial paragraph, describes a suitable in vitro assay of Potier, M.; et al.; "Analyt. Biochem.", 94:287–296 (1979), as modified by Chong, A. K. J.; et al.; "Biochem. Biophys. Acta", 1077:65–71 (1991); and Colman, P. M.; et al.; International Publication No. WO 92/06691 (Int. App. No. PCT/AU90/00501, publication date Apr. 30, 1992) page 34, line 13, to page 35, line 16, describes another useful in vitro screen.

In vivo screens have also been described in detail, see Itzstein, M. von et al.; op. cit., in particular page 421, column 2, first full paragraph, to page 423, column 2, first partial paragraph, and Colman, P. M.; et al.; op. cit. page 36, lines 1–38, describe suitable in vivo screens.

Pharmaceutical Formulations and Routes of Administration

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally; it is not necessary to administer them by intrapulmonary or intranasal routes. Surprisingly, the anti-influenza compounds of WO 91/16320, WO 92/06691 and U.S. Pat. No. 5,360,817 are successfully administered by the oral or intraperitoneal routes. See Example 161 infra.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient (s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth;

pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

Active ingredients of the invention are also used in combination with other active ingredients. Such combinations are selected based on the condition to be treated, cross-reactivities of ingredients and pharmacoproperties of the combination. For example, when treating viral infections of the respiratory system, in particular influenza infection, the compositions of the invention are combined with antivirals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of this invention.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $C^{14}$ or $H^3$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Additional Uses for the Compounds of This Invention

The compounds of this invention, or the biologically active substances produced from these compounds by hydrolysis or metabolism in vivo, are used as immunogens or for conjugation to proteins, whereby they serve as components of immunogenic compositions to prepare antibodies capable of binding specifically to the protein, to the compounds or to their metabolic products which retain immunologically recognized epitopes (sites of antibody binding). The immunogenic compositions therefore are useful as intermediates in the preparation of antibodies for use in diagnostic, quality control, or the like, methods or in assays for the compounds or their novel metabolic products. The compounds are useful for raising antibodies against otherwise non-immunogenic polypeptides, in that the compounds serve as haptenic sites stimulating an immune response that cross-reacts with the unmodified conjugated protein.

The hydrolysis products of interest include products of the hydrolysis of the protected acidic and basic groups discussed above. As noted above, the acidic or basic amides comprising immunogenic polypeptides such as albumin or keyhole limpet hemocyanin generally are useful as immunogens. The metabolic products described above may retain a substantial degree of immunological cross reactivity with the compounds of the invention. Thus, the antibodies of this invention will be capable of binding to the unprotected compounds of the invention without binding to the protected compounds; alternatively the metabolic products, will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1–100, typically, 1–25, more typically 1–10 carbon atoms to the immunogenic substance. The conjugates are separated from starting materials and by products using chromatography or the like, and then are sterile filtered and vialed for storage.

The compounds of this invention are cross-linked for example through any one or more of the following groups: a hydroxyl group of $U_1$; a carboxyl group of $E_1$; a carbon atom of $U_1$, $E_1$, $G_1$, or $T_1$, in substitution of H; and an amine group of $G_1$. Included within such compounds are amides of polypeptides where the polypeptide serves as an above-described $R_{6c}$ or $R_{6b}$ groups.

Animals are typically immunized against the immunogenic conjugates or derivatives and antisera or monoclonal antibodies prepared in conventional fashion.

The compounds of the invention are useful for maintaining the structural integrity of glycoproteins in recombinant cell culture, i.e., they are added to fermentations in which glycoproteins are being produced for recovery so as to inhibit neuraminidase-catalyzed cleavage of the desired glycoproteins. This is of particular value in the recombinant synthesis of proteins in heterologous host cells that may disadvantageously degrade the carbohydrate portion of the protein being synthesized.

The compounds of the invention are polyfunctional. As such they represent a unique class of monomers for the synthesis of polymers. By way of example and not limitation, the polymers prepared from the compounds of this invention include polyamides and polyesters.

The present compounds are used as monomers to provide access to polymers having unique pendent functionalities. The compounds of this invention are useful in homopolymers, or as comonomers with monomers which do not fall within the scope of the invention. Homopolymers of the compounds of this invention will have utility as cation exchange agents (polyesters or polyamides) in the preparation of molecular sieves (polyamides), textiles, fibers, films, formed articles and the like where the acid functionality $E_1$ is esterified to a hydroxyl group in $U_1$, for example, whereby the pendant basic group $G_1$ is capable of binding acidic functionalities such as are found in polypeptides whose purification is desired. Polyamides are prepared by cross-linking $E_1$ and $G_1$, with $U_1$ and the adjacent portion of the ring remaining free to function as a hydrophilic or hydrophobic affinity group, depending up the selection of the $U_1$ group. The preparation of these polymers from the compounds of the invention is conventional per se.

The compounds of the invention are also useful as a unique class of polyfunctional surfactants. Particularly when $U_1$ does not contain a hydrophilic substituent and is, for example, alkyl or alkoxy, the compounds have the properties of bi-functional surfactants. As such they have useful surfactant, surface coating, emulsion modifying, rheology modifying and surface wetting properties.

As polyfunctional compounds with defined geometry and carrying simultaneously polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms in groups $U_1$, $E_1$, $G_1$, and $T_1$. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters or amides with a compound of the invention wherein $U_1$ is an asymmetric hydroxyalkane or amino alkane group; 2) separating the diastereomers; and 3) hydrolyzing the ester structure. Racemic alcohols are separated by ester formation with an acid group of $E_1$. Further, such a method can be used to resolve the compounds of the invention themselves if optically active acids or alcohols are used instead of racemic starting materials.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups in the compounds of this invention are suitable for use in cross-linking. For example, the carboxylic or phosphonic acid of group $E_1$ is used to form esters with alcohols or amides with amines of the reagent to be cross-linked. The $G_1$ sites substituted with OH, $NHR_1$, SH, azido (which is reduced to amino if desired before cross-linking), CN, $NO_2$, amino, guanidino, halo and the like are suitable sites. Suitable protection of reactive groups will be used where necessary while assembling the cross-linked reagent to prevent polymerization of the bifunctional compound of this invention. In general, the compounds here are used by linking them through carboxylic or phosphonic acid to the hydroxyl or amino groups of the first linked partner, then covalently bonded to the other binding partner through a $T_1$ or $G_1$ group. For example a first binding partner such as a steroid hormone is esterified to the carboxylic acid of a compound of this invention and then this conjugate is cross-linked through a $G_1$ hydroxyl to cyanogen bromide activated Sepaharose, whereby immobilized steroid is obtained. Other chemistries for conjugation are well known. See for example Maggio, "Enzyme-Immunoassay" (CRC, 1988, pp 71–135) and references cited therein.

As noted above, the therapeutically useful compounds of this invention in which the $W_1$, or $G_1$ carboxyl, hydroxyl or amino groups are protected are useful as oral or sustained release forms. In these uses the protecting group is removed in vivo, e.g., hydrolyzed or oxidized, so as to yield the free carboxyl, amino or hydroxyl. Suitable esters or amides for this utility are selected based on the substrate specificity of esterases and/or carboxypeptidases expected to be found within cells where precursor hydrolysis is desired. To the extent that the specificity of these enzymes is unknown, one will screen a plurality of the compounds of this invention until the desired substrate specificity is found. This will be apparent from the appearance of free compound or of antiviral activity. One generally selects amides or esters of the invention compound that are (i) not hydrolyzed or hydrolyzed comparatively slowly in the upper gut, (ii) gut and cell permeable and (iii) hydrolyzed in the cell cytoplasm and/or systemic circulation. Screening assays preferably use cells from particular tissues that are susceptible to influenza infection, e.g. the mucous membranes of the bronchopulmonary tract. Assays known in the art are suitable for determining in vivo bioavailability including intestinal lumen stability, cell permeation, liver homogenate stability and plasma stability assays. However, even if the ester, amide or other protected derivatives are not converted in vivo to the free carboxyl, amino or hydroxyl groups, they remain useful as chemical intermediates.

Exemplary Methods of Making the Compounds of the Invention

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be –100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to –100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to –100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

One exemplary method of preparing the compounds of the invention is shown in Scheme 1 below. A detailed description of the methods is found in the Experimental section below.

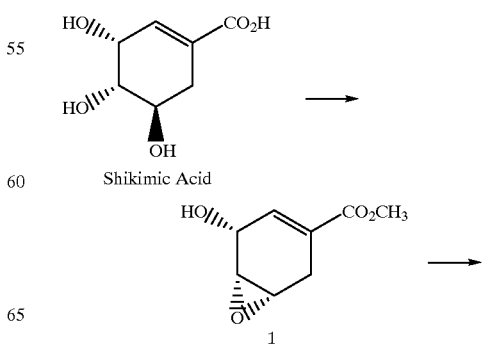

Scheme 1

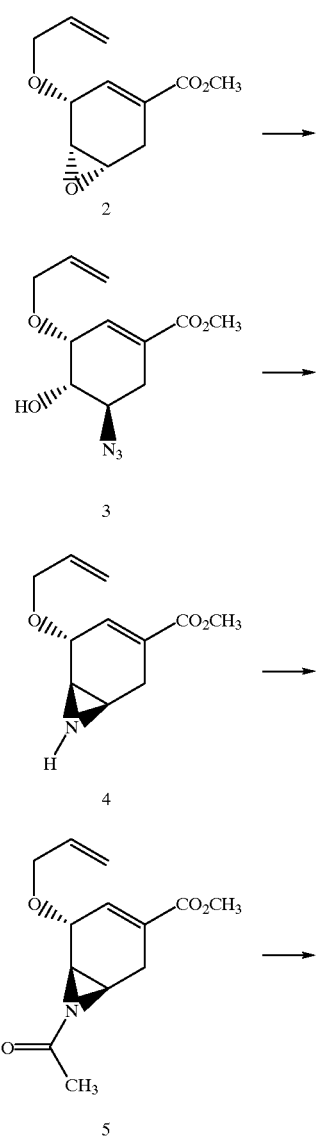
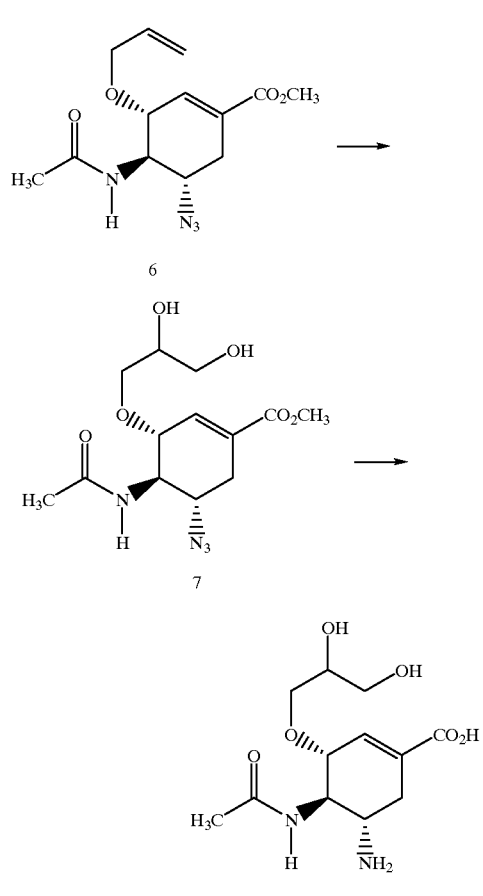
Modifications of Scheme 1 to form additional embodiments is shown in Schemes 2–4.
Scheme 2
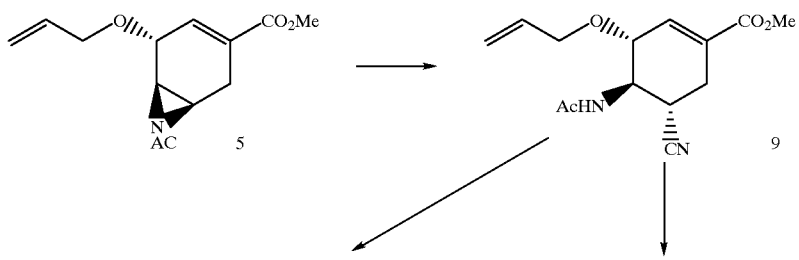

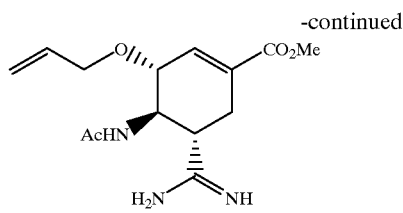

10

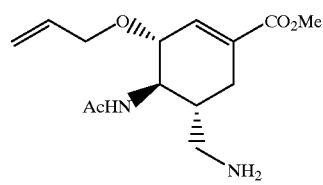

11

↓

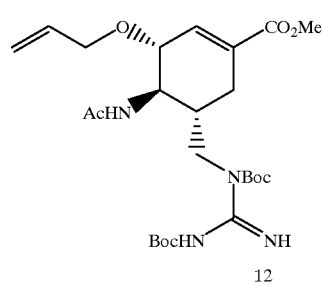

12

Scheme 2

Aziridine 5 is converted to the amino nitrile 9 by Yb(CN)$_3$ catalyzed addition of TMSCN according to the procedure of Utimoto and co-workers, "Tetrahedron Lett.", 31:6379 (1990).

Conversion of nitrile 9 to the corresponding amidine 10 is accomplished using a standard three step sequence: i) H$_2$S; ii) CH$_3$I; iii) NH$_4$OAc. A typical conversion is found in "J. Med. Chem.", 36:1811 (1993).

Nitrile 9 is converted to the amino methyl compound 11 by reduction using any of the available methods found in "Modern Synthetic Reactions" 2nd ed. H.O. House, Benjamin/Cummings Publishing Co., 1972.

Amino methyl compound 11 is converted to the bis-Boc protected guanidino compound 12 by treating 11 with N,N'-bis-Boc-1H-pyrazole-1-carboxamidine according to the method found in "Tetrahedron Lett.", 36:299 (1995).

Scheme 3

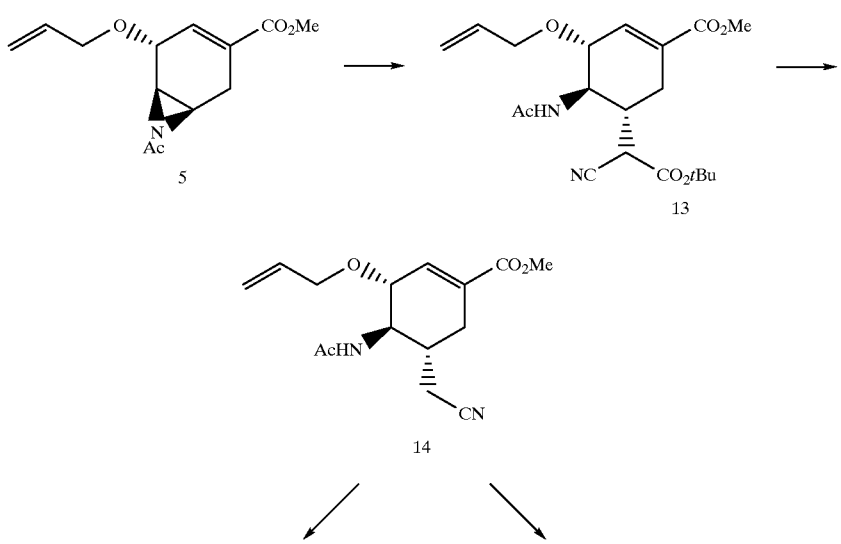

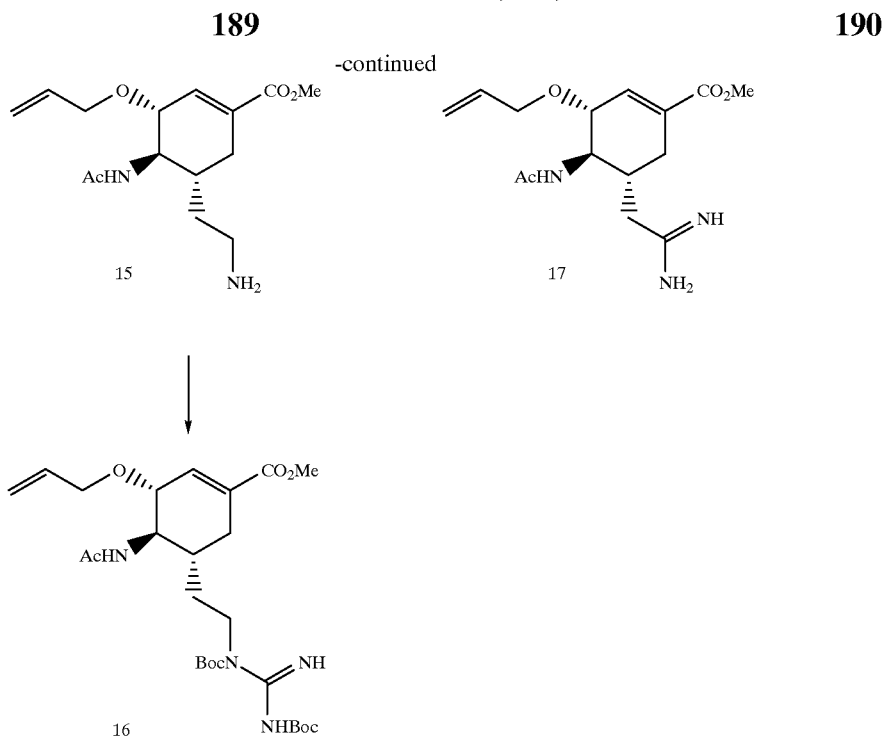

Scheme 3

The aziridine 5 is opened with α-cyano acetic acid t-butyl ester to give 13. Aziridine openings of this type are found in "Tetrahedron Lett.", 23:5021 (1982). Selective hydrolysis of the t-butyl ester moiety under acidic condtions followed by decarboxylation gives nitrile 14.

Reduction of 14 to the amino ethyl derivative 15 is accomplished in the same fashion as the conversion of 9 to 11. The amine 15 is then converted into the guanidino derivative 16 with N,N'-bis-Boc-1H-pyrazole-1-carboxamidine according to the method found in "Tetrahedron Lett.", 36:299 (1995).

The nitrile 14 is converted to the corresponding amidine 17 using the same sequence described above for the conversion of 9 to 10.

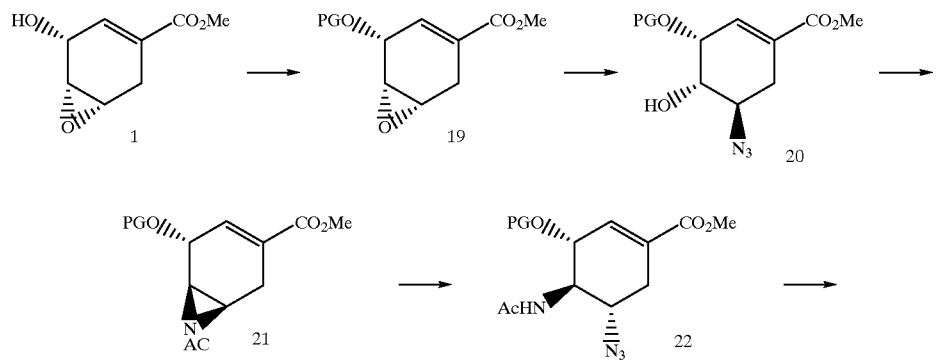

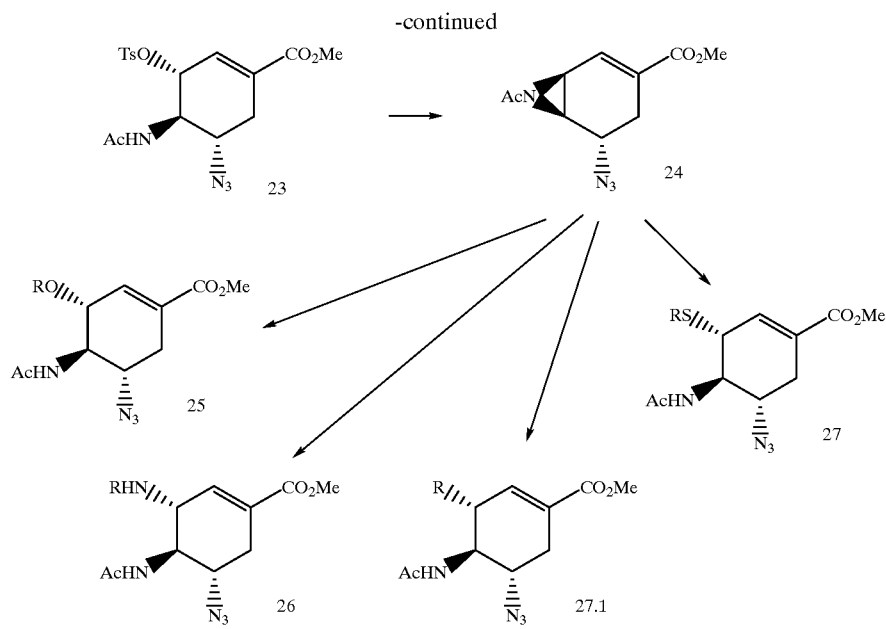

Scheme 4

The epoxy alcohol 1 is protected (PG=protecting group), for example with MOMCl. Typical conditions are found in "Protective Groups in Organic Synthesis" 2nd ed., T. W. Greene and P. G. M. Wuts, John Wiley & Sons, New York, N.Y., 1991.

The epoxide 19 is opened with $NaN_3/NH_4Cl$ to the amino alcohol 20 according to the procedure of Sharpless and co-workers, "J. Org. Chem.", 50:1557 (1985).

Reduction of 20 to the N-acetyl aziridine 21 is accomplished in a three step sequence: 1) MsCl/triethyl amine; 2) $H_2$/Pd; 3) AcCl/pyridine. Such transformations can be found in "Angew. Chem. Int. Ed. Engl.", 33:599 (1994).

Aziridine 21 is converted to the azido amide 22 by opening with $NaN_3/NH_4Cl$ in DMF at 65° C. as described in "J. Chem. Soc. Perkin Trans I", 801 (1976).

Removal of the MOM protecting group of 22 is accomplished using the methods described in "Protective Groups in Organic Synthesis" 2nd ed., T. W. Greene and P. G. M. Wuts, John Wiley & Sons, New York, N.Y., 1991. The resulting alcohol is converted directly to aziridine 24 with TsCl in pyridine. Such transformations are found in "Angew. Chem. Int. Ed. Engl.", 33:599 (1994).

Aziridine 24 is then reacted with ROH, $RNH_2$, RSH or an organometallic (metal-R) to give the corresponding ring opened derivatives 25, 26, 27 and 27.1 respectively. Aziridine openings of this type are found in "Tetrahedron Lett.", 23:5021 (1982) and "Angew. Chem. Int. Ed. Engl.", 33:599 (1994).

Scheme 5

Another class of compounds of the invention are prepared by the method of Schemes 5a and 5b. Quinic acid is converted to 28 by the method of Shing, T. K. M.; et al.; "Tetrahedron", 47(26):4571 (1991). Mesylation with MsCl in $TEA/CH_2Cl_2$ will give 29 which is reacted with $NaN_3$ in DMF to give 30. Reaction of 30 with TFA in $CH_2Cl_2$ will give 31 which is mesylated with MsCl in $TEA/CH_2Cl_2$ to give 32. Reaction with triphenylphosphine in water will give 33 which is converted to 35 by sequential application of: 1) $CH_3C(O)Cl$ in pyridine, 2) $NaN_3$ in DMF, and 3) NaH in THF. Alkylation of 35 with a wide variety of nucleophiles common in the art will provide a number of compounds such as 36. Methods for elaboration of the compounds such as 36 to other embodiments of the invention will be similar to those described above.

Scheme 5a

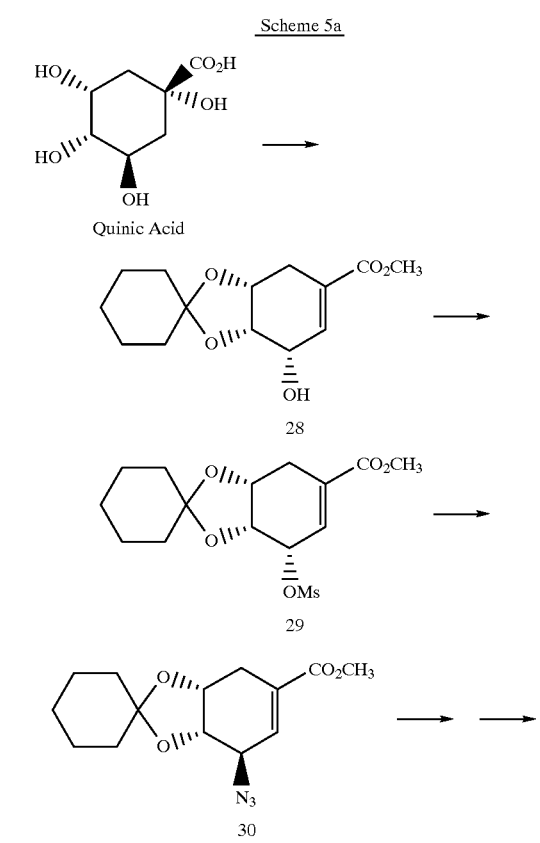

5,952,375
193
-continued
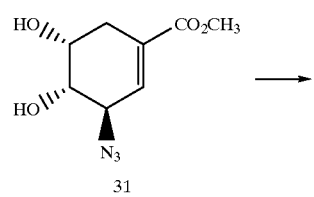
31
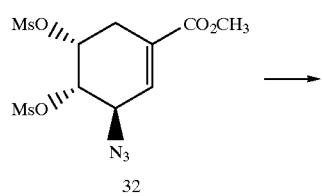
32
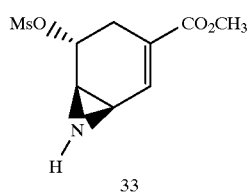
33
Scheme 5b
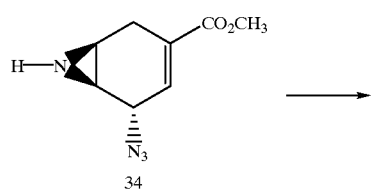
34
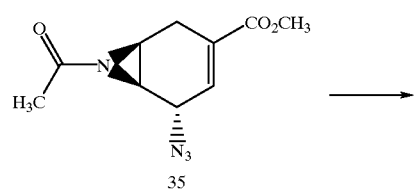
35
194
-continued
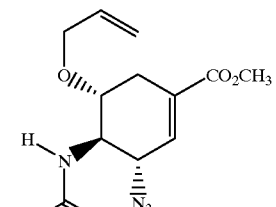
36
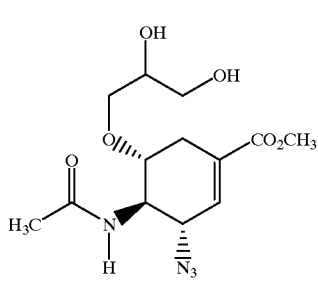
37
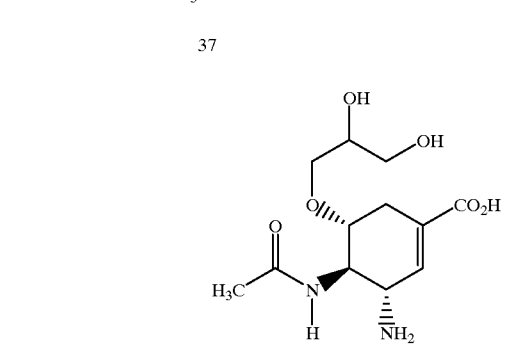
38
Scheme 6
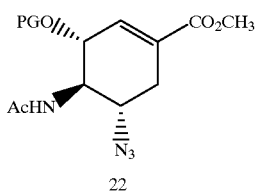
22
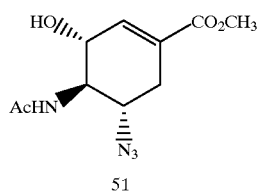
51

-continued

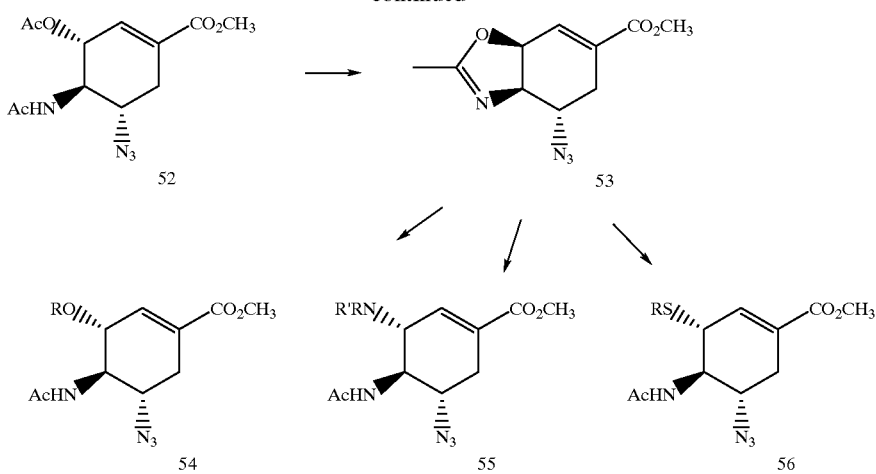

Scheme 6

Another class of compounds of the invention are prepared by the method of Scheme 6. Protected alcohol 22 (PG=methoxymethyl ether) is deprotected under standard conditions described in "Protective Groups in Organic Synthesis" 2nd ed., T. W. Greene and P. G. M. Wuts, John Wiley & Sons, New York, N.Y., 1991. Alcohol 51 is converted to acetate 52 with acetic anhydride and pyridine under standard conditions. Acetate 52 is treated with TMSOTf or $BF_3 \cdot OEt$ to afford oxazoline 53. Such transformations are described in "Liebigs Ann. Chem.", 129 (1991) and "Carbohydrate Research", 181 (1993), respectively. Alternatively, alcohol 51 is transformed to oxazoline 53 by conversion to the corresponding mesylate or tosylate 23 and subsequently cyclized to the oxazoline under standard conditions, as described in "J. Org. Chem.", 50:1126 (1985) and "J. Chem. Soc.", 1385 (1970). Oxazoline 53 is reacted with ROH, RR'NH, or RSH (wherein R and R' are selected to be consistent with the definition of $W_6$ above) provide the corresponding ring opened derivatives 54, 55, and 56 respectively. Such transformations are described in "J. Org. Chem.", 49:4889 (1984) and "Chem. Rev.", 71:483 (1971).

Schemes 7–35

Other exemplary methods of preparing the compounds of the invention are shown in Schemes 7–35 below. A detailed description of the methods is found in the Experimental section below.

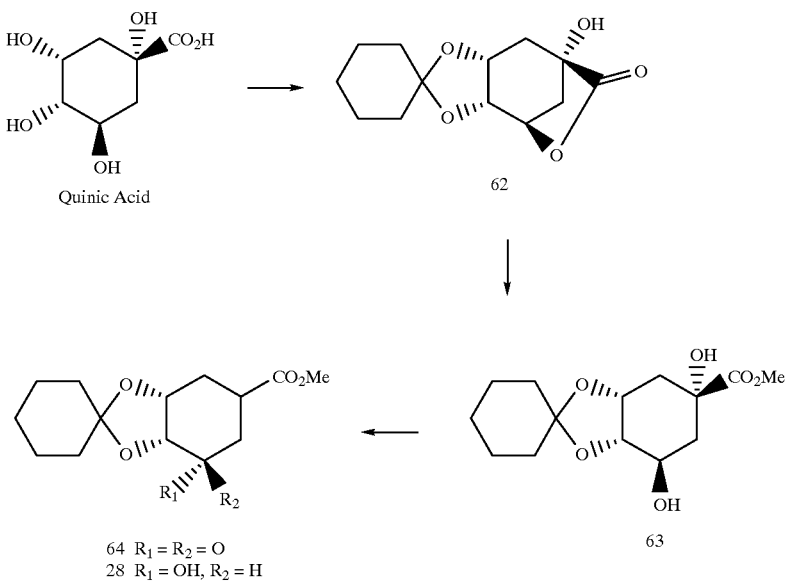

-continued
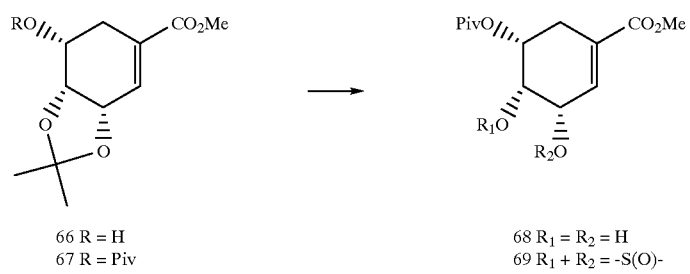
66 R = H
67 R = Piv
68 R₁ = R₂ = H
69 R₁ + R₂ = -S(O)-
Scheme 7b
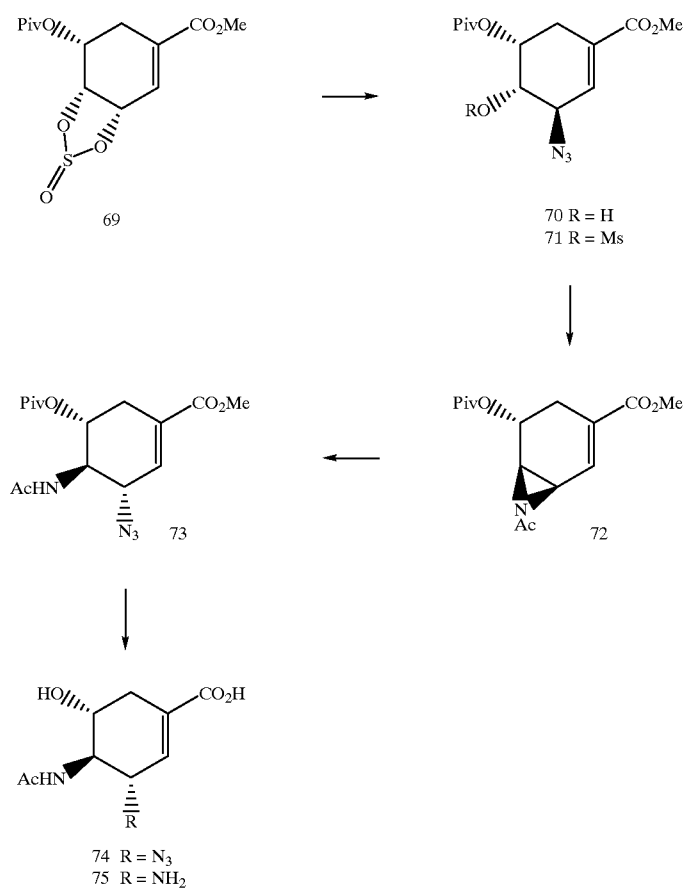
69
70 R = H
71 R = Ms
72
73
74 R = N₃
75 R = NH₂

Scheme 7c
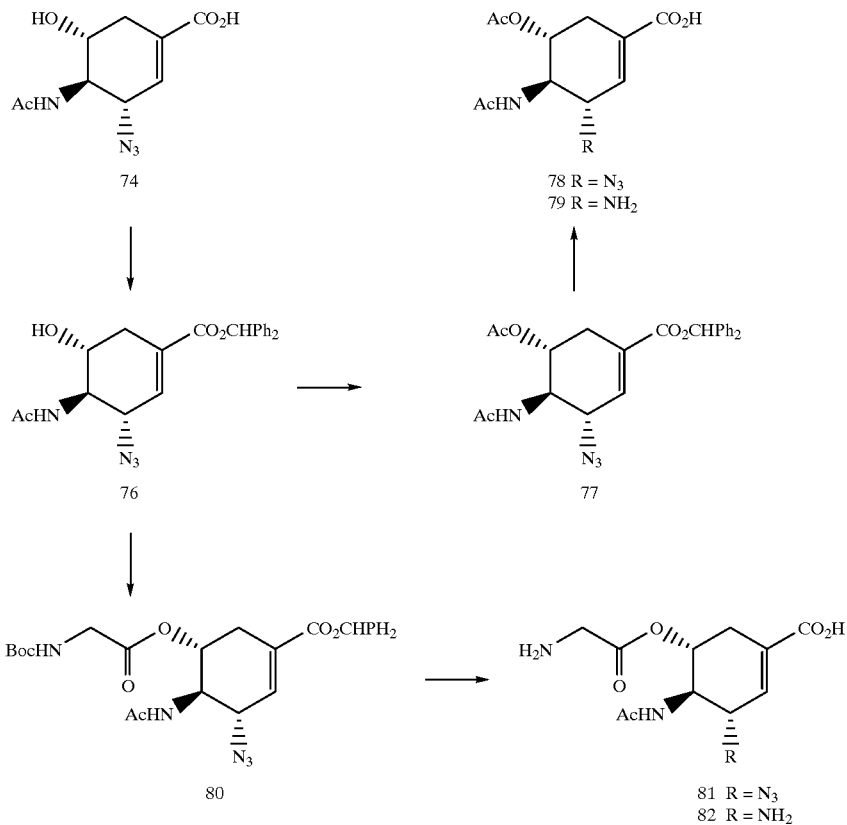
Scheme 8
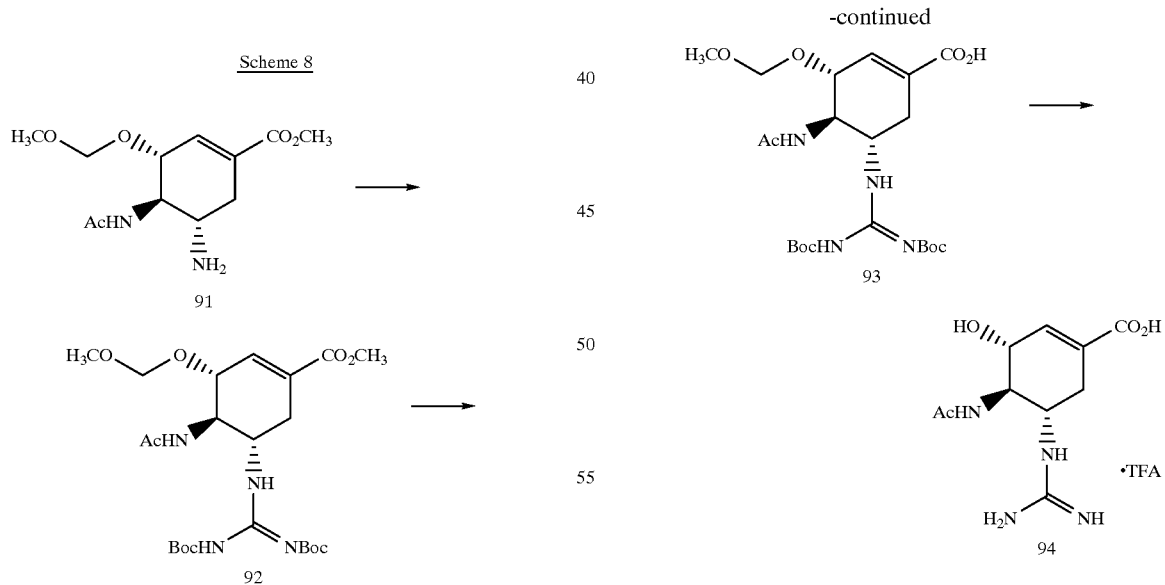

Scheme 9
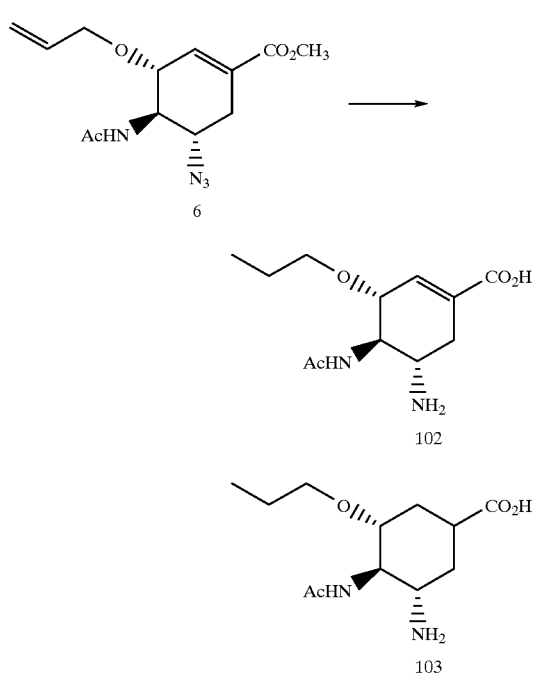
Scheme 10
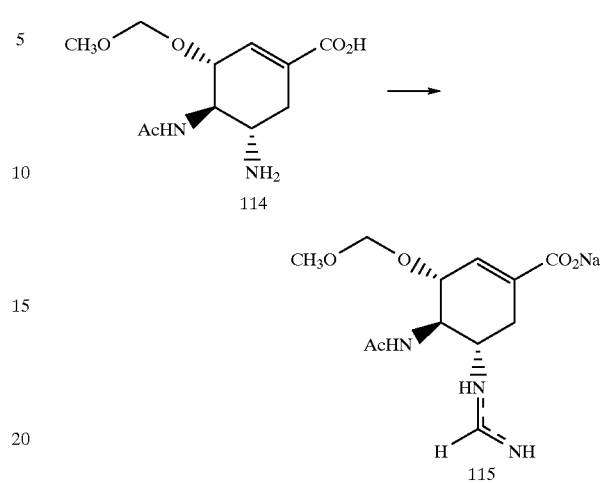
Scheme 11
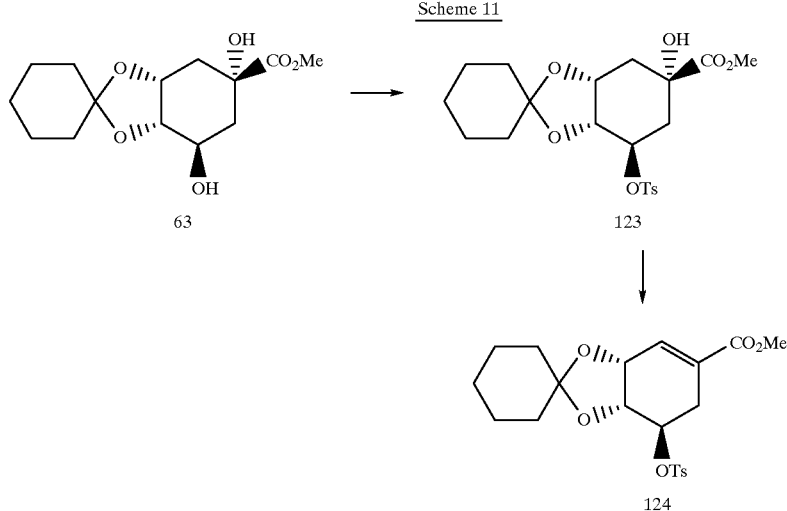

Scheme 12
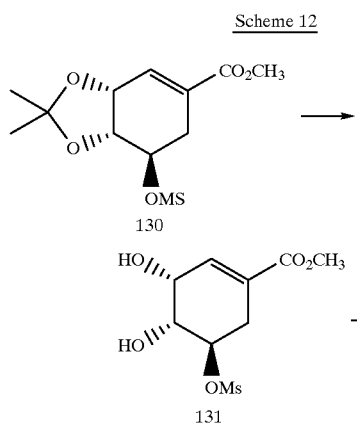
Scheme 13
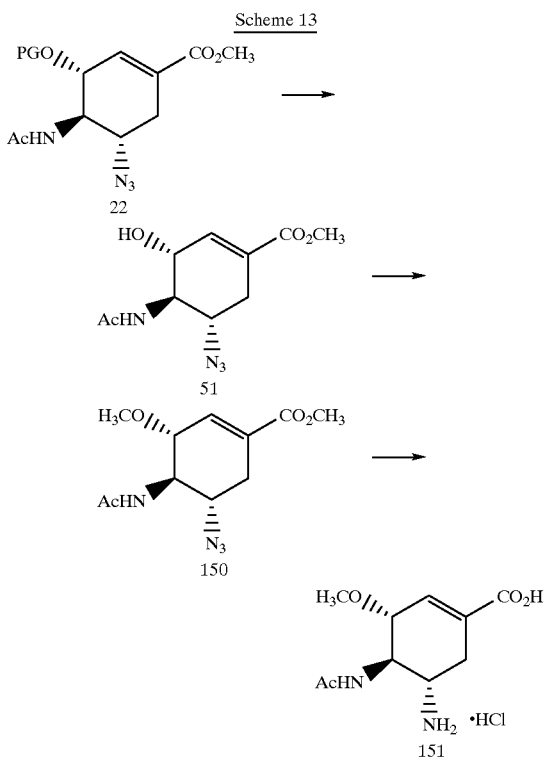
Scheme 14
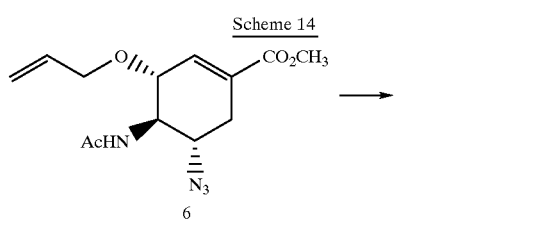
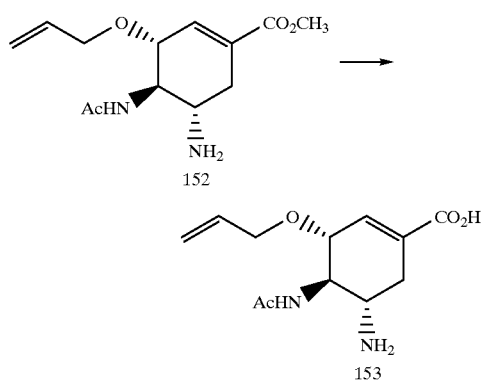
Scheme 15a
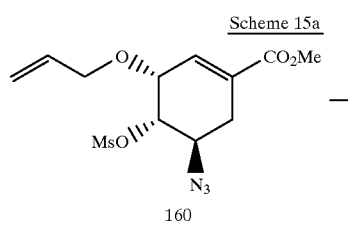

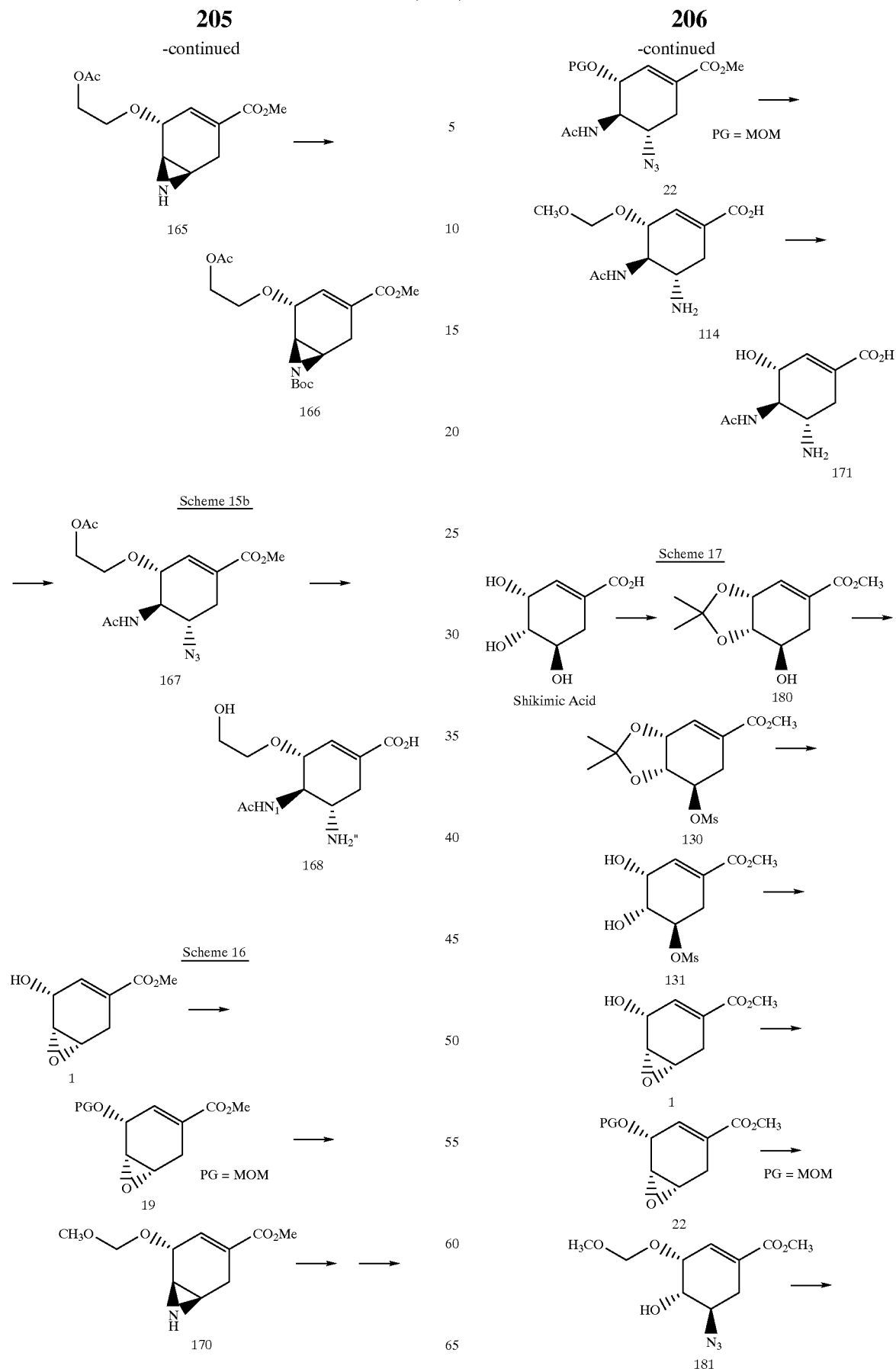

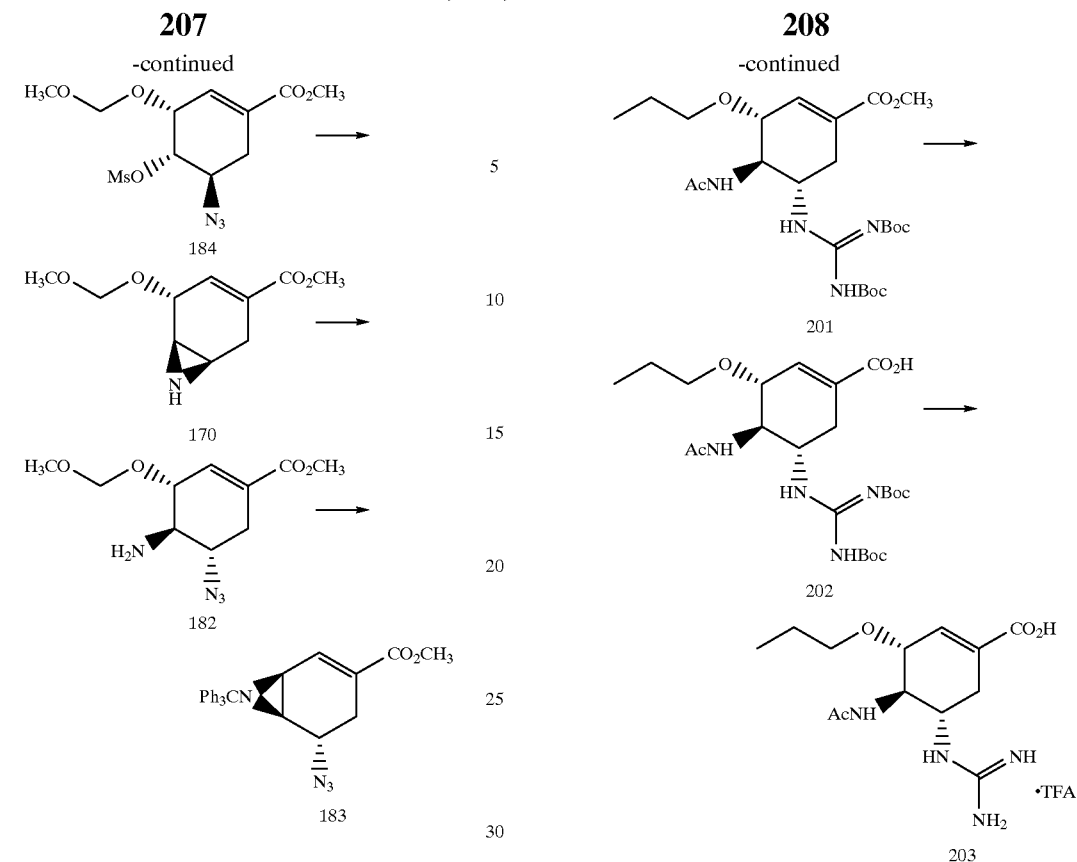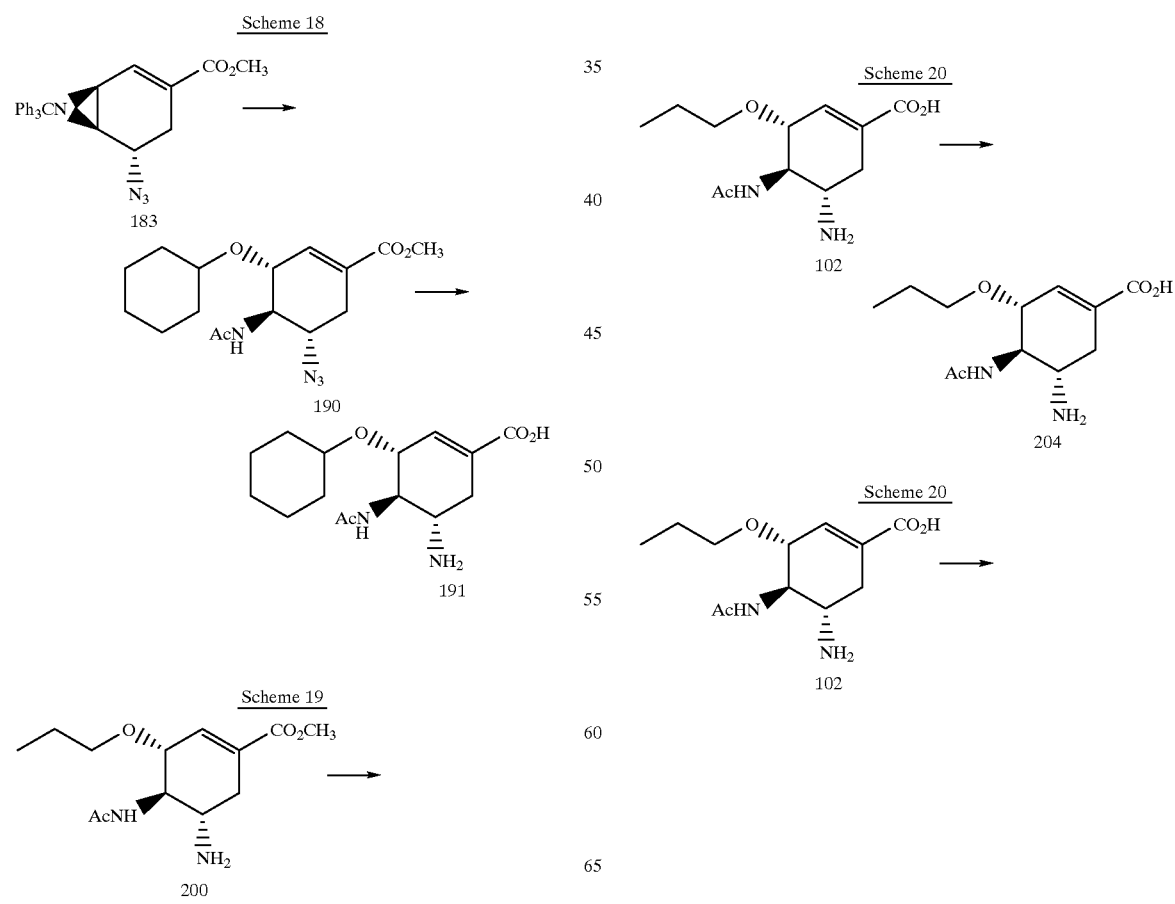

209
-continued
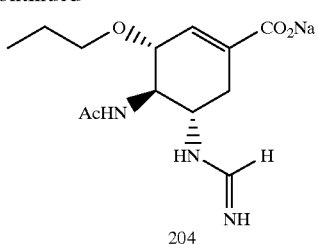
204
Scheme 21
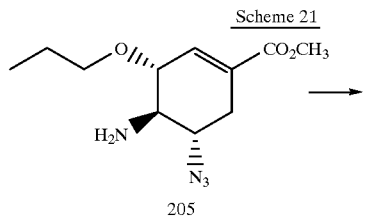
205
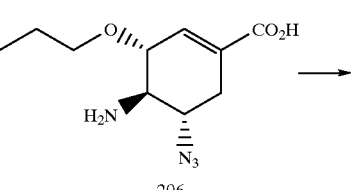
206
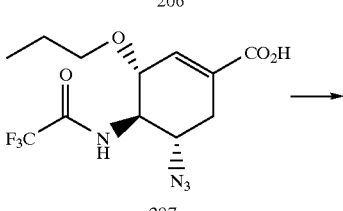
207
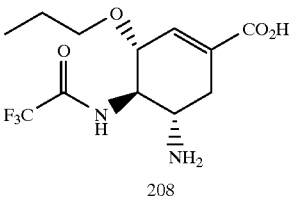
208
Scheme 22
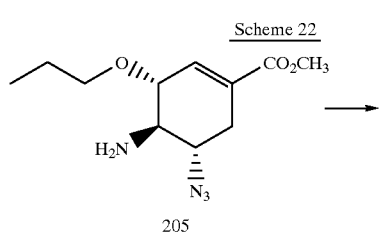
205
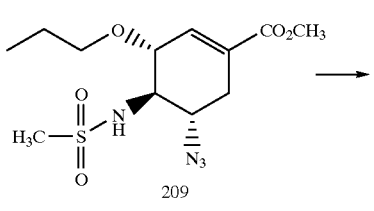
209
210
-continued
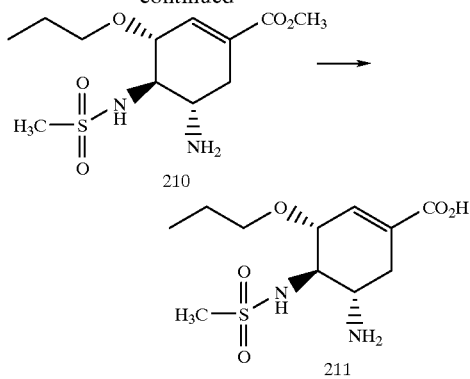
210
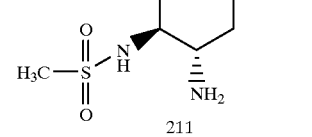
211
Scheme 23
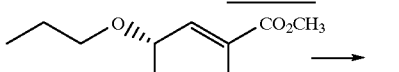
210
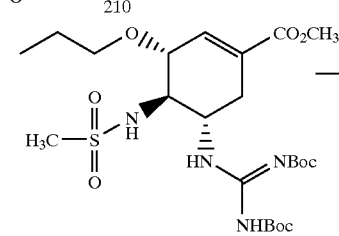
212
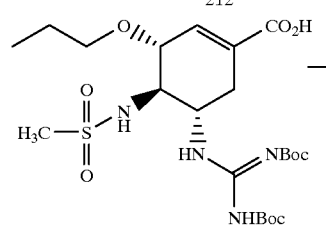
213
214
Scheme 24
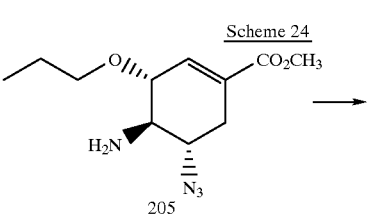
205

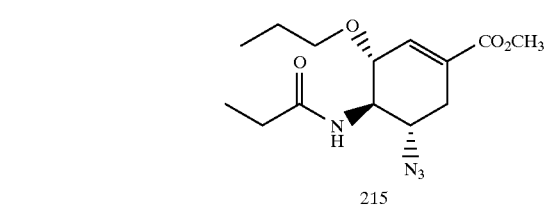
215
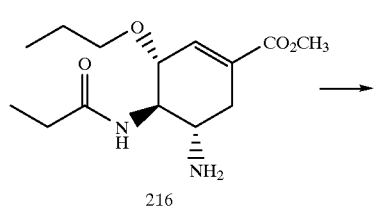
216
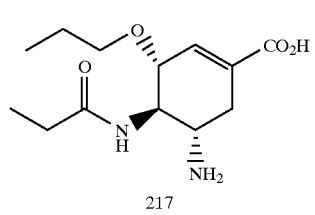
217
Scheme 25
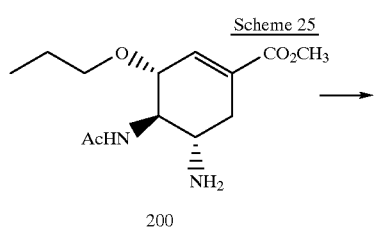
200
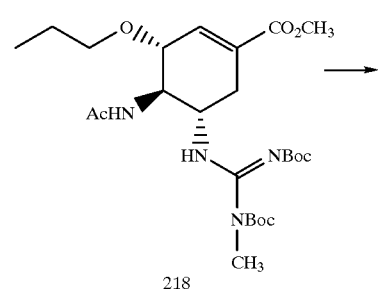
218
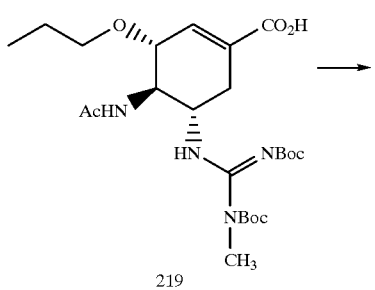
219
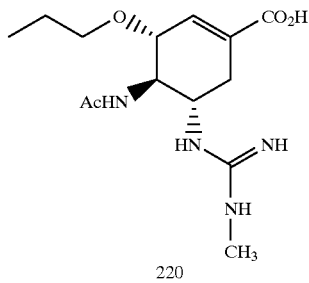
220
Scheme 26
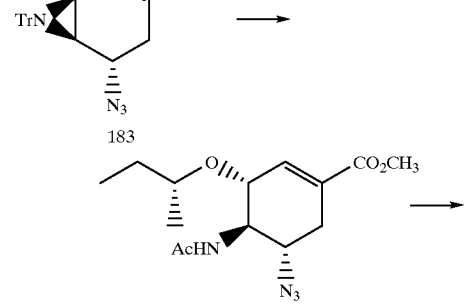
183
221
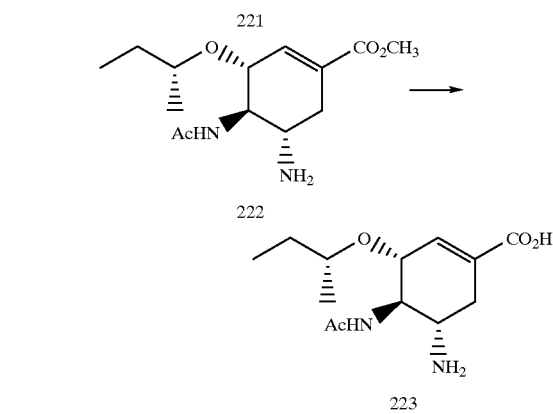
222
223
Scheme 27
222
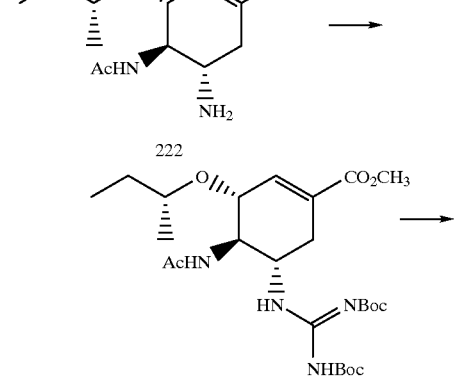
224

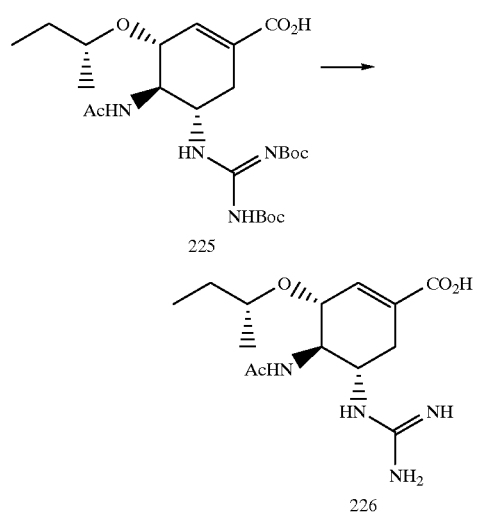
225
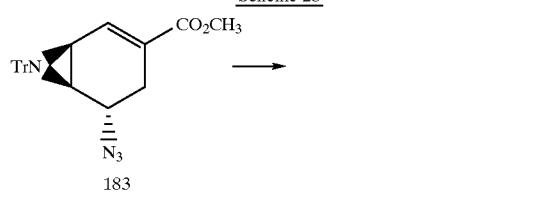
226
Scheme 28
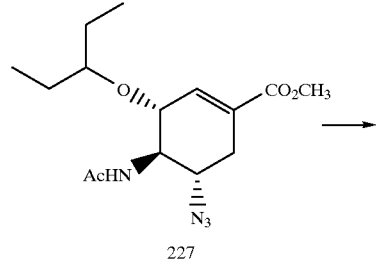
183
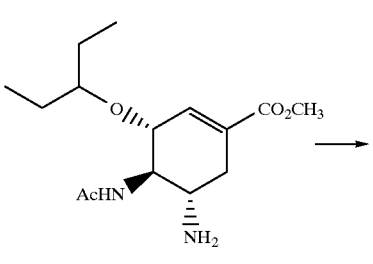
227
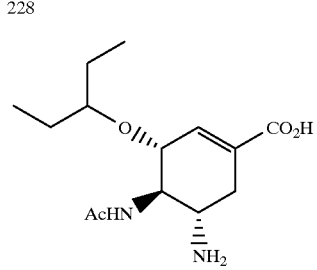
228
229
Scheme 29
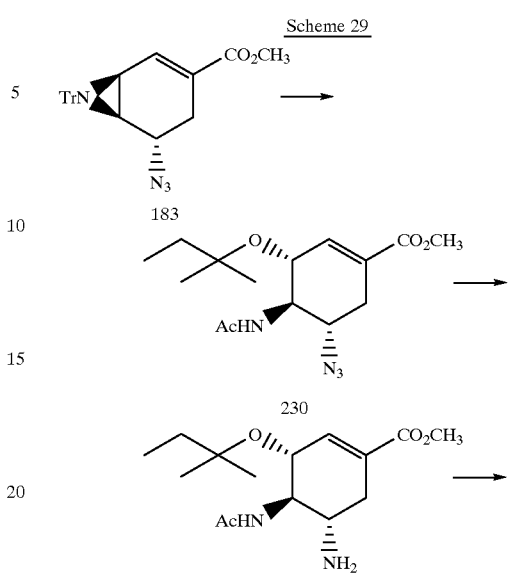
183
230
231
232
Scheme 30
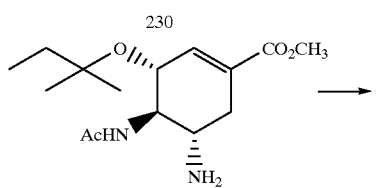
183
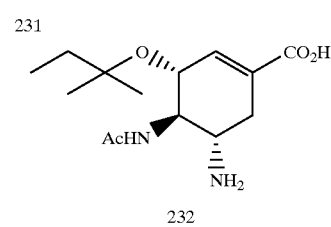
233
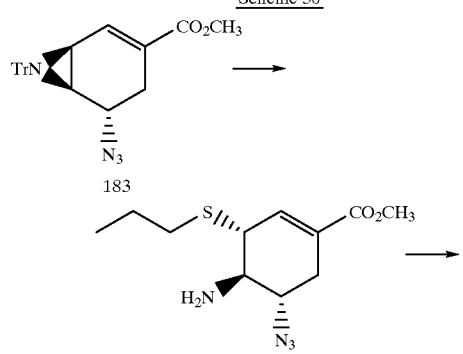
234
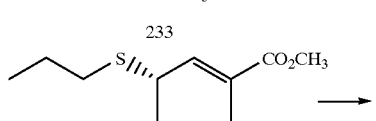
235
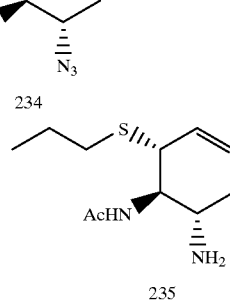

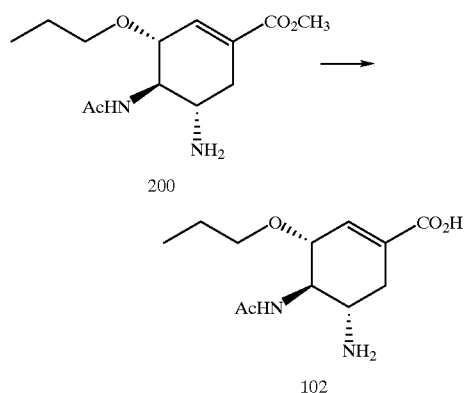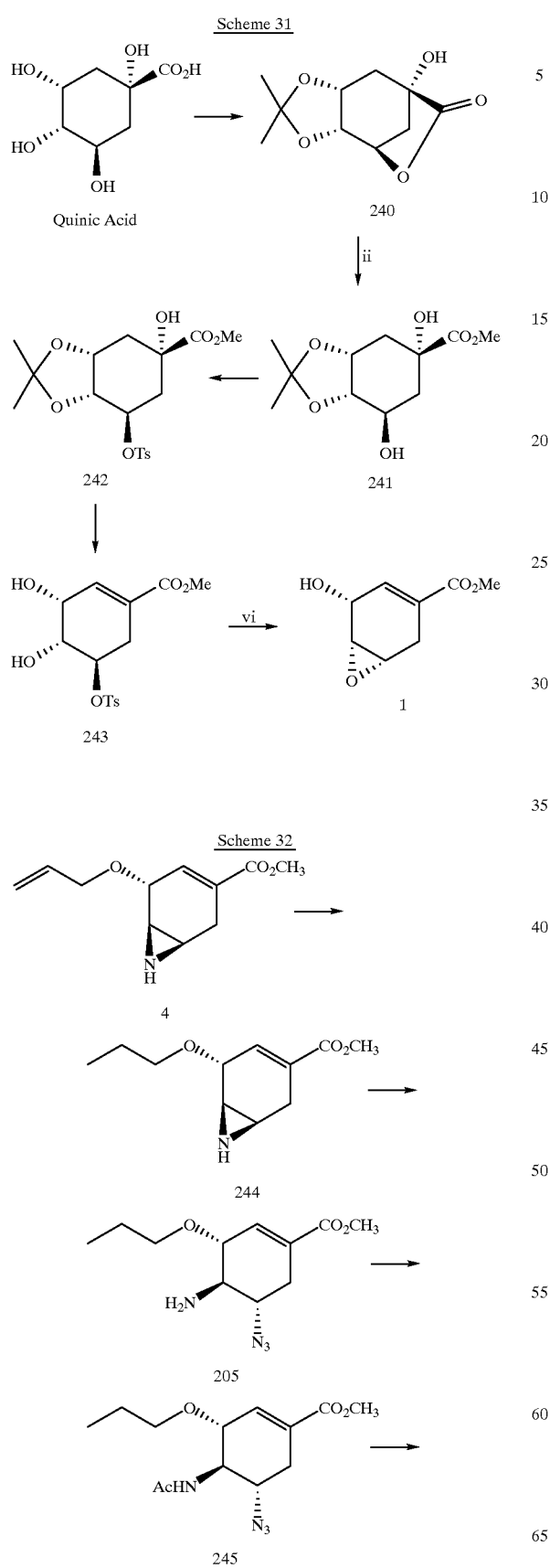

217
-continued
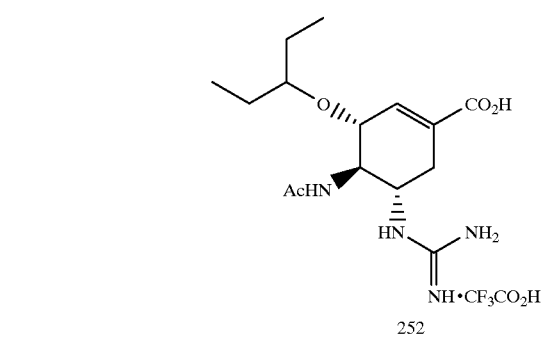
Scheme 34
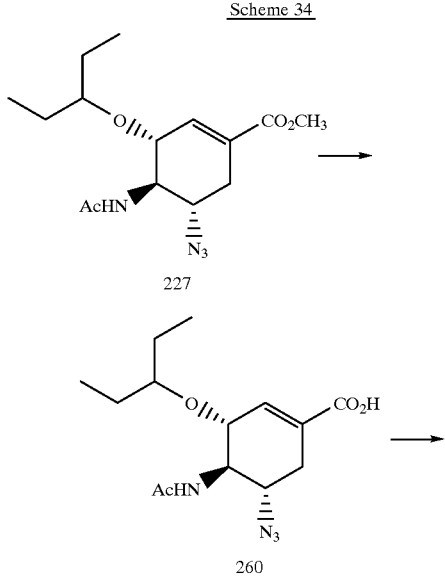
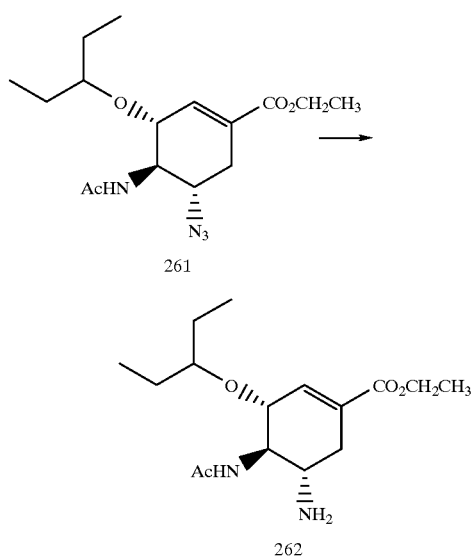
218
Scheme 35
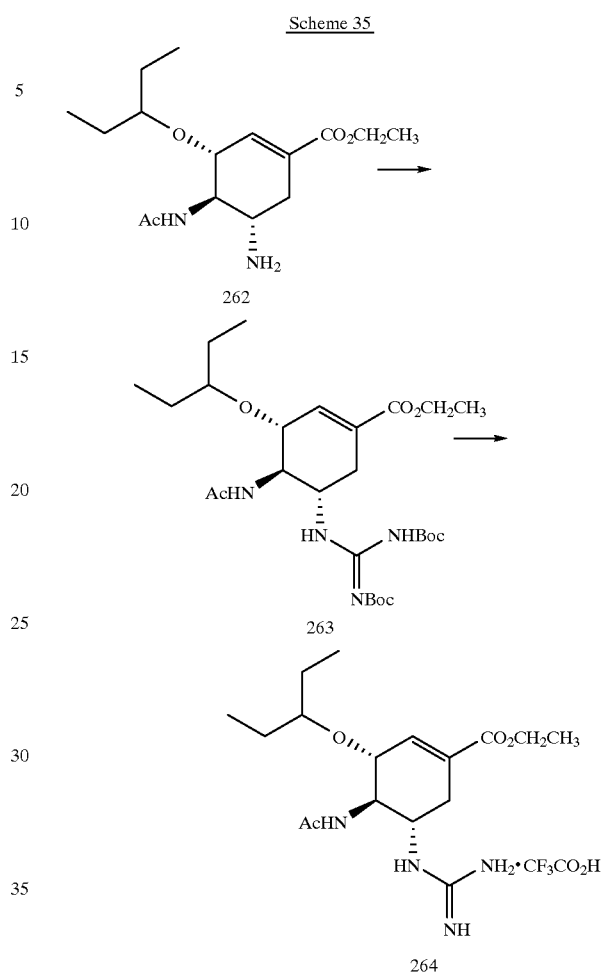
Scheme 36
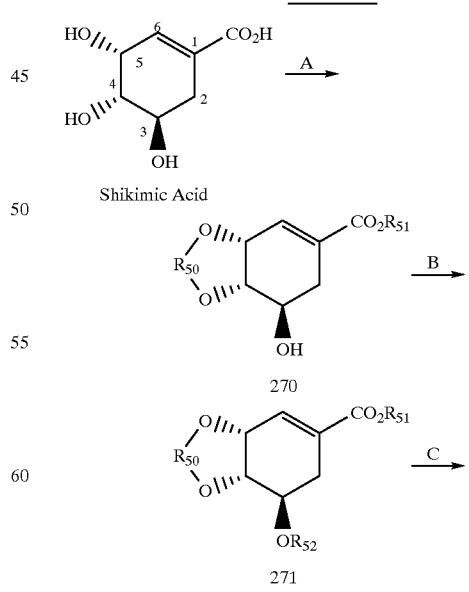

-continued
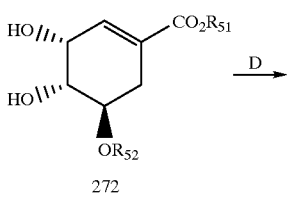
272
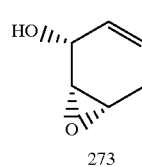
273
Scheme 37
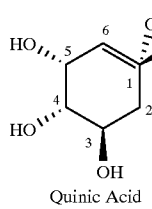
Quinic Acid
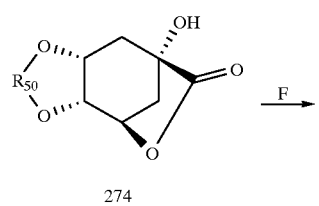
274
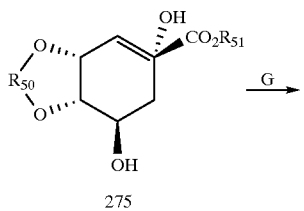
275
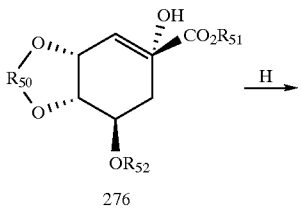
276
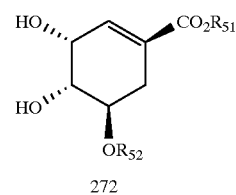
272
Scheme 38
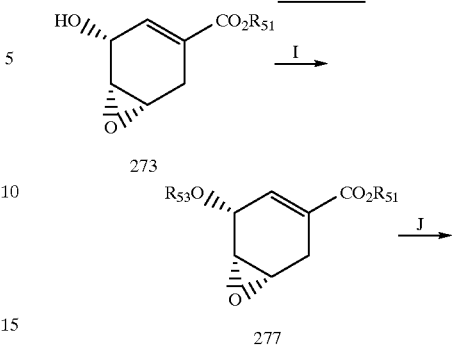
273
277
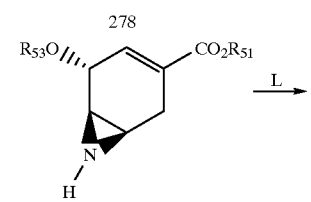
278
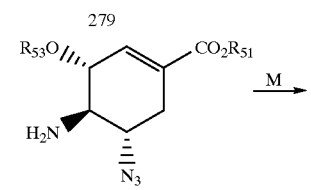
279
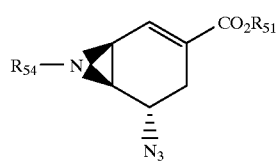
280
281
Scheme 39
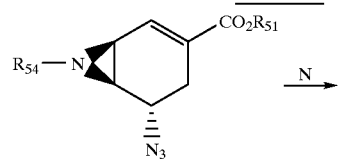
281
282

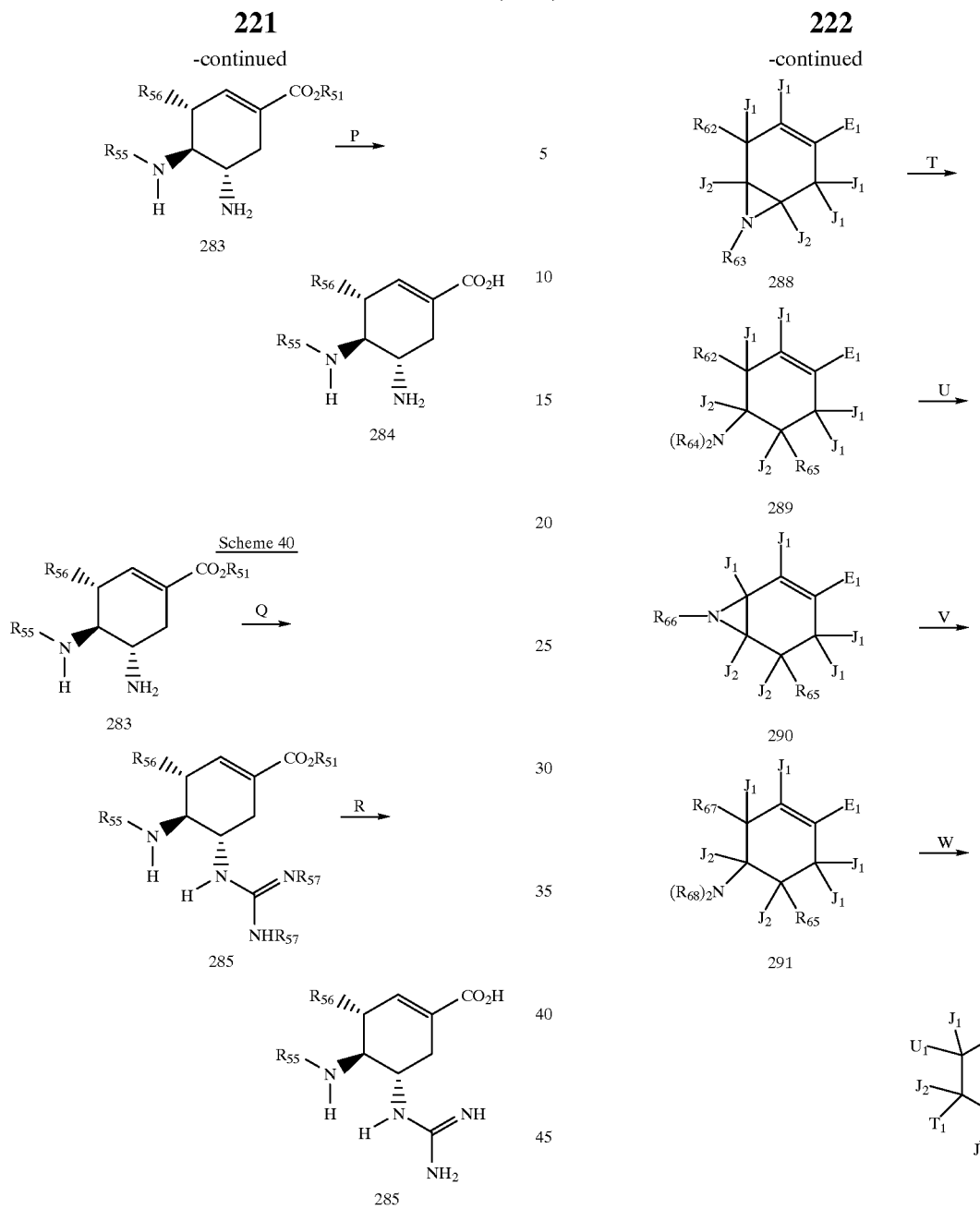
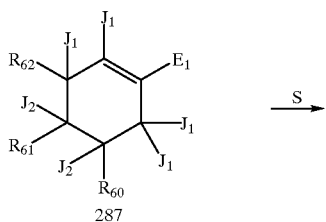

Additional embodiments of methods of making and using compositions of the invention are depicted in Schemes 36–40.1. One aspect of the invention is directed to methods of making compounds of the invention comprising processes A, B, C, D, E, F, G, H, I, J, K, L, M, N, O, P, Q, R, S, T, U, V or W of Schemes 36–40.1, alone or in combination with each other. Table 27 describes exemplary method embodiments of processes A–W. Each embodiment is an individual method using the unit processes A–W alone or in combination. Each method embodiment of Table 27 is separated by a ";". If the embodiment is a single letter than it corresponds to one of the processes A–W. If it is more than one letter than it corresponds to each of the processes performed sequentially in the order indicated.

Other aspects of the invention are directed to methods of using shikimic acid to prepare compound 270 shown as A in Schemes 36, methods of using compound 270 to prepare compound 271 shown as B in Schemes 36, methods of using compound 271 to prepare compound 272 shown as C in Schemes 36, methods of using compound 272 to prepare compound 273 shown as D in Schemes 36, methods of using quinic acid to prepare compound 274 shown as E in Schemes 37, methods of using compound 274 to prepare compound 275 shown as F in Schemes 37, methods of using compound 275 to prepare compound 276 shown as G in Schemes 37, methods of using compound 276 to prepare compound 272 shown as H in Schemes 37, methods of using compound 273 to prepare compound 277 shown as I in Schemes 38, methods of using compound 277 to prepare compound 278 shown as J in Schemes 38, methods of using compound 278 to prepare compound 279 shown as K in Schemes 38, methods of using compound 279 to prepare compound 280 shown as L in Schemes 38, methods of using compound 280 to prepare compound 281 shown as M in Schemes 38, methods of using compound 281 to prepare compound 282 shown as N in Schemes 39, methods of using compound 282 to prepare compound 283 shown as O in Schemes 39, methods of using compound 283 to prepare compound 284 shown as P in Schemes 39, methods of using compound 283 to prepare compound 285 shown as Q in Schemes 40, methods of using compound 285 to prepare compound 286 shown as R in Schemes 40, methods of using compound 287 to prepare compound 288 shown as S in Schemes 40.1, methods of using compound 288 to prepare compound 289 shown as T in Schemes 40.1, methods of using compound 289 to prepare compound 290 shown as U in Schemes 40.1, methods of using compound 290 to prepare compound 291 shown as V in Schemes 40.1, and methods of using compound 291 to prepare compound 292 shown as W in Schemes 40.1.

General aspects of these exemplary methods are described below and in the Example. Each of the products of the following processes is optionally separated, isolated, and/or purified prior to its use in subsecquent processes.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic sysnthesis selects conditions and apparatus reasonably expected to successfully carry out the chemical reactions of the described processes based on the knowledge in the art.

Process A, Scheme 36

Shikimic acid is used to prepare compound 270 by the following process.

The cis-4,5-diol function of shikimic acid is differentiated from the carboxylic acid at carbon 1 by selective protection of these two functionalities. Typically the cis-4,5-diol function is protected as a cyclic ketal and the carboxylic acid function is protected as an ester.

$R_{50}$ is an acid labile 1,2-diol protecting group such as those described in the above cited work of Greene, typically a cyclic ketal or acetal, more typically, a ketal of cyclohexanone or acetone. $R_{51}$ is an acid stable carboxylic acid protecting group such as those described in the above cited work of Greene, typically a linear, branched or cyclic alkyl, alkenyl, or alkynyl of 1 to 12 carbon atoms such as those shown as groups 2–7, 9–10, 15, or 100–660 of Table 2, more typically a linear or branched alkyl of 1 to 8 carbon atoms such as those shown as groups 2–5, 9, or 100–358 of Table 2, still more typically a linear or branched alkyl of 1 to 6 carbon atoms such as those shown as groups 2–5, 9, or 100–141 of Table 2, more typically yet, $R_{51}$ is methyl, ethyl, n-propyl, i-propyl, n-butyl, sec-butyl, i-butyl, or t-butyl.

Shikimic acid is reacted to protect the carboxylic acid with group $R_{51}$ and the cis-4,5-diol with group $R_{50}$. Typically shikimic acid is treated with an alcohol, such as methanol, ethanol, n-propanol, or i-propanol, and an acid catalyst, such as a mineral acid or a sulfonic acid such as methane, benzene or toluene sulfonic acid, followed by a dialkyl ketal or acetal of a ketone or aldehyde, such as 2,2-dimethoxy-propane, or 1,1-dimethoxy-cyclohexane, in the presence of the corresponding ketone or aldehyde, such as acetone or cyclohexanone. Optionally, the product of the alcohol and acid catalyst treatment is separated, isolated and/or purified prior to treatment with dialkyl ketal or acetal. Alternatively shikimic acid is treated with $CH_2N_2$.

Typically, the process comprises treating shikimic acid with an alkanol and a sulfonic acid followed by treating with a geminal-dialkoxyalkane or geminal dialkoxycycloalkane and an alkanone or cycloalkanone to form compound 270. More typically, the process comprises treating shikimic acid with an alkanol and a sulfonic acid; evaporating excess alkanol to form a residue; treating the residue with a geminal-dialkoxyalkane or geminal-dialkoxycycloalkane and an alkanone or cycloalkanone to form compound 270. Still more typically, the process comprises treating shikimic acid with methanol and para-toluenesulfonic acid; evaporating excess methanol to form a residue; treating the residue with 2,2-dimethoxypropane and acetone to form compound 270.

An exemplary embodiment of this process is given as Example 55 below.

Process B, Scheme 36

Compound 270 is used to prepare compound 271 by the following process.

The hydroxy group at position 3 is activated, typically, activated toward displacement reactions, more typically, activated toward epoxide ring forming displacement with an alcohol at position 4.

$R_{52}$ is an alcohol activating group, typically, an activating group toward displacement reactions, more typically, an activating group toward epoxide ring forming displacement with an alcohol at position 4. Such groups include those typical in the art such as sulfonic acid esters, more typically, methane, benzene or toluene sulfonic acid esters. In one embodiment, $R_{52}$, taken together with O (i.e. —$OR_{52}$), is a leaving group such as those common in the art.

Typically the process comprises treating compound 270 with an acid halide to form compound 271. More typically, the process comprises treating compound 270 with a sulfonic acid halide in a suitable solvent to form compound 271. Still more typically, the process comprises treating compound 270 with a sulfonic acid halide in a suitable solvent such as an amine, optionally, in the presence of a cosolvent, such as a haloalkane, to form compound 271. More typically yet, the process comprises treating compound 270 with methane sulfonyl chloride in triethylamine/dichloromethane to form compound 271.

An exemplary embodiment of this process is given as Example 56 below.

Process C, Scheme 36

Compound 271 is used to prepare compound 272 by the following process.

The acid labile protecting group ($R_{50}$) for the hydroxy groups at positions 4 and 5 is removed. Typically, $R_{50}$ is removed without substaintially removing base labile carboxylic acid protecting groups (e.g. $R_{51}$) or hydroxy activating groups (e.g. $R_{52}$). Still more typically, $R_{50}$ is cleaved under acidic conditions.

Typically the process comprises treating compound 271 with a protic solvent, more typically, in the presence of an acid catalyst as described above. Still more typically, the process comprises treating compound 271 with an alkanol as described above and an acid catalyst as described above. More typically yet, the process comprises treating compound 271 with methanol and para-toluene sulfonic acid to produce compound 272.

An exemplary embodiment of this process is given as Example 57 below.

Process D, Scheme 36

Compound 272 is used to prepare compound 273 by the following process.

The activated hydroxy group at position 3 of compound 272 is displaced by the hydroxy at position 4 of compound 272 to produce epoxide compound 273. Typically the displacement is catalyzed by a suitable base, more typically, an amine base such as DBU or DBN.

Typically the process comprises treating compound 272 with a basic catalyst, optionally in the presecnce of a suitable solvent. Still more typically, the process comprises treating compound 272 with an amine base in a polar, non-protic solvent such as diethyl ether or THF. More typically yet, the process comprises treating compound 272 with DBU in THF to produce compound 273.

An exemplary embodiment of this process is given as Example 58 below.

Process E, Scheme 37

Quinic acid is used to prepare compound 274 by the following process.

The cis-4,5-diol function of quinic acid is differentiated from the carboxylic acid at carbon 1 by selective protection of these two functionalities. Typically the cis-4,5-diol function is protected as a cyclic ketal and the carboxylic acid function is protected as a lactone with the hydroxy group at position 3.

$R_{50}$ is as described above.

Typically, the process comprises treating quinic acid with a geminal-dialkoxyalkane or geminal dialkoxycycloalkane, as described above, and an alkanone or cycloalkanone, as described above, optionally, in the presence of an acid catalyst, as described above, to form compound 274. More typically, the process comprises treating quinic acid with a geminal-dialkoxyalkane or geminal-dialkoxycycloalkane, an alkanone or cycloalkanone, and an acid catalyst to form compound 270. Still more typically, the process comprises treating quinic acid with 2,2-dimethoxypropane, acetone, and para-toluenesulfonic acid to form compound 274.

An exemplary embodiment of this process is given as Example 101 below.

Process F, Scheme 37

Compound 274 is used to prepare compound 275 by the following process.

The lactone is opened to form compound 275. Typically, the lactone is opened to produce a protected carboxylic acid at position 1 and a free hydroxy at position 3. More typically, the lactone is opened under basic conditions to produce an $R_{51}$ protected carboxylic acid at position 1 and a free hydroxy group at position 3.

$R_{51}$ is as described above.

Typically compound 274 is treated with a suitable base in a suitable protic solvent. More typically compound 275 is treated with a metal alkoxide base, such as sodium, potassium or lithium alkoxide, in an alkanol, as described above. Still more typically, compound 274 is treated with NaOMe in MeOH to produce compound 275.

An exemplary embodiment of this process is given as Example 102 below.

Process G, Scheme 37

Compound 275 is used to prepare compound 276 by the following process.

The hydroxy group at position 3 is activated, typically, activated toward displacement reactions, more typically, activated toward epoxide ring forming displacement with an alcohol at position 4.

$R_{52}$ is an alcohol activating group, typically, an activating group toward displacement reactions, more typically, an activating group toward epoxide ring forming displacement with an alcohol at position 4. Such groups include those typical in the art such as sulfonic acid esters, more typically, methane, benzene or toluene sulfonic acid esters. In one embodiment, $R_{52}$, taken together with O (i.e. —$OR_{52}$), is a leaving group such as those common in the art.

Typically the process comprises treating compound 275 with an acid halide to form compound 276. More typically, the process comprises treating compound 275 with a sulfonic acid halide in a suitable solvent to form compound 276. Still more typically, the process comprises treating compound 275 with a sulfonic acid halide in a suitable solvent such as an amine, optionally, in the presence of a cosolvent, such as a haloalkane, to form compound 276. More typically yet, the process comprises treating compound 275 with p-toluene sulfonyl chloride in pyridine dichloromethane to form compound 276.

An exemplary embodiment of this process is given as Example 103 below.

Process H, Scheme 37

Compound 276 is used to prepare compound 272 by the following process.

The hydroxy group at position 1 is eliminated and the cis-4,5-diol protecting group is removed. The hydroxy group at position 1 is eliminated to form an olefinic bond between positions 1 and 6 and the cis-4,5-diol protecting group is removed to regenerate the cis-4,5-diol.

Typically the process comprises treating compound 276 with a suitable dehydrating agent, such as a mineral acid (HCl, $H_2SO_4$) or $SO_2Cl_2$. More typically, compound 276 is treated with $SO_2Cl_2$, followed by an alkanol, optionally in the presence of an acid catalyst. Still more typically, compound 276 is treated with $SO_2Cl_2$ in a suitable polar, aprotic solvent, such as an amine to form an olefin; the olefin is treated with an alkanol, as described above, and an acid catalyst, as described above, to form compound 272. More typically yet, compound 276 is treated with $SO_2Cl_2$ in pyridine/$CH_2Cl_2$ at a temperature between $-100°$ C. and $0°$ C., typically $-100°$ C. and $-10°$ C., more typically $-78°$ C., to form an olefin; the olefin is treated with methanol and para-toluene sulfonic acid to form compound 272.

An exemplary embodiment of this process is given as Example 104 below.

Process I, Scheme 38

Compound 273 is used to prepare compound 277 by the following process.

The hydroxy group at position 5 is protected. Typically the protecting group is an acid labile hydroxy protecting. More typically, the protecting group resists transfer to adjacent hydroxy groups.

$R_{53}$ is an acid labile hydroxy protecting group such as those described in the above cited work of Greene. More typically, $R_{53}$ is an acid cleavable ether, still more typically, $R_{53}$ is methoxymethyl (MOM, $CH_3$—O—$CH_2$—).

Typically the process comprises treating compound 273 with a hydroxy protecting group reagent as described in Greene. More typically the process comprises treating compound 273 with a substituted or unsubstituted haloalkane or alkene, such as methoxymethyl chloride (MOM chloride, $CH_3$—O—$CH_2$—Cl), in a suitable solvent, such as a polar, aprotic solvent. Still more typically, the process comprises treating compound 273 with MOM chloride in an amine solvent. More typically yet, the process comprises treating compound 273 with MOM chloride in diisoproply ethyl amine.

An exemplary embodiment of this process is given as Example 59 below.

Process J, Scheme 38

Compound 277 is used to prepare compound 278 by the following process.

The epoxide at positions 3 and 4 is opened to form an azide. More typically, the epoxide at positions 3 and 4 is opened to form a 3-azido-4-hydroxy compound 278.

Typically the process comprises treating compound 277 with an azide salt in a suitable solvent. More typically, the process comprises treating compound 277 with sodium azide and a mild base, such as an ammonium halide, in a polar, protic solvent, such as an alkanol or water. Still more typically, the process comprises treating compound 277 with sodium azide and ammonium chloride in water/methanol solution to produce compound 278.

An exemplary embodiment of this process is given as Example 60 below.

Process K, Scheme 38

Compound 278 is used to prepare compound 279 by the following process.

The hydroxy group at position 4 of compound 278 is displaced by the 3-azido group to form the aziridine compound 279.

Typically the process comprises treating compound 278 with a hydroxy activating group as described above, an organophosphine and a base. More typically the process comprises treating compound 278 with a sulfonic acid halide, such as those described above, to form an activated hydroxy compound, treating the activated hydroxy compound with trialkyl or tri arylphosphine, such as triphenylphosphine, to form a phosphonium salt, and treating the phosphonium salt with a base, such as an amine, to form compound 279. Still more typically, the process comprises treating compound 278 with mesyl chloride, to form an activated hydroxy compound, treating the activated hydroxy compound with triphenylphosphine, to form a phosphonium salt, and treating the phosphonium salt with triethylamine and $H_2O$, to form compound 279.

An exemplary embodiment of this process is given as Examples 61 and 62 below.

Process L, Scheme 38

Compound 279 is used to prepare compound 280 by the following process.

The aziridine compound 279 is opened with azide to form azido amine 280.

Typically the process comprises treating compound 279 with with an azide salt in a suitable solvent. More typically, the process comprises treating compound 279 with sodium azide and a mild base, such as an ammonium halide, in a polar, aprotic solvent, such as an ether, amine, or amide. Still more typically, the process comprises treating compound 279 with sodium azide and ammonium chloride in DMF solution to producee compound 280.

An exemplary embodiment of this process is given as Example 63 below.

Process M, Scheme 38

Compound 280 is used to prepare compound 281 by the following process.

The protected hydroxy group at position 5 is displaced by the amine at position 4 to form aziridine 281. Typically the aziridine 281 is substituted with an acid labile group, more typically an aziridine activating group.

$R_{54}$ is an acid labile group, typically an acid labile amine protecting group such as those described in the above cited work of Greene. More typically, $R_{54}$ is an aziridine activating group, still more typically, a group capable of activating an aziridine toward acid catalyzed ring opening. Typical $R_{54}$ groups include by way of example and not limitation, a linear or branched 1-oxo-alk-1-yl group of 1 to 12 carbons wherein the alkyl portion is a 1 to 11 carbon linear or branched chain alkyl group (such as $CH_3(CH_2)_zC(O)$—, z is an integer from 0 to 10, i.e. acetyl $CH_3C(O)$—, etc.), substituted methyl (e.g. triphenylmethyl, $Ph_3C$—, trityl, Tr), or a carbamate such as BOC or Cbz or a sulfonate (e.g. alkyl sulphonates such as methyl sulphonate). More typical $R_{54}$ groups include triphenylmethyl and 1-oxo-alk-1-yl groups having 1 to 8, still more typically, 1, 2, 3, 4, 5, or 6, more typically yet, 2 or 3 carbon atoms.

Typically the process comprises treating compound 280 with a deprotecting agent to remove group $R_{53}$, an $R_{54}$ producing reagent such as those described in Greene ($R_{54}$-halide, such as acetylchloride, or Tr-Cl, or $R_{54}$—O—$R_{54}$, such as acetic anhydride), and a hydroxy activating group such as those described in process B, Scheme 36. More typically the process comprises treating compound 280 with a polar, protic solvent, optionally in the presence of an acid catalyst as described above, to form a first intermediate; treating the first intermediate with Tr-Cl in a polar, aprotic solvent, such as an amine, to form a second intermediate; and treating the second intermediate with a sulfonic acid halide, such as mesyl chloride or para toluene sulfonyl chloride, in a polar aprotic solvent, such as an amine, to produce compound 281. Still more typically, the process comprises treating compound 280 with methanol and HCl, to form a first intermediate; treating the first intermediate with Tr-Cl and triethylamine, to form a second intermediate; and treating the second intermediate with mesyl chloride and triethylamine, to produce compound 281.

An exemplary embodiment of this process is given as Example 64 below.

Process N, Scheme 39

Compound 281 is used to prepare compound 282 by the following process.

Aziridine 281 is opened and the resulting amine is substituted with an $R_{55}$ group to form compound 282. Typically, aziridine 281 is opened by acid catalyzed ring opening and the resulting amine is acylated.

$R_{55}$ is $W_3$ as defined above. Typically $R_{55}$ is —C(O)$R_5$. More typically, $R_{55}$ is —C(O)$R_1$. Still more typically, $R_{55}$ is —C(O)CH$_3$.

$R_{56}$ is $U_1$ as described above. Typically $R_{56}$ is $W_6$—O—, $W_6$—S—, or $W_6$—N(H)—. More typically, $R_{56}$ is $R_5$—O—, $R_5$—S—, or $R_5$—N(H)—, still more tyically, $R_{56}$ is $R_5$—O—, still more typically yet, $R_{56}$ is $R_1$—O—.

Typically the process comprises treating compound 281 with an acid catalyst and a compound of the formula $W_6$—$X_1$—H, wherein $X_1$ is as defined above to form an amine intermediate; and treating the amine intermediate with a compound of the formula $W_3$—$X_1$—$W_3$, $W_3$—$X_{10}$, wherein $X_{10}$ is a leaving group, to form compound 282. The acid catalyst is typically a Lewis acid catalyst common in the art, such as BF$_3$.Et$_2$O, TiCl$_3$, TMSOTf, SmI$_2$(THF)$_2$, LiClO$_4$, Mg(ClO$_4$)$_2$, Ln(OTf)$_3$ (where Ln=Yb, Gd, Nd), Ti(Oi-Pr)$_4$, AlCl$_3$, AlBr$_3$, BeCl$_2$, CdCl$_2$, ZnCl$_2$, BF$_3$, BCl$_3$, BBr$_3$, GaCl$_3$, GaBr$_3$, TiCl$_4$, TiBr$_4$, ZrCl$_4$, SnCl$_4$, SnBr$_4$, SbCl$_5$, SbCl$_3$, BiCl$_3$, FeCl$_3$, UCl$_4$, ScCl$_3$, YCl$_3$, LaCl$_3$, CeCl$_3$, PrCl$_3$, NdCl$_3$, SmCl$_3$, EuCl$_3$, GdCl$_3$, TbCl$_3$, LuCl$_3$, DyCl$_3$, HoCl$_3$, ErCl$_3$, TmCl$_3$, YbCl$_3$, ZnI$_2$, Al(OPr$^i$)$_3$, Al(acac)$_3$, ZnBr$_2$, for SnCl$_4$. $X_1$ is typically —O—, —S—, or —N(H)—. $X_{10}$ is typically a halide such as Cl, Br, or I. More typically, the process comprises treating compound 281 with a compound of the formula $R_5$—OH, $R_5$—SH, or $R_5$—NH$_2$, and BF$_3$.Et$_2$O to form an intermediate; and treating the intermediate with an alkanoic acid anhydride to form compound 282. Still more typically, the process comprises treating compound 281 with a compound of the formula $R_5$—OH and BF$_3$.Et$_2$O to form an intermediate; and treating the intermediate with a substituted or unsubstituted acetic anhydride to form compound 282. Exemplary compounds of the formula $R_5$—OH include those described by Table 2, groups 2–7, 9–10, 15, and 100–660 wherein $Q_1$ is —OH. Further exemplary compounds of the formula $R_5$—OH include those shown in Table 25 below (together with their Chemical Abstracts Service Registry Numbers) and those shown in Table 26 below (together with their Chemical Abstracts Service Registry Numbers, and Aldrich Chemical Company Product Numbers). More typical exemplary compounds of the formula $R_5$—OH are those described by Table 2, groups 2–5, 9, and 100–141 wherein $Q_1$ is —OH.

In another embodiment of Process N, Scheme 39, $R_{55}$ is H.

Typically this process embodiment comprises treating compound 281 with an acid catalyst and a compound of the formula $R_{56}$—$X_1$—H, wherein $X_1$ is as defined above to form an amine intermediate to form compound 282. The acid catalyst and $X_1$ are as described above. More typically, the process comprises treating compound 281 with a compound of the formula $R_5$—OH, $R_5$—SH, or $R_5$—NH$_2$, and BF$_3$.Et$_2$O to form compound 282. Still more typically, the process comprises treating compound 281 with a compound of the formula $R_5$—OH and BF$_3$.Et$_2$O to form compound 282. Exemplary compounds of the formula $R_5$—OH are described above.

Exemplary embodiments of this process are given as Examples 65, 86, 92, and 95 below.

Process O, Scheme 39

Compound 282 is used to prepare compound 283 by the following process.

The azide of compound 282 is reduced to form amino compound 283.

Typically the process comprises treating compound 282 with a reducing agent to form compound 283. More typically the process comprises treating compound 282 with hydrogen gas and a catalyst (such as platinum on carbon or Lindlar's catalyst), or reducing reagents (such as a trialkyl or triaryl phosphine as described above). More typically still, the process comprises treating compound 282 with triphenylphosphine in water/THF to form compound 283.

Exemplary embodiments of this process are given as Examples 87, 93, and 96 below.

Process P, Scheme 39

Compound 283 is used to prepare compound 284 by the following process.

The carboxylic acid protecting group is removed.

Typically the process comprises treating compound 283 with a base. More typically, the process comprises treating compound 283 with a metal hydroxide in a suitable solvent such as an aprotic, polar solvent. More typically still, the process comprises treating compound 283 with aqueous potassium hydroxide in THF to produce compound 284.

Exemplary embodiments of this process are given as Examples 88, 94, and 97 below.

Process O, Scheme 40

Compound 283 is used to prepare compound 285 by the following process.

The amine is converted to a protected guanidine.

$R_{57}$ is a guanidine protecting group common in the art, such as BOC or Me.

Typically the process comprises treating compound 283 with a guanidylating reagent such as those common in the art. Exemplary reagents include Bis-BOC Thio-Urea aminoiminomethanesulfonic acid (Kim; et al.; "Tet. Lett." 29(26):3183–3186 (1988) and 1-guanylpyrazoles (Bernatowicz; et al.; "Tet. Lett." 34(21):3389–3392 (1993). More typically, the process comprises treating compound 283 with Bis-BOC Thio-Urea acid. Still more typically, the process comprises treating compound 283 with Bis-BOC Thio-Urea acid and HgCl$_2$ to form compound 285.

An exemplary embodiment of this process is given as Example 67 below.

Process R, Scheme 40

Compound 285 is used to prepare compound 286 by the following process.

The carboxylic acid and guanidine protecting groups are removed.

Typically the process comprises treating compound 285 with a base; followed by treating with an acid, as described above. More typically the process comprises treating compound 285 with a metal hydroxide base, described above, to form an intermediate; and treating the intermediate with acid to form compound 286. Still more typically the process comprises treating compound 285 with aqueous potassium hydroxide and THF, to form an intermediate; and treating the intermediate with TFA to form compound 286.

Process S, Scheme 40.1

Compound 287 is used to prepare compound 288 by the following process.

$E_1$, $J_1$ and $J_2$ of compounds 287 and 288 are as described above. Typically, $E_1$ is —$CO_2R_{51}$ as described above. Typically, $J_1$ is H, F, or methyl, more typically, H. Typically, $J_2$ is H or a linear or branched alkyl of 1 to 6 carbon atoms, more typically, H, methyl, ethyl, n-propyl, or i-propyl, still more typically, H.

$R_{60}$ and $R_{61}$ are groups capable of reacting to form the $R_{63}$ (defined below) substituted aziridine ring of compound 288. Typically, one of $R_{60}$ or $R_{61}$ is a primary or secondary amine, or a group capable of being converted to a primary or secondary amine. Such groups for $R_{60}$ and $R_{61}$ include by way of example and not limitation, —$NH_2$, —$N(H)(R_{6b})$, —$N(R_{6b})_2$, —$N(H)(R_1)$, —$N(R_1)(R_{6b})$, and —$N_3$. The other of $R_{60}$ and $R_{61}$ is typically a group capable of being displaced by a primary or secondary amine to form an aziridine. Such groups include by way of example and not limitation, —OH, —$OR_{6a}$, Br, Cl, and I. Typically, $R_{60}$ and $R_{61}$ are in a trans configuration. More typically, $R_{60}$ is a primary or secondary amine, or a group capable of being converted to a primary or secondary amine and $R_{61}$ is a group capable of being displaced by a primary or secondary amine to form an aziridine. Still more typically, $R_{60}$ is β-azido or β-$NH_2$, and $R_{61}$ is α-OH, α-OMesyl, or α-OTosyl.

$R_{62}$ is described below in Process U, Scheme 40.1.

The process comprises treating compound 287 to form compound 288. This is typically accomplished by treating compound 287 to displace $R_{61}$ by $R_{60}$. More typically, compound 287 is treated to activate $R_{61}$ toward displacement by $R_{60}$. Still more typically, compound 287 is treated to activate $R_{61}$ toward displacement by $R_{60}$, and $R_{60}$ is activated toward displacement of $R_{61}$. If both $R_{60}$ and $R_{61}$ are activated, the activations can be performed simultaneously or sequentially. If the activations are performed sequentially, they can be performed in any order, typically the activation of $R_{61}$ precedes the activation of $R_{60}$.

Activation of $R_{61}$ toward displacement by $R_{60}$ is typically accomplished by treating compound 287 with a hydroxy activating reagent such as mesyl or tosyl chloride. Activation of $R_{60}$ toward displacement of $R_{61}$ is typically accomplished by treating compound 287 to form a primary or secondary amine and treating the amine with a base. By way of example and not limitation, compound 287 is treated with a reducing agent capable of reducing an azide to an amine and a base.

In one embodiment of this process, compound 287 is treated with an $R_{61}$ activating reagent, and an $R_{60}$ activating reagent to produce compound 288. In another embodiment, compound 287 is treated in a suitable solvent with an $R_{61}$ activating reagent, and an $R_{60}$ activating reagent to produce compound 288. In another embodiment, compound 287 is treated with an $R_{61}$ activating reagent, an $R_{60}$ activating reagent, and a base to produce compound 288. In another embodiment, compound 287 is treated in a suitable solvent with an $R_{61}$ activating reagent, an $R_{60}$ activating reagent, and a base to produce compound 288. In another embodiment, compound 287 wherein $R_{60}$ is an azide is treated with an $R_{61}$ activating reagent, and an azide reducing reagent to produce compound 288. In another embodiment, compound 287 wherein $R_{60}$ is an azide is treated in a suitable solvent with an $R_{61}$ activating reagent, and an azide reducing reagent to produce compound 288. In another embodiment, compound 287 wherein $R_{60}$ is an azide is treated with an $R_{61}$ activating reagent, an azide reducing reagent, and a base to produce compound 288. In another embodiment, compound 287 wherein $R_{60}$ is an azide is treated in a suitable solvent with an $R_{61}$ activating reagent, an azide reducing reagent, and a base to produce compound 288. In another embodiment, compound 287 wherein $R_{60}$ is an azide and $R_{61}$ is a hydroxy, is treated with a hydroxy activating reagent, and an azide reducing reagent to produce compound 288. In another embodiment, compound 287 wherein $R_{60}$ is an azide and $R_{61}$ is a hydroxy, is treated in a suitable solvent with an hydroxy activating reagent, and an azide reducing reagent to produce compound 288. In another embodiment, compound 287 wherein $R_{60}$ is an azide and $R_{61}$ is a hydroxy, is treated with a hydroxy activating reagent, an azide reducing reagent, and a base to produce compound 288. In another embodiment, compound 287 wherein $R_{60}$ is an azide and $R_{61}$ is a hydroxy, is treated in a suitable solvent with a hydroxy activating reagent, an azide reducing reagent, and a base to produce compound 288.

An exemplary embodiments of this process are given as Process K, Scheme 38, above.

Process T, Scheme 40.1

Compound 288 is used to prepare compound 289 by the following process.

$R_{64}$ is typically H, $R_{6b}$ or a group capable of being converted to H or $R_{6b}$. More typically, $R_{64}$ is H. $R_{65}$ is typically $G_1$ or a group capable of being converted to $G_1$. More typically, $R_{65}$ is —$N_3$, —CN, or —$(CR_1R_1)_{m1}W_2$. More typically $R_{65}$ is —$N_3$, —$NH_2$, —$N(H)(R_{6b})$, —$N(R_{6b})_2$, —$CH_2N_3$, or —$CH_2CN$.

Typically, compound 288 is treated to form amine 289. More typically, compound 288 is treated with a nucleophile, typically a nitrogen nucleophile such as $R_{65}$, a cationic salt of $R_{65}$, or a protonated analog of $R_{65}$, such as by way of example and not limitation, $NH_3$, an azide salt (such as $NaN_3$, $KN_3$, or the like), HCN, a cyanide salt (such as NaCN, KCN, or the like), or a salt of a cyanoalkyl (e.g. $(CH_2CN)^-$) (such as $NaCH_2CN$, $KCH_2CN$, or the like). Still more typically, compound 288 is treated with an azide salt. Optionally a base, typically a mild base such as an ammonium halide and a solvent, typically a polar, aprotic solvent, such as an ether, amine, or amide are used.

In one embodiment, compound 288 is treated with a nucleophile. In another embodiment, compound 288 is treated with a nucleophile in a suitable solvent to produce compound 289. In another embodiment, compound 288 is treated with a nucleophile and a base to produce compound 289. In another embodiment, compound 288 is treated with a nucleophile and a base in a suitable solvent to produce compound 289. In another embodiment, compound 288 is treated with a nitrogen nucleophile to produce compound 289. In another embodiment, compound 288 is treated with a nitrogen nucleophile in a suitable solvent to produce compound 289. In another embodiment, compound 288 is treated with a nitrogen nucleophile and a base to produce compound 289. In another embodiment, compound 288 is treated with a nitrogen nucleophile and a base in a suitable solvent to produce compound 289. In another embodiment, compound 288 is treated with an azide salt to produce compound 289. In another embodiment, compound 288 is treated with an azide salt in a suitable solvent to produce compound 289. In another embodiment, compound 288 is treated with an azide salt and a base to produce compound 289. In another embodiment, compound 288 is treated with an azide salt and a base in a suitable solvent to produce compound 289.

An exemplary embodiment of this process is given as Process L, Scheme 38, above.

Process U, Scheme 40.1

Compound 289 is used to prepare compound 290 by the following process.

$R_{62}$ is a group capable of reacting with an amine to form the $R_{66}$ (defined below) substituted aziridine ring of compound 290. Typically, $R_{62}$ is a group capable of being displaced by a primary or secondary amine to form an aziridine. Such groups include by way of example and not limitation, —$OR_{53}$, —OH, —$OR_{6a}$, Br, Cl, and I. Typically, $R_{62}$ is in a trans configuration relative to the nitrogen in position 4. More typically, $R_{62}$ is —$OR_{53}$.

$R_{64}$ is H or $R_{6b}$, typically an acid labile protecting group such as $R_{54}$.

$R_{66}$ is H, $R_{6b}$ or $R_{54}$.

The process comprises treating compound 289 to form compound 290. This is typically accomplished by treating compound 289 to displace $R_{62}$ by the amine at position 4. More typically, compound 289 is treated to activate the amine at position 4 toward displacement of $R_{62}$. Still more typically, compound 289 is treated to activate the amine at position 4 toward displacement of $R_{62}$, and $R_{62}$ is activated toward displacement by the amine at position 4. If both $R_{62}$ and the amine at position 4 are activated, the activations can be performed simultaneously or sequentially. If the activations are performed sequentially, they can be performed in any order, typically the activation of $R_{62}$ precedes the activation of the amine at position 4.

Activation of $R_{62}$ toward displacement by the amine at position 4 is typically accomplished by treating compound 289 with a hydroxy activating agent such as those described in process B, Scheme 36. Optionally, $R_{62}$ is deprotected prior to activation. Activation of the amine at position 4 toward $R_{62}$ displacement is typically accomplished by treating compound 289 to form a primary or secondary amine and treating the amine with an acid catalyst such as those described in Process N, Scheme 39, above.

Typically when $R_{62}$ is —$OR_{53}$ and $R_{66}$ is $R_{56}$, the process comprises treating compound 289 with a deprotecting agent to remove group $R_{53}$, an $R_{54}$ producing reagent such as those described in Greene ($R_{54}$-halide, such as acetylchloride, or Tr-Cl, or $R_{54}$—O—$R_{54}$, such as acetic anhydride), and a hydroxy activating group such as those described in Process B, Scheme 36. More typically the process comprises treating compound 289 with a polar, protic solvent, optionally in the presence of an acid catalyst as described above, to form a first intermediate; treating the first intermediate with Tr-Cl in a polar, aprotic solvent, such as an amine, to form a second intermediate; and treating the second intermediate with a sulfonic acid halide, such as mesyl chloride or para toluene sulfonyl chloride, in a polar aprotic solvent, such as an amine, to produce compound 290. Still more typically, the process comprises treating compound 289 with methanol and HCl, to form a first intermediate; treating the first intermediate with Tr-Cl and triethylamine, to form a second intermediate; and treating the second intermediate with mesyl chloride and triethylamine, to produce compound 290.

In one embodiment compound 289 is treated with an acid catalyst to produce compound 290. In another embodiment compound 289 is treated with an acid catalyst in a suitable solvent to produce compound 290. In another embodiment compound 289 is treated with a hydroxy activating reagent and an acid catalyst to produce compound 290. In another embodiment compound 289 is treated with a hydroxy activating reagent and an acid catalyst in a suitable solvent to produce compound 290. In another embodiment compound 289 is treated with a hydroxy deprotecting reagent, a hydroxy activating reagent and an acid catalyst to produce compound 290. In another embodiment compound 289 is treated with a hydroxy activating reagent and an acid catalyst in a suitable solvent to produce compound 290.

An exemplary embodiment of this process is given as Process M, Scheme 38, above.

Process V, Scheme 40.1

Compound 290 is used to prepare compound 291 by the following process.

Aziridine 290 is treated to form compound 291. Typically, aziridine 290 is opened by acid catalyzed ring opening and the resulting amine is acylated.

$R_{68}$ is independently H, $R_{6b}$, $R_1$ or $R_{55}$ as defined above. Typically $R_{55}$ is —$C(O)R_5$. Typically one $R_{68}$ is H or $R_{6b}$ and the other is $W_3$.

$R_{67}$ is $U_1$ as described above. Typically $R_{67}$ is $W_6$—O—, $W_6$—S—, or $W_6$—N(H)—. More typically, $R_{67}$ is $R_5$—O—, $R_5$—S—, or $R_5$—N(H)—.

Typically the process comprises treating compound 290 with an acid catalyst and a compound of the formula $W_6$—$X_1$—H, wherein $X_1$ is as defined above to form an amine intermediate; and treating the amine intermediate with a compound of the formula $W_3$—$X_1$—$W_3$, or $W_3$—$X_{10}$, wherein $X_{10}$ is a leaving group, to form compound 291. The treatment with a compound of the formula W6—X1—H and an acid catalyst may be prior to or simultaneous with the treatment with a compound of the formula $W_3$—$X_1$—$W_3$, or $W_3$—$X_{10}$. The acid catalyst is typically one of those described in Process N, Scheme 39, above. More typically, the process comprises treating compound 290 with a compound of the formula $R_5$—OH, $R_5$—SH, or $R_5$—$NH_2$ and an acid catalyst; and treating the intermediate with an alkanoic acid anhydride to form compound 291.

One embodiment comprises treating compound 290 with a compound of the formula $W_6$—$X_1$—H and an acid catalyst to produce compound 291. Another embodiment comprises treating compound 290 with a compound of the formula $W_6$—$X_1$—H and an acid catalyst in a suitable solvent to produce compound 291. Another embodiment comprises treating compound 290 with a compound of the formula $W_6$—$X_1$—H, an acid catalyst and a compound of the formula $W_3$—$X_1$—$W_3$ or $W_3$—$X_{10}$ to produce compound 291. Another embodiment comprises treating compound 290 with a compound of the formula $W_6$—$X_1$—H, an acid catalyst and a compound of the formula $W_3$—$X_1$—$W_3$ or $W_3$—$X_{10}$ in a suitable solvent to produce compound 291.

Exemplary embodiments of this process are given as Process N, Scheme 39, above.

Process W, Scheme 40.1

Compound 291 is used to prepare compound 292 by the following process.

Compound 291 is treated to form compound 292. Typically $R_{65}$ is converted to form $G_1$. $U_1$ is an embodiment of $R_{67}$ and $T_1$ is an embodiment of —$N(R_{68})_2$ prepared in Process V, Scheme 40.1, above.

In one embodiment, $R_{65}$ is deprotected, alkylated, guanidinylated, oxidized or reduced to form $G_1$. Any number of such treatments can be performed in any order or simultaneously. By way of example and not limitation, when $R_{65}$ is azido, embodiments of this process include Processes O, OQ, OQR, and OP. Typical alkylating agents are those common in the art including, by way of example and not limitation, an alkyl halide such as methyl iodide, methyl bromide, ethyl iodide, ethyl bromide, n-propyl iodide, n-propyl bromide, i-propyl iodide, i-propyl bromide; and an olefin oxide such as ethylene oxide or propylene oxide. A base catalyst as described herein maybe optionally employed in the alkylation step.

One embodiment comprises treating compound 291 wherein $R_{65}$ is azido with a reducing agent to produce compound 292. Another embodiment comprises treating compound 291 wherein $R_{65}$ is azido with a reducing agent to produce compound 292 in a suitable solvent. Another embodiment comprises treating compound 291 wherein $R_{65}$ is amino with an alkylating agent to produce compound 292. Another embodiment comprises treating compound 291 wherein $R_{65}$ is amino with an alkylating agent to produce compound 292 in a suitable solvent. Another embodiment comprises treating compound 291 wherein $R_{65}$ is azido with a reducing agent and an alkylating agent to produce compound 292. Another embodiment comprises treating compound 291 wherein $R_{65}$ is azido with a reducing agent and an alkylating agent to produce compound 292 in a suitable solvent. Another embodiment comprises treating compound 291 wherein $R_{65}$ is amino with an alkylating agent and a base catalyst to produce compound 292. Another embodiment comprises treating compound 291 wherein $R_{65}$ is amino with an alkylating agent and a base catalyst to produce compound 292 in a suitable solvent. Another embodiment comprises treating compound 291 wherein $R_{65}$ is azido with a reducing agent, an alkylating agent and a base catalyst to produce compound 292. Another embodiment comprises treating compound 291 wherein $R_{65}$ is azido with a reducing agent, an alkylating agent and a base catalyst to produce compound 292 in a suitable solvent.

Exemplary embodiments of this process are given as Process O, Scheme 39, above.

Exemplary embodiments of this process are given as Examples 68 and 69 below.

TABLE 25

Exemplary Compounds of Formula $R_5$-OH (CAS No.)

C4 Fluoro Alcohols (R*,R*)-(±)-3-fluoro-2-Butanol (139755-61-6)
1-fluoro-2-Butanol (124536-12-5)
(R)-3-fluoro-1-Butanol (120406-57-7)
3-fluoro-1-Butanol (19808-95-8)
4-fluoro-2-Butanol (18804-31-4)
(R*,S*)-3-fluoro-2-Butanol (6228-94-0)
(R*,R*)-3-fluoro-2-Butanol (6133-82-0)
2-fluoro-1-Butanol (4459-24-9)
2-fluoro-2-methyl-1-Propanol (3109-99-7)
3-fluoro-2-Butanol (1813-13-4)
4-fluoro-1-Butanol (372-93-0)
1-fluoro-2-methyl-2-Propanol (353-80-0)
C5 Fluoro Alcohols 2-fluoro-1-Pentanol (123650-81-7)
(R)-2-fluoro-3-methyl-1-Butanol (113943-11-6)
(S)-2-fluoro-3-methyl-1-Butanol (113942-98-6)
4-fluoro-3-methyl-1-Butanol (104715-25-5)
1-fluoro-3-Pentanol (30390-84-2)
4-fluoro-2-Pentanol (19808-94-7)
5-fluoro-2-Pentanol (18804-35-8)

TABLE 25-continued

Exemplary Compounds of Formula $R_5$-OH (CAS No.)

3-fluoro-2-methyl-2-Butanol (7284-96-0)
2-fluoro-2-methyl-1-Butanol (4456-02-4)
3-fluoro-3-methyl-2-Butanol (1998-77-2)
5-fluoro-1-Pentanol (592-80-3)
C6 Fluoro Alcohols (R-(R*,S*))-2-fluoro-3-methyl-1-Pentanol (168749-88-0)
1-fluoro-2,3-dimethyl-2-Butanol (161082-90-2)
2-fluoro-2,3-dimethyl-1-Butanol (161082-89-9)
(R)-2-fluoro-4-methyl-1-Pentanol (157988-30-2)
(S-(R*,R*))-2-fluoro-3-methyl-1-Pentanol (151717-18-9)
(R*,S*)-2-fluoro-3-methyl-1-Pentanol (151657-14-6)
(S)-2-fluoro-3,3-dimethyl-1-Butanol (141022-94-8)
(M)-2-fluoro-2-methyl-1-Pentanol (137505-57-8)
(S)-2-fluoro-1-Hexanol (127608-47-3)
3-fluoro-3-methyl-1-Pentanol (112754-22-0)
3-fluoro-2-methyl-2-Pentanol (69429-54-5)
2-fluoro-2-methyl-3-Pentanol (69429-53-4)
1-fluoro-3-Hexanol (30390-85-3)
5-fluoro-2-methyl-2-Pentanol (21871-78-3)
5-fluoro-3-Hexanol (19808-92-5)
4-fluoro-3-methyl-2-Pentanol (19808-90-3)
4-fluoro-4-methyl-2-Pentanol (19031-69-7)
1-fluoro-3,3-dimethyl-2-Butanol (4604-66-4)
2-fluoro-2-methyl-1-Pentanol (4456-03-5)
2-fluoro-4-methyl-1-Pentanol (4455-95-2)
2-fluoro-1-Hexanol (1786-48-7)
3-fluoro-2,3-dimethyl-2-Butanol (661-63-2)
6-fluoro-1-Hexanol (373-32-0)
C7 Fluoro Alcohols 5-fluoro-5-methyl-1-Hexanol (168268-63-1)
(R)-1-fluoro-2-methyl-2-Hexanol (153683-63-7)
(S)-3-fluoro-1-Heptanol (141716-56-5)
(S)-2-fluoro-2-methyl-1-Hexanol (132354-09-7)
(R)-3-fluoro-1-Heptanol (120406-54-4)
(S)-2-fluoro-1-Heptanol (110500-31-7)
1-fluoro-3-Heptanol (30390-86-4)
7-fluoro-2-Heptanol (18804-38-1)
2-ethyl-2-(fluoromethyl)-1-Butanol (14800-35-2)
2-(fluoromethyl)-2-methyl-1-Pentanol (13674-80-1)
2-fluoro-5-methyl-1-Hexanol (4455-97-4)
2-fluoro-1-Heptanol (1786-49-8)
7-fluoro-1-Heptanol (408-16-2)
C8 Fluoro Alcohols (M)-2-fluoro-2-methyl-1-Heptanol (137505-55-6)
6-fluoro-6-methyl-1-Heptanol (135124-57-1)
1-fluoro-2-Octanol (127296-11-1)
(R)-2-fluoro-1-Octanol (118205-91-7)
(±)-2-fluoro-2-methyl-1-Heptanol (117169-40-1)
(S)-2-fluoro-1-Octanol (110500-32-8)
(S)-1-fluoro-2-Octanol (110270-44-5)
(R)-1-fluoro-2-Octanol (110270-42-3)
(±)-1-fluoro-2-Octanol (110229-70-4)
2-fluoro-4-methyl-3-Heptanol (87777-41-1)
2-fluoro-6-methyl-1-Heptanol (4455-99-6)
2-fluoro-1-Octanol (4455-93-0)
8-fluoro-1-Octanol (408-27-5)
C9 Fluoro Alcohols 6-fluoro-2,6-dimethyl-2-Heptanol (160981-64-6)
(S)-3-fluoro-1-Nonanol (160706-24-1)
(R-(R*,R*))-3-fluoro-2-Nonanol (137909-46-7)
(R-(R*,S*))-3-fluoro-2-Nonanol (137909-45-6)
3-fluoro-2-Nonanol (137639-20-4)
(S-(R*,R*))-3-fluoro-2-Nonanol (137639-19-1)
(S-(R*,S*))-3-fluoro-2-Nonanol (137639-18-0)
(±)-3-fluoro-1-Nonanol (134056-76-1)
2-fluoro-1-Nonanol (123650-79-3)
2-fluoro-2-methyl-1-Octanol (120400-89-7)
(R)-2-fluoro-1-Nonanol (118243-18-8)
(S)-1-fluoro-2-Nonanol (111423-41-7)
(S)-2-fluoro-1-Nonanol (110500-33-9)
1-fluoro-3-Nonanol (30390-87-5)
2-fluoro-2,6-dimethyl-3-Heptanol (684-74-2)
9-fluoro-1-Nonanol (463-24-1)

TABLE 25-continued

Exemplary Compounds of Formula $R_5$-OH (CAS No.)

C10 Fluoro Alcohols 4-fluoro-1-Decanol (167686-45-5)
(P)-10-fluoro-3-Decanol (145438-91-1)
(R-(R*,R*))-3-fluoro-5-methyl-1-Nonanol (144088-79-9)
(P)-10-fluoro-2-Decanol (139750-57-5)
1-fluoro-2-Decanol (130876-22-1)
(S)-2-fluoro-1-Decanol (127608-48-4)
(R)-1-fluoro-2-Decanol (119 105-16-7)
(S)-1-fluoro-2-Decanol (119105-15-6)
2-fluoro-1-Decanol (110500-35-1)
1-fluoro-5-Decanol (106533-31-7)
4-fluoro-2,2,5,5-tetramethyl-3-Hexanol (24212-87-1)
10-fluoro-1-Decanol (334-64-5)

C11 Fluoro Alcohols 10-fluoro-2-methyl-1-Decanol (139750-53-1)
2-fluoro-1-Undecanol (110500-34-0)
8-fluoro-5,8-dimethyl-5-Nonanol (110318-90-6)
11-fluoro-2-Undecanol (101803-63-8)
11-fluoro-1-Undecanol (463-36-5)

C12 Fluoro Alcohols 11-fluoro-2-methyl-1-Undecanol (139750-52-0)
1-fluoro-2-Dodecanol (132547-33-2)
(R*,S*)-7-fluoro-6-Dodecanol (130888-52-7)
(R*,R*)-7-fluoro-6-Dodecanol (130876-18-5)
(S)-2-fluoro-1-Dodecanol (127608-49-5)
12-fluoro-2-pentyl--Heptanol (120400-91-1)
(R*,S*)-(±)-7-fluoro-6-Dodecanol (119174-39-9)
(R*,R*)-(±)-7-fluoro-6-Dodecanol (119174-38-8)
2-fluoro-1-Dodecanol (110500-36-2)
11-fluoro-methyl-2-Undecanol (101803-67-2)
1-fluoro-1-Dodecanol (100278-87-3)
12-fluoro-1-Dodecanol (353-31-1)

C4 Nitro Alcohols (R)-4-nitro-2-Butanol (129520-34-9)
(S)-4-nitro-2-Butanol (120293-74-5)
4-nitro-1-Butanol radical ion(1-) (83051-13-2)
(R*,S*)-3-nitro-2-Butanol (829 78-02-7)
(R*,R*)-3-nitro-2-Butanol (82978-01-6)
4-nitro-1-Butanol (75694-90-5)
(±)-4-nitro-2-Butanol (72959-86-5)
4-nitro-2-Butanol (55265-82-2),
1-aci-nitro-2-Butanol (22916-75-2)
3-aci-nitro2-Butanol (22916-74-1)
2-methyl-3-nitro-1-Propanol (21527-52-6)
3-nitro-2-Butanol (6270-16-2)
2-methyl-1-nitro-2-Propanol (5447-98-3)
2-aci-nitro-1-Butanol (4167-97-9)
1-nitro-2-Butanol (3156-74-9)
2-nitro-1-Butanol (609-31-4)
2-methyl-2-nitro-1-Propanol (76-39-1)

C5 Nitro Alcohols (R)-3-methyl-3-nitro-2-Butanol (154278-27-0)
3-methyl-1-nitro-1-Butanol (153977-20-9)
(±)-1-nitro-3-Pentanol (144179-64-6)
(S)-1-nitro-3-Pentanol (144139-35-5)
(R)-1-nitro-3-Pentanol (144139-34-4)
(R)-3-methyl-1-nitro-2-Butanol (141434-98-2)
(±)-3-methyl-1-nitro-2-Butanol (141377-55-1)
(R*,R*)-3-nitro-2-Pentanol (13875 1-72-1)
(R*,S*)-3-nitro-2-Pentanol (138751-71-0)
(R*,R*)-2-nitro-3-Pentanol (138668-26-5)
(R*,S*)-2-nitro-3-Pentanol (138668-19-6)
3-nitro-1-Pentanol (135462-98-5)
(R)-5-nitro-2-Pentanol (129520-35-0)
(S)-5-nitro-2-Pentanol (120293-75-6)
4-nitro-1-Pentanol (116435-64-4)
(±)-3-methyl-3-nitro-2-Butanol (114613-30-8)
(S)-3-methyl-3-nitro-2-Butanol (109849-50-5)
3-methyl-4-nitro-2-Butanol (96597-30-7)
(±)-5-nitro-2-Pentanol (78174-81-9)
2-methyl-2-nitro-1-Butanol (77392-55-3)
3-methyl-2-nitro-1-Butanol (77392-54-2)

3-methyl-4-nitro-1-Butanol (75694-89-2)
2-methyl-4-nitro-2-Butanol (72183-50-7)
3-methyl-3-nitro-1-Butanol (65102-50-3)
5-nitro-2-Pentanol (54045-33-9)
2-methyl-3-aci-nitro-2-Butanol (22916-79-6)
2-methyl-1-aci-nitro-2-Butanol (22916-78-5)
2-methyl-3-nitro-2-Butanol (22916-77-4)
2-methyl-1-nitro-2-Butanol (22916-76-3)
5-nitro-1-Pentanol (21823-27-8)
2-methyl-3-nitro-1-Butanol (21527-53-7)
2-nitro-3-Pentanol (20575-40-0)
3-methyl-3-nitro-2-Butanol (20575-38-6)
3-nitro-2-Pentanol (5447-99-4)
2-nitro-1-Pentanol (2899-90-3)
3-methyl-1-nitro-2-Butanol (2224-38-6)
1-nitro-2-Pentanol (2224-37-5)

C6 Nitro Alcohols (–)-4-methyl-1-nitro-2-Pentanol (158072-33-4)
3-(nitromethyl)-3-Pentanol (156544-56-8)
(R*,R*)-3-methyl-2-nitro-3-Pentanol (148319-17-9)
(R*,S*)-3-methyl-2-nitro-3-Pentanol (148319-16-8)
6-nitro-2-Hexanol (146353-95-9)
(±)-6-nitro-3-Hexanol (144179-63-5)
(S)-6-nitro-3-Hexanol (144139-33-3)
(R)-6-nitro-3-Hexanol (144139-32-2)
3-nitro-2-Hexanol (127143-52-6)
5-nitro-2-Hexanol (110364-37-9)
4-methyl-1-nitro-2-Pentanol (102014-44-8)
(R*,S*)-2-methyl-4-nitro-3-Pentanol (82945-29-7)
(R*,R*)-2-methyl-4-nitro-3-Pentanol (82945-20-8)
2-methyl-5-nitro-2-Pentanol (79928-61-3)
2,3-dimethyl-1-nitro-2-Butanol (68454-59-1)
2-methyl-3-nitro-2-Pentanol (59906-62-6)
3,3-dimethyl-1-nitro-2-Butanol (58054-88-9)
2,3-dimethyl-3-nitro-2-Butanol (51483-61-5)
2-methyl-1-nitro-2-Pentanol (49746-26-1)
3,3-dimethyl-2-nitro-1-Butanol (37477-66-0)
6-nitro-1-Hexanol (31968-54-4)
2-methyl-3-nitro-1-Pentanol (21527-55-9)
2,3-dimethyl-3-nitro-1-Butanol (21527-54-8)
2-methyl-4-nitro-3-Pentanol (20570-70-1)
2-methyl-4-nitro-3-Pentanol (20570-67-6)
2-nitro-3-Hexanol (5448-00-0)
4-nitro-3-Hexanol (5342-71-2)
4-methyl-4-nitro-1-Pentanol (5215-92-9)
1-nitro-2-Hexanol (2224-40-0)

C7 Nitro Alcohols 1-nitro-4-Heptanol (167696-66-4)
(R)-1-nitro-2-Heptanol (146608-19-7)
7-nitro-1-Heptanol (133088-94-5)
(R*,S*)-3-nitro-2-Heptanol (127143-73-1)
(R*,R*)-3-nitro-2-Heptanol (127143-72-0)
(R*,S*)-2-nitro-3-Heptanol (127143-71-9)
(R*,R*)-2-nitro-3-Heptanol (127143-70-8)
(R*,S*)-2-methyl-5-nitro-3-Hexanol (103077-95-8)
(R*,R*)2-methyl-5-nitro-3-Hexanol (103077-87-8)
3-ethyl-4-nitro-1-Pentanol (92454-38-1)
3-ethyl-2-nitro-3-Pentanol (77922-54-4)
2-nitro-3-Heptanol (61097-77-6)
2-methyl-1-nitro-3-Hexanol (35469-17-1)
2-methyl-4-nitro-3-Hexanol (20570-71-2)
2-methyl-2-nitro-3-Hexanol (20570-69-8)
5-methyl-5-nitro-2-Hexanol (7251-87-8)
1-nitro-2-Heptanol (6302-74-5)
3-nitro-4-Heptanol (5462-04-4)
4-nitro-3-Heptanol (5342-70-1)

C8 Nitro Alcohols (±)-1-nitro-3-Octanol (141956-93-6)
1-nitro-4-Octanol (167642-45-7)
(S)-1-nitro-4-Octanol (167642-18-4)
6-methyl-6-nitro-2-Heptanol (142991-77-3)
(R*,S*)-2-nitro-3-Octanol (135764-74-8)
(R*,R*)-2-nitro-3-Octanol (135764-73-7)
5-nitro-4-Octanol (132272-46-9)

TABLE 25-continued

Exemplary Compounds of Formula R₅-OH (CAS No.)

(R*,R*)-3-nitro-4-Octanol (130711-79-4)
(R*,S*)-3-nitro-4-Octanol (130711-78-3)
4-ethyl-2-nitro-3-Hexanol (126939-74-0)
2-nitro-3-Octanol (126939-73-9)
1-nitro-3-Octanol (126495-48-5)
(R*,R*)-(±)-3-nitro-4-Octanol (118869-22-0)
(R*,S*)-(±)-3-nitro-4-Octanol (118869-21-9)
3-nitro-2-Octanol (127143-53-7)
(R*,S*)-2-methyl-5-nitro-3-Heptanol (103078-03-1)
(R*,R*)-2-methyl-5-nitro-3-Heptanol (103077-90-3)
8-nitro-1-Octanol (101972-90-1)
(±)-2-nitro-1-Octanol (96039-95-1)
3,4-dimethyl-1-nitro-2-Hexanol (64592-02-5)
3-(nitromethyl)-4-Heptanol (35469-20-6)
2,5-dimethyl-1-nitro-3-Hexanol (35469-19-3)
2-methyl-1-nitro-3-Heptanol (35469-18-2)
2,4,4-trimethyl-1-nitro-2-Pentanol (35223-67-7)
2,5-dimethyl-4-nitro-3-Hexanol (22482-65-1)
2-nitro-1-Octanol (2882-67-9)
1-nitro-2-Octanol (2224-39-7)

C9 Nitro Alcohols 4-nitro-3-Nonanol (160487-89-8)
(R*,R*)-3-ethyl-2-nitro-3-Heptanol (148319-18-0)
2,6-dimethyl-6-nitro-2-Heptanol (117030-50-9)
(R*,S*)-2-nitro-4-Nonanol (103077-93-6)
(R*,R*)-2-nitro-4-Nonanol (103077-85-6)
2-nitro-3-Nonanol (99706-65-7)
9-nitro-1-Nonanol (81541-84-6)
2-methyl-1-nitro-3-Octanol (53711-06-1)
4-nitro-5-Nonanol (34566-13-7)
2-methyl-3-(nitromethyl)-3-Heptenol (5582-88-7)
1-nitro-2-Nonanol (4013-87-0)

C10 Nitro Alcohols 2-nitro-4-Decanol (141956-94-7)
(R*,S*)-3-nitro-4-Decanol (135764-76-0)
(R*,R*)-3-nitro-4-Decanol (135764-75-9)
5,5-dimethyl-4-(2-nitroethyl)-1-Hexanol (133088-96-7)
(R*,R*)-(±)-3-nitro-4-Decanol (118869-20-8)
(R*,S*)-(±)-3-nitro-4-Decanol (18869-19-5)
5-nitro-2-Decanol (112882-29-8)
3-nitro-4-Decanol (93297-82-6)
4,6,6-trimethyl-1-nitro-2-Heptanol (85996-72-1)
2-methyl-2-nitro-3-Nonanol (80379-17-5)
1-nitro-2-Decanol (65299-35-6)
2,2,4,4-tetramethyl-3-(nitromethyl)-3-Pentanol (58293-26-8)

C11 Nitro Alcohols 11-nitro-5-Undecanol (167696-69-7)
(R*,R*)-2-nitro-3-Undecanol (144434-56-0)
(R*,S*)-2-nitro-3-Undecanol (144434-55-9)
2-nitro-3-Undecanol (143464-92-0)
2,2-dimethyl-4-nitro-3-Nonanol (126939-76-2)
4,8-dimethyl-2-nitro-1-Nonanol (118304-30-6)
11-nitro-1-Undecanol (81541-83-5)

C12 Nitro Alcohols 2-methyl-2-nitro-3-Undecanol (126939-75-1)
2-nitro-1-Dodecanol (62322-32-1)
1-nitro-2-Dodecanol (62322-31-0)
2-nitro-3-Dodecanol (82981-40-6)
12-nitro-1-Dodecanol (81541-78-8)

TABLE 6

| Exemplary Compounds of Formula R₅-OH | (CAS No. | /Aldrich No.) |
|---|---|---|
| 3-BROMO-1-PROPANOL | 627189 | 167169 |
| 1,3-DICHLORO-2-PROPANOL | 96231 | 184489 |
| 3-CHLORO-2,2-DIMETHYL-1-PROPANOL | 13401564 | 189316 |
| 2,2-BIS(CHLOROMETHYL)-1-PROPANOL | 5355544 | 207691 |
| 1,3-DIFLUORO-2-PROPANOL | 453134 | 176923 |
| 2-(METHYLTHIO)ETHANOL | 5271385 | 226424 |

TABLE 6-continued

| Exemplary Compounds of Formula R₅-OH | (CAS No. | /Aldrich No.) |
|---|---|---|
| 2-(DIBUTYLAMINO)ETHANOL | 102818 | 168491 |
| 2-(DIISOPROPYLAMINO)ETHANOL | 96800 | 168726 |
| 3-METHYL-3-BUTEN-1-OL | 763326 | 129402 |
| 2-METHYL-3-BUTEN-2-OL | 115184 | 136816 |
| 3-METHYL-2-BUTEN-1-OL | 556821 | 162353 |
| 4-HEXEN-1-OL | 928927 | 237604 |
| 5-HEXEN-1-OL | 821410 | 230324 |
| CIS-2-HEXEN-1-OL | 928949 | 224707 |
| TRANS-3-HEXEN-1-OL | 928972 | 224715 |
| TRANS-2-HEXEN-1-OL | 928950 | 132667 |
| (+/-)-6-METHYL-5-HEPTEN-2-OL | 4630062 | 195871 |
| DIHYDROMYRCENOL | 18479588 | 196428 |
| TRANS,TRANS-2,4-HEXADIEN-1-OL | 17102646 | 183059 |
| 2,4-DIMETHYL-2,6-HEPTADIEN-1-OL | 80192569 | 238767 |
| GERANIOL | 106241 | 163333 |
| 3-BUTYN-1-OL | 927742 | 130850 |
| 3-PENTYN-1-OL | 10229104 | 208698 |
| ISETHIONIC ACID, SODIUM SALT | 1562001 | 220078 |
| (4-(2-HYDROXYETHYL)-1-PIPERAZINE-PROPANESULFONIC ACID) | 16052065 | 163740 |
| HEPES, SODIUM SALT | 75277393 | 233889 |
| 1-METHYLCYCLOPROPANEMETHANOL | 2746147 | 236594 |
| 2-METHYLCYCLOPROPANEMETHANOL | 6077721 | 233811 |
| (+/-)-CHRYSANTHEMYL ALCOHOL | 18383590 | 194654 |
| CYCLOBUTANEMETHANOL | 4415821 | 187917 |
| 3-CYCLOPENTYL-1-PROPANOL | 767055 | 187275 |
| 1-ETHYNYLCYCLOPENTANOL | 17356193 | 130869 |
| 3-METHYLCYCLOHEXANOL | 591231 | 139734 |
| 3,3,5,5-TETRAMETHYLCYCLOHEXANOL | 2650400 | 190624 |
| 4-CYCLOHEXYL-1-BUTANOL | 4441570 | 197408 |
| DIHYDROCARVEOL | 619012 | 218421 |
| (1S,2R,5S)-(±)-MENTHOL | 15356704 | 224464 |
| (1S,2S,5R)-(±)-NEOMENTHOL | 2216526 | 235180 |
| (1S,2R,5R)-(±)-ISOMENTHOL | 23283978 | 242195 |
| (+/-)-3-CYCLOHEXENE-1'-METHANOL | 72581329 | 162167 |
| (±)-P-MENTH-1-EN-9-OL | 13835308 | 183741 |
| (S)-(-)-PERILLYL ALCOHOL | 536594 | 218391 |
| TERPINEN-4-OL | 562743 | 218383 |
| ALPHA-TERPINEOL | 98555 | 218375 |
| (+/-)-TRANS-P-MENTH-6-ENE-2,8-DIOL | 32226543 | 247774 |
| CYCLOHEPTANEMETHANOL | 4448753 | 138657 |
| TETRAHYDROFURFURYL ALCOHOL | 97994 | 185396 |
| (S)-(+)-2-PYRROLIDINEMETHANOL | 23356969 | 186511 |
| 1-METHYL-2-PYRROLIDINEETHANOL | 67004642 | 139513 |
| 1-ETHYL-4-HYDROXYPIPERIDINE | 3518830 | 224634 |
| 3-HYDROXYPIPERIDINE HYDROCHLORIDE | 64051792 | 174416 |
| (+/-)-2-PIPERIDINEMETHANOL | 3433372 | 155225 |
| 3-PIPERIDINEMETHANOL | 4606659 | 155233 |
| 1-METHYL-2-PIPERIDINEMETHANOL | 20845345 | 155241 |
| 1-METHYL-3-PIPERIDINEMETHANOL | 7583531 | 146145 |
| 2-PIPERIDINEETHANOL | 1484840 | 131520 |
| 4-HYDROXYPIPERIDINE | 5382161 | 128775 |
| 4-METHYL-1-PIPERAZINEPROPANOL | 5317339 | 238716 |
| EXO-NORBORNEOL | 497370 | 179590 |
| ENDO-NORBORNEOL | 497369 | 186457 |
| 5-NORBORNENE-2-METHANOL | 95125 | 248533 |
| (+/-)-3-METHYL-2-NORBORNANEMETHANOL | 6968758 | 130575 |
| ((1S)-ENDO)-(-)-BORNEOL | 464459 | 139114 |
| (1R)-ENDO-(±)-FENCHYL ALCOHOL | 2217029 | 196444 |
| 9-ETHYLBICYCLO(3.3.1)NONAN-9-OL | 21951333 | 193895 |
| (+/-)-ISOPINOCAMPHEOL | 51152115 | 183229 |
| (S)-CIS-VERBENOL | 18881044 | 247065 |
| (1R,2R,3R,5S)-(-)-ISOPINOCAMPHEOL | 25465650 | 221902 |
| (1R)-(-)-MYRTENOL | 515004 | 188417 |
| 1-ADAMANTANOL | 768956 | 130346 |
| 3,5-DIMETHYL-1-ADAMANTANOL | 707379 | 231290 |
| 2-ADAMANTANOL | 700572 | 153826 |
| 1-ADAMANTANEMETHANOL | 770718 | 184209 |
| 1-ADAMANTANEETHANOL | 6240115 | 188115 |
| 3-FURANMETHANOL | 4412913 | 196398 |
| FURFURYL ALCOHOL | 98000 | 185930 |
| 2-(3-THIENYL)ETHANOL | 13781674 | 228796 |
| 4-METHYL-5-IMIDAZOLEMETHANOL HYDROCHLORIDE | 38585625 | 227420 |
| METRONIDAZOLE | 443481 | 226742 |
| 4-(HYDROXYMETHYL)IMIDAZOLE HYDROCHLORIDE | 32673419 | 219908 |

TABLE 6-continued

Exemplary Compounds of Formula $R_5$-OH (CAS No. /Aldrich No.)

| Compound | CAS No. | Aldrich No. |
|---|---|---|
| 4-METHYL-5-THIAZOLEETHANOL | 137008 | 190675 |
| 2-(2-HYDROXYETHYL)PYRIDINE | 103742 | 128643 |
| 2-HYDROXY-6-METHYLPYRIDINE | 3279763 | 128740 |
| 4-PYRIDYLCARBINOL | 586958 | 151629 |
| 3-PYRIDYLCARBINOL N-OXIDE | 6968725 | 184446 |
| 1-BENZYL-4-HYDROXYPIPERIDINE | 4727724 | 152986 |
| 1-(4-CHLOROPHENYL)-1-CYCLOPENTANEMETHANOL | 80866791 | 188697 |
| (4S,5S)-(−)-2-METHYL-5-PHENYL-2-OXAZOLINE-4-METHANOL | 53732415 | 187666 |
| 6-(4-CHLOROPHENYL)-4,5-DIHYDRO-2-(2-HYDROXYBUTYL)-3(2H)-PYRIDAZINONE | 38958826 | 243728 |
| N-(2-HYDROXYETHYL)PHTHALIMIDE | 3891074 | 138339 |
| 2-NAPHTHALENEETHANOL | 1485070 | 188107 |
| 1-NAPHTHALENEETHANOL | 773999 | 183458 |
| 2-ISOPROPYLPHENOL | 88697 | 129526 |
| 4-CHLORO-ALPHA,ALPHA-DIMETHYLPHENETHYL ALCOHOL | 5468973 | 130559 |
| 4-FLUORO-ALPHA-METHYLBENZYL ALCOHOL | 403418 | 132705 |
| 3-PHENYL-1-PROPANOL | 122974 | 140856 |
| 3-(4-METHOXYPHENYL)-1-PROPANOL | 5406188 | 142328 |
| 4-FLUOROPHENETHYL ALCOHOL | 7589277 | 154172 |
| 4-METHOXYPHENETHYL ALCOHOL | 702238 | 154180 |
| TRANS-2-METHYL-3-PHENYL-2-PROPEN-1-OL | 1504558 | 155888 |
| 2-ANILINOETHANOL | 122985 | 156876 |
| 3-FLUOROBENZYL ALCOHOL | 456473 | 162507 |
| 2-FLUOROBENZYL ALCOHOL | 446515 | 162515 |
| 2-METHYL-1-PHENYL-2-PROPANOL | 100867 | 170275 |
| ALPHA-(CHLOROMETHYL)-2,4-DICHLOROBENZYL ALCOHOL | 13692143 | 178403 |
| 2-PHENYL-1-PROPANOL | 1123859 | 179817 |
| 4-CHLOROPHENETHYL ALCOHOL | 1875883 | 183423 |
| 4-BROMOPHENETHYL ALCOHOL | 4654391 | 183431 |
| 4-NITROPHENETHYL ALCOHOL | 100276 | 183466 |
| 2-NITROPHENETHYL ALCOHOL | 15121843 | 183474 |
| BETA-ETHYLPHENETHYL ALCOHOL | 2035941 | 183482 |
| 4-PHENYL-1-BUTANOL | 3360496 | 184756 |
| 2-METHOXYPHENETHYL ALCOHOL | 7417187 | 187925 |
| 3-METHOXYPHENETHYL ALCOHOL | 5020417 | 187933 |
| 3-PHENYL-1-BUTANOL | 2722363 | 187976 |
| 2-METHYLPHENETHYL ALCOHOL | 19819988 | 188123 |
| 3-METHYLPHENETHYL ALCOHOL | 1875894 | 188131 |
| 4-METHYLPHENETHYL ALCOHOL | 699025 | 188158 |
| 5-PHENYL-1-PENTANOL | 10521912 | 188220 |
| 4-(4-METHOXYPHENYL)-1-BUTANOL | 22135508 | 188239 |
| 4-(4-NITROPHENYL)-1-BUTANOL | 79524202 | 188751 |
| 3,3-DIPHENYL-1-PROPANOL | 20017678 | 188972 |
| 1-PHENYL-2-PROPANOL | 14898874 | 189235 |
| (+/−)-ALPHA-ETHYLPHENETHYL ALCOHOL | 701702 | 190136 |
| 1,1-DIPHENYL-2-PROPANOL | 29338496 | 190756 |
| 3-CHLOROPHENETHYL ALCOHOL | 5182445 | 193518 |
| 2-CHLOROPHENETHYL ALCOHOL | 19819955 | 193844 |
| (+/−)-1-PHENYL-2-PENTANOL | 705737 | 195286 |
| 2,2-DIPHENYLETHANOL | 1883325 | 196568 |
| 4-ETHOXY-3-METHOXYPHENETHYL ALCOHOL | 77891293 | 197599 |
| 3,4-DIMETHOXYPHENETHYL ALCOHOL | 7417212 | 197653 |
| 3-(3,4-DIMETHOXYPHENYL)-1-PROPANOL | 3929473 | 197688 |
| 2-(4-BROMOPHENOXY)ETHANOL | 34743889 | 198765 |
| 2-FLUOROPHENETHYL ALCOHOL | 50919067 | 228788 |
| 3-(TRIFLUOROMETHYL)PHENETHYL ALCOHOL | 455016 | 230359 |
| 2-(PHENYLTHIO)ETHANOL | 699127 | 232777 |
| 1-(2-METHOXYPHENYL)-2-PROPANOL | 1554261 | 233773 |

TABLE 27

Exemplary Method Embodiments of Processes A–R

A; B; C; D; I; J; K; L; M; N; O; P; Q; R; E; F; G; H; AB; BC; CD; DI; IJ; JK; KL; LM; MN; NO; OP; OQ; QR; EF; FG; GH; HI; ABC; BCD; CDI; DIJ; IJK; JKL; KLM; LMN; MNO; NOP; NOQ; OQR; EFG; FGH; GHI;

TABLE 27-continued

Exemplary Method Embodiments of Processes A–R

HIJ; ABDC; BCDI; CDIJ; DIJK; IJKL; JKLM; KLMN; LMNO; MNOP; MNOQ; NOQR; EFHG; FGHI; GHIJ; HIJK; ABCDI; BCDIJ; CDIJK; DIJKL; IJKLM; JKLMN; KLMNO; LMNOP; LMNOQ; MNOQR; EFGHI; FGHIJ; GHIJK; HIJKL; ABCDIJ; BCDIJK; CDIJKL; DIJKLM; IJKLMN; JKLMNO; KLMNOP; KLMNOQ; LMNOQR; EFGHIJ; FGHIJK; GHIJKL; HIJKLM; ABCDIJK; BCDIJKL; CDIJKLM; DIJKLMN; IJKLMNO; JKLMNOP; JKLMNOQ; KLMNOQR; EFGHIJK; FGHIJKL; GHIJKLM; HIJKLMN; ABCDIJKL; BCDIJKLM; CDIJKLMN; DIJKLMNO; IJKLMNOP; IJKLMNOQ; JKLMNOQR; EFGHIJKL; FGHIJKLM; GHIJKLMN; HIJKLMNO; ABCDIJKLM; BCDIJKLMN; CDIJKLMNO; DIJKLMNOP; DIJKLMNOQ; IJKLMNOQR; EFGHIJKLM; FGHIJKLMN; GHIJKLMNO; HIJKLMNOP; HIJKLMNOQ; ABCDIJKLMN; BCDIJKLMNO; CDIJKLMNOP; CDIJKLMNOQ; DIJKLMNOQR; EFGHIJKLMN; FGHIJKLMNO; GHIJKLMNOP; GHIJKLMNOQ; HIJKLMNOQR; ABCDIJKLMNO; BCDIJKLMNOP; BCDIJKLMNOQ; CDIJKLMNOQR; EFGHIJKLMNO; FGHIJKLMNOP; FGHIJKLMNOQ; GHIJKLMNOQR; ABCDIJKLMNOP; ABCDIJKLMNOQ; BCDIJKLMNOQR; EFGHIJKLMNOP; EFGHIJKLMNOQ; FGHIJKLMNOQR; ABCDIJKLMNOQR; EFGHIJKLMNOQR; S; T; U; V; W; ST; TU; UV; VW; STU; TUV; UVW; STUV; TUVW; STUVW.

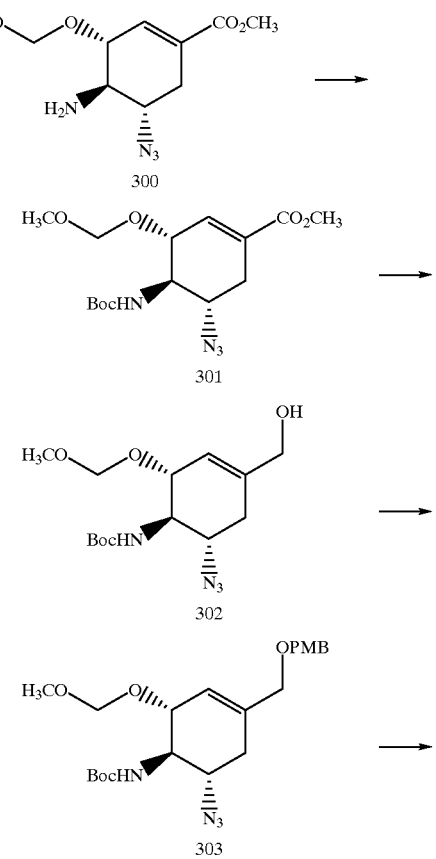

Scheme 41

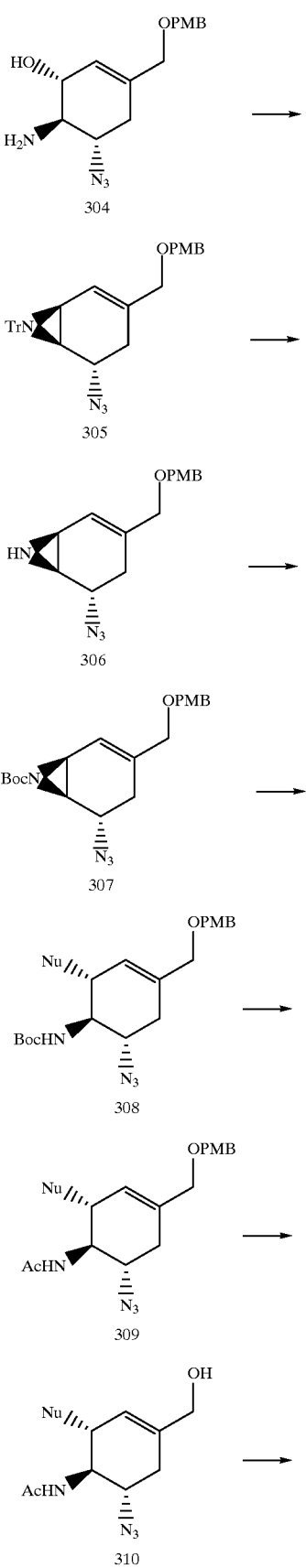

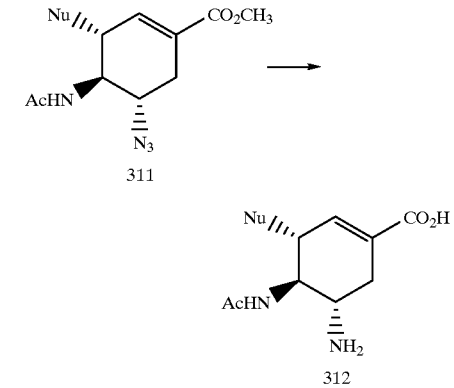

The amine 300 (an intermediate in Example 52, optionally purified prior to use) is treated with Boc anhydride to give the mono Boc protected amine 301. Such a transformation is found in Greene, T. W. "Protective Groups in Organic Synthesis" 2nd Ed. (John Wiley & Sons, New York, 1991) pages 327–328.

Methyl ester 301 is reduced to the corresponding primary allylic alcohol 302 with DIBAL at low temperature. Such a conversion is described by Garner, P. and Park, I. M., "J. Org. Chem.", 52:2361 (1987).

The primary alcohol 302 is protected as its p-methoxy benzyl ether derivative 303 by treatment with 4-methoxybenzyl chloride under basic conditions. Such a conversion is described in Horita, K. et. al., "Tetrahedron", 42:3021 (1986).

The MOM and Boc protecting groups of 303 are removed by treatment with TFA/$CH_2Cl_2$ to give the amino alcohol 304. Such transformations are found in Greene, T. W "Protective Groups in Organic Synthesis", 2nd. Ed. (John Wiley & Sons, New York, 1991).

Conversion of 304 into the corresponding trityl protected aziridine 305 is accomplished in a one pot reaction two step sequence: 1) TrCl/TEA, 2) MsCl/TEA. Such a transformation has been previously described.

Aziridine 305 is then converted the corresponding Boc protected derivative 307 by first removal of the trityl group with HCl/acetone to give 306. Such a transformation is described in Hanson, R. W. and Law, H. D. "J. Chem. Soc.", 7285 (1965). Aziridine 306 is then converted into the corresponding Boc derivative 307 by treatment with Boc anhydride. Such a conversion is described in Fitremann, J., et. al. "Tetrahedron Lett.", 35:1201 (1994).

The allylic aziridine 307 is opened selectively at the allylic position with a carbon nucleophile delivered via a higher order organocuprate in the presence of $BF_3.Et_2O$ at low temperature to give the opened adduct 308. Such an opening is described in Hudlicky, T., et. al. "Synlett." 1125 (1995).

The Boc protected amine 308 is converted into the N-acetyl derivative 309 in a two step sequence: 1) TFA/$CH_2Cl_2$; 2) $Ac_2O$/pyridine. Such transformations can be found in Greene, T. W., ",Protective Groups in Organic Synthesis", 2nd. Ed. (John Wiley & Sons, New York, 1991) pages 327–328 and pages 351–352.

Benzyl ether 309 is deprotected with DDQ at room temperature to give the primary allylic alcohol 310. Such a transformation is found in Horita, K., et. al. "Tetrahedron" 42:3021 (1986).

Alcohol 310 is oxidized and converted in a one pot reaction into the methyl ester 311 via a Corey oxidation using MnO2/AcOH/MeOH/NaCN. Such a transformation can be found in Corey, E. J., et. al. "J. Am. Chem. Soc.", 90:5616 (1968).

Azido ester 311 is converted into amino acid 312 in a two step sequence 1) Ph$_3$P/H$_2$O/THF; 2) KOH/THF. Such a conversion has been described previously.

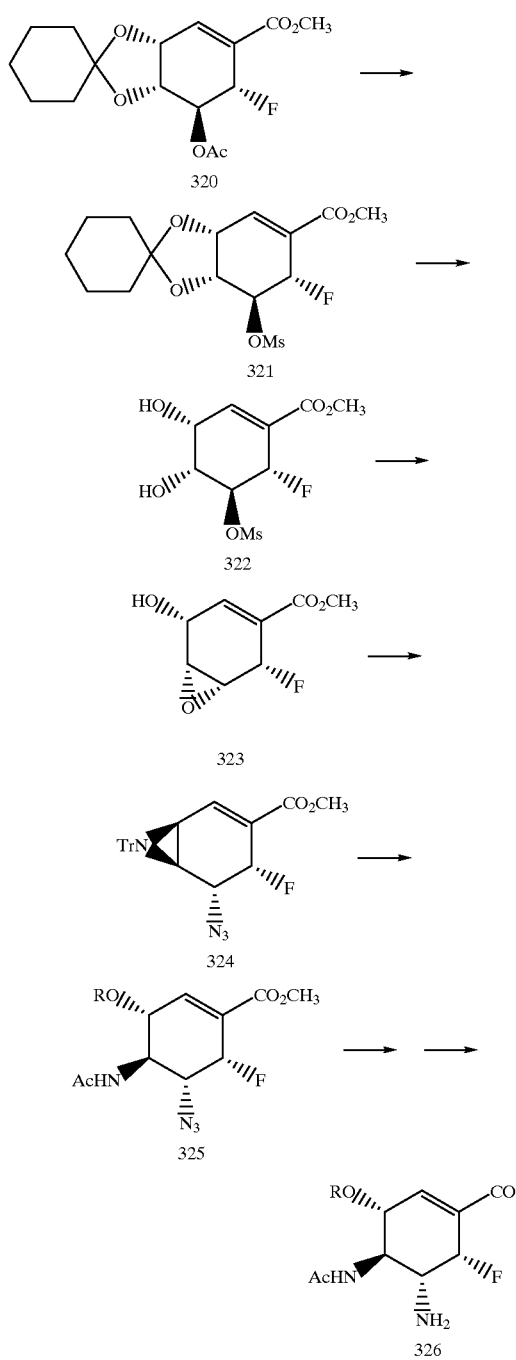

the free alcohol and then converted into the corresponding mesylate 321 in two steps: 1) NaOMe; 2) MsCl/TEA. Such transformations are described in Greene, T. W., "Protective Groups in Organic Synthesis", 2nd. Ed. (John Wiley & Sons, New York, 1991).

Deprotection of 321 under acidic conditions gives diol 322 which is cyclized to the epoxy alcohol 323 under basic conditions. Such a conversion has been previously described.

Conversion of 323 to the N-trityl protected aziridine 324 is accomplished with the following sequence: 1) MOMCl/TEA; 2) NaN$_3$/NH$_4$Cl; 3) MsCl/TEA; 4) PPh$_3$/TEA/H$_2$O; 5) NaN$_3$/NH$_4$Cl; 6) HCl/MeOH; 7) i) TrCl, ii) MsCl/TEA. Such a sequence has been previously described.

The aziridine 324 is then opened with the appropriate alcohol under Lewis acid conditions and then treated with Ac$_2$O/pyridine to give the acetylated product 325. Such a transformation has been previously described.

The ester 325 is converted to the corresponding amino acid 326 in a two step sequence: 1) PPh$_3$/H$_2$O/THF; 2) KOH/THF. Such a transformation has been previously described.

U.S. Pat. No. 5,214,165, and in particular, the "Descriptions and Examples" at column 9, line 61 to column 18, line 26, describes the preparation of 6α and 6β fluoro Shikimic acid. These fluoro compounds are suitable starting materials for methods of making compounds of the invention that use Shikimic acid.

Scheme 43

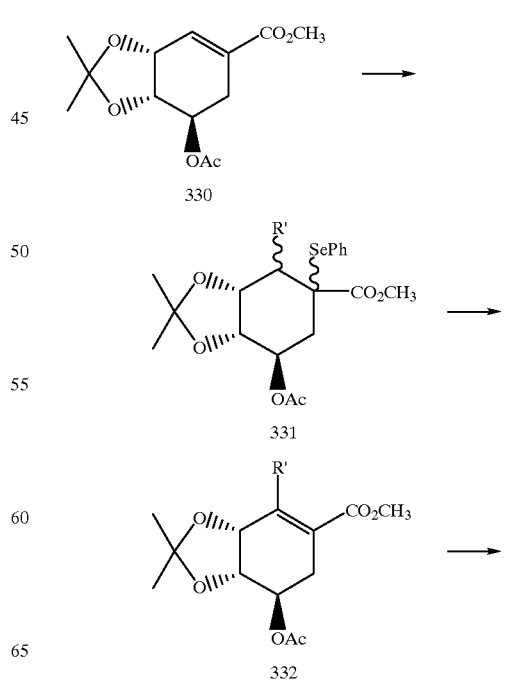

Scheme 42

The known fluoro acetate 320 (Sutherland, J. K., et.al. "J. Chem. Soc. Chem. Commun." 464 (1993) is deprotected to

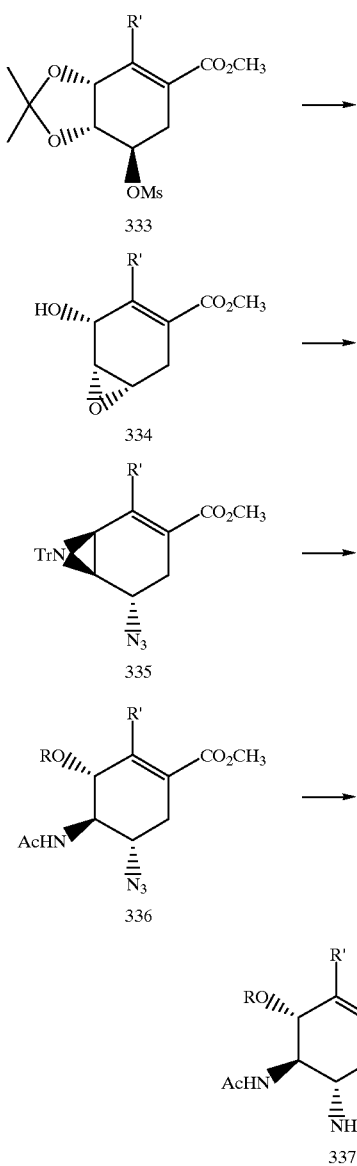

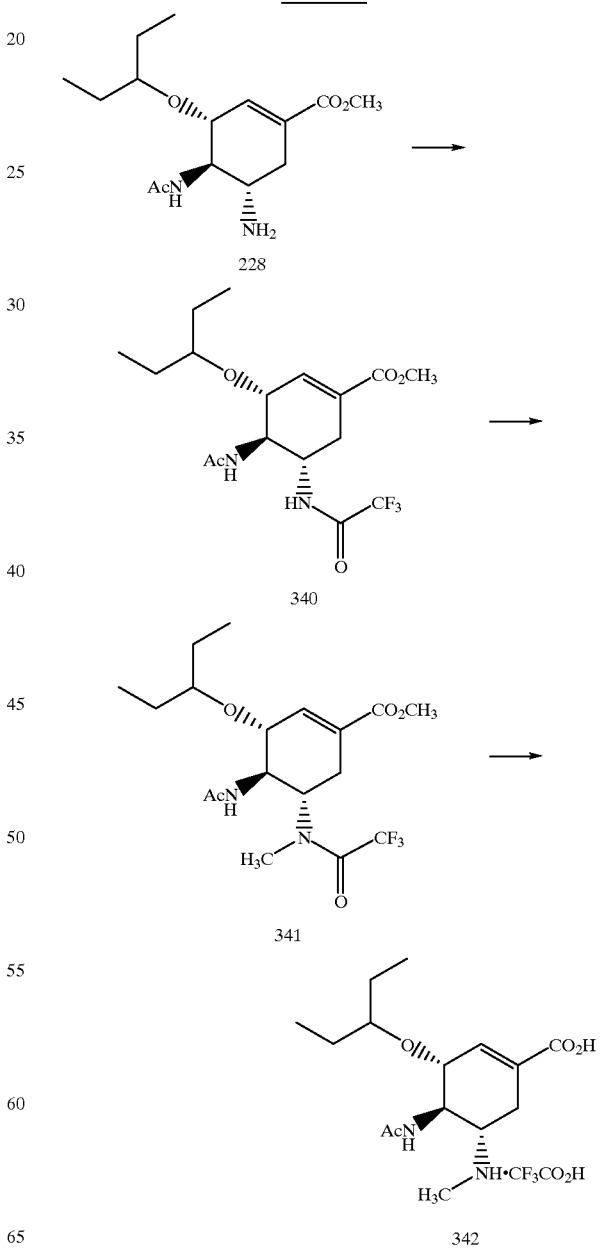

Conversion of epoxide 334 into N-trityl aziridine 335 is accomplished by the following sequence: 1) MOMCl/TEA; 2) NaN₃/NH₄Cl; 3) MsCl/TEA; 4) PPh₃/TEA/H₂O; 5) NaN₃/NH₄Cl; 6) HCl/MeOH; 7) i) TrCl, ii) MsCl/TEA. Such a sequence has been previously described.

The aziridine 335 is then opened with the appropriate alcohol under Lewis acid conditions and then treated with Ac₂O/pyridine to give the acetylated product 336. Such a transformation has been previously described.

The azido ester 336 is converted to the corresponding amino acid 337 in a two step sequence: 1) PPh₃/H₂O/THF; 2) KOH/THF. Such a transformation has been previously described.

Schemes 44 and 45 are referred to in the examples.

Scheme 43

Unsaturated ester 330 (obtainable by standard actetylation methods from the acetonide alcohol described in Campbell, M. M., et. al., "Synthesis", 179 (1993)) is reacted with the appropriate organocuprate where R' is the ligand to be transferred from the organocuprate. The resultant intermediate is then trapped with PhSeCl to give 331 which is then treated with 30% H₂O₂ to give the α,β-unsaturated ester 332. Such a transformation can be found in Hayashi, Y., et. al, "J. Org. Chem." 47:3428 (1982).

Acetate 332 is then converted into the corresponding mesylate 333 in a two step sequence: 1) NaOMe/MeOH; 2) MsCl/TEA. Such a transformation has been previously described and can also be found in Greene, T. W., "Protective Groups in Organic Synthesis", 2nd. Ed. (John Wiley & Sons, New York, 1991).

The acetonide 333 is then converted into the epoxy alcohol 334 in a two step sequence: 1) p-TsOH/MeOH/Δ; 2) DBU/THF. Such a transformation has been previously described.

Scheme 45

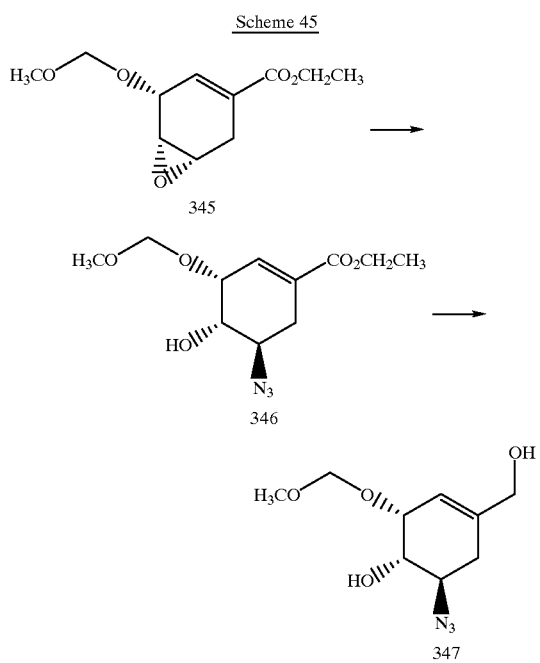

Modification of the exemplary starting materials to form different $E_1$ groups has been described in detail and will not be elaborated here. See Fleet, G. W. J. et al.; "J. Chem. Soc. Perkin Trans. I", 905–908 (1984), Fleet, G. W. J. et al.; "J. Chem. Soc., Chem. Commun.", 849–850 (1983), Yee, Ying K. et al.; "J. Med. Chem.", 33:2437–2451 (1990); Olson, R. E. et al.; "Bioorganic & Medicinal Chemistry Letters", 4(18):2229–2234 (1994); Santella, J. B. III et al.; "Bioorganic & Medicinal Chemistry Letters", 4(18):2235–2240 (1994); Judd, D. B. et al.; "J. Med. Chem.", 37:3108–3120 (1994) and Lombaert, S. De et al.; "Bioorganic & Medicinal Chemistry Letters", 5(2):151–154 (1994).

The $E_1$ sulfur analogs of the carboxylic acid compounds of the invention are prepared by any of the standard techniques. By way of example and not limitation, the carboxylic acids are reduced to the alcohols by standard methods. The alcohols are converted to halides or sulfonic acid esters by standard methods and the resulting compounds are reacted with NaSH to produce the sulfide product. Such reactions are described in Patai, "The Chemistry of the Thiol Group" (John Wiley, New York, 1974), pt. 2, and in particular pages 721–735.

Modifications of each of the above schemes leads to various analogs of the specific exemplary materials produced above. The above cited citations describing suitable methods of organic synthesis are applicable to such modifications.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

EXAMPLES

General

The following Examples refer to the Schemes.

Some Examples have been performed multiple times. In repeated Examples, reaction conditions such as time, temperature, concentration and the like, and yields were within normal experimental ranges. In repeated Examples where significant modifications were made, these have been noted where the results varied significantly from those described. In Examples where different starting materials were used, these are noted. When the repeated Examples refer to a "corresponding" analog of a compound, such as a "corresponding ethyl ester", this intends that an otherwise present group, in this case typically a methyl ester, is taken to be the same group modified as indicated. For example, the "corresponding ethyl ester of compound 1" is

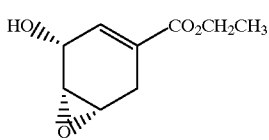

500

Example 1

Epoxy alcohol 1: Prepared from shikimic acid by the procedure of McGowan and Berchtold, "J. Org. Chem.", 46:2381 (1981).

Example 2

Epoxy allyl ether 2: To a solution of epoxy alcohol 1 (2.37 g, 14.08 mmol) in dry benzene (50 mL) was added thallium (I)ethoxide (1.01 mL) in one portion. After 2 hr the reaction was concentrated in vacuo and the residue dissolved in acetonitrile. Allyl iodide (3.0 mL) was added and the mixture was stirred in the dark for 16 h. The solids were filtered thru a celite pad and washed with chloroform. Concentration in vacuo followed by flash chromatography (40% EtOAc in hexane) gave 1.24 g (42%) of 2 as a pale viscous oil. $^1$H NMR (300 MHz, CDCl$_3$): δ 6.75 (1H, m); 6.10–5.90 (1H, m, —CH=, allyl); 5.40–5.15 (2H, m, =CH$_2$, allyl); 4.47–4.43 (1H, m); 4.30–4.15 (2H, m, —CH$_2$—, allyl); 3.73 (3H, s); 3.55–3.50 (1H, m); 3.45–3.40 (1H, m); 3.15–3.00 (1H, dm, J=19.5 Hz), 2.50–2.35 (1H, dm, J=2.7, 19.5 Hz).

Example 3

Azido alcohol 3: Epoxide 2 (1.17 g, 5.57 mmol), sodium azide (1.82 g) and ammonium chloride (658 mg) were refluxed in MeOH/H$_2$O (8:1) (35 mL) for 18 h. The reaction was then concentrated in vacuo and the residue partitioned between ethyl ether and water. The organic layer was washed with brine and dried. Concentration in vacuo gave 3 as a pale oil 1.3 g (92%) which was used without further purification. $^1$H NMR (300 MHz, CDCl$_3$): δ 6.95–6.85 (1H, m); 6.00–5.85 (1H, m, —CH=, allyl); 5.35–5.25 (2H, m, =CH$_2$, allyl); 4.25–4.10 (2H, m, —CH$_2$—, allyl); 4.12 (1H, bt, J=4.2 Hz); 3.95–3.75 (2H, m); 3.77 (3H, s); 2.85 (1H, dd, J=5.3, 18.3 Hz); 2.71 (1H, bs); 2.26 (1H, dd, J=7.2, 18.3 Hz).

Example 4

Aziridine 4: To a solution of alcohol 3 (637 mg, 2.52 mmol) in CH$_2$Cl$_2$ (20 mL) cooled to 0° C. was added DMAP (few crystals) and triethyl amine (442 μL). MsCl (287 μL) was then added and the reaction stirred for 2 h at 0° C. Volatiles were removed and the residue partitioned between ethyl ether and water. The organic layer was washed with saturated bicarbonate, brine and then dried. Concentration in vacuo gave 881 mg of crude mesylate. $^1$H NMR (300 MHz, CDCl$_3$): δ 6.87–6.84 (1H, s); 6.00–5.85 (1H, m, —CH=, allyl); 5.40–5.25 (2H, m, =CH$_2$, allyl); 4.72 (1H, dd, J=3.9, 8.5 Hz); 4.32 (1H, bt, J=3.9 Hz); 4.30–4.15 (2H, m, —CH$_2$—, allyl); 3.77 (3H, s); 3.14 (3H, s); 2.95 (1H, dd, J=5.7, 18.6 Hz); 2.38 (1H, dd, J=6.7, 18.6 Hz).

The crude mesylate was dissolved in dry THF (20 mL) and treated with Ph$_3$P (727 mg). After stirring for 3 h at room temperature, water (15 mL) and solid NaHCO$_3$ (1.35 g) was added and the mixture stirred overnight at room temperature. The reaction was then concentrated in vacuo and the residue partitioned between EtOAc, saturated bicarbonate and brine. The organic layer was separated and dried over MgSO$_4$. Concentration in vacuo and flash chromatography of the residue gave the aziridine 4 170 mg (33%) as a pale yellow oil. $^1$H NMR (300 MHz, CDCl$_3$): δ 6.82–6.80 (1H, m); 6.04–5.85 (1H, m, —CH=, allyl); 5.35–5.20 (2H, m, =CH$_2$, allyl); 4.39 (1H, bd, J=2.4 Hz); 4.20–4.05 (2H, m, —CH$_2$-allyl); 3.73 (3H, s); 2.90–2.80 (1H, bd, J=18.9 Hz); 2.65–2.40 (2H, m).

Example 5

N-acetyl aziridine 5: Aziridine 4 (170 mg, 0.814 mmol) was dissolved in CH$_2$Cl$_2$ (2 mL) and pyridine (4 mL) and cooled to 0° C. Acetyl chloride (87 μL) was then added and the reaction stirred at 0° C. for 1 h. Volatiles were removed in vacuo and the residue partitioned between ethyl ether, saturated bicarbonate and brine. The organic layer was separated and dried over MgSO$_4$. Concentration gave crude 5 196 mg (96%) which was used without further purification. $^1$H NMR (300 MHz, CDCl$_3$): δ 6.88–6.86 (1H, m); 6.00–5.85 (1H, m, —CH=, allyl); 5.40–5.20 (2H, m, =CH$_2$, allyl); 4.45–4.40 (1H, m); 4.16 (2H, d, J=6.0 Hz, —CH$_2$—, allyl); 3.76 (3H, s); 3.00–2.95 (2H, m); 2.65 (1H, bd, J=18.5 Hz); 2.14 (3H, s).

Example 6

Azido allyl ether 6: Aziridine 5 (219 mg, 0.873 mmol), sodium azide (426 mg) and ammonium chloride (444 mg) in dry DMF (7 mL) was heated at 65° C. under argon overnight. The reaction was poured into saturated bicarbonate/brine and extracted with ethyl ether several times. The combined ether layers were washed with brine and dried. Concentration followed by flash chromatography (EtOAc only) gave the azido amine 77 mg (35%) which was dissolved in CH$_2$Cl$_2$ (1 mL) and pyridine (1 mL) and cooled to 0° C. Acetyl chloride (38 μL) was added and after 45 min solid NaHCO$_3$ was added and the volatiles removed under vacuum. The residue was partitioned between EtOAc and brine. The organic layer was dried over MgSO$_4$ and concentrated in vacuo. Flash chromatography (EtOAc only) gave 6 90 mg (99%). $^1$H NMR (500 MHz, CDCl$_3$): δ 6.86 (1H, bt, J=2.2 Hz); 5.95–5.82 (1H, m, CH=, allyl); 5.68 (1H, bd, J=7.3 Hz); 5.35–5.20 (2H, m, =CH$_2$, allyl); 4.58–4.52 (1H, m); 4.22–4.10 (2H, m); 4.04 (1H, dd, J=5.9, 12.5 Hz); 3.77 (3H, s); 3.54–3.52 (1H, m); 2.89 (1H, dd, J=5.9, 17.6 Hz); 2.32–2.22 (1H, m); 2.06 (3H, s).

Example 7

Azido diol 7: To a solution of olefin 6 (90 mg, 0.306 mmol) in acetone (3 ml) and water (258 μL) was added N-methyl morpholine-N-oxide (39 mg) and OsO$_4$ (73 μL of a 2.5% w/w in t-butanol). The reaction was then stirred at room temperature for 3 days. Solid sodium hydrosulfite was added and after stirring for 20 min the reaction was filtered thru a celite pad and washed with copious amounts of acetone. Concentration in vacuo followed by flash chromatography (10% MeOH in CH$_2$Cl$_2$) gave the diol 7 50 mg (50%). $^1$H NMR (300 MHz, CD$_3$CN): δ 6.80–6.70 (1H, m); 4.20–4.15 (1H, bm); 3.95–3.80 (1H, m); 3.80–3.25 (6H, m); 3.70 (3H, s); 3.10 (1H, bs); 2.85 (1H, bs); 2.85–2.75 (1H, m); 2.30–2.15 (1H, m); 2.16 (1H, bs); 1.92 (3H, s).

Example 8

Amino acid diol 8: A solution of the diol 7 (23 mg, 0.07 mmol) in THF (1 mL) was treated with aq. KOH (223 μL, of 0.40 M solution) at room temperature. After stirring for 1.5 h the reaction was acidified to pH=4 with Amberlite IR-120 (plus) ion exchange resin. The resin was filtered and washed with MeOH. Concentration in vacuo gave the crude carboxylic acid which was dissolved in ethanol (1.5 mL). To this solution was added Lindlar's catalyst (20 mg) and the reaction stirred over a hydrogen atmosphere (1 atm via a balloon) for 20 h. The reaction mixture was filtered thru a celite pad and washed with hot ethanol and water. The ethanol was removed under vacuum and the resulting aqueous layer lyophilized to give a mixture of the desired amino acid 8 and the starting azide 7 as a white powder. Compound 8: $^1$H NMR (500 MHz, D$_2$O): δ 6.5 (1H, s); 4.24–4.30 (2H, m); 4.25–4.18 (1H, m); 3.90–3.55 (5H, complex m); 2.96–2.90 (1H, m); 2.58–2.50 (1H, complex m); 2.12 (3H, s).

Example 9

Compound 62: A suspension of Quinic acid (60 g), cyclohexanone (160 mL) and toluenesulfonic acid (600 mg)

in benzene (450 mL) was refluxed with Dean-Stark for 14 hrs. The reaction mixture was cooled to room temperature and poured into saturated NaHCO$_3$ solution (150 mL). The aqueous layer was extracted with CH$_2$Cl$_2$ (3×). The combined organic layers were washed with water (2×), brine (1×), and dried over Na$_2$SO$_4$. Concentration gave a whited solid, which was recrystallized from ether (75 g, 95%): $^1$H NMR (CDCl$_3$) δ 4.73 (dd, J=6.1, 2.5 Hz, 1 H), 4.47 (ddd, J=7.0, 7.0, 3.0 Hz, 1H), 4.30 (ddd, J=5.4, 2.6, 1.4 Hz, 1 H), 2.96 (s, 1H), 2.66 (d, J=11.7 Hz, 1H), 2.40–2.15 (m, 3 H), 1.72–1.40 (m, 10 H).

Example 10

Compound 63: To a solution of lactone 62 (12.7 g, 50 mmol) in methanol (300 mL) was added sodium methoxide (2.7 g, 50 mmol) in one portion. The mixture was stirred at room temperature for 3 hrs, and quenched with acetic acid (3 mL) and stirred for 10 min. The mixture was poured into saturated NH$_4$Cl solution (300 mL), and extracted with CH$_2$Cl$_2$ (3×). The combined organic phase was washed with brine (1×), and dried over MgSO$_4$. Purification by flash column chromatography (Hexane/EtOAc=1/1 to 1/2) gave diol (11.5 g, 80%) and starting material (1.2 g, 10%): $^1$H NMR (CDCl$_3$) δ 4.47 (ddd, J=7.4, 5.8, 3.5 Hz, 1 H), 4.11 (m, 1 H), 3.98 (m, 1 H), 3.81 (s, 3 H), 3.45 (s, 1 H), 2.47 (d, J=3.3 Hz, 1 H), 2.27 (m, 2 H), 2.10 (dd, J=11.8, 4.3 Hz, 1 H), 1.92–1.26 (m, 10 H).

Example 11

Compound 64: To a mixture of diol 63 (1.100 g, 3.9 mmol), molecule sieves (3 A, 2.2 g) and pyridine (1.1 g) in CH$_2$Cl$_2$ (15 mL) was added PCC (3.3 g, 15.6 mmol) in one portion. The mixture was stirred at room temperature for 26 hrs, and diluted with ether (30 mL). The suspension was filtered through a pad of celite, and washed with ether (2×20 mL). The combined ether was washed with brine (2×), and dried over MgSO$_4$. Concentration and purification was by flash column chromatography (Hexane/EtOAc=3/1) gave the ketone (0.690 g, 67%): $^1$H NMR (CDCl$_3$) δ 6.84 (d, J=2.8 Hz, 1 H), 4.69 (ddd, J=6.4, 4.9, 1.6 Hz, 1 H), 4.30 (d, J=5.0 Hz, 1 H), 3.86 (s, 3 H), 3.45 (d, J=22.3 Hz, 1 H), 2.86 (m, 1 H), 1.69–1.34 (m, 10 H).

Example 12

Compound 28: To a solution of ketone 64 (0.630 g, 2.4 mmol) in MeOH (12 mL) at 0° C. was added NaBH$_4$ in 30 min. The mixture was stirred for additional 1.5 hrs at 0° C., and quenched with 15 mL of saturated NH$_4$Cl solution. The solution was extracted with CH$_2$Cl$_2$ (3×), and the combined organic extract was dried over MgSO$_4$. Purification by flash column chromatography (Hexane/EtOAc=2/1) gave the alcohol (0.614 g, 97%): $^1$H NMR (CDCl$_3$) δ 6.94 (d, J=0.5 Hz, 1 H), 4.64 (ddd, J=9.8, 6.7, 3.2 Hz, 1 H), 4.55 (dd, J=7.1, 4.2 Hz, 1 H), 4.06 (m, 1 H), 3.77 (s, 3 H), 3.04 (dd, J=16.5, 2.1 Hz, 1 H), 2.73 (d, J=10.2 Hz, 1 H), 1.94 (m, 1 H), 1.65–1.29 (m, 10 H).

Example 13

Compound 66: Alcohol 28 (2.93 g, 10.9 mmol) and toluenesulfonic acid (1.5 g) were dissolved in acetone (75 mL), and the mixture was stirred at room temperature for 15 hrs. The reaction was quenched with water (30 mL), and basified with concentrated NH$_3$—H$_2$O until PH=9. Acetone was removed under reduced pressure, and the water phase was extracted with CH$_2$Cl$_2$ (3×). The combined organic extracts were washed with brine (1×), and dried over Na$_2$SO$_4$. Concentration gave the desired product: $^1$H NMR (CDCl$_3$) δ 7.01 (m, 1 H), 4.73 (m, 1 H), 4.42 (m, 1 H), 3.97 (m, 1 H), 3.76 (s, 3 H), 2.71–2.27 (m, 2 H), 2.02 (s, 3 H), 1.98 (s, 3 H).

Example 14

Compound 67: To a solution of alcohol 66 (10.9 mmol) in CH$_2$Cl$_2$ (60 mL) at 0° C. was added pyridine (4.4 mL, 54.5 mmol), followed by addition of trimethylacetyl chloride (2.7 mL, 21.8 mmol). The mixture was warmed to room temperature and stirred for 14 hrs. The mixture was diluted with CH$_2$Cl$_2$, and washed with water (2×), brine (1×), and dried over MgSO$_4$. Purification by flash column chromatography (Hexane/EtOAc=9/1) gave the diester (2.320 g, 68%): $^1$H NMR (CDCl$_3$) δ 6.72 (m, 1 H), 5.04 (m, 1 H), 4.76 (m, 1 H), 4.40 (m, 1 H), 3.77 (s, 3 H), 2.72–2.49 (m, 2 H), 1.37 (s, 3 H), 1.35 (s, 3 H), 1.23 (s, 9 H).

Example 15

Compound 68: Diester 67 (2.32 g, 2.3 mmol) was dissolved in acetone/H$_2$O (1/1, 100 mL) and heated at 55° C. for 16 hrs. Solvents were removed, water (2×50 mL) was added and evaporated. Concentration with toluene (2×50 mL) gave diol, which was used without further purification: $^1$H NMR (CDCl$_3$) δ 6.83 (m, 1 H), 5.06 (m, 1 H), 4.42 (m, 1 H), 4.09 (m, 1 H), 3.77 (s, 3 H), 2.68–2.41 (m, 2 H), 1.22 (s, 9 H).

Example 16

Compound 69: To a solution of diol 68 (0.410 g, 1.5 mmol) in THF (8 mL) at 0° C. was added triethylamine (0.83 mL, 6.0 mmol), followed by slow addition of thionyl chloride (0.33 mL, 4.5 mmol). The mixture was warmed to room temperature and stirred for 3 hrs. The mixture was diluted with CHCl$_3$, and washed with water (3×), brine (1×), and dried over MgSO$_4$. Purification by flash column chromatography (Hexanes/EtOAc=5/1) gave a exo/endo mixture (0.430 g, 90%): $^1$H NMR (CDCl$_3$) δ 6.89–6.85 (m, 1 H), 5.48–4.84 (m, 3 H), 3.80, 3.78 (s, 3 H), 2.90–2.60 (m, 2 H), 1.25, 1.19 (s, 9 H).

Example 17

Compound 70: The mixture of sulfone 69 (0.400 g, 1.3 mmol) and sodium azide (0.410 g, 6.29 mmol) in DMF (10 mL) was stirred for 20 hrs. The reaction mixture was then diluted with ethyl acetate, washed with saturated NH$_4$Cl solution, water, brine, and dried over MgSO$_4$. Concentration gave the azide (0.338 g, 90%): $^1$H NMR (CDCl$_3$) δ 6.78 (m, 1 H), 5.32 (m, 1 H), 4.20 (m, 1 H), 3.89 (m, 1 H), 3.78 (s, 3 H), 3.00–2.60 (m, 2 H), 1.21 (s, 9 H).

Example 18

Compound 71: To a solution of alcohol 70 (0.338 g, 1.1 mmol) in CH$_2$Cl$_2$ (11 mL) at 0° C. was added triethylamine (0.4 mL, 2.9 mmol), followed by slow addition of methylsulfonic chloride (0.18 mL, 2.3 mmol). The mixture was stirred at 0° C. for 30 min., and diluted with CH$_2$Cl$_2$. The organic layer was washed with water (2×), brine, and dried over MgSO$_4$. Purification by flash column chromatography (Hexane/EtOAc=3/1) gave the desired compound (0.380 g, 82%): $^1$H NMR (CDCl$_3$) δ 6.82 (m, 1 H), 5.44 (m, 1 H), 4.76 (dd, J=7.3, 1.4 Hz, 1 H), 4.48 (m, 1 H), 3.80 (s, 3 H), 3.11 (s, 3 H), 2.82–2.61 (m, 2 H), 1.21 (s, 9 H).

Example 19

Compound 72: The mixture of azide 71 (0.380 g, 0.94 mmol) and triphenylphosphine (0.271 g, 1.04 mmol) in THF (19 mL) was stirred for 2 hrs. The reaction was quenched with water (1.9 mL) and triethylamine (0.39 mL, 2.82 mmol), and the mixture was stirred for 14 hrs. Solvents were removed under reduced pressure, and the mixture was used for next step. To a solution of above mixture in $CH_2Cl_2$ (20 mL) at 0° C. was added pyridine (0.68 mL, 8.4 mmol), followed by slow addition of acetyl chloride (0.30 mL, 4.2 mmol). The mixture was stirred at 0° C. for 5 min., and diluted with ethyl acetate. The mixture was washed with water (2×), brine (1×), dried over $MgSO_4$. Purification by flash column chromatography (Hexanes/EtOAc=3/1) gave the aziridine (0.205 g, 83%): $^1H$ NMR ($CDCl_3$) δ 7.19 (m, 1 H), 5.58 (m, 1 H), 3.77 (s, 3 H), 3.14 (m, 2 H), 2.85 (dd, J=7.0, 1.6 Hz, 1 H), 2.34 (m, 1 H), 2.16 (s, 3 H), 1.14 (s, 9 H).

Example 20

Compound 73: The mixture of aziridine 72 (0.200 g, 0.68 mmol), sodium azide (0.221 g, 3.4 mmol), and ammonium chloride (0.146 g, 2.7 mmol) in DMF (10 mL) was stirred at room temperature for 14 hrs. Then the mixture was diluted with ethyl acetate, and washed with water (5×), brine (1×), and dried over $MgSO_4$. Purification by flash column chromatography (hexanes/EtOAc=2/1) gave desired product and deacetyl amine (0.139 g). The mixture was dissolved in acetic anhydride (2 mL), and stirred for 2 hrs. Excess anhydride was removed under reduced pressure, and give the desired product (149 mg): $^1H$ NMR ($CDCl_3$) δ 6.76 (m, 1 H), 5.53 (d, J=8.5 Hz, 1 H), 5.05 (m, 1 H), 4.31 (m, 1 H), 4.08 (m, 1 H), 3.79 (s, 3 H), 2.91 (m, 1 H), 2.51 (m, 1 H), 1.99 (s, 3 H), 1.20 (s, 9 H).

Example 21

Compound 74: A solution of potassium hydroxide in $MeOH/H_2O$ (0.5 M, 4.4 mL, 2.2 mmol) was added to ester 73 (149 mg, 0.44 mmol) and the mixture was stirred at room temperature for 3 hrs. The mixture was cooled to 0° C., and acidified with Amberlite (acidic) to PH=3–4. The mixture was filtered, and washed with MeOH. Concentration gave the carboxylic acid as a white solid (73 mg, 69%): $^1H$ NMR ($CD_3OD$) δ 6.62 (m, 1 H), 4.15 (m, 1 H), 3.95–3.72 (m, 2 H), 2.84 (dd, J=6.7, 1.4 Hz, 1 H), 2.23 (m, 1 H), 1.99 (s, 3 H).

Example 22

Compound 75: The mixture of azide 74 (8 mg) and Pd-C (Lindlar) (15 mg) in ethanol (2 mL) was stirred under hydrogen for 16 hrs. The mixture was filtered through celite, washed with hot $MeOH-H_2O$ (1/1). Concentration gave a solid. The solid was dissolved in water, and passed through a short C-8 column, and washed with water. Concentration gave a white solid (6 mg): $^1H$ NMR ($D_2O$) δ 6.28 (m, 1 H), 4.06–3.85 (m, 3 H), 2.83 (dd, J=17.7, 5.4 Hz, 1 H), 2.35 (m, 1 H), 2.06 (s, 3 H).

Example 23

Compound 76: Carboxylic acid 74 (68 mg, 0.28 mmol) and diphenyldiazomethane (61 mg, 0.31 mmol) were dissolved in ethanol (12 mL), and stirred for 16 hrs. The reaction was quenched with acetic acid (0.5 mL), and the mixture was stirred for 10 min. Solvents were removed under reduced pressure. Purification by flash column chromatography (EtOAc) gave the ester (56 mg, 50%): $^1H$ NMR ($CD_3OD$) δ 7.36–7.23 (m, 10 H), 6.88 (s, 1 H), 6.76 (s, 1 H), 4.21 (m, 1 H), 3.93–3.79 (m, 2 H), 2.89 (dd, J=17.7, 5.0 Hz, 1 H), 2.34 (m, 1 H), 2.00 (s, 3 H).

Example 24

Compound 77: To a solution of alcohol 76 (20 mg, 0.05 mmol) in $CH_2Cl_2$ (1 mL) was added pyridine (40 μL, 0.5 mmol), followed by addition of acetic anhydride (24 μL, 0.25 mmol). The mixture was stirred for 24 hrs, and solvents and reagents were removed under reduced pressure. Purification by flash column chromatography (Hexane/EtOAc=1/2) gave the diester (20 mg, 91%): $^1H$ NMR ($CDCl_3$) δ 7.40–7.27 (m, 10 H), 6.95 (s, 1 H), 6.87 (m, 1 H), 5.60 (m, 1 H), 5.12 (ddd, J=16.4, 10.2, 5.9 Hz, 1 H), 4.28 (dd, J=20.0, 9.4 Hz, 1 H), 4.15 (m, 1 H), 2.93 (dd, J=17.8, 5.2 Hz, 1 H), 2.57 (m, 1 H), 2.09 (s, 3 H), 2.01 (s, 3 H).

Example 25

Compound 78: The mixture of diester 77 (20 mg, 0.045 mmol), anisole (50 μL, 0.45 mmol), and TFA (1 mL) in $CH_2Cl_2$ (1 mL) was stirred for 20 min. Solvents and reagents were removed under reduced pressure. Purification by flash column chromatography (EtOAc to EtOAc/AcOH=100/1) gave the carboxylic acid (6 mg): $^1H$ NMR ($CDCl_3$) δ 6.85 (m, 1 H), 5.54 (m, 1 H), 5.12 (m, 1 H), 4.31–4.03 (m, 2 H), 2.89 (m, 1 H), 2.60–2.41 (m, 1 H), 2.11 (s, 3 H), 2.03 (s, 3 H).

Example 26

Compound 79: The mixture of azide 78 (6 mg, 0.02 mmol) and Pd-C (Lindlar) (15 mg) in $EtOH/H_2O$ (2.2 mL, 10/1) was stirred under hydrogen for 3 hrs. The mixture was filtered through a pad of celite, washed with hot $MeOH/H_2O$ (1/1). Evaporation gave a white solid. The solid was dissolved in water, and passed through a C-8 column. Evaporation of water gave a white powder (3 mg): $^1H$ NMR ($D_2O$) δ 6.32 (m, 1 H), 5.06 (m, 1 H), 4.06 (t, J=10.4 Hz, 1 H), 3.84 (m, 1 H), 2.83 (m, 1 H), 2.42 (m, 1 H), 2.06 (s, 3 H), 2.00 (s, 3 H).

Example 27

Compound 80: To a solution of alcohol 76 (35 mg, 0.086 mmol), Boc-glycine (30 mg, 0.172 mmol), and catalytic amount DMAP in $CH_2Cl_2$ (1 mL) was added DCC (35 mg, 0.172 mmol). The mixture was stirred for 30 min, and filtered and washed with $CHCl_3$. The $CHCl_3$ solution was washed with water (2×). Concentration gave a white solid. Purification by flash column chromatography (Hexane/EtOAc=1/2) gave product (30 mg): $^1H$ NMR ($CDCl_3$) δ 7.39–7.26 (m, 10 H), 6.95 (s, 1 H), 6.86 (m, 1 H), 5.77 (m, 1 H), 5.27 (m, 1 H), 4.99 (m, 1 H), 4.18–4.01 (m, 2 H), 3.94–3.84 (m, 2 H), 2.96 (dd, J=7.8, 5.9 Hz, 1 H), 2.57 (m, 1 H), 2.02 (s, 3 H), 1.45 (s, 9 H).

Example 28

Compound 81: The mixture of diester 80 (30 mg, 0.05 mmol), anisole (150 μL), and TFA (1 mL) in $CH_2Cl_2$ (1 mL) was stirred for 3 hrs. Solvents and reagents were evaporated. The mixture was dissolved in water, and washed with $CHCl_3$ (3×). Water phase was evaporated to gave a white solid (15 mg): $^1H$ NMR ($CD_3OD$) δ 6.73 (m, 1 H), 5.25–5.15 (m, 1 H), 4.35 (m, 1 H), 4.17 (m, 1 H), 3.82 (m, 2 H), 2.93 (dd, J=17.7, 5.6 Hz, 1 H), 2.42 (m, 1 H), 1.97 (s, 3 H).

Example 29

Compound 82: The mixture of azide 81 (15 mg, 0.05 mmol) and Pd-C (Lindlar) (30 mg) in $EtOH/H_2O$ (4 mL, 1/1) was stirred under hydrogen for 3 hrs. The mixture was filtered through a pad of celite, and washed with hot MeOH/H$_2$O (1/1). Concentration gave a glass-like solid. The solid was dissolved in water, and passed through C-8 column. Evaporation of water gave the amino acid: $^1$H NMR (D$_2$O) δ 6.68 (m, 1 H), 5.28 (m, 1 H), 4.29 (m, 1 H), 4.08–3.79 (m, 3 H), 2.85 (m, 1 H), 2.41 (m, 1 H); 2.04 (s, 3 H).

Example 30 bis-Boc guanidinyl methyl ester 92: Treated according to the procedure of Kim and Qian, "Tetrahedron Lett.", 34:7677 (1993). To a solution of amine 91 (42 mg, 0.154 mmol), bis-Boc thiourea (43 mg, 0.155 mmol) and triethylamine (72 μL) in dry DMF (310 μL) cooled to 0° C. was added mercury chloride (46 mg, 0.170 mmol) in one portion. After 30 min the reaction was warmed to room temperature and stirred for an additional 2.5 h. The reaction mixture was then filtered through a celite pad, concentrated and purified by flash column chromatography (100% ethyl acetate) to give 70 mg (89%) of 92 as a colorless foam. $^1$H NMR (CDCl$_3$, 300 MHz): δ 11.37 (s, 1H); 8.60 (d, 1H, J=7.8 Hz); 6.83 (t, 1H, J=2.1 Hz); 6.63 (d, 1H, J=8.4 Hz); 4.76 (d, 1H, J=7.0 Hz); 4.71 (d, 1H, J=7.0 Hz); 4.45–4.10 (complex m, 2H); 3.76 (s, 3H); 3.39 (s, 3H); 2.84 (dd, 1H, J=5.4, 17.4 Hz); 2.45–2.30 (m, 1H); 1.92 (s, 3H); 1.49 (s, 18H).

Example 31 bis-Boc guanidinyl carboxylic acid 93: To a solution of ester 92 (70 mg, 0.136 mmol) in THF (3 mL) cooled to 0° C. was added aq. KOH (350 μL of a 0.476 M solution). The reaction was then warmed to room temperature and stirred for 2 h. The reaction was then acidified to pH=4.5 with Amberlite IR-120 (plus) acidic resin. The resin was then filtered and washed with ethanol and H$_2$O. Concentration in vacuo gave 66 mg (97%) of carboxylic acid 93 as a white solid. $^1$H NMR (CDCl$_3$, 300 MHz): δ 11.40 (br s, 1H); 8.67 (d, 1H, J=7.8 Hz); 6.89 (s, 1H); 6.69 (br d, 1H, J=8.4 Hz); 4.77 (d, 1H, J=7.2 Hz); 4.70 (d, 1H, J=7.2 Hz); 4.40–4.15 (m, 2H); 3.39 (s, 3H); 2.84 (dd, 1H, J=4.8, 17.1 Hz); 2.45–2.30 (m, 1H); 1.95 (s, 3H); 1.49 (s, 9H); 1.48 (s, 9H).

Example 32

Guanidine carboxylic acid TFA salt 94: To a solution of bis-Boc guanidinyl carboxylic acid 93 (23 mg, 0.046 mmol) in CH$_2$Cl$_2$ (1 mL) cooled to 0° C. was added neat trifluoroacetic acid (500 μL). After 30 min the reaction was warmed to room temperature and stirred for an additional 1.25 h. Volatiles were removed under vacuum and the residue co-evaporated with several portions of H$_2$O to give a pale orange solid. The residue was purified by reverse phase C$_{18}$ chromatography using H$_2$O as an eluent. Fractions containing the desired product were pooled and lyophilized to give 15 mg of 93 as a white powder. $^1$H NMR (D$_2$O, 500 MHz): δ 6.82 (t, 1H, J=2.0 Hz); 4.51–4.47 (m, 1H); 3.93 (dd, 1H, J=9.0, 11.2 Hz); 3.87–3.80 (apparent ddd, 1H); 2.88 (m, 1H); 2.48–2.45 (complex m); 2.07 (s, 3H). $^{13}$C NMR (D$_2$O): δ 176.1; 170.0; 157.1; 139.2; 129.5; 69.4; 56.2; 50.9; 30.3; 22.2.

Example 33

Synthesis of 102: A solution of azido allyl ether 6 (24 mg, 0.082 mmol) in ethanol (1 mL) was treated with hydrogen gas (1 atm) over Lindlar's catalyst (30 mg) for 1.5 h. The reaction mixture was filtered through a celite pad and washed with hot ethanol. Concentration in vacuo gave a pale solid which was dissolved in THF (1.5 mL) and treated with aqueous KOH (246 μL of a 0.50 M solution). After stirring at ambient temperature for 2 h the reaction was acidified to pH=4.0 with Amberlite IR-120 (plus) acidic resin, filtered and washed with ethanol and H$_2$O. Concentration in vacuo gave an orange solid which was purified by a C$_{18}$ column chromatography eluting with H$_2$O. Fractions containing the product were pooled and lyophilized to give a 2 to 1 mixture of 102 and the fully saturated compound 103 as a white powder. $^1$H NMR data for compound 102: $^1$H NMR (D$_2$O, 500 MHz): δ: 7.85 (s, 1H); 4.29 (br d, 1H, J=9.2 Hz); 4.16 (dd, 1H, J=11.6, 11.6 Hz); 3.78–3.72 (m, 2H); 3.62 (apparent ddd, 1H); 2.95 (apparent dd, 1H); 2.58–2.52 (m, 1H); 2.11 (s, 3H); 1.58 (q, 2H, J=7.3 Hz); 0.91 (t, 3H, J=7.3 Hz).

Example 34

Synthesis of 115: A solution of amino acid 114 (10.7 mg, 0.038 mmol) in water (1.3 mL) cooled to 0° C. was adjusted to pH=9.0 with 1.0 M NaOH. Benzyl formimidate hydrochloride (26 mg, 0.153 mmol) was then added in one portion and the reaction stirred between 0–5° C. for 3 h while maintaining the pH between 8.5–9.0 with 1.0 M NaOH. The reaction was then concentrated in vacuo and the residue applied to a C$_{18}$ column and eluted with water. Fractions containing the product were pooled and lyophilized to give the formamidine carboxylic acid 115 (10 mg) as a white powder. $^1$H NMR (D$_2$O, 300 MHz, mixture isomers): δ 7.83 (s, 1H); [6.46 (s) & 6.43 (s); 1 H total]; 4.83 (d, 1H, J=7.3 Hz); 4.73 (d, 1H, J=7.3 Hz); 4.50–4.35 (m, 1H); 4.10–4.05 (m, 1H); [4.03–3.95 (m) & 3.80–3.65 (m), 1 H total]; 3.39 (s, 3H); 2.90–2.75 (m, 1H); 2.55–2.30 (m, 1H); [2.03 (s) & 2.01 (s), 3H total].

Example 35

Compound 123: To a solution of alcohol 63 (5.842 g, 20.5 mmol) and DMAP (200 mg) in pyridine (40 mL) was added tosyl chloride (4.3 g, 22.6 mmol). The mixture was stirred at room temperature for 40 hrs, and pyridine was removed under reduced pressure. The reaction was quenched with water, and extracted with EtOAc (3×). The combined organic extracts were washed with water, brine, and dried over MgSO$_4$. Purification by flash column chromatography (Hexanes/EtOAc=2/1) gave the tosylate (8.04 g, 89%): $^1$H NMR (CDCl$_3$) δ 7.84 (d, J=8.3 Hz, 2H), 7.33 (d, J=8.1 Hz, 2 H), 4.78 (m, 1 H), 4.43 (m, 1 H), 4.06 (m, 1 H), 3.79 (s, 3 H), 2.44 (s, 3 H), 2.43–1.92 (m, 4 H), 1.61–1.22 (m, 10 H).

Example 36

Compound 124: To a solution of alcohol 123 (440 mg, 1.0 mmol) in pyridine (3 mL) was added POCl$_3$ (100 μL, 1.1 mmol). The mixture was stirred at room temperature for 12 hrs, and quenched with saturated NH$_4$Cl solution. The water phase was extracted with ether (3×). The combined ether layers were washed with water (2×), 2 N HCl solution (2×), brine, and dried over MgSO$_4$. Purification by flash column chromatography (Hexane/EtOAc=2/1) gave a mixture of the desired product 124 and some inpurity (350 mg, 83%, 2/1).

Example 37

Compound 1: To a solution of the known acetonide of methyl shikimate (877 mg, 3.85 mmol, "Tetrahedron Lett.", 26:21 (1985)) in dichloromethane (15 mL) at −10° C. was added methanesulfonyl chloride (330 μL, 4.23 mmol) followed by the dropwise addition of triethylamine (640 μL, 4.62 mmol). The solution was stirred at −10° C. for 1 h then at 0° C. for 2 h, at which time methanesulfonyl chloride (30

µL), triethylamine (64 µL) was added. After 1 h cold water was added, the organic phase was separated, washed with water, dried (MgSO$_4$), and evaporated. The crude product was chromatographed on silica gel (1/1-hexane/ethyl acetate) to provide mesylate 130 (1.1 g, 93%) as an oil. Mesylate 130 (990 mg, 3.2 mmol) was dissolved in tetrahydrofuran (5 mL) and was treated with 1M HCl (5 mL). The solution was stirred at room temperature for 19 h, diluted with water (5 mL) and stirred an additional 7 h. Evaporation of the organic solvent precipitated an oily residue which was extracted into ethyl acetate. The combined organic extracts were washed with brine, dried (MgSO$_4$), and evaporated. Addition of CH$_2$Cl$_2$ to the crude residue precipitated a white solid which was filtered and washed with CH$_2$Cl$_2$ to afford diol 131 (323 mg, 38%). To a partial suspension of diol 131 (260 mg, 0.98 mmol) in THF (5 mL) at 0° C. was added DBU (154 µL, 1.03 mmol). The solution was stirred at 0° C. for 3 h and then was warmed to room temperature stirring for 5 h. The solvent was evaporated and the crude residue was partitioned between ethyl acetate (40 mL) and 5% citric acid (20 mL). The organic phase was washed with brine. Aqueous phases were back extracted with ethyl acetate (15 mL) and the combined organic extracts were dried (MgSO$_4$) and evaporated to afford the epoxide (117 mg, 70%) as a white solid which gave an $^1$H NMR spectrum consistent with structure 1 prepared by literature method.

Example 38

Alcohol 51: To a solution of protected alcohol (PG=methoxymethyl) (342 mg, 1.15 mmol) in CH$_2$Cl$_2$ (10 mL) at 0° C. was added trifluoroacetic acid (8 mL). After 5 min at 0° C., the solution was stirred 1 h at room temperature and was evaporated. The crude product was purified on silica gel (ethyl acetate) to afford alcohol 51 (237 mg, 82%) as an oil: $^1$H NMR (300 MHz, CDCl$_3$) δ 2.11 (s, 3H), 2.45 (m, 1H), 2.97 (dd, 1H, J=3.8, 18.8), 3.66 (m, 2H), 3.78 (s, 3H), 4.40 (br s, 1H), 5.22 (br s, 1H), 6.19 (br s, 1H), 6.82 (m, 1H).

Example 39

Methyl ether 150: To a solution of alcohol 51 (46 mg, 0.18 mmol) and methyl iodide (56 µL, 0.90 mmol) in THF (0.7 mL) at 0° C. was added NaH as a 60% mineral oil dispersion (8 mg, 0.20 mmol). The solution was stirred at 0° C. for 2.5 h, and a second portion of NaH (2 mg) was added. After an additional 1 h at 0° C. and 4 h at room temperature the solution was cooled to 0° C. and 5% citric acid (0.5 mL) was added. The mixture was extracted with ethyl acetate (4×2 mL) and the combined organic extracts were dried (MgSO$_4$), and evaporated. Purification of the crude residue on silica gel (ethyl acetate) gave methyl ether 150 (12 mg, 25%) as a solid: $^1$H NMR (300 MHz, CDCl$_3$) δ 2.07 (s, 3H), 2.23–2.34 (m, 1H), 2.89 (app ddd, 1H), 3.43 (s, 3H), 3.58 (m, 1H), 3.78 (s, 3H), 4.13 (m, 1H), 4.40 (m, 1H), 5.73 (d, 1H, J=7.6), 6.89 (m, 1H).

Example 40

Amino acid 151: To a solution of methyl ether 150 (12 mg, 0.45 mmol) in THF(1 mL)/water (100 µL) was added polymer support Ph$_3$P (75 mg, 3 mmol P/g resin). The mixture was stirred at room temperature for 19 h. The resin was filtered, washed several times with THF and the combined filtrate and washings were evaporated to provide 8 mg of a crude residue. The residue was dissolved in THF (0.5 mL), and 0.5 M KOH (132 µL)/water (250 µL) was added. The solution was stirred at room temperature for 1.25 h and the pH was adjusted to 3–4 with IR120 ion exchange resin. The resin was filtered and was stirred with 1M HCl. After filtration, the resin was subjected to the same treatment with 1M HCl until the acidic washes no longer tested positive for amine with ninhydrin. The combined resin washings were evaporated and the residue was purified on C-18 reverse phase silica eluting with water to afford after lyophilization, amino acid 151 (1.8 mg, 15%) as a white solid: $^1$H NMR (300 MHz, D$_2$O) δ 2.09 (s, 3H), 2.48–2.59 (app qt, 1H), 2.94 (dd, 1H, J=5.7, 17.4), 3.61 (m, 1H), 4.14–4.26 (m, 2H), 6.86 (br s, 1H).

Example 41

Amino acid allyl ether 153: To a solution of azide 6 (16 mg, 0.054 mmol) in THF (0.50 mL) and H$_2$O (35 µL) was added polystyrene supported PPh$_3$ (50 mg). The reaction was stirred at ambient temperature for 24 h, filtered through a sintered glass funnel and washed with hot methanol. Concentration in vacuo gave the crude amino ester which was dissolved in THF (1.0 mL) and treated with aqueous KOH (220 µL of a 0.5 M solution). After stirring at ambient temperature for 2 h Amberlite IR-120 (plus) acidic resin was added until the solution attained pH=4.5. The resin was filtered and washed with ethanol and H$_2$O. Concentration in vacuo gave a pale orange solid which was purified by reverse phase C$_{18}$ chromatography using H$_2$O as an eluent. Fractions containing the desired product were pooled and lyophilized to give the amino acid as a white powder. $^1$H NMR (D$_2$O, 300 MHz): δ 6.51 (br t, 1H); 6.05–5.80 (m, 1H, —CH=, allyl); 5.36–5.24 (m, 2H,=CH$_2$, allyl); 4.35–4.25 (m, 1H); 4.25–4.05 (m, 2H, —CH$_2$—, allyl); 4.02–3.95 (m, 1H); 3.81–3.70 (m, 1H); 2.86–2.77 (apparent dd, 1H); 2.35–2.24 (complex m, 1H); 2.09 (s, 3H).

Example 42

Epoxide 161: MCPBA (690 mg) was added to a solution of olefin 160 (532 mg, 1.61 mmol, prepared by Example 14, crude mesylate was filtered through silica gel using 30% EtOAc/Hexanes prior to use) in dichloromethane (15 mL) cooled to 0° C. The mixture was warmed to room temperature and stirred overnight. The bulk of the solvent was removed under vacuum and the mixture diluted with ethyl acetate. The organic layer was washed with aqueous sodium bisulfite, saturated sodium bicarbonate, brine and dried over MgSO$_4$. Concentration in vacuo followed by flash column chromatography of the residue (30% hexanes in ethyl acetate) gave 437 mg (78%) of 161 as a pale oil. $^1$H NMR (CDCl$_3$, 300 MHz): [1:1 mixture of diastereomers] δ [4.75 (dd, J=3.9, 8.2 Hz) & 4.71 (dd, J=3.9, 8.4 Hz), 1H total]; 4.37 (m, 1H); 4.25–4.00 (m, 2H); 3.78 (s, 3H); [3.68 (dd, J=5.7, 11.7 Hz) & 3.51 (dd, J=6.6, 11.7 Hz), 1H total]; [3.17 (s) & 3.16 (s), 3H total]; [2.99 (m) & 2.93 (m), 1H total]; [2.83 (t, J=4.1 Hz) & 2.82 (t, J=4.5 Hz), 1H total]; 2.70–2.60 (m, 1H); 2.45–2.30 (m, 1H).

Example 43

Diol 162: The epoxide 161 (437 mg, 1.23 mmol) was gently reluxed for 1 h in THF (20 mL) and H$_2$O (10 mL) containing 5 drops of 70% HClO$_4$. Solid NaHCO$_3$ was added and the mixture concentrated in vacuo. The residue was dissolved in EtOAc, washed with brine and dried. Concentration in vacuo gave the crude diol 162 as a pale oil in quantitative yield. Used without any purification for the next reaction.

Example 44

Aldehyde 163: Oxidation of diol 162 was carried out according to the procedure of Vo-Quang and co-workers, "Synthesis", 68 (1988). To a slurry of silica gel (4.3 g) in dichloromethane (30 mL) was added a solution of $NaIO_4$ (4.4 mL of a 0.65 M aqueous solution). To this slurry was added a solution of the crude diol 162 (520 mg) in EtOAc (5 mL) and dichloromethane (15 mL). After 1 h the solids were filtered and washed with 20% hexanes/EtOAc. Concentration gave an oily residue which was dissolved in EtOAc and dried over $MgSO_4$. Concentration in vacuo gave the aldehyde 163 as a pale oil which was used immediately for the next reaction. $^1H$ NMR ($CDCl_3$, 300 MHz): δ 9.69 (s, 1H); 6.98 (m, 1H); 4.72 (dd, 1H, J=3.7, 9.1 Hz); 4.53 (d, 1H, J=18.3 Hz); 4.45 (d, 1H, J=18.3 Hz); 4.31 (m, 1H); 4.26–4.18 (m, 1H); 3.79 (s, 3H); 3.19 (s, 3H); 3.05 (dd, 1H, J=5.7, 18.6 Hz); 2.20–2.45 (m, 1H).

Example 45

Alcohol 164: The crude aldehyde 163 was treated with $NaCNBH_3$ according to the procedure of Borch and co-workers, "J. Amer. Chem. Soc.", 93:2897 (1971) to give 269 mg (65%) of the alcohol 164 after flash chromatography (40% hexanes in ethyl acetate). $^1H$ NMR ($CDCl_3$, 300 MHz): δ 6.91 (m, 1H); 4.75 (dd, 1H, J=3.9, 8.7 Hz); 4.34 (br t, 1H, J=4.1 Hz); 4.25–4.15 (m, 1H); 3.85–3.70 (m, 4H); 3.77 (s, 3H); 3.16 (s, 3H); 2.95 (dd, 1H, J=5.7, 18.6 Hz); 2.37 (dd, 1H, J=7.1, 18.6 Hz); 2.26 (br s, 1H).

Example 46

Aziridine 165: The alcohol 164 (208 mg, 0.62 mmol) was acetylated in the usual manner (AcCl, pyridine, dichloromethane, cat. DMAP) to give the acetate (241 mg, 100%). The crude acetate (202 mg, 0.54 mmol) was treated at room temperature with $Ph_3P$ (155 mg) in THF (12 mL) for 2 h. $H_2O$ (1.1 mL) and triethylamine (224 μL) were then added and the solution stirred overnight. The reaction mixture was concentrated and the residue partitioned between ethyl acetate and saturated bicarbonate/brine. The organic layer was dried, concentrated in vacuo and purified by flash chromatography (10% MeOH in EtOAc) to give 125 mg (90%) of aziridine 165 as a white solid. $^1H$ NMR ($CDCl_3$, 300 MHz): δ 6.80 (m, 1H); 4.44 (br s, 1H); 4.23 (t, 2H, J=4.8 Hz); 3.82–3.65 (m, 2H); 3.74 (s, 3H); 2.85 (br d, 1H, J=19.2 Hz); 2.65–2.40 (m, 3H); 2.09 (s, 3H); 1.25 (br s, 1H).

Example 47

N-Boc aziridine 166: Boc anhydride (113 mg, 0.52 mmol) was added to a solution of aziridine 165 (125 mg, 0.49 mmol), triethylamine (70 μL), DMAP (cat. amount) in dichloromethane (7 mL). After 1 h the reaction was concentrated and the residue subjected to flash chromatography (40% EtOAc in hexanes) to give 154 mg (88%) of the N Boc aziridine 166 as a pale oil. $^1H$ NMR ($CDCl_3$, 300 MHz): δ 6.82 (m, 1H); 4.47 (br m, 1H); 4.23 (t, 2H, J=4.7 Hz); 3.81 (t, 2H, J=4.7 Hz); 3.75 (s, 3H); 3.00 (br d, 1H, J=18.0 Hz); 2.90–2.85 (m, 2H); 2.65–2.55 (m, 1H); 2.10 (s, 3H); 1.44 (s, 9H).

Example 48

Azido ester 167: Aziridine 166 (154 mg, 0.43 mmol), sodium azide (216 mg), and ammonium chloride (223 mg) was heated at 100° C. in DMF (5 mL) for 18 h. The cooled reaction mixture was partitioned between ethyl ether and brine. The ether layer was washed with $H_2O$, brine and dried over $MgSO_4$. Concentration gave a crude residue which was treated with 40% TFA in dichloromethane at room temperature. After 2 h the reaction was concentrated in vacuo to give a pale oil which was passed through a short column of silica gel eluting with EtOAc. The product was then acylated in the usual manner (AcCl, pyridine, dichloromethane, cat. DMAP) to give the azido ester 167 as a pale yellow oil 16 mg (11% for 3 steps) after flash chromatography (5% MeOH in chloroform). $^1H$ NMR ($CDCl_3$, 300 MHz): δ 6.85 (m, 1H); 5.80 (br d, 1H, J=7.8 Hz); 4.55 (m, 1H); 4.25–4.10 (m, 3H); 3.90–3.85 (m, 2H); 3.78 (s, 3H); 3.55 (m, 1H); 2.90 (dd, 1H, J=5.4, 17.0 Hz); 2.45–2.25 (m, 1H); 2.10 (s, 3H); 2.05 (s, 3H).

Example 49

Amino acid 168: To a solution of ester 167 (16 mg, 0.047 mmol) in THF (1 ml) cooled to 0° C. was added aq. KOH (208 μl of a 0.476 M solution). The reaction was then warmed to room temperature and stirred for 2 h. The reaction was then acidified to pH=4.0 with Amberlite IR-120 (plus) acidic resin. The resin was then filtered and washed with ethanol and $H_2O$. Concentration in vacuo gave a 14 mg (100%) of the azido carboxylic acid as a white solid. The azido acid was dissolved in ethanol (2 mL) and treated with hydrogen gas (1 atm) over Lindlar's catalyst (15 mg) for 16 h according to the procedure of Corey and co-workers, "Synthesis", 590 (1975). The reaction mixture was filtered through a celite pad and washed with hot ethanol and $H_2O$. Concentration in vacuo gave a pale orange solid which was purified by a $C_{18}$ column chromatography eluting with $H_2O$. The fractions containing the product were pooled and lyophilzed to give 9.8 mg of 168 as a white powder. $^1H$ NMR ($D_2O$, 500 MHz): δ: 6.53 (br s, 1H); 4.28 (br m, 1H); 4.08 (dd, 1H, J=11.0, 11.0 Hz); 3.80–3.65 (complex m, 4H); 3.44 (m, 1H); 2.84 (apparent dd, 1H); 2.46–2.39 (complex m, 1H); 2.08 (s, 3H).

Example 50

Epoxy MOM ether 19 (PG=methoxymethyl): Prepared in 74% from epoxy alcohol 1 according to the procedure of Mordini and co-workers, "J. Org. Chem.", 59:4784 (1994). $^1H$ NMR ($CDCl_3$, 300 MHz): δ 6.73 (m, 1H); 4.87 (s, 2H); 4.59 (t, 1H, J=2.4 Hz); 3.76 (s, 3H); 3.57 (m, 1H); 3.50–3.40 (m, 1H); 3.48 (s, 3H); 3.10 (d, J=19.5 Hz); 2.45 (m, 1H).

Example 51

Aziridine 170: Prepared in 77% overall from epoxide 19 (PG=methoxymethyl) according to the general protocol described in Examples 3 and 4: $^1H$ NMR ($CDCl_3$, 300 MHz): δ 6.85 (m, 1H); 4.78 (s, 2H); 4.54 (m, 1H); 3.73 (s, 3H); 3.41 (s, 3H); 2.87 (d, 1H, J=18.9 Hz); 2.70–2.45 (m, 3H).

Example 52

Azido ester 22 (PG=methoxymethyl): The aziridine 170 (329 mg, 1.54 mmol), $NaN_3$ (446 mg) and $NH_4Cl$ (151 mg) was heated at 65° C. in DMF (20 mL) for 18 h. The cooled reaction mixture was partitioned between ethyl ether and brine. The ether layer was washed with $H_2O$, brine and dried over $MgSO_4$. Concentration in vacuo gave the crude azido amine as a pale oil which was taken up in $CH_2Cl_2$ (15 mL) and treated with pyridine (4 mL) and AcCl (150 μL). Aqueous work up followed by flash chromatography of the residue gave 350 mg (76%) of azido ester 22 (PG=methoxymethyl) as a pale oil. $^1H$ NMR ($CDCl_3$, 300 MHz): δ 6.78 (s, 1H); 6.39 (br d, 1H, J=7.8 Hz); 4.72 (d, 1H, J=6.9 Hz); 4.66 (d, 1H, J=6.9 Hz); 4.53 (br d, 1H, J=8.4 Hz); 4.00–3.90 (m, 1H); 3.80–3.65 (m, 1H); 3.75 (s, 3H); 3.37 (s, 3H); 2.85 (dd, 1H, J=5.4, 17.7 Hz); 2.35–2.20 (m, 1H); 2.04 (s, 3H).

Example 53

Amino acid 114: The azide 22 (PG=methoxymethyl) (39 mg, 0.131 mmol) was treated with hydrogen gas at 1 atmosphere over Lindlar's catalyst (39 mg) in ethanol for 2.5 h according to the procedure of Corey and co-workers, "Synthesis", 590 (1975). The reaction mixture was filtered through a celite pad, washed with hot ethanol and concentrated to give the crude amine 33 mg (92%) as a pale foam. The amine in THF (1 mL) was treated with aq. KOH (380 $\mu$L of a 0.476 M solution). After 1 h the reaction was acidified to pH=4.0 with Amberlite IR-120 (plus) acidic resin. The resin was then filtered, washed with $H_2O$ and concentrated to give a pale solid which was purified by a $C_{18}$ column chromatography eluting with $H_2O$. The fractions containing the product were pooled and lyophilzed to give 20 mg of 114 as a white powder. $^1$H NMR ($D_2O$, 300 MHz): $\delta$ 6.65 (s, 1H); 4.87 (d, 1H, J=7.5 Hz); 4.76 (d, 1H, J=7.5 Hz); 4.47 (br d, 1H, J=8.7 Hz); 4.16 (dd, 1H, J=11.4, 11.4 Hz); 3.70–3.55 (m, 1H); 3.43 (s, 3H); 2.95 (dd, 1H, J=5.7, 17.4 Hz); 2.60–2.45 (m, 1H); 2.11 (s, 3H).

Example 54

Amino acid 171: To solid amino acid 114 (4 mg, 0.015 mmol) was added 40% TFA in $CH_2Cl_2$ (1 mL, cooled to 0° C. prior to addition). After stirring at room temperature for 1.5 h the reaction mixture was concentrated to give a white foam. Co-evaporation from $H_2O$ several times followed by lyophilization gave a white solid, 5.5 mg of 117 as the TFA salt. $^1$H NMR ($D_2O$, 300 MHz): $\delta$ 6.85 (m, 1H); 4.45 (m, 1H); 4.05 (dd, 1H, J=11.4, 11.4 Hz); 3.65–3.55 (m, 1H); 3.00–2.90 (m, 1H); 2.60–2.45 (m, 1H); 2.09 (s, 3H).

Example 55

Acetonide 180: To a suspension of shikimic acid (25 g, 144 mmol, Aldrich) in methanol (300 mL) was added p-toluenesulfonic acid (274 mg, 1.44 mmol, 1 mol %) and the mixture was heated to reflux for 2 h. After adding more p-toluenesulfonic acid (1 mol %) the reaction was refluxed for 26 h and was evaporated. The crude methyl ester (28.17 g) was suspended in acetone (300 mL) and was treated with dimethoxypropane (35 mL, 288 mmol) and was stirred at room temperature for 6 h and then was evaporated. The crude product was dissolved in ethyl acetate (400 mL) and was washed with saturated $NaHCO_3$ (3×125 mL) and saturated NaCl. The organic phase was dried ($MgSO_4$), filtered, and evaporated to afford crude acetonide 180 (~29.4 g) which was used directly: $^1$H NMR ($CDCl_3$) $\delta$ 6.91 (t, 1H, J=1.1), 4.74 (t, 1H, J=4.8), 4.11 (t, 1H, J=6.9), 3.90 (m, 1H), 2.79 (dd, 1H, J=4.5, 17.4), 2.25 (m, 2H), 1.44 (s, 3H), 1.40 (s, 3H).

Example 56

Mesylate 130: To a solution of acetonide 180 (29.4 g, 141 mmol) in $CH_2Cl_2$, (250 mL) at 0° C. was added triethylamine (29.5 mL, 212 mmol) followed by the addition of methanesulfonyl chloride (13.6 mL, 176 mmol) over a period of 10 min. The reaction was stirred at 0° C. for 1 h and ice cold water (250 mL) was added. After transfer to a separatory funnel, the organic phase was washed with water, 5% citric acid (300 mL), saturated $NaHCO_3$ (300 mL) and was dried ($MgSO_4$), filtered, and evaporated. The crude product was filtered through a short plug of silica gel on a fritted glass funnel eluting with ethyl acetate. The filtrate was evaporated to afford mesylate 130 (39.5 g, 91%) as a viscous oil which was used directly in the next step: $^1$H NMR ($CDCl_3$) $\delta$ 6.96 (m, 1H), 4.80 (m, 2H), 4.28 (dd, 1H, J=6.6, 7.5), 3.79 (s, 3H), 3.12 (s, 3H), 3.01 (dd, 1H, J=5, 17.7), 2.56–2.46 (m, 1H).

Example 57

Diol 131: To a solution of mesylate 130 (35.85 g, 117 mmol) in methanol (500 mL) was added p-toluenesulfonic acid (1.11 g, 5.85 mmol, 5 mol %) and the solution was refluxed for 1.5 h and was evaporated. The residue was redissolved in methanol (500 mL) and was refluxed an additional 4 h. The solvent was evaporated and the crude oil was triturated with diethyl ether (250 mL). After completing the crystallization overnight at 0° C., the solid was filtered and was washed with cold diethyl ether, and dried to afford diol 131 (24.76 g) as a white solid. Evaporation of the filtrate and crystallization of the residue from methanol/diethyl ether gave an additional 1.55 g. Obtained 26.3 g (85%) of diol 131: $^1$H NMR ($CD_3OD$) $\delta$ 6.83 (m, 1H), 4.86 (m, 1H), 4.37 (t, 1H, J=4.2), 3.87 (dd, 1H, J=4.2, 8.4), 3.75 (s, 3H), 3.13 (s, 3H), 2.98–2.90 (m, 1H), 2.53–2.43 (m, 1H).

Example 58

Epoxy alcohol 1: A suspension of diol 131 (20.78 g, 78 mmol) in tetrahydrofuran (400 mL) at 0° C. was treated with 1,8-diazabicyclo[5.4.0]undec-7-ene (11.7 mL, 78 mmol) and was stirred at room temperature for 9 h at which time the reaction was complete. The reaction was evaporated and the crude residue was dissolved in $CH_2Cl_2$ (200 mL) and was washed with saturated NaCl (300 mL). The aqueous phase was extracted with $CH_2Cl_2$ (2×200 mL). The combined organic extracts were dried ($MgSO_4$), filtered, and evaporated. The crude product was purified on silica gel (ethyl acetate) to afford epoxy alcohol 1 (12 g, 90%) as a white solid whose $^1$H NMR spectrum was consistent with that reported in the literature: McGowan, D. A.; Berchtold, G. A., "J. Org. Chem.", 46:2381 (1981).

Example 59

Methoxymethyl ether 22 (PG=methoxymethyl): To a solution of epoxy alcohol 1 (4 g, 23.5 mmol) in $CH_2Cl_2$ (100 mL) was added N, N'-diisopropylethylamine (12.3 mL, 70.5 mmol) followed by chloromethyl methyl ether (3.6 mL, 47 mmol, distilled from tech. grade). The solution was refluxed for 3.5 h and the solvent was evaporated. The residue was partitioned between ethyl acetate (200 mL) and water (200 mL). The aqueous phase was extracted with ethyl acetate (100 mL). The combined organic extracts were washed with saturated NaCl (100 mL), dried ($MgSO_4$), filtered, and evaporated to afford 4.9 g of a solid residue which was of suitable purity to use directly in the next step: mp 62–65° (crude); mp 64–66° C. (diethyl ether/hexane); $^1$H NMR ($CDCl_3$) $\delta$ 6.73 (m, 1H), 4.87 (s, 2H), 4.59 (m, 1H), 3.75 (s, 3H), 3.57 (m, 1H), 3.48 (m overlapping s, 4H), 3.07 (dd, 1H, J=1.2, 19.8), 2.47 (dq, 1H, J=2.7, 19.5).

Ethyl Ester Analog of Compound 22:

To a solution of the corresponding ethyl ester of compound 1 (12.0 g, 0.065 mol) in $CH_2Cl_2$ (277 mL) at room temperature was added diisopropylethyl amine (34.0 mL, 0.13 mol) followed by chloromethyl methyl ether (10.0 mL, 0.19 mol). The reaction mixture was then gently refluxed for 2 h, cooled, concentrated in vacuo, and partitioned between EtOAc and water. The organic layer was separated and washed successively with dil. HCl, saturated bicarb, brine and dried over $MgSO_4$. Concentration in vacuo followed by flash chromatography on silica gel (50% hexanes in EtOAc) gave 13.3 g (90%) of the corresponding ethyl ester of compound 22 as a colorless liquid. $^1$H NMR (300 MHz, CDCl$_3$) δ 6.73–6.71 (m, 1H); 4.87 (s, 2H); 4.61–4.57 (m, 1H); 4.21 (q, 2H, J=7.2 Hz); 3.60–3.55 (m, 1H); 3.50–3.45 (m, 1H); 3.48 (s, 3H); 3.12–3.05 (m, 1H); 2.52–2.42 (m, 1H); 1.29 (t, 3H, J=7.2 Hz).

Example 60

Alcohol 181: To a solution of methoxymethyl ether 22 (PG=methoxymethyl) (4.9 g, 22.9 mmol) in 8/1-MeOH/H$_2$O (175 mL, v/v) was added sodium azide (7.44 g, 114.5 mmol) and ammonium chloride (2.69 g, 50.4 mmol) and the mixture was refluxed for 15 h. The reaction was diluted with water (75 mL) to dissolve precipitated salts and the solution was concentrated to remove methanol. The resulting aqueous phase containing a precipitated oily residue was diluted to a volume of 200 mL with water and was extracted with ethyl acetate (3×100 mL). The combined organic extracts were washed with saturated NaCl (100 mL), dried (MgSO$_4$), filtered and evaporated. The crude was purified on silica gel (1/1-hexane/ethyl acetate) to afford alcohol 181 (5.09 g, 86%) as a pale yellow oil. Subsequent preparations of alcohol 181 provided material which was of sufficient purity to use in the next step without further purification: $^1$H NMR (CDCl$_3$) δ 6.86 (m, 1H), 4.79 (s, 2H), 4.31 (br t, 1H, J=4.2), 3.90–3.75, 3.77 (m overlapping s, 5H), 3.43 (s, 3H), 2.92 (d, 1H, J=6.6), 2.87 (dd, 1H, J=5.4, 18.6), 2.21–2.30 (m, 1H).

Example 61

Mesylate 184: To a solution of alcohol 181 (6.47 g, 25.2 mmol) in CH$_2$Cl$_2$ (100 mL) at 0° C. was added first triethyl amine (4.4 mL, 31.5 mmol) then methanesulfonyl chloride (2.14 mL, 27.7 mmol). The reaction was stirred at 0° C. for 45 min then was warmed to room temperature stirring for 15 min. The reaction was evaporated and the residue was partitioned between ethyl acetate (200 mL) and water (100 mL). The organic phase was washed with water (100 mL), saturated NaHCO$_3$ (100 mL), saturated NaCl (100 mL). The water washes were extracted with a single portion of ethyl acetate which was washed with the same NaHCO$_3$/NaCl solutions. The combined organic extracts were dried (MgSO$_4$), filtered, and evaporated. The crude product was of suitable purity to be used directly in the next step: $^1$H NMR (CDCl$_3$) δ 6.85 (m, 1H), 4.82 (d, 1H, J=6.9), 4.73 (d, 1H, J=6.9), 4.67 (dd, 1H, J=3.9, 9.0), 4.53 (br t, 1H, J=4.2), 3.78 (s, 3H), 3.41 (s, 3H), 3.15 (s, 3H), 2.98 (dd, 1H, J=6.0, 18.6), 2.37 (m, 1H); $^{13}$C NMR (CDCl$_3$) δ 165.6, 134.3, 129.6, 96.5, 78.4, 69.6, 55.8, 55.7, 52.1, 38.2, 29.1.

Example 62

Aziridine 170: To a solution of mesylate 184 (8.56 g, 25 mmol) in THF (150 mL) at 0° C. was added Ph$_3$P (8.2 g, 31 mmol), initially adding a third of the amount while cooling and then after removing the ice bath adding the remainder of the Ph$_3$P over a period of 10–15 min. After complete addition of the Ph$_3$P the reaction was stirred at room temperature for 3 h with the formation of a white precipitate. To this suspension was added triethyl amine (5.2 mL, 37.5 mmol) and water (10 mL) and the mixture was stirred at room temperature for 12 h. The reaction was concentrated to remove THF and the residue was partitioned between CH$_2$Cl$_2$ (200 mL) and saturated NaCl (200 mL). The aqueous phase was extracted with several portions of CH$_2$Cl$_2$ and the combined organic extracts were dried (Na$_2$SO$_4$), filtered, and evaporated to afford a crude product which was purified on silica gel (10% MeOH/EtOAc) to afford aziridine 170 (4.18 g, 78%) as an oil which typically contained trace amounts of triphenylphosphine oxide impurity: $^1$H NMR (CDCl$_3$) δ 6.81 (m, 1H), 4.78 (s, 2H), 4.54 (m, 1H), 3.73 (s, 3H), 3.41 (s, 3H), 2.87 (app dd, 1H), 2.64 (br s, 1H), 2.56–2.47 (m, 2H), NH signal was not apparent; $^{13}$C NMR (CDCl$_3$) δ 166.9, 132.5, 128.0, 95.9, 69.5, 55.2, 51.6, 31.1, 27.7, 24.1.

Example 63

Amine 182: To a solution of aziridine 170 (3.2 g, 15 mmol) in DMF (30 mL) was applied a vacuum on a rotary evaporator (40° C.) for several minutes to degas the solution. To the solution was added sodium azide (4.9 g, 75 mmol) and ammonium chloride (1.6 g, 30 mmol) and the mixture was heated at 65–70° C. for 21 h. The reaction mixture was cooled to room temperature, diluted with ethyl acetate (~100 mL) and was filtered. The filtrate was evaporated and the residue was partitioned between diethyl ether (100 mL) and saturated NaCl (100 mL). The organic phase was washed again with saturated NaCl (100 mL), dried (MgSO$_4$), filtered, and was evaporated. Additional crude product was obtained from the aqueous washings by extraction with ethyl acetate and treated in the same manner as described above. The crude product was purified on silica gel (5% MeOH/CH$_2$Cl$_2$) to afford amine 182 (2.95 g) as an oil which contained a small amount of triphenylphosphine oxide impurity from the previous step: $^1$H NMR (CDCl$_3$) δ 6.82 (t, 1H, J=2.3), 4.81 (d, 1H, J=7.2), 4.77 (d, 1H, J=6.9), 4.09–4.04 (m, 1H), 3.76 (s, 3H), 3.47 and 3.44 (m overlapping s, 4H), 2.94–2.86 (m, 2H), 2.36–2.24 (m, 1H); $^{13}$C NMR (CDCl$_3$) δ 165.9, 137.3, 128.2, 96.5, 79.3, 61.5, 55.7, 55.6, 51.9, 29.5.

Example 64

N-Trityl aziridine 183: Amine 182 (2.59 g, 10.2 mmol) was dissolved in 5% HCl/MeOH (30 mL) and the solution was stirred for 3 h at room temperature. Additional 5% HCl/MeOH (10 mL) was added stirring 1 h and the solvent was evaporated to afford 2.52 g of the HCl salt as a tan solid after high vacuum. To a suspension of the HCl salt in CH$_2$Cl$_2$ (50 mL) at 0° C. was added triethylamine (3.55 mL, 25.5 mmol) followed by the addition of solid trityl chloride (5.55 g, 12.8 mmol) in one portion. The mixture was stirred at 0° C. for 1 h and then was warmed to room temperature stirring for 2 h. The reaction was cooled to 0° C., triethylamine (3.6 mL, 25.5 mmol) was added and methane sulfonyl chloride (0.97 mL, 12.5 mmol) was added, stirring the resulting mixture for 1 h at 0° C. and for 22 h at room temperature. The reaction was evaporated and the residue was partitioned between diethyl ether (200 mL) and water (200 mL). The organic phase was washed with water (200 mL) and the combined aqueous phases were extracted with diethyl ether (200 mL). The combined organic extracts were washed with water (100 mL), saturated NaCl (200 mL) and were dried (Na$_2$SO$_4$), filtered, and evaporated. The crude product was purified on silica gel (1/1-hexane/CH$_2$Cl$_2$) to afford N-trityl aziridine 183 (3.84 g, 86%) as a white foam: $^1$H NMR (CDCl$_3$) δ 7.4–7.23 (m, 16H), 4.32 (m, 1H), 3.81 (s, 3H), 3.06 (dt, 1H, J=1.8, 17.1), 2.94–2.86 (m, 1H), 2.12 (m, 1H), 1.85 (t, 1H, J=5.0).

Example 65

Compound 190: A solution of N-trityl aziridine 183 (100 mg, 0.23 mmol), cyclohexanol (2 mL) and boron trifluoride etherate (42 μL, 0.35 mmol) was heated at 70° C. for 1.25 h and was evaporated. The residue was dissolved in pyridine (2 mL) and was treated with acetic anhydride (110 μL, 1.15 mmol) and catalytic DMAP. After stirring for 3 h at room temperature the reaction was evaporated. The residue was partitioned between ethyl acetate and 5% citric acid. The aqueous phase was extracted with ethyl acetate and the combined organic extracts were washed with saturated NaHCO$_3$, and saturated NaCl. The organic phase was dried (MgSO$_4$), filtered, and evaporated. The crude product was purified on silica gel (1/1-hexane/ethyl acetate) to afford compound 190 (53 mg, 69%) as a solid: mp 105–107° C. (ethyl acetate/hexane); $^1$H NMR (CDCl$_3$) δ 6.78 (m, 1H), 6.11 (d, 1H, J=7.4), 4.61 (m, 1H), 4.32–4.23 (m, 1H), 3.76 (s, 3H), 3.44–3.28 (m, 2H), 2.85 (dd, 1H, J=5.7, 17.6), 2.28–2.17 (m, 1H), 2.04 (s, 3H), 1.88–1.19 (m, 10H).

Example 66

Compound 191: To a solution of compound 190 (49 mg, 0.15 mmol) in THF was added triphenylphosphine (57 mg, 0.22 mmol) and water (270 μL) and the solution was heated at 50° C. for 10 h. The reaction was evaporated and the residue was dissolved in ethyl acetate, dried (Na$_2$SO$_4$), filtered and evaporated. The crude product was purified on silica gel (1/1-methanol/ethyl acetate) to afford the amine (46 mg) as a pale yellow solid. The a solution of the amine in THF (1.5 mL) was added 1.039N KOH solution (217 μL) and water (200 μL). The mixture was stirred at room temperature for 1 h and was then cooled to 0° C. and acidified to pH 6–6.5 with IR 120 ion exchange resin. The resin was filtered, washed with methanol and the filtrate was evaporated. The solid residue was dissolved in water and was passed through a column (4×1 cm) of C-18 reverse phase silica gel eluting with water and then 2.5% acetonitrile/water. Product fractions were combined and evaporated and the residue was dissolved in water and lyophilized to afford amino acid 191 (28 mg) as a white solid: $^1$H NMR (D$_2$O) δ 6.47 (br s, 1H), 4.80 (br d, 1H), 4.00 (dd, 1H, J=8.9, 11.6), 3.59–3.50 (m, 2H), 2.87 (dd, 1H, J=5.5, 17.2), 2.06 (s, 3H), 1.90–1.15 (series of m, 10H); Anal. Calcd for C$_{15}$H$_{24}$N$_2$O$_4$.H$_2$O: C, 57.31; H, 8.34; N, 8.91. Found: C, 57.38; H, 8.09; N, 8.77.

Example 67 bis-Boc guanidino ester 201: Treated according to the procedure of Kim and Qian, "Tetrahedron Lett.", 34:7677 (1993). To a solution of amine 200 (529 mg, 1.97 mmol, prepared by the method of Example 109, bis-Boc thiourea (561 mg, 2.02 mmol) and Et$_3$N (930 μL) in dry DMF (5.0 mL) cooled to 0° C. was added HgCl$_2$ (593 mg, 2.18 mmol) in one portion. The heterogeneous reaction mixture was stirred for 45 min at 0° C. and then at room temperature for 15 min, after which the reaction was diluted with EtOAc and filtered through a pad of celite. Concentration in vacuo followed by flash chromatography of the residue on silica gel (10% hexanes in ethyl acetate) gave 904 mg (90%) of 201 as a pale oil. $^1$H NMR (CDCl$_3$, 300 MHz): δ 11.39 (s, 1H); 8.63 (d, 1H, J=7.8 Hz); 6.89 (t, 1H, J=2.4 Hz); 6.46 (d, 1H, J=8.7 Hz); 4.43–4.32 (m, 1H); 4.27–4.17 (m, 1H); 4.13–4.06 (m, 1H); 3.77 (s, 3H); 3.67–3.59 (m, 2H); 2.83 (dd, 1H, J=5.1, 17.7 Hz); 2.45–2.33 (m, 1H); 1.95 (s, 3H); 1.65–1.50 (m, 2H); 1.45 (s, 18H); 0.90 (t, 3H, J=7.5 Hz).

Example 68

Carboxylic acid 202: To a solution of methyl ester 201 (904 mg, 1.77 mmol) in THF (10 mL) was added aqueous KOH (3.45 mL of a 1.039 N solution). The reaction mixture was stirred at room temperature for 17 h, cooled to 0° C. and acidified to pH 4.0 with Amberlite IR-120 (H$^+$) acidic resin. The resin was filtered and washed with water and methanol. Concentration in vacuo gave the free acid as a pale foam which was used without further purification in the next reaction.

Example 69

Guanidine carboxylic acid 203: To a solution of bis-Boc guanidnyl acid 202 (crude from previous reaction) in CH$_2$Cl$_2$ (40 mL) cooled to 0° C. was added neat trifluoroacetic acid (25 mL). The reaction mixture was stirred at 0° C. for 1 h and then at room temperature for 2 h. Concentration in vacuo gave a pale orange solid which was purified by C$_{18}$ reverse phase chromatography eluting with water. Fractions containing the desired product were pooled and lyophilized to give 495 mg (68%, 2 steps) of the guanidine carboxylic acid 203 as the trifluoroacetic acid salt. $^1$H NMR (D$_2$O, 300 MHz): δ 6.66 (s, 1H); 4.29 (bd, 1H, J=9.0 Hz); 4.01 (dd, 1H, J=10.8, 10.8 Hz); 3.87–3.79 (m, 1H); 3.76–3.67 (m, 1H); 3.60–3.50 (m, 1H); 2.83 (dd, 1H, J=5.1, 17.4 Hz); 2.47–2.36 (m, 1H); 2.06 (s, 3H); 1.65–1.50 (m, 2H); 0.90 (t, 3H, J=7.2 Hz). Anal. Calcd for C$_{15}$H$_{23}$O$_6$N$_4$F$_3$: C, 43.69; H, 5.62; N, 13.59. Found: C, 43.29; H, 5.90; N, 13.78.

Example 70

Formamidine carboxylic acid 204: A solution of amino acid 102 (25 mg, 0.10 mmol, prepared by the method of Example 110) in water (500 μL) at 0–5° C. was adjusted to pH 8.5 with 1.0 N NaOH. Benzyl formimidate hydrochloride (45 mg, 0.26 mmol) was added in one portion and the reaction mixture was stirred for 3 h at this temperature while maintaining the pH at 8.5–9.0 with 1.0 N NaOH. The reaction was then concentrated in vacuo and purified by C$_{18}$ reverse phase chromatography eluting with water. Fractions containing the desired product were pooled and lyophilized to give 4.0 mg (13%) of the formamidine carboxylic acid 204. $^1$H NMR (D$_2$O, 300 MHz): δ 7.85 (s, 1H); 6.53 (bd, 1H, J=7.8 Hz); 4.32–4.25 (bm, 1H); 4.10–3.97 (m, 1H); 3.76–3.67 (m, 2H); 3.57–3.49 (m, 1H); 2.86–2.81 (m, 1H); 2.55–2.40 (m, 1H); 2.04 (s, 3H); 1.65–1.50 (m, 2H); 0.90 (t, 3H, J=7.4 Hz).

Example 71

Amino acid 206: To a solution of amino methyl ester 205 (84 mg, 0.331 mmol, prepared by Example 107) in THF (1.0 mL) was added aqueous KOH (481 μL of a 1.039 N solution). The reaction mixture was stirred at room temperature for 2.5 h and acidified to pH 6.5 with Amberlite IR-120 (H$^+$) acidic resin. The resin was filtered and washed with water and methanol. Concentration in vacuo gave the amino acid as a white solid which was purified by C$_{18}$ reverse phase chromatography eluting with water. Fractions containing the desired product were pooled and lyophilized to give 59 mg (74%) of the amino acid 206. $^1$H NMR (CD$_3$OD, 300 MHz): δ 6.60 (bd, 1H, J=1.8 Hz); 4.01–3.95 (m, 1H); 3.71–3.60 (m, 2H); 3.50–3.42 (m, 1H); 3.05–2.85 (m, 2H); 2.39–2.28 (m, 1H); 1.70–1.55 (m, 2H); 0.95 (t, 3H, J=7.5 Hz).

Example 72

Trifluoroacetamide 207: To a degassed solution of amino acid 206 (59 mg, 0.246 mmol) in dry methanol (1.0 mL) under argon was added Et$_3$N (35 μL) followed by methyl trifluoroacetate (35 μL). The reaction was stirred for one week at room temperature and concentrated. Analysis by $^1$H NMR showed that reaction was 40% complete. The crude reaction product was redissolved in dry methanol (1.0 mL), methyl trifluoroacetate (1.0 mL) and Et$_3$N (0.5 mL) and stirred at room temperature for 5 days. The reaction was then concentrated in vacuo and dissolved in 50% aqueous THF (2.0 mL), acidified to pH 4 with Amberlite IR-120 (H$^+$) acidic resin and filtered. Concentration gave the crude trifluoroacetamide carboxylic acid which was used without further purification for the next reaction.

Example 73

Amino acid 208: A solution of azide 207 (crude from previous reaction) in THF (2.0 mL) and water (160 μL) was treated with polymer supported triphenyl phosphine (225 mg) at room temperature. After stirring for 20 h the polymer was filtered and washed with methanol. Concentration in vacuo gave a pale solid which was purified by C$_{18}$ reverse phase chromatography eluting with water. Fractions containing the desired product were pooled and lyophilized to give 6.5 mg (9%) of the trifluoroacetamide amino acid 208. $^1$H NMR (D$_2$O, 300 MHz): δ 6.59 (bs, 1H); 4.40–4.30 (m, 1H); 4.26 (t, 1H, J=10.1 Hz); 3.80–3.66 (m, 2H); 3.56–3.47 (m, 1H); 2.96 (bdd, 1H, J=5.4, 17.7 Hz); 2.58–2.45 (m, 1H); 1.62–1.50 (m, 2H); 0.89 (t, 3H, J=7.5 Hz).

Example 74

Methylsulfonamide methyl ester 209: Methanesulfonyl chloride (19 μL) was added to a solution of amine 205 (58 mg, 0.23 mmol, prepared by Example 107), Et$_3$N (97 μL) and a catalytic amount of DMAP (few crystals) in CH$_2$Cl$_2$ (1.0 mL) at 0° C. After 30 min the reaction mixture was warmed to room temperature and stirred for an additional 1 h. Concentration in vacuo followed by flash chromatography of the residue on silica gel (50% hexanes in ethyl acetate) gave 61 mg (79%) of the sulfonamide 209. $^1$H NMR (CDCl$_3$, 300 MHz): δ 6.87 (t, 1H, J=2.3 Hz); 5.08 (d, 1H, J=7.5 Hz); 4.03–3.90 (m, 1H); 3.78 (s, 3H); 3.75–3.45 (m, 4H); 3.14 (s, 3H); 2.95 (dd, 1H, J=5.2, 17.3 Hz); 2.42–2.30 (m, 1H); 1.75–1.55 (m, 2H); 0.95 (t, 3H, J=7.5 Hz).

Example 75

Amino ester 210: A solution of azide 209 (61 mg, 0.183 mmol) in THF (2.0 mL) and water (118 μL) was treated with polymer supported triphenyl phosphine (170 mg) at room temperature. After stirring for 17.5 h the polymer was filtered and washed with methanol. Concentration in vacuo followed by flash chromatography of the residue through a short silica gel column (100% methanol) gave 45 mg (80%) of the amino ester 210 as a pale foam. $^1$H NMR (CDCl$_3$, 300 MHz): δ 6.85 (s, 1H); 3.94 (bd, 1H, J=7.8 Hz); 3.77 (s, 3H); 3.74–3.60 (m, 2H); 3.55–3.45 (m, 1H); 3.25–3.15 (m, 1H); 3.11 (s, 3H); 2.94–2.85 (m, 1H); 2.85 (bs, 2H); 2.22–2.10 (m, 1H); 1.70–1.56 (m, 2H); 0.94 (t, 3H, J=7.5 Hz).

Example 76

Amino acid 211: A solution of methyl ester 210 (21 mg, 0.069 mmol) in THF (200 μL) was treated with aqueous KOH (135 μL of a 1.039 N solution). The reaction mixture was stirred at room temperature for 40 min and neutralized to pH 7.0 with Amberlite IR-120 (H$^+$) acidic resin. The resin was filtered and washed with water and methanol. Concentration in vacuo gave the amino acid as a pale solid which was purified by C$_{18}$ reverse phase chromatography eluting with water. Fractions containing the desired product were pooled and lyophilized to give 3.5 mg (17%) of the amino acid 211. $^1$H NMR (D$_2$O, 300 MHz): δ 6.60 (d, 1H, J=1.8 Hz); 4.30–4.20 (m, 1H); 3.84–3.75 (m, 1H); 3.68–3.58 (m, 1H); 3.60–3.40 (m, 2H); 3.20 (s, 3H); 2.96–2.88 (m, 1H); 2.55–2.45 (m, 1H); 1.72–1.59 (m, 2H); 0.93 (t, 3H, J=7.4 Hz).

Example 77

Bis-Boc guanidino ester 212: Treated according to the procedure of Kim and Qian, "Tetrahedron Lett." 34:7677 (1993). To a solution of amine 210 (31 mg, 0.101 mmol), bis-Boc thiourea (28.5 mg, 0.103 mmol) and Et$_3$N (47 μL) in dry DMF (203 μL) cooled to 0° C. was added HgCl$_2$ (30 mg, 0.11 mmol) in one portion. The heterogeneous reaction mixture was stirred for 30 min at 0° C. and then at room temperature for 30 min, after which the reaction was diluted with EtOAc and filtered through a pad of celite. Concentration in vacuo followed by flash chromatography of the residue on silica gel (40% hexanes in ethyl acetate) gave 49 mg (89%) of 212 as a pale oil. $^1$H NMR (CDCl$_3$, 300 MHz): δ 11.47 (s, 1H); 8.66 (d, 1H, J=8.4 Hz); 6.87 (s, 1H); 6.01 (bs, 1H); 4.50–4.35 (m, 1H); 4.04 (bd, 1H, J=8.4 Hz); 3.76 (s, 3H); 3.70–3.60 (m, 1H); 3.53–3.45 (m, 2H); 3.02 (s, 3H); 2.85 (dd, 1H, J=5.3, 17.3 Hz); 2.42–2.30 (m, 1H); 1.66–1.55 (m, 2H); 1.49 (s, 9H); 1.48 (s, 9H); 0.93 (t, 3H, J=7.3 Hz).

Example 78

Carboxylic acid 213: To a solution of methyl ester 212 (49 mg, 0.090 mmol) in THF (1.0 mL) was added aqueous KOH (260 μL of a 1.039 N solution). The reaction mixture was stirred at room temperature for 16 h, cooled to 0° C. and acidified to pH 4.0 with Amberlite IR-120 (H$^+$) acidic resin. The resin was filtered and washed with water and methanol. Concentration in vacuo gave the free acid as a pale foam which was used without further purification in the next reaction.

Example 79

Guanidine carboxylic acid 214: To a solution of bis-Boc guanidnyl acid 213 (crude from previous reaction) in CH$_2$Cl$_2$ (2.0 mL) cooled to 0° C. was added neat trifluoroacetic acid (2.0 mL). The reaction mixture was stirred at 0° C. for 1 h and then at room temperature for 1 h. Concentration in vacuo gave a pale orange solid which was purified by C$_{18}$ reverse phase chromatography eluting with water. Fractions containing the desired product were pooled and lyophilized to give 10 mg (25%, 2 steps) of the guanidine carboxylic acid 214. $^1$H NMR (D$_2$O, 300 MHz): δ 6.60 (bs, 1H); 4.22 (bd, 1H, J=9.0 Hz); 3.82–3.66 (m, 2H); 3.65–3.54 (m, 1H); 3.43 (bt, 1H, J=9.9 Hz); 3.15 (s, 3H); 2.82 (dd, 1H, J=5.0, 17.5 Hz); 2.48–2.30 (m, 1H); 1.71–1.58 (m, 2H); 0.93 (t, 3H, J=7.3 Hz).

Example 80

Propionamide methyl ester 215: Propionyl chloride (96 μL, 1.1 mmol) was added to a solution of amine 205 (178 mg, 0.70 mmol, prepared by Example 107) and pyridine (1.5 mL) in CH$_2$Cl$_2$ (2.0 mL) cooled to 0° C. After 30 min at 0° C. the reaction was concentrated and partitioned between ethyl acetate and brine. The organic layer was separated and washed sequentially with saturated sodium bicarbonate, brine and dried over MgSO$_4$. Concentration in vacuo followed by flash chromatography of the residue on silica gel (40% hexanes in ethyl acetate) gave 186 mg (86%) of the propionamide methyl ester 215 as a pale yellow solid. $^1$H NMR (CDCl$_3$, 300 MHz): δ 6.86 (t, 1H, J=2.3 Hz); 5.72 (bd, 1H, J=7.8 Hz); 4.52–4.49 (m, 1H); 4.25–4.15 (m, 1H); 3.77 (s, 3H); 3.65–3.37 (complex m, 3H); 2.87 (dd, 1H, J=5.7, 17.7 Hz); 2.28 (q, 2H, J=7.5 Hz); 2.25–2.20 (m, 1H); 1.65–1.50 (m, 2H); 1.19 (t, 3H, J=7.5 Hz); 0.92 (t, 3H, J=7.5 Hz).

Example 81

Amino methyl ester 216: A solution of azide 215 (186 mg, 0.60 mmol) in THF (5.0 mL) and water (400 µL) was treated with polymer supported triphenyl phosphine (560 mg) at room temperature. After stirring for 21 h the polymer was filtered and washed with methanol. Concentration in vacuo gave the crude amino ester 216 which was used without any further purification for the next step.

Example 82

Amino acid 217: A solution of methyl ester 216 (crude from previous reaction) in THF (500 µL) was treated with aqueous KOH (866 µL of a 1.039 N solution). The reaction mixture was stirred at room temperature for 3 h and neutralized to pH 7.0 with Amberlite IR-120 (H$^+$) acidic resin. The resin was filtered and washed with water and methanol. Concentration in vacuo gave the amino acid as a pale solid which was purified by $C_{18}$ reverse phase chromatography eluting with water. Fractions containing the desired product were pooled and lyophilized to give 49 mg (31% 2 steps) of the amino acid 217. $^1$H NMR (D$_2$O, 300 MHz): δ 6.54 (s, 1H); 4.25 (bd, 1H, J=8.7 Hz); 4.13 (dd, 1H, J=9.0, 11.3 Hz); 3.74–3.60 (m, 1H); 3.61–3.40 (m, 2H); 2.85 (dd, 1H, J=5.9, 17.1 Hz); 2.55–2.40 (m, 1H); 2.35 (q, 2H, J=7.5 Hz); 1.65–1.45 (m, 2H); 1.13 (t, 3H, J=7.5 Hz); 0.88 (t, 3H, J=7.5 Hz).

Example 83

(mono methyl) bis-Boc guanidino ester 218: To a solution of amine 200 (51 mg, 0.19 mmol) and mono methyl bis-Boc thiourea (36 mg, 0.19 mmol) in dry DMF (1.0 mL), was added 1-(3-Dimethylaminopropyl)-3-ethylcarbodiimide hydrochloride (38 mg) and Et$_3$N (56 µL) at room temperature. After 1.5 h at room temperature HgCl$_2$ (~75 mg, excess) was added in one portion. The heterogeneous reaction mixture was stirred for 45 min, diluted with ethyl acetate and filtered through a pad of celite. The filtrate was diluted with additional ethyl acetate and washed with dilute HCl, saturated sodium bicarbonate, brine and dried over MgSO$_4$. Concentration in vacuo followed by flash chromatography of the residue on silica gel (10% methanol in ethyl acetate) gave 13 mg (16%) of the (mono methyl) bis-Boc guanidino ester 218 as a colorless foam. $^1$H NMR (CDCl$_3$, 300 MHz): δ 6.84 (s, 1H); 6.20 (bd, 1H, J=5.1 Hz); 5.45 (bs, 1H); 4.25–4.40 (bm, 1H); 4.20–4.05 (bm, 2H); 3.76 (s, 3H); 3.60–3.50 (m, 1H); 3.43–3.30 (m, 1H); 2.90 (dd, 1H, J=5.4, 17.7 Hz); 2.77 (d, 3H, J=4.8 Hz); 2.35–2.25 (m, 1H); 1.96 (s, 3H); 1.60–1.50 (m, 2H); 1.47 (s, 9H); 0.91 (t, 3H, J=7.2 Hz).

Example 84

(mono methyl) bis-Boc guanidino acid 219: To a solution of methyl ester 218 (13 mg, 0.031 mmol) in THF (500 µL) was added aqueous KOH (60 µL of a 1.039 N solution). The reaction mixture was stirred at room temperature for 1 h and then gently refluxed for 1 h. The reaction was cooled to 0° C. and acidified to pH 6.0 with Amberlite IR-120 (H$^+$) acidic resin. The resin was filtered and washed with water and methanol. Concentration in vacuo gave the free acid 219 which was used without further purification in the next reaction.

Example 85

(mono methyl) guanidino amino acid 220: To a solution of (mono methyl) bis-Boc guanidnyl acid 219 (crude from previous reaction) in CH$_2$Cl$_2$ (1.0 mL) cooled to 0° C. was added neat trifluoroacetic acid (1.0 mL). The reaction mixture was stirred at 0° C. for 1 h and then at room temperature for 1 h. Concentration in vacuo gave a pale solid which was purified by $C_{18}$ reverse phase chromatography eluting with water. Fractions containing the desired product were pooled and lyophilized to give 4.4 mg (33%, 2 steps) of the guanidine carboxylic acid 220. $^1$H NMR (D$_2$O, 300 MHz): δ 6.52 (bs, 1H); 4.27 (bd, 1H, J=8.4 Hz); 4.01 (dd, 1H, J=9.2, 10.3 Hz); 3.86–3.75 (m, 1H); 3.75–3.67 (m, 1H); 3.60–3.49 (m, 1H); 2.85 (s, 3H); 2.80 (dd, 1H, J=5.1, 17.7 Hz); 2.47–2.37 (m, 1H); 2.04 (s, 3H); 1.64–1.50 (m, 2H); 0.90 (t, 3H, J=7.2 Hz).

Example 86

(R)-methyl propyl ester 221: BF$_3$.Et$_2$O (63 µL, 0.51 mmol) was added to a solution of N-trityl aziridine 183 (150 mg, 0.341 mmol) in (R)-(–)-2-butanol (1.2 mL) under argon with stirring at room temperature. The pale solution was heated at 70° C. for 2 h and then concentrated in vacuo to give a brown residue which was dissolved in dry pyridine (2.0 mL) and treated with acetic anhydride (225 µL) and a catalytic amount of DMAP (few crystals) at 0° C. The reaction was allowed to warm to room temperature and stirred for 2 h, concentrated in vacuo and partitioned between ethyl acetate and brine. The organic layer was separated and washed sequentially with dilute HCl, saturated sodium bicarbonate, brine and dried over MgSO$_4$. Concentration in vacuo followed by flash chromatography of the residue on silica gel (50% hexanes in ethyl acetate) gave 75 mg (72%) of the (R)-methyl propyl ester 221 as a pale solid. $^1$H NMR (CDCl$_3$, 300 MHz): δ 6.79 (t, 1H, J=2.2 Hz); 6.14 (d, 1H, J=7.3 Hz); 4.55 (bd, 1H, J=8.7 Hz); 4.33–4.23 (m, 1H); 3.77 (s, 3H); 3.56–3.45 (m, 1H); 3.40–3.27 (m, 1H); 2.85 (dd, 1H, J=5.5, 17.5 Hz); 2.30–2.15 (m, 1H); 2.04 (s, 3H); 1.5901.40 (m, 2H); 1.10 (d, 3H, J=6.0 Hz); 0.91 (t, 3H, J=7.4 Hz).

Example 87

(R)-methyl propyl amino ester 222: Ph$_3$P (95 mg, 0.36 mmol) was added in one portion to a solution of azide 221 (75 mg, 0.24 mmol) and water (432 µL) in THF (3.0 mL). The pale yellow solution was then heated at 50° C. for 10 h, cooled and concentrated in vacuo to give a pale solid. Purification by flash chromatography on silica gel (50% methanol in ethyl acetate) gave 66 mg (97%) of the amino ester 222 as a pale solid.

Example 88

Amino acid 223: A solution of methyl ester 222 (34 mg, 0.12 mmol) in THF (1.0 mL) was treated with aqueous KOH (175 µL of a 1.039 N solution). The reaction mixture was stirred at room temperature for 3 h and acidified to pH 6.0 with Amberlite IR-120 (H$^+$) acidic resin. The resin was filtered and washed with water and methanol. Concentration in vacuo gave the amino acid as a pale solid which was purified by $C_{18}$ reverse phase chromatography eluting with water. Fractions containing the desired product were pooled and lyophilized to give 11.5 mg (36%) of the amino acid 223. $^1$H NMR (D$_2$O, 300 MHz): δ 6.52 (bs, 1H); 4.28 (bd, 1H, J=8.7 Hz); 4.04 (dd, 1H, J=8.8, 11.5 Hz); 3.74–3.65 (m, 1H); 3.50–3.60 (m, 1H); 2.90 (dd, 1H, J=5.5, 17.2 Hz);

2.50–2.40 (m, 1H0; 2.10 (s, 3H); 1.60–1.45 (m, 2H); 1.14 (d, 3H, J=6.2 Hz); 0.91 (t, 3H, J=7.4 Hz).

Example 89 bis-Boc guanidino ester 224: Treated according to the procedure of Kim and Qian, "Tetrahedron Lett.", 34:7677 (1993). To a solution of amine 222 (32 mg, 0.113 mmol), bis-Boc thiourea (32 mg, 0.115 mmol) and Et$_3$N (53 µL) in dry DMF (350 µL) cooled to 0° C. was added HgCl$_2$ (34 mg, 0.125 mmol) in one portion. The heterogeneous reaction mixture was stirred for 45 min at 0° C. and then at room temperature for 1 h, after which the reaction was diluted with EtOAc and filtered through a pad of celite. Concentration in vacuo followed by flash chromatography of the residue on silica gel (20% hexanes in ethyl acetate) gave 57 mg (96%) of 224 as a colorless foam. $^1$H NMR (CDCl$_3$, 300 MHz): δ 11.40 (s, 1H); 8.65 (d, 1H, J=7.8 Hz); 6.82 (s, 1H); 6.36 (d, 1H, J=8.7 Hz); 4.46–4.34 (m, 1H); 4.20–4.10 (m, 1H); 4.10–3.95 (m, 1H); 3.76 (s, 3H); 2.79 (dd, 1H, J=5.4, 17.7 Hz); 2.47–2.35 (m, 1H); 1.93 (s, 3H); 1.60–1.45 (m, 2H); 1.49 (s, 18H); 1.13 (d, 3H, J=6.0 Hz); 0.91 (t, 3H, J=7.5 Hz).

Example 90

Carboxylic acid 225: To a solution of methyl ester 224 (57 mg, 0.11 mmol) in THF (1.5 mL) was added aqueous KOH (212 µL of a 1.039 N solution). The reaction mixture was stirred at room temperature for 16 h, cooled to 0° C. and acidified to pH 4.0 with Amberlite IR-120 (H$^+$) acidic resin. The resin was filtered and washed with water and methanol. Concentration in vacuo gave the free acid as a pale foam which was used without further purification in the next reaction.

Example 91

Guanidine carboxylic acid 226: To a solution of bis-Boc guanidnyl acid 225 (crude from previous reaction) in CH$_2$Cl$_2$ (4.0 mL) cooled to 0° C. was added neat trifluoroacetic acid (4.0 mL). The reaction mixture was stirred at 0° C. for 1 h and then at room temperature for 2 h. Concentration in vacuo gave a pale orange solid which was purified by C$_{18}$ reverse phase chromatography eluting with water. Fractions containing the desired product were pooled and lyophilized to give 18.4 mg (40%, 2 steps) of the guanidine carboxylic acid 226. $^1$H NMR (D$_2$O, 300 MHz): δ 6.47 (s, 1H); 4.28 (bd, 1H, J=8.4 Hz); 3.93–3.74 (m, 2H); 3.72–3.63 (m, 1H); 2.78 (dd, 1H, J=4.8, 17.4 Hz); 2.43–2.32 (m, 1H); 1.58–1.45 (m, 2H); 1.13 (d, 3H, J=6.0 Hz); 0.90 (t, 3H, J=7.4 Hz).

Example 92

(Diethyl) methyl ether ester 227: BF$_3$.Et$_2$O (6.27 mL, 51 mmol) was added to a solution of N-trityl aziridine 183 (15 g, 34 mmol) in 3-pentanol (230 mL) under argon with stirring at room temperature. The pale solution was heated at 70–75° C. for 1.75 h and then concentrated in vacuo to give a brown residue which was dissolved in dry pyridine (2.0 mL) and treated with acetic anhydride (16 mL, 170 mmol) and a catalytic amount of DMAP 200 mg. The reaction was stirred at room temperature for 18 h, concentrated in vacuo and partitioned between ethyl acetate and 1M HCl. The organic layer was separated and washed sequentially with saturated sodium bicarbonate, brine and dried over MgSO$_4$. Concentration in vacuo followed by flash chromatography of the residue on silica gel (50% hexanes in ethyl acetate) gave 7.66 g of the (Diethyl) methyl ether ester which was recrystallized from ethylacetate/hexane to afford 227 (7.25 g, 66%,)) as colorless needles: $^1$H NMR (CDCl$_3$, 300 MHz): δ 6.79 (t, 1H, J=2.1 Hz); 5.92 (d, 1H, J=7.5 Hz); 4.58 (bd, 1H, J=8.7 Hz); 4.35–4.25 (m, 1H); 3.77 (s, 3H); 3.36–3.25 (m, 2H); 2.85 (dd, 1H, J=5.7, 17.4 Hz); 2.29–2.18 (m, 1H); 2.04 (s, 3H); 1.60–1.45 (m, 4H); 0.91 (t, 3H, J=3.7 Hz); 0.90 (t, 3H, J=7.3 Hz).

Example 93

(Diethyl) methyl ether amino ester 228: Ph$_3$P (1.21 g, 4.6 mmol) was added in one portion to a solution of azide 227 (1 g, 3.1 mmol) and water (5.6 mL) in THF (30 mL). The pale yellow solution was then heated at 50° C. for 10 h, cooled and concentrated in vacuo . The aqueous oily residue was partitioned between EtOAc and saturated NaCl. The organic phase was dried (MgSO$_4$), filtered, and evaporated. Purification by flash chromatography on silica gel (50% methanol in ethyl acetate) gave 830 mg (90%) of the amino ester 228 as a pale white solid. $^1$H NMR (CDCl$_3$, 300 MHz): δ 6.78 (t, 1H, J=2.1 Hz); 5.68 (bd, 1H, J=7.8 Hz); 4.21–4.18 (m, 1H); 3.75 (s, 3H); 3.54–3.45 (m, 1H); 3.37–3.15 (m, 2H); 2.74 (dd, 1H, J=5.1, 17.7 Hz); 2.20–2.07 (m, 1H); 2.03 (s, 3H); 1.69 (bs, 2H, —NH$_2$); 1.57–1.44 (m, 4H); 0.90 (t, 3H, J=7.5 Hz); 0.89 (t, 3H, J=7.5 Hz).

Example 94

Amino acid 229: A solution of methyl ester 228 (830 mg, 2.8 mmol) in THF (15 mL) was treated with aqueous KOH (4 mL of a 1.039 N solution). The reaction mixture was stirred at room temperature for 40 min and acidified to pH 5.5–6.0 with Dowex 50WX8 acidic resin. The resin was filtered and washed with water and methanol. Concentration in vacuo gave the amino acid as a pale solid which was purified by C$_{18}$ reverse phase chromatography eluting with water and then with 5% CH$_3$CN/water. Fractions containing the desired product were pooled and lyophilized to give 600 mg (75%) of the amino acid 229. $^1$H NMR (D$_2$O, 300 MHz): δ 6.50 (t, 1H, J=2.1 Hz); 4.30–4.26 (m, 1H); 4.03 (dd, 1H, J=9.0, 11.7 Hz); 3.58–3.48 (m, 2H); 2.88 (dd, 1H, J=5.4, 16.8 Hz); 2.53–2.41 (m, 1H); 1.62–1.40 (m, 4H); 0.90 (t, 3H, J=7.5 Hz); 0.85 (t, 3H, J=7.5 Hz).

Example 95 t-amyl ether ester 230: BF$_3$.Et$_2$O (43 µL, 0.35 mmol) was added to a solution of N-trityl aziridine 183 (104 mg, 0.24 mmol) in t-amyl alcohol (2.5 mL) under argon with stirring at room temperature. The pale solution was heated at 75° C. for 3 h and then concentrated in vacuo to give a brown residue which was dissolved in dry pyridine (2.0 mL) and treated with acetic anhydride (250 µL) and a catalytic amount of DMAP (few crystals). The reaction was stirred at room temperature for 1.5 h, concentrated in vacuo and partitioned between ethyl acetate and brine. The organic layer was separated and washed sequentially with dilute HCl, saturated sodium bicarbonate, brine and dried over MgSO$_4$. Concentration in vacuo followed by flash chromatography of the residue on silica gel (50% hexanes in ethyl acetate) gave 27 mg (35%) of the t-amyl ether ester 230 as a pale orange oil. $^1$H NMR (CDCl$_3$, 300 MHz): δ 6.72 (t, 1H, J=2.1 Hz); 5.83 (d, 1H, J=7.2 Hz); 4.71 (bd, 1H, J=8.1 Hz); 4.45–4.35 (m, 1H); 3.75 (s, 3H); 3.27–3.17 (m, 1H); 2.84 (dd, 1H, J=5.7, 17.4 Hz); 2.27–2.15 (m, 1H); 2.05 (s, 3H); 1.57–1.47 (m, 2H); 1.19 (s, 3H); 1.15 (s, 3H); 0.90 (t, 3H, J=7.5 Hz).

Example 96 t-amyl ether amino ester 231: Ph$_3$P (35 mg, 0.133 mmol) was added in one portion to a solution of azide 230 (27 mg, 0.083 mmol) and water (160 μL) in THF (1.5 mL). The pale orange solution was then heated at 50° C. for 10 h, cooled and concentrated in vacuo to give a pale solid. Purification by flash chromatography on silica gel (50% methanol in ethyl acetate) gave 20 mg (82%) of the amino ester 231 as a pale oil.

Example 97

Amino acid 232: A solution of methyl ester 231 (20 mg, 0.068 mmol) in THF (1.0 mL) was treated with aqueous KOH (131 μL of a 1.039 N solution). The reaction mixture was stirred at room temperature for 2.5 h and acidified to pH 5.0 with Amberlite IR-120 (H$^+$) acidic resin. The resin was filtered and washed with water and methanol. Concentration in vacuo gave the amino acid as a pale solid which was purified by $C_{18}$ reverse phase chromatography eluting with water. Fractions containing the desired product were pooled and lyophilized to give 8.6 mg (45%) of the amino acid 232. $^1$H NMR (D$_2$O, 300 MHz): δ 6.47 (bs, 1H); 4.42 (bd, 1H, J=8.1 Hz); 3.97 (dd, 1H, J=8.4, 11.4 Hz); 3.65–3.54 (m, 1H); 2.88 (dd, 1H, J=5.5, 17.3 Hz); 2.51–2.39 (m, 1H); 2.08 (s, 3H); 1.61–1.46 (m, 2H); 1.23 (s, 3H); 1.18 (s, 3H), 0.86 (t, 3H, J=7.5 Hz).

Example 98 n-Propyl thio ether ester 233: BF$_3$.Et$_2$O (130 μL, 1.06 mmol) was added to a solution of N-trityl aziridine 183 (300 mg, 0.68 mmol) in 1-propanethiol (8.0 mL) under argon with stirring at room temperature. The pale solution was then heated at 65° C. for 45 min, concentrated and partitioned between ethyl acetate and brine. The organic layer was separated and washed with saturated sodium bicarbonate, brine and dried over MgSO$_4$. Concentration in vacuo followed by flash chromatography of the residue on silica gel (30% hexanes in ethyl acetate) gave 134 mg (73%) of the n-propyl thio ether ester 233 as a pale oil. $^1$H NMR (CDCl$_3$, 300 MHz): δ 6.87 (t, 1H, J=2.4 Hz); 3.77 (s, 3H); 3.48–3.38 (m, 1H); 3.22–3.18 (m, 1H), 2.93 (dd, 1H, J=5.4, 17.4 Hz); 2.80 (t, 1H, J=9.9 Hz); 2.51 (t, 2H, J=7.2 Hz); 2.32–2.20 (m, 1H); 1.96 (bs, 2H, —NH$_2$), 1.69–1.56 (m, 2H); 1.00 (t, 3H, J=7.2 Hz).

Example 99 n-Propyl thio ether azido ester 234: To a solution of amine 233 (134 mg, 0.50 mmol) in pyridine (1.5 mL) cooled to 0° C. was added neat acetyl chloride (60 μL, 0.84 mmol). After stirring for 1 h the reaction mixture was warmed to room temperature and stirred for an additional 15 min. The reaction was concentrated and partitioned between ethyl acetate and brine and washed sequentially with dilute HCl, water, saturated sodium bicarbonate, brine and dried over MgSO$_4$. Concentration in vacuo followed by flash chromatography of the residue on silica gel (30% hexanes in ethyl acetate) gave 162 mg (100%) of the n-Propyl thio ether azido ester 234 as a pale yellow solid. $^1$H NMR (CDCl$_3$, 300 MHz): δ 6.90 (t, 1H, J=2.7 Hz); 5.87 (bd, 1H, J=7.8 Hz); 4.07–3.98 (m, 1H); 3.77 (s, 3H); 3.65–3.55 (m, 1H); 2.95–2.85 (m, 1H); 2.60–2.45 (m, 2H); 2.30–2.18 (m, 1H); 2.08 (s, 3H); 1.65–1.53 (m, 2H); 0.98 (t, 3H, J=7.2 Hz).

Example 100 n-Propyl thio ether amino ester 235: The azide 234 (130 mg, 0.416 mmol) in ethyl acetate (10 mL) was hydrogenated (1 atmosphere) over Lindlar's catalyst (150 mg) for 18 h at room temperature. The catalyst was then filtered through a celite pad and washed with hot ethyl acetate and methanol. Concentration in vacuo followed by flash chromatography of the orange residue gave 62 mg (53%) of the n-propyl thio ether amino ester 235. $^1$H NMR (CDCl$_3$, 300 MHz): δ 6.88 (t, 1H, J=2.7 Hz); 5.67 (bd, 1H, J=8.7 Hz); 3.76 (s, 3H); 3.75–3.65 (m, 1H); 3.45–3.35 (bm, 1H); 3.05–2.95 (m, 1H); 2.87–2.78 (m, 1H); 2.56–2.40 (m, 2H); 2.18–2.05 (m, 1H); 2.09 (s, 3H); 1.65–1.50 (m, 2H); 1.53 (bs, 2H, —NH$_2$); 0.98 (t, 3H, J=7.2 Hz).

Example 101

Compound 240: A suspension of Quinic acid (103 g), 2,2-dimethoxypropane (200 mL) and toluenesulfonic acid (850 mg) in acetone (700 mL) was stirred at room temperature for 4 days. Solvents and excess reagents were removed under reduced pressure. Purification by flash column chromatography (Hexanes/EtOAc=2/1–1.5/1) gave lactone 240 (84 g, 73%): $^1$H NMR (CDCl$_3$) δ 4.72 (dd, J=2.4, 6.1 Hz, 1 H), 4.50 (m, 1 H), 4.31 (m, 1 H), 2.67 (m, 2 H), 2.4–2.2 (m, 3 H), 1.52 (s, 3 H), 1.33 (s, 3 H). Performing the reaction at reflux temperatures for 4 h afforded lactone 240 in 71% yield after aqueous work-up (ethyl acetate/water partition) and recrystallization of the crude product from ethyl acetate/hexane.

Example 102

Compound 241: To a solution of lactone 240 (43.5 g, 203 mmol) in methanol (1200 mL) was added sodium methoxide (4.37 M, 46.5 ml, 203 mmol) in one portion. The mixture was stirred at room temperature for 3 hrs, and quenched with acetic acid (11.62 mL). Methanol was removed under reduced pressure. The mixture was diluted with water, and extracted with EtOAc (3×). The combined organic phase was washed with water (1×) and brine (1×), and dried over MgSO$_4$. Purification by flash column chromtography (Hexanes/EtOAc=1/1 to 1/4) gave diol (43.4 g, 87%): $^1$H NMR (CDCl$_3$) δ 4.48 (m, 1 H), 4.13 (m, 1 H), 3.99 (t, J=6.4 Hz, 1 H), 3.82 (s, 3 H), 3.34 (s, 1 H), 2.26 (d, J=3.8 Hz, 2 H), 2.08 (m, 1 H), 1.91 (m, 1 H), 1.54 (s, 3 H), 1.38 (s, 3 H). Alternatively, treatment of lactone 240 with catalytic sodium ethoxide (1 mol %) in ethanol gave the corresponding ethyl ester in 67% after crystallization of the crude product from ethyl acetate/hexane. The residue obtained from the mother liquor (consisting of starting material and product) was subjected again to the same reaction conditions, affording additional product after recrystallization. Overall yield was 83%.

Example 103

Compound 242: To a solution of diol 241 (29.8 g, 121 mmol) and 4-(N,N-dimethylamino)pyridine (500 mg) in pyridine (230 mL) was added tosyl chloride (27.7 g, 145 mmol). The mixture was stirred at room temperature for 3 days, and pyridine was removed under reduced pressure. The mixture was diluted with water, and extracted with EtOAc (3×). The combined organic phase was washed with water (2×) and brine (1×), and dried over MgSO$_4$. Concentration and purification by flash column chromatography (Hexanes/EtOAc=2/1–1/1) gave tosylate 242 (44.6 g, 92%): $^1$H NMR (CDCl$_3$) δ 7.84 (d, J=8.4 Hz, 2 H), 7.33 (d, J=8.1 Hz, 2 H), 4.76 (m, 1 H), 4.42 (m, 1 H), 4.05 (dd, J=5.5, 7.5 Hz, 1 H), 3.80 (s, 3 H), 2.44 (s, 3 H), 2.35 (m, 1 H), 2.24 (m, 2 H), 1.96 (m, 1 H), 1.26 (s, 3 H), 1.13 (s, 3 H). The corresponding ethyl ester of compound 241 was treated with methanesulfonyl chloride and triethylamine in CH$_2$Cl$_2$ at 0° C. to afford the mesylate derivative in quantitative yield after aqueous work-up. The mesylate was used directly without any further purification.

Example 104

Compound 243: To a solution of tosylate 242 (44.6 g, 111.5 mmol) in $CH_2Cl_2$ (450 mL) at $-78°$ C. was added pyridine (89 mL), followed by slow addition of $SO_2Cl_2$ (26.7 mL, 335 mmol). The mixture was stirred at $-78°$ C. for 5 hrs, and methanol (45 mL) was added dropwise. The mixture was warmed to room temperature and stirred for 12 hrs. Ethyl ether was added, and the mixture was washed with water (3×) and brine (1×), and dried over $MgSO_4$. Concentration gave the intermediate as a oil (44.8 g). To a solution of the intermediate (44.8 g, 111.5 mmol) in MeOH (500 mL) was added TsOH (1.06 g, 5.6 mmol). The mixture was refluxed for 4 hrs. The reaction mixture was cooled to room temperature, and methanol was removed under reduced pressure. Fresh methanol (500 mL) was added, and the whole mixture was refluxed for another 4 hrs. The reaction mixture was cooled to room temperature, and methanol was removed under reduced pressure. Purification by flash column chromatography (Hexanes/EtOAc=3/1–1/3) gave a mixture of the two isomers (26.8 g). Recrystalization from EtOAc/Hexanes afforded the pure desired product 243 (20.5 g, 54%): $^1H$ NMR ($CDCl_3$) δ 7.82 (d, J=8.3 Hz, 2 H), 7.37 (d, J=8.3 Hz, 2 H), 6.84 (m, 1 H), 4.82 (dd, J=5.8, 7.4 Hz, 1 H), 4.50 (m, 1 H), 3.90 (dd, J=4.4, 8.2 Hz, 1 H), 3.74 (s, 3 H), 2.79 (dd, J=5.5, 18.2 Hz, 1 H), 2.42 (dd, J=6.6, 18.2 Hz, 1 H). The corresponding mesylate-ethyl ester derivative of compound 242 was treated in the same manner as described. Removal of the acetonide protecting group was accomplished with acetic acid in refluxing ethanol to afford the diol in 39% yield by direct precipitation with ether from the crude reaction mixture.

Example 105

Compound 1: To a solution of diol 243 (20.0 g, 58.5 mmol) in THF (300 mL) at 0° C. was added DBU (8.75 mL, 58.5 mmol). The reaction mixture was warmed to room temperature, and stirred for 12 hrs. Solvent (THF) was removed under reduced pressure. Purification by flash column chromatography (Hexanes/EtOAc=1/3) gave epoxide 1 (9.72 g, 100%): $^1H$ NMR ($CDCl_3$) δ 6.72 (m, 1 H), 4.56 (td, J=2.6, 10.7 Hz, 1 H), 3.76 (s, 3 H), 3.56 (m, 2 H), 3.0 (d, J=21 Hz, 1 H), 2.50 (d, J=20 Hz, 1 H), 2.11 (d, 10.9 Hz, 1 H). The corresponding mesylate-ethyl ester derivative of compound 243 was treated in the same manner as described, affording the epoxide in nearly quantitative yield.

Example 106

Aziridine 244: A solution of allyl ether 4 (223 mg, 1.07 mmol) and Lindlar's catalyst (200 mg) in absolute ethanol (8.0 mL) was treated with hydrogen gas (1 atmosphere) at room temperature for 50 min. The catalyst was then filtered through a celite pad and washed with hot methanol. Concentration in vacuo gave ~230 mg of 244 as pale yellow oil which was used for the next reaction without any further purification.

Example 107

Azido amine 205: Crude aziridine 244 (230 mg), sodium azide (309 mg, 4.75 mmol) and ammonium chloride (105 mg, 1.96 mmol) in dry DMF (10 mL) was heated at 70° C. for 16 h under an argon atmosphere. The reaction was cooled, filtered through a fritted glass funnel to remove solids and partitioned between ethyl acetate and brine. The organic layer was separated and dried over $MgSO_4$. Concentration in vacuo followed by flash chromatography of the residue on silica gel (10% hexanes in ethyl acetate) gave 154 mg (57%, 2 steps) of 205 as a yellow viscous oil of sufficient purity for the next reaction.

Example 108

N-acetyl azide 245: Acetyl chloride (70 μl, 0.98 mmol) was added to a solution of amine 205 (154 mg, 0.61 mmol) and pyridine (1.3 mL) in $CH_2Cl_2$ (4.0 mL) cooled to 0° C. After 1.5 h at 0° C. the reaction was concentrated and partitioned between ethyl acetate and brine. The organic layer was separated and washed sequentially with saturated sodium bicarbonate, brine and dried over $MgSO_4$. Concentration in vacuo followed by flash chromatography of the residue on silica gel (ethyl acetate) gave 167 mg (93%) of 245 as a pale yellow solid.

Example 109

Amino ester 200: Triphenyl phosphine (1.7 g, 6.48 mmol) was added in several portions to a solution of 245 (1.78 g, 6.01 mmol) in THF (40 mL) and water (1.5 mL). The reaction was then stirred at room temperature for 42.5 h. Volatiles were removed under vaccum and the crude solid absorbed onto silica gel and purified by flash chromatography on silica gel (100% ethyl acetate then 100% methanol) to give 1.24 g (77%) of 200 as a pale solid.

Example 110

Amino acid 102: To a solution of methyl ester 200 (368 mg, 1.37 mmol) in THF (4.0 mL) cooled to 0° C. was added aqueous NaOH (1.37 mL of a 1.0 N solution). The reaction mixture was stirred at 0° C. for 10 min, room temperature for 1.5 h and then acidified to pH 7.0–7.5 with Amberlite IR-120 ($H^+$) acidic resin. The resin was filtered and washed with water and methanol. Concentration in vacuo gave the amino acid as a white solid which was purified by $C_{18}$ reverse phase chromatography eluting with water. Fractions containing the desired product were pooled and lyophilized to give 290 mg (83%) of amino acid 102.

Example 111

Amine hydrochloride 250: Amine 228 (15.6 mg, 0.05 mmol) was treated with 0.1 N HCl and was evaporated. The residue was dissolved in water and was filtered through a small column of C-18 reverse phase silica gel. The hydrochloride salt 250 (12 mg) was obtained as a solid after lyophilization: $^1H$ NMR ($D_2O$) δ 6.86 (s, 1H), 4.35 (br d, J=9.0), 4.06 (dd, 1H, J=9.0, 11.6), 3.79 (s, 3H), 3.65–3.52 (m, 2H), 2.97 (dd, 1H, J=5.5, 17.2), 2.58–2.47 (m, 1H), 2.08 (s, 3H), 1.61–1.41 (m, 4H), 0.88 (t, 3H, J=7.4), 0.84 (t, 3H, J=7.4).

Example 112

Bis-Boc-guanidine 251: To a solution of amine 228 (126 mg, 0.42 mmol), N, N'-bis-tert-butoxycarbonylthiourea (127 mg, 0.46 mmol), and triethylamine (123 μL, 0.88 mmol) in DMF (4 mL) at 0° C. was added $HgCl_2$ (125 mg, 0.46 mmol). The mixture was stirred at 0° C. for 30 min and at room temperature for 1.5 h. The reaction was diluted with ethyl acetate and filtered through celite. The solvent was evaporated and the residue was partitioned between ethyl acetate and water. The organic phase was washed with saturated NaCl, dried ($MgSO_4$), filtered and the solvent was evaporated. The crude product was purified on silica gel (2/1, 1/1-hexane/ethyl acetate) to afford bis-Boc-guanidine 251 (155 mg, 69%) as a solid: $^1$H NMR (CDCl$_3$) δ 11.40 (s, 1H), 8.66 (d, 1H, J=7.9), 6.8 (s, 1H), 6.22 (d, 1H, J=8.9), 4.43–4.34 (m, 1H), 4.19–4.08 (m, 1H), 4.03 (m, 1H), 3.76 (s, 3H), 3.35 (m, 1H), 2.79 (dd, 1H, J=5.4, 17.7), 2.47–2.36 (m, 1H), 1.92 (s, 3H), 1.50, 1.49 (2s, 18H), 0.89 (m, 6H).

Example 113

Guanidino-acid 252: To a solution of bis-Boc-guanidine 251 (150 mg, 0.28 mmol) in THF (3 mL) was added 1.039N KOH solution (337 μL) and water (674 μL). The mixture was stirred for 3 h, additional 1.039N KOH solution (67 μL) was added and stirring was continued for 2 h. The reaction was filtered to remove a small amount of dark precipitate. The filtrate was cooled to 0° C. and was acidified with IR 120 ion exchange resin to pH 4.5–5.0. The resin was filtered and washed with methanol. The filtrate was evaporated to a residue which was dissolved in CH$_2$Cl$_2$ (3 mL), cooled to 0° C., and was treated with trifluoroacetic acid (3 mL). After stirring 10 min. at 0° C., the reaction was stirred at room temperature for 2.5 h. The solvents were evaporated and the residue was dissolved in water and was chromatographed on a short column (3×1.5 cm) of C-18 reverse phase silica gel eluting initially with water and then 5% acetonitrile/water. Product fractions were combined and evaporated. The residue was dissolved in water and lyophilized to afford guanidino-acid 252 (97 mg, 79%) as a white solid.

Example 114

Azido acid 260: To a solution of methyl ester 227 (268 mg, 0.83 mmol) in THF (7.0 mL) was added aqueous KOH (1.60 mL of a 1.039 N solution) at room temperature. After stirring for 19 h at room temperature the reaction was acidified to pH 4.0 with Amberlite IR-120 (H$^+$) acidic resin. The resin was filtered and washed with water and ethanol. Concentration in vacuo gave the crude azido acid 260 as a pale orange foam which was used for the next reaction without any further purification.

Example 115

Azido ethyl ester 261: To a solution of carboxylic acid 260 (crude from previous reaction, assume 0.83 mmol), ethyl alcohol (150 μL), and catalytic DMAP in CH$_2$Cl$_2$ (6.0 mL) was added DCC (172 mg, 0.83 mmol) in one portion at room temperature. After several minutes a precipitate formed and after an additional 1 h of stirring the reaction was filtered and washed with CH$_2$Cl$_2$. Concentration in vacuo afforded a pale solid which was purified by flash chromatography on silica gel (50% hexanes in ethyl acetate) to give 272 mg (96%, small amount of DCU impurity present) of 261 as a white solid. When DCC was replaced by diisopropyl carbodiimide than the yield of 261 was 93% but the chromatographic purification eliminated urea impurities present when DCC was used.

Example 116

Amino ethyl ester 262: Triphenyl phosphine (342 mg, 1.30 mmol) was added in one portion to a solution of 261 (272 g, 0.80 mmol) in THF (17 mL) and water (1.6 mL). The reaction was then heated at 50° C. for 10 h, cooled and concentrated in vacuo to give a pale white solid. Purification of the crude solid by flash chromatography on silica gel (50% methanol in ethyl acetate) gave 242 mg (96%) of the amino ethyl ester 262 as a pale solid. The amino ethyl ester is dissolved in 3N HCl and lyophilized to give the corresponding water soluble HCl salt form. $^1$H NMR (D$_2$O, 300 MHz): δ 6.84 (s, 1H); 4.36–4.30 (br m, 1H); 4.24 (q, 2H, J=7.2 Hz); 4.05 (dd, 1H, J=9.0, 11.7 Hz); 3.63–3.50 (m, 2H); 2.95 (dd, 1H, J=5.7, 17.1 Hz); 2.57–2.45 (m, 1H); 1.60–1.39 (m, 4H); 1.27 (t, 3H, J=7.2 Hz); 0.89–0.80 (m, 6H).

Example 117 bis-Boc guanidino ethyl ester 263: Treated according to the procedure of Kim and Qian, "Tetrahedron Lett." 34:7677 (1993). To a solution of amine 262 (72 mg, 0.23 mmol), bis-Boc thiourea (66 mg, 0.24 mmol) and Et$_3$N (108 μL) in dry DMF (600 μL) cooled to 0° C. was added HgCl$_2$ (69 mg, 0.25 mmol) in one portion. The heterogeneous reaction mixture was stirred for 1 h at 0° C. and then at room temperature for 15 min, after which the reaction was diluted with EtOAc and filtered through a pad of celite. Concentration in vacuo followed by flash chromatography of the residue on silica gel (20% hexanes in ethyl acetate) gave 113 mg (89%) of 263 as a colorless foam. $^1$H NMR (CDCl$_3$, 300 MHz): δ 11.41 (s, 1H); 8.65 (d, 1H, J=8.1 Hz); 6.83 (s, 1H); 6.22 (d, 1H, J=9.0 Hz); 4.46–4.34 (m, 1H); 4.21 (q, 2H, J=6.9 Hz); 4.22–4.10 (m, 1H); 4.04–4.00 (m, 1H); 3.36 (quintet, 1H, J=5.7 Hz); 2.78 (dd, 1H, J=5.4, 17.7 Hz); 2.46–2.35 (m, 1H); 1.94 (s, 3H); 1.60–1.40 (m, 4H); 1.49 (s, 9H); 1.50 (s, 9H); 1.30 (t, 3H, J=6.9 Hz); 0.93–0.84 (m, 6H).

Example 118

Guanidino ethyl ester 264: To a solution of bis-Boc guanidnyl ethyl ester 263 (113 mg, 0.20 mmol) in CH$_2$Cl$_2$ (5.0 mL) cooled to 0° C. was added neat trifluoroacetic acid (5.0 mL). The reaction mixture was stirred at 0° C. for 30 min and then at room temperature for 1.5 h. The reaction was then concentrated in vacuo to give a pale orange solid which was purified by C$_{18}$ reverse phase chromatography eluting with water. Fractions containing the desired product were pooled and lyophilized to give 63 mg (66%) of the guanidine ethyl ester 264 as white solid. $^1$H NMR (D$_2$O, 300 MHz): δ 6.82 (s, 1H); 4.35–4.31 (m, 1H); 4.24 (q, 2H, J=7.1 Hz); 3.95–3.87 (m, 1H); 3.85–3.76 (m, 1H); 3.57–3.49 (m, 1H); 2.87 (dd, 1H, J=5.1, 17.7 Hz); 2.46–2.34 (m, 1H); 2.20 (s, 3H); 1.60–1.38 9M, 4H); 1.28 (t, 3H, J=7.1 Hz); 0.90–0.80 (m, 6H).

Example 119

Enzyme Inhibition: Using the methods of screening in vitro activity described above, the following activities were observed (+10–100 μm, ++1–10 μm, +++<1.0 μm):

| Compound | IC$_{50}$ |
| --- | --- |
| 102/103 (2:1) | +++ |
| 8 | ++ |
| A.17.a.4.i | ++ |
| 114 | ++ |
| A.1.a.4.i | ++ |
| 79 | + |
| 82/75 (1.2:1) | + |
| 94 | +++ |
| A.100.a.11.i | +++ |
| A.101.a.11.i | +++ |
| A.113.a.4.i | +++ |

Example 120

Compounds A.113.b.4.i and A.113.x.4.i were incubated separately in enzyme assay buffey and tested for activity as described in Example 119. Activity was >100 μm for both. When each compound was separately incubated in rat plasma prior to testing as described in Example 119, activity of both was similar to compound A.113.a.4.i.

Example 121

Studies were conducted under the supervision of Dr. Robert Sidwell at the Institute for Antiviral Research of Utah State University to determine the comparative anti-influenza A activity of compound 203 (example 69), GG167 and ribavirin in vivo in mice by i.p. or p.o. routes of administration. GG167 and ribavirin are known anti-influenza virus compounds.

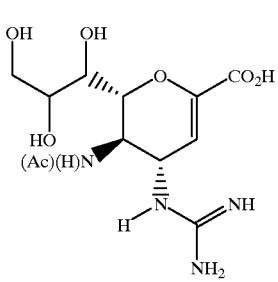

GG167

Mice: Female 13–15 g specific-pathogen free BALB/c mice were obtained from Simonsen Laboratories (Gilroy, Calif.). They were quarantined 24 hr prior to use, and maintained on Wayne Lab Blox and tap water. Once infected, the drinking water contained 0.006% oxytetracycline (Pfizer, New York, N.Y.) to control possible secondary bacterial infections.

Virus: Influenza A/NWS/33 (H1N1) was obtained from K.W. Cochran, University of Michigan (Ann Arbor, Mich.). A virus pool was prepared by infecting confluent monolayers of Madin Darby canine kidney (MDCK) cells, incubating them at 37° C. in 5% $CO_2$, and harvesting the cells at 3 to 5 days when the viral cytopathic effect was 90 to 100%. The virus stock was ampuled and stored at −80° C. until used.

Compounds: Compound 203 and GG167 were dissolved in sterile physiological saline for this study.

Arterial Oxygen Saturation ($SaO_2$) Determinations: $SaO_2$ was determined using the Ohmeda Biox 3740 pulse oximeter (Ohmeda, Louisville, Ohio). The ear probe attachment was used, the probe placed on the thigh of the animal, with the slow instrument mode selected. Readings were made after a 30 second stabilization time on each animal. Use of this device for measuring effects of influenza virus on arterial oxygen saturation has been described by Sidwell et al., *Antimicrob. Agents Chemother.* 36:473–476 (1992).

Experiment Design for Oral Administration Study: Groups of eleven mice infected intranasally with an approximate 95% lethal dose of virus received each dose of test compound. Doses of both 203 and GG167 were 50, 10, 2 and 0.5 mg/kg/day. Treatments were i.p. twice daily for 5 days beginning 4 hr pre-virus exposure. Eight of the infected, treated mice at each dosage and 16 infected, saline-treated controls were assayed for $SaO_2$ level on days 3 through 10; deaths were recorded daily in these animals for 21 days. The remaining three animals in each group as well as six saline-treated control mice were killed on day 6 and their lungs removed, weighed, assigned a consolidation score based on extent of plum color in the lungs (0=normal, 4=100% of lung affected). Since no toxicity had been seen at a dose of 300 mg/kg/day of 203 and literature reports indicate GG167 to be similarly nontoxic, toxicity controls were not included in this study.

Experiment Design for Intraperitoneal Administration Study: Groups of 11 mice were infected intranasally with an approximate 95% lethal dose of virus and treated with 250, 50, or 10 mg/kg/day of 203 or GG167 or with 100, 32 or 10 mg/kg/day of ribavirin. Treatment was by oral gavage (p. o.) twice daily for 5 days beginning 4 hr pre-virus exposure. Eight of the animals in each group were held for 21 days, with deaths noted daily and $SaO_2$ levels determined on days 3–10. The remaining 3 infected mice in each group were killed on day 6 and their lungs removed, weighed, assigned a consolidation score of 0 (normal) to 4 (100% lung affected). Fifteen infected mice were treated with saline only and held 21 days with $SaO_2$ determined as above, and 6 additional infected, saline treated mice were killed on day 6 for lung assay. Three normal controls were held 21 days, with $SaO_2$ determined in parallel with the above, and an additional 3 normal animals were killed on day 6 for lung weight and score.

Experiment Design for Low Dose Oral Administration Study: Groups of 8 mice infected intranasally with an approximate 90% lethal concentration of virus received each dosage of compound. Doses of each compound were 10, 1, and 0.1 mg/kg/day. Treatments were p.o. twice daily for 5 days beginning 4 hr pre-virus exposure. Eight of the infected, treated mice at each dosage and 16 infected, saline-treated controls were assayed for $SaO_2$ level on days 3 through 11; deaths were recorded daily in these animals for 21 days.

Statistical Evaluation: Increase in survivor number was evaluated by chi square analysis with Yates' correction. Mean survival time increases and differences in $SaO_2$, lung weight and lung virus titers were analyzed by t-test. Lung score differences were evaluated by ranked sum analysis. In all cases, differences between drug-treated and saline-treated controls were studied.

Figure 2:
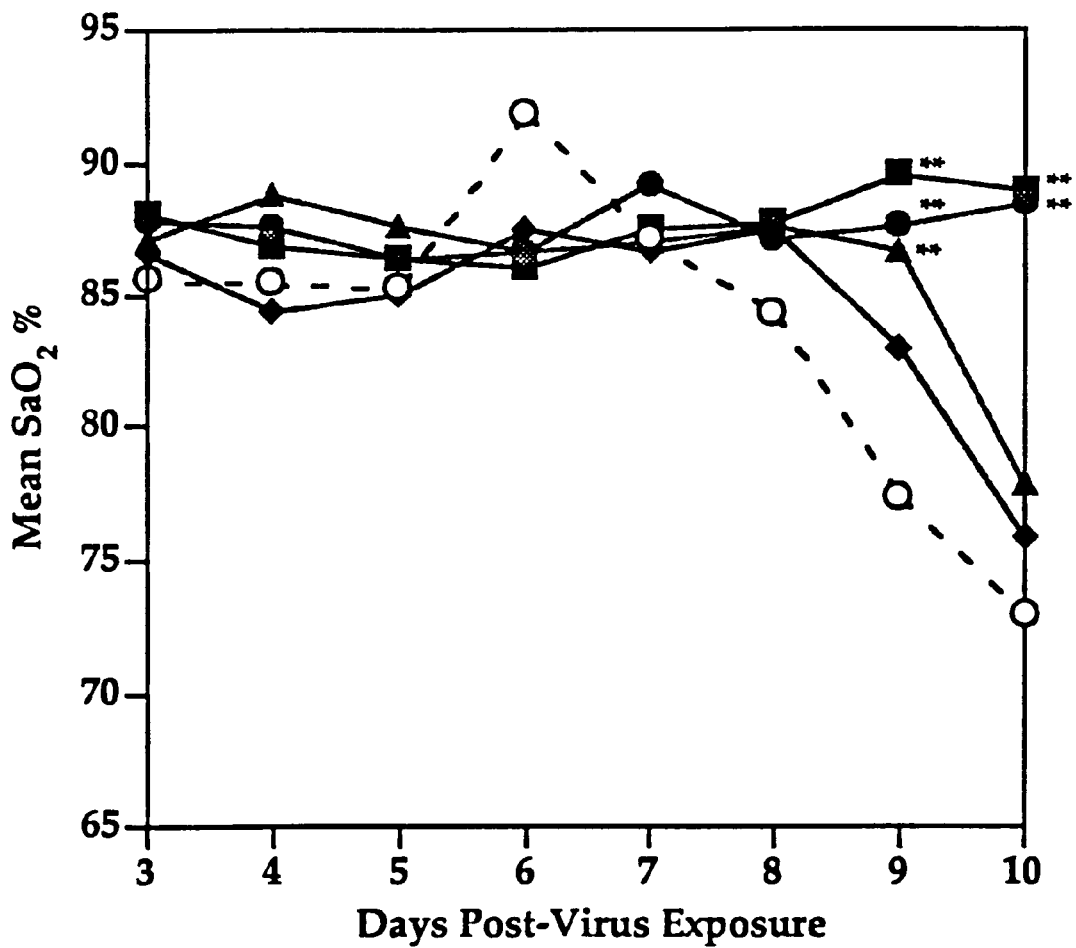

The results of the i.p. dosing experiment are summarized in Table I and in FIGS. 1 and 2. While in this model both compounds were significantly inhibitory at the high dose used, 203 treatment also resulted in significant survivors at a dose of 10 mg/kg/day. $SaO_2$ decline was particularly inhibited by both compounds at the 50 mg/kg/day dose, and again GG167 appeared to also prevent this decline at 10 and even 2 mg/kg/day. The lung score data appear to show the same trend of GG167 being effective at more than one dose. Some erraticism was seen in lung weights, with lungs taken from the mice receiving the highest dose of GG167 having a greater mean weight than the saline-treated controls.

Figure 3:
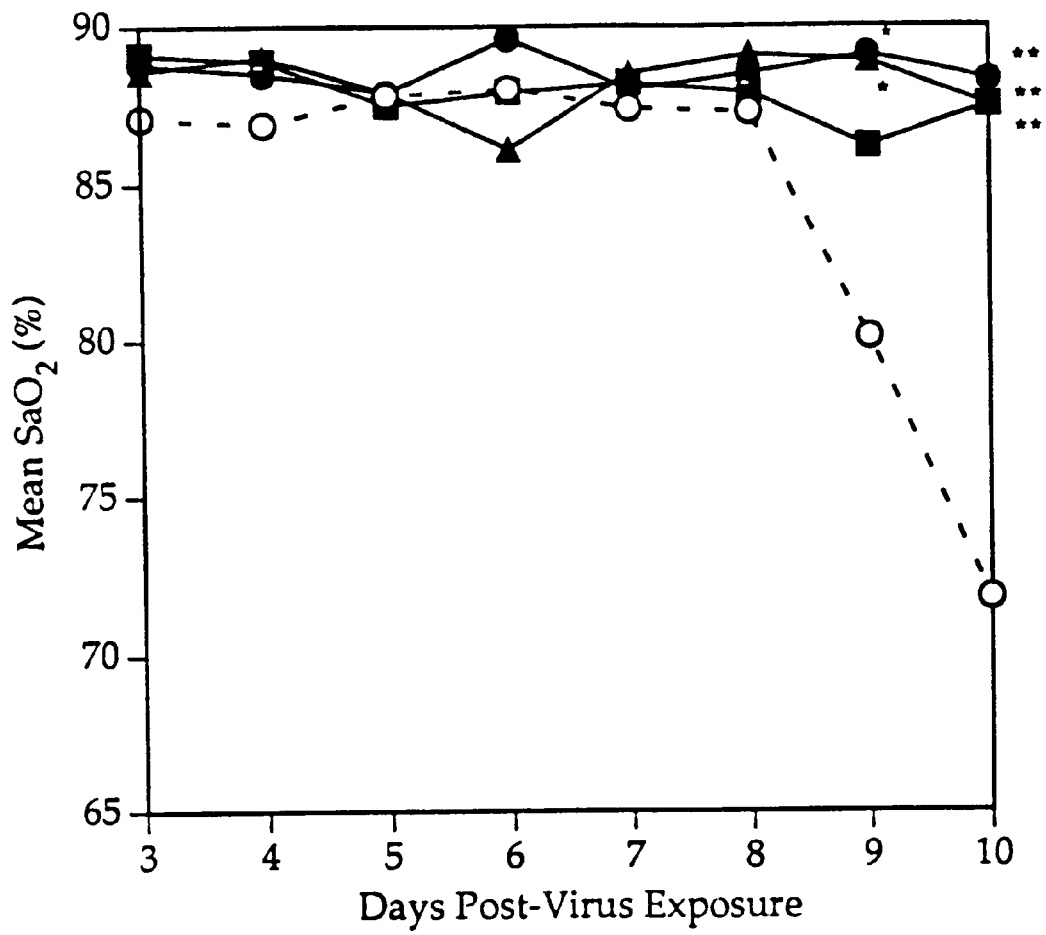
FIGS. 3–5 compare the $SaO_2$ levels achieved in influenza A infected mice treated with p.o. doses of ribavirin (triangles), compound 203 (squares) and GG167 (solid circles); saline controls are open circles.
Figure 4:
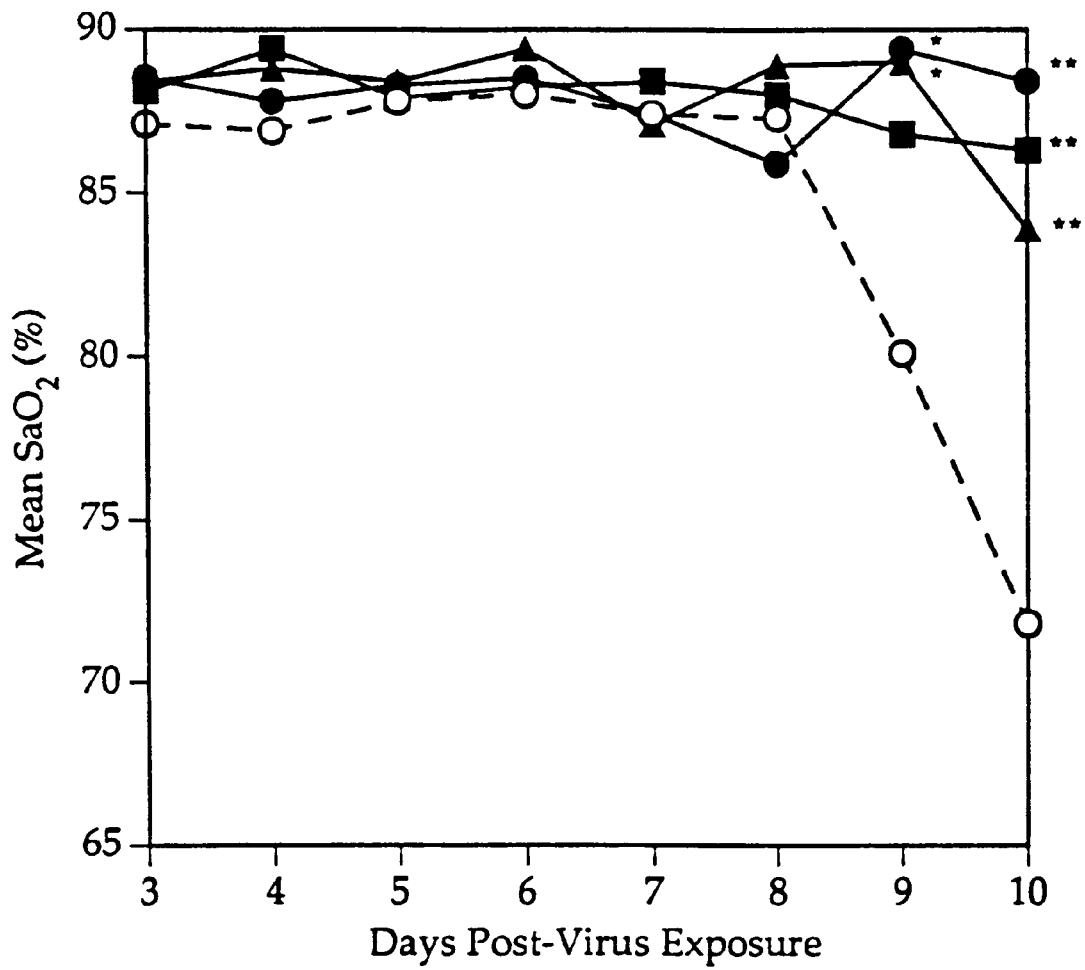
Figure 5:
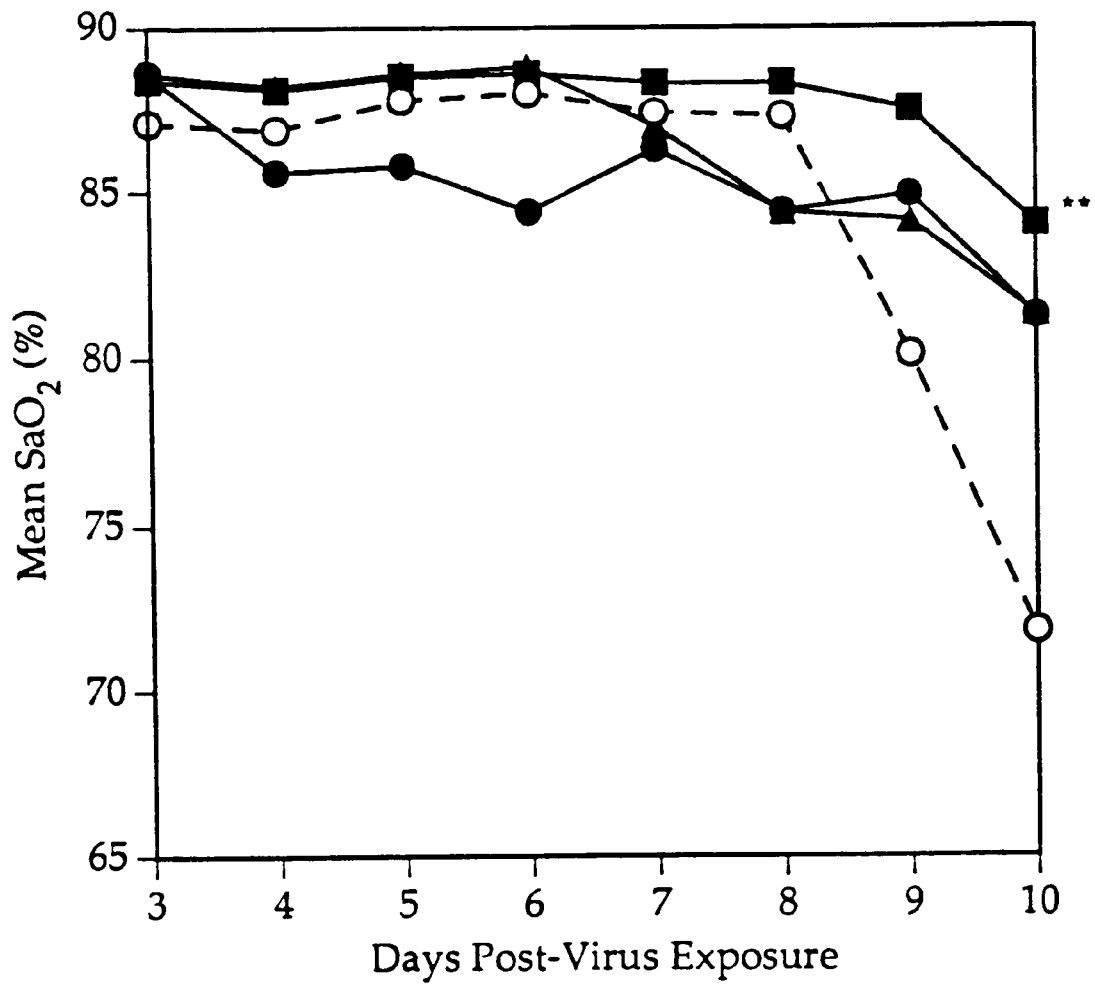

The p.o. dosing study is summarized in Table II, with daily $SaO_2$ values shown in FIGS. 3–5. Oral treatment with all three drugs in this model was significantly inhibitory to the influenza virus infection, preventing death, lowering lung scores and infection-associated lung weights, and inhibiting the usual decline in $SaO_2$.

Figure 6:
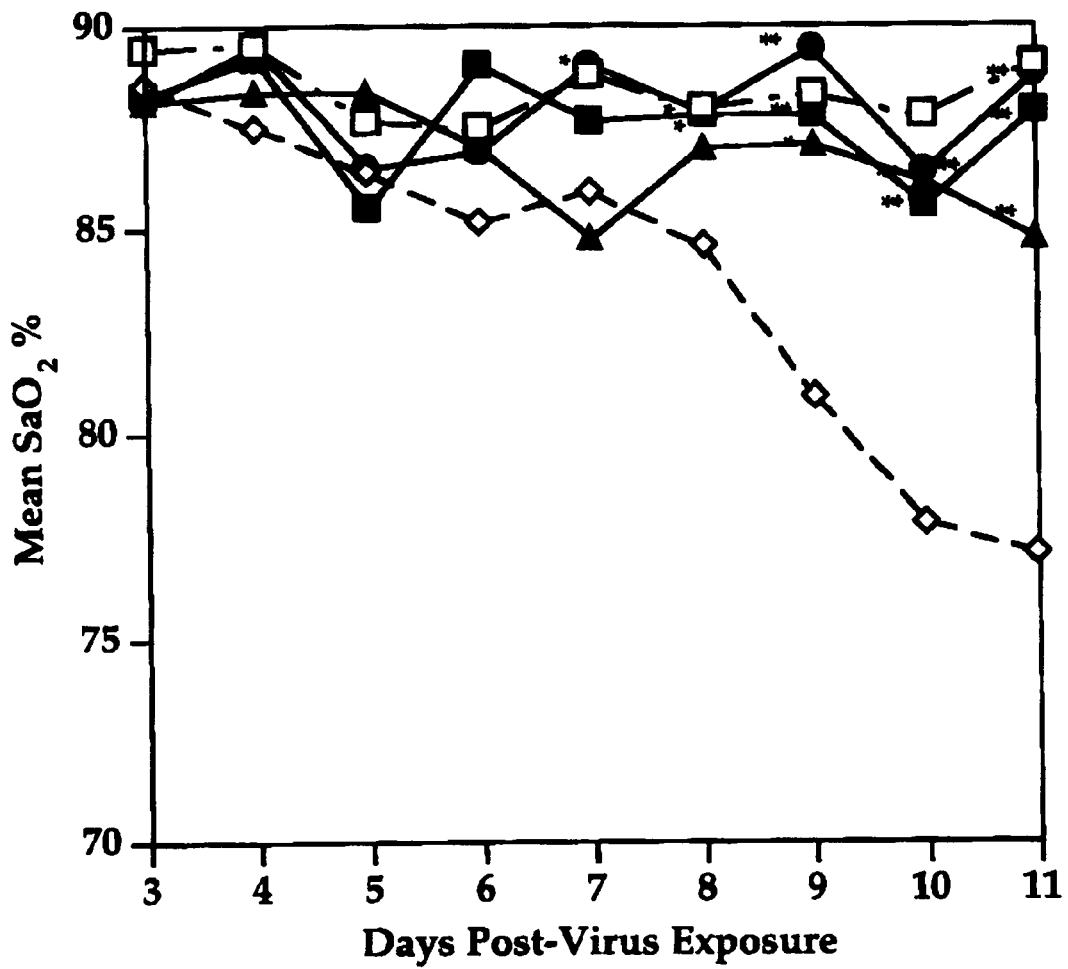
FIGS. 6–8 depict the $SaO_2$ levels in influenza A infected mice treated with low p.o. doses of compounds 262 (circles) and 260 (solid squares) and GG167 (triangles); saline controls are open circles and uninfected controls are open squares.
Figure 7:
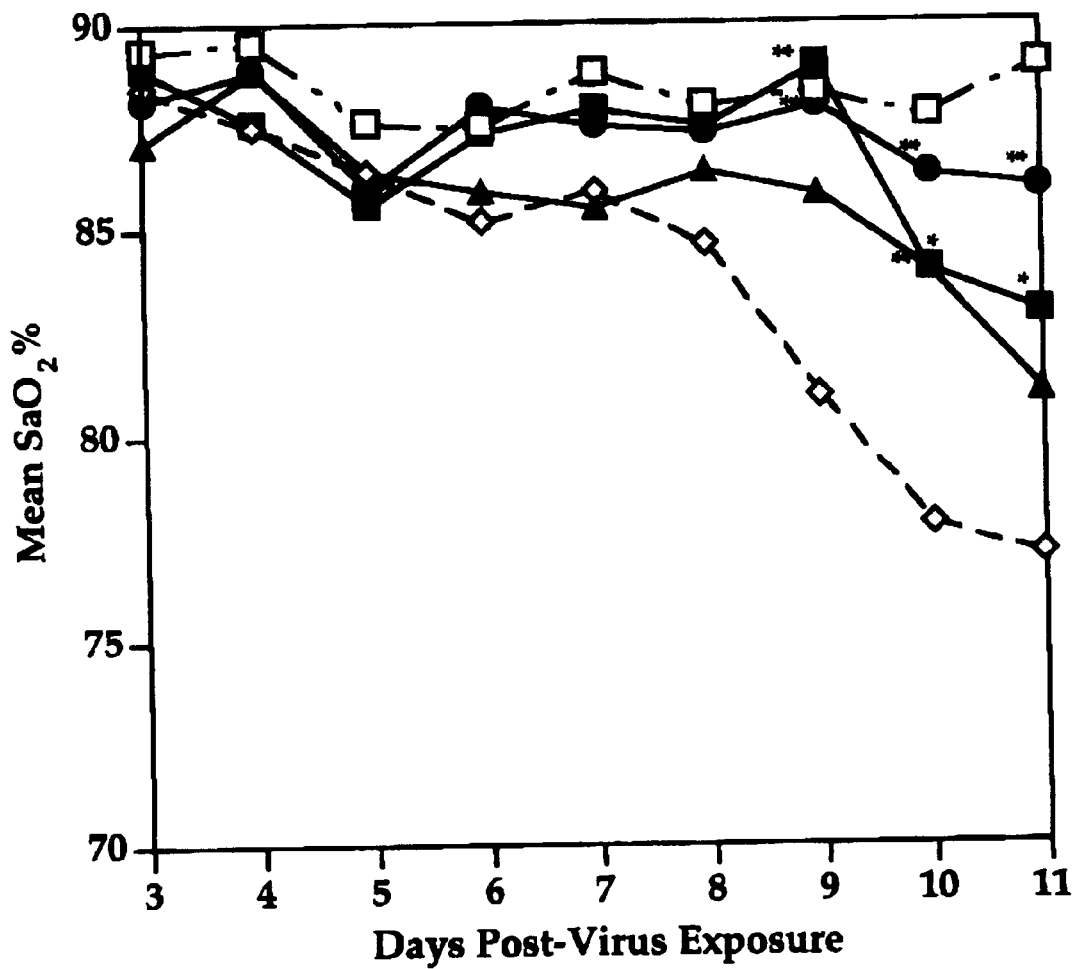
Figure 8:
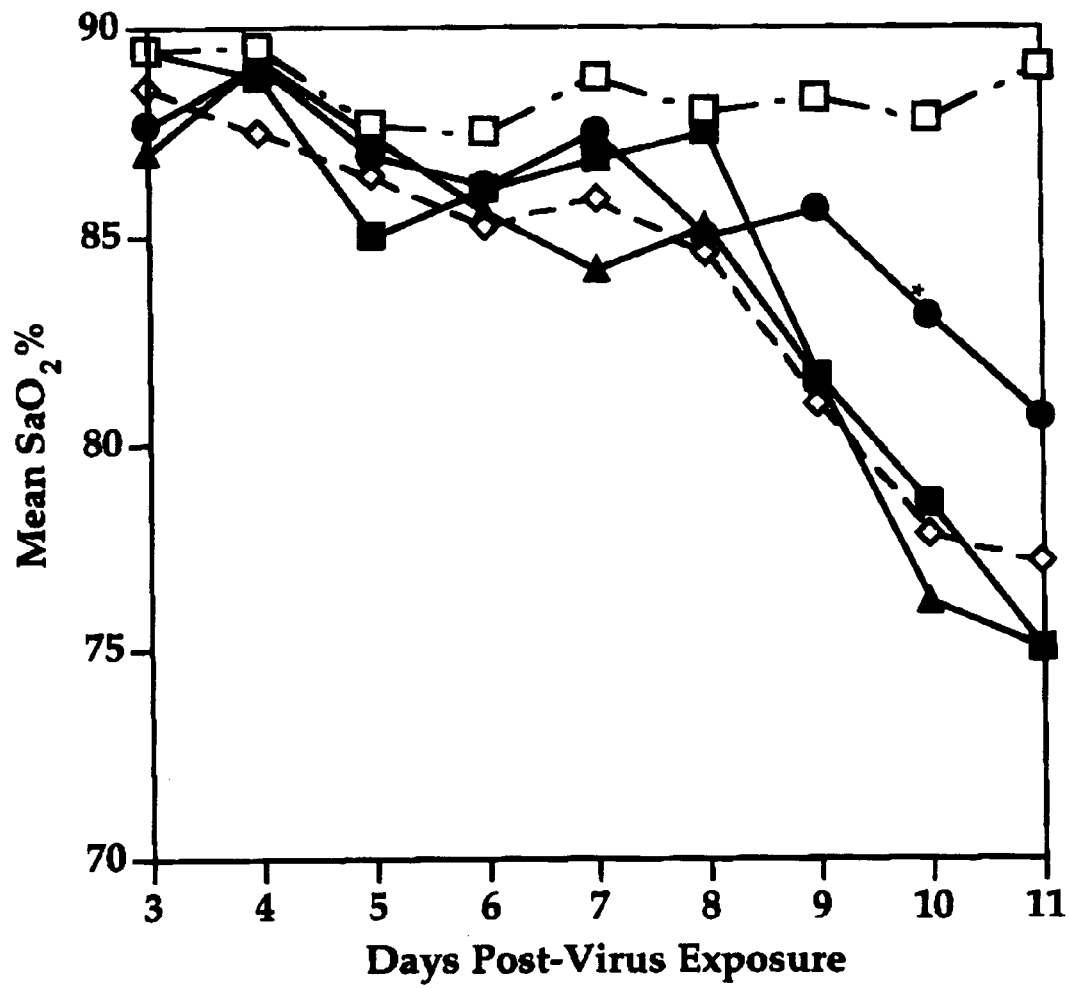

The p.o. low dose study results are summarized in Table III and in FIGS. 6–8. In this experiment, the infection was lethal to 14 of 16 saline-treated animals, the mean survival time being 9.6 days in this group. While all three compounds exhibited some degree of inhibitory effect on the virus infection, 262 (the ethyl ester prodrug) was the most effective at every dose as evidenced by number of survivors, mean survival time, and prevention of $SaO_2$ decline.

Table III shows the mean $SaO_2\%$ for all assay time taken together. The daily values for each compound are graphically represented in FIGS. 6 through 8. FIG. 6 illustrates the SaO$_2$ data with the highest concentrations of each compound; FIG. 7 shows the values at the median dose of each compound, and the SaO$_2$ values for the low dose of each compound are compared in FIG. 8.

Table III and FIGS. 6–8 indicate that while all three compounds were active orally against an experimentally induced influenza A (H1N1) virus infection, 262 was considered most effective. It was not determined whether the improved antiviral potency of 262 was unaccompanied with a concomitant increased animal toxicity, but this is unlikely since its greater efficacy is expected to be a result of its elevated oral bioavailability.

TABLE I

Comparison of the Effect of 203 and GG167 Administered i.p.[a] to Influenza A (H1N1) Virus-Infected Mice

| Compound | Dosage (mg/kg/day) | Surv/Total | Mean Surv. Time[b] (days) | Mean SaO$_2$[c] % | Infected, Treated Mean Lung Parameters[d] Score | Weight mg |
|---|---|---|---|---|---|---|
| 203 | 50 | 8/8** | >21.0** | 87.2** | 0.7* | 173* |
|  | 10 | 3/8* | 10.8 | 84.7 | 2.5 | 217 |
|  | 2 | 0/7 | 12.6 | 84.4 | 2.0 | 203 |
|  | 0.5 | 0/8 | 11.1 | 85.2* | 2.0 | 230 |
| GG167 | 50 | 8/8** | >21.0** | 87.6** | 0.7* | 230 |
|  | 10 | 7/8** | 15.0 | 87.5** | 1.7 | 170* |
|  | 2 | 1/8 | 12.6 | 86.0** | 1.3 | 213 |
|  | 0.5 | 0/8 | 12.3 | 84.5 | 2.3 | 227 |
| Saline | — | 0/16 | 11.0 | 82.9 | 2.0 | 220 |

TABLE II

Comparison of the Effect of Orally Administered[a] 203, GG167 and Ribavirin on Influenza A (H1N1) Virus Infections in Mice.

| Compound | Dosage (mg/kg/day) | Surv/Total | Mean Surv.[b] Time (days) | Mean SaO$_2$[c] % | Infected, Treated Mean Lung Parameters[d] Score | Weight (mg) |
|---|---|---|---|---|---|---|
| 203 | 250 | 8/8** | >21.0** | 87.9* | 0.8** | 160** |
|  | 50 | 8/8** | >21.0** | 87.9* | 1.3* | 200 |
|  | 10 | 4/8* | 12.8* | 87.7* | 1.3* | 240 |
| GG167 | 250 | 8/8** | >21.0** | 88.6* | 0.3** | 163** |
|  | 50 | 8/8** | >21.0** | 88.0* | 1.5* | 187* |
|  | 10 | 5/7* | 10.5 | 85.2 | 1.5* | 250 |
| Ribavirin | 100 | 8/8** | >21.0** | 88.2* | 0.3** | 140** |
|  | 32 | 6/8* | 13.0 | 88.0* | 0.8** | 163** |
|  | 10 | 3/8 | 11.0 | 86.4 | 2.2 | 267 |
| Saline | — | 1/16 | 10.9 | 84.5 | 2.4 | 203 |

TABLE III

Comparison of the Effect of Orally Administered[a] 260, 262 and GG167 on Influenza A (H1N1) Virus Infections in Mice.

| Compound | Dosage (mg/kg/day) | Surv/total | % Survivors | Mean Surv. Time[b] (days) | Mean SaO$_2$[c] (%) |
|---|---|---|---|---|---|
| 260 | 10 | 6/8** | 75** | 13.5** | 87.6* |
|  | 1 | 3/5 | 38 | 11.8 | 86.8 |
|  | 0.1 | 0/8 | 0 | 10.0 | 84.3 |
| 262 | 10 | 8/8*** | 100*** | >21.0** | 88.1** |
|  | 1 | 7/8*** | 88*** | 14.0* | 87.4* |
|  | 0.1 | 2/8 | 25 | 11.1** | 85.7 |

TABLE III-continued

Comparison of the Effect of Orally Administered[a] 260, 262 and GG167 on Influenza A (H1N1) Virus Infections in Mice.

| Compound | Dosage (mg/kg/day) | Surv/total | % Survivors | Mean Surv. Time[b] (days) | Mean SaO$_2$[c] (%) |
|---|---|---|---|---|---|
| GG167 | 10 | 5/8* | 63* | 12.3** | 86.9 |
|  | 1 | 2/8 | 25 | 11.7** | 85.7 |
|  | 0.1 | 0/8 | 0 | 9.8 | 83.5 |
| Saline | 0 | 2/16 | 13 | 9.6 | 83.8 |

Footnotes for Tables I-III
[a]Bid × 5 beginning 4 hr pre-virus exposure.
[b]Animals dying on or before day 21.
[c]Mean of values determined on days 3–10.
[d]Determined on day 6.
*P < 0.05, P < 0.01, *P < 0.001 compared to saline-treated controls Surprisingly, the foregoing demonstrates that in this model the oral or i.p. administration of GG167 was effective in practical therapeutic doses at reducing mortality in influenza-infected mice, despite the conclusion of Ryan et al. (*Antimicrob. Agents Chemother.*, 38(10):2270–2275) [1994]) that "it is likely that the relatively poor in vivo activity seen with GG167 in mice following intraperitoneal administration, despite good bioavailability, is due to its rapid clearance from the plasma, permitting poor penetration into respiratory secretions, coupled with its inability to penetrate and persist inside cells. . . . Similarly, the poor efficacy following oral dosing is probably a consequence of poor oral bioavailability in addition to these other factors." (p.2274). These observations are consistent with Von Izstein et al., WO 91/16320, WO 92/06691 and U.S. Pat. No. 5,360,817, which cover or are directed specifically to GG167. These patent documents are devoid of any teaching or suggestion to administer GG167 by any other route than intranasal. However, intranasal administration is believed to be inconvenient and costly in some circumstances. It would be advantageous if more facile routes of administration could be employed for GG167 and its related compounds set forth in WO 91/16320, WO 92/06691 and U.S. Pat. No. 5,360,817.

Thus, an embodiment of this invention is a method for the treatment or prophylaxis of influenza virus infection in a host comprising administering to the host, by a route other than topically to the respiratory system, a therapeutically effective dose of an antivirally active compound having formula (X) or (Y)

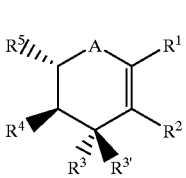

(x)

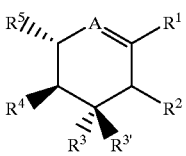

(y)

where in general formula (x), A is oxygen, carbon or sulphur, and in general formula (y), A is nitrogen or carbon;

R$^1$ denotes COOH, P(O)(OH)$_2$, NO$_2$, SOOH, SO$_3$H, tetrazol, CH$_2$CHO, CHO or CH(CHO)$_2$, $R^2$ denotes H, $OR^6$, F, Cl, Br, CN, $NHR^6$, $SR^6$, or $CH_2X$, wherein X is $NHR^6$, halogen or $OR^6$ and $R^6$ is hydrogen; an acyl group having 1 to 4 carbon atoms; a linear or cyclic alkyl group having 1 to 6 carbon atoms, or a halogen-substituted analogue thereof; an allyl group or an unsubstituted aryl group or an aryl substituted by a halogen, an OH group, an $NO_2$ group, an $NH_2$ group or a COOH group, $R^3$ and $R^{3'}$ are the same or different, and each denotes hydrogen, CN, $NHR^6$, $N_3$, $SR^6$, =N—$OR^6$, $OR^6$, guanidino,

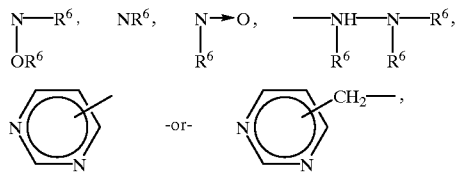

$R^4$ denotes $NHR^6$, $SR^6$, $OR^6$, $COOR^6$, $NO_2$, $C(R^6)_3$, $CH_2COOR^6$, $CH_2NO_2$ or $CH_2NHR^6$, and $R^5$ denotes $CH_2YR^6$, $CHYR^6CH_2YR^6$ or $CHYR^6CHYR^6CH_2YR^6$, where Y is O, S, NH or H, and successive Y moieties in an $R^5$ group are the same or different, and pharmaceutically acceptable salts or derivatives thereof, provided that in general formula (x)
(i) when $R^3$ or $R^{3'}$ is $OR^6$ or hydrogen, and A is oxygen or sulphur, then said compound cannot have both
(a) an $R^2$ that is hydrogen and
(b) an $R^4$ that is NH-acyl, and
(ii) $R^6$ represents a covalent bond when Y is hydrogen, and that in general formula (y),
(i) when $R^3$ or $R^{3'}$ is $OR^6$ or hydrogen, and A is nitrogen, then said compound cannot have both
(a) an $R^2$ that is hydrogen, and
(b) an $R^4$ that is NH-acyl, and
(ii) $R^6$ represents a covalent bond when Y is hydrogen.

The compounds of formulas x and y are more fully described in WO 91/16320, at page 3, line 23 to page 7, line 1, WO 92/06691 and U.S. Pat. No. 5,360,817, x and y are described therein as "I" and "Ia", respectively.

For the purposes herein, administration by a route "other than topically to the respiratory tract means" does not exclude administration of compound by buccal or sublingual routes, and does not exclude incidental adsorption of compound in the esophagus during oral, buccal or sublingual administration, provided however, that such as buccal, oral, sublingual or esophageal adsorption is not incidental to administration to the lungs or nasal passages by inhalers or the like. Usually, compound is administered as a formed article, a slurry or a solution.

In typical embodiments of this invention, the compound is GG167, the host is an animal other than mice (such as ferrets or humans), the route of administration is oral, and the objective of treatment and prophylaxis is reduction in mortality. Optionally, a prodrug of the compound of formula (X) or (Y) is employed, although as shown above it is not necessary to do so to achieve antiviral effect by oral administration. As prodrugs of GG167 and its co-disclosed compounds, any of the esters, amides or other prodrugs described elsewhere herein for the compounds of this invention are suitable for use with the analogous groups of the compounds of formula (X) and (Y), e.g., carboxyl esters or amides.

The therapeutically effective dose of GG167 and its related compounds, when administered by oral or other non-nasal administration routes, will be determined by the ordinarily skilled clinician in light of the considerations set forth in connection with dosing the compounds of this invention. For the most part the principal considerations are the route of administration and the host species. In general, larger doses will be required as one proceeds from intravenous to subcutaneous to oral administration routes, and in accord with conventional pharmacologic scaling principles as one proceeds to larger animals. Determination of therapeutically active doses is well within the ordinary skill in the art, but in general the doses will be substantially the same as those employed for the compounds of this invention.

Example 122

Each of the reactions shown in Table 50 were preformed according to Scheme 50. The preformed reactions are indicated with a "✓". Unless otherwise indicated in Table 50, steps AA, AB and AC were preformed according to Examples 92, 93 and 94, respectively, and step AD was preformed according to the combination of Examples 112 and 113.

Scheme 50

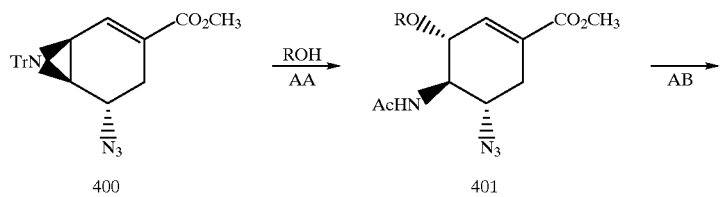

-continued

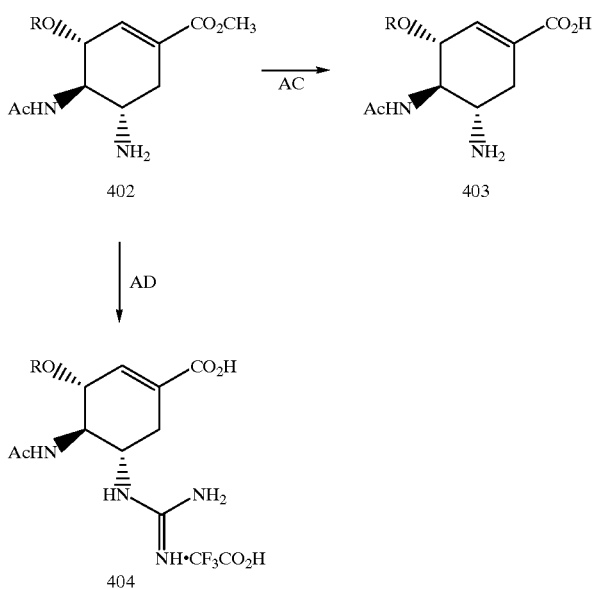

TABLE 50

| ROH | AA | AB | AC | AD |
|---|---|---|---|---|
| ethanol (EtOH) | ✓ | ✓ a,b | ✓ c | |
| butanol | ✓ | ✓ a,d | ✓ c,e | ✓ |
| pentanol | ✓ | ✓ | ✓ | |
| $F_3C$-CH$_2$CH$_2$OH | ✓ | ✓ | ✓ | |
| isobutanol | ✓ | ✓ d | ✓ c | ✓ |
| isopropanol | ✓ | ✓ f | ✓ | |
| (R)-2-butanol | ✓ g | ✓ | ✓ | ✓ |
| (S)-2-butanol | ✓ g | ✓ | ✓ | ✓ |
| 2-methyl-2-butanol | | ✓ | ✓ | ✓ |
| 3-pentanol | ✓ | ✓ | ✓ | ✓ |
| 4-heptanol | ✓ | ✓ | ✓ | |
| cyclopentanol | ✓ | ✓ h | ✓ | ✓ |
| cyclohexanol | ✓ | ✓ | ✓ | |
| benzyl alcohol | ✓ | ✓ b,d | ✓ | ✓ |
| phenol | ✓ i,j | ✓ | ✓ | |

Table 50 (notes)
a) ester hydrolysis prior to azide reduction
b) azide reduction using Ph$_3$P at room temperature
c) ester hydrolysis using aqueous KOH/MeOH
d) azide reduction using polymer-support Ph$_3$P at room temperature
e) isolated as the HCl salt
f) azide reduction using Ph$_3$P in MeOH/THF/H$_2$O
g) diastereomeric mixture, major diastereomer indicated
h) azide reduction also performed with Me$_3$P
i) aziridine opening performed at 55° C.
j) C-alkylated products were isolated

TABLE 50-continued

| ROH | AA | AB | AC | AD |
|---|---|---|---|---|

Structure 405 (phenyl-OAc, cyclohexene with CO$_2$CH$_3$, AcNH, N$_3$ substituents)

Structure 406 (AcO-phenyl, cyclohexene with CO$_2$CH$_3$, AcNH, N$_3$ substituents)

Example 123

Trifluoroacetamide 340: To a solution of amine 228 (100 mg, 0.34 mmol) in CH$_2$Cl$_2$ (3.5 mL) at 0° C. was added pyridine (41 μL, 0.51 mmol) and trifluroacetic anhydride (TFAA) (52 μL, 0.37 mmol) and the solution was stirred for 45 min at which time additional TFAA (0.5 eq) was added. After 15 min the reaction was evaporated under reduced pressure and the residue was partitioned between ethyl acetate and 1M HCl. The organic phase was washed with saturated NaHCO$_3$, saturated NaCl, and was dried (MgSO$_4$), filtered, and evaporated. The residue was chromatographed on silica gel (2/1-hexane/ethyl acetate) to afford trifluoroacetamide 340 (105 mg, 78%): $^1$H NMR (CDCl$_3$) δ 8.64 (d, 1H, J=7.7), 6.81 (s, 1H), 6.48 (d, 1H, J=8.2), 4.25–4.07 (m, 3H), 3.75 (s, 3H), 3.37 (m, 1H), 2.76 (dd, 1H, J=4.5, 18.7), 2.54 (m, 1H), 1.93 (s, 3H), 1.48 (m, 4H), 0.86 (m, 6H).

Example 124

N-Methyl trifluoroacetamide 341: To a solution of trifluoroacetamide 340 (90 mg, 0.23 mmol) in DMF (2 mL) at 0° C. was added sodium hydride (10 mg, 60% dispersion in mineral oil, 0.25 mmol). After 15 min at 0° C., methyl iodide (71 μL, 1.15 mmol) was added and the reaction was stirred for 2 h at 0° C. and for 1 h at room temperature. Acetic acid (28 μL) was added was the solution was evaporated. The residue was partitioned between ethyl acetate and water. The organic phase was washed with saturated NaCl, dried (MgSO$_4$), filtered, and evaporated. The residue was chromatographed on silica gel (1/1-hexane/ethyl acetate) to afford N-methyl trifluoroacetamide 341 (81 mg, 87%) as a colorless glass: $^1$H NMR (CDCl$_3$) δ 6.80 (s, 1H), 6.26 (d, 1H, J=9.9), 4.67 (m, 1H), 4.32 (m, 1H), 4.11 (m, 1H), 3.78 (s, 3H), 3.32 (m, 1H), 3.07 (br s, 3H), 2.60 (m, 2H), 1.91 (s, 3H), 1.48 (m, 4H), 0.87 (m, 6H).

Example 125

N-Methyl amine 342: To a solution of N-methyl trifluoroacetamide 341 (81 mg, 0.20 mmol) if THF (3 mL) was added 1.04 N KOH (480 μL, 0.50 mmol) and the mixture was stirred at room temperature for 14 h. The reaction was acidified with IR 120 ion exchange resin to pH~4. The resin was filtered, washed with THF, and the filtrate was evaporated. The residue was dissolved in 10% TFA/water (5 mL) and was evaporated. The residue was passed through a column (1.5×2.5 cm) of C-18 reverse phase silica gel eluting with water. Product fractions were pooled and lyophilized to afford N-methyl amine 342 (46 mg, 56%) as a white solid: $^1$H NMR (D$_2$O) δ 6.80 (s, 1H), 4.31 (br d, 1H, J=8.8), 4.09 (dd, 1H, J=8.9, 11.6), 3.53 (m, 2H), 2.98 (dd, 1H, J=5.4, 16.9), 2.73 (s, 3H), 2.52–2.41 (m, 1H), 2.07 (s, 3H), 1.61–1.39 (m, 4H), 0.84 (m, 6H).

Example 126

Compound 346: To a solution of epoxide 345 (13.32 g, 58.4 mmol) in 8/1-MeOH/H$_2$O (440 mL, v/v) was added sodium azide (19.0 g, 292.0 mmol) and ammonium chloride (2.69 g, 129.3 mmol) and the mixture was refluxed for 15 h. The reaction was cooled, concentrated under reduced pressure and partitioned between EtOAc and H$_2$O. The organic layer was washed successively with satd. bicarb, brine and dried over MgSO$_4$. Concentration in vacuo followed by flash chromatography on silica gel (30% EtOAc in hexanes) gave 11.81 g (75%) of azido alcohol 346 as a viscous oil. $^1$H NMR (300 MHz, CDCl$_3$) δ 6.90–6.86 (m, 1H); 4.80 (s, 2H); 4.32 (bt, 1H, J=4.2 Hz); 4.22 (q, 2H, J=7.2 Hz); 3.90–3.74 (overlapping m, 2H); 3.44 (s, 3H); 2.90 (d, 1H, J=6.9 Hz); 2.94–2.82 (m, 1H); 2.35–2.21 (m, 1H); 1.30 (t, 3H, J=7.2 Hz).

Example 127

Compound 347: To a solution of ethyl ester 346 (420 mg, 1.55 mmol) in dry THF (8.0 mL) cooled to -78° C. was added DIBAL (5.1 mL of a 1.0 M solution in toluene) dropwise via syringe. The bright yellow reaction mixture was stirred at -78° C. for 1.25 h and then slowly hydrolyzed with the slow addition of MeOH (1.2 mL). Volatiles were removed under reduced pressure and the residue partitioned between EtOAc and cold dilute HCl. The organic layer was separated and the aqueous layer back extracted with EtOAc. The organic layers were combined and washed successively with satd. bicarb, brine and dried over MgSO$_4$. Concentration in vacuo followed by flash chromatography on silica gel (20% hexanes in EtOAc) gave 127 mg (36%) of the diol 347 as a colorless viscous oil. $^1$H NMR (300 MHz, CDCl$_3$) δ 5.83–5.82 (m, 1H); 4.78 (s, 2H); 4.21 (bt, 1H, J=4.4 Hz); 4.06 (bs, 2H); 3.85–3.65 (overlapping m, 2H); 3.43 (s, 3H); 3.18 (d, 1H, J=8.1 Hz); 2.51 (dd, 1H, J=5.5, 17.7 Hz); 2.07–1.90 (m, 1H); 1.92 (bs, 1H).

The following claims are directed to embodiments of the invention and shall be construed to cover insubstantial variations thereof.

What is claimed is:

1. A composition comprising a compound of the formula:

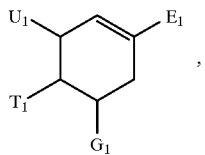

wherein:
  E$_1$ is —CO$_2$H, —CO$_2$R$_5$, —CO$_2$R$_{5a}$W$_5$ or —CO$_2$W$_5$;
  G$_1$ is —N(R$_{11}$)$_2$, —N(R$_{11}$)C(N(R$_{11}$))(N(R$_{11}$)$_2$), or —C(R$_{11}$)$_2$—N(R$_{11}$)$_2$;

$T_1$ is —NH(C(O)CH$_3$), —NH(C(O)CH$_2$F), —NH(C(O)CHF$_2$), or —NH(C(O)CF$_3$);

$U_1$ is —OR$_4$, —SR$_4$, NHR$_4$ or N(R$_4$)$_2$;

$R_1$ is independently H or alkyl of 1 to 12 carbon atoms;

$R_2$ is independently $R_3$ or $R_4$ wherein each $R_4$ is independently substituted with 0 to 3 $R_3$ groups;

$R_3$ is independently F, Cl, Br, I, —CN, N$_3$, —NO$_2$, —OR$_{6a}$, —OR$_1$, —N(R$_1$)$_2$, —N(R$_1$)(R$_{6b}$), —N(R$_{6b}$)$_2$, —SR$_1$, —SR$_{6a}$, —S(O)R$_1$, —S(O)$_2$R$_1$, —S(O)OR$_1$, —S(O)OR$_{6a}$, —S(O)$_2$OR$_1$, —S(O)$_2$OR$_{6a}$, —C(O)OR$_1$, —C(O)R$_{6c}$, —C(O)OR$_{6a}$, —OC(O)R$_1$, —N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_{6b}$))(N(R$_1$)$_2$), —N(R$_{6b}$)C(N(R$_1$))(N(R$_1$)(R$_{6b}$)), —N(R$_1$)C(N(R$_{6b}$))(N(R$_1$)(R$_{6b}$), —N(R$_1$)C(N(R$_1$))(N(R$_{6b}$)$_2$), —N(R$_{6b}$)C(N(R$_{6b}$))(N(R$_1$)R$_{6b}$)), —N(R$_{6b}$)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), =O, =S, =N(R$_1$) or =N(R$_{6b}$);

$R_4$ is independently alkyl of 1 to 12 carbon atoms, alkenyl of 2 to 12 carbon atoms, or alkynyl of 2 to 12 carbon atoms; and $R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_5$ is carbocycle or heterocycle wherein $W_5$ is independently substituted with 0 to 3 $R_2$ groups; and $R_{11}$ is independently H or $R_5$.

2. The composition of claim 1 wherein:

$G_1$ is —NH$_2$, —N(H)C(N(H))(NH$_2$), —NHCH$_3$, —NHCH$_2$CH$_3$, —N(CH$_3$)$_2$, —N(CH$_2$CH$_3$)$_2$, —N(CH$_3$)(CH$_2$CH$_3$), —NHCH$_2$CH$_2$OH, —NHCH$_2$CH$_2$NH$_2$, or —CH$_2$—NH$_2$;

$T_1$ is —N(H)(C(O)CH$_3$), —N(H)(C(O)CH$_2$F), —N(H)(C(O)CHF$_2$), or —N(H)(C(O)CF$_3$); and $R_4$ is —OR$_4$, —SR$_4$ or NHR$_4$ is branched chain.

3. The composition of claim 1 wherein $R_4$ is alkyl of 1 to 12 carbon atoms, and $R_{11}$ is $R_4$.

4. The composition of claim 1 wherein $R_4$ is alkyl of 1 to 8 carbon atoms, or alkenyl or alkynyl of 2 to 8 carbon atoms, and $R_{11}$ is $R_4$.

5. The composition of claim 1 wherein $R_4$ is alkyl of 1 to 6 carbon atoms, or alkenyl or alkynyl of 2 to 6 carbon atoms, and $R_{11}$ is $R_4$.

6. The composition of claim 1 wherein $R_4$ is alkyl of 1 to 6 carbon atoms, and $R_{11}$ is $R_4$.

7. The composition of claim 1 wherein $R_4$ is alkyl of 1 to 6 carbon atoms and each $R_{11}$ is H.

8. The composition of claim 1 wherein $E_1$ is C(O)OCH$_2$CH$_3$; $G_1$ is NH$_2$, NHCH$_3$ or NHCH$_2$CH$_3$; $T_1$ is NH(C(O)CH$_3$); and $U_1$ is OCH(CH$_2$CH$_3$)$_2$.

* * * * *